United States Patent
Kane, Jr. et al.

(10) Patent No.: US 11,274,108 B2
(45) Date of Patent: Mar. 15, 2022

(54) COLONY STIMULATING FACTOR-1 RECEPTOR (CSF-1R) INHIBITORS

(71) Applicant: Genzyme Corporation, Cambridge, MA (US)

(72) Inventors: John L. Kane, Jr., Maynard, MA (US); Claude Barberis, Ayer, MA (US); Mark Czekaj, Doylestown, PA (US); Paul Erdman, Evanston, IL (US); Barret Giese, Wyckoff, NJ (US); Michael Kothe, Medway, MA (US); Tieu-Binh Le, Waltham, MA (US); Jinyu Liu, Acton, MA (US); Liang Ma, Hillsborough, NJ (US); Markus Metz, Encinitas, CA (US); Vinod Patel, Acton, MA (US); Andrew Scholte, Somerville, MA (US); Patrick Wai-Kwok Shum, Holliston, MA (US); Linli Wei, Waltham, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 15/745,223

(22) PCT Filed: Jul. 19, 2016

(86) PCT No.: PCT/US2016/042917
§ 371 (c)(1),
(2) Date: Jan. 16, 2018

(87) PCT Pub. No.: WO2017/015267
PCT Pub. Date: Jan. 26, 2017

(65) Prior Publication Data
US 2019/0016707 A1 Jan. 17, 2019

Related U.S. Application Data

(60) Provisional application No. 62/194,619, filed on Jul. 20, 2015.

(51) Int. Cl.
| | | |
|---|---|---|
| C07D 519/00 | (2006.01) | |
| C07D 471/04 | (2006.01) | |
| C07D 405/06 | (2006.01) | |
| C07D 487/04 | (2006.01) | |
| A61P 37/06 | (2006.01) | |

(52) U.S. Cl.
CPC ............ C07D 519/00 (2013.01); A61P 37/06 (2018.01); C07D 405/06 (2013.01); C07D 471/04 (2013.01); C07D 487/04 (2013.01)

(58) Field of Classification Search
CPC ... C07D 471/04; C07D 487/04; C07D 519/00
See application file for complete search history.

(56) References Cited

U.S. PATENT DOCUMENTS

| | | | |
|---|---|---|---|
| 4,612,323 A | | 9/1986 | Kisida et al. |
| 5,187,159 A | * | 2/1993 | Greenlee .............. C07D 405/06 514/234.2 |
| 6,060,480 A | | 5/2000 | Nakamura et al. |
| 6,130,333 A | * | 10/2000 | Huang ............... A61K 31/4184 546/118 |
| 2003/0114468 A1 | | 6/2003 | Wilde et al. |
| 2003/0176400 A1 | | 9/2003 | Torisu et al. |
| 2005/0004097 A1 | | 1/2005 | Torisu et al. |
| 2005/0107343 A1 | | 5/2005 | Kasibhatla et al. |
| 2006/0025383 A1 | | 2/2006 | Wishart et al. |
| 2006/0116402 A1 | | 6/2006 | Crew et al. |
| 2006/0235222 A1 | | 10/2006 | Bell et al. |
| 2007/0043068 A1 | | 2/2007 | Arnold et al. |
| 2008/0013095 A1 | | 1/2008 | Tai et al. |
| 2008/0108648 A1 | | 5/2008 | Alcouffe et al. |
| 2008/0221148 A1 | | 9/2008 | Ibrahim et al. |

(Continued)

FOREIGN PATENT DOCUMENTS

| | | |
|---|---|---|
| CN | 101558070 A | 10/2009 |
| CN | 104321322 A | 1/2015 |

(Continued)

OTHER PUBLICATIONS

Kubinyi (3D QSAR in Drug Design: Ligand-Protein Interactions and Molecular Similarity, vol. 2-3, Springer, 1998, 800 pages.*
Wermuth, The Practice of Medicinal Chemsitry, 2d ed. (2003), 768 pages, for example p. 142.*
The Chemical Abstracts Registry—(PD Feb. 9, 2014 and Dec. 25, 2013).*
Harrison et al. (Hypertension 2011; 57:132-140—Abstract published on Dec. 2010).*
John L. Kane at the 2018 (ACS-NE) American Chemical Society—Northeastern Section: Medicinal Chemistry Symposium on Dec. 13, 2018.

(Continued)

Primary Examiner — Valerie Rodriguez-Garcia
(74) Attorney, Agent, or Firm — McNeill Baur PLLC

(57) ABSTRACT

Compounds of the formulas

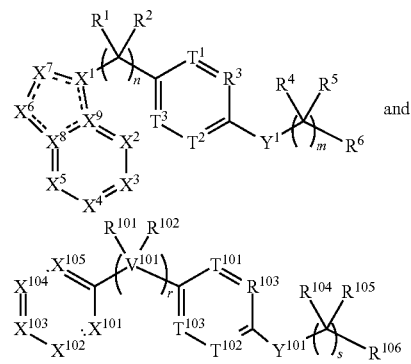

which are useful as colony stimulating factor-1 receptor inhibitors ("CSF-1R inhibitors").

15 Claims, 17 Drawing Sheets

(56) References Cited

U.S. PATENT DOCUMENTS

| | | |
|---|---|---|
| 2009/0093516 A1 | 4/2009 | Li et al. |
| 2009/0274698 A1 | 11/2009 | Bhagwat et al. |
| 2009/0286782 A1 | 11/2009 | Ibrahim et al. |
| 2010/0324011 A1 | 12/2010 | Bian et al. |
| 2011/0166174 A1 | 7/2011 | Zhang et al. |
| 2011/0281865 A1* | 11/2011 | Muthuppalaniappan ............ A61P 37/00 514/234.2 |
| 2012/0129829 A1 | 5/2012 | Sinha et al. |
| 2012/0252778 A1 | 10/2012 | Miltz et al. |
| 2013/0018049 A1 | 1/2013 | Rosa et al. |
| 2013/0196967 A1 | 8/2013 | Bartolozzi et al. |
| 2014/0155398 A1 | 6/2014 | Verma et al. |
| 2014/0309227 A1* | 10/2014 | Bungard ............ C07D 215/48 514/236.5 |

FOREIGN PATENT DOCUMENTS

| | | |
|---|---|---|
| EA | 7157 B1 | 8/2006 |
| EP | 0186190 A2 | 7/1986 |
| FR | 2693197 * | 7/1992 |
| JP | 2002507996 A | 3/2002 |
| JP | 2007500253 A | 1/2007 |
| JP | 2007505933 A | 3/2007 |
| JP | 2007520559 A | 7/2007 |
| JP | 2008503473 A | 2/2008 |
| JP | 2008521903 A | 6/2008 |
| JP | 2008533111 A | 8/2008 |
| JP | 2008545652 A | 12/2008 |
| JP | 2008546797 A | 12/2008 |
| JP | 2010510321 A | 4/2010 |
| JP | 2010514695 A | 5/2010 |
| JP | 2010532756 A | 10/2010 |
| JP | 2010540643 A | 12/2010 |
| JP | 2012524800 A | 10/2012 |
| JP | 2013543892 A | 12/2013 |
| JP | 2014514293 A | 6/2014 |
| JP | 2014515368 A | 6/2014 |
| JP | 2014522858 A | 9/2014 |
| WO | WO 94/00450 * | 1/1994 |
| WO | 9413676 A1 | 6/1994 |
| WO | 1994014434 A1 | 7/1994 |
| WO | 9901454 A1 | 1/1999 |
| WO | 2001066520 A1 | 9/2001 |
| WO | 200250062 A2 | 6/2002 |
| WO | 02092575 A1 | 11/2002 |
| WO | 03092595 A2 | 11/2003 |
| WO | 2004067529 A1 | 8/2004 |
| WO | 2005028434 A2 | 3/2005 |
| WO | 2005028448 A1 | 3/2005 |
| WO | 2005074603 A2 | 8/2005 |
| WO | 2006009755 A2 | 1/2006 |
| WO | 2006009797 A1 | 1/2006 |
| WO | 2006025715 A1 | 3/2006 |
| WO | 2006060381 A2 | 6/2006 |
| WO | 2006097625 A1 | 9/2006 |
| WO | 2007002325 A1 | 1/2007 |
| WO | 2007002433 A1 | 1/2007 |
| WO | 2007013896 A2 | 2/2007 |
| WO | 2007132308 A1 | 11/2007 |
| WO | 2008008539 A2 | 1/2008 |
| WO | 2008051805 A2 | 5/2008 |
| WO | 2008063888 A2 | 5/2008 |
| WO | 2008064255 A2 | 5/2008 |
| WO | 2008064265 A2 | 5/2008 |
| WO | 2008080001 A2 | 7/2008 |
| WO | 2008130951 A1 | 10/2008 |
| WO | 2009008992 A2 | 1/2009 |
| WO | 2009045753 A2 | 4/2009 |
| WO | 2009062118 A2 | 5/2009 |
| WO | 2010124082 A1 | 10/2010 |
| WO | 2011145035 A1 | 11/2011 |
| WO | 2011156632 A2 | 12/2011 |
| WO | 2012071184 A1 | 5/2012 |
| WO | 2012107500 A1 | 8/2012 |
| WO | 2012131633 A1 | 10/2012 |
| WO | 2012160464 A1 | 11/2012 |
| WO | 2013012649 A1 | 1/2013 |
| WO | 2013056070 A2 | 4/2013 |
| WO | 2013142427 A1 | 9/2013 |
| WO | 2014081820 A1 | 5/2014 |
| WO | 2015089139 A1 | 6/2015 |
| WO | 2015103137 A1 | 7/2015 |
| WO | 2015168269 A1 | 11/2015 |
| WO | WO 2013/144737 * | 10/2016 |

OTHER PUBLICATIONS

Cassia S. Mizuno et al, "Design, Synthesis, and Docking Studies of Novel Benzimidazoles for the Treatment of Metabolic Syndrome", Journal of Medicinal Chemistry,vol. 53, No. 3, Feb. 11, 2010 (Feb. 11, 2010), p. 1076-1085.

Conway James G et al, "Inhibition of colony-stimulating-factor-1 signaling in vivo with the orally bioavailable cFMS kinase inhibitor GW2580", Proceedings of the National Academy of Sciences, National Academy of Sciences, US,vol. 102, No. 44, Nov. 1, 2005 (Nov. 1, 2005), p. 16078-16083.

International Preliminary Report on Patentability in International Application No. PCT/US2016/042917, dated Jan. 23, 2018 (14 pages).

International Search Report and Written Opinion in International Application No. PCT/US2016/042917, dated Jan. 26, 2017 (30 pages).

Wu Z et al, "Design and synthesis of 3,7-diarylimidazopyridines as inhibitors of the VEGF-receptor KDR", Bioorganic & Medicinal Chemistry Letters, Pergamon, Amsterdam, NL,vol. 14, No. 4, Feb. 23, 2004 (Feb. 23, 2004), p. 909-912.

Chemical Abstract Service Registration No. 1788907-60-7 (Jun. 25, 2015).

Chemical Abstract Service Registration No. 1788907-62-9 (Jun. 25, 2015).

Chemical Abstract Service Registration No. 1788907-64-1 (Jun. 25, 2015).

Weidel, E. et al., "Composing compound libraries for hit discovery—rationality-driven preselection or random choice by structural diversity?", Future Medicinal Chemistry, 6(18), pp. 2057-2072 (2014) (downloaded on Sep. 1, 2020, http://hdl.handle.net/10033/345823).

Yuan, H. et al., "Molecular modeling of exquisitely selective c-Met inhibitors through #D-QSAR and molecular dynamics simulations", Journal of Chemical Information and Modeling, 54, pp. 2544-2554 (2014).

The Chemical Abstract Service Registration No. 1347291-61-5 (Dec. 2, 2011).

The Chemical Abstract Service Registration No. 1347338-13-9 (Dec. 2, 2011).

The Chemical Abstract Service Registration No. 1347343-41-2 (Dec. 2, 2011).

The Chemical Abstract Service Registration No. 1347464-55-4 (Dec. 2, 2011).

The Chemical Abstract Service Registration No. 1347528-83-9 (Dec. 2, 2011).

The Chemical Abstract Service Registration No. 1347650-16-1 (Dec. 2, 2011).

The Chemical Abstract Service Registration No. 1347673-50-0 (Dec. 2, 2011).

The Chemical Abstract Service Registration No. 1347698-95-6 (Dec. 2, 2011).

The Chemical Abstract Service Registration No. 1348223-10-8 (Dec. 4, 2011).

The Chemical Abstract Service Registration No. 1348621-97-5 (Dec. 4, 2011).

The Chemical Abstract Service Registration No. 1348052-74-3 (Dec. 4, 2011).

The Chemical Abstract Service Registration No. 1349276-26-1 (Dec. 5, 2011).

The Chemical Abstract Service Registration No. 1349135-12-1 (Dec. 5, 2011).

(56) References Cited

OTHER PUBLICATIONS

The Chemical Abstract Service Registration No. 1348972-34-8 (Dec. 5, 2011).
The Chemical Abstract Service Registration No. 1349470-05-8 (Dec. 6, 2011).
The Chemical Abstract Service Registration No. 1349831-67-9 (Dec. 6, 2011).
Hao et al., "Alumina-supported heteropoly acid: An efficient catalyst for the synthesis of azaarene substituted 3-hydroxy-2-oxindole derivatives via C(sp3)—H bond functionalization", Chinese Chemical Letters, 26, pp. 599-602 (2015).
Kumar et al., "β-Cyclodextrin catalysed C—C bond formation via C(sp3)—H functionalization of 2-methyl azaarenes with diones in aqueous medium", Green Chemistry, vol. 17, pp. 848-851 (Dec. 5, 2014).
Zeng et al., "Discovery of potent dipeptidyl peptidase IV inhibitors through pharmacophore hybridization and hit-to-lead optimization", Bioorganic & Medicinal Chemistry, vol. 21, pp. 1749-1755 (Feb. 8, 2013).
The Chemical Abstract Service Registration No. 1787486-49-0 (Jun. 24, 2015).
The Chemical Abstract Service Registration No. 1387586-18-6 (Aug. 7, 2012).
The Chemical Abstract Service Registration No. 1390476-30-8 (Aug. 13, 2012).
The Chemical Abstract Service Registration No. 1424499-72-8 (Mar. 17, 2013).
The Chemical Abstract Service Registration No. 1424601-42-2 (Mar. 17, 2013).
The Chemical Abstract Service Registration No. 1445131-94-1 (Jul. 17, 2013).
The Chemical Abstract Service Registration No. 1646259-46-2 (Feb. 10, 2015).
The Chemical Abstract Service Registration No. 1648159-37-8 (Feb. 16, 2015).
The Chemical Abstract Service Registration No. 1648351-85-2 (Feb. 16, 2015).
The Chemical Abstract Service Registration No. 1787479-54-2 (Jun. 24, 2015).

* cited by examiner

Figure 1: Inhibition of Proliferation of Murine Bone Marrow-Derived Macrophages (BMDMs) Treated with CSF-1 and CSF-1R Inhibitors (Group 1)
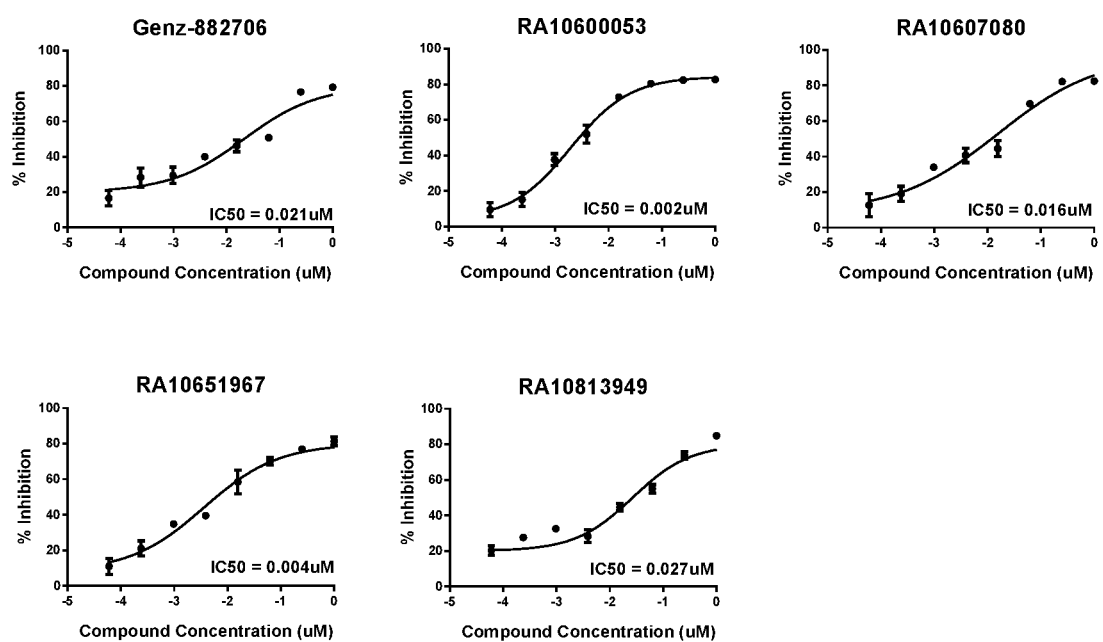

Figure 2: Inhibition of Proliferation of Murine Bone Marrow-Derived Macrophages (BMDMs) Treated with CSF-1 and CSF-1R Inhibitors (Group 2)
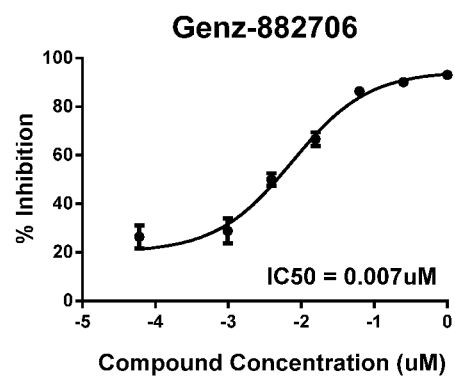
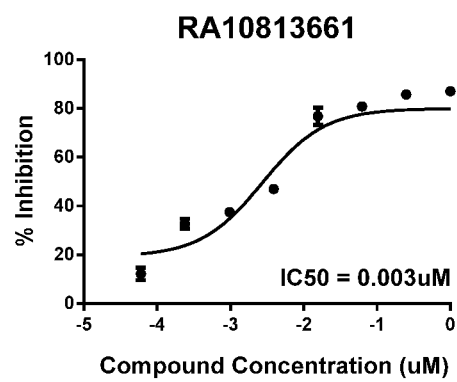
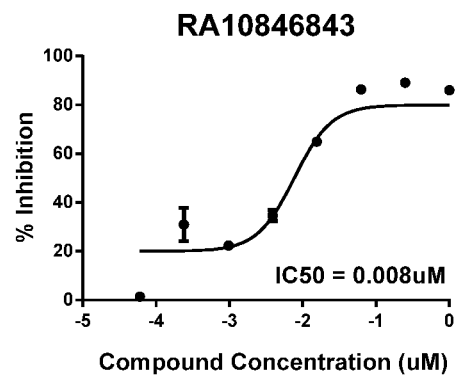
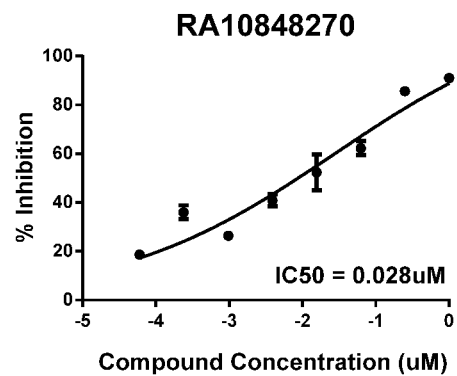

Figure 3: Inhibition of Proliferation of Murine Bone Marrow-Derived Macrophages (BMDMs) Treated with CSF-1 and CSF-1R Inhibitors (Group 3)
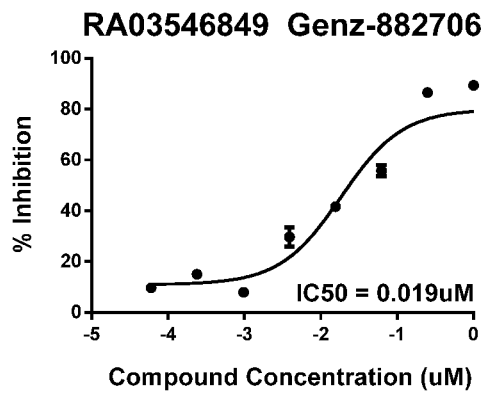
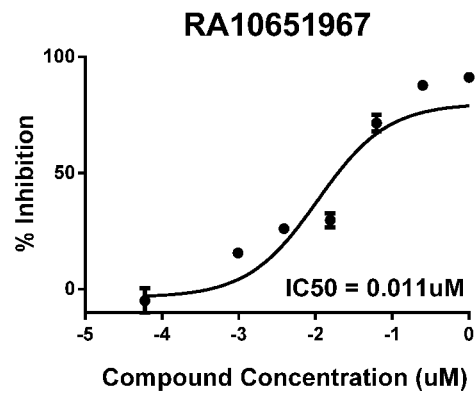
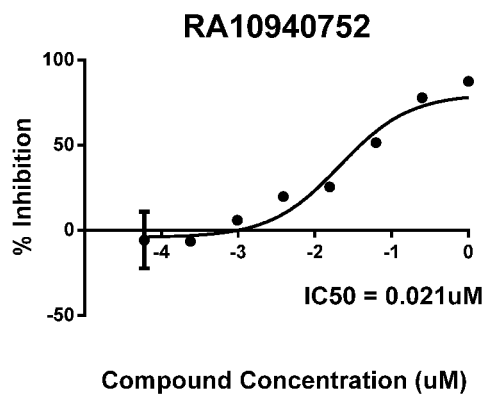
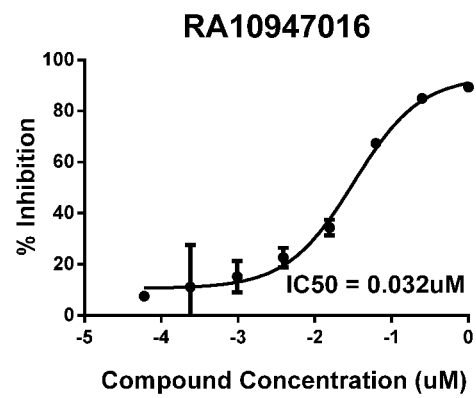
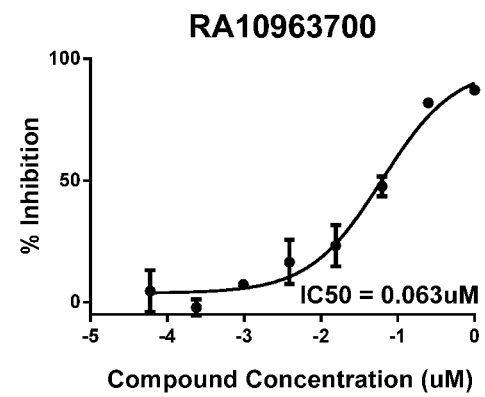
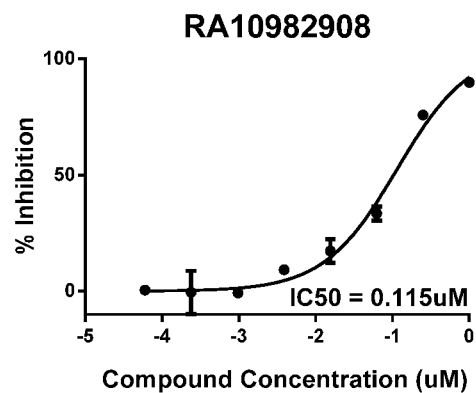

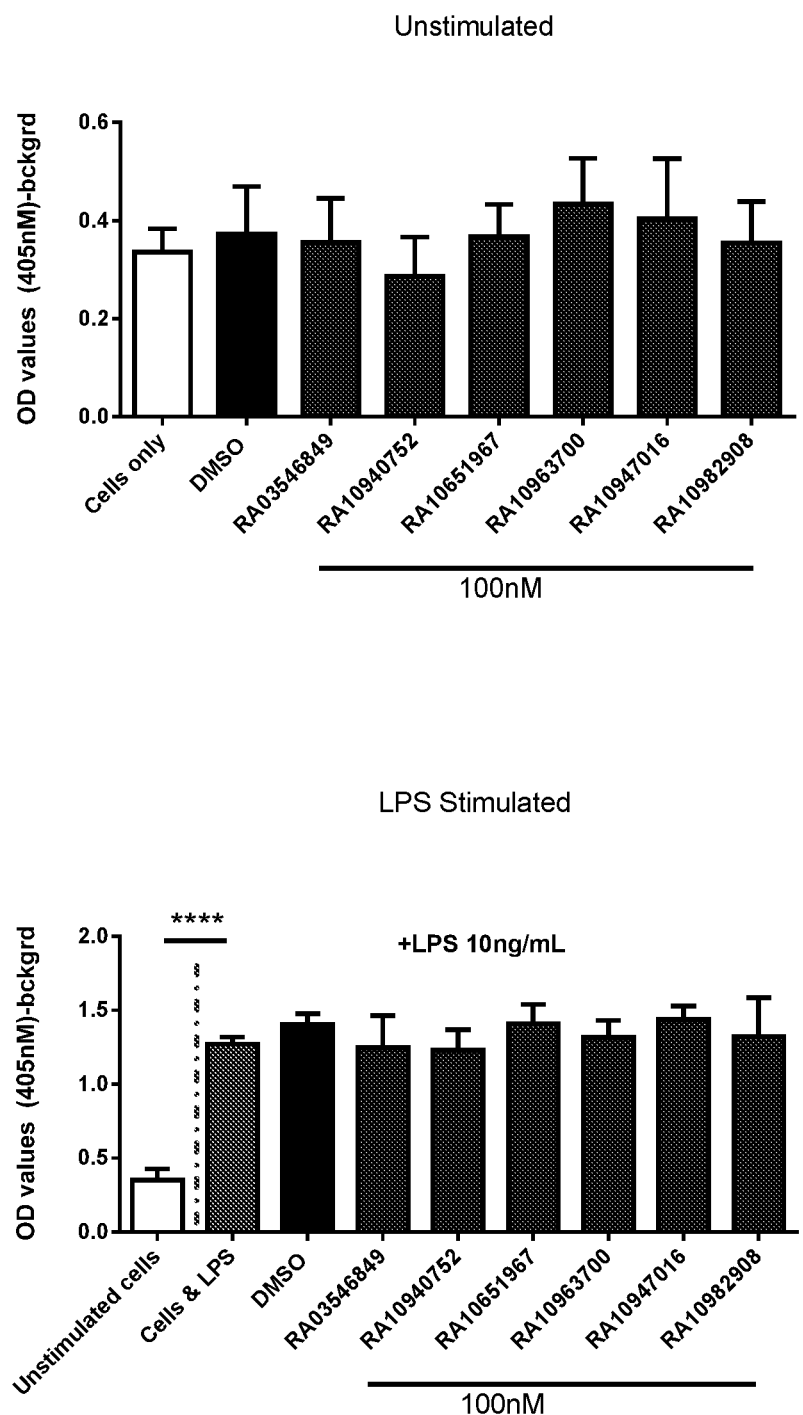
Figure 4: Phagocytic Activity of Murine Bone Marrow Derived Macrophages

Figure 5: Phagocytic Activity of Primary Murine Microglia Cells
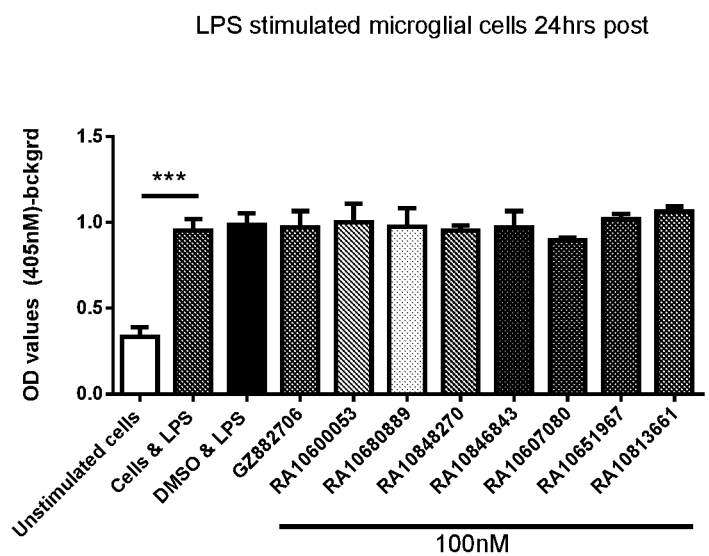

Figure 6: Phagocytic Activity of Primary Murine Microglial Cells following Incubation with DMSO or CSF-1R Inhibitors with LPS
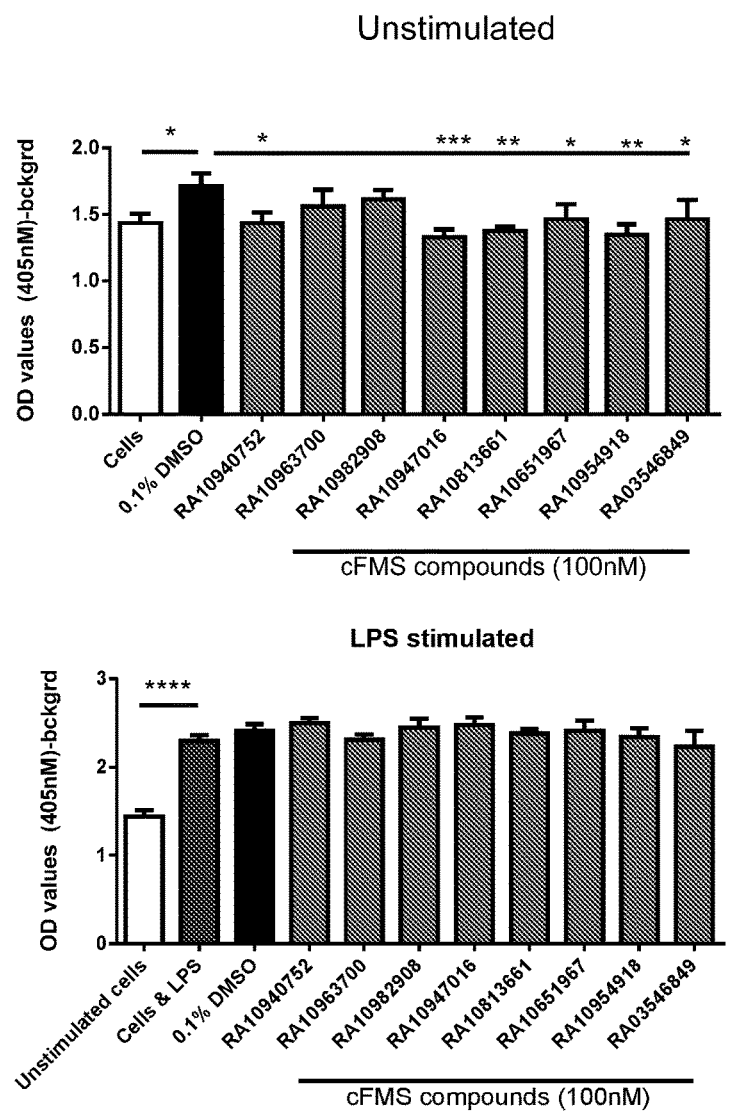

Figure 7: Effect of CSF-1R Inhibitors and Laquinimod on the Proliferation of Unstimulated Primary Murine Microglial Cells
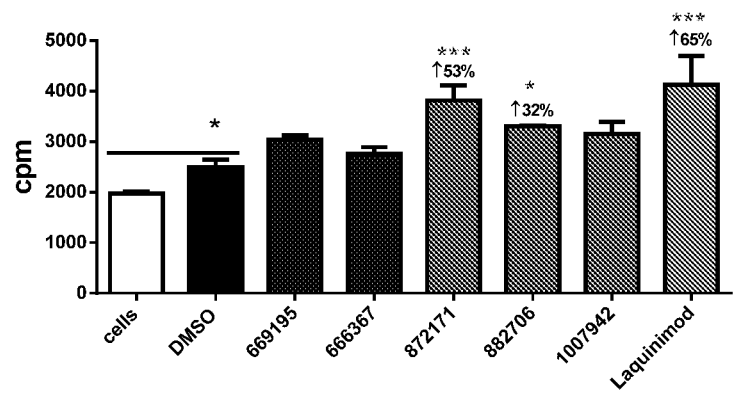

Figure 8: Effect of CSF-1R Inhibitors and Laquinimod on the Proliferation of CSF-1-Stimulated Primary Murine Microglial Cells
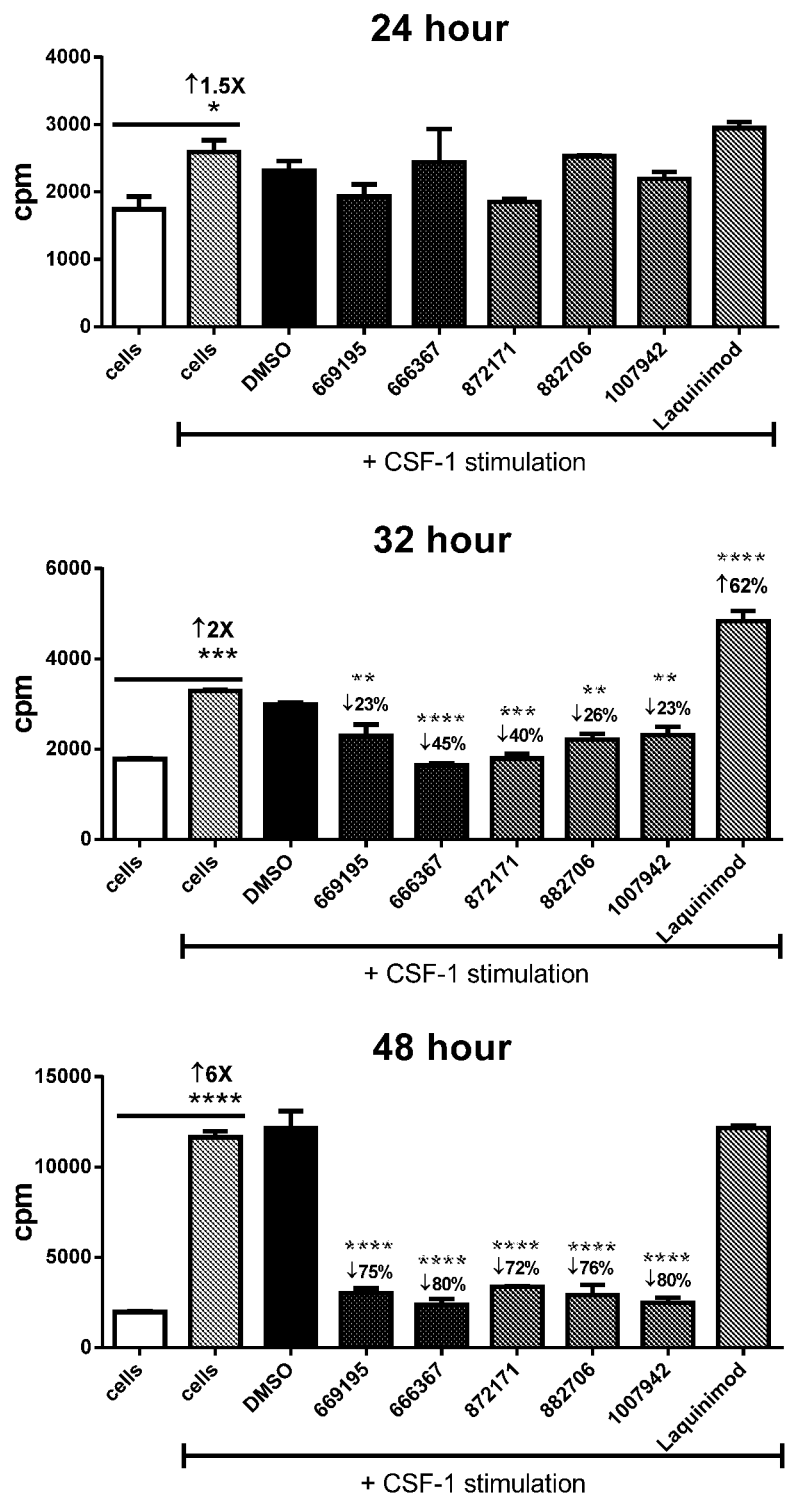

Figure 9: Comparison of GENZ-882706-Treated and Vehicle MOG-Induced NOD Progressive EAE Mice
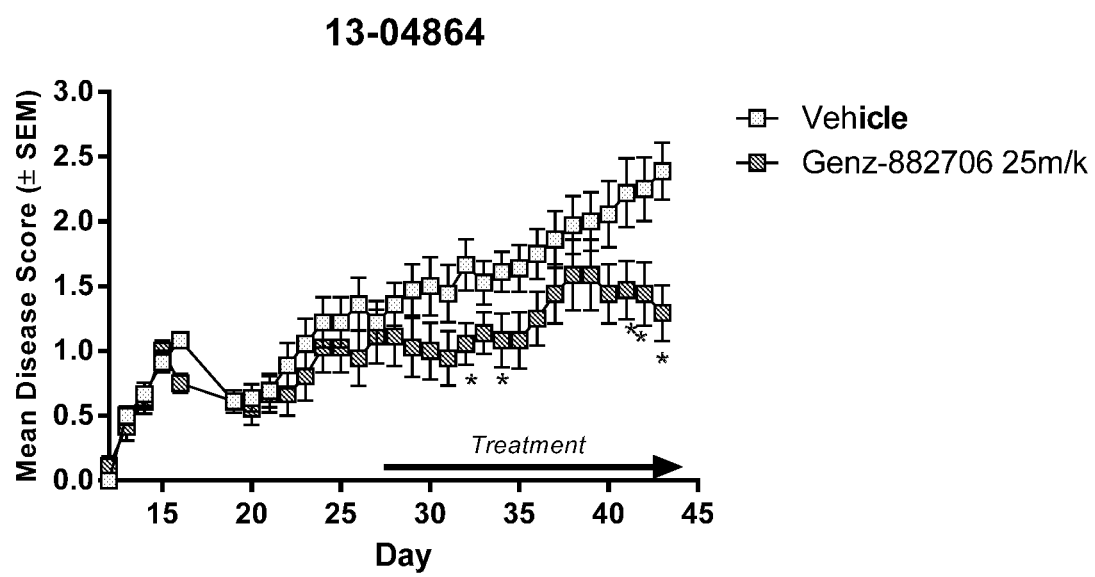

Figure 10: Gene Expression of Anti-Inflammatory and Inflammatory Markers in Spinal Cords from MOG-Induced NOD Progressive EAE Mice
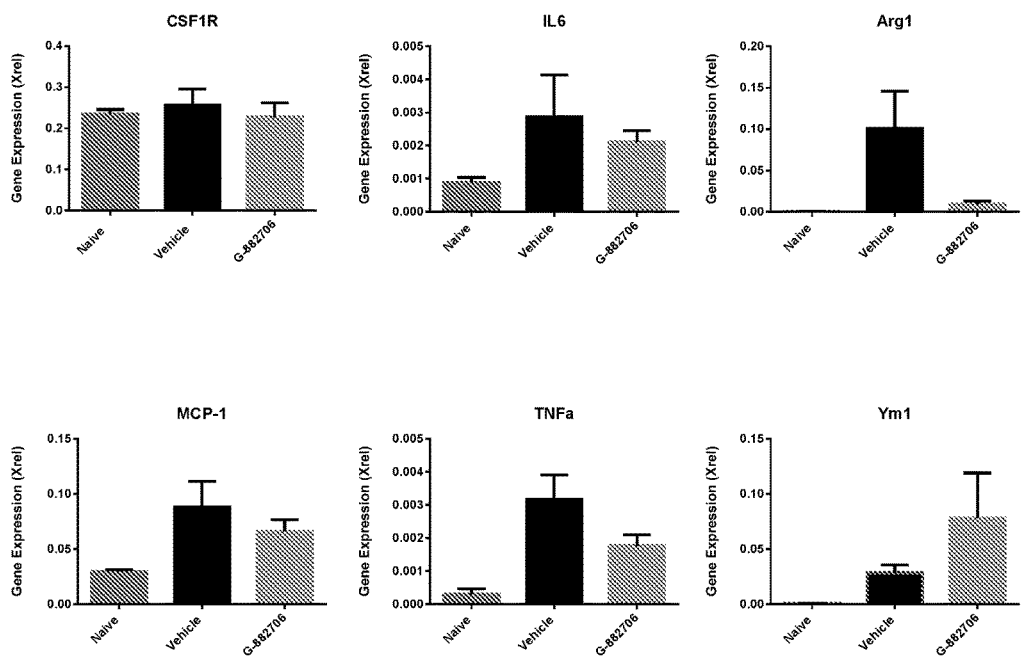

Figure 11: Inflammatory Cytokine Production in the Spinal Cord Following Treatment with Genz-882706
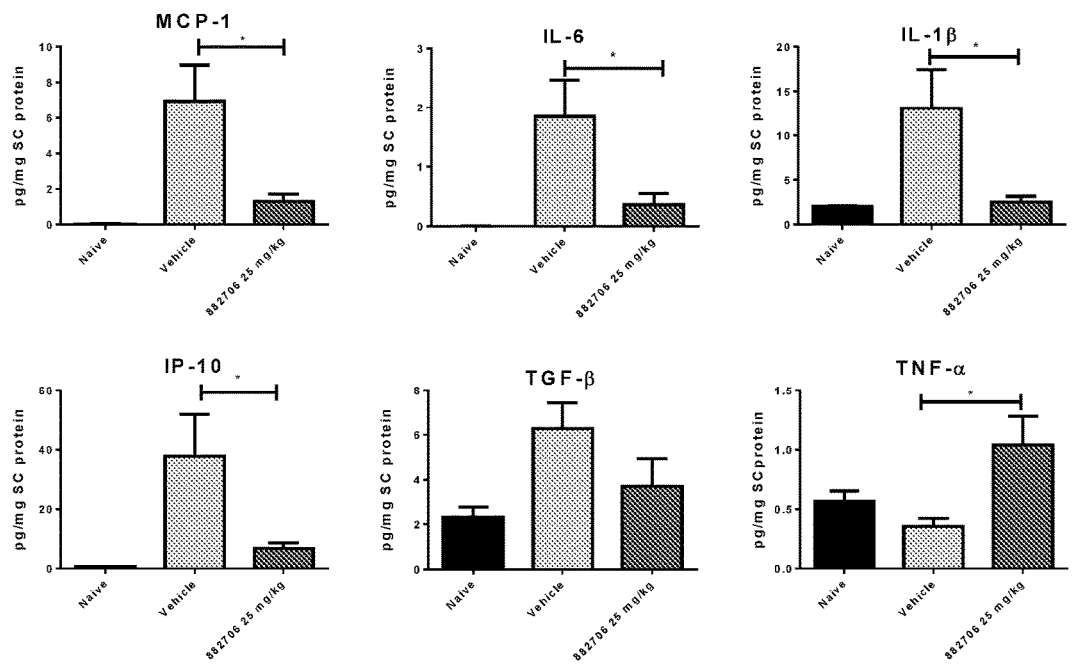
Figure 12: Regulatory Cytokine Production in the Spinal Cord Following Treatment with Genz-882706
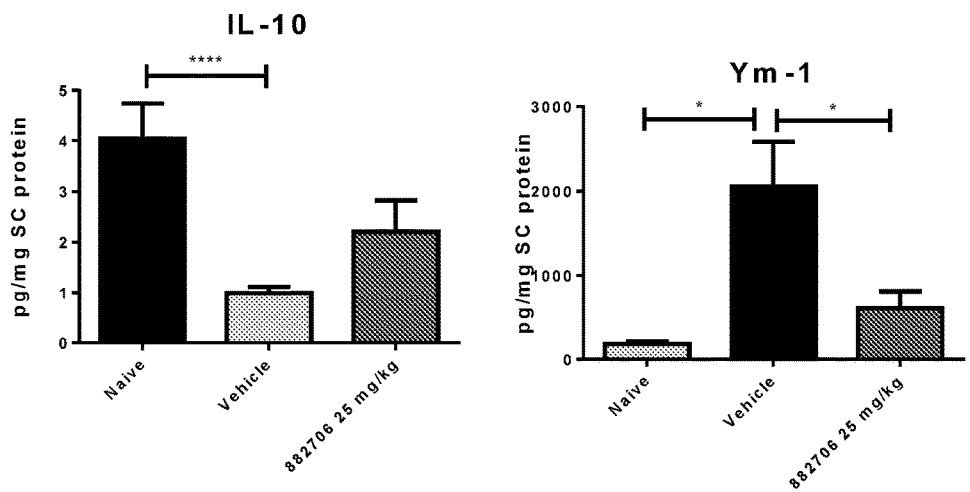

Figure 13: Microglia, Monocyte/Macrophage and Lymphocyte Populations in the Brain and Spinal cord after LPS Challenge and Prophylactic Treatment with Genz-882706
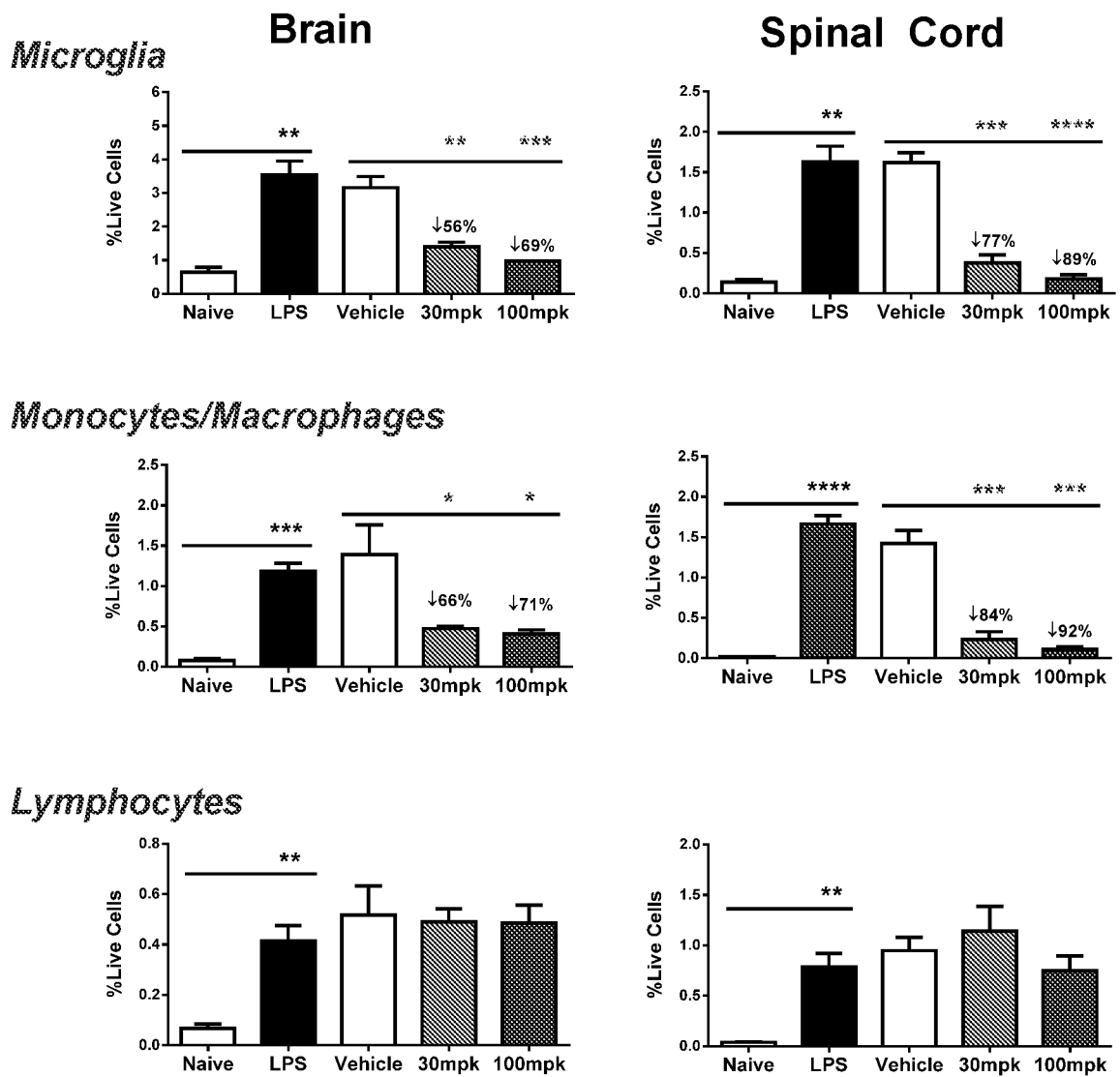

Figure 14: Mean Fluorescence Intensities (MFIs) of Activation Markers on Microglia and Monocyte/Macrophage Cell Populations in the Brain after *in vivo* LPS Challenge and Prophylactic Treatment with Genz-882706
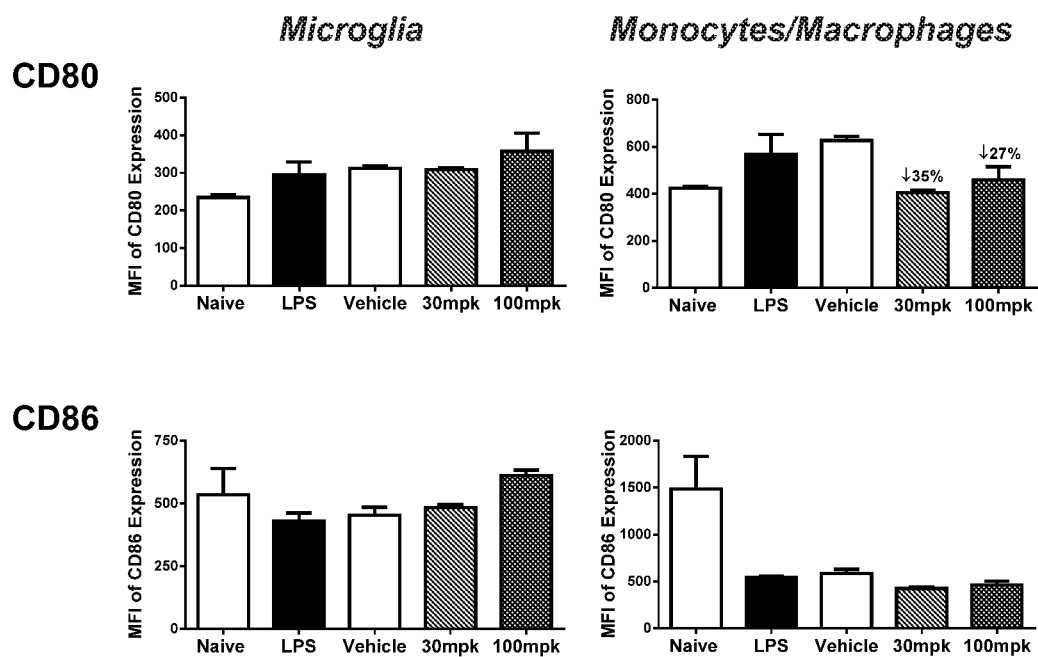

Figure 15: Mean Fluorescence Intensities (MFIs) of Activation Markers on Microglia and Monocyte/Macrophage Cell Populations in the Spinal Cord after *in vivo* LPS Challenge and Prophylactic Treatment with Genz-882706
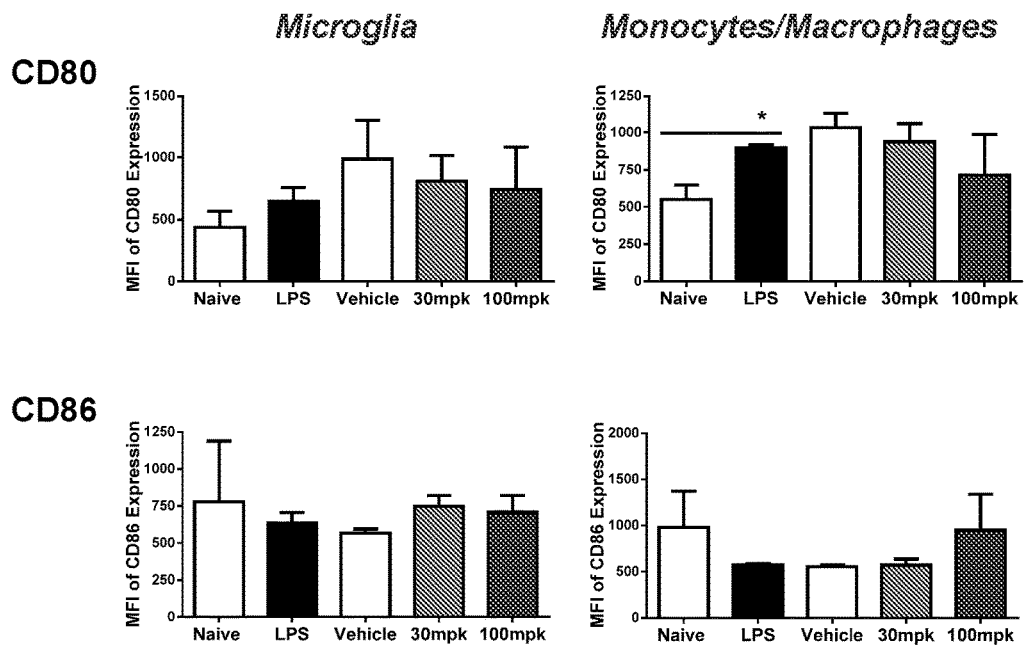
Figure 16: Cell Populations in the Blood after LPS Challenge and Prophylactic Treatment with Genz-882706
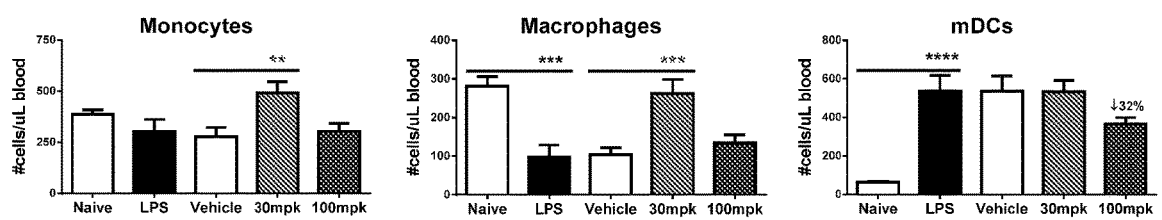

Figure 17: Therapeutic treatment with Genz-882706 (100mg/kg or 25mg/kg, top) and Inhibitor A (150mg/kg, bottom).
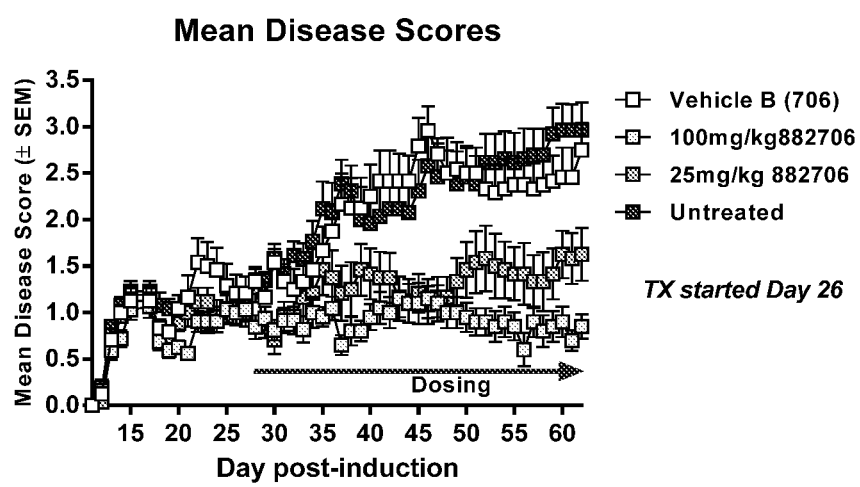
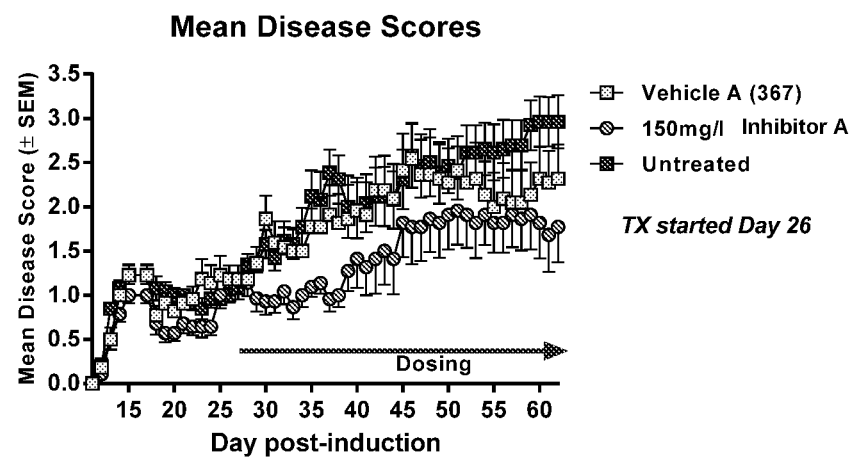

Figure 18: Histopathology Scoring of Spinal Cord Sections of GENZ-882706-Treated, Vehicle, and Untreated MOG-Induced NOD Progressive EAE Mice
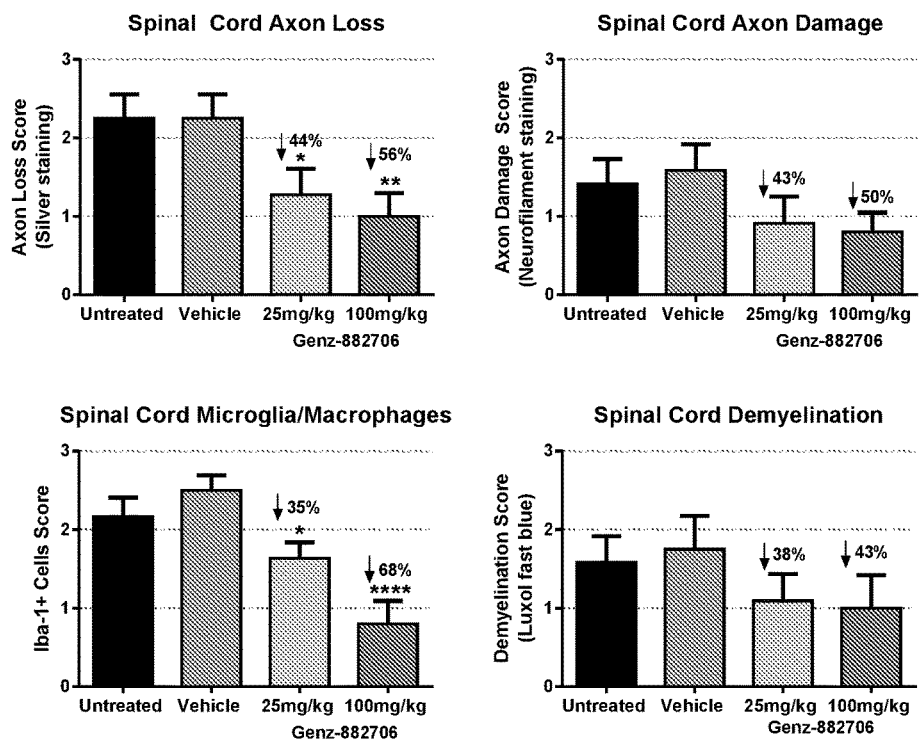
Figure 19: Microglia, Monocyte/Macrophage and Lymphocyte Populations in the Brain after LPS challenge and Prophylactic Treatment with RA10651967
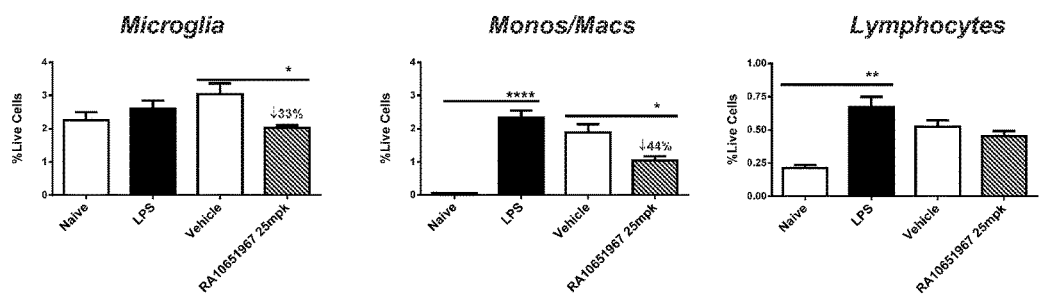

Figure 20: Mean Fluorescence Intensities (MFIs) of Activation Markers on Microglia and Monocyte/Macrophage Populations in the Brain after LPS challenge and Prophylactic Treatment with RA10651967
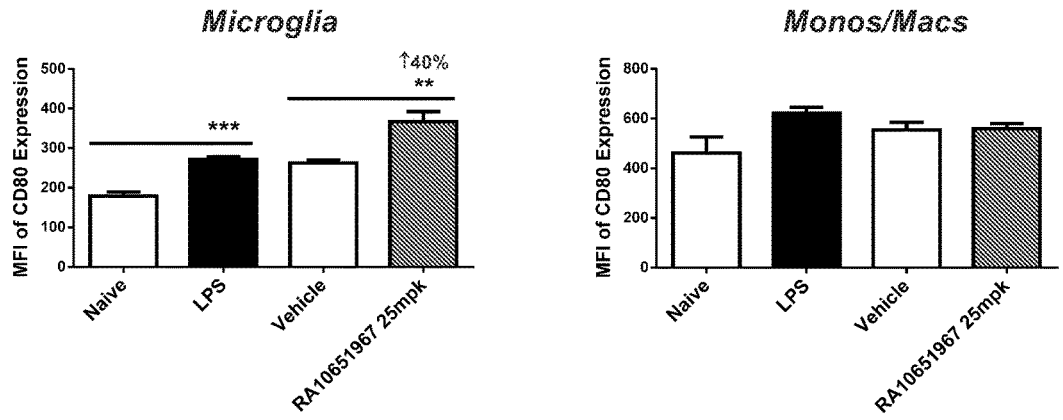
Figure 21: Cell Populations in the Blood after LPS Challenge and Prophylactic Treatment with RA10651967
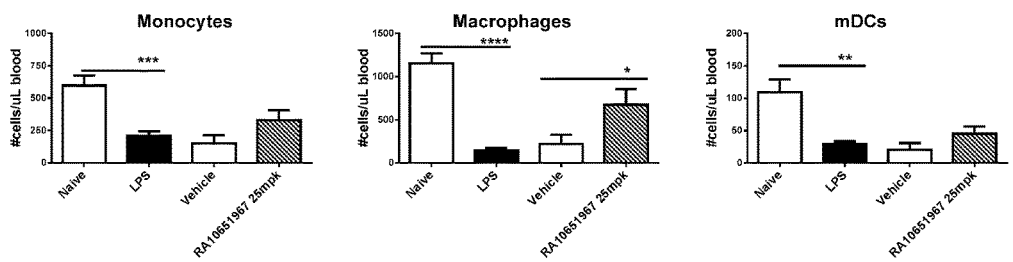

COLONY STIMULATING FACTOR-1 RECEPTOR (CSF-1R) INHIBITORS

CROSS-REFERENCE TO RELATED APPLICATION

This application is a § 371 National Stage Application of the International Application No. PCT/US2016/042917, filed Jul. 19, 2016, which claims the benefit of priority to U.S. Provisional Application No. 62/194,619 filed Jul. 20, 2015, all of which are incorporated herein in their entirety.

BACKGROUND OF THE INVENTION

Field of the Invention

This invention relates to colony stimulating factor-1 receptor inhibitors ("CSF-1R inhibitors"). The CSF-1R inhibitors of the invention are small molecules capable of penetrating the blood-brain barrier to reach the central nervous system (CNS). This invention also relates to pharmaceutical formulations comprising CSF-1R inhibitors and to the use of CSF-1R inhibitors and pharmaceutical compositions comprising CSF-1R inhibitors to treat disease. This invention further relates to the use of CSF-1R inhibitors and pharmaceutical compositions comprising CSF-1R inhibitors to treat immune-mediated diseases, including but not limited to multiple sclerosis, lupus nephritis, rheumatoid arthritis, and to treat neurological diseases, including but not limited to amyotrophic lateral sclerosis (ALS) and Hunington's disease. The CSF-1R inhibitors of the present invention can be used to inhibit c-FMS, the cellular receptor for colony stimulating factor-1 (CSF-1).

BRIEF SUMMARY OF THE INVENTION

The present invention refers to a compound comprising the structure of Formula (I):

or the pharmaceutically acceptable salt thereof, wherein:
n is 0, 1, 2, 3, 4 or 5;
m is 1, 2, 3 or 4;
$X^1$ is C, N or $CR^7$,
$X^2, X^3, X^4, X^5, X^6$ and $X^7$ are each independently selected from N, $NR^7$ or $CR^7$,
wherein each $R^7$ is independently selected from the group consisting of H, $(C_1\text{-}C_{10})$alkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_2\text{-}C_{10})$alkylnyl, $(C_1\text{-}C_{10})$alkylamine, $((C_1\text{-}C_{10})$alkyl$)_2$amine, $(C_2\text{-}C_{10})$alkynylamine, C(O)—, $(C_1\text{-}C_{10})$alkyl-C(O)O—, COOH—$(C_1\text{-}C_{10})$alkyl-, COOH—$(C_3\text{-}C_{10})$cycloalkyl-, $(C_1\text{-}C_{10})$alkoxy-, $R^8$-$(C_1\text{-}C_{10})$alkyl-, $R^8$-$(C_3\text{-}C_{10})$cycloalkyl, $R^8$-$(C_2\text{-}C_9)$heterocycloalkyl, $R^8$-$(C_6\text{-}C_{14})$aryl, $R^8$-$(C_2\text{-}C_9)$heteroaryl, $R^8$-$(C_2\text{-}C_{10})$alkylnyl, $R^8$-$(C_1\text{-}C_{10})$alkylamine, $R^8$-$((C_1\text{-}C_{10})$alkyl$)_2$amine, $R^8$-$(C_2\text{-}C_{10})$alkynylamine, $R^8$-C(O)—, $R^8$-$(C_1\text{-}C_{10})$alkyl-C(O)O—, $R^8$-$(C_1\text{-}C_{10})$alkoxy-, $(C_3\text{-}C_{10})$cycloalkyl-O—, $(C_2\text{-}C_9)$heterocycloalkyl-O—, $(C_6\text{-}C_{14})$aryl-O—, $(C_2\text{-}C_9)$heteroaryl-O—, $R^8$-$(C_3\text{-}C_{10})$cycloalkyl-O—, $R^8$-$(C_2\text{-}C_9)$heterocycloalkyl-O—, $R^8$-$(C_6\text{-}C_{14})$aryl-O—, $R^8$-$(C_2\text{-}C_9)$heteroaryl-O—, HO—, halo, cyano, $H_2N$—, $(CH_3)HN$—, $(CH_3)_2N$—, $R^8R^9N$—, $R^8R^9N(O)C$—, $R^8(R^9C(O))N$—, $R^8R^9NC(O)O$—, $R^8C(O)$—, $R^8R^9NC(O)R^8N$—, $(C_1\text{-}C_{10})$alkyl-OC(O)$R^8N$—, $(C_3\text{-}C_{10})$cycloalkyl-OC(O)$R^8N$—, $(C_2\text{-}C_9)$heterocycloalkyl-OC(O)$R^8N$—, $(C_6\text{-}C_{14})$aryl-OC(O)$R^8N$—, $(C_2\text{-}C_9)$heteroaryl-OC(O)$R^8N$—, $F_3C$—, $F_2HC$—, $CH_3F_2C$—, $FH_2C$—, $CH_3FHC$—, $(CH_3)_2FC$—; NC—, $(C_1\text{-}C_{10})$alkyl(O)P—, $(C_1\text{-}C_{10})$alkyl-S—, $(C_1\text{-}C_{10})$alkyl-S—$(C_1\text{-}C_{10})$alkyl-, $(C_3\text{-}C_{10})$cycloalkyl-S—, $(C_6\text{-}C_{14})$aryl-S—, $(C_2\text{-}C_9)$heteroalkyl-S—, $(C_2\text{-}C_9)$heterocycloalkyl-S—, $(C_2\text{-}C_9)$heteroaryl-S—, $(C_1\text{-}C_{10})$alkyl-S(O)—, $(C_3\text{-}C_{10})$cycloalkyl-S(O)—, $(C_6\text{-}C_{14})$aryl-S(O)—, $(C_2\text{-}C_9)$heterocycloalkyl-S(O)—, $(C_2\text{-}C_9)$heteroaryl-S(O)—, $(C_3\text{-}C_{10})$alkyl-S(O)$_2$—, $(C_3\text{-}C_{10})$cycloalkyl-S(O)$_2$—, $(C_6\text{-}C_{14})$aryl-S(O)$_2$—, $(C_2\text{-}C_9)$heterocycloalkyl-S(O)$_2$—, $(C_2\text{-}C_9)$heteroaryl-S(O)$_2$—, $R^8R^9NS(O)_2$—, $(C_1\text{-}C_{10})$alkyl-S(O)$_2R^8N$—, $(C_3\text{-}C_{10})$cycloalkyl-S(O)$_2R^8N$—, $(C_6\text{-}C_{14})$aryl-S(O)$_2R^8N$—, $(C_2\text{-}C_9)$heterocycloalkyl-SO$_2R^8N$—, and $(C_2\text{-}C_9)$heteroaryl-S(O)$_2R^8N$—;
wherein $R^8$ and $R^9$ are each independently selected from the group consisting of H, $(C_1\text{-}C_{10})$alkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_1\text{-}C_{10})$alkylamine, $((C_1\text{-}C_{10})$alkyl$)_2$amine, $(C_1\text{-}C_3)$alkynylamine, $(C_1\text{-}C_{10})$alkyl-C(O)O—, COOH—$(C_1\text{-}C_{10})$alkyl, COOH—$(C_3\text{-}C_{10})$cycloalkyl, $(C_1\text{-}C_{10})$alkoxy-, $(C_1\text{-}C_{10})$alkoxy-$(C_1\text{-}C_{10})$alkyl-, $(C_3\text{-}C_{10})$cycloalkyl-O—, $(C_2\text{-}C_9)$heterocycloalkyl-O—, $(C_6\text{-}C_{14})$aryl-O—, $(C_2\text{-}C_9)$heteroaryl-O—, HO—, halo, $(CH_3)_2N$—, and $H_2N$—;
or $R^8$ and $R^9$ are taken together to form a 3 to 10 member cycloalkyl, heterocycloalkyl, aryl or heteroaryl ring;
wherein each $(C_1\text{-}C_{10})$alkyl, $(C_6\text{-}C_{14})$aryl, $(C_2\text{-}C_9)$heteroaryl, $(C_3\text{-}C_{10})$cycloalkyl, or $(C_2\text{-}C_9)$heterocycloalkyl are further optionally substituted by one to four groups selected from $(C_1\text{-}C_{10})$alkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_1\text{-}C_{10})$alkylamine, $((C_1\text{-}C_{10})$alkyl$)_2$amine, $(C_1\text{-}C_3)$alkynylamine, $(C_1\text{-}C_{10})$alkyl-C(O)O—, COOH—$(C_1\text{-}C_{10})$alkyl, COOH—$(C_3\text{-}C_{10})$cycloalkyl, $(C_1\text{-}C_{10})$alkoxy-, $(C_1\text{-}C_{10})$alkoxy-$(C_1\text{-}C_{10})$alkyl-, $(C_3\text{-}C_{10})$cycloalkyl-O—, $(C_2\text{-}C_9)$heterocycloalkyl-O—, $(C_6\text{-}C_{14})$aryl-O—, $(C_2\text{-}C_9)$heteroaryl-O—, HO—, halo, or $H_2N$—;
$X^8$ and $X^9$ are each independently selected from N or C;
$T^1$, $T^2$, and $T^3$ is each independently selected from are each independently selected from N or $CR^{10}$,
wherein each $R^{10}$ is independently selected from the group consisting of H, $(C_1\text{-}C_{10})$alkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_2\text{-}C_{10})$alkylnyl, $(C_1\text{-}C_{10})$alkylamine, $((C_1\text{-}C_{10})$alkyl$)_2$amine, $(C_2\text{-}C_{10})$alkynylamine, C(O)—, $(C_1\text{-}C_{10})$alkyl-C(O)O—, COOH—$(C_1\text{-}C_{10})$alkyl-, COOH—$(C_3\text{-}C_{10})$cycloalkyl-, $(C_1\text{-}C_{10})$alkoxy-, $R^{10A}$-$(C_1\text{-}C_{10})$alkyl-, $R^{10A}$-$(C_3\text{-}C_{10})$cycloalkyl, $R^{10A}$-$(C_2\text{-}C_9)$heterocycloalkyl, $R^{10A}$-$(C_6\text{-}C_{14})$aryl, $R^{10A}$-$(C_2\text{-}C_9)$heteroaryl, $R^{10A}$-$(C_2\text{-}C_{10})$alkylnyl, $R^{10A}$-$(C_1\text{-}C_{10})$alkylamine, $R^{10A}$-$((C_1\text{-}C_{10})$alkyl$)_2$amine, $R^{10A}$-$(C_2\text{-}C_{10})$alkynylamine, $R^{10A}$-C(O)—, $R^{10A}$-$(C_1\text{-}C_{10})$alkyl- C(O)O—, $R^{10A}$-($C_1$-$C_{10}$)alkoxy-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, $R^{10A}$-($C_3$-$C_{10}$)cycloalkyl-O—, $R^{10A}$-($C_2$-$C_9$)heterocycloalkyl-O—, $R^{10A}$-($C_6$-$C_{14}$)aryl-O—, $R^{10A}$-($C_2$-$C_9$)heteroaryl-O—, HO—, halo, cyano, $H_2N$—, ($CH_3$)HN—, ($CH_3$)$_2$N—, $R^{10A}R^{11}N$—, $R^{10A}R^{11}N(O)C$—, $R^{10A}(R^{11}C(O))N$—, $R^{10A}R^{11}NC(O)O$—, $R^{10A}C(O)$—, $R^{10A}R^{11}NC(O)R^{10A}N$—, ($C_1$-$C_{10}$)alkyl-OC(O)$R^{10A}N$—, ($C_3$-$C_{10}$)cycloalkyl-OC(O)$R^{10A}N$—, ($C_2$-$C_9$)heterocycloalkyl-OC(O)$R^{10A}N$—, ($C_6$-$C_{14}$)aryl-OC(O)$R^{10A}N$—, ($C_2$-$C_9$)heteroaryl-OC(O)$R^{10A}N$—, $F_3C$—, $F_2HC$—, $CH_3F_2C$—, $FH_2C$—, $CH_3FHC$—, ($CH_3$)$_2FC$—; NC—, ($C_1$-$C_{10}$)alkyl(O)P—, ($C_1$-$C_{10}$)alkyl-S—, ($C_1$-$C_{10}$)alkyl-S-($C_1$-$C_{10}$)alkyl-, ($C_3$-$C_{10}$)cycloalkyl-S—, ($C_6$-$C_{14}$)aryl-S—, ($C_2$-$C_9$)heteroalkyl-S—, ($C_2$-$C_9$)heterocycloalkyl-S—, ($C_2$-$C_9$)heteroaryl-S—, ($C_1$-$C_{10}$)alkyl-S(O)—, ($C_3$-$C_{10}$)cycloalkyl-S(O)—, ($C_6$-$C_{14}$)aryl-S(O)—, ($C_2$-$C_9$)heterocycloalkyl-S(O)—, ($C_2$-$C_9$)heteroaryl-S(O)—, ($C_3$-$C_{10}$)alkyl-S(O)$_2$—, ($C_3$-$C_{10}$)cycloalkyl-S(O)$_2$—, ($C_6$-$C_{14}$)aryl-S(O)$_2$—, ($C_2$-$C_9$)heterocycloalkyl-S(O)$_2$—, ($C_2$-$C_9$)heteroaryl-S(O)$_2$—, $R^{10A}R^{11}NS(O)_2$—, ($C_1$-$C_{10}$)alkyl-S(O)$_2R^{10A}N$—, ($C_3$-$C_{10}$)cycloalkyl-S(O)$_2R^{10A}N$—, ($C_6$-$C_{14}$)aryl-S(O)$_2R^{10A}N$—, ($C_2$-$C_9$)heterocycloalkyl-SO$_2R^{10A}N$—, and ($C_2$-$C_9$)heteroaryl-S(O)$_2R^{10A}N$—;

wherein $R^{10A}$ and $R^{11}$ are each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, ($CH_3$)$_2$N—, and $H_2N$—;

or $R^{10A}$ and $R^{11}$ are taken together to form a 3 to 10 member cycloalkyl, heterocycloalkyl, aryl or heteroaryl ring;

wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, or $H_2N$—

$Y^1$ is O, S, $NR^{12}$, or $CR^{12}R^{13}$, wherein $R^{12}$ is absent or $R^{12}$ and $R^{13}$ are each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, and $H_2N$—;

$R^1$ together with the carbon to which it is attached to form a carbonyl and $R^2$ is absent, or $R^1$ and $R^2$ are each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, and $H_2N$—, or $R^1$ and $R^2$ are taken together with the carbon to which they are attached to form a 3 to 10 member ring;

$R^4$ is selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, and $H_2N$—, or $R^4$ and $R^5$ can be taken together with the carbon to which they are attached to form a 3 to 10 member ring;

$R^5$ is absent or selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, and $H_2N$—;

$R^6$ is selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_2$-$C_{10}$)alkylnyl, ($C_1$-$C_{10}$)alkylamine, (($C_1$-$C_{10}$)alkyl)$_2$amine, ($C_2$-$C_{10}$)alkynylamine, C(O)—, ($C_1$-$C_{10}$)alkyl-C(O)O—, COOH—($C_1$-$C_{10}$)alkyl-, COOH—($C_3$-$C_{10}$)cycloalkyl-, ($C_1$-$C_{10}$)alkoxy-, $R^{14}$-($C_1$-$C_{10}$)alkyl-, $R^{14}$-($C_3$-$C_{10}$)cycloalkyl, $R^{14}$-($C_2$-$C_9$)heterocycloalkyl, $R^{14}$-($C_6$-$C_{14}$)aryl, $R^{14}$-($C_2$-$C_9$)heteroaryl, $R^{14}$-($C_2$-$C_{10}$)alkylnyl, $R^{14}$-($C_1$-$C_{10}$)alkylamine, $R^{14}$-(($C_1$-$C_{10}$)alkyl)$_2$amine, $R^{14}$-($C_2$-$C_{10}$)alkynylamine, $R^{14}$-C(O)—, $R^{14}$-($C_1$-$C_{10}$)alkyl-C(O)O—, $R^{14}$-($C_1$-$C_{10}$)alkoxy-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, $R^{14}$-($C_3$-$C_{10}$)cycloalkyl-O—, $R^{14}$-($C_2$-$C_9$)heterocycloalkyl-O—, $R^{14}$-($C_6$-$C_{14}$)aryl-O—, $R^{14}$-($C_2$-$C_9$)heteroaryl-O—, HO—, halo, cyano, $H_2N$—, ($CH_3$)HN—, ($CH_3$)$_2$N—, $R^{14}R^{15}N$—, $R^{14}R^{15}N(O)C$—, $R^{14}(R^{15}C(O))N$—, $R^{14}R^{15}NC(O)O$—, $R^{14}C(O)$—, $R^{14}R^{15}NC(O)R^{14}N$—, ($C_1$-$C_{10}$)alkyl-OC(O)$R^{14}N$—, ($C_3$-$C_{10}$)cycloalkyl-OC(O)$R^{14}N$—, ($C_2$-$C_9$)heterocycloalkyl-OC(O)$R^{14}N$—, ($C_6$-$C_{14}$)aryl-OC(O)$R^{14}N$—, ($C_2$-$C_9$)heteroaryl-OC(O)$R^{14}N$—, $F_3C$—, $F_2HC$—, $CH_3F_2C$—, $FH_2C$—, $CH_3FHC$—, ($CH_3$)$_2FC$—; NC—, ($C_1$-$C_{10}$)alkyl(O)P—, ($C_1$-$C_{10}$)alkyl-S—, ($C_1$-$C_{10}$)alkyl-S-($C_1$-$C_{10}$)alkyl-, ($C_3$-$C_{10}$)cycloalkyl-S—, ($C_6$-$C_{14}$)aryl-S—, ($C_2$-$C_9$)heteroalkyl-S—, ($C_2$-$C_9$)heterocycloalkyl-S—, ($C_2$-$C_9$)heteroaryl-S—, ($C_1$-$C_{10}$)alkyl-S(O)—, ($C_3$-$C_{10}$)cycloalkyl-S(O)—, ($C_6$-$C_{14}$)aryl-S(O)—, ($C_2$-$C_9$)heterocycloalkyl-S(O)—, ($C_2$-$C_9$)heteroaryl-S(O)—, ($C_3$-$C_{10}$)alkyl-S(O)$_2$—, ($C_3$-$C_{10}$)cycloalkyl-S(O)$_2$—, ($C_6$-$C_{14}$)aryl-S(O)$_2$—, ($C_2$-$C_9$)heterocycloalkyl-S(O)$_2$—, ($C_2$-$C_9$)heteroaryl-S(O)$_2$—, $R^{14}R^{15}NS(O)_2$—, ($C_1$-$C_{10}$)alkyl-S(O)$_2R^{14}N$—, ($C_3$-$C_{10}$)cycloalkyl-S(O)$_2$ $R^{14}N$—, ($C_6$-$C_{14}$)aryl-S(O)$_2R^{14}N$—, ($C_2$-$C_9$)heterocycloalkyl-SO$_2R^{14}N$—, and ($C_2$-$C_9$)heteroaryl-S(O)$_2R^{14}N$—;

wherein $R^{14}$ and $R^{15}$ are each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)

aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, $F_2$HC—O—, halo, $(CH_3)_2$N—, $H_2$N—, $F_3$C—C(O)—, $F_3$C—, and $F_2$HC—;

or $R^{14}$ and $R^{15}$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2$N—; and $R^3$ is N or $CR^{16}$, wherein $R^{16}$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, and $H_2$N—, or when m is 1, $R^{16}$ and $R^4$ are taken together with the carbons to which they are attached to form a compound according to Formula (II):

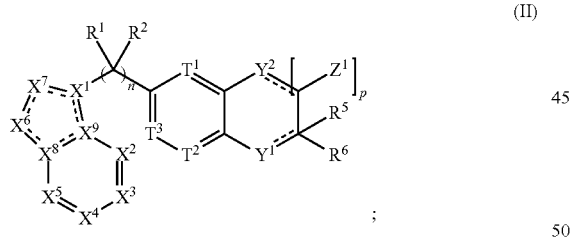

(II)

wherein the dashed lines represent optional double bonds and:

p is 0, 1, 2, 3, 4 or 5;

$Z^1$ is each independently selected from H, halo, $(C_1-C_{10})$alkyl, $(C_2-C_9)$heteroalkyl, $(C_1-C_{10})$alkylamine, $((C_1-C_{10})$alkyl$)_2$amine, $(C_2-C_{10})$alkynylamine, $(C_1-C_{10})$alkoxy-, or $H_2$N—;

$Y^2$ is O, S, $NR^{17}$, or $CR^{17}R^{18}$, and wherein $R^{17}$ is absent or $R^{17}$ and $R^{18}$ are each independently selected from H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2$N—.

The present invention also refers to a compound comprising the structure of Formula (XIII):

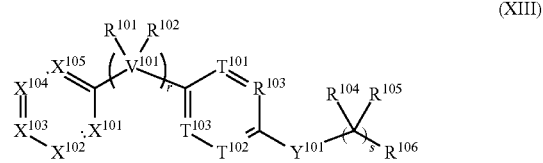

(XIII)

wherein:

$V^{101}$ is C, N, O, or S, r is 0, 1, 2, 3, 4 or 5;

wherein when $V^{101}$ is C, then r is 0, 1, 2, 3, 4 or 5, wherein when $V^{101}$ is N, then r is 1 and $R^{102}$ is absent;

wherein when $V^{101}$ is O, r is 1 and $R^{101}$ and $R^{102}$ are absent; and wherein when $V^{101}$ is S, r is 1 and $R^{101}$ and $R^{102}$ are absent;

s is 1, 2, 3 or 4;

$X^{101}$, $X^{102}$, $X^{103}$, $X^{105}$ are each independently selected from N, $NR^{107}$ or $CR^{107}$, wherein each $R^{107}$ is independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, C(O)—, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{108}$-$(C_1-C_{10})$alkyl-, $R^{108}$-$(C_3-C_{10})$cycloalkyl, $R^{108}$-$(C_2-C_9)$heterocycloalkyl, $R^{108}$-$(C_6-C_{14})$aryl, $R^{108}$-$(C_2-C_9)$heteroaryl, $R^{108}$-$(C_2-C_{10})$alkylnyl, $R^{108}$-$(C_1-C_{10})$alkylamine, $R^{108}$-$((C_1-C_{10})$alkyl$)_2$amine, $R^{108}$-$(C_2-C_{10})$alkynylamine, $R^{108}$-C(O)—, $R^{108}$-$(C_1-C_{10})$alkyl-C(O)O—, $R^{108}$-$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^{108}$-$(C_3-C_{10})$cycloalkyl-O—, $R^{108}$-$(C_2-C_9)$heterocycloalkyl-O—, $R^{108}$-$(C_6-C_{14})$aryl-O—, $R^{108}$-$(C_2-C_9)$heteroaryl-O—, HO—, halo, cyano, $H_2$N—, $(CH_3)$HN—, $(CH_3)_2$N—, $R^{108}R^{109}$N—, $R^{108}R^{109}$N(O)C—, $R^{108}(R^{109}$C(O))N—, $R^{108}R^{109}$NC(O)O—, $R^{108}$C(O)—, $R^{108}R^{109}$NC(O)$R^{108}$N—, $(C_1-C_{10})$alkyl-OC(O)$R^{108}$N—, $(C_3-C_{10})$cycloalkyl-OC(O)$R^{108}$N—, $(C_2-C_9)$heterocycloalkyl-OC(O)$R^{108}$N—, $(C_6-C_{14})$aryl-OC(O)$R^{108}$N—, $(C_2-C_9)$heteroaryl-OC(O)$R^{108}$N—, $F_3$C—, $F_2$HC—, $CH_3F_2$C—, $FH_2$C—, $CH_3$FHC—, $(CH_3)_2$FC—; NC—, $(C_1-C_{10})$alkyl(O)P—, $(C_1-C_{10})$alkyl-S—, $(C_1-C_{10})$alkyl-S—$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^{108}R^{109}$NS(O)$_2$—, $(C_1-C_{10})$alkyl-S(O)$_2R^{108}$N—, $(C_3-C_{10})$cycloalkyl-S(O)$_2R^{108}$N—, $(C_6-C_{14})$aryl-S(O)$_2R^{108}$N—, $(C_2-C_9)$heterocycloalkyl-SO$_2R^{108}$N—, and $(C_2-C_9)$heteroaryl-S(O)$_2R^{108}$N—;

wherein $R^{108}$ and $R^{109}$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $(CH_3)_2N$—, and $H_2N$—;

or $R^{108}$ and $R^{109}$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—;

$T^{101}$, $T^{102}$, and $T^{103}$ is each independently selected from are each independently selected from N or $CR^{110}$, wherein each $R^{110}$ is independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, C(O)—, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{110A}$-$(C_1-C_{10})$alkyl-, $R^{110A}$-$(C_3-C_{10})$cycloalkyl, $R^{110A}$-$(C_2-C_9)$heterocycloalkyl, $R^{110A}$-$(C_6-C_{14})$aryl, $R^{110A}$-$(C_2-C_9)$heteroaryl, $R^{110A}$-$(C_2-C_{10})$alkylnyl, $R^{110A}$-$(C_1-C_{10})$alkylamine, $R^{110A}$-$((C_1-C_{10})$alkyl$)_2$amine, $R^{110A}$-$(C_2-C_{10})$alkynylamine, $R^{110A}$-C(O)—, $R^{110A}$-$(C_1-C_{10})$alkyl-C(O)O—, $R^{110A}$-$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^{110A}$-$(C_3-C_{10})$cycloalkyl-O—, $R^{110A}$-$(C_2-C_9)$heterocycloalkyl-O—, $R^{110A}$-$(C_6-C_{14})$aryl-O—, $R^{110A}$-$(C_2-C_9)$heteroaryl-O—, HO—, halo, cyano, $H_2N$—, $(CH_3)HN$—, $(CH_3)_2N$—, $R^{110A}R^{111}N$—, $R^{110A}R^{111}N(O)C$—, $R^{110A}(R^{111}C(O))N$—, $R^{110A}R^{111}NC(O)O$—, $R^{110A}C(O)$—, $R^{110A}R^{111}NC(O)R^{110A}N$—, $(C_1-C_{10})$alkyl-OC(O)$R^{110A}N$—, $(C_3-C_{10})$cycloalkyl-OC(O)$R^{110A}N$—, $(C_2-C_9)$heterocycloalkyl-OC(O)$R^{110A}N$—, $(C_6-C_{14})$aryl-OC(O)$R^{110A}N$—, $(C_2-C_9)$heteroaryl-OC(O)$R^{110A}N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S-$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^{110A}R^{111}NS(O)_2$—, $(C_1-C_{10})$alkyl-S(O)$_2R^{110A}N$—, $(C_3-C_{10})$cycloalkyl-S(O)$_2R^{110A}N$—, $(C_6-C_{14})$aryl-S(O)$_2R^{110A}N$—, $(C_2-C_9)$heterocycloalkyl-SO$_2R^{110A}N$—, and $(C_2-C_9)$heteroaryl-S(O)$_2R^{110A}N$—;

wherein $R^{110A}$ and $R^1$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $(CH_3)_2N$—, and $H_2N$—;

or $R^{110A}$ and $R^{111}$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—

$Y^{101}$ is O, S, $NR^{112}$, or $CR^{112}R^{113}$, wherein $R^{112}$ is absent or $R^{112}$ and $R^{113}$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, and $H_2N$—;

$R^{101}$ together with the carbon to which it is attached to form a carbonyl and $R^{102}$ is absent, or $R^{101}$ and $R^{102}$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, and $H_2N$—, or $R^{101}$ and $R^{102}$ are taken together with the carbon to which they are attached to form a 3 to 10 member ring;

$R^{104}$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, and $H_2N$—, or $R^{104}$ and $R^{105}$ can be taken together with the carbon to which they are attached to form a 3 to 10 member ring;

$R^{105}$ is absent or selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, and $H_2N$—;

$R^{106}$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, C(O)—, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{114}$-$(C_1-C_{10})$alkyl-, $R^{114}$-$(C_3-C_{10})$cycloalkyl, $R^{114}$-$(C_2-C_9)$heterocycloalkyl, $R^{114}$-$(C_6-C_{14})$aryl, $R^{114}$-$(C_2-C_9)$heteroaryl, $R^{114}$-$(C_2-C_{10})$alkylnyl, $R^{114}$-$(C_1-C_{10})$alkylamine, $R^{114}$-$((C_1-C_{10})$alkyl$)_2$amine, $R^{114}$-$(C_2-C_{10})$alkynylamine, $R^{114}$-C(O)—, $R^{114}$-$(C_1-C_{10})$alkyl-C(O)O—, $R^{114}$-$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^{114}$-$(C_3-C_{10})$cycloalkyl-O—, $R^{114}$-$(C_2-C_9)$heterocycloalkyl-O—, $R^{114}$-$(C_6-C_{14})$aryl-O—, $R^{114}$-$(C_2-C_9)$heteroaryl-O—, HO—, halo, cyano, $H_2N$—, $(CH_3)HN$—, $(CH_3)_2N$—, $R^{114}R^{115}N$—, $R^{114}R^{115}N(O)C$—, $R^{114}(R^{115}C(O))N$—, $R^{114}R^{115}NC(O)O$—, $R^{114}C(O)$—, $R^{114}R^{115}NC(O)R^{114}N$—, $(C_1-C_{10})$alkyl-OC(O)$R^{114}N$—, $(C_3-C_{10})$cycloalkyl-OC(O)$R^{114}N$—, $(C_2-C_9)$heterocycloalkyl-OC(O)$R^{114}N$—, $(C_6-C_{14})$aryl-OC(O)$R^{114}N$—, $(C_2-C_9)$heteroaryl-OC(O)$R^{114}N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S-$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^{114}R^{115}NS(O)_2$—, $(C_1-C_{10})$alkyl-S(O)$_2R^{114}N$—, $(C_3-C_{10})$cycloalkyl-S(O)$_2R^{114}N$—, $(C_6-C_{14})$aryl-S(O)$_2R^{114}N$—, $(C_2-C_9)$heterocycloalkyl-SO$_2R^{114}N$—, and $(C_2-C_9)$heteroaryl-S(O)$_2R^{114}N$—;

wherein $R^{114}$ and $R^{115}$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, $F_2HC$—O—, halo, $(CH_3)_2N$—, $H_2N$—, $F_3C$—C(O)—, $F_3C$—, and $F_2HC$—;

or $R^{114}$ and $R^{115}$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—; and $R^{103}$ is N or $CR^{116}$, wherein $R^{116}$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, and $H_2N$—, or when s is 1, $R^{116}$ and $R^{104}$ are taken together with the carbons to which they are attached to form a compound according to Formula (XIV):

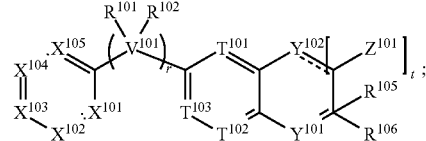

(XIV)

wherein the dashed lines represent optional double bonds and:

t is 0, 1, 2, 3, 4 or 5;

$Z^{101}$ is each independently selected from H, halo, $(C_1-C_{10})$alkyl, $(C_2-C_9)$heteroalkyl, $(C_1-C_{10})$alkylamine, $((C_1-C_{10})$alkyl$)_2$amine, $(C_2-C_{10})$alkynylamine, $(C_1-C_{10})$alkoxy-, or $H_2N$—;

$Y^{102}$ is O, S, $NR^{117}$, or $CR^{117}R^{118}$, and wherein $R^{117}$ is absent or $R^{117}$ and $R^{118}$ are each independently selected from H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (I) or Formula (II) wherein $X^1$ is N; $X^2$ is N; $X^3$ is $CR^7$; $X^4$ is $CR^7$; $X^5$ is $CR^7$; $X^6$ is N; $X^7$ is $CR^7$; $X^8$ is C; and $X^9$ is C; or wherein $X^3$ is CH; $X^4$ is $CR^7$; $X^5$ is CH; and $X^7$ is CH.

The present invention further relates to a compound according to Formula (I) or Formula (II) wherein $X^1$ is N; $X^2$ is $CR^7$; $X^3$ is $CR^7$; $X^4$ is $CR^7$; $X^5$ is $CR^7$; $X^6$ is N; $X^7$ is $CR^7$; $X^8$ is C; and $X^9$ is C; or wherein $X^2$ is CH; $X^3$ is CH; $X^4$ is $CR^7$; $X^5$ is CH; $X^7$ is CH.

The present invention further relates to a compound according to Formula (I) or Formula (II) wherein $X^1$ is N; $X^2$ is $CR^7$; $X^3$ is N; $X^4$ is $CR^7$; $X^5$ is $CR^7$; $X^6$ is N; $X^7$ is $CR^7$; $X^8$ is C; and $X^9$ is C; or wherein $X^2$ is CH; $X^4$ is $CR^7$; $X^5$ is CH; and $X^7$ is CH.

The present invention further relates to a compound according to Formula (I) or Formula (II) wherein $X^1$ is N; $X^2$ is $CR^7$; $X^3$ is $CR^7$; $X^4$ is N; $X^5$ is $CR^7$; $X^6$ is N; $X^7$ is $CR^7$; $X^8$ is C; and $X^9$ is C.

The present invention further relates to a compound according to Formula (I) or Formula (II) wherein $X^1$ is N; $X^2$ is $CR^7$; $X^3$ is $CR^7$; $X^4$ is $CR^7$; $X^5$ is N; $X^6$ is N; $X^7$ is $CR^7$; $X^8$ is C; and $X^9$ is C; or wherein $X^2$ is CH; $X^3$ is CH; $X^4$ is $CR^7$; and $X^7$ is CH.

The present invention further relates to a compound according to Formula (I) or Formula (II) wherein $X^1$ is N; $X^2$ is N; $X^3$ is N; $X^4$ is $CR^7$; $X^5$ is $CR^7$; $X^6$ is N; $X^7$ is $CR^7$; $X^8$ is C; and $X^9$ is C; or wherein $X^4$ is $CR^7$; $X^5$ is CH; and $X^7$ is $CR^7$.

The present invention further relates to a compound according to Formula (I) or Formula (II) wherein $X^1$ is N; $X^2$ is N; $X^3$ is $CR^7$; $X^4$ is N; $X^5$ is $CR^7$; $X^6$ is N; $X^7$ is $CR^7$; $X^8$ is C; and $X^9$ is C.

The present invention further relates to a compound according to Formula (I) or Formula (II) wherein $X^1$ is N; $X^2$ is N; $X^3$ is $CR^7$; $X^4$ is $CR^7$; $X^5$ is N; $X^6$ is N; $X^7$ is $CR^7$; $X^8$ is C; and $X^9$ is C; or wherein $X^3$ is CH; $X^4$ is $CR^7$; and $X^7$ is CH.

The present invention further relates to a compound according to Formula (I) or Formula (II) wherein $X^1$ is N; $X^2$ is N; $X^3$ is N; $X^4$ is $CR^7$; $X^5$ is N; $X^6$ is N; $X^7$ is $CR^7$; $X^8$ is C; and $X^9$ is C; or wherein $X^4$ is $CR^7$ and $X^7$ is CH.

The present invention further relates to a compound according to Formula (I) or Formula (II) wherein $X^1$ is N; $X^2$ is N; $X^3$ is $CR^7$; $X^4$ is N; $X^5$ is N; $X^6$ is N; $X^7$ is $CR^7$; $X^8$ is C; and $X^9$ is C.

The present invention further relates to a compound according to Formula (I) or Formula (II) wherein $X^1$ is C; $X^2$ is N; $X^3$ is $CR^7$; $X^4$ is $CR^7$; $X^5$ is $CR^7$; $X^6$ is N; $X^7$ is $CR^7$; $X^8$ is C; and $X^9$ is C; or wherein $X^3$ is CH; $X^4$ is $CR^7$; $X^5$ is CH; and $X^7$ is CH.

The present invention further relates to a compound according to Formula (I) or Formula (II) wherein $X^1$ is C; $X^2$ is $CR^7$; $X^3$ is $CR^7$; $X^4$ is $CR^7$; $X^5$ is $CR^7$; $X^6$ is N; $X^7$ is $CR^7$; $X^8$ is C; and $X^9$ is C; or wherein $X^2$ is CH; $X^3$ is CH; $X^4$ is $CR^7$; $X^5$ is CH; $X^7$ is CH.

The present invention further relates to a compound according to Formula (I) or Formula (II) wherein $X^1$ is C; $X^2$ is $CR^7$; $X^3$ is N; $X^4$ is $CR^7$; $X^5$ is $CR^7$; $X^6$ is N; $X^7$ is $CR^7$; $X^8$ is C; and $X^9$ is C; or wherein $X^2$ is CH; $X^4$ is $CR^7$; $X^5$ is CH; and $X^7$ is CH.

The present invention further relates to a compound according to Formula (I) or Formula (II) wherein $X^1$ is C; $X^2$ is $CR^7$; $X^3$ is $CR^7$; $X^4$ is N; $X^5$ is $CR^7$; $X^6$ is N; $X^7$ is $CR^7$; $X^8$ is C; and $X^9$ is C.

The present invention further relates to a compound according to Formula (I) or Formula (II) wherein $X^1$ is C; $X^2$ is $CR^7$; $X^3$ is $CR^7$; $X^4$ is $CR^7$; $X^5$ is N; $X^6$ is N; $X^7$ is $CR^7$; $X^8$ is C; and $X^9$ is C; or wherein $X^2$ is CH; $X^3$ is CH; $X^4$ is $CR^7$; and $X^7$ is CH.

The present invention further relates to a compound according to Formula (I) or Formula (II) wherein $X^1$ is C; $X^2$ is N; $X^3$ is N; $X^4$ is $CR^7$; $X^5$ is $CR^7$; $X^6$ is N; $X^7$ is $CR^7$; $X^8$ is C; and $X^9$ is C; or wherein $X^4$ is $CR^7$; $X^5$ is CH; and $X^7$ is $CR^7$.

The present invention further relates to a compound according to Formula (I) or Formula (II) wherein $X^1$ is C; $X^2$ is N; $X^3$ is $CR^7$; $X^4$ is N; $X^5$ is $CR^7$; $X^6$ is N; $X^7$ is $CR^7$; $X^8$ is C; and $X^9$ is C.

The present invention further relates to a compound according to Formula (I) or Formula (II) wherein $X^1$ is C; $X^2$ is N; $X^3$ is $CR^7$; $X^4$ is $CR^7$; $X^5$ is N; $X^6$ is N; $X^7$ is $CR^7$; $X^8$ is C; and $X^9$ is C; or wherein $X^3$ is CH; $X^4$ is $CR^7$; $X^5$ is N; and $X^7$ is CH.

The present invention further relates to a compound according to Formula (I) or Formula (II) wherein $X^1$ is C; $X^2$ is N; $X^3$ is N; $X^4$ is $CR^7$; $X^5$ is N; $X^6$ is N; $X^7$ is $CR^7$; $X^8$ is C; and $X^9$ is C; or wherein $X^4$ is $CR^7$ and $X^7$ is CH.

The present invention further relates to a compound according to Formula (I) or Formula (II) wherein $X^1$ is C; $X^2$ is N; $X^3$ is $CR^7$; $X^4$ is N; $X^5$ is N; $X^6$ is N; $X^7$ is $CR^7$; $X^8$ is C; and $X^9$ is C.

The present invention further relates to a compound according to Formula (I) or Formula (II) wherein $X^1$ is C; $X^2$ is N; $X^3$ is $CR^7$; $X^4$ is $CR^7$; $X^5$ is $CR^7$; $X^6$ is N; $X^7$ is $CR^7$; $X^8$ is N; and $X^9$ is C; or wherein $X^3$ is CH; $X^4$ is $CR^7$; $X^5$ is CH; and $X^7$ is CH.

The present invention further relates to a compound according to Formula (I) or Formula (II) wherein $X^1$ is C; $X^2$ is $CR^7$; $X^3$ is $CR^7$; $X^4$ is $CR^7$; $X^5$ is $CR^7$; $X^6$ is N; $X^7$ is $CR^7$; $X^8$ is N; and $X^9$ is C; or wherein $X^2$ is CH; $X^3$ is CH; $X^4$ is $CR^7$; $X^5$ is CH; $X^7$ is CH.

The present invention further relates to a compound according to Formula (I) or Formula (II) wherein $X^1$ is C; $X^2$ is $CR^7$; $X^3$ is N; $X^4$ is $CR^7$; $X^5$ is $CR^7$; $X^6$ is N; $X^7$ is $CR^7$; $X^8$ is N; and $X^9$ is C; or wherein $X^2$ is CH; $X^4$ is $CR^7$; $X^5$ is CH; and $X^7$ is CH.

The present invention further relates to a compound according to Formula (I) or Formula (II) wherein $X^1$ is C; $X^2$ is $CR^7$; $X^3$ is $CR^7$; $X^4$ is N; $X^5$ is $CR^7$; $X^6$ is N; $X^7$ is $CR^7$; $X^8$ is N; and $X^9$ is C.

The present invention further relates to a compound according to Formula (I) or Formula (II) wherein $X^1$ is C; $X^2$ is N; $X^3$ is N; $X^4$ is $CR^7$; $X^5$ is $CR^7$; $X^6$ is N; $X^7$ is $CR^7$; $X^8$ is N; and $X^9$ is C; or wherein $X^4$ is $CR^7$; $X^5$ is CH; and $X^7$ is $CR^7$.

The present invention further relates to a compound according to Formula (I) or Formula (II) wherein $X^1$ is C; $X^2$ is N; $X^3$ is $CR^7$; $X^4$ is N; $X^5$ is $CR^7$; $X^6$ is N; $X^7$ is $CR^7$; $X^8$ is N; and $X^9$ is C.

The present invention further relates to a compound according to Formula (I) or Formula (II) wherein $X^1$ is C; $X^2$ is N; $X^3$ is $CR^7$; $X^4$ is $CR^7$; $X^5$ is $CR^7$; $X^6$ is N; $X^7$ is $CR^7$; $X^8$ is C; and $X^9$ is N; or wherein $X^3$ is CH; $X^4$ is $CR^7$; $X^5$ is CH; and $X^7$ is CH.

The present invention further relates to a compound according to Formula (I) or Formula (II) wherein $X^1$ is C; $X^2$ is $CR^7$; $X^3$ is $CR^7$; $X^4$ is $CR^7$; $X^5$ is $CR^7$; $X^6$ is N; $X^7$ is $CR^7$; $X^8$ is C; and $X^9$ is N; or wherein $X^2$ is CH; $X^3$ is CH; $X^4$ is $CR^7$; $X^5$ is CH; $X^7$ is CH.

The present invention further relates to a compound according to Formula (I) or Formula (II) wherein $X^1$ is C; $X^2$ is $CR^7$; $X^3$ is N; $X^4$ is $CR^7$; $X^5$ is $CR^7$; $X^6$ is N; $X^7$ is $CR^7$; $X^8$ is C; and $X^9$ is N; or wherein $X^2$ is CH; $X^4$ is $CR^7$; $X^5$ is CH; and $X^7$ is CH.

A compound according to Formula (I) or Formula (II), wherein $X^1$ is C; $X^2$ is $CR^7$; $X^3$ is $CR^7$; $X^4$ is N; $X^5$ is $CR^7$; $X^6$ is N; $X^7$ is $CR^7$; $X^8$ is C; and $X^9$ is N.

The present invention further relates to a compound according to Formula (I) or Formula (II) wherein $X^1$ is C; $X^2$ is $CR^7$; $X^3$ is $CR^7$; $X^4$ is $CR^7$; $X^5$ is N; $X^6$ is N; $X^7$ is $CR^7$; $X^8$ is C; and $X^9$ is N; or wherein $X^2$ is CH; $X^3$ is CH; $X^4$ is $CR^7$; and $X^7$ is CH.

The present invention further relates to a compound according to Formula (I) or Formula (II) wherein $X^1$ is C; $X^2$ is N; $X^3$ is $CR^7$; $X^4$ is N; $X^5$ is $CR^7$; $X^6$ is N; $X^7$ is $CR^7$; $X^8$ is C; and $X^9$ is N.

The present invention further relates to a compound according to Formula (I) or Formula (II) wherein $X^1$ is C; $X^2$ is N; $X^3$ is $CR^7$; $X^4$ is $CR^7$; $X^5$ is N; $X^6$ is N; $X^7$ is $CR^7$; $X^8$ is C; and $X^9$ is N; or wherein $X^3$ is CH; $X^4$ is $CR^7$; and $X^7$ is CH.

The present invention further relates to a compound according to Formula (I) or Formula (II) wherein $X^1$ is C; $X^2$ is N; $X^3$ is $CR^7$; $X^4$ is N; $X^5$ is N; $X^6$ is N; $X^7$ is $CR^7$; $X^8$ is C; and $X^9$ is N.

The present invention further relates to a compound according to Formula (I) or Formula (II) wherein $X^1$ is C; $X^2$ is $CR^7$; $X^3$ is N; $X^4$ is N; $X^5$ is $CR^7$; $X^6$ is N; $X^7$ is $CR^7$; $X^8$ is C; and $X^9$ is N.

The present invention further relates to a compound according to Formula (I) or Formula (II) wherein $X^1$ is C; $X^2$ is $CR^7$; $X^3$ is N; $X^4$ is $CR^7$; $X^5$ is N; $X^6$ is N; $X^7$ is $CR^7$; $X^8$ is C; and $X^9$ is N; or wherein $X^2$ is CH; $X^4$ is $CR^7$; and $X^7$ is CH.

The present invention further relates to a compound according to Formula (I) or Formula (II) wherein $X^1$ is C; $X^2$ is $CR^7$; $X^3$ is $CR^7$; $X^4$ is N; $X^5$ is N; $X^6$ is N; $X^7$ is $CR^7$; $X^8$ is C; and $X^9$ is N.

The present invention further relates to a compound according to Formula (I) or Formula (II) wherein $X^1$ is N; $X^2$ is $CR^7$; $X^3$ is N; $X^4$ is N; $X^5$ is $CR^7$; $X^6$ is N; $X^7$ is $CR^7$; $X^8$ is C; and $X^9$ is C.

The present invention further relates to a compound according to Formula (I) or Formula (II) wherein $X^1$ is N; $X^2$ is $CR^7$; $X^3$ is N; $X^4$ is $CR^7$; $X^5$ is N; $X^6$ is N; $X^7$ is $CR^7$; $X^8$ is C; and $X^9$ is C; or wherein $X^2$ is CH; $X^4$ is $CR^7$; and $X^7$ is CH.

The present invention further relates to a compound according to Formula (I) or Formula (II) wherein $X^1$ is N; $X^2$ is $CR^7$; $X^3$ is $CR^7$; $X^4$ is N; $X^5$ is N; $X^6$ is N; $X^7$ is $CR^7$; $X^8$ is C; and $X^9$ is C.

The present invention further relates to a compound according to Formula (I) or Formula (II) wherein $X^1$ is C; $X^2$ is $CR^7$; $X^3$ is N; $X^4$ is N; $X^5$ is $CR^7$; $X^6$ is N; $X^7$ is $CR^7$; $X^8$ is C; and $X^9$ is C.

The present invention further relates to a compound according to Formula (I) or Formula (II) wherein $X^1$ is C; $X^2$ is $CR^7$; $X^3$ is N; $X^4$ is $CR^7$; $X^5$ is N; $X^6$ is N; $X^7$ is $CR^7$; $X^8$ is C; and $X^9$ is C; or wherein $X^2$ is CH; $X^4$ is $CR^7$; and $X^7$ is CH.

The present invention further relates to a compound according to Formula (I) or Formula (II) wherein $X^1$ is C; $X^2$ is $CR^7$; $X^3$ is $CR^7$; $X^4$ is N; $X^5$ is N; $X^6$ is N; $X^7$ is $CR^7$; $X^8$ is C; and $X^9$ is C.

The present invention further relates to a compound according to Formula (I) or Formula (II) wherein $X^1$ is C; $X^2$ is $CR^7$; $X^3$ is N; $X^4$ is N; $X^5$ is $CR^7$; $X^6$ is N; $X^7$ is $CR^7$; $X^8$ is N; and $X^9$ is C.

The present invention further relates to a compound according to Formula (I) or Formula (II) wherein $X^1$ is N; $X^2$ is N; $X^3$ is $CR^7$; $X^4$ is $CR^7$; $X^5$ is $CR^7$; $X^6$ is N; $X^7$ is N; $X^8$ is C; and $X^9$ is C; or wherein $X^3$ is CH; $X^4$ is $CR^7$; and $X^5$ is CH.

The present invention further relates to a compound according to Formula (I) or Formula (II) wherein $X^1$ is N; $X^2$ is $CR^7$; $X^3$ is $CR^7$; $X^4$ is $CR^7$; $X^5$ is $CR^7$; $X^6$ is N; $X^7$ is N; $X^8$ is C; and $X^9$ is C; or wherein $X^2$ is CH; $X^3$ is CH; $X^4$ is $CR^7$; and $X^5$ is CH.

The present invention further relates to a compound according to Formula (I) or Formula (II) wherein $X^1$ is N; $X^2$ is $CR^7$; $X^3$ is N; $X^4$ is $CR^7$; $X^5$ is $CR^7$; $X^6$ is N; $X^7$ is N; $X^8$ is C; and $X^9$ is C; or wherein $X^1$ is $X^2$ is CH; $X^4$ is $CR^7$; and $X^5$ is CH.

The present invention further relates to a compound according to Formula (I) or Formula (II) wherein $X^1$ is N; $X^2$ is $CR^7$; $X^3$ is $CR^7$; $X^4$ is N; $X^5$ is $CR^7$; $X^6$ is N; $X^7$ is N; $X^8$ is C; and $X^9$ is C.

The present invention further relates to a compound according to Formula (I) or Formula (II) wherein $X^1$ is N; $X^2$ is $CR^7$; $X^3$ is $CR^7$; $X^4$ is $CR^7$; $X^5$ is N; $X^6$ is N; $X^7$ is N; $X^8$ is C; and $X^9$ is C; or wherein $X^2$ is CH; $X^3$ is CH; and $X^4$ is $CR^7$.

The present invention further relates to a compound according to Formula (I) or Formula (II) wherein $X^1$ is N; $X^2$ is N; $X^3$ is N; $X^4$ is $CR^7$; $X^5$ is $CR^7$; $X^6$ is N; $X^7$ is N; $X^8$ is C; and $X^9$ is C; or wherein $X^4$ is $CR^7$; and $X^5$ is CH.

The present invention further relates to a compound according to Formula (I) or Formula (II) wherein $X^1$ is N; $X^2$ is N; $X^3$ is $CR^7$; $X^4$ is N; $X^5$ is $CR^7$; $X^6$ is N; $X^7$ is N; $X^8$ is C; and $X^9$ is C.

The present invention further relates to a compound according to Formula (I) or Formula (II) wherein $X^1$ is N; $X^2$ is N; $X^3$ is $CR^7$; $X^4$ is $CR^7$; $X^5$ is N; $X^6$ is N; $X^7$ is N; $X^8$ is C; and $X^9$ is C; or wherein $X^3$ is CH; and $X^4$ is $CR^7$.

The present invention further relates to a compound according to Formula (I) or Formula (II) wherein $X^1$ is N; $X^2$ is N; $X^3$ is N; $X^4$ is $CR^7$; $X^5$ is N; $X^6$ is N; $X^7$ is N; $X^8$ is C; and $X^9$ is C.

The present invention further relates to a compound according to Formula (I) or Formula (II) wherein $X^1$ is N; $X^2$ is N; $X^3$ is $CR^7$; $X^4$ is N; $X^5$ is N; $X^6$ is N; $X^7$ is N; $X^8$ is C; and $X^9$ is C.

The present invention further relates to a compound according to Formula (I) or Formula (II) wherein $X^1$ is N; $X^2$ is $CR^7$; $X^3$ is N; $X^4$ is N; $X^5$ is $CR^7$; $X^6$ is N; $X^7$ is N; $X^8$ is C; and $X^9$ is C.

The present invention further relates to a compound according to Formula (I) or Formula (II), wherein $X^1$ is N; $X^2$ is $CR^7$; $X^3$ is N; $X^4$ is N; $X^5$ is N; $X^6$ is N; $X^7$ is N; $X^8$ is C; and $X^9$ is C; or wherein $X^2$ is CH; and $X^4$ is $CR^7$.

The present invention further relates to a compound according to Formula (I) or Formula (II) wherein $X^1$ is N; $X^2$ is $CR^7$; $X^3$ is $CR^7$; $X^4$ is N; $X^5$ is N; $X^6$ is N; $X^7$ is N; $X^8$ is C; and $X^9$ is C.

The present invention further relates to a compound according to Formula (I) or Formula (II) wherein $X^1$ is C; $X^2$ is N; $X^3$ is $CR^7$; $X^4$ is $CR^7$; $X^5$ is $CR^7$; $X^6$ is N; $X^7$ is N; $X^8$ is C; and $X^9$ is C; or wherein $X^3$ is CH; $X^4$ is $CR^7$; and $X^5$ is CH.

The present invention further relates to a compound according to Formula (I) or Formula (II) wherein $X^1$ is C; $X^2$ is $CR^7$; $X^3$ is $CR^7$; $X^4$ is $CR^7$; $X^5$ is $CR^7$; $X^6$ is N; $X^7$ is N; $X^8$ is C; and $X^9$ is C; or wherein $X^2$ is CH; $X^3$ is CH; $X^4$ is $CR^7$; and $X^5$ is CH.

The present invention further relates to a compound according to Formula (I) or Formula (II) wherein $X^1$ is C; $X^2$ is $CR^7$; $X^3$ is N; $X^4$ is $CR^7$; $X^5$ is $CR^7$; $X^6$ is N; $X^7$ is N; $X^8$ is C; and $X^9$ is C; or wherein $X^2$ is CH; $X^4$ is $CR^7$; and $X^5$ is CH.

The present invention further relates to a compound according to Formula (I) or Formula (II) wherein $X^1$ is C; $X^2$ is $CR^7$; $X^3$ is $CR^7$; $X^4$ is N; $X^5$ is $CR^7$; $X^6$ is N; $X^7$ is N; $X^8$ is C; and $X^9$ is C.

The present invention further relates to a compound according to Formula (I) or Formula (II) wherein $X^1$ is C; $X^2$ is $CR^7$; $X^3$ is $CR^7$; $X^4$ is $CR^7$; $X^5$ is N; $X^6$ is N; $X^7$ is N; $X^8$ is C; and $X^9$ is C; or wherein $X^2$ is CH; $X^3$ is CH; and $X^4$ is $CR^7$.

The present invention further relates to a compound according to Formula (I) or Formula (II) wherein $X^1$ is C; $X^2$ is N; $X^3$ is N; $X^4$ is $CR^7$; $X^5$ is $CR^7$; $X^6$ is N; $X^7$ is N; $X^8$ is C; and $X^9$ is C; or wherein $X^4$ is $CR^7$; and $X^5$ is CH.

The present invention further relates to a compound according to Formula (I) or Formula (II) wherein $X^1$ is C; $X^2$ is N; $X^3$ is $CR^7$; $X^4$ is N; $X^5$ is $CR^7$; $X^6$ is N; $X^7$ is N; $X^8$ is C; and $X^9$ is C.

The present invention further relates to a compound according to Formula (I) or Formula (II) wherein $X^1$ is C; $X^2$ is N; $X^3$ is $CR^7$; $X^4$ is $CR^7$; $X^5$ is N; $X^6$ is N; $X^7$ is N; $X^8$ is C; and $X^9$ is C; or wherein $X^3$ is CH; and $X^4$ is $CR^7$.

The present invention further relates to a compound according to Formula (I) or Formula (II) wherein $X^1$ is C; $X^2$ is N; $X^3$ is N; $X^4$ is $CR^7$; $X^5$ is N; $X^6$ is N; $X^7$ is N; $X^8$ is C; and $X^9$ is C.

The present invention further relates to a compound according to Formula (I) or Formula (II) wherein $X^1$ is C; $X^2$ is N; $X^3$ is $CR^7$; $X^4$ is N; $X^5$ is N; $X^6$ is N; $X^7$ is N; $X^8$ is C; and $X^9$ is C.

The present invention further relates to a compound according to Formula (I) or Formula (II) wherein $X^1$ is C; $X^2$ is $CR^7$; $X^3$ is N; $X^4$ is N; $X^5$ is $CR^7$; $X^6$ is N; $X^7$ is N; $X^8$ is C; and $X^9$ is C.

The present invention further relates to a compound according to Formula (I) or Formula (II) wherein $X^1$ is C; $X^2$ is $CR^7$; $X^3$ is N; $X^4$ is $CR^7$; $X^5$ is N; $X^6$ is N; $X^7$ is N; $X^8$ is C; and $X^9$ is C; or wherein $X^2$ is CH; and $X^4$ is $CR^7$.

The present invention further relates to a compound according to Formula (I) or Formula (II) wherein $X^1$ is C; $X^2$ is $CR^7$; $X^3$ is $CR^7$; $X^4$ is N; $X^5$ is N; $X^6$ is N; $X^7$ is N; $X^8$ is C; and $X^9$ is C.

The present invention further relates to a compound according to Formula (I) or Formula (II) wherein $R^7$ is each independently selected from H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, C(O)—, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^8(C_1-C_{10})$alkyl-, $R^8(C_3-C_{10})$cycloalkyl, $R^8(C_2-C_9)$heterocycloalkyl, $R^8(C_6-C_{14})$aryl, $R^8(C_2-C_9)$heteroaryl, $R^8(C_2-C_{10})$alkylnyl, $R^8(C_1-C_{10})$alkylamine, $R^8((C_1-C_{10})$alkyl$)_2$amine, $R^8(C_2-C_{10})$alkynylamine, $R^8$C(O)—, $R^8(C_1-C_{10})$alkyl-C(O)O—, $R^8(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^8(C_3-C_{10})$cycloalkyl-O—, $R^8(C_2-C_9)$heterocycloalkyl-O—, $R^8(C_6-C_{14})$aryl-O—, $R^8(C_2-C_9)$heteroaryl-O—, HO—, halo, cyano, $H_2N$—, $(CH_3)HN$—, $(CH_3)_2N$—, $R^8R^9N$—, $R^9R^9N(O)C$—, $F_3C$—, $F_2HC$—, $CH_3F_2C$—, $FH_2C$—, $CH_3FHC$—, or $(CH_3)_2FC$—,
wherein $R^8$ and $R^9$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $(CH_3)_2N$—, and $H_2N$—;
or $R^8$ and $R^9$ are taken together to form a 3 to 10 member cycloalkyl, heterocycloalkyl, aryl or heteroaryl ring; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_2-C_{10})$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $H_2N$—, $(CH_3)HN$—, $(CH_3)_2N$—, $F_3C$—, $F_2HC$—, $CH_3F_2C$—, $FH_2C$—, $CH_3FHC$—, or $(CH_3)_2FC$—.

The present invention further relates to a compound according to Formula (I) or Formula (II) wherein $R^7$ is each independently selected from H, $(C_2-C_9)$heteroaryl, $(C_2-C_{10})$alkynylamine, $(C_1-C_{10})$alkoxy-, $(C_1-C_{10})$alkyl-$(C_2-C_9)$heterocycloalkyl, $(C_2-C_9)$heterocycloalkyl-$(C_1-C_{10})$alkoxy-, $(C_1-C_{10})$alkoxy-$(C_2-C_9)$heterocycloalkyl-, $(C_2-C_9)$heteroalkyl-C(O)—, or $F_2HC$—, wherein each $(C_1-C_{10})$alkyl, $(C_2-C_9)$heteroaryl, or $(C_2-C_9)$heterocycloalkyl are further optionally substituted by one to four groups selected from $(C_1-C_{10})$alkyl.

The present invention further relates to a compound according to Formula (I) or Formula (II) wherein $R^7$ is H.

The present invention further relates to a compound according to Formula (I) or Formula (II) wherein n is 1, 2 or 3.

The present invention further relates to a compound according to Formula (I) or Formula (II) wherein n is 1.

The present invention further relates to a compound according to Formula (I) or Formula (II) wherein $R^1$ and $R^2$ are each independently selected from H, $(C_1-C_{10})$alkyl, $(C_1-C_{10})$alkylamine, $(C_1-C_{10})$alkoxy-, or $NH_2$.

The present invention further relates to a compound according to Formula (I) or Formula (II) wherein $R^1$ is H.

The present invention further relates to a compound according to Formula (I) or Formula (II) wherein $R^2$ is H.

The present invention further relates to a compound according to Formula (I) or Formula (II) wherein $R^1$ and $R^2$ are each H.

The present invention further relates to a compound according to Formula (I) wherein $T^1$ is $CR^{10}$; $T^2$ is $CR^{10}$; $T^3$ is $CR^{10}$; and $R^3$ is $CR^{16}$.

The present invention further relates to a compound according to Formula (I) wherein $T^1$ is $CR^{10}$; $T^2$ is $CR^{10}$; $T^3$ is $CR^{10}$; and $R^3$ is N.

The present invention further relates to a compound according to Formula (I) wherein $T^1$ is N; $T^2$ is $CR^{10}$; $T^3$ is $CR^{10}$; and $R^3$ is $CR^{16}$.

The present invention further relates to a compound according to Formula (I) wherein $T^1$ is N; $T^2$ is N; $T^3$ is $CR^{10}$; and $R^3$ is $CR^{16}$.

The present invention further relates to a compound according to Formula (I) wherein $T^1$ is N; $T^2$ is $CR^{10}$; $T^3$ is N; and $R^3$ is $CR^{16}$.

The present invention further relates to a compound according to Formula (I) wherein $T^1$ is $CR^{10}$; $T^2$ is N; $T^3$ is $CR^{10}$; and $R^3$ is N.

The present invention further relates to a compound according to Formula (I) wherein $T^1$ is $CR^{10}$; $T^2$ is $CR^{10}$; $T^3$ is N; and $R^3$ is N.

The present invention further relates to a compound according to Formula (I) wherein $T^1$ is $CR^{10}$; $T^2$ is N; $T^3$ is N; and $R^3$ is N.

The present invention further relates to a compound according to Formula (I) wherein $T^1$ is N; $T^2$ is N; $T^3$ is N; and $R^3$ is $CR^{16}$.

The present invention further relates to a compound according to Formula (I) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (I) wherein $R^{10}$ is selected from the group consisting of H, $(C_1-C_{10})$alkyl, $(C_3-C_{10})$cycloalkyl, $(C_1-C_{10})$alkoxy and halo.

The present invention further relates to a compound according to Formula (I) wherein $R^{16}$ is selected from the group consisting of H, $(C_1-C_{10})$alkyl, $(C_3-C_{10})$cycloalkyl, $(C_1-C_{10})$alkoxy and halo.

The present invention further relates to a compound according to Formula (I) wherein $R^{16}$ is selected from the group consisting of H, $(C_1-C_{10})$alkyl, $(C_3-C_{10})$cycloalkyl, $(C_1-C_{10})$alkoxy and halo.

The present invention further relates to a compound according to Formula (I) wherein $R^{10}$ and $R^{16}$ are each independently selected from the group consisting of H, $(C_1-C_{10})$alkyl, $(C_3-C_{10})$cycloalkyl, $(C_1-C_{10})$alkoxy and halo.

The present invention further relates to a compound according to Formula (I) wherein $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy and halo; $T^3$ is CH; and $R^3$ is CH.

The present invention further relates to a compound according to Formula (I) wherein $T^1$ is CH; $T^2$ is $CR^{10}$ wherein $R^{10}$ is $(C_1-C_{10})$alkoxy; $T^3$ is CH and $R^3$ is CH.

The present invention further relates to a compound according to Formula (I) wherein $T^1$ is $CR^{10}$ wherein $R^{10}$ is H. $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy and halo; $T^3$ is CH; and $R^3$ is N.

The present invention further relates to a compound according to Formula (I) wherein $T^1$ is CH; $T^2$ is $CR^{10}$ wherein $R^{10}$ is $(C_1-C_{10})$alkoxy; $T^3$ is CH and $R^3$ is N.

The present invention further relates to a compound according to Formula (I) wherein $Y^1$ is O, $NR^{18}$, or $CR^{18}R^{19}$.

The present invention further relates to a compound according to Formula (I) wherein $Y^1$ is O.

The present invention further relates to a compound according to Formula (I) wherein $Y^1$ is $CR^{18}R^{19}$.

The present invention further relates to a compound according to Formula (I) wherein $R^{18}$ and $R^{19}$ are each H.

The present invention further relates to a compound according to Formula (I) wherein $Y^1$ is $NR^{18}$ The present invention further relates to a compound according to Formula (I) wherein m is 0, 1, or 2.

The present invention further relates to a compound according to Formula (I), wherein m is 1

The present invention further relates to a compound according to Formula (I) wherein $R^4$ and $R^5$ are each independently selected from the group consisting of H, $(C_1-C_{10})$alkyl, hydroxy, halo, and amino.

The present invention further relates to a compound according to Formula (I) wherein $R^4$ is H.

The present invention further relates to a compound according to Formula (I) wherein $R^5$ is H.

The present invention further relates to a compound according to Formula (I) wherein $R^4$ and $R^5$ are each H.

The present invention further relates to a compound according to Formula (I) wherein
$R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (I) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (I) wherein $R^{16}$ and $R^4$ are taken together with the carbons to which they are attached to form a compound of Formula (II):

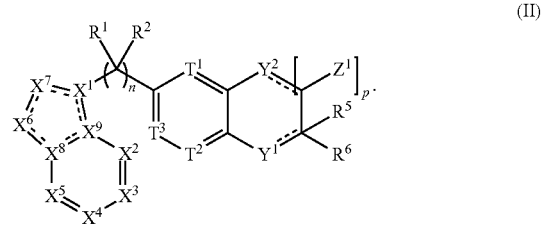

(II)

The present invention further relates to a compound according to Formula (II) wherein $T^1$ is $CR^{10}$; $T^2$ is $CR^{10}$; and $T^3$ is $CR^{10}$.

The present invention further relates to a compound according to Formula (II) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (II) wherein $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy and halo; and $T^3$ is CH.

The present invention further relates to a compound according to Formula (II) wherein $T^1$ is CH; $T^2$ is $CR^{10}$ wherein $R^{10}$ is $(C_1-C_{10})$alkoxy; and $T^3$ is CH.

The present invention further relates to a compound according to Formula (II) wherein $T^1$ is CH; $T^2$ is $CR^{10}$ wherein $R^{10}$ is halo; and $T^3$ is CH.

The present invention further relates to a compound according to Formula (II) wherein $Y^1$ and $Y^2$ are each independently selected from O, S, $NR^{18}$, or $CR^{18}R^{19}$.

The present invention further relates to a compound according to Formula (II) wherein $Y^1$ is O.

The present invention further relates to a compound according to Formula (II) wherein $Y^2$ is O.

The present invention further relates to a compound according to Formula (II) wherein $Y^1$ is $CR^{18}R^{19}$.

The present invention further relates to a compound according to Formula (II) wherein $R^{18}$ and $R^{19}$ are each H.

The present invention further relates to a compound according to Formula (II) wherein $Y^2$ is $CR^{18}R^{19}$. The present invention further relates to a compound according to Formula (II) wherein $R^{18}$ and $R^{19}$ are each H.

The present invention further relates to a compound according to Formula (II) wherein $Y^1$ is S.

The present invention further relates to a compound according to Formula (II) wherein $Y^2$ is S.

The present invention further relates to a compound according to Formula (II) wherein $Y^1$ is $NR^{18}$ wherein $R^{18}$ is H or $(C_1-C_{10})$alkyl.

The present invention further relates to a compound according to Formula (II) wherein $Y^2$ is $NR^{18}$ wherein $R^{18}$ is H or $(C_1-C_{10})$alkyl.

The present invention further relates to a compound according to Formula (II) wherein $Y^1$ is O; and $Y^2$ is O, S, $NR^{18}$, or $CR^{18}R^{19}$.

The present invention further relates to a compound according to Formula (II) wherein $Y^2$ is O.

The present invention further relates to a compound according to Formula (II) wherein p is 0, 1 or 2.

The present invention further relates to a compound according to Formula (II) wherein p is 1.

The present invention further relates to a compound according to Formula (II) wherein $Z^1$ is each independently selected from H, halo or $(C_1-C_{10})$alkyl.

The present invention further relates to a compound according to Formula (II) wherein $R^5$ is selected from the group consisting of H, $(C_1-C_{10})$alkyl, HO—, halo, and $H_2N$—

The present invention further relates to a compound according to Formula (II) wherein $R^5$ is H or $(C_1-C_{10})$alkyl.

The present invention further relates to a compound according to Formula (II) wherein $R^5$ is H.

The present invention further relates to a compound according to Formula (II) wherein $R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (II) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (II) wherein $R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (II) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (III):

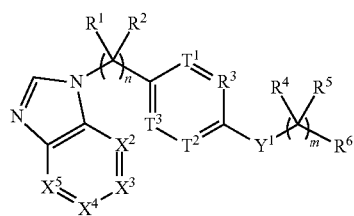

(III)

wherein n is 1, 2 or 3;
m is 0, 1, or 2;
$R^1$ and $R^2$ are each independently selected from H, $(C_1-C_{10})$alkyl, $(C_1-C_{10})$alkylamine, $(C_1-C_{10})$alkoxy-, or $NH_2$;
$T^1$ is $CR^{10}$; $T^2$ is $CR^{10}$; $T^3$ is $CR^{10}$; and $R^3$ is $CR^{16}$ or N;
$Y^1$ is O, $NR^{18}$, or $CR^{18}R^{19}$;
$R^4$ and $R^5$ are each independently selected from the group consisting of H, $(C_1-C_{10})$alkyl, hydroxy, halo, and amino; and
$R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (III) wherein $X^2$ is N; $X^3$ is $CR^7$; $X^4$ is $CR^7$ and $X^5$ is $CR^7$.

The present invention further relates to a compound according to Formula (III) wherein $X^2$ is $CR^7$; $X^3$ is $CR^7$; $X^4$ is $CR^7$ and $X^5$ is $CR^7$.

The present invention further relates to a compound according to Formula (III) wherein $X^2$ is $CR^7$; $X^3$ is N; $X^4$ is $CR^7$ and $X^5$ is $CR^7$.

The present invention further relates to a compound according to Formula (III) wherein $X^1$ is N; $X^2$ is $CR^7$; $X^3$ is $CR^7$; $X^4$ is N and $X^5$ is $CR^7$.

The present invention further relates to a compound according to Formula (III) wherein $X^2$ is $CR^7$; $X^3$ is $CR^7$; $X^4$ is $CR^7$ and $X^5$ is N.

The present invention further relates to a compound according to Formula (III) wherein $X^2$ is N; $X^3$ is N; $X^4$ is $CR^7$ and $X^5$ is $CR^7$.

The present invention further relates to a compound according to Formula (III) wherein $X^2$ is N; $X^3$ is $CR^7$; $X^4$ is N and $X^5$ is $CR^7$.

The present invention further relates to a compound according to Formula (III) wherein $X^2$ is N; $X^3$ is $CR^7$; $X^4$ is $CR^7$ and $X^5$ is N.

The present invention further relates to a compound according to Formula (III) wherein $X^2$ is N; $X^3$ is N; $X^4$ is $CR^7$ and $X^5$ is N.

The present invention further relates to a compound according to Formula (III) wherein $X^2$ is N; $X^3$ is $CR^7$; $X^4$ is N and $X^5$ is N.

The present invention further relates to a compound according to Formula (III) wherein $X^2$ is $CR^7$; $X^3$ is N; $X^4$ is N and $X^5$ is $CR^7$.

The present invention further relates to a compound according to Formula (III) wherein $X^2$ is $CR^7$; $X^3$ is N; $X^4$ is $CR^7$ and $X^5$ is N.

The present invention further relates to a compound according to Formula (III) wherein $X^2$ is $CR^7$; $X^3$ is $CR^7$; $X^4$ is N and $X^5$ is N.

The present invention further relates to a compound according to Formula (III) wherein n is 1.

The present invention further relates to a compound according to Formula (III) wherein $R^1$ and $R^2$ are each H.

The present invention further relates to a compound according to Formula (III) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (III) wherein $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy and halo; $T^3$ is CH; and $R^3$ is CH or N.

The present invention further relates to a compound according to Formula (III) wherein $Y^1$ is O.

The present invention further relates to a compound according to Formula (III) wherein m is 1.

The present invention further relates to a compound according to Formula (III) wherein $R^4$ and $R^5$ are each H.

The present invention further relates to a compound according to Formula (III) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (III) wherein n is 1; m is 1; $R^1$ and $R^2$ are each H; $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy or halo; $T^3$ is CH; and $R^3$ is CH or N; $Y^1$ is O; $R^4$ and $R^5$ are each H; and $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;
  wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
  wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (IV)

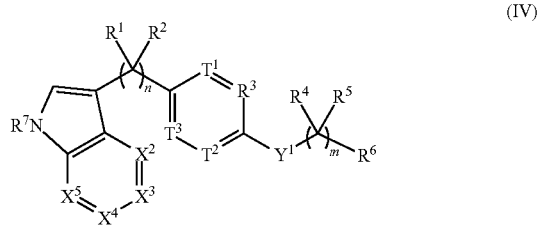

wherein n is 1, 2 or 3;
m is 0, 1, or 2;
$R^1$ and $R^2$ are each independently selected from H, $(C_1-C_{10})$alkyl, $(C_1-C_{10})$alkylamine, $(C_1-C_{10})$alkoxy-, or $NH_2$;
$T^1$ is $CR^{10}$; $T^2$ is $CR^{10}$; $T^3$ is $CR^{10}$; and $R^3$ is $CR^{16}$ or N;
$Y^1$ is O, $NR^{18}$, or $CR^{18}R^{19}$;
$R^4$ and $R^5$ are each independently selected from the group consisting of H, $(C_1-C_{10})$alkyl, hydroxy, halo, and amino; and
$R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;
  wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
  wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (IV) wherein $X^2$ is N; $X^3$ is $CR^7$; $X^4$ is $CR^7$ and $X^5$ is $CR^7$.

The present invention further relates to a compound according to Formula (IV) wherein $X^2$ is $CR^7$; $X^3$ is $CR^7$; $X^4$ is $CR^7$ and $X^5$ is $CR^7$.

The present invention further relates to a compound according to Formula (IV) wherein $X^2$ is $CR^7$; $X^3$ is N; $X^4$ is $CR^7$ and $X^5$ is $CR^7$.

The present invention further relates to a compound according to Formula (IV) wherein $X^2$ is $CR^7$; $X^3$ is $CR^7$; $X^4$ is N and $X^5$ is $CR^7$.

The present invention further relates to a compound according to Formula (IV) wherein $X^2$ is $CR^7$; $X^3$ is $CR^7$; $X^4$ is $CR^7$ and $X^5$ is N.

The present invention further relates to a compound according to Formula (IV) wherein $X^2$ is N; $X^3$ is N; $X^4$ is $CR^7$ and $X^5$ is $CR^7$.

The present invention further relates to a compound according to Formula (IV) wherein $X^2$ is N; $X^3$ is $CR^7$; $X^4$ is N and $X^5$ is $CR^7$.

The present invention further relates to a compound according to Formula (IV) wherein $X^2$ is N; $X^3$ is $CR^7$; $X^4$ is $CR^7$ and $X^5$ is N.

The present invention further relates to a compound according to Formula (IV) wherein $X^2$ is N; $X^3$ is N; $X^4$ is $CR^7$ and $X^5$ is N.

The present invention further relates to a compound according to Formula (IV) wherein $X^2$ is N; $X^3$ is $CR^7$; $X^4$ is N and $X^5$ is N.

The present invention further relates to a compound according to Formula (IV) wherein $X^2$ is $CR^7$; $X^3$ is N; $X^4$ is N and $X^5$ is $CR^7$.

The present invention further relates to a compound according to Formula (IV) wherein $X^2$ is $CR^7$; $X^3$ is N; $X^4$ is $CR^7$ and $X^5$ is N.

The present invention further relates to a compound according to Formula (IV) wherein $X^2$ is $CR^7$; $X^3$ is $CR^7$; $X^4$ is N and $X^5$ is N.

The present invention further relates to a compound according to Formula (IV) wherein n is 1.

The present invention further relates to a compound according to Formula (IV) wherein $R^1$ and $R^2$ are each H.

The present invention further relates to a compound according to Formula (IV) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (IV) wherein $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy or halo; $T^3$ is CH; and $R^3$ is CH or N.

The present invention further relates to a compound according to Formula (IV) wherein $Y^1$ is O.

The present invention further relates to a compound according to Formula (IV) wherein m is 1.

The present invention further relates to a compound according to Formula (IV) wherein $R^4$ and $R^5$ are each H.

The present invention further relates to a compound according to Formula (IV) wherein $R^6$ is selected from the group consisting of H, $(C_1-C_{10})$alkyl, $(C_3-C_{10})$cycloalkyl, $(C_2-C_9)$heteroaryl, $R^{14}-(C_6-C_{14})$aryl, $R^{14}-(C_2-C_9)$heteroaryl, and $R^{14}-(C_1-C_{10})$alkylamine;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (IV) wherein n is 1; m is 1; $R^1$ and $R^2$ are each H; $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy or halo; $T^3$ is CH; and $R^3$ is CH or N; $Y^1$ is O; $R^4$ and $R^5$ are each H; and $R^6$ is selected from the group consisting of H, $(C_1-C_{10})$alkyl, $(C_3-C_{10})$cycloalkyl, $(C_2-C_9)$heteroaryl, $R^{14}-(C_6-C_{14})$aryl, $R^{14}-(C_2-C_9)$heteroaryl, and $R^{14}-(C_1-C_{10})$alkylamine;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (V)

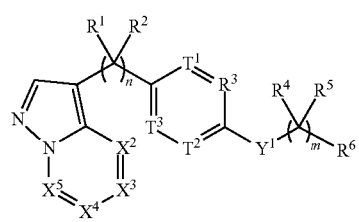

(V)

wherein n is 1, 2 or 3;
m is 0, 1, or 2;
$R^1$ and $R^2$ are each independently selected from H, $(C_1-C_{10})$alkyl, $(C_1-C_{10})$alkylamine, $(C_1-C_{10})$alkoxy-, or $NH_2$;
$T^1$ is $CR^{10}$; $T^2$ is $CR^{10}$; $T^3$ is $CR^{10}$; and $R^3$ is $CR^{16}$ or N;
$Y^1$ is O, $NR^{18}$, or $CR^{18}R^{19}$;
$R^4$ and $R^5$ are each independently selected from the group consisting of H, $(C_1-C_{10})$alkyl, hydroxy, halo, and amino; and $R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}-(C_1-C_{10})$alkyl-, $R^{14}-(C_3-C_{10})$cycloalkyl, $R^{14}-(C_2-C_9)$heterocycloalkyl, $R^{14}-(C_6-C_{14})$aryl, $R^{14}-(C_2-C_9)$heteroaryl, $R^{14}-(C_2-C_{10})$alkylnyl, $R^{14}-(C_1-C_{10})$alkylamine, $R^{14}-((C_1-C_{10})$alkyl$)_2$amine, and $R^{14}-C(O)$—;
wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (V) wherein $X^2$ is N; $X^3$ is $CR^7$; $X^4$ is $CR^7$ and $X^5$ is $CR^7$.

The present invention further relates to a compound according to Formula (V) wherein $X^2$ is $CR^7$; $X^3$ is $CR^7$; $X^4$ is $CR^7$ and $X^5$ is $CR^7$.

The present invention further relates to a compound according to Formula (V) wherein $X^2$ is $CR^7$; $X^3$ is N; $X^4$ is $CR^7$ and $X^5$ is $CR^7$.

The present invention further relates to a compound according to Formula (V) wherein $X^2$ is $CR^7$; $X^3$ is $CR^7$; $X^4$ is N and $X^5$ is $CR^7$.

The present invention further relates to a compound according to Formula (V) wherein $X^2$ is N; $X^3$ is N; $X^4$ is $CR^7$ and $X^5$ is $CR^7$.

The present invention further relates to a compound according to Formula (V) wherein $X^2$ is N; $X^3$ is $CR^7$; $X^4$ is N and $X^5$ is $CR^7$.

The present invention further relates to a compound according to Formula (V) wherein $X^2$ is $CR^7$; $X^3$ is N; $X^4$ is N and $X^5$ is $CR^7$.

The present invention further relates to a compound according to Formula (V) wherein n is 1.

The present invention further relates to a compound according to Formula (V) wherein $R^1$ and $R^2$ are each H.

The present invention further relates to a compound according to Formula (V) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (V) wherein $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy or halo; $T^3$ is CH; and $R^3$ is CH or N.

The present invention further relates to a compound according to Formula (V) wherein $Y^1$ is O.

The present invention further relates to a compound according to Formula (V) wherein m is 1.

The present invention further relates to a compound according to Formula (V) wherein $R^4$ and $R^5$ are each H.

The present invention further relates to a compound according to Formula (V) wherein $R^6$ is selected from the group consisting of H, $(C_1-C_{10})$alkyl, $(C_3-C_{10})$cycloalkyl, $(C_2-C_9)$heteroaryl, $R^{14}-(C_6-C_{14})$aryl, $R^{14}-(C_2-C_9)$heteroaryl, and $R^{14}-(C_1-C_{10})$alkylamine;
- wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
- wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (V) wherein n is 1; m is 1; $R^1$ and $R^2$ are each H; $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy or halo; $T^3$ is CH; and $R^3$ is CH or N; $Y^1$ is O; $R^4$ and $R^5$ are each H; and $R^6$ is selected from the group consisting of H, $(C_1-C_{10})$alkyl, $(C_3-C_{10})$cycloalkyl, $(C_2-C_9)$heteroaryl, $R^{14}-(C_6-C_{14})$aryl, $R^{14}-(C_2-C_9)$heteroaryl, and $R^{14}-(C_1-C_{10})$alkylamine;
- wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
- wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (VI)

(VI)

wherein n is 1, 2 or 3;
m is 0, 1, or 2;
$R^1$ and $R^2$ are each independently selected from H, $(C_1-C_{10})$alkyl, $(C_1-C_{10})$alkylamine, $(C_1-C_{10})$alkoxy-, or $NH_2$;
$T^1$ is $CR^{10}$; $T^2$ is $CR^{10}$; $T^3$ is $CR^{10}$; and $R^3$ is $CR^{16}$ or N;
$Y^1$ is O, $NR^{18}$, or $CR^{18}R^{19}$;
$R^4$ and $R^5$ are each independently selected from the group consisting of H, $(C_1-C_{10})$alkyl, hydroxy, halo, and amino; and
$R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}-(C_1-C_{10})$alkyl-, $R^{14}-(C_3-C_{10})$cycloalkyl, $R^{14}-(C_2-C_9)$heterocycloalkyl, $R^{14}-(C_6-C_{14})$aryl, $R^{14}-(C_2-C_9)$heteroaryl, $R^{14}-(C_2-C_{10})$alkylnyl, $R^{14}-(C_1-C_{10})$alkylamine, $R^{14}-((C_1-C_{10})$alkyl$)_2$amine, and $R^{14}-C(O)$—;
- wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
- wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (VI) wherein $X^2$ is N; $X^3$ is $CR^7$; $X^4$ is $CR^7$ and $X^5$ is $CR^7$.

The present invention further relates to a compound according to Formula (VI) wherein $X^2$ is $CR^7$; $X^3$ is $CR^7$; $X^4$ is $CR^7$ and $X^5$ is $CR^7$.

The present invention further relates to a compound according to Formula (VI) wherein $X^2$ is $CR^7$; $X^3$ is N; $X^4$ is $CR^7$ and $X^5$ is $CR^7$.

The present invention further relates to a compound according to Formula (VI) wherein $X^2$ is $CR^7$; $X^3$ is $CR^7$; $X^4$ is N and $X^5$ is $CR^7$.

The present invention further relates to a compound according to Formula (VI) wherein $X^2$ is $CR^7$; $X^3$ is $CR^7$; $X^4$ is $CR^7$ and $X^5$ is N.

The present invention further relates to a compound according to Formula (VI) wherein $X^2$ is N; $X^3$ is $CR^7$; $X^4$ is N and $X^5$ is $CR^7$.

The present invention further relates to a compound according to Formula (VI) wherein $X^2$ is N; $X^3$ is $CR^7$; $X^4$ is $CR^7$ and $X^5$ is N.

The present invention further relates to a compound according to Formula (VI) wherein $X^2$ is N; $X^3$ is $CR^7$; $X^4$ is N and $X^5$ is N.

The present invention further relates to a compound according to Formula (VI) wherein $X^2$ is $CR^7$; $X^3$ is N; $X^4$ is N and $X^5$ is $CR^7$.

The present invention further relates to a compound according to Formula (VI) wherein $X^2$ is $CR^7$; $X^3$ is N; $X^4$ is $CR^7$ and $X^5$ is N.

The present invention further relates to a compound according to Formula (VI) wherein $X^2$ is $CR^7$; $X^3$ is $CR^7$; $X^4$ is N and $X^5$ is N.

The present invention further relates to a compound according to Formula (VI) wherein n is 1.

The present invention further relates to a compound according to Formula (VI) wherein $R^1$ and $R^2$ are each H.

The present invention further relates to a compound according to Formula (VI) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (VI) wherein $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy or halo; $T^3$ is CH; and $R^3$ is CH or N.

The present invention further relates to a compound according to Formula (VI) wherein $Y^1$ is O.

The present invention further relates to a compound according to Formula (VI) wherein m is 1.

The present invention further relates to a compound according to Formula (VI) wherein $R^4$ and $R^5$ are each H.

The present invention further relates to a compound according to Formula (VI) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;
  wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
  wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (VI) wherein n is 1; m is 1; $R^1$ and $R^2$ are each H; $T^1$ is $CR^{10}$ wherein $R^{10}$ is H, $(C_1-C_{10})$alkyl or $(C_3-C_{10})$cycloalkyl; $T^2$ is $CR^{10}$ wherein $R^{10}$ is $(C_1-C_{10})$alkyl, $(C_3-C_{10})$cycloalkyl, $(C_1-C_{10})$alkoxy or halo; $T^3$ is CH; and $R^3$ is CH or N; $Y^1$ is O; $R^4$ and $R^5$ are each H; and $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;
  wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
  wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (VII)

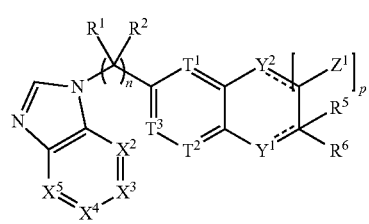

(VII)

wherein n is 1, 2 or 3;
p is 0, 1 or 2;

$R^1$ and $R^2$ are each independently selected from H, $(C_1-C_{10})$alkyl, $(C_1-C_{10})$alkylamine, $(C_1-C_{10})$alkoxy-, or $NH_2$, $T^1$ is $CR^{10}$; $T^2$ is $CR^{10}$; $T^3$ is $CR^{10}$;

$Y^1$ and $Y^2$ are each independently selected from O, S, $NR^{18}$, or $CR^{18}R^{19}$;

$Z^1$ is each independently selected from H, halo or $(C_1-C_{10})$alkyl;

$R^5$ is selected from the group consisting of H, $(C_1-C_{10})$alkyl, HO—, halo, and $H_2N$—; and $R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;
  wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
  wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (VII) wherein $X^2$ is N; $X^3$ is $CR^7$; $X^4$ is $CR^7$ and $X^5$ is $CR^7$.

The present invention further relates to a compound according to Formula (VII) wherein $X^2$ is $CR^7$; $X^3$ is $CR^7$; $X^4$ is $CR^7$ and $X^5$ is $CR^7$.

The present invention further relates to a compound according to Formula (VII) wherein $X^2$ is $CR^7$; $X^3$ is N; $X^4$ is $CR^7$ and $X^5$ is $CR^7$.

The present invention further relates to a compound according to Formula (VII) wherein $X^1$ is N; $X^2$ is $CR^7$; $X^3$ is $CR^7$; $X^4$ is N and $X^5$ is $CR^7$.

The present invention further relates to a compound according to Formula (VII) wherein $X^2$ is $CR^7$; $X^3$ is $CR^7$; $X^4$ is $CR^7$ and $X^5$ is N.

The present invention further relates to a compound according to Formula (VII) wherein $X^2$ is N; $X^3$ is N; $X^4$ is $CR^7$ and $X^5$ is $CR^7$.

The present invention further relates to a compound according to Formula (VII) wherein $X^2$ is N; $X^3$ is $CR^7$; $X^4$ is N and $X^5$ is $CR^7$.

The present invention further relates to a compound according to Formula (VII) wherein $X^2$ is N; $X^3$ is $CR^7$; $X^4$ is $CR^7$ and $X^5$ is N.

The present invention further relates to a compound according to Formula (VII) wherein $X^2$ is N; $X^3$ is N; $X^4$ is $CR^7$ and $X^5$ is N.

The present invention further relates to a compound according to Formula (VII) wherein $X^2$ is N; $X^3$ is $CR^7$; $X^4$ is N and $X^5$ is N.

The present invention further relates to a compound according to Formula (VII) wherein $X^2$ is $CR^7$; $X^3$ is N; $X^4$ is N and $X^5$ is $CR^7$.

The present invention further relates to a compound according to Formula (VII) wherein $X^2$ is $CR^7$; $X^3$ is N; $X^4$ is $CR^7$ and $X^5$ is N.

The present invention further relates to a compound according to Formula (VII) wherein $X^2$ is $CR^7$; $X^3$ is $CR^7$; $X^4$ is N and $X^5$ is N.

The present invention further relates to a compound according to Formula (VII) wherein n is 1.

The present invention further relates to a compound according to Formula (VII) wherein $R^1$ and $R^2$ are each H.

The present invention further relates to a compound according to Formula (VII) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (VII) wherein each $R^{10}$ is H.

The present invention further relates to a compound according to Formula (VII) wherein $Y^1$ is O; and $Y^2$ is O, S, $NR^{18}$, or $CR^{18}R^{19}$.

The present invention further relates to a compound according to Formula (VII) wherein $Y^2$ is O.

The present invention further relates to a compound according to Formula (VII) wherein p is 1.

The present invention further relates to a compound according to Formula (VII) wherein $R^5$ is H or $(C_1-C_{10})$alkyl.

The present invention further relates to a compound according to Formula (VII) wherein $R^5$ is H.

The present invention further relates to a compound according to Formula (VII) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;
  wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
  wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (VII) wherein n is 1; p is 1; $R^1$ and $R^2$ are each H; $R^{10}$ is selected from the group consisting of H, $(C_1-C_{10})$alkyl, $(C_3-C_{10})$cycloalkyl, $(C_1-C_{10})$alkoxy, and halo; $Y^1$ is O; $Y^2$ is O, S, $NR^{18}$, or $CR^{18}R^{19}$; $R^5$ is H or $(C_1-C_{10})$alkyl; and $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;
  wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (VII) wherein $R^5$ is H and $Y^2$ is O.

The present invention further relates to a compound according to Formula (VIII):

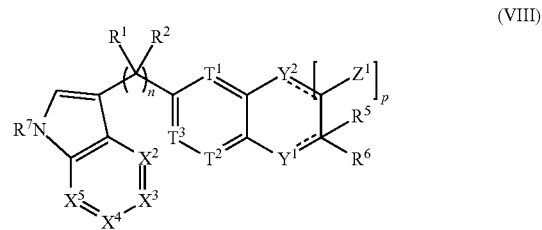

(VIII)

wherein n is 1, 2 or 3;

p is 0, 1 or 2;

$R^1$ and $R^2$ are each independently selected from H, $(C_1-C_{10})$alkyl, $(C_1-C_{10})$alkylamine, $(C_1-C_{10})$alkoxy-, or $NH_2$;

$T^1$ is $CR^{10}$; $T^2$ is $CR^{10}$; $T^3$ is $CR^{10}$;

$Y^1$ and $Y^2$ are each independently selected from O, S, $NR^{18}$, or $CR^{18}R^{19}$;

$Z^1$ is each independently selected from H, halo or $(C_1-C_{10})$alkyl;

$R^5$ is selected from the group consisting of H, $(C_1-C_{10})$alkyl, HO—, halo, and $H_2N$—; and $R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;
  wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and
  wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (VIII) wherein $X^2$ is N; $X^3$ is $CR^7$; $X^4$ is $CR^7$ and $X^5$ is $CR^7$.

The present invention further relates to a compound according to Formula (VIII) wherein $X^2$ is $CR^7$; $X^3$ is $CR^7$; $X^4$ is $CR^7$ and $X^5$ is $CR^7$.

The present invention further relates to a compound according to Formula (VIII) wherein $X^2$ is $CR^7$; $X^3$ is N; $X^4$ is $CR^7$ and $X^5$ is $CR^7$.

The present invention further relates to a compound according to Formula (VIII) wherein $X^2$ is $CR^7$; $X^3$ is $CR^7$; $X^4$ is N and $X^5$ is $CR^7$.

The present invention further relates to a compound according to Formula (VIII) wherein $X^2$ is $CR^7$; $X^3$ is $CR^7$; $X^4$ is $CR^7$ and $X^5$ is N.

The present invention further relates to a compound according to Formula (VIII) wherein $X^2$ is N; $X^3$ is N; $X^4$ is $CR^7$ and $X^5$ is $CR^7$.

The present invention further relates to a compound according to Formula (VIII) wherein $X^2$ is N; $X^3$ is $CR^7$; $X^4$ is N and $X^5$ is $CR^7$.

The present invention further relates to a compound according to Formula (VIII) wherein $X^2$ is N; $X^3$ is $CR^7$; $X^4$ is $CR^7$ and $X^5$ is N.

The present invention further relates to a compound according to Formula (VIII) wherein $X^2$ is N; $X^3$ is N; $X^4$ is $CR^7$ and $X^5$ is N.

The present invention further relates to a compound according to Formula (VIII) wherein $X^2$ is $CR^7$; $X^3$ is $CR^7$; $X^4$ is N and $X^5$ is N.

The present invention further relates to a compound according to Formula (VIII) wherein $X^2$ is $CR^7$; $X^3$ is N; $X^4$ is N and $X^5$ is $CR^7$.

The present invention further relates to a compound according to Formula (VIII) wherein $X^2$ is $CR^7$; $X^3$ is N; $X^4$ is $CR^7$ and $X^5$ is N.

The present invention further relates to a compound according to Formula (VIII) wherein $X^2$ is $CR^7$; $X^3$ is $CR^7$; $X^4$ is N and $X^5$ is N.

The present invention further relates to a compound according to Formula (VIII) wherein n is 1.

The present invention further relates to a compound according to Formula (VIII) wherein $R^1$ and $R^2$ are each H.

The present invention further relates to a compound according to Formula (VIII) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (VIII) wherein each $R^{10}$ is H.

The present invention further relates to a compound according to Formula (VIII) wherein $Y^1$ is O; and $Y^2$ is O, S, $NR^{18}$, or $CR^{18}R^{19}$.

The present invention further relates to a compound according to Formula (VIII) wherein $Y^2$ is O.

The present invention further relates to a compound according to Formula (VIII) wherein p is 1.

The present invention further relates to a compound according to Formula (VIII) wherein $R^5$ is H or $(C_1-C_{10})$alkyl.

The present invention further relates to a compound according to Formula (VIII) wherein $R^5$ is H.

The present invention further relates to a compound according to Formula (VIII) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (VIII) wherein n is 1; p is 1; $R^1$ and $R^2$ are each H; $R^{10}$ is selected from the group consisting of H, $(C_1-C_{10})$alkyl, $(C_3-C_{10})$cycloalkyl, $(C_1-C_{10})$alkoxy, and halo; $Y^1$ is O; $Y^2$ is O, S, $NR^{18}$, or $CR^{18}R^{19}$; $R^5$ is H or $(C_1-C_{10})$alkyl; and $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—; and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (VIII) wherein $R^5$ is H and $Y^2$ is O.

The present invention further relates to a compound according to Formula (IX):

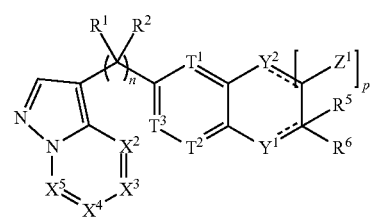

(IX)

wherein n is 1, 2 or 3;

p is 0, 1 or 2;

$R^1$ and $R^2$ are each independently selected from H, $(C_1-C_{10})$alkyl, $(C_1-C_{10})$alkylamine, $(C_1-C_{10})$alkoxy-, or $NH_2$, $T^1$ is $CR^{10}$; $T^2$ is $CR^{10}$; $T^3$ is $CR^{10}$;

$Y^1$ and $Y^2$ are each independently selected from O, S, $NR^{18}$, or $CR^{18}R^{19}$;

$Z^1$ is each independently selected from H, halo or $(C_1-C_{10})$alkyl;

$R^5$ is selected from the group consisting of H, $(C_1-C_{10})$alkyl, HO—, halo, and $H_2N$—; and $R^6$ is selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-$ $C_{14}$)aryl, $R^{14}$-($C_2$-$C_9$)heteroaryl, $R^{14}$-($C_2$-$C_{10}$)alkylnyl, $R^{14}$-($C_1$-$C_{10}$)alkylamine, $R^{14}$-(($C_1$-$C_{10}$)alkyl)$_2$amine, and $R^{14}$-C(O)—;

wherein $R^{14}$ is each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, ($C_1$-$C_{10}$)alkoxy-, HO—, $F_2$HC—O—, $F_3$C—C(O)—, $F_3$C—, and $F_2$HC—; and wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, or $H_2$N—.

The present invention further relates to a compound according to Formula (IX) wherein $X^2$ is N; $X^3$ is $CR^7$; $X^4$ is $CR^7$ and $X^5$ is $CR^7$.

The present invention further relates to a compound according to Formula (IX) wherein $X^2$ is $CR^7$; $X^3$ is $CR^7$; $X^4$ is $CR^7$ and $X^5$ is $CR^7$.

The present invention further relates to a compound according to Formula (IX) wherein $X^2$ is $CR^7$; $X^3$ is N; $X^4$ is $CR^7$ and $X^5$ is $CR^7$.

The present invention further relates to a compound according to Formula (IX) wherein $X^2$ is $CR^7$; $X^3$ is $CR^7$; $X^4$ is N and $X^5$ is $CR^7$.

The present invention further relates to a compound according to Formula (IX) wherein $X^2$ is N; $X^3$ is N; $X^4$ is $CR^7$ and $X^5$ is $CR^7$.

The present invention further relates to a compound according to Formula (IX) wherein $X^2$ is N; $X^3$ is $CR^7$; $X^4$ is N and $X^5$ is $CR^7$.

The present invention further relates to a compound according to Formula (IX) wherein $X^2$ is $CR^7$; $X^3$ is N; $X^4$ is N and $X^5$ is $CR^7$.

The present invention further relates to a compound according to Formula (IX) wherein n is 1.

The present invention further relates to a compound according to Formula (IX) wherein $R^1$ and $R^2$ are each H.

The present invention further relates to a compound according to Formula (IX) wherein $R^{10}$ is selected from the group consisting of H, ($C_1$-$C_{10}$)alkyl, ($C_3$-$C_{10}$)cycloalkyl, ($C_1$-$C_{10}$)alkoxy, and halo.

The present invention further relates to a compound according to Formula (IX) wherein each $R^{10}$ is H.

The present invention further relates to a compound according to Formula (IX) wherein $Y^1$ is O; and $Y^2$ is O, S, $NR^{18}$, or $CR^{18}R^{19}$.

The present invention further relates to a compound according to Formula (IX) wherein $Y^2$ is O.

The present invention further relates to a compound according to Formula (IX) wherein p is 1.

The present invention further relates to a compound according to Formula (IX) wherein $R^5$ is H or ($C_1$-$C_{10}$)alkyl.

The present invention further relates to a compound according to Formula (IX) wherein $R^5$ is H.

The present invention further relates to a compound according to Formula (IX) wherein $R^6$ is selected from the group consisting of H, ($C_1$-$C_{10}$)alkyl, ($C_3$-$C_{10}$)cycloalkyl, ($C_2$-$C_9$)heteroaryl, $R^{14}$-($C_6$-$C_{14}$)aryl, $R^{14}$-($C_2$-$C_9$)heteroaryl, and $R^{14}$-($C_1$-$C_{10}$)alkylamine;

wherein $R^{14}$ is each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, ($C_1$-$C_{10}$)alkoxy-, HO—, $F_2$HC—O—, $F_3$C—C(O)—, $F_3$C—, and $F_2$HC—; and wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, HO—, halo, or $H_2$N—.

The present invention further relates to a compound according to Formula (IX) wherein n is 1; p is 1; $R^1$ and $R^2$ are each H; $R^{10}$ is selected from the group consisting of H, ($C_1$-$C_{10}$)alkyl, ($C_3$-$C_{10}$)cycloalkyl, ($C_1$-$C_{10}$)alkoxy, and halo; $Y^1$ is O; $Y^2$ is O, S, $NR^{18}$, or $CR^{18}R^{19}$; $R^5$ is H or ($C_1$-$C_{10}$)alkyl; and $R^6$ is selected from the group consisting of H, ($C_1$-$C_{10}$)alkyl, ($C_3$-$C_{10}$)cycloalkyl, ($C_2$-$C_9$)heteroaryl, $R^{14}$-($C_6$-$C_{14}$)aryl, $R^{14}$-($C_2$-$C_9$)heteroaryl, and $R^{14}$-($C_1$-$C_{10}$)alkylamine;

wherein $R^{14}$ is each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, ($C_1$-$C_{10}$)alkoxy-, HO—, $F_2$HC—O—, $F_3$C—C(O)—, $F_3$C—, and $F_2$HC—; and wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, HO—, halo, or $H_2$N—.

The present invention further relates to a compound according to Formula (IX) wherein $R^5$ is H and $Y^2$ is O.

The present invention further relates to a compound according to Formula (X):

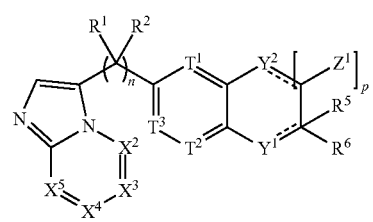

wherein n is 1, 2 or 3;
p is 0, 1 or 2;
$R^1$ and $R^2$ are each independently selected from H, ($C_1$-$C_{10}$)alkyl, ($C_1$-$C_{10}$)alkylamine, ($C_1$-$C_{10}$)alkoxy-, or $NH_2$,
$T^1$ is $CR^{10}$; $T^2$ is $CR^{10}$; $T^3$ is $CR^{10}$;
$Y^1$ and $Y^2$ are each independently selected from O, S, $NR^{18}$, or $CR^{18}R^{19}$;
$Z^1$ is each independently selected from H, halo or ($C_1$-$C_{10}$)alkyl;
$R^5$ is selected from the group consisting of H, ($C_1$-$C_{10}$)alkyl, HO—, halo, and $H_2$N—; and
$R^6$ is selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, $((C_1-C_{10})alkyl)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2$HC—O—, $F_3$C—C(O)—, $F_3$C—, and $F_2$HC—; and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2$N—.

The present invention further relates to a compound according to Formula (X) wherein $X^2$ is N; $X^3$ is $CR^7$; $X^4$ is $CR^7$ and $X^5$ is $CR^7$.

The present invention further relates to a compound according to Formula (X) wherein $X^2$ is $CR^7$; $X^3$ is $CR^7$; $X^4$ is $CR^7$ and $X^5$ is $CR^7$.

The present invention further relates to a compound according to Formula (X) wherein $X^2$ is $CR^7$; $X^3$ is N; $X^4$ is $CR^7$ and $X^5$ is $CR^7$.

The present invention further relates to a compound according to Formula (X) wherein $X^2$ is $CR^7$; $X^3$ is $CR^7$; $X^4$ is N and $X^5$ is $CR^7$.

The present invention further relates to a compound according to Formula (X) wherein $X^2$ is $CR^7$; $X^3$ is $CR^7$; $X^4$ is $CR^7$ and $X^5$ is N.

The present invention further relates to a compound according to Formula (X) wherein $X^2$ is N; $X^3$ is $CR^7$; $X^4$ is N and $X^5$ is $CR^7$.

The present invention further relates to a compound according to Formula (X) wherein $X^2$ is N; $X^3$ is $CR^7$; $X^4$ is $CR^7$ and $X^5$ is N.

The present invention further relates to a compound according to Formula (X) wherein $X^2$ is N; $X^3$ is $CR^7$; $X^4$ is N and $X^5$ is N.

The present invention further relates to a compound according to Formula (X) wherein $X^2$ is $CR^7$; $X^3$ is N; $X^4$ is N and $X^5$ is $CR^7$.

The present invention further relates to a compound according to Formula (X) wherein $X^2$ is $CR^7$; $X^3$ is N; $X^4$ is $CR^7$ and $X^5$ is N.

The present invention further relates to a compound according to Formula (X) wherein $X^2$ is $CR^7$; $X^3$ is $CR^7$; $X^4$ is N and $X^5$ is N.

The present invention further relates to a compound according to Formula (X) wherein n is 1.

The present invention further relates to a compound according to Formula (X) wherein $R^1$ and $R^2$ are each H.

The present invention further relates to a compound according to Formula (X) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (X) wherein each $R^{10}$ is H.

The present invention further relates to a compound according to Formula (X) wherein $Y^1$ is O; and $Y^2$ is O, S, $NR^{18}$, or $CR^{18}R^{19}$.

The present invention further relates to a compound according to Formula (X) wherein $Y^2$ is O.

The present invention further relates to a compound according to Formula (X) wherein p is 1.

The present invention further relates to a compound according to Formula (X) wherein $R^5$ is H or $(C_1-C_{10})$alkyl.

The present invention further relates to a compound according to Formula (X) wherein $R^5$ is H.

The present invention further relates to a compound according to Formula (X) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2$HC—O—, $F_3$C—C(O)—, $F_3$C—, and $F_2$HC—; and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2$N—.

The present invention further relates to a compound according to Formula (X) wherein n is 1; p is 1; $R^1$ and $R^2$ are each H; $R^{10}$ is selected from the group consisting of H, $(C_1-C_{10})$alkyl, $(C_3-C_{10})$cycloalkyl, $(C_1-C_{10})$alkoxy, and halo; $Y^1$ is O; $Y^2$ is O, S, $NR^{18}$, or $CR^{18}R^{19}$; $R^5$ is H or $(C_1-C_{10})$alkyl; and $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2$HC—O—, $F_3$C—C(O)—, $F_3$C—, and $F_2$HC—; and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2$N—.

The present invention further relates to a compound according to Formula (X) wherein $R^5$ is H and $Y^2$ is O.

The present invention further relates to a compound according to Formula (XI)

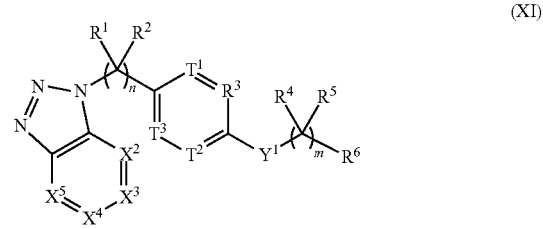

(XI)

wherein n is 1, 2 or 3;

p is 0, 1 or 2;

$R^1$ and $R^2$ are each independently selected from H, ($C_1$-$C_{10}$)alkyl, ($C_1$-$C_{10}$)alkylamine, ($C_1$-$C_{10}$)alkoxy-, or $NH_2$, $T^1$ is $CR^{10}$; $T^2$ is $CR^{10}$; $T^3$ is $CR^{10}$;

$Y^1$ and $Y^2$ are each independently selected from O, S, $NR^{18}$, or $CR^{18}R^{19}$;

$Z^1$ is each independently selected from H, halo or ($C_1$-$C_{10}$)alkyl;

$R^5$ is selected from the group consisting of H, ($C_1$-$C_{10}$) alkyl, HO—, halo, and $H_2N$—; and $R^6$ is selected from the group consisting of H, ($C_1$-$C_{10}$) alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_{10}$)alkyl-C(O)O—, COOH—($C_1$-$C_{10}$)alkyl-, COOH—($C_3$-$C_{10}$)cycloalkyl-, ($C_1$-$C_{10}$)alkoxy-, $R^{14}$-($C_1$-$C_{10}$)alkyl-, $R^{14}$-($C_3$-$C_{10}$)cycloalkyl, $R^{14}$-($C_2$-$C_9$)heterocycloalkyl, $R^{14}$-($C_6$-$C_{14}$)aryl, $R^{14}$-($C_2$-$C_9$)heteroaryl, $R^{14}$-($C_2$-$C_{10}$)alkylnyl, $R^{14}$-($C_1$-$C_{10}$)alkylamine, $R^{14}$-(($C_1$-$C_{10}$)alkyl)$_2$amine, and $R^{14}$-C(O)—;

wherein $R^{14}$ is each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, ($C_1$-$C_{10}$)alkoxy-, HO—, $F_2HC$—O—, $F_3C$—C(O)—, $F_3C$—, and $F_2HC$—; and wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, or $H_2N$—.

The present invention further relates to a compound according to Formula (XI) wherein $X^2$ is N; $X^3$ is $CR^7$; and $X^4$ is $CR^7$; $X^5$ is $CR^7$.

The present invention further relates to a compound according to Formula (XI) wherein $X^2$ is $CR^7$; $X^3$ is $CR^7$; $X^4$ is $CR^7$; and $X^5$ is $CR^7$.

The present invention further relates to a compound according to Formula (XI) wherein $X^2$ is $CR^7$; $X^3$ is N; $X^4$ is $CR^7$; and $X^5$ is $CR^7$.

The present invention further relates to a compound according to Formula (XI) wherein $X^2$ is $CR^7$; $X^3$ is $CR^7$; $X^4$ is N; and $X^5$ is $CR^7$.

The present invention further relates to a compound according to Formula (XI) wherein $X^2$ is $CR^7$; $X^3$ is $CR^7$; $X^4$ is $CR^7$; and $X^5$ is N.

The present invention further relates to a compound according to Formula (XI) wherein $X^2$ is N; $X^3$ is N; $X^4$ is $CR^7$; and $X^5$ is $CR^7$.

The present invention further relates to a compound according to Formula (XI) wherein $X^2$ is N; $X^3$ is $CR^7$; $X^4$ is N; and $X^5$ is $CR^7$.

The present invention further relates to a compound according to Formula (XI) wherein $X^2$ is N; $X^3$ is $CR^7$; $X^4$ is $CR^7$; and $X^5$ is N.

The present invention further relates to a compound according to Formula (XI) wherein $X^2$ is N; $X^3$ is N; $X^4$ is $CR^7$; and $X^5$ is N.

The present invention further relates to a compound according to Formula (XI) wherein $X^2$ is N; $X^3$ is $CR^7$; $X^4$ is N; and $X^5$ is N.

The present invention further relates to a compound according to Formula (XI) wherein $X^2$ is $CR^7$; $X^3$ is N; $X^4$ is N; and $X^5$ is $CR^7$.

The present invention further relates to a compound according to Formula (XI) wherein $X^2$ is $CR^7$; $X^3$ is N; $X^4$ is $CR^7$; and $X^5$ is N.

The present invention further relates to a compound according to Formula (XI) wherein $X^2$ is $CR^7$; $X^3$ is $CR^7$; $X^4$ is N; and $X^5$ is N.

The present invention further relates to a compound according to Formula (XI) wherein n is 1.

The present invention further relates to a compound according to Formula (XI) wherein $R^1$ and $R^2$ are each H.

The present invention further relates to a compound according to Formula (XI) wherein $R^{10}$ is selected from the group consisting of H, ($C_1$-$C_{10}$)alkyl, ($C_3$-$C_{10}$)cycloalkyl, ($C_1$-$C_{10}$)alkoxy, and halo.

The present invention further relates to a compound according to Formula (XI) wherein each $R^{10}$ is H.

The present invention further relates to a compound according to Formula (XI) wherein $Y^1$ is O; and $Y^2$ is O, S, $NR^{18}$, or $CR^{18}R^{19}$.

The present invention further relates to a compound according to Formula (XI) wherein $Y^2$ is O.

The present invention further relates to a compound according to Formula (XI) wherein p is 1.

The present invention further relates to a compound according to Formula (XI) wherein $R^5$ is H or ($C_1$-$C_{10}$)alkyl.

The present invention further relates to a compound according to Formula (XI) wherein $R^5$ is H.

The present invention further relates to a compound according to Formula (XI) wherein $R^6$ is selected from the group consisting of H, ($C_1$-$C_{10}$)alkyl, ($C_3$-$C_{10}$)cycloalkyl, ($C_2$-$C_9$)heteroaryl, $R^{14}$-($C_6$-$C_{14}$)aryl, $R^{14}$-($C_2$-$C_9$)heteroaryl, and $R^{14}$-($C_1$-$C_{10}$)alkylamine;

wherein $R^{14}$ is each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, ($C_1$-$C_{10}$)alkoxy-, HO—, $F_2HC$—O—, $F_3C$—C(O)—, $F_3C$—, and $F_2HC$—; and wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, HO—, halo, or $H_2N$—.

The present invention further relates to a compound according to Formula (XI) wherein n is 1; p is 1; $R^1$ and $R^2$ are each H; $R^{10}$ is selected from the group consisting of H, ($C_1$-$C_{10}$)alkyl, ($C_3$-$C_{10}$)cycloalkyl, ($C_1$-$C_{10}$)alkoxy, and halo; $Y^1$ is O; $Y^2$ is O, S, $NR^{18}$, or $CR^{18}R^{19}$; $R^5$ is H or ($C_1$-$C_{10}$)alkyl; and $R^6$ is selected from the group consisting of H, ($C_1$-$C_{10}$)alkyl, ($C_3$-$C_{10}$)cycloalkyl, ($C_2$-$C_9$)heteroaryl, $R^{14}$-($C_6$-$C_{14}$)aryl, $R^{14}$-($C_2$-$C_9$)heteroaryl, and $R^{14}$-($C_1$-$C_{10}$) alkylamine;

wherein $R^{14}$ is each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, ($C_1$-$C_{10}$)alkoxy-, HO—, $F_2HC$—O—, $F_3C$—C(O)—, $F_3C$—, and $F_2HC$—; and wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (XI) wherein $R^5$ is H and $Y^2$ is O.

The present invention further relates to a compound according to Formula (XII)

$$(XII)$$

wherein n is 1, 2 or 3;

p is 0, 1 or 2;

$R^1$ and $R^2$ are each independently selected from H, $(C_1-C_{10})$alkyl, $(C_1-C_{10})$alkylamine, $(C_1-C_{10})$alkoxy-, or $NH_2$, $T^1$ is $CR^{10}$; $T^2$ is $CR^{10}$; $T^3$ is $CR^{10}$;

$Y^1$ and $Y^2$ are each independently selected from O, S, $NR^{18}$, or $CR^{18}R^{19}$;

$Z^1$ is each independently selected from H, halo or $(C_1-C_{10})$alkyl;

$R^5$ is selected from the group consisting of H, $(C_1-C_{10})$ alkyl, HO—, halo, and $H_2N$—; and $R^6$ is selected from the group consisting of H, $(C_1-C_{10})$ alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, and $R^{14}$-C(O)—;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$ alkoxy-, HO—, $F_2HC$—O—, $F_3C$—C(O)—, $F_3C$—, and $F_2HC$—;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$ cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$ cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

The present invention further relates to a compound according to Formula (XII) wherein $X^2$ is N; $X^3$ is $CR^7$; and $X^4$ is $CR^7$; $X^5$ is $CR^7$.

The present invention further relates to a compound according to Formula (XII) wherein $X^2$ is $CR^7$; $X^3$ is $CR^7$; $X^4$ is $CR^7$; and $X^5$ is $CR^7$.

The present invention further relates to a compound according to Formula (XII) wherein $X^2$ is $CR^7$; $X^3$ is N; $X^4$ is $CR^7$; and $X^5$ is $CR^7$.

The present invention further relates to a compound according to Formula (XII) wherein $X^2$ is $CR^7$; $X^3$ is $CR^7$; $X^4$ is N; and $X^5$ is $CR^7$.

The present invention further relates to a compound according to Formula (XII) wherein $X^2$ is $CR^7$; $X^3$ is $CR^7$; $X^4$ is $CR^7$; and $X^5$ is N.

The present invention further relates to a compound according to Formula (XII) wherein $X^2$ is N; $X^3$ is N; $X^4$ is $CR^7$; and $X^5$ is $CR^7$.

The present invention further relates to a compound according to Formula (XII) wherein $X^2$ is N; $X^3$ is $CR^7$; $X^4$ is N; and $X^5$ is $CR^7$.

The present invention further relates to a compound according to Formula (XII) wherein $X^2$ is N; $X^3$ is $CR^7$; $X^4$ is $CR^7$; and $X^5$ is N.

The present invention further relates to a compound according to Formula (XII) wherein $X^2$ is N; $X^3$ is N; $X^4$ is $CR^7$; and $X^5$ is N.

The present invention further relates to a compound according to Formula (XII) wherein $X^2$ is N; $X^3$ is $CR^7$; $X^4$ is N; and $X^5$ is N.

The present invention further relates to a compound according to Formula (XII) wherein $X^2$ is $CR^7$; $X^3$ is N; $X^4$ is N; and $X^5$ is $CR^7$.

The present invention further relates to a compound according to Formula (XII) wherein $X^2$ is $CR^7$; $X^3$ is N; $X^4$ is $CR^7$; and $X^5$ is N.

The present invention further relates to a compound according to Formula (XII) wherein $X^2$ is $CR^7$; $X^3$ is $CR^7$; $X^4$ is N; and $X^5$ is N.

The present invention further relates to a compound according to Formula (XII) wherein n is 1.

The present invention further relates to a compound according to Formula (XII) wherein $R^1$ and $R^2$ are each H.

The present invention further relates to a compound according to Formula (XII) wherein $R^{10}$ is selected from the group consisting of H, $(C_1-C_{10})$alkyl, $(C_3-C_{10})$cycloalkyl, $(C_1-C_{10})$alkoxy, and halo.

The present invention further relates to a compound according to Formula (XII) wherein each $R^{10}$ is H.

The present invention further relates to a compound according to Formula (XII) wherein $Y^1$ is O; and $Y^2$ is O, S, $NR^{18}$, or $CR^{18}R^{19}$.

The present invention further relates to a compound according to Formula (XII) wherein $Y^2$ is O.

The present invention further relates to a compound according to Formula (XII) wherein p is 1.

The present invention further relates to a compound according to Formula (XII) wherein $R^5$ is H or $(C_1-C_{10})$ alkyl.

The present invention further relates to a compound according to Formula (XII) wherein $R^5$ is H.

The present invention further relates to a compound according to Formula (XII) wherein $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (XII) wherein n is 1; p is 1; $R^1$ and $R^2$ are each H; $R^{10}$ is selected from the group consisting of H, $(C_1-C_{10})$alkyl, $(C_3-C_{10})$cycloalkyl, $(C_1-C_{10})$alkoxy, and halo; $Y^1$ is O; $Y^2$ is O, S, $NR^{18}$, or $CR^{18}R^{19}$; $R^5$ is H or $(C_1-C_{10})$alkyl; and $R^6$ is selected from the group consisting of H, $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and $R^{14}$-$(C_1-C_{10})$alkylamine;

wherein $R^{14}$ is each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $(C_1-C_{10})$alkoxy-, HO—, $F_2HC$—O—, $F_3C$—C(O)—, $F_3C$—, and $F_2HC$—;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2N$—.

The present invention further relates to a compound according to Formula (XII) wherein $R^5$ is H and $Y^2$ is O.

The present invention further relates to a compound according to Formula (I) or Formula (II) wherein the compound is selected from:

3-(3-methoxy-4-((6-methoxypyridin-3-yl)methoxy)benzyl)-6-(4-methylpiperazin-1-yl)-3H-imidazo[4,5-b]pyridine,
(S)-4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine,
6-methoxy-3-((8-methoxy-2-(6-methoxypyridin-3-yl)-2,3-dihydrobenzo[b][1,4]dioxin-6-yl)methyl)-3H-imidazo[4,5-b]pyridine,
(S)-6-methoxy-3-((8-methoxy-2-(6-methoxypyridin-3-yl)-2,3-dihydrobenzo[b][1,4]dioxin-6-yl)methyl)-3H-imidazo[4,5-b]pyridine,
(R)-6-methoxy-3-((8-methoxy-2-(6-methoxypyridin-3-yl)-2,3-dihydrobenzo[b][1,4]dioxin-6-yl)methyl)-3H-imidazo[4,5-b]pyridine,
3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine,
6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine,
(S)-6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine,
(R)-6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine,
3-((8-methoxy-2-(6-methoxypyridin-3-yl)-3-methyl-2,3-dihydrobenzo[b][1,4]dioxin-6-yl)methyl)-3H-imidazo[4,5-b]pyridine,
3-(((2R,3S)-8-methoxy-2-(6-methoxypyridin-3-yl)-3-methyl-2,3-dihydrobenzo[b][1,4]dioxin-6-yl)methyl)-3H-imidazo[4,5-b]pyridine,
3-(((2S,3R)-8-methoxy-2-(6-methoxypyridin-3-yl)-3-methyl-2,3-dihydrobenzo[b][1,4]dioxin-6-yl)methyl)-3H-imidazo[4,5-b]pyridine,
3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine,
3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine,
3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine,
(R)-3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine,
(S)-3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine,
3-((8-methoxy-2-(6-(trifluoromethyl)pyridin-3-yl)-2,3-dihydrobenzo[b][1,4]dioxin-6-yl)methyl)-3H-imidazo[4,5-b]pyridine,
(S)-3-((8-methoxy-2-(6-(trifluoromethyl)pyridin-3-yl)-2,3-dihydrobenzo[b][1,4]dioxin-6-yl)methyl)-3H-imidazo[4,5-b]pyridine,
(R)-3-((8-methoxy-2-(6-(trifluoromethyl)pyridin-3-yl)-2,3-dihydrobenzo[b][1,4]dioxin-6-yl)methyl)-3H-imidazo[4,5-b]pyridine,
azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone,
(S)-azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone,
(S)-azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone,
3-((2-(6-cyclopropylpyridin-3-yl)-8-methoxy-2,3-dihydrobenzo[b][1,4]dioxin-6-yl)methyl)-3H-imidazo[4,5-b]pyridine,
(S)-3-((2-(6-cyclopropylpyridin-3-yl)-8-methoxy-2,3-dihydrobenzo[b][1,4]dioxin-6-yl)methyl)-3H-imidazo[4,5-b]pyridine,
(R)-3-((2-(6-cyclopropylpyridin-3-yl)-8-methoxy-2,3-dihydrobenzo[b][1,4]dioxin-6-yl)methyl)-3H-imidazo[4,5-b]pyridine,
3-((8-fluoro-2-(6-methoxypyridin-3-yl)-2,3-dihydrobenzo[b][1,4]dioxin-6-yl)methyl)-6-(2-methyl-1H-imidazol-1-yl)-3H-imidazo[4,5-b]pyridine,
3-((8-methoxy-2-(6-methoxypyridin-3-yl)-2,3-dihydrobenzo[b][1,4]dioxin-6-yl)methyl)-6-(3-methoxyazetidin-1-yl)-3H-imidazo[4,5-b]pyridine;
4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine;
(R)-4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine;
(R)-3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine;
(S)-3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine;
(R)-azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone;

3-((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine, (S)-3-((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine, and (R)-3-((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine.

The present invention further relates to a compound according to Formula (XIII):

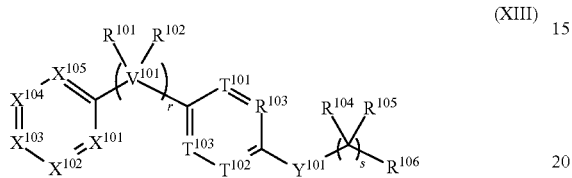

(XIII)

wherein:

$V^{101}$ is C, N, O, or S, r is 0, 1, 2, 3, 4 or 5;
   wherein when $V^{101}$ is C, then r is 0, 1, 2, 3, 4 or 5,
   wherein when $V^{101}$ is N, then r is 1 and $R^{102}$ is absent;
   wherein when $V^{101}$ is O, r is 1 and $R^{101}$ and $R^{102}$ are absent; and
   wherein when $V^{101}$ is S, r is 1 and $R^{101}$ and $R^{102}$ are absent;

s is 1, 2, 3 or 4;

$X^{101}$, $X^{102}$, $X^{103}$, $X^{105}$ and $X^{105}$ are each independently selected from N, $NR^{107}$ or $CR^{107}$, wherein each $R^{107}$ is independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, C(O)—, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{108}$-$(C_1-C_{10})$alkyl-, $R^{108}$-$(C_3-C_{10})$cycloalkyl, $R^{108}$-$(C_2-C_9)$heterocycloalkyl, $R^{108}$-$(C_6-C_{14})$aryl, $R^{108}$-$(C_2-C_9)$heteroaryl, $R^{108}$-$(C_2-C_{10})$alkylnyl, $R^{108}$-$(C_1-C_{10})$alkylamine, $R^{108}$-$((C_1-C_{10})$alkyl$)_2$amine, $R^{108}$-$(C_2-C_{10})$alkynylamine, $R^{108}$-C(O)—, $R^{108}$-$(C_1-C_{10})$alkyl-C(O)O—, $R^{108}$-$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^{108}$-$(C_3-C_{10})$cycloalkyl-O—, $R^{108}$-$(C_2-C_9)$heterocycloalkyl-O—, $R^{108}$-$(C_6-C_{14})$aryl-O—, $R^{108}$-$(C_2-C_9)$heteroaryl-O—, HO—, halo, cyano, $H_2N$—, $(CH_3)HN$—, $(CH_3)_2N$—, $R^{108}R^{109}N$—, $R^{108}R^{109}N(O)C$—, $R^{108}(R^{109}C(O))N$—, $R^{108}R^{109}NC(O)O$—, $R^{108}C(O)$—, $R^{108}R^{109}NC(O)R^8N$—, $(C_1-C_{10})$alkyl-OC(O)$R^{108}N$—, $(C_3-C_{10})$cycloalkyl-OC(O)$R^{108}N$—, $(C_2-C_9)$heterocycloalkyl-OC(O)$R^{108}N$—, $(C_6-C_{14})$aryl-OC(O)$R^{108}N$—, $(C_2-C_9)$heteroaryl-OC(O)$R^{108}N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S—$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^{108}R^{109}NS(O)_2$—, $(C_1-C_{10})$alkyl-S(O)$_2R^{108}N$—, $(C_3-C_{10})$cycloalkyl-S(O)$_2R^{108}N$—, $(C_6-C_{14})$aryl-S(O)$_2R^{108}N$—, $(C_2-C_9)$heterocycloalkyl-SO$_2R^{108}N$—, and $(C_2-C_9)$heteroaryl-S(O)$_2R^{108}N$—;

wherein $R^{108}$ and $R^{109}$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $(CH_3)_2N$—, and $H_2N$—;

or $R^{108}$ and $R^{109}$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—;

$T^{101}$, $T^{102}$, and $T^{103}$ is each independently selected from are each independently selected from N or $CR^{110}$, wherein each $R^{110}$ is independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, C(O)—, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{110A}$-$(C_1-C_{10})$alkyl-, $R^{110A}$-$(C_3-C_{10})$cycloalkyl, $R^{110A}$-$(C_2-C_9)$heterocycloalkyl, $R^{110A}$-$(C_6-C_{14})$aryl, $R^{110A}$-$(C_2-C_9)$heteroaryl, $R^{110A}$-$(C_2-C_{10})$alkylnyl, $R^{110A}$-$(C_1-C_{10})$alkylamine, $R^{110A}$-$((C_1-C_{10})$alkyl$)_2$amine, $R^{110A}$-$(C_2-C_{10})$alkynylamine, $R^{110A}$-C(O)—, $R^{110A}$-$(C_1-C_{10})$alkyl-C(O)O—, $R^{110A}$-$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^{110A}$-$(C_3-C_{10})$cycloalkyl-O—, $R^{110A}$-$(C_2-C_9)$heterocycloalkyl-O—, $R^{110A}$-$(C_6-C_{14})$aryl-O—, $R^{110A}$-$(C_2-C_9)$heteroaryl-O—, HO—, halo, cyano, $H_2N$—, $(CH_3)HN$—, $(CH_3)_2N$—, $R^{110A}R^{111}N$—, $R^{110A}R^{111}N(O)C$—, $R^{110A}(R^{111}C(O))N$—, $R^{110A}R^{111}NC(O)O$—, $R^{110A}C(O)$—, $R^{110A}R^{111}NC(O)R^{110A}N$—, $(C_1-C_{10})$alkyl-OC(O)$R^{110A}N$—, $(C_3-C_{10})$cycloalkyl-OC(O)$R^{110A}N$—, $(C_2-C_9)$heterocycloalkyl-OC(O)$R^{110A}N$—, $(C_6-C_{14})$aryl-OC(O)$R^{110A}N$—, $(C_2-C_9)$heteroaryl-OC(O)$R^{110A}N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S-$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, ($C_6$-$C_{14}$)aryl-S(O)$_2$—, ($C_2$-$C_9$)heterocycloalkyl-S(O)$_2$—, ($C_2$-$C_9$)heteroaryl-S(O)$_2$—, $R^{110A}R^{111}$NS(O)$_2$—, ($C_1$-$C_{10}$)alkyl-S(O)$_2R^{110A}$N—, ($C_3$-$C_{10}$)cycloalkyl-S(O)$_2R^{110A}$N—, ($C_6$-$C_{14}$)aryl-S(O)$_2R^{110A}$N—, ($C_2$-$C_9$)heterocycloalkyl-SO$_2R^{110A}$N—, and ($C_2$-$C_9$)heteroaryl-S(O)$_2R^{110A}$N—;

wherein $R^{110A}$ and $R^{111}$ are each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, (CH$_3$)$_2$N—, and H$_2$N—;

or $R^{110A}$ and $R^{111}$ are taken together to form a 3 to 10 member cycloalkyl, heterocycloalkyl, aryl or heteroaryl ring;

wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, or H$_2$N—

$Y^{101}$ is O, S, NR$^{112}$, or CR$^{112}R^{113}$, wherein $R^{112}$ is absent or $R^{112}$ and $R^{113}$ are each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, and H$_2$N—;

$R^{101}$ together with the carbon to which it is attached to form a carbonyl and $R^{102}$ is absent, or $R^{101}$ and $R^{102}$ are each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkoxy-, ($C_1$-$C_{10}$)alkoxy-($C_1$-$C_{10}$)alkyl-, ($C_3$-$C_9$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, and H$_2$N—, or $R^{101}$ and $R^{102}$ are taken together with the carbon to which they are attached to form a 3 to 10 member ring;

$R^{104}$ is selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, and H$_2$N—, or $R^{104}$ and $R^{105}$ can be taken together with the carbon to which they are attached to form a 3 to 10 member ring;

$R^{105}$ is absent or selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, halo, and H$_2$N—;

$R^{106}$ is selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_2$-$C_{10}$)alkylnyl, ($C_1$-$C_{10}$)alkylamine, (($C_1$-$C_{10}$)alkyl)$_2$amine, ($C_2$-$C_{10}$)alkynylamine, C(O)—, ($C_1$-$C_{10}$)alkyl-C(O)O—, COOH—($C_1$-$C_{10}$)alkyl-, COOH—($C_3$-$C_{10}$)cycloalkyl-, ($C_1$-$C_{10}$)alkoxy-, $R^{114}$-($C_1$-$C_{10}$)alkyl-, $R^{114}$-($C_3$-$C_{10}$)cycloalkyl, $R^{114}$-($C_2$-$C_9$)heterocycloalkyl, $R^{114}$-($C_6$-$C_{14}$)aryl, $R^{114}$-($C_2$-$C_9$)heteroaryl, $R^{114}$-($C_2$-$C_{10}$)alkylnyl, $R^{114}$-($C_1$-$C_{10}$)alkylamine, $R^{114}$-(($C_1$-$C_{10}$)alkyl)$_2$amine, $R^{114}$-($C_2$-$C_{10}$)alkynylamine, $R^{114}$-C(O)—, $R^{114}$-($C_1$-$C_{10}$)alkyl-C(O)O—, $R^{114}$-($C_1$-$C_{10}$)alkoxy-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, $R^{114}$-($C_3$-$C_{10}$)cycloalkyl-O—, $R^{114}$-($C_2$-$C_9$)heterocycloalkyl-O—, $R^{114}$-($C_6$-$C_{14}$)aryl-O—, $R^{114}$-($C_2$-$C_9$)heteroaryl-O—, HO—, halo, cyano, H$_2$N—, (CH$_3$)HN—, (CH$_3$)$_2$N—, $R^{114}R^{115}$N—, $R^{114}R^{115}$N(O)C—, $R^{114}$($R^{115}$C(O))N—, $R^{114}R^{115}$NC(O)O—, $R^{114}$C(O)—, $R^{114}R^{115}$NC(O)$R^{114}$N—, ($C_1$-$C_{10}$)alkyl-OC(O)$R^{114}$N—, ($C_3$-$C_{10}$)cycloalkyl-OC(O)$R^{114}$N—, ($C_2$-$C_9$)heterocycloalkyl-OC(O)$R^{114}$N—, ($C_6$-$C_{14}$)aryl-OC(O)$R^{114}$N—, ($C_2$-$C_9$)heteroaryl-OC(O)$R^{114}$N—, F$_3$C—, F$_2$HC—, CH$_3$F$_2$C—, FH$_2$C—, CH$_3$FHC—, (CH$_3$)$_2$FC—; NC—, ($C_1$-$C_{10}$)alkyl(O)P—, ($C_1$-$C_{10}$)alkyl-S—, ($C_1$-$C_{10}$)alkyl-S-($C_1$-$C_{10}$)alkyl-, ($C_3$-$C_{10}$)cycloalkyl-S—, ($C_6$-$C_{14}$)aryl-S—, ($C_2$-$C_9$)heteroalkyl-S—, ($C_2$-$C_9$)heterocycloalkyl-S—, ($C_2$-$C_9$)heteroaryl-S—, ($C_1$-$C_{10}$)alkyl-S(O)—, ($C_3$-$C_{10}$)cycloalkyl-S(O)—, ($C_6$-$C_{14}$)aryl-S(O)—, ($C_2$-$C_9$)heterocycloalkyl-S(O)—, ($C_2$-$C_9$)heteroaryl-S(O)—, ($C_3$-$C_{10}$)alkyl-S(O)$_2$—, ($C_3$-$C_{10}$)cycloalkyl-S(O)$_2$—, ($C_6$-$C_{14}$)aryl-S(O)$_2$—, ($C_2$-$C_9$)heterocycloalkyl-S(O)$_2$—, ($C_2$-$C_9$)heteroaryl-S(O)$_2$—, $R^{114}R^{115}$NS(O)$_2$—, ($C_1$-$C_{10}$)alkyl-S(O)$_2R^{114}$N—, ($C_3$-$C_{10}$)cycloalkyl-S(O)$_2R^{114}$N—, ($C_6$-$C_{14}$)aryl-S(O)$_2R^{114}$N—, ($C_2$-$C_9$)heterocycloalkyl-SO$_2R^{114}$N—, and ($C_2$-$C_9$)heteroaryl-S(O)$_2R^{114}$N—;

wherein $R^{114}$ and $R^{115}$ are each independently selected from the group consisting of H, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, COOH—($C_3$-$C_{10}$)cycloalkyl, ($C_1$-$C_{10}$)alkoxy-, ($C_1$-$C_{10}$)alkoxy-($C_1$-$C_{10}$)alkyl-, ($C_3$-$C_{10}$)cycloalkyl-O—, ($C_2$-$C_9$)heterocycloalkyl-O—, ($C_6$-$C_{14}$)aryl-O—, ($C_2$-$C_9$)heteroaryl-O—, HO—, F$_2$HC—O—, halo, (CH$_3$)$_2$N—, H$_2$N—, F$_3$C—C(O)—, F$_3$C—, and F$_2$HC—;

or $R^{114}$ and $R^{115}$ are taken together to form a 3 to 10 member cycloalkyl, heterocycloalkyl, aryl or heteroaryl ring;

wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, (C$_1$-C$_3$)alkynylamine, (C$_1$-C$_{10}$)alkyl-C(O)O—, COOH—(C$_1$-C$_{10}$)alkyl, COOH—(C$_3$-C$_{10}$)cycloalkyl, (C$_1$-C$_{10}$)alkoxy-, (C$_1$-C$_{10}$)alkoxy-(C$_1$-C$_{10}$)alkyl-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, halo, or H$_2$N—; and R$^{103}$ is N or CR$^{116}$, wherein R$^{116}$ is selected from the group consisting of H, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_3$)alkynylamine, (C$_1$-C$_{10}$)alkyl-C(O)O—, COOH—(C$_1$-C$_{10}$)alkyl, COOH—(C$_3$-C$_{10}$)cycloalkyl, (C$_1$-C$_{10}$)alkoxy-, (C$_1$-C$_{10}$)alkoxy-(C$_1$-C$_{10}$)alkyl-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, halo, and H$_2$N—, or when s is 1, R$^{116}$ and R$^{104}$ are taken together with the carbons to which they are attached to form a compound according to Formula (XIV):

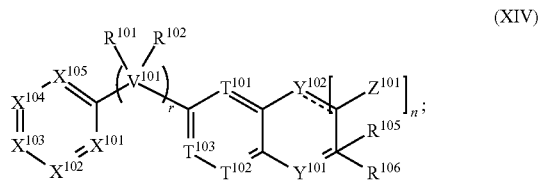

(XIV)

wherein the dashed lines represent optional double bonds and:

t is 0, 1, 2, 3, 4 or 5;

Z$^{101}$ is each independently selected from H, halo, (C$_1$-C$_{10}$)alkyl, (C$_2$-C$_9$)heteroalkyl, (C$_1$-C$_{10}$)alkylamine, ((C$_1$-C$_{10}$)alkyl)$_2$amine, (C$_2$-C$_{10}$)alkynylamine, (C$_1$-C$_{10}$)alkoxy-, or H$_2$N—;

Y$^{102}$ is O, S, NR$^{117}$, or CR$^{117}$R$^{118}$, wherein R$^{117}$ is absent or R$^{117}$ and R$^{118}$ are each independently selected from H, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_3$)alkynylamine, (C$_1$-C$_{10}$)alkyl-C(O)O—, COOH—(C$_1$-C$_{10}$)alkyl, COOH—(C$_3$-C$_{10}$)cycloalkyl, (C$_1$-C$_{10}$)alkoxy-, (C$_1$-C$_{10}$)alkoxy-(C$_1$-C$_{10}$)alkyl-, (C$_1$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, halo, or H$_2$N—.

The present invention further relates to a compound according to Formula (XIII) or Formula (XIV) wherein X$^1$ is N; X$^2$ is N; X$^3$ is CR$^7$; X$^4$ is CR$^7$; X$^5$ is CR$^7$; X$^6$ is N; X$^7$ is CR$^7$; X$^8$ is C; and X$^9$ is C; and/or wherein X$^3$ is CH; X$^4$ is CR$^7$; X$^5$ is CH; and X$^7$ is CH.

The present invention further relates to a compound according to Formula (XIII) or Formula (XIV) wherein X$^1$ is N; X$^2$ is CR$^7$; X$^3$ is CR$^7$; X$^4$ is CR$^7$; X$^5$ is CR$^7$; X$^6$ is N; X$^7$ is CR$^7$; X$^8$ is C; and X$^9$ is C; and/or wherein X$^2$ is CH; X$^3$ is CH; X$^4$ is CR$^7$; X$^5$ is CH; X$^7$ is CH.

A method for treating a disease or disorder mediated by colony stimulating factor-1 receptors (CSF-1R) or a disease or disorder in which CSF-1R is implicated in a subject in need of such treatment comprising administering to the subject an effective amount of a compound according to Formula (I) or Formula (II).

The method for treating a disease or disorder, wherein the disease or disorder is neurological and immune mediated diseases including Multiple Sclerosis, ALS, Huntington's disease, lupus, lupus nephritis, and rheumatoid arthritis in a subject in need of such treatment comprising administering to the subject an effective amount of a compound according to Formula (I) or Formula (II).

A pharmaceutical composition comprising a compound according to Formula (I) or Formula (II).

BRIEF DESCRIPTION OF THE FIGURES

FIG. 1 shows inhibitition of proliferation of Murine Bone Marrow-Dervied Macrophages (BMDMs) treated with CSF-1 and CSF-1R Inhibitors (Group 1).

FIG. 2 shows inhibitition of proliferation of Murine Bone Marrow-Dervied Macrophages (BMDMs) treated with CSF-1 and CSF-1R Inhibitors (Group 2).

FIG. 3 shows inhibitition of proliferation of Murine Bone Marrow-Dervied Macrophages (BMDMs) treated with CSF-1 and CSF-1R Inhibitors (Group 3).

FIG. 4 shows phagocytic activity of Murine Bone Marrow Derived Macrophages.

FIG. 5 shows phagocytic activity of primary Murine Microgalia Cells.

FIG. 6 shows phagocytic activity of primary Murine Microglial Cells following incubation with DMSO or CSF-1R Inhibitors with LPS.

FIG. 7 shows the effect of CSF-1R Inhibitors and laquinimod on the proliferation of unstimulated primary Murine Microglial Cells.

FIG. 8 shows the effects of CSF-1R Inhibitors and laquinimod on the proliferation of CSF-1-stimulated primary Murine Microglial Cells.

FIG. 9 shows the comparison of GENZ-882706-treated and vehicle MOG-induced NOD progressive EAE mice.

FIG. 10 shows gene expression of anti-inflammatory and inflammatory markers in spinal cords from MOG-induced NOD progressive EAE mice.

FIG. 11 shows inflammatory cytokine production in the spinal cord following treatment with Genz-882706.

FIG. 12 shows regulatory cytokine production in the spinal cord following treatment with Genz-882706.

FIG. 13 shows microglia, monocyte/macrophage and lymphocyte populations in the brain and spinal cord after LPS challenge and prophylactic treatment with Genz-882706.

FIG. 14 shows Mean Fluorescence Intensitites (MFIs) of activitation markers on microglia and monocyte/macrophage cell populations in the brain after in vivo LPS challenge and prophylactic treatment with Genz-882706.

FIG. 15 shows Mean Fluorescence Intensitites (MFIs) of activitation markers on microglia and monocyte/macrophage cell populations in the spinal cord after in vivo LPS challenge and prophylactic treatment with Genz-882706.

FIG. 16 shows cell populations in the blood after LPS challenge and prophylactic treatment with Genz-882706.

FIG. 17 shows therapeutic treatment with Genz-882706 (100 mg/kg or 25 mg/kg, top) and Inhibitor A (150 mg/kg, bottom).

FIG. 18 shows histopathology scoring of spinal cord sections of Genz-882706-treated, vehicle, and untreated MOG-induced NOD progressive EAE mice.

FIG. 19 shows microglia, monocyte/macrophage and lymphocyte populations in the brain after LPS challenge and prophylactic treatment with RA10651967.

FIG. 20 shows Mean Fluorescence Intensitites (MFIs) of activation markers on microglia and monocyte/macrophage populations in the brain after LPS challenge and prophylactic treatment with RA10651967.

FIG. 21 shows cell populations in the blood after LPS challenge and prophylactic treatment with RA10651967.

DETAILED DESCRIPTION OF THE INVENTION

This invention relates to colony stimulating factor-1 receptor inhibitors ("CSF-1R inhibitors"). The CSF-1R inhibitors of the invention are small molecules capable of penetrating the blood-brain barrier to reach the central nervous system (CNS). This invention also relates to pharmaceutical formulations comprising CSF-1R inhibitors and to the use of CSF-1R inhibitors and pharmaceutical compositions comprising CSF-1R inhibitors to treat disease. This invention further relates to the use of CSF-1R inhibitors and pharmaceutical compositions comprising CSF-1R inhibitors to treat immune-mediated diseases, including but not limited to multiple sclerosis, lupus nephritis, rheumatoid arthritis, and to treat neurological diseases, including but not limited to amyotrophic lateral sclerosis (ALS) and Huntington's disease. The CSF-1R inhibitors of the present invention can be used to inhibit c-FMS, the cellular receptor for colony stimulating factor-1 (CSF-1).

Multiple sclerosis is a chronic, inflammatory, demyelinating disease of the CNS that causes intermittent relapses and progressive neurological deterioration. Activated microglial cells and macrophages contribute to CNS damage and play a significant role in disease progression and neurodegeneration in multiple sclerosis. These activated innate immune cells can participate in antigen presentation and produce inflammatory and neurotoxic mediators that are destructive to neurons and oligodendrocytes. CSF-1R is a receptor-tyrosine kinase expressed on macrophages, monocytes, and microglial cells and represents a potential target for therapeutic modulation of effector function.

The CSF-1R inhibitors of the instant invention are particularly useful in the treatment of multiple sclerosis, and have demonstrated in preclinical in vitro and in vivo studies: a reduction of inflammatory cytokines/chemokines and nitric oxide production, inhibition of the expansion and activation of macrophages/microglial cells, a preservation of phagocytic activity of macrophages and microglial cells, an inhibition of CNS infiltration in multiple in vivo disease models, protection against demyelination in a rat brain slice culture, and a therapeutic benefit in mouse disease models. These data suggest that inhibition of CNS macrophage/microglia effector functions through CSF-1R antagonism provide neuroprotection in multiple sclerosis by reducing inflammation, demyelination, and axonal loss.

In one embodiment, the invention relates to a pharmaceutical composition comprising CSF-1R inhibitors according to Formula (I) and Formula (II). In another embodiment of the invention, the pharmaceutical composition comprising CSF-1R inhibitors according to Formula (I) and Formula (II) are administered in an effective amount to achieve the desired therapeutic effect. The skilled artisan will be able to determine the effective amount of the pharmaceutical composition comprising CSF-1R inhibitors according to Formula (I) and Formula (II) depending on the individual and the condition being treated.

In one embodiment of the invention, the CSF-1R inhibitors and pharmaceutical compositions comprising CSF-1R inhibitors can be for use in treating immune-mediated disease. In another embodiment of the invention, the CSF-1R inhibitors and pharmaceutical compositions comprising CSF-1R inhibitors can be for use in treating multiple sclerosis. In yet another embodiment of the invention, the CSF-1R inhibitors and pharmaceutical compositions comprising CSF-1R inhibitors can be for use in treating lupus nephritis.

In one embodiment of the invention, the CSF-1R inhibitors and pharmaceutical compositions comprising CSF-1R inhibitors can be for use in treating neurological diseases. In another embodiment of the invention, the CSF-1R inhibitors and pharmaceutical compositions comprising CSF-1R inhibitors can be for use in treating ALS.

In one embodiment of the invention, the CSF-1R inhibitors and pharmaceutical compositions comprising CSF-1R inhibitors can be for use in inhibiting c-FMS, the cellular receptor for colony stimulating factor-1 (CSF-1).

The CSF-1R inhibitors of the present invention may be administered alone or in a pharmaceutical composition comprising a CSF-1R inhibitor or multiple CSF-1R inhibitors. Suitable pharmaceutical compositions may comprise a CSF-1R inhibitor and one or more pharmaceutically acceptable excipients. The form in which CSF-1R inhibitors are administered, for example, powder, tablet, capsule, solution, suspension or emulsion, depends in part on the route by which it is administered. The CSF-1R inhibitors can be administered, for example, orally or by injection. Suitable excipients include, but are not limited to, are inorganic or organic materials such as gelatin, albumin, lactose, starch, stabilizers, melting agents, emulsifying agents, salts and buffers. Suitable pharmaceutically acceptable excipients for intra-articular formulations such as solutions or suspensions include, but are not limited to, commercially available inert gels or liquids.

The CSF-1R inhibitors and pharmaceutical compositions comprising CSF-1R inhibitors can be administered alone or in combination with one or more additional drugs. Additional drugs administered in combination with the CSF-1R inhibitors and pharmaceutical compositions comprising CSF-1R inhibitors of the present invention include therapies for the treatment of immune-mediated and neurological diseases, including multiple sclerosis, lupus nephritis and ALS. The additional drugs may be administered concomitantly with the CSF-1R inhibitors and pharmaceutical compositions comprising CSF-1R inhibitors. The additional drugs may also be administered in series with the CSF-1R inhibitors and pharmaceutical compositions comprising CSF-1R inhibitors.

In vitro and in vivo effects of CSF-1R inhibitors and methods of preparing the preferred CSF-1R inhibitors of the invention are described in the Examples.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

Scheme 1: Preparation A
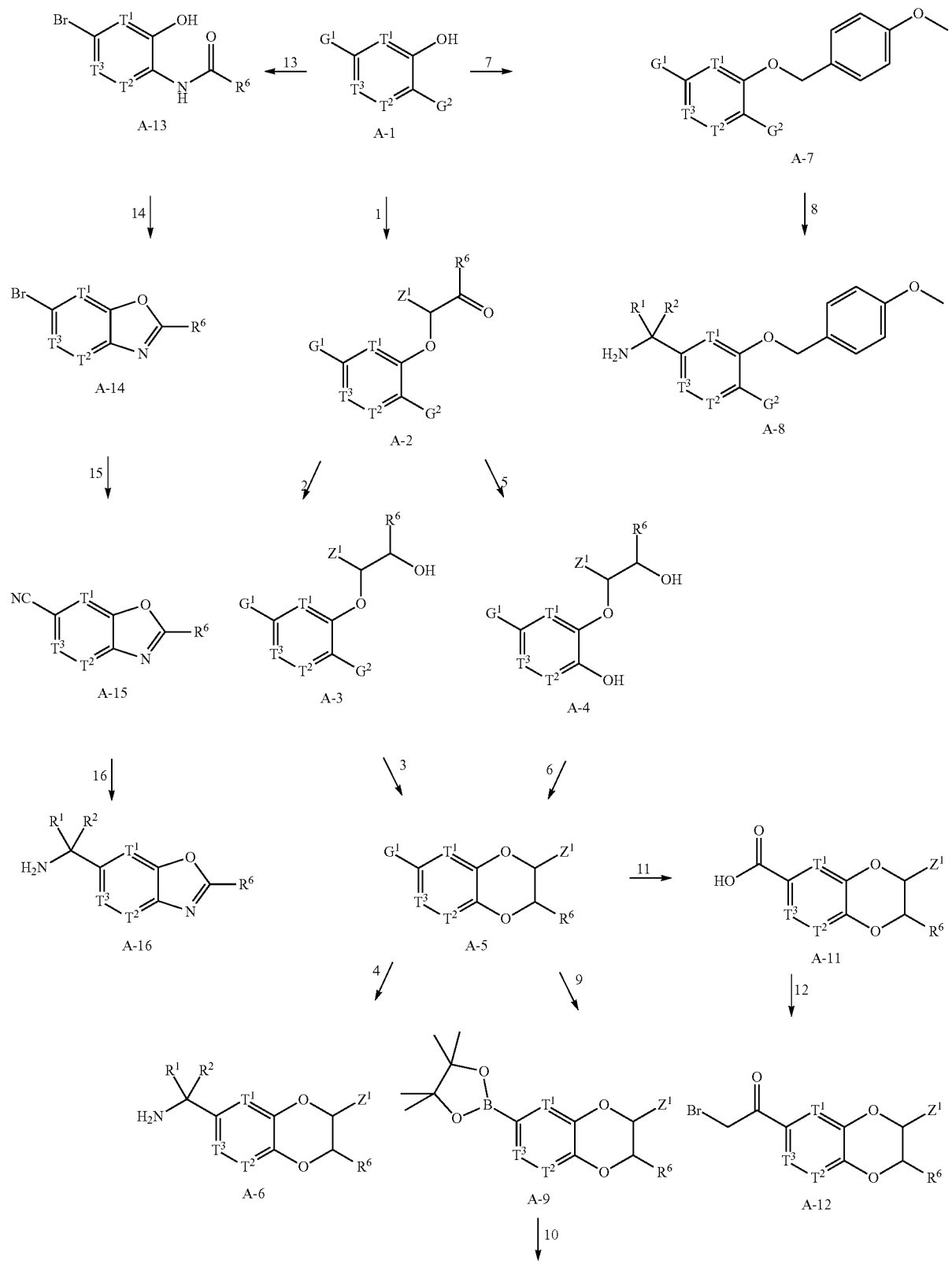

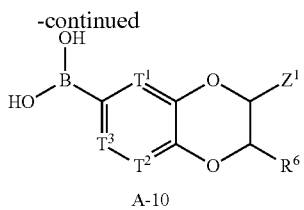

A-10

In Reaction 1 of Preparation A, the compound A-1 (wherein $T^1$, $T^2$, and $T^3$ are as defined above; and wherein $G^1$ is —CN, —CO$_2$Me, —CONH$_2$, or —CH$_2$NHBOC, and $G^2$ is —F, —I, or —OBn; or wherein $G^1$ is —Br, and $G^2$ is —Br or —OPMB) is converted to the corresponding compound A-2 by reacting A-1 with an alpha-haloketone, such as bromoketone $R^6$(CO)CH(Br)($Z^1$), in a polar aprotic solvent, such as acetonitrile in the presence of a base, such as cesium carbonate, at room temperature for 1-24 hours.

In Reaction 2 of Preparation A, the compound A-2 (wherein $G^1$ is —CN or —CONH$_2$, and $G^2$ is —F or —I; or wherein $G^1$ is —Br, and $G^2$ is —Br or —OPMB) is converted to compound A-3 by reducing the ketone of A-2 in an appropriate solvent or solvent mixture, such as methanol or methanol/tetrahydrofuran, with a reducing agent, such as sodium borohydride, at 0° C. for 1 hour.

In Reaction 3 of Preparation A, the compound A-3 (wherein $G^1$ is —CN, and $G^2$ is —F) is converted to compound A-5 by cyclizing A-3 in a polar aprotic solvent, such as dimethylformamide, in the presence of a base, such as potassium carbonate, at 80° C. for 24 hours. Alternatively, in Reaction 3 of Preparation A, the compound A-3 (wherein $G^1$ is —Br, and $G^2$ is —Br) is converted to compound A-5 by cyclizing A-3 in a polar aprotic solvent, such as dimethylformamide, in the presence of a catalyst, such as copper(I) iodide, a base, such as cesium carbonate, and a diamine ligand, such as N,N-dimethylethylenediamine, at reflux for 48 hours. Alternatively, in Reaction 3 of Preparation A, the compound A-3 (wherein $G^1$ is —CONH$_2$, and $G^2$ is —I) is converted to compound A-5 by cyclizing A-3 in a polar aprotic solvent, such as dimethylformamide, in the presence of a catalyst, such as copper(I) iodide, and a base, such as sodium hydride, at 80° C. for 2 hours.

In Reaction 4 of Preparation A, the compound A-5 (wherein $G^1$ is —CN or —CONH$_2$) is converted to compound A-6 by reducing A-4 in an ethereal solvent, such as tetrahydrofuran, in the presence of a reducing agent, such as borane-tetrahydrofuran complex, at reflux for 1-16 hours, or by reducing A-5 in an ethereal solvent, such as tetrahydrofuran, in the presence of a reducing agent, such as lithium aluminum hydride, starting at 0° C. and warming to room temperature over 1-5 hours. Alternatively, in Reaction 4 of Preparation A, the compound A-5 (wherein $G^1$ is —CH$_2$NHBOC) is converted to compound A-6 by deprotecting A-5 in a halogenated solvent, such as dichloromethane, in the presence of an acid, such as trifluoroacetic acid, at room temperature for 1 hour. Alternatively, in Reaction 4 of Preparation A, the compound A-5 (wherein $G^1$ is —CO$_2$Me) is converted to compound A-6 by first reducing A-4 in an ethereal solvent, such as tetrahydrofuran, in the presence of a reducing agent, such as lithium aluminum hydride, starting at 0° C. for 1 hour, second converting to an azide by reacting with an a phosphoryl azide, such as diphenylphosphoryl azide, and a base, such as 1,8-diazabicycloundec-7-ene, in an ethereal solvent, such as tetrahydrofuran, at room temperature to reflux over 1-16 hour, and third reducing with a phosphine, such as resin-bound triphenylphosphine in an aqueous solvent mixture, such as tetrahydrofuran/water mixture, at reflux for 1-3 hours.

In Reaction 5 of Preparation A, the compound A-2 (wherein $G^1$ is —CO$_2$Me or —CH$_2$NHBOC, and $G^2$ is —OBn) is converted to compound A-4 by first deprotecting under hydrogenation conditions in an ethereal solvent, such as tetrahydrofuran, with a solid-supported catalyst, such as palladium on carbon, in the presence of hydrogen at room temperature for 1-5 hours, and second, reducing with a reducing agent, such as sodium borohydride, in a solvent mixture, such as tetrahydrofuran/methanol mixture, at 0° C. for 30 minutes. Alternatively, in Reaction 5 of Preparation A, the compound A-2 (wherein $G^1$ is —Br, and $G^2$ is —OPMB) is converted to compound A-4 by first deprotecting with an acid, such as trifluoroacetic acid, in a halogenated solvent, such as dichloromethane, at room temperature for 1-5 hours, and second, reducing with a reducing agent, such as sodium borohydride, in a solvent mixture, such as tetrahydrofuran/methanol mixture, at 0° C. for 30 minutes.

In Reaction 6 of Preparation A, the compound A-4 is converted to compound A-5 by reacting with a phosphine, such as resin-bound triphenylphosphine, a carbon tetrahalide, such as carbon tetrachloride, and a base, such as triethylamine, in a polar aprotic solvent, such as acetonitrile, at reflux for 1-15 hours. Alternatively, in Reaction 6 of Preparation A, the compound A-4 is converted to compound A-5 by reacting with a phosphine, such as triphenylphosphine and an azodicarboxylate, such as bis(2-methoxyethyl) azodicarboxylate in an ethereal solvent, such as tetrahydrofuran, from room temperature to reflux over 3-20 hours.

In Reaction 7 of Preparation A, the compound A-1 (wherein $T^1$, $T^2$, and $T^3$ are as defined above, wherein $G^1$ is —CO$_2$Me, and wherein $G^2$ is —OBn) is converted to compound A-7 by reacting A-1 with an alkylating reagent, such as p-methoxy-benzyl chloride, in a polar aprotic solvent, such as acetonitrile, in the presence of a base, such as potassium carbonate, at reflux for 20 hours.

In Reaction 8 of Preparation A, the compound A-7 is converted to compound A-8 by reacting A-7 first with a base, such as lithium hydroxide, in an aqueous solvent mixture, such as tetrahydrofuran/water mixture, at room temperature for 45 minutes, second reacting with an amine or amine salt, such as ammonium chloride, an amide coupling reagent, such as 1-[bis(dimethylamino)methylene-1H-1,2,3-triazolo[4,5-b]pyridinium 3-oxid hexafluorophosphate, and a base, such as triethylamine, in a polar aprotic solvent, such as dimethylformamide, at 50° C. for 20 hours, and third reducing in an ethereal solvent, such as tetrahydrofuran, in the presence of a reducing agent, such as lithium aluminum hydride, starting at 0° C. to reflux over 20 hours.

In Reaction 9 of Preparation A, the compound A-5 (wherein $G^1$ is —Br) is converted to compound A-9 by reacting A-5 with an organoboran compound, such as 4,4,4',4',5,5,5',5'-octamethyl-2,2'-bi(1,3,2-dioxaborolane), in the presence of a catalyst, such as (1,1'-bis(diphenylphosphino)

ferrocene)palladium(II) chloride, and a base, such as potassium acetate, in an ethereal solvent, such as 1,4-dioxane, at reflux for 2 hours.

In Reaction 10 of Preparation A, the compound A-9 is converted to compound A-10 by reacting A-9 with an oxidizing agent, such as sodium periodate, in an acidic aqueous solvent mixture, such as tetrahydrofuran/water/hydrochloric acid mixture at room temperature for 16 hours.

In Reaction 11 of Preparation A, the compound A-5 (wherein $G^1$ is an ester, such as —$CO_2Me$) is converted to compound A-11 by hydrolyzing A-5 with a base, such as lithium hydroxide, in an aqueous alcohol mixture, such as methanol/water mixture, at room temperature for 16 hours.

In Reaction 12 of Preparation A, the compound A-11 is converted to compound A-12 by reacting A-11 first with a chlorination reagent, such as oxalyl chloride, in the presence of a catalyst, such as dimethylformamide, in a halogenated solvent, such as dichloromethane, at room temperature for 1.5 hours, second reacting with a diazoalkane, such as (trimethylsilyl)diazomethane, in an aprotic solvent or solvent mixture, such as tetrahydrofuran/acetonitrile mixture, at 0° C. to room temperature over 19 hours, and third reacting with an acid, such as 48% aqueous hydrobromic acid in an aprotic solvent or solvent mixture, such as tetrahydrofuran/acetonitrile mixture, at 0° C. for 10 minutes.

In Reaction 13 of Preparation A, the compound A-1 (wherein $G^1$ is Br and $G^2$ is $NH_2$) is converted to compound A-13 by reacting A-1 with a carboxylic acid, such as $R^6CO_2H$ (wherein $R^6$ is defined above), an amide coupling reagent, such as 1-[bis(dimethylamino)methylene]-1H-1,2,3-triazolo[4,5-b]pyridinium 3-oxid hexafluorophosphate, and a base, such as triethylamine, in a polar aprotic solvent, such as dimethylformamide, at room temperature for 3 hours.

In Reaction 14 of Preparation A, the compound A-13 is converted to compound A-14 by reacting A-13 with an azodicarboxylate, such as diethyl azodicarboxylate, and a phosphine, such as triphenylphosphine, in an aprotic solvent, such as tetrahydrofuran, at room temperature for 16 hours.

In Reaction 15 of Preparation A, the compound A-14 is converted to compound A-14 by reacting A-14 with a cyanide salt, such as zinc(II) cyanide, a catalyst, such as tris(dibenzylideneacetone)dipalladium, and a ligand, such as 1,1'-bis(diphenylphosphino)ferrocene, in a polar aprotic solvent, such as dimethylsulfoxide, at 100° C. for 3 hours.

In Reaction 16 of Preparation A, the compound A-15 is converted to compound A-16 by reacting A-15 with a reducing agent, such as Raney nickel, in the presence of ammonia and hydrogen and in an alcohol, such as methanol, at room temperature for 2 hours.

Scheme 2: Preparation B

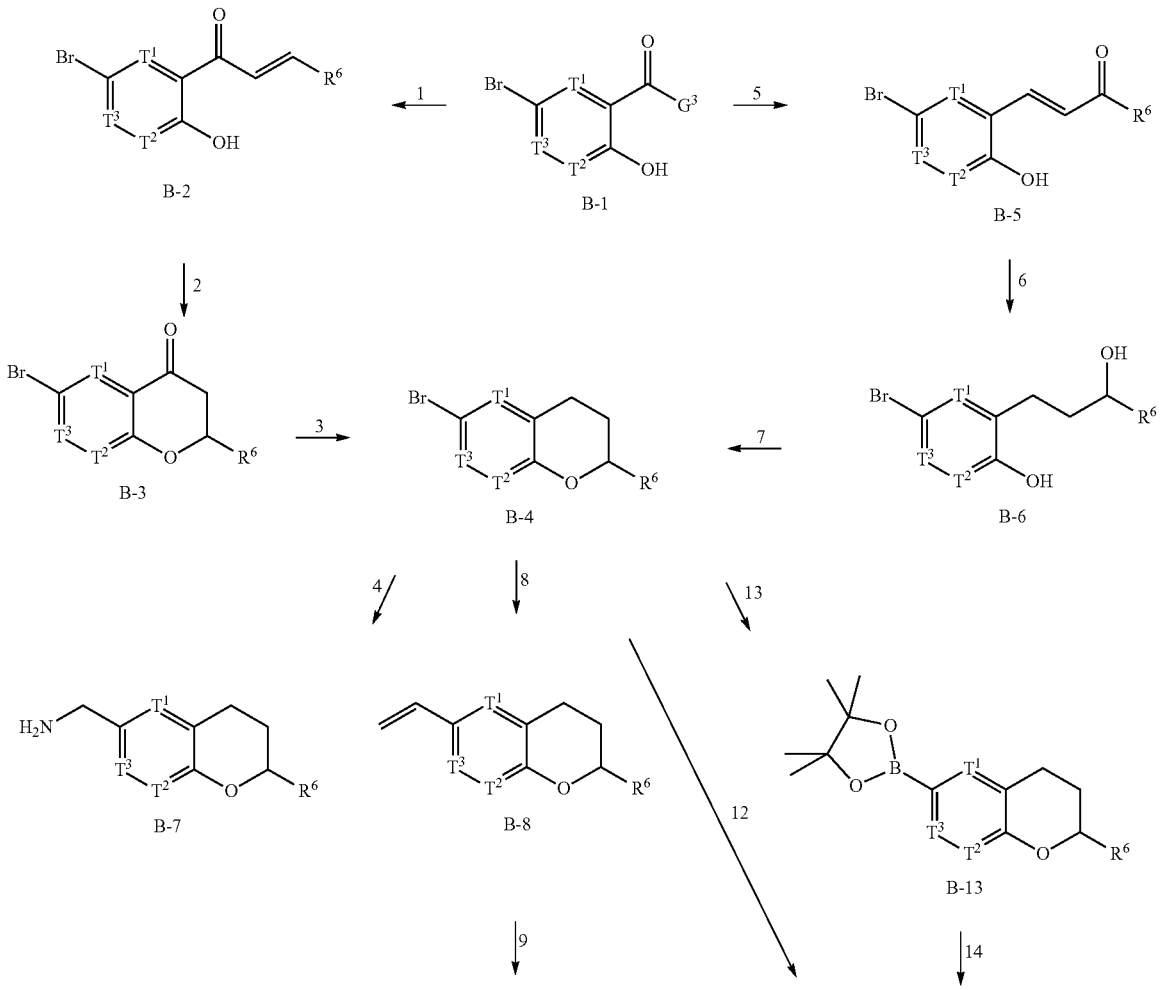

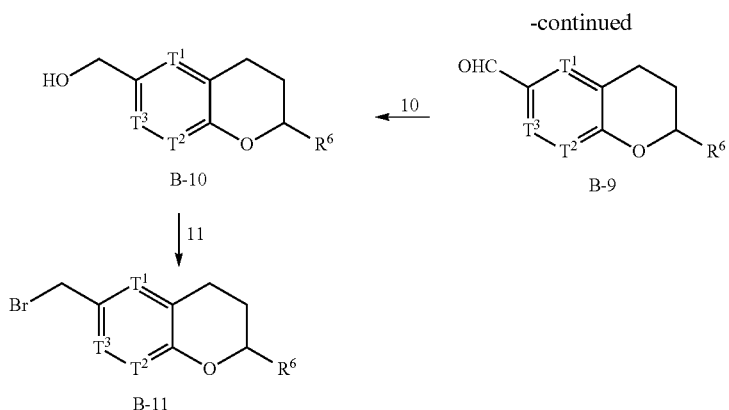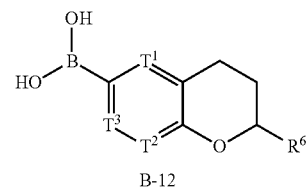

In Reaction 1 of Preparation B, the compound B-1 (wherein $T^1$, $T^2$, and $T^3$, are as defined above, and wherein $G^3$ is —$CH_3$) is converted to the corresponding compound B-2 by reacting B-1 with a carbonyl compound, such as aldehyde $R^6$(CHO) (wherein $R^6$ is as defined above), in an aqueous alcohol mixture, such as ethanol/water mixture, in the presence of a base, such as potassium hydroxide, at room temperature for 16 hours.

In Reaction 2 of Preparation B, the compound B-2 is converted to compound B-3 by cyclizing compound B-2 in an aqueous alcohol mixture, such as ethanol/water mixture, in the presence of a base, such as sodium acetate, at reflux for 17 hours.

In Reaction 3 of Preparation B, the compound B-3 is converted to compound B-4 by reducing the ketone of compound B-3 with an organosilane, such as triethylsilane, in an acid, such as trifluoroacetic acid, at 65° C. for 20 hours.

In Reaction 4 of Preparation B, the compound B-4 is converted to compound B-7 by first reacting with an organoborane, such as potassium vinyltrifluoroborate, a catalyst, such as palladium(II) chloride, a phosphine, such as triphenylphosphine, and a base, such as cesium carbonate, in an aqueous ethereal solvent mixture, such as tetrahydrofuran/water mixture, at reflux, second reacting with oxidizing reagent system, such as osmium tetraoxide and sodium periodate, in an aqueous ethereal solvent mixture, such as tetrahydrofuran/water mixture, at room temperature for 1 hour, third reacting with an amine or amine salt, such as hydroxylaminehydrochloride and a base, such as sodium acetate, in an alcohol solvent, such as methanol, at reflux for 2 hours, and fourth reacting with a reducing agent, such as zinc dust, in an acid, such as acetic acid, at 40° C. for 2 h. Alternatively, in Reaction 4 of Preparation B, the compound B-4 is converted to compound B-7 by first reacting with a cyanating reagent, such as potassium hexacyanoferrate(II) trihydrate, a catalyst, such as palladium(II) acetate, a base, such as sodium carbonate, and an polar solvent or solvent mixture, such as N-methyl-2-pyrrolidone/isopropanol mixture, at room temperature to 140° C., over 16 hours, and second reducing with a solid supported catalyst, such as palladium on carbon (10%), in the presence of hydrogen in an acidic aqueous alcohol mixture, such as methanol and concentrated HCl, at room temperature for 20 hours.

In Reaction 5 of Preparation B, the compound B-1 (wherein $T^1$, $T^2$, $T^3$, and $Z^1$, are as defined above, and wherein $G^3$ is —H) is converted to the corresponding compound B-5 by reacting B-1 with a carbonyl compound, such as ketone $R^6$(CO)$CH_3$ (wherein $R^6$ is as defined above) in an alcohol, such as ethanol, in the presence of a base, such as 10 N sodium hydroxide, at reflux for 3 hours.

In Reaction 6 of Preparation B, the compound B-5 is converted to compound B-6 by first reacting B-5 with a reducing reagent system, such as zinc and ammonium chloride, in an aqueous ethereal solvent mixture, such as tetrahydrofuran/water mixture, at room temperature for 10 minutes, and second reducing the carbonyl moiety with a reducing agent, such as sodium borohydride, in an alcohol, such as methanol, at 0° C. for 15 minutes. Alternatively, in Reaction 6 of Preparation B, the compound B-5 is converted to compound B-6 by reacting B-5 with a reducing reagent system, such as cobalt(II) chloride and sodium borohydride, in an ethereal solvent, such as tetrahydrofuran, at 0° C. to room temperature over 2 hours.

In Reaction 7 of Preparation B, the compound B-6 is converted to compound B-7 by cyclizing B-6 with an acid, such as glacial acetic acid, at 110° C. for 45 minutes. Alternatively, in Reaction 7 of Preparation B, the compound B-6 is converted to B-7 by cyclizing B-6 with a phosphine, such as triphenylphosphine, and an azodicarboxylate, such as bis(2-methoxyethyl) azodicarboxylate, in an ethereal solvent, such as tetrahydrofuran, at room temperature to reflux over 3-20 hours.

In Reaction 8 of Preparation B, the compound B-4 is converted to compound B-8 by reacting B-4 with an organoboran compound, such as ($CH_2CH$)$BF_3K$, in the presence of a catalyst, such as palladium(II) chloride, a phosphine, such as triphenylphosphine, and a base, such as cesium carbonate, in an aqueous ethereal solvent mixture, such as tetrahydrofuran/water mixture, at reflux for 16 hours.

In Reaction 9 of Preparation B, the compound B-8 is converted to compound B-9 by oxidizing B-8 with an oxidizing reagent system, such as osmium tetraoxide and sodium periodate, in an aqueous ethereal solvent mixture, such as tetrahydrofuran/water mixture, at room temperature for 1 hour.

In Reaction 10 of Preparation B, the compound B-9 is converted to compound B-10 by reacting B-9 with a reducing agent, such as sodium borohydride, in an alcohol, such as methanol, at 0° C. for 1 hour.

In Reaction 11 of Preparation B, the compound B-10 is converted to compound B-11 by reacting B-10 with a carbon tetrahalide, such as carbon tetrabromide, in the presence of a phosphine, such as resin-bound triphenylphosphine, in an ethereal solvent, such as tetrahydrofuran, at reflux for 2 hours.

In Reaction 12 of Preparation B, the compound B-4 is converted to compound B-12 by reacting B-4 with an organolithium reagent, such as n-butyl lithium, and an organoborate, such as tri-isopropoxy borate, in an ethereal solvent, such as tetrahydrofuran, at −78° C. to room temperature over 30 minutes.

In Reaction 13 of Preparation B, the compound B-4 is converted to compound B-13 by reacting B-4 with an organoborane compound, such as 4,4,4',4',5,5,5',5'-octamethyl-2,2'-bi(1,3,2-dioxaborolane), in the presence of a catalyst, such as (1,1'-bis(diphenylphosphino)ferrocene)palladium(II) chloride and a base, such as potassium acetate, in an ethereal solvent, such as 1,4-dioxane, at reflux for 2 hours.

In Reaction 14 of Preparation B, the compound B-13 is converted to compound B-12 by reacting B-13 with an oxidizing reagent, such as sodium periodate, in an aqueous ethereal solvent mixture, such as tetrahydrofuran/water mixture at room temperature for 16 hours.

In Reaction 4 of Preparation C, the compound C-4 is converted to compound C-5 by reacting C-4 with a cyanide salt, such as zinc(II) cyanide, and tetrakis(triphenylphosphine)palladium(0), in a polar aprotic solvent, such as dimethylformamide, at 80° C. for 16 hours. In Reaction 5 of Preparation C, the compound C-5 is converted to compound C-6 by reacting C-5 with a reducing agent system, such as nickel(II) chloride hexahydrate and sodium borohydride, and di-t-butyl dicarbonate, in an alcohol, such as methanol, at 0° C. to room temperature for 4 hours.

In Reaction 6 of Preparation C, the compound C-6 is converted to compound C-7 by reacting C-6 with an acid, such as 4N hydrogen chloride in 1,4-dioxane, in a halogenated solvent, such as dichloromethane, at room temperature for 1 hour.

Scheme 3: Preparation C

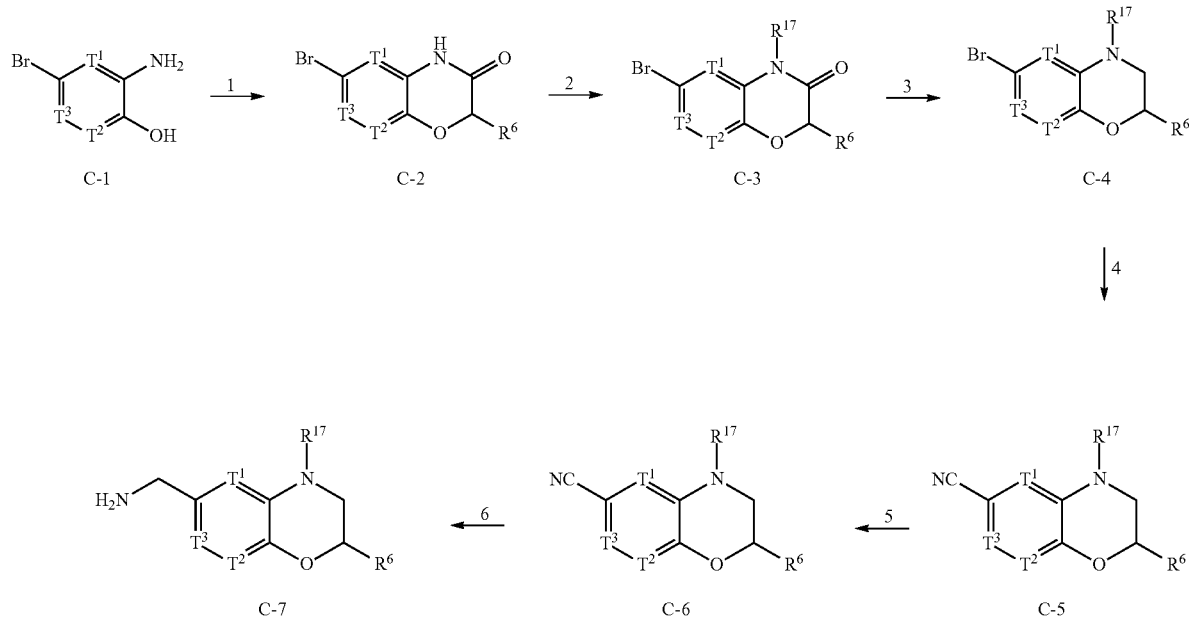

In Reaction 1 of Preparation C, the compound C-1 (wherein $T^1$, $T^2$, and $T^3$, are as defined above) is converted to the corresponding compound C-2 by reacting C-1 with an alpha-halo ester, such as bromo ester $CH_3O(CO)CH(Br)$ ($R^6$) (wherein $R^6$ is as defined above), in an aprotic solvent, such as acetone, in the presence of a base, such as potassium carbonate, at reflux for 16 hours.

In Reaction 2 of Preparation C, the compound C-2 is converted to compound C-3 (wherein $R^{17}$ is as defined above) by reacting C-2 with an alkylating reagent, such as methyl iodide (e.g., wherein $R^{17}$ is methyl) in the presence of a base, such as potassium hydroxide, in an aprotic solvent, such as acetone, at reflux for 45 minutes.

In Reaction 3 of Preparation C, the compound C-3 is converted to compound C-4 by reacting C-3 with a reducing agent, such as borane-methyl sulfide complex, in an ethereal solvent, such as tetrahydrofuran, at 50° C. for 16 hours.

Scheme 4: Preparation D

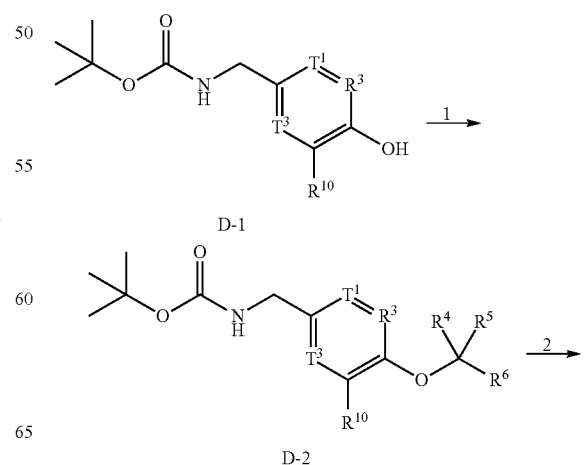

-continued

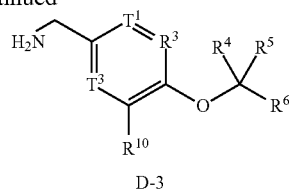

D-3

In Reaction 1 of Preparation D, the compound D-1 (wherein $T^1$, $T^3$, $R^3$, and —$R^{10}$, are as defined above, such as —$R^{10}$ is —H, halo, cyano, or $(C_1-C_{10})$alkoxy-) is converted to compound D-2 by reacting D-1 with an alkyl chloride $(R^4)(R^5)(R^6)$CCl (wherein $R^4$, $R^5$, and $R^6$ are as defined above) in a polar aprotic solvent, such as acetonitrile, in the presence of a base, such as potassium carbonate, at reflux for 23 hours.

In Reaction 2 of Preparation D, the compound D-2 is converted to compound D-3 by deprotecting D-2 with an acid, such as trifluoroacetic acid, in a halogenated solvent, such as dichloromethane, at room temperature for 30 minutes.

In Reaction 1 of Preparation E, the compound E-1 (wherein $T^1$ and $T^2$ are as defined above) is converted to compound E-2 (wherein $R^{10}$ is as defined above, such as a $(C_1-C_{10})$alkyoxy-) by reacting E-1 with $(C_1-C_{10})$ alkyl iodide in a polar aprotic solvent, such as acetonitrile, in the presence of a base, such as potassium carbonate, at reflux for 16 hours.

In Reaction 2 of Preparation E, the compound E-2 (wherein $R^{10}$ is as defined above, such as a —H, halo, cyano, or $(C_1-C_{10})$alkyoxy-) is converted to compound E-3 by reacting E-2 with alcohol $(R^4)(R^5)(R^6)$COH (wherein $R^4$, $R^5$, and $R^6$ are as defined above) in a polar aprotic solvent, such as dimethylsulfoxide, in the presence of a base, such as sodium hydride, at room temperature for 2 hours.

In Reaction 3 of Preparation E, the compound E-3 is converted to compound E-4 by reacting E-3 first, with an organoboron compound, such as potassium (N-Boc-aminomethyl)trifluoroborate, a catalyst, such as 2nd Gen XPhos precatalyst, and a base, such as cesium carbonate, in a biphasic solvent system, such as toluene/water mixture, at reflux for 20 hours, and second deprotecting with an acid, such as trifluoroacetic acid, in a halogenated solvent, such as dichloromethane, at room temperature for 30 minutes.

Scheme 5: Preparation E

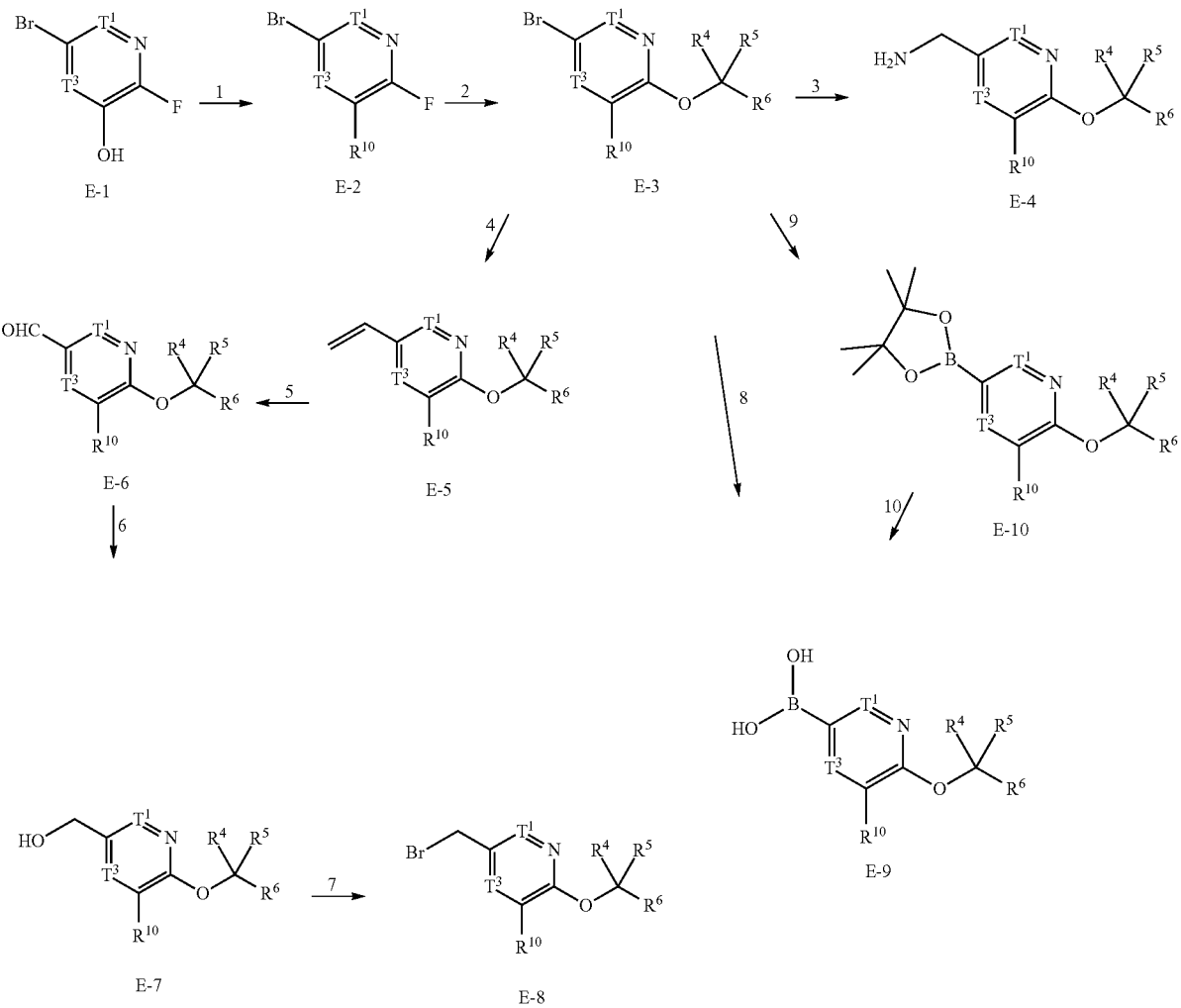

In Reaction 4 of Preparation E, the compound E-3 is converted to compound E-5 by reacting E-3 with an organoboron compound, such as potassium vinyltrifluoroborate, in the presence of a catalyst, such as palladium(II) chloride, a phosphine, such as triphenylphosphine, and a base, such as cesium carbonate, in an aqueous ethereal solvent mixture, such as tetrahydrofuran/water mixture, at reflux for 16 hours.

In Reaction 5 of Preparation E, the compound E-5 is converted to compound E-6 by reacting E-5 with an oxidizing agent system, such as osmium tetraoxide and sodium periodate, in an aqueous ethereal solvent mixture, such as tetrahydrofuran/water mixture, at room temperature for 1 hour.

In Reaction 6 of Preparation E, the compound E-6 is converted to compound E-7 by reacting E-6 with a reducing agent, such as sodium borohydride, in an alcohol, such as methanol, at 0° C. for 1 hour.

In Reaction 7 of Preparation E, the compound E-7 is converted to compound E-8 by reacting E-7 with a carbon tetrahalide, such as carbon tetrabromide, in the presence of a phosphine, such as resin-bound triphenylphosphine, in an ethereal solvent, such as tetrahydrofuran, at reflux for 2 hours.

In Reaction 8 of Preparation E, the compound E-3 is converted to compound E-9 by reacting E-3 with an organolithium reagent, such as n-butyl lithium, and an organoborate, such as tri-isopropoxy borate, in an ethereal solvent, such as tetrahydrofuran, at −78° C. to room temperature over 30 minutes.

In Reaction 9 of Preparation E, the compound E-3 is converted to compound E-10 by reacting E-3 with an organoboron compound, such as 4,4,4',4',5,5,5',5'-octamethyl-2,2'-bi(1,3,2-dioxaborolane), in the presence of a catalyst, such as (1,1'-bis(diphenylphosphino)ferrocene)palladium(II) chloride and a base, such as potassium acetate, in an ethereal solvent, such as 1,4-dioxane, at reflux for 2 hours.

In Reaction 10 of Preparation E, the compound E-10 is converted to compound E-9 by reacting E-10 with an oxidizing agent, such as sodium periodate, in an aqueous ethereal solvent mixture, such as tetrahydrofuran/water mixture, at room temperature for 16 hours.

In Reaction 1 of Preparation F, the compound F-1 (wherein $T^1$, $T^2$, and $T^3$, are as defined above) is converted to compound F-2 by reacting F-1 with an alpha-haloketone, such as bromo ketone $R^6(CO)CH_2Br$ (wherein $R^6$ is as defined above), in the presence of a base, such as potassium carbonate, in a polar aprotic solvent, such as dimethylformamide, at 0° C. to room temperature over 1.5 hours.

In Reaction 2 of Preparation F, the compound F-2 is converted to compound F-3 by reacting F-2 with a reducing agent, such as sodium borohydride, in an alcohol, such as methanol, at 0° C. for 1 hour.

In Reaction 3 of Preparation F, the compound F-3 is converted to compound F-4 by reacting F-3 with a cyanide salt, such as zinc(II) cyanide, in the presence of a catalyst, such as tetrakis(triphenylphosphine)palladium(0), in a polar aprotic solvent, such as dimethylformamide, at 90° C. for 4 hours.

In Reaction 4 of Preparation F, the compound F-4 is converted to compound F-5 by cyclizing F-4 in the presence of a base, such as potassium carbonate, in a polar aprotic solvent, such as dimethylformamide, at 80° C. for 24 hours.

In Reaction 5 of Preparation F, the compound F-5 is converted to compound F-6 by reacting F-5 with a reducing agent, such as lithium aluminum hydride, in an ethereal solvent, such as tetrahydrofuran, at 0° C. for 1 hour.

In Reaction 6 of Preparation F, the compound F-6 is converted to compound F-7 by reacting F-6 with a reducing agent, such as sodium borohydride, in an alcohol, such as methanol, at 0° C. for 1 hour. In Reaction 7 of Preparation F, the compound F-7 is converted to compound F-8 by reacting F-7 with a carbon tetrahalide, such as carbon tetrabromide, in the presence of a phosphine, such as resin-bound triphenylphosphine, in an ethereal solvent, such as tetrahydrofuran, at reflux for 2 hours.

Scheme 6: Preparation F

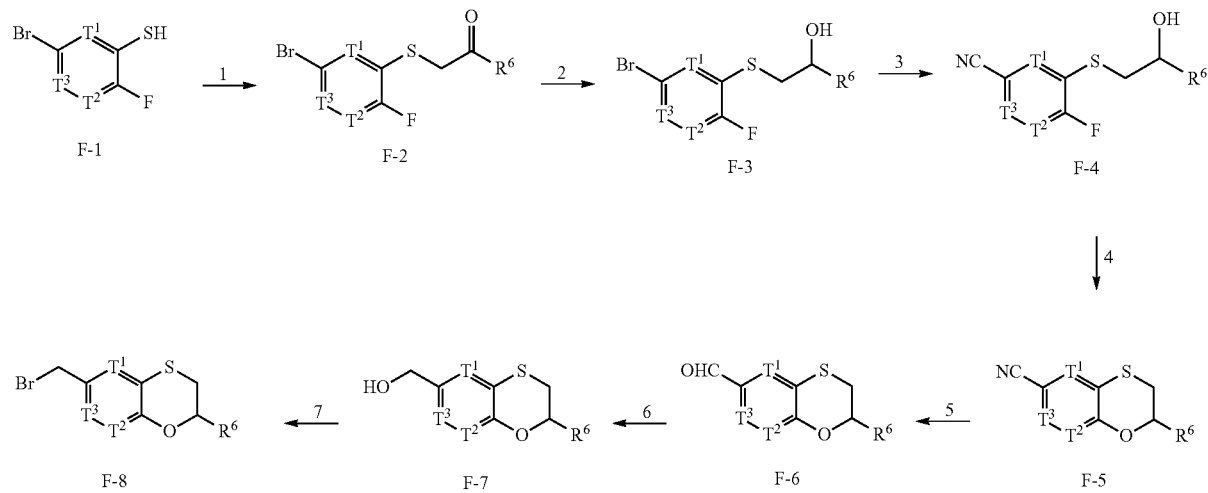

Scheme 7: Preparation G

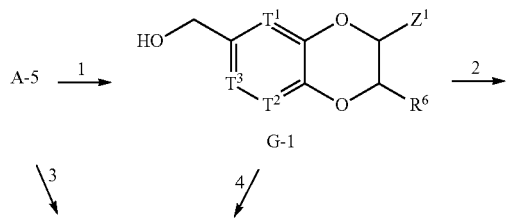

Scheme 8: Preparation H

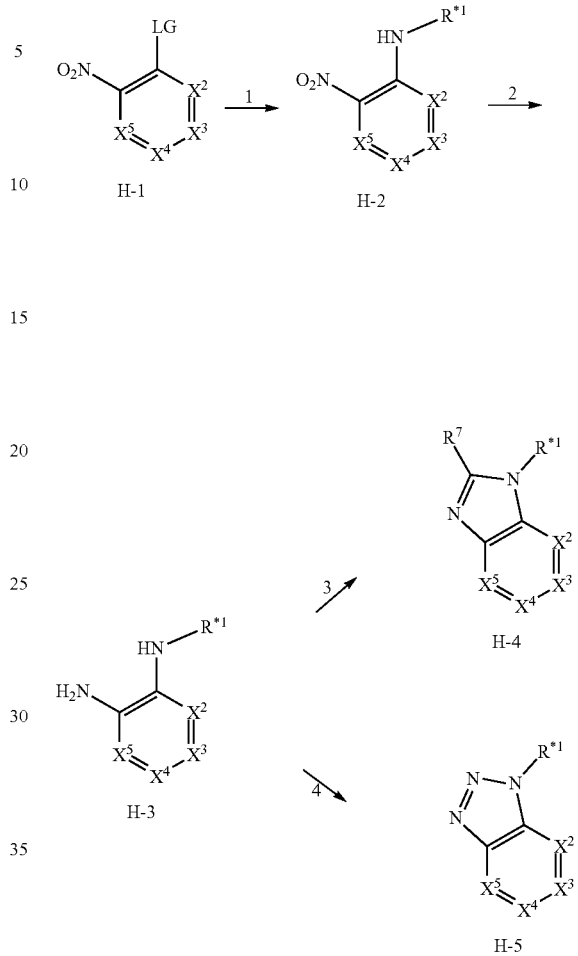

In Reaction 1 of Preparation G, the compound A-5 (wherein $T^1$, $T^2$, $T^3$, $R^6$, and $Z^1$, are as defined above, and wherein $G^1$ is —$CO_2Me$) is converted to the compound G-1 by reacting A-5 with a reducing agent, such as lithium aluminum hydride, in an ethereal solvent, such as tetrahydrofuran, at 0° C. for 1 hour.

In Reaction 2 of Preparation G, the compound G-1 is converted to compound G-2 by reacting G-1 with a carbon tetrahalide, such as carbon tetrabromide, in the presence of a phosphine, such as resin-bound triphenylphosphine, in an ethereal solvent, such as tetrahydrofuran, at reflux for 2 hours.

In Reaction 3 of Preparation G, the compound A-5 (wherein $T^1$, $T^2$, $T^3$, $R^6$, and $Z^1$, are as defined above, and wherein $G^1$ is Br) is converted to compound G-3 by reacting A-5 with an organolithium reagent, such as n-butyl lithium, followed by dimethylformamide in in an ethereal solvent, such as tetrahydrofuran, at −78° C. to room temperature over 1 hour.

In Reaction 4 of Preparation G, the compound G-1 is converted to compound G-3 by reacting G-1 with an oxidizing reagent, such as the Dess-Martin periodinane, in a halogenated solvent, such as dichloromethane, at room temperature for 30 minutes, or alternatively by reacting G-1 with an oxidizing reagent, such as manganese(IV)oxide, in a halogenated solvent, such as dichloromethane, at room temperature for 22 hours.

In Reaction 1 of Preparation H, the compound H-1 (wherein $X^2$, $X^3$, $X^4$, and $X^5$, are as defined above; and wherein LG represents a leaving group, such as —F or —Cl) is converted to compound H-2 by reacting H-1 with amine $R^{*1}NH_2$ (wherein $R^{*1}NH_2$ represents, for example, compound A-6, A-8, B-7, C-7, D-3, or E-4 as defined above) in the presence of a base, such as diisopropylethylamine, in acetonitrile at reflux for 2-16 hours.

In Reaction 2 of Preparation H, the compound H-2 is converted to compound H-3 by reacting H-2 with a reducing agent system, such as zinc and ammonium chloride, in an aqueous ethereal/alcohol mixture, such as tetrahydrofuran/methanol/water mixture, at room temperature for 1 hour, or alternatively, reacting H-2 with a reducing agent, such as iron, in an acid, such as acetic acid, at 100° C. for 30 minutes.

In Reaction 3 of Preparation H, the compound H-3 is converted to compound H-4 by reacting H-3 with an orthoester $(EtO)_3CR^7$ (wherein $R^7$ is as defined above), such as triethyl orthoformate, in the presence of an acid, such as p-toluenesulfonic acid, in an alcohol, such as ethanol, at reflux for 1-4 hours.

In Reaction 4 of Preparation H, the compound H-3 is converted to compound H-5 by reacting H-3 with sodium nitrite in the presence of an acid, such as acetic acid, at room temperature for 2 hours.

Scheme 9: Preparation I

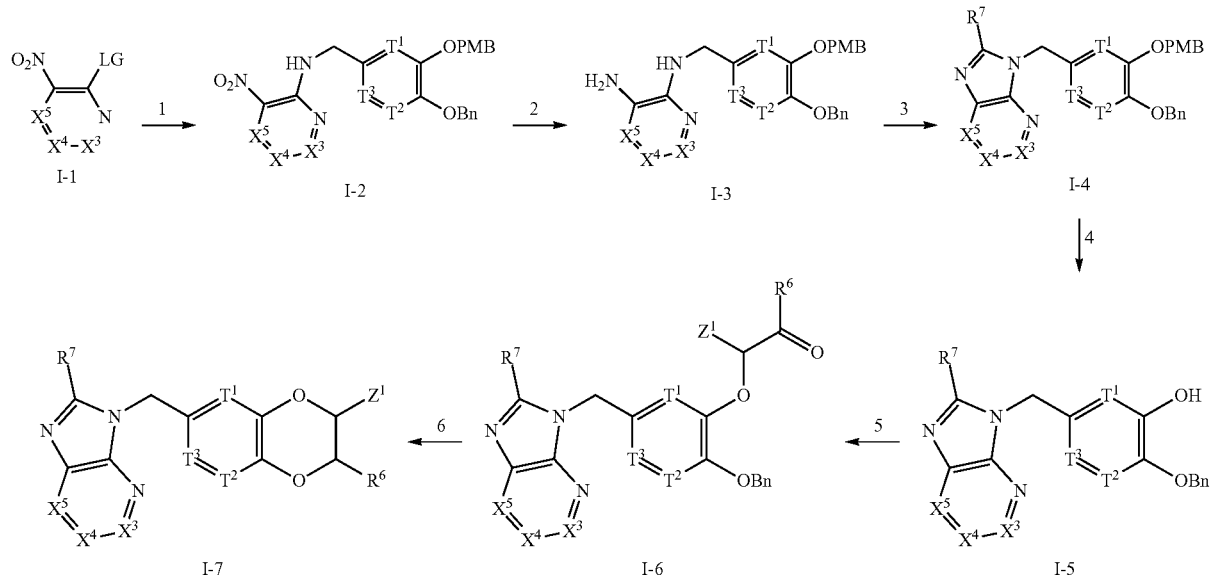

In Reaction 1 of Preparation I, the compound I-1 (wherein $X^3$, $X^4$, and $X^5$, are as defined above) is converted to compound I-2 (wherein $X^3$, $X^4$, $X^5$, $T^1$, $T^2$, and $T^3$, are as defined above) by reacting I-1 with amine compound A-8 (wherein $R^1$ and $R^2$ each independently represent H, and $G^2$ is —OBn, as defined above) in the presence of a base, such as diisopropylethylamine, in a polar aprotic solvent, such as acetonitrile, at reflux for 2-16 hours.

In Reaction 2 of Preparation I, the compound I-2 is converted to compound I-3 by reacting I-2 with a reducing agent system, such as zinc and ammonium chloride, in an aqueous ethereal/alcohol mixture, such as tetrahydrofuran/methanol/water mixture, at room temperature for 1 hour.

In Reaction 3 of Preparation I, the compound I-3 is converted to compound I-4 by reacting I-3 with orthoester $(EtO)_3CR^7$ (wherein $R^7$ is as defined above), such as triethyl orthoformate, in the presence of an acid, such as p-toluenesulfonic acid, in an alcohol, such as ethanol, at reflux for 1-4 hours.

In Reaction 4 of Preparation I, the compound I-4 is converted to compound I-5 by reacting I-4 with an acid, such as glacial acetic acid, at 110° C. for 20 hours.

In Reaction 5 of Preparation I, the compound I-5 is converted to compound I-6 by reacting I-5 with an alpha-haloketone, such as bromoketone $R^6(CO)CH(Br)(Z^1)$, in a polar aprotic solvent, such as acetonitrile in the presence of a base, such as cesium carbonate, at room temperature for 1-24 hours.

In Reaction 6 of Preparation I, the compound I-6 is converted to the compound I-7 by first deprotecting under hydrogenation conditions in an ethereal solvent, such as tetrahydrofuran, with a solid-supported catalyst, such as palladium on carbon, in the presence of hydrogen at room temperature for 1-5 hours, and second, reducing with a reducing agent, such as sodium borohydride, in a solvent mixture, such as tetrahydrofuran/methanol mixture, at 0° C. for 30 minutes, and third reacting with a phosphine, such as resin-bound triphenylphosphine, a carbon tetrahalide, such as carbon tetrachloride, a base, such as triethylamine, in acetonitrile, at reflux for 1-15 hours.

Scheme 10: Preparation J

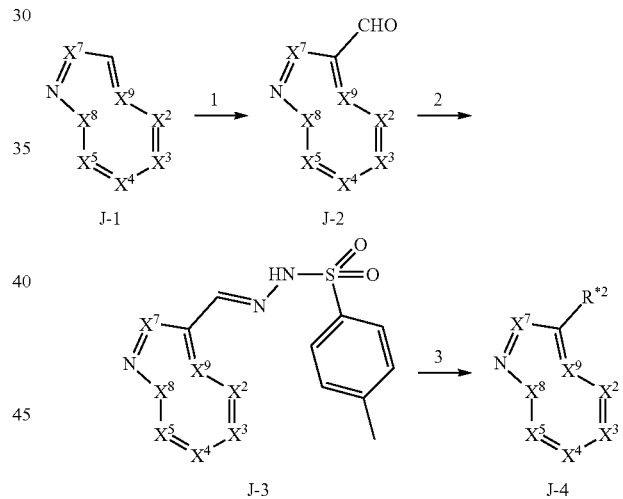

In Reaction 1 of Preparation J, the compound J-1 (wherein $X^3$, $X^4$, $X^5$, $X^7$, and $X^8$, are as defined above, such as wherein $X^2$ and $X^8$ are independently C or N and $X^9$ is C) is converted to compound J-2 by reacting J-1 with a formylation reagent, such as phosphorous oxychloride in dimethylformamide, at 0° C. to room temperature over 16 hours. In Reaction 2 of Preparation J, the compound J-2 is converted to the compound J-3 by reacting J-2 with a sulfonyl hydrazide, such as p-toluenesulfonyl hydrazide, in an ethereal solvent, such as 1,4-dioxane, at 100° C. for 2 hours.

In Reaction 3 of Preparation J, the compound J-3 is converted to the compound J-4 by reacting J-3 with boronic acid compound $R^{*2}B(OH)_2$ (wherein $R^{*2}B(OH)_2$ represents, for example, compound A-10, B-12, or E-9 as defined above) in the presence of a base, such as potassium carbonate, in an etheral solvent, such as 1,4-dioxane, at 100° C. for 16 hours.

Scheme 11: Preparation K

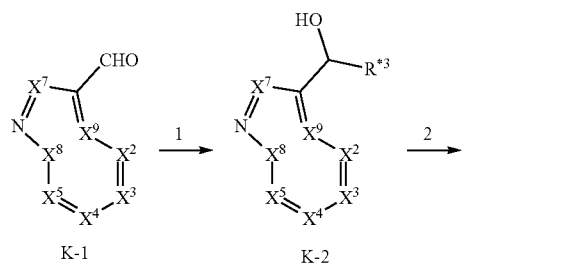

In Reaction 1 of Preparation K, the compound K-1 (wherein $X^2$, $X^3$, $X^4$, $X^5$, $X^7$, and $X^8$, are as defined above, such as wherein $X^2$ and $X^8$ are independently C or N and $X^9$ is C) is converted to compound K-2 by reacting K-1 with bromide compound $R^{*3}Br$ (wherein $R^{*3}Br$ represents, for example, compound A-5 (wherein $G^1$ is Br), B-4, C-4, E-2, or E-3 as defined above) in the presence of a base, such as n-butyl lithium, in tetrahydrofuran at −78° C. for 30 minutes.

In Reaction 2 of Preparation K, the compound K-2 is converted to compound K-3 by reacting K-2 with an organosilane, such as triethylsilane, in an acid, such as trifluoroacetic acid, at room temperature for 30 minutes.

Scheme 12: Preparation L

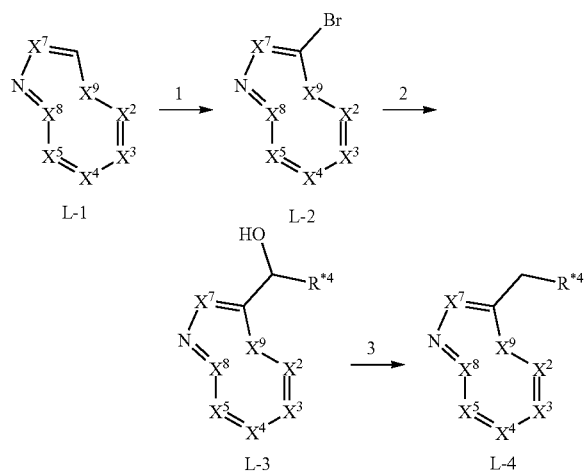

In Reaction 1 of Preparation L, the compound L-1 (wherein $X^2$, $X^3$, $X^4$, $X^5$, and $X^7$, are as defined above, such as wherein $X^2$ and $X^8$ are independently C and $X^9$ is C or N, or such as wherein $X^2$ and $X^8$ are independently C or N and $X^9$ is C) is converted to compound L-2 by reacting L-1 with brominating reagent, such as N-bromosuccinimide, in a polar aprotic solvent, such as dimethylformamide, at 0° C. to room temperature for 1.5 hours.

In Reaction 2 of Preparation L, the compound L-2 is converted to compound L-3 by first reacting L-2 with an organometallic reagent, such as ethyl magnesium bromide, in an ethereal solvent, such as tetrahydrofuran, at room temperature for 30 minutes, and second reacting with aldehyde compound $R^{*4}CHO$ (wherein $R^{*4}CHO$ represents, for example, compound B-9, E-6, F-6, or G-3, as defined above) at room temperature for 0.5-3 hours.

In Reaction 3 of Preparation L, the compound L-3 is converted to the compound L-4 by reacting L-3 with an organosilane, such as triethylsilane, in an acid, such as trifluoroacetic acid, at room temperature for 30 minutes.

Scheme 13: Preparation M

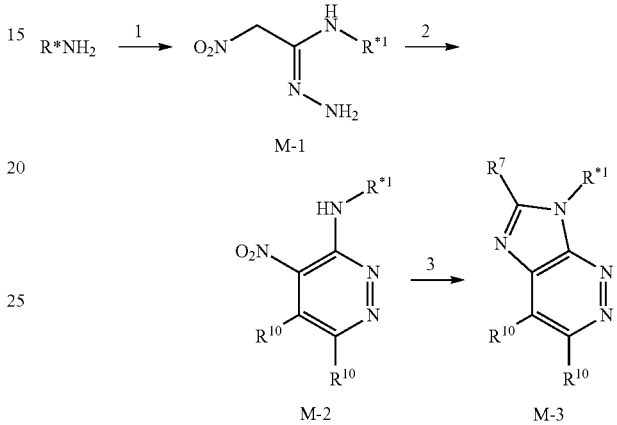

In Reaction 1 of Preparation M, the amine compound $R^*NH_2$ (wherein $R^{*1}NH_2$ represents, for example, compound A-6, A-8, B-7, C-7, D-3, or E-4 as defined above) is converted to compound M-1 by first reacting $R^{*1}NH_2$ with 1,1-bis(methylthio)-2-nitroethylene in an alcohol, such as ethanol, at reflux for 19 hours, and second reacting with a hydrazine, such as hydrazine hydrate, in an alcohol, such as ethanol, at reflux for 2.5 hours.

In Reaction 2 of Preparation M, the compound M-1 is converted to compound M-2 (wherein each $R^{10}$ independently is as defined above) by reacting M-1 with a 1,2-dicarbonyl compound, such as gyloxal, in the presence of a base, such as sodium carbonate, in an aqueous ethereal alcohol mixture, such as tetrahydrofuran/ethanol/water mixture, at room temperature for 19 hours.

In Reaction 3 of Preparation M, the compound M-2 is converted to the compound M-3 by first reacting M-1 with a reducing agent, such as iron, in an acid, such as glacial acetic acid, at 125° C. for 10 minutes, and second reacting with orthoester $(EtO)_3CR^7$ (wherein $R^7$ is as defined above), such as triethyl orthoformate, in the presence of an acid, such as p-toluenesulfonic acid, in an alcohol, such as ethanol, at reflux for 1 hour.

Scheme 14: Preparation N

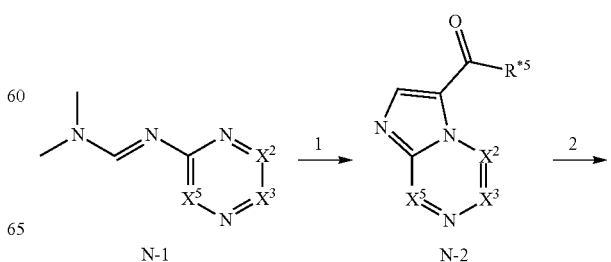

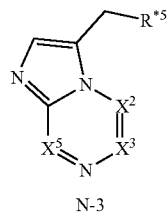

N-3

In Reaction 1 of Preparation N, the compound N-1 (wherein $X^2$, $X^3$, and $X^5$, are as defined above) is converted to compound N-2 by reacting N-1 with alpha-bromo ketone compound $BrCH_2(CO)R^{*5}$ (wherein $BrCH_2(CO)R^{*5}$ represents, for example, compound A-12 as defined above) in an polar aprotic solvent, such as acetonitrile, at reflux for 42 hours.

In Reaction 2 of Preparation N, the compound N-2 is converted to the compound N-3 by first reacting N-2 with a reducing agent, such as sodium borohydride, in an alcohol, such as methanol, at room temperature for 30 minutes, and second reacting with an organosilane, such as triethylsilane, in an acid, such as trifluoroacetic acid, at room temperature for 2 hours.

Scheme 15: Preparation O

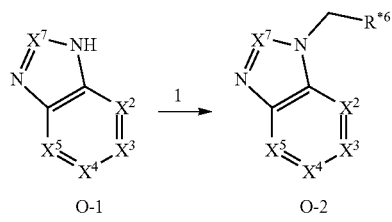

O-1      O-2

In Reaction 1 of Preparation O, the compound O-1 (wherein $X^2$, $X^3$, $X^4$, $X^5$, and $X^7$, are as defined above) is converted to the compound O-2 by reacting O-1 with an azodicarboxylate, such as bis(2-methoxyethyl) azodicarboxylate, a phosphine, such as triphenylphosphine, and alcohol compound $HOCH_2R^{*6}$ (wherein $HOCH_2R^{*6}$ represents, for example, compound B-10, E-7, F-7, or G-1, as defined above) in an ethereal solvent, such as tetrahydrofuran, at room temperature for 3 hours, or alternatively, by reacting O-1 with (tributylphosphoranylidene)acetonitrile and alcohol compound $HOCH_2R^{*6}$ (wherein $HOCH_2R^{*6}$ represents, for example, compound B-10, E-7, F-7, or G-1, as defined above), in an aromatic solvent, such as toluene at 100° C. for 1 hour.

Scheme 16: Preparation P

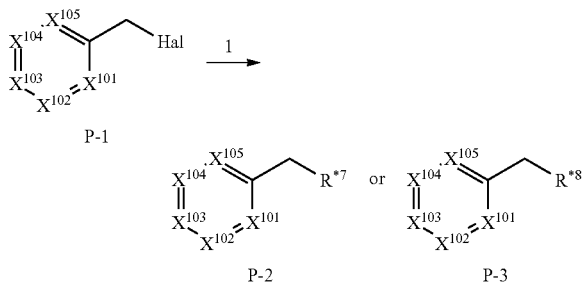

P-1

P-2      P-3

In Reaction 1 of Preparation P, the compound P-1 (wherein $X^{101}$, $X^{102}$, $X^{103}$, $X^{104}$, and $X^{105}$, are as defined above, such as wherein $X^{102}$, $X^{103}$, or $X^{104}$, are independently N; and wherein Hal represents a halogen) is converted to either compound P-2 by reacting P-1 with a catalyst, such as 2nd Gen XPhos palladium precatalyst, a base, such as potassium phosphate, and an organoborate compound, such as (4,4,5,5-tetramethyl-1,3,2-dioxaborolyl)-$R^{*7}$ (wherein (4,4,5,5-tetramethyl-1,3,2-dioxaborolyl)-$R^{*7}$ represents, for example, compound A-9, B-13, or E-10, as defined above) in an aqueous ethereal solvent mixture, such as tetrahydrofuran/water mixture, at 80° C. for 15 hours, or alternatively converted to the compound P-3 by reacting P-1 with a catalyst, such as 2nd Gen XPhos palladium precatalyst, a base, such as potassium phosphate, and a boronic acid compound $(HO)_2BR^{*8}$ (wherein $(HO)_2BR^{*8}$ represents, for example, compound A-10, B-12, or E-9, as defined above, respectively) in an aqueous ethereal solvent mixture, such as tetrahydrofuran/water mixture at 80° C. for 15 hours.

Scheme 17: Preparation Q

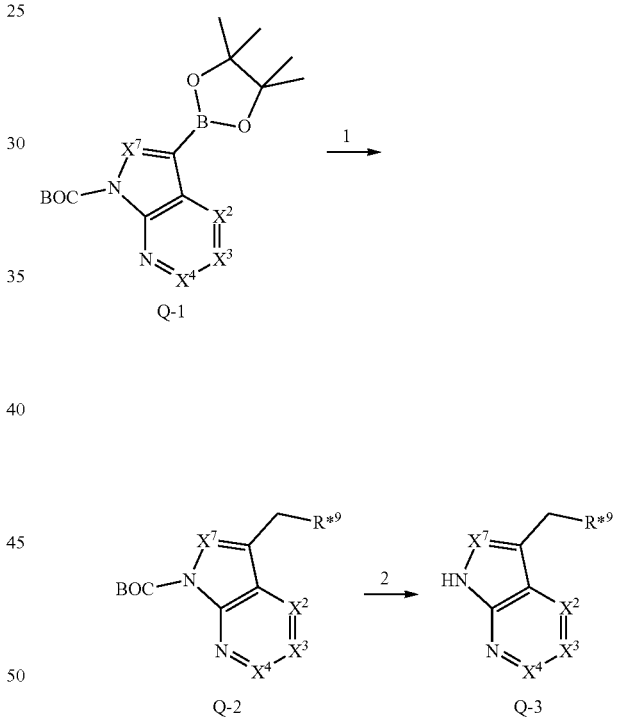

Q-1

Q-2      Q-3

In Reaction 1 of Preparation Q, the compound Q-1 (wherein $X^2$, $X^3$, $X^4$, and $X^7$, are as defined above) is converted to compound Q-2 by reacting Q-1 with a catalyst, such as palladium(II) acetate, a phosphine, such as tricyclohexylphosphine, a base, such as potassium phosphate, and a bromide compound $BrCH_2R^{*9}$ (wherein $BrCH_2R^{*9}$ represents, for example, compound B-11, E-8, F-8, or G-2 as defined above) in a biphasic solvent mixture, such as toluene/water mixture, at reflux for 18 hours.

In Reaction 2 of Preparation Q, the compound Q-2 is converted to compound Q-3 by reacting Q-2 with an acid, such as trifluoroacetic acid, in a halogenated solvent, such as dichloromethane at room temperature for 30 minutes.

Scheme 18: Preparation R

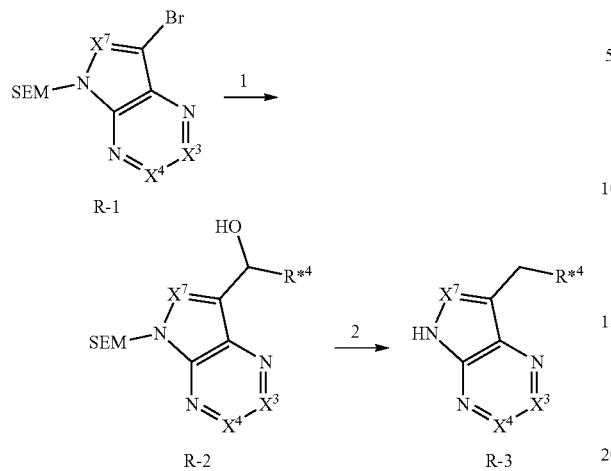

In Reaction 1 of Preparation R, the compound R-1 (wherein $X^3$, $X^4$, and $X^7$, are as defined above) is converted to compound R-2 by first reacting R-1 with an organometallic reagent, such as ethyl magnesium bromide, in an ethereal solvent, such as tetrahydrofuran, at room temperature for 30 minutes, and second reacting with aldehyde compound R*⁴CHO (wherein R*⁴CHO represents, for example, compound B-9, E-6, F-6, or G-3, as defined above) at room temperature for 0.5-3 hours.

In Reaction 2 of Preparation R, the compound R-2 is converted to the compound R-3 by reacting R-2 with an organosilane, such as triethylsilane, in an acid, such as trifluoroacetic acid, at room temperature for 30 minutes.

Scheme 19: Preparation S

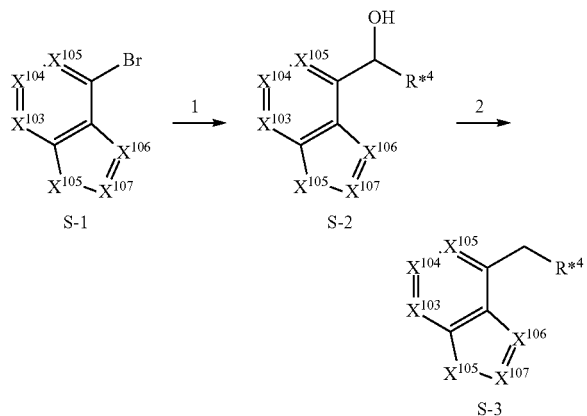

In Reaction 1 of Preparation S, the compound S-1 (wherein $X^{103}$, $X^{104}$, $X^{105}$, $X^{106}$, $X^{107}$, and $X^{108}$, are as defined above, such as wherein $X^{103}$ is N and $X^{108}$ is $NR^{117}$, such as wherein $R^{117}$ is H) is converted to compound S-2 by first reacting S-1 with a first molar equivalent of an organometallic reagent, such as n-butyl lithium, in an ethereal solvent, such as tetrahydrofuran, at −78° C. for 30 minutes, second reacting with a second molar equivalent of an organometallic reagent, such as t-butyl lithium, in an ethereal solvent, such as tetrahydrofuran, at −78° C. for 15 minutes, and third reacting with aldehyde compound R*⁴CHO (wherein R*⁴CHO represents, for example, compound B-9, E-6, F-6, or G-3, as defined above) at −78° C. to room temperature over 40 minutes.

In Reaction 2 of Preparation S, the compound S-2 is converted to the compound S-3 by reacting S-2 with an organosilane, such as triethylsilane, in an acid, such as trifluoroacetic acid, at room temperature for 30 minutes.

Scheme 20: Preparation T

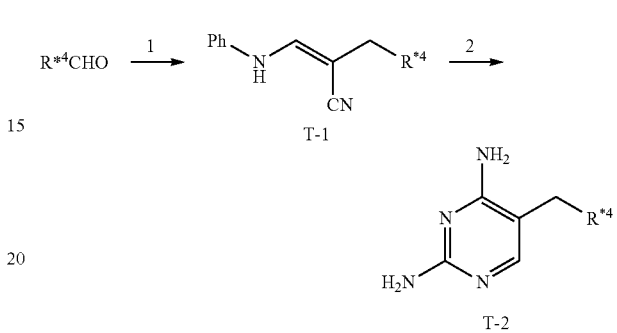

In Reaction 1 of Preparation T, the aldehyde compound R*⁴CHO (wherein R*⁴CHO represents, for example, compound B-9, E-6, F-6, or G-3, as defined above) is converted to compound T-1 by reacting R*⁴CHO with 3-(phenylamino)propanenitrile in the presence of a base, such as sodium methoxide, in a polar aprotic solvent, such as dimethylsulfoxide, at 95° C. for 1 hour.

In Reaction 2 of Preparation T, the compound T-1 is converted to compound T-2 by reacting T-2 with guanidine hydrochloride in the presence of a base, such as potassium t-butoxide, in an alcohol, such as ethanol, at 70° C. for 48 hours.

Scheme 21: Preparation U

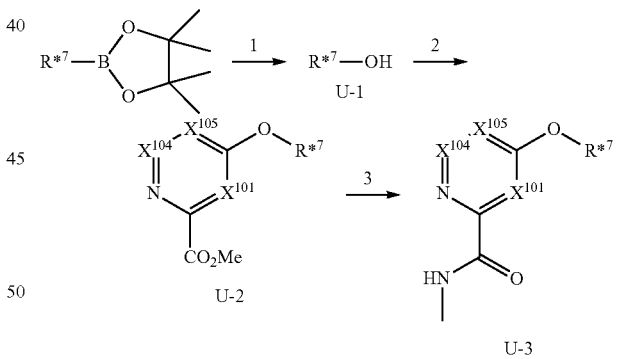

In Reaction 1 of Preparation U, the organoborate compound, such as (4,4,5,5-tetramethyl-1,3,2-dioxaborolyl)-R*⁷ (wherein (4,4,5,5-tetramethyl-1,3,2-dioxaborolyl)-R*⁷ represents, for example, compound A-9, B-13, or E-10, as defined above) is converted to alcohol compound U-1 (R*⁷—OH) by reacting (4,4,5,5-tetramethyl-1,3,2-dioxaborolyl)-R*⁷ with sodium borate-hydrate in a tetrahydrofuran/water mixture at room temperature for 16 hours.

In Reaction 2 of Preparation U, the alcohol compound U-1 (R*⁷—OH) is converted to compound U-2 (wherein $X^{101}$, $X^{104}$, and $X^{105}$, are as defined above) by reacting U-1 (R*⁷—OH) with methyl 4-chloropicolinate in the presence of sodium hydride in dimethylsulfoxide at room temperature to 100° C. over 5 hours.

In Reaction 3 of Preparation U, the compound U-2 is converted to compound U-3 by reacting U-2 with an amine, such as methyl amine, in the presence of sodium cyanide in ethanol at 125° C. for 30 minutes.

cloalkyl, $R^8$-$(C_6$-$C_{14})$aryl, or $R^8$-$(C_2$-$C_9)$heteroaryl, as defined above) by reacting V-1 with an organoboron compound, a catalyst, such as palladium(II) acetate, a ligand, such as tricyclohexylphosphine, a base, such as potassium

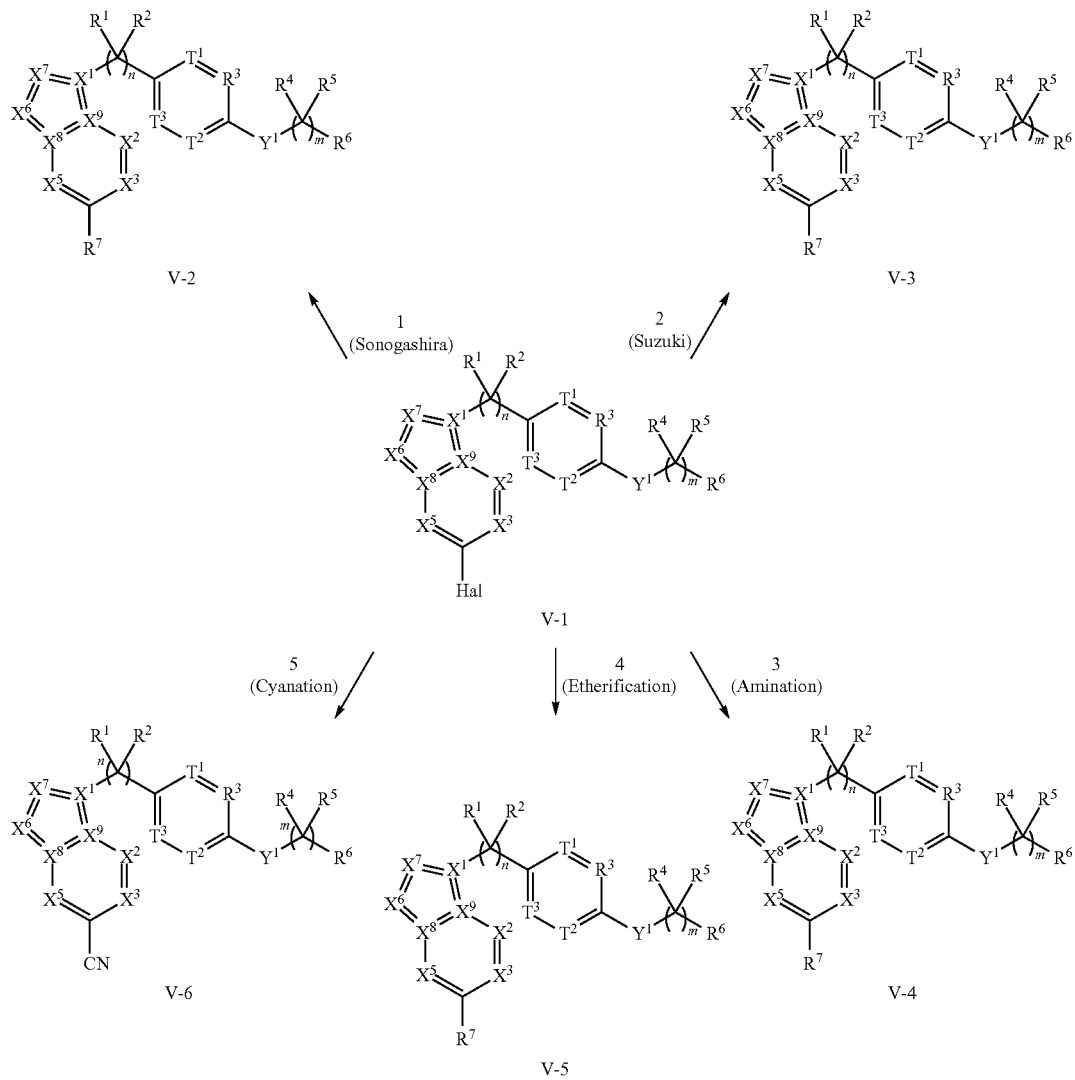

Scheme 22: Preparation V

Sonogashira Coupling: In Reaction 1 of Preparation V, the compound V-1 (wherein $X^1$, $X^2$, $X^3$, $X^5$, $X^6$, $X^7$, $X^8$, $X^9$, $R^1$, $R^2$, $R^3$, $R^4$, $R^5$, $R^6$, $T^1$, $T^2$, $T^3$, $Y^1$, n, and m, are as defined above, and Hal is I, Br, or Cl) is converted to compound V-2 (wherein $R^7$ is $(C_2$-$C_{10})$alkylnyl, $(C_2$-$C_{10})$alkynylamine, $R^8$-$(C_2$-$C_{10})$alkylnyl, or $R^8$-$(C_2$-$C_{10})$alkynylamine, as defined above) by reacting V-1 with an alkyne, a catalyst system, such as copper(I) iodide and bis(triphenylphosphine)palladium(II) chloride, and an amine, such as piperidine at 100° C. in a microwave reactor for 30 minutes.

Suzuki Coupling: In Reaction 2 of Preparation V, the compound V-1 (wherein $X^1$, $X^2$, $X^3$, $X^5$, $X^6$, $X^7$, $X^8$, $X^9$, $R^1$, $R^2$, $R^3$, $R^4$, $R^5$, $R^6$, $T^1$, $T^2$, $T^3$, $Y^1$, n, and m, are as defined above, and Hal is I, Br, or Cl) is converted to compound V-3 (wherein $R^7$ is $(C_1$-$C_{10})$alkyl, $(C_3$-$C_{10})$cycloalkyl, $(C_2$-$C_9)$heterocycloalkyl, $(C_6$-$C_{14})$aryl, $(C_2$-$C_9)$heteroaryl, $R^8$-$(C_1$-$C_{10})$alkyl-, $R^8$-$(C_3$-$C_{10})$cycloalkyl, $R^8$-$(C_2$-$C_9)$heterocyphosphate tribasic, in a biphasic solvent mixture, such as toluene/water mixture, at reflux for 1-18 hours.

Amination Coupling Reaction: In Reaction 3 of Preparation V, the compound V-1 (wherein $X^1$, $X^2$, $X^3$, $X^5$, $X^6$, $X^7$, $X^8$, $X^9$, $R^1$, $R^2$, $R^3$, $R^4$, $R^5$, $R^6$, $T^1$, $T^2$, $T^3$, $Y^1$, n, and m, are as defined above, and Hal is I, Br, or Cl) is converted to compound V-4 (wherein $R^7$ is $H_2N$—, $(CH_3)HN$—, or $(CH_3)_2N$—, or $R^8R^9N$—, as defined above) by reacting V-1 with a primary or secondary amine, a catalyst, such as $3^{rd}$ generation BrettPhos precatalyst, a ligand, such as RuPhos, a base, such as sodium t-butoxide, in an ethereal solvent, such as 1,4-dioxane, at 100° C. for 1-16 hours, or alternatively converted to V-4 by reacting V-1 with a primary or secondary amine, a catalyst, such as copper(I) iodide, a ligand, such as L-proline, a base, such as potassium carbonate, in a polar aprotic solvent, such as dimethylsulfoxide, at 150° C. for 1-16 hours, or alternatively converted to V-4 by reacting V-1 with an aromatic heterocycle, such as a 1-H-imidazole, a catalyst, such as copper(I) iodide, a diamine ligand, such as N,N'-dimethyl-1,2-cyclohexanediamine, a base, such as potassium carbonate, in a polar aprotic solvent, such as dimethylformamide, at 135° C. for 3-16 hours.

Etherification Coupling Reaction: In Reaction 4 of Preparation V, the compound V-1 (wherein $X^1$, $X^2$, $X^3$, $X^5$, $X^6$, $X^7$, $X^8$, $X^9$, $R^1$, $R^2$, $R^3$, $R^4$, $R^5$, $R^6$, $T^1$, $T^2$, $T^3$, $Y^1$, n, and m, are as defined above, and Hal is I, Br, or Cl) is converted to compound V-5 (wherein $R^7$ is $(C_1-C_{10})$alkoxy-, $R^8$-$(C_1-C_{10})$alkoxy-, $(C_2-C_9)$heterocycloalkyl-O—, $(C_6-C_{14})$aryl-O—, $(C_2-C_9)$heteroaryl-O—, $R^8$-$(C_3-C_{10})$cycloalkyl-O—, $R^8$-$(C_2-C_9)$heterocycloalkyl-O—, $R^8$-$(C_6-C_{14}$aryl-O—, or $R^8$-$(C_2-C_9)$heteroaryl-O—, as defined above) by reacting V-1 with an alcohol, a catalyst, such as copper(I)iodide, a ligand, such as 1,10-phenanthroline, a base, such as cesium carbonate, in a polar solvent, such as an alcohol or dimethylsulfoxide, at 110° C. for 1-20 hours, or alternatively converted to V-5 by reacting V-1 with an alcohol, a catalyst, such as $3^{RD}$ generation RockPhos, a base, such as cesium carbonate, in a non-polar solvent, such as toluene, at 100° C. for 5-20 hours.

Cyanation Reaction: In Reaction 5 of Preparation V, the compound V-1 (wherein $X^1$, $X^2$, $X^3$, $X^5$, $X^6$, $X^7$, $X^8$, $X^9$, $R^1$, $R^2$, $R^3$, $R^4$, $R^5$, $R^6$, $T^1$, $T^2$, $T^3$, $Y^1$, n, and m, are as defined above, and Hal is I, Br, or Cl) is converted to compound V-6 by reacting V-1 with a cyanide salt, such as zinc(II)cyanide, a catalyst, such as tetrakis(triphenylphosphine)palladium(0), in a polar aprotic solvent, such as dimethylformamide, at 100° C. for 3 hours.

Scheme 23: Preparation W

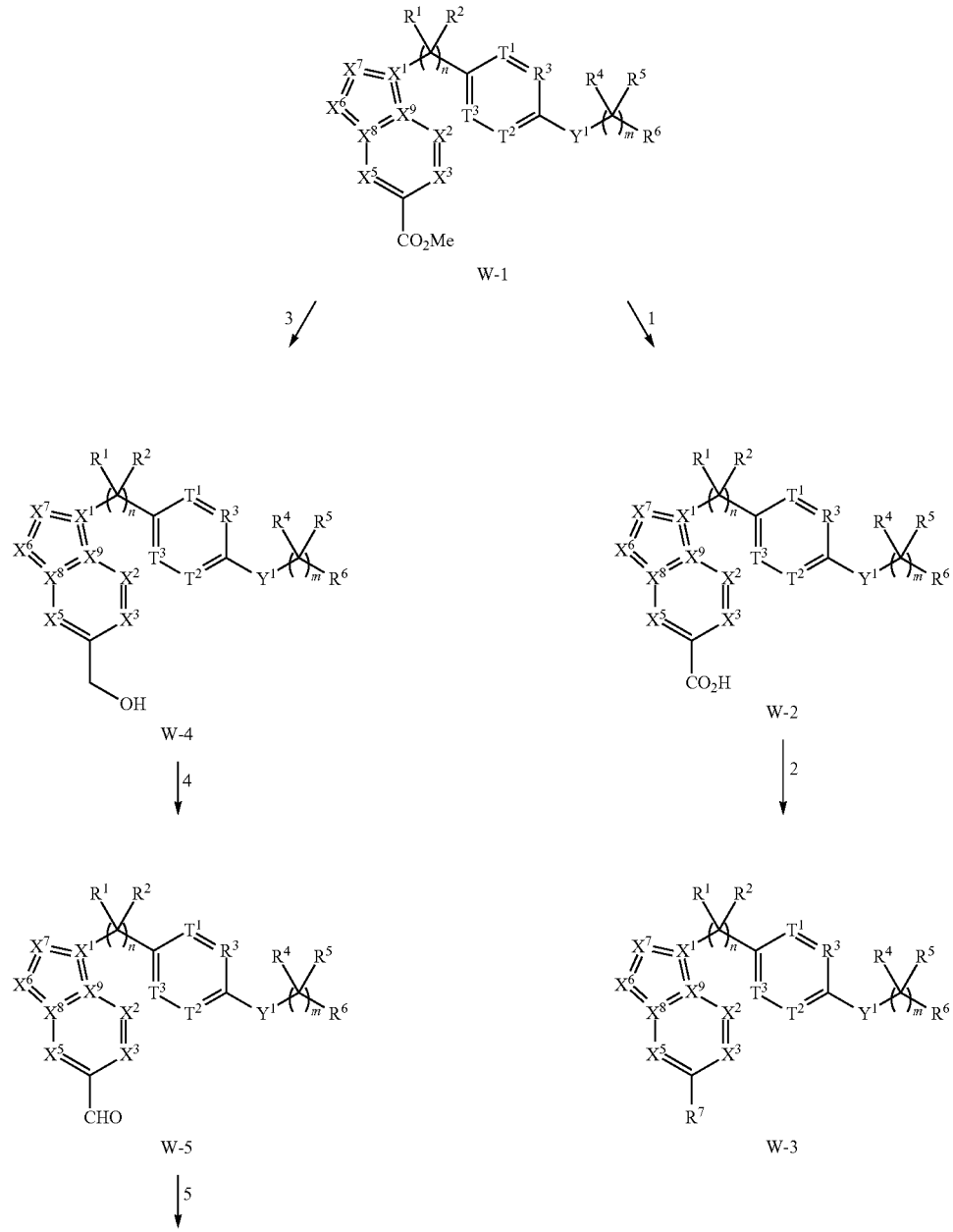

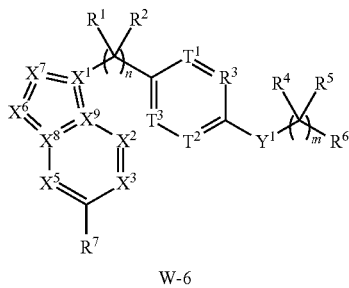

W-6

In Reaction 1 of Preparation W, the compound W-1 (wherein $X^1$, $X^2$, $X^3$, $X^5$, $X^6$, $X^7$, $X^8$, $X^9$, $R^1$, $R^2$, $R^3$, $R^4$, $R^5$, $R^6$, $T^1$, $T^2$, $T^3$, $Y^1$, n, and m, are as defined above) is converted to compound W-2 by reacting W-1 with a base, such as lithium hydroxide monohydrate, in an aqueous ethereal alcohol mixture, such as water/tetrahydrofuran/methanol mixture, at room temperature for 1 hour.

In Reaction 2 of Preparation W, the compound W-2 is converted to compound W-3 (wherein $R^7$ is $R^8R^9N(O)C$—, as defined above) by reacting W-2 with an amine, an amide coupling reagent, such as O-(benzotriazol-1-yl)-N,N,N',N'-tetramethyluronium tetrafluoroborate, and a base, such as diisopropylethylamine, in a halogenated solvent, such as dichloromethane, at room temperature for 30 minutes.

In Reaction 3 of Preparation W, the compound W-1 is converted to compound W-4 by reacting W-1 with a reducing agent, such as lithium aluminum hydride, in an ethereal solvent, such as tetrahydrofuran, at room temperature for 30 minutes.

In Reaction 4 of Preparation W, the compound W-4 is converted to compound W-5 by reacting W-4 with an oxidizing reagent, such as manganese(IV) oxide, in a halogenated solvent, such as dichloromethane, at room temperature for 22 hours.

In Reaction 5 of Preparation W, the compound W-5 is converted to compound W-6 (wherein $R^7$ is $(C_2-C_9)$heteroaryl or $R^8$-$(C_2-C_9)$heteroaryl, as defined above) by reacting W-5 with a 1,2-dicarbonyl compound, such as glyoxal, and an amine salt, such as ammonium acetate, in a polar aprotic solvent, such as N-methyl-2-pyrrolidone, at 120° C. for 16 hours.

As used herein, the term "amino" means a functional group having a nitrogen atom and 1 to 2 hydrogen atoms. "Amino" generally may be used herein to describe a primary, secondary, or tertiary amine, and those of skill in the art will readily be able to ascertain the identification of which in view of the context in which this term is used in the present disclosure. The term "amine" or "amine group" or "ammonia group" means a functional group containing a nitrogen atom derived from ammonia ($NH_3$). The amine groups are preferably primary amines, meaning the nitrogen is bonded to two hydrogen atoms and one substituent group comprising a substituted or unsubstituted alkyl or aryl group or an aliphatic or aromatic group. The amine groups may be secondary amines meaning, the nitrogen is bonded to one hydrogen atom and two substituent groups comprising a substituted or unsubstituted alkyl or aryl groups or an aliphatic or aromatic group, as defined below. The amine groups may be tertiary amines meaning the nitrogen is bonded to three substituent groups comprising a substituted or unsubstituted alkyl or aryl groups or an aliphatic or aromatic group. The amine groups may also be quaternary amines meaning the designated amine group is bonded to a fourth group, resulting in a positively charged ammonium group.

It is understood that any or all of the amines in the present invention may be in the free amine form (that is, as —$NH_2$ for a primary amine) or in a protonated form with a pharmaceutically acceptable anion (that is, as —$NH_3^+Y^-$ for a primary amine, where $Y^-$ is the pharmaceutically acceptable anion).

As used herein, the term "amide group" means a functional group comprising a carbonyl group linked to a nitrogen. A "carbonyl group" means a functional group comprising a carbon atom double bonded to an oxygen atom, represented by (C=O).

The term "alkane" means a saturated hydrocarbon, bonded by single bonds. Alkanes can be linear or branched. "Cycloalkanes" are saturated hydrocarbons rings bonded by single bonds.

As used herein, the term "$(C_1-C_{10})$alkyl" means a saturated straight chained or branched or cyclic hydrocarbon consisting essentially of 1 to 10 carbon atoms and a corresponding number of hydrogen atoms. Typically straight chained or branched groups have from one to ten carbons, or more typically one to five carbons. Exemplary $(C_1-C_{10})$alkyl groups include methyl (represented by —$CH_3$), ethyl (represented by —$CH_2$—$CH_3$), n-propyl, isopropyl, n-butyl, isobutyl, etc. Other $(C_1-C_{10})$alkyl groups will be readily apparent to those of skill in the art given the benefit of the present disclosure.

As used herein, the term "$(C_2-C_9)$heteroalkyl" means a saturated straight chained or branched or cyclic hydrocarbon consisting essentially of 2 to 10 atoms, wherein 2 to 9 of the atoms are carbon and the remaining atom(s) is selected from the group consisting of nitrogen, sulfur, and oxygen. Exemplary $(C_2-C_9)$heteroalkyl groups will be readily apparent to those of skill in the art given the benefit of the present disclosure.

As used herein, the term "$(C_3-C_{10})$cycloalkyl" means a nonaromatic saturated hydrocarbon group, forming at least one ring consisting essential of 3 to 10 carbon atoms and a corresponding number of hydrogen atoms. $(C_3-C_{10})$cycloalkyl groups can be monocyclic or multicyclic. Individual rings of multicyclic cycloalkyl groups can have different connectivities, for example, fused, bridged, spiro, etc., in addition to covalent bond substitution. Exemplary $(C_3-C_{10})$ cycloalkyl groups include cyclopropyl, cyclobutyl, cyclopentyl, cyclohexyl, norbornanyl, bicyclo-octanyl, octahydro-pentalenyl, spiro-decanyl, cyclopropyl substituted with cyclobutyl, cyclobutyl substituted with cyclopentyl, cyclohexyl substituted with cyclopropyl, etc. Other $(C_3-C_{10})$ cycloalkyl groups will be readily apparent to those of skill in the art given the benefit of the present disclosure.

As used herein, the term "$(C_2-C_9)$heterocycloalkyl" means a nonaromatic group having 3 to 10 atoms that form at least one ring, wherein 2 to 9 of the ring atoms are carbon and the remaining ring atom(s) is selected from the group consisting of nitrogen, sulfur, and oxygen. $(C_2-C_9)$heterocycloalkyl groups can be monocyclic or multicyclic. Individual rings of such multicyclic heterocycloalkyl groups can have different connectivities, for example, fused, bridged, spiro, etc., in addition to covalent bond substitution. Exemplary $(C_2-C_9)$heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl, 2-azaspiro[4.4]nonanyl, 7-oxa-1-aza-spiro[4.4]nonanyl, 7-azabicyclo[2.2.2]heptanyl, octahydro-1H-indolyl, etc. The $(C_2-C_9)$heterocycloalkyl group is typically attached to the main structure via a carbon atom or a nitrogen atom. Other $(C_2-C_9)$heterocycloalkyl groups will be readily apparent to those of skill in the art given the benefit of the present disclosure.

The term "aliphatic group" or "aliphatic" means a nonaromatic group consisting of carbon and hydrogen, and may optionally include one or more double and/or triple bonds. In other words, an aliphatic group is any group consisting of carbon and hydrogen which contains no aromatic functionality. An aliphatic group may be straight chained, branched or cyclic and typically contains between about one and about 24 carbon atoms.

The term "aryl group" may be used interchangeably with "aryl," "aryl ring," "aromatic," "aromatic group," and "aromatic ring." Aryl groups include carbocyclic aromatic groups, typically with six to fourteen ring carbon atoms. Aryl groups also include heteroaryl groups, which typically have five to fourteen ring atoms with one or more heteroatoms selected from nitrogen, oxygen and sulfur.

As used herein, the term "$(C_6-C_{14})$aryl" means an aromatic functional group having 6 to 14 carbon atoms that form at least one ring.

As used herein, the term "$(C_2-C_9)$heteroaryl" means an aromatic functional group having 5 to 10 atoms that form at least one ring, wherein 2 to 9 of the ring atoms are carbon and the remaining ring atom(s) is selected from the group consisting of nitrogen, sulfur, and oxygen. $(C_2-C_9)$heteroaryl groups can be monocyclic or multicyclic. Individual rings of such multicyclic heteroaryl groups can have different connectivities, for example, fused, etc., in addition to covalent bond substitution. Exemplary $(C_2-C_9)$heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. The $(C_2-C_9)$heteroaryl group is typically attached to the main structure via a carbon atom, however, those of skill in the art will realize when certain other atoms, for example, hetero ring atoms, can be attached to the main structure. Other $(C_2-C_9)$heteroaryl groups will be readily apparent to those of skill in the art given the benefit of the present disclosure.

The term "alkynyl" means a functional group containing triple bonded carbons, represented by $(C_2-C_{10})$alkynyl-.

As used herein, the term "alkylamine" means an $(C_1-C_{10})$ alkyl containing a primary, secondary, or tertiary amine group in place of one hydrogen atom, represented by $(C_1-C_{10})$alkyl amine and $((C_1-C_{10})alkyl)_2$amine.

The term "alkynylamine" means a $(C_2-C_{10})$ group containing triple bonded carbons and an amine group, represented by $(C_2-C_{10})$alkynylamine.

The term "alkoxy" means a $(C_1-C_{10})$alkyl bound to an oxygen, represented by $(C_1-C_{10})$alkyl-O— or $(C_1-C_{10})$ alkoxy-. The term "alkoxyalkyl" means a $(C_1-C_{10})$alkyl bound to an oxygen bound to another $(C_1-C_{10})$alkyl, represented by $(C_1-C_{10})$alkyl-O—$(C_1-C_{10})$alkyl- or $(C_1-C_{10})$alkoxy-$(C_1-C_{10})$alkyl-.

The term "alkyl ester" means a $(C_1-C_{10})$alkyl containing an ester group in place of one hydrogen atom, represented by —O(O)C—$(C_1-C_{10})$alkyl.

The term "alkyl acid" means an $(C_1-C_{10})$alkyl containing a carboxylic acid group in place of one hydrogen atom, represented by $(C_1-C_{10})$alkyl-COOH.

The term "aliphatic acid" means an acid of nonaromatic hydrocarbons, represented by $(C_1-C_{10})$alkyl-COOH and $(C_3-C_{10})$cycloalkyl-COOH.

The term "dicarbonyl" refers to an organic molecule containing two or more adjacent carbonyl groups. Carbonyl groups, represented by C═O, can be, for example, aldehydes, ketones, and other groups with an oxygen atom doubly bonded to a carbon atom. Examples include but are not limited to glyoxal, methylglyoxal, dimethyl glyoxal, and 3-deoxyglucosone.

The term "halo" or "Hal" means a fluorine (F), chlorine (Cl), bromine (Br), iodine (I), or astatine (At) ion.

The term "methoxy" means a $(C_1)$alkyl containing an oxygen in place of one hydrogen atom, represented by —(O)CH$_3$.

The term "polyol" means an alcohol containing multiple hydroxyl (—OH) groups.

"Substituted" means the substitution of a carbon in alkyl, heterocyclic or aryl groups with one or more non-carbon substituents. Non-carbon substituents are selected from nitrogen, oxygen and sulfur.

"Unsubstituted" means the group is comprised of only hydrogen and carbon.

A 3 to 10 member ring means a closed ring; the 3 to 10 member ring may be acyclic, aromatic or heterocyclic.

The term "pharmaceutically acceptable anion" means an anion that is suitable for pharmaceutical use. Pharmaceutically acceptable anions include but are not limited to halides, carbonate, bicarbonate, sulfate, bisulfate, hydroxide, nitrate, persulfate, phosphate, sulfite, acetate, ascorbate, benzoate, citrate, dihydrogen citrate, hydrogen citrate, oxalate, succinate, tartrate, taurocholate, glycocholate, and cholate.

All pharmaceutically acceptable salts, prodrugs, tautomers, hydrates and solvates of the compounds presently disclosed are also within the scope of the present disclosure.

Presently disclosed compounds that are basic in nature are generally capable of forming a wide variety of different salts with various inorganic and/or organic acids. Although such salts are generally pharmaceutically acceptable for administration to animals and humans, it is often desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g., by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

Acids which can be used to prepare the pharmaceutically acceptable acid addition salts of the base compounds are those which can form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Presently disclosed compounds that are acidic in nature, e.g., contain a COOH or tetrazole moiety, are generally capable of forming a wide variety of different salts with various inorganic and/or organic bases. Although such salts are generally pharmaceutically acceptable for administration to animals and humans, it is often desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations, and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields of the desired solid salt.

Bases which can be used to prepare the pharmaceutically acceptable base addition salts of the base compounds are those which can form non-toxic base addition salts, i.e., salts containing pharmacologically acceptable cations, such as, alkali metal cations (e.g., potassium and sodium), alkaline earth metal cations (e.g., calcium and magnesium), ammonium or other water-soluble amine addition salts such as N-methylglucamine-(meglumine), lower alkanolammonium and other such bases of organic amines.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts and prodrugs thereof, can be prepared by any means known in the art.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

The compounds, salts, prodrugs, hydrates, and solvates presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

The present disclosure also provides pharmaceutical compositions comprising at least one presently disclosed compound and at least one pharmaceutically acceptable carrier. The pharmaceutically acceptable carrier can be any such carrier known in the art including those described in, for example, Remington's Pharmaceutical Sciences, Mack Publishing Co., (A. R. Gennaro edit. 1985). Pharmaceutical compositions of the compounds presently disclosed may be prepared by conventional means known in the art including, for example, mixing at least one presently disclosed compound with a pharmaceutically acceptable carrier.

Presently disclosed pharmaceutical compositions can be used in an animal or human. Thus, a presently disclosed compound can be formulated as a pharmaceutical composition for oral, buccal, parenteral (e.g., intravenous, intramuscular or subcutaneous), topical, rectal or intranasal administration or in a form suitable for administration by inhalation or insufflation.

The compounds presently disclosed may also be formulated for sustained delivery according to methods well known to those of ordinary skill in the art. Examples of such formulations can be found in U.S. Pat. Nos. 3,119,742, 3,492,397, 3,538,214, 4,060,598, and 4,173,626.

For oral administration, the pharmaceutical composition may take the form of, for example, a tablet or capsule prepared by conventional means with a pharmaceutically acceptable excipient(s) such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); and/or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive(s) such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and/or preservative (e.g., methyl or propyl p-hydroxybenzoates or sorbic acid).

For buccal administration, the composition may take the form of tablets or lozenges formulated in a conventional manner.

Presently disclosed compounds may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent recognized by those of skill in the art. Alternatively, the active ingredient may be in powder form for reconstitution with a suitable vehicle, e.g., sterile pyrogen-free water, before use.

For topical administration, a presently disclosed compound may be formulated as an ointment or cream.

Presently disclosed compounds may also be formulated in rectal compositions such as suppositories or retention enemas, e.g., containing conventional suppository bases such as cocoa butter or other glycerides.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

A proposed dose of a presently disclosed compound for oral, parenteral or buccal administration to the average adult human for the treatment or prevention of a CSF-1R-related disease state is about 0.1 mg to about 2000 mg. In certain embodiments, the proposed dose is from about 0.1 mg to about 200 mg of the active ingredient per unit dose. Irrespective of the amount of the proposed dose, administration of the compound can occur, for example, 1 to 4 times per day.

Aerosol formulations for the treatment or prevention of the conditions referred to above in the average adult human are preferably arranged so that each metered dose or "puff" of aerosol contains about 20 mg to about 10,000 mg, preferably, about 20 mg to about 1000 mg of a presently disclosed compound. The overall daily dose with an aerosol will be within the range from about 100 mg to about 100 mg. In certain embodiments, the overall daily dose with an aerosol generally will be within the range from about 100 mg to about 10 mg. Administration may be several times daily, for example 2, 3, 4 or 8 times, giving for example, 1, 2 or 3 doses each time.

Aerosol combination formulations for the treatment or prevention of the conditions referred to above in the average adult human are preferably arranged so that each metered dose or "puff" of aerosol contains from about 0.01 mg to about 1000 mg of a combination comprising a presently disclosed compound. In certain embodiments, each metered dose or "puff" of aerosol contains about 0.01 mg to about 100 mg of a combination comprising a presently disclosed compound. In certain embodiments, each metered dose or "puff" of aerosol contains about 1 mg to about 10 mg of a combination comprising a presently disclosed compound. Administration may be several times daily, for example 2, 3, 4 or 8 times, giving for example, 1, 2 or 3 doses each time.

Pharmaceutical compositions and methods of treatment or prevention comprising administering prodrugs of at least one presently disclosed compound are also within the scope of the present disclosure.

Non-limiting examples of suitable CSF-1R inhibitors according to Formula (I) and Formula (II) are presented in the Examples below. It is understood that any or all of the amines of the structures presented in inhibitors according to Formula (I) and Formula (II) are presented in the Examples below may be in the free amine form or in a protonated form with a pharmaceutically acceptable anion. Preferred pharmaceutically acceptable anions include but are not limited to halides, carbonate, bicarbonate, sulfate, bisulfate, hydroxide, nitrate, persulfate, phosphate, sulfite, acetate, ascorbate, benzoate, citrate, dihydrogen citrate, hydrogen citrate, oxalate, succinate, tartrate, taurocholate, glycocholate, and cholate. Most preferred pharmaceutically acceptable anions include chloride, carbonate, and bicarbonate. It is also understood that any or all of the CSF-1R inhibitors according to Formula (I) and Formula (II) may be the racemate or an enantiomer of the racemate.

EXAMPLES

Example 1: Methods of Synthesis

The specific embodiments of the present disclosure are described with reference to the preparations and schemes presented below; it should be understood that such embodiments are by way of example only and merely illustrative of but a small number of the many possible specific embodiments which can represent applications of the principles of the present disclosure. Various changes and modifications to the preparations, schemes and examples will be obvious to those of skill in the art given the benefit of the present disclosure.

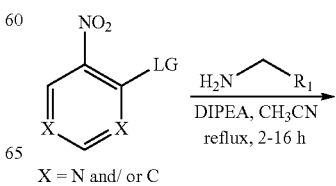

X = N and/ or C

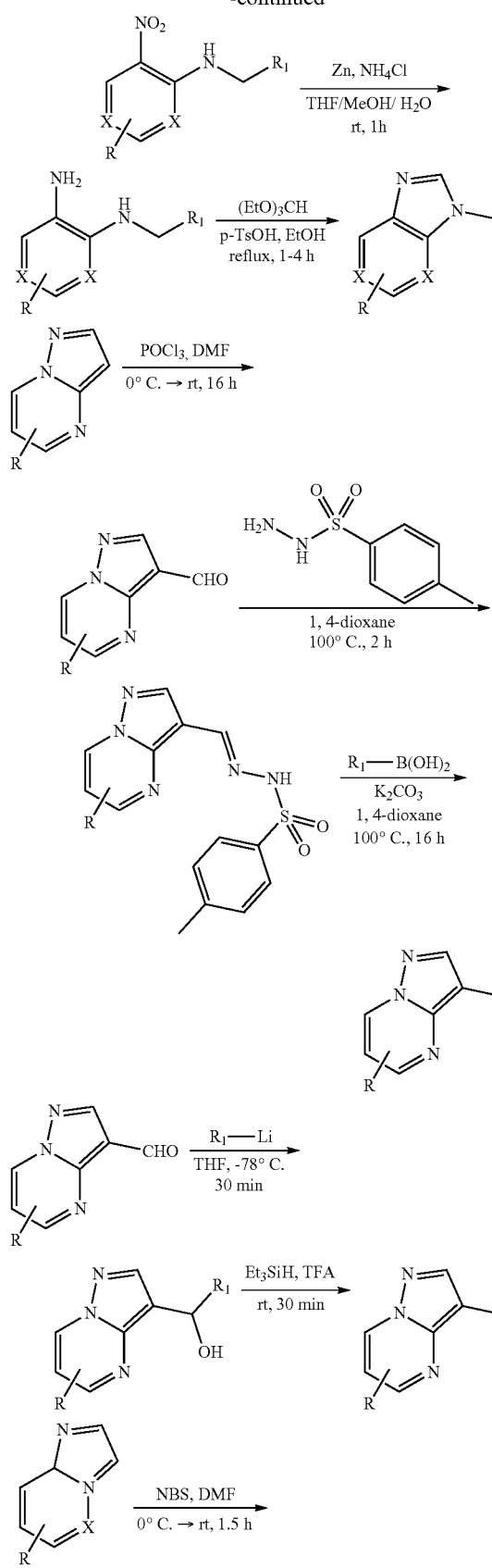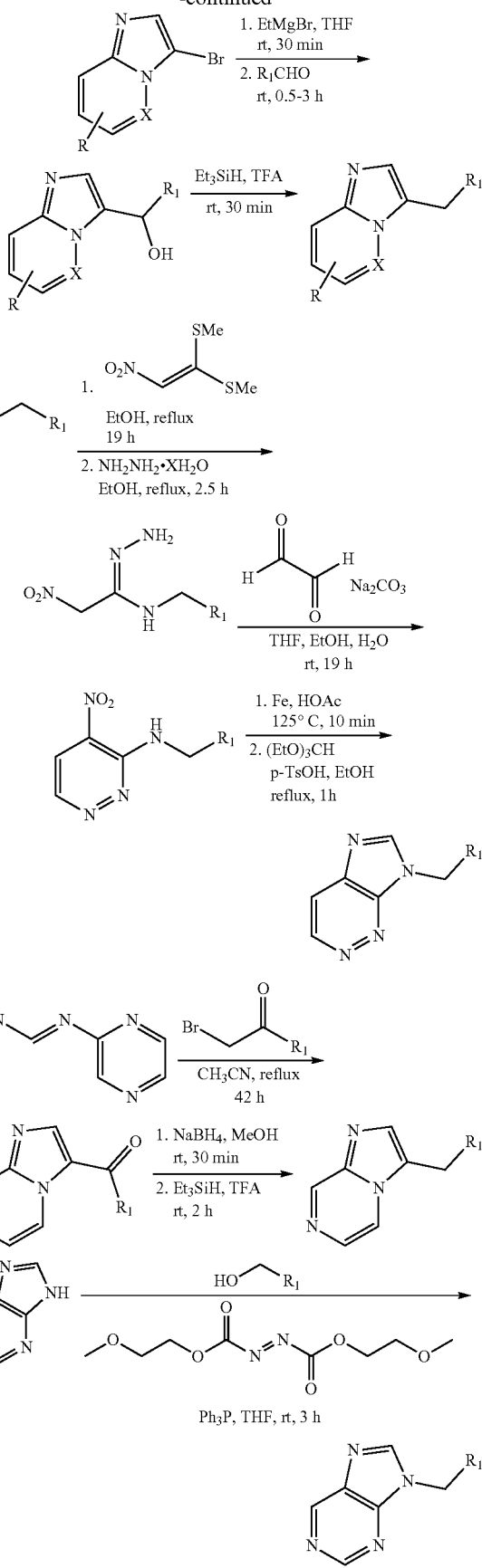

-continued

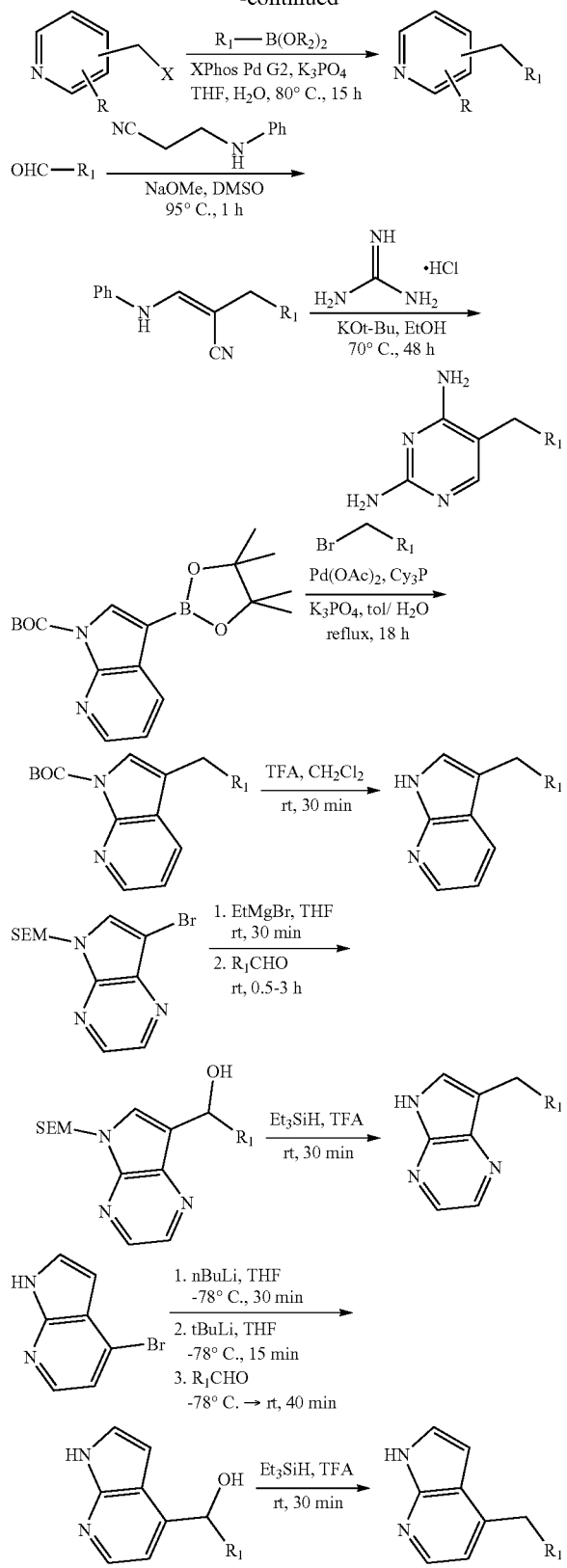

The examples below present compounds of Formula (I) and Formula (XIII) as synthesized according to the above schemes.

Example 1-1: Synthesis of 4-(1-((2-(4-methoxyphenyl)-2,3-dihydrobenzo[b][1,4]dioxin-6-yl)methyl)-1H-benzo[d]imidazol-5-yl)-2-methylbut-3-yn-2-amine

Example 1-1-1: Preparation of 4-iodo-3-(2-(4-methoxyphenyl)-2-oxoethoxy)benzamide To a stirred solution of 3-hydroxy-4-iodobenzamide (1.90 g, 7.23 mmol) in N,N-dimethylformamide (20 mL) was added 2-bromo-1-(4-methoxyphenyl)ethan-1-one (1.80 g, 7.86 mmol) and potassium carbonate (2.00 g, 14.47 mmol). The mixture was allowed to stir at room temperature. After 1 h, the mixture was diluted with brine (50 mL) and extracted with ethyl acetate (2×50 mL). The combined organic phases were dried over magnesium sulfate, filtered, and concentrated. Chromatographic purification of the crude product (silica gel, 5% methanol in dichloromethane elute) afforded 1.60 g (55%) of 4-iodo-3-(2-(4-methoxyphenyl)-2-oxoethoxy)benzamide as a yellow solid.

Example 1-1-2: Preparation of 3-(2-hydroxy-2-(4-methoxyphenyl)ethoxy)-4-iodobenzamide To a stirred solution of 4-iodo-3-(2-(4-methoxyphenyl)-2-oxoethoxy)benzamide (1.60 g, 3.89 mmol) in methanol (25 mL) at 0° C. was slowly added sodium borohydride (0.158 g, 4.18 mmol). The resulting mixture was allowed to stir at 0° C. After 1 h, the mixture was diluted with brine (50 mL) and extracted with ethyl acetate (2×50 mL). The combined organic phases were dried over magnesium sulfate, filtered, and concentrated. Chromatographic purification of the crude product (silica gel, 5% methanol in dichloromethane elute) afforded 1.50 g (94%) of 3-(2-hydroxy-2-(4-methoxyphenyl)ethoxy)-4-iodobenzamide as a yellow solid.

Example 1-1-3: Preparation of 2-(4-methoxyphenyl)-2,3-dihydrobenzo[b][1,4]dioxine-6-carboxamide To a stirred solution of 3-(2-hydroxy-2-(4-methoxyphenyl)ethoxy)-4-iodobenzamide (0.78 g, 1.88 mmol) in N,N-dimethylformamide (15 mL) was added sodium hydride (60% dispersion in mineral oil, 0.23 g, 5.75 mmol) and copper(I) iodide (0.36 g, 1.88 mmol). The resulting mixture was heated to 80° C. After 2 h, the mixture was allowed to cool to room temperature and was filtered through Celite. The filtrate was concentrated. Chromatographic purification of the crude product (silica gel, 1-2% methanol in dichloromethane elute) afforded 0.41 g (76%) of 2-(4-methoxyphenyl)-2,3-dihydrobenzo[b][1,4]dioxine-6-carboxamide as a white solid.

Example 1-1-4: Preparation of (2-(4-methoxyphenyl)-2,3-dihydrobenzo[b][1,4]dioxin-6-yl)methanamine To a stirred solution of 2-(4-methoxyphenyl)-2,3-dihydrobenzo[b][1,4]dioxine-6-carboxamide (0.43 g, 1.51 mmol) in tetrahydrofuran (10 mL) was added 1.0 M borane-tetrahydrofuran complex (30 mL, 30 mmol) The resulting mixture was heated to reflux. After 16 h, the mixture was allowed to cool to room temperature and was quenched by the slow addition of methanol (20 mL). The mixture was allowed to stir at room temperature. After 2 h, the mixture was concentrated. Chromatographic purification of the crude product (silica gel, 10% methanol in dichloromethane elute) afforded 0.32 g (75%) of (2-(4-methoxyphenyl)-2,3-dihydrobenzo[b][1,4]dioxin-6-yl)methanamine as a yellow solid.

Example 1-1-5: Preparation of 4-iodo-N-((2-(4-methoxyphenyl)-2,3-dihydrobenzo[b][1,4]dioxin-6-yl)methyl)-2-nitroaniline To a stirred solution of (2-(4-methoxyphenyl)-2,3-dihydrobenzo [b][1,4]dioxin-6-yl)methanamine (0.25 g, 0.92 mmol) in acetonitrile (25 mL) was added 2-fluoro-4-iodo-1-nitrobenzene (0.27 g, 1.01 mmol) and potassium carbonate (0.26 mg, 1.85 mmol). The resulting mixture heated to reflux. After 1 h, the mixture was allowed to cool to room temperature and was filtered. The filtrate was concentrated. Chromatographic purification of the crude product (silica gel, 10% methanol in dichloromethane elute) afforded 0.24 g (50%) of 4-iodo-N-((2-(4-methoxyphenyl)-2,3-dihydrobenzo[b][1,4]dioxin-6-yl)methyl)-2-nitroaniline as a yellow solid.

Example 1-1-6: Preparation of 4-iodo-$N^1$-((2-(4-methoxyphenyl)-2,3-dihydrobenzo[b][1,4]dioxin-6-yl)methyl)benzene-1,2-diamine To a stirred suspension of 4-iodo-N-((2-(4-methoxyphenyl)-2,3-dihydrobenzo[b][1,4]dioxin-6-yl)methyl)-2-nitroaniline (0.26 g, 0.51 mmol) in ethanol (20 mL) and water (5 mL) was added iron powder (0.14 g, 2.52 mmol) and ammonium chloride (0.13 g, 2.52 mmol). The resulting mixture was heated to reflux. After 1 h, the mixture was allowed to cool to room temperature and was filtered. The filtrate was concentrated. Chromatographic purification of the crude product (neutral alumina, 5% methanol in dichloromethane elute) afforded 0.23 g (91%) of 4-iodo-$N^1$-((2-(4-methoxyphenyl)-2,3-dihydrobenzo[b][1,4]dioxin-6-yl)methyl)benzene-1,2-diamine as a yellow solid.

Example 1-1-7: Preparation of 5-iodo-1-((2-(4-methoxyphenyl)-2,3-dihydrobenzo[b][1,4]dioxin-6-yl)methyl)-1H-benzo[d]imidazole To a stirred solution of 4-iodo-$N^1$-((2-(4-methoxyphenyl)-2,3-dihydrobenzo[b][1,4]dioxin-6-yl)methyl)benzene-1,2-diamine (0.22 g, 0.42 mmol) in in N,N-dimethylformamide (30 mL) was added triethyl orthoformate (0.46 g, 3.09 mmol) and p-toluenesulfonic acid monohydrate (0.038 g, 0.22 mmol). The mixture was allowed to stir at room temperature. After 1 h, the mixture was diluted with water (150 mL), and the resulting precipitate was isolated by filtration. Chromatographic purification of the crude product (neutral alumina, 2% methanol in dichloromethane elute) afforded 0.20 g (93%) of 5-iodo-1-((2-(4-methoxyphenyl)-2,3-dihydrobenzo[b][1,4]dioxin-6-yl)methyl)-1H-benzo[d]imidazole as a yellow solid.

Example 1-1-8: Preparation of 4-(1-((2-(4-methoxyphenyl)-2,3-dihydrobenzo[b][1,4]dioxin-6-yl)methyl)-1H-benzo[d]imidazol-5-yl)-2-methylbut-3-yn-2-amine To a stirred solution of 5-iodo-1-((2-(4-methoxyphenyl)-2,3-dihydrobenzo[b][1,4]dioxin-6-yl)methyl)-1H-benzo[d]imidazole (0.17 g, 0.34 mmol) in tetrahydrofuran (3 mL) was added 2-methylbut-3-yn-2-amine (0.057 g, 0.68 mmol), copper(I) iodide (0.026 g, 0.14 mmol), piperidine (0.15 g, 1.70 mmoL), and bis(triphenylphosphine)palladium(II) dichloride (0.048 g, 0.068 mmol). The mixture was heated to 60° C. in a microwave reactor. After 30 min, the mixture was allowed to cool to room temperature and was filtered. Chromatographic purification of the crude product (prep-HPLC) afforded 0.029 g (19%) of 4-(1-((2-(4-methoxyphenyl)-2,3-dihydrobenzo[b][1,4]dioxin-6-yl)methyl)-1H-benzo[d]imidazol-5-yl)-2-methylbut-3-yn-2-amine as a yellow solid: $^1$H NMR (500 MHz, CDCl$_3$) δ 7.96 (s, 1H), 7.88 (s, 1H), 7.35-7.30 (m, 3H), 7.25 (d, J=8.5 Hz, 1H), 6.97-6.93 (m, 3H), 6.77 (d, J=2.0 Hz, 1H), 6.73 (dd, J=8.5, 2.0 Hz, 1H), 5.26 (s, 2H), 5.07-5.05 (m, 1H), 4.32-4.30 (m, 1H), 4.03-3.99 (m, 1H), 3.84 (s, 3H), 1.54 (s, 6H) ppm; (M+1)=454.

Example 1-2: Synthesis of 4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine Example 1-2-1: Preparation of 5-iodo-N-((2-(4-methoxyphenyl)-2,3-dihydrobenzo[b][1,4]dioxin-6-yl)methyl)-3-nitropyridin-2-amine To a stirred solution of (2-(4-methoxyphenyl)-2,3-dihydrobenzo[b][1,4]dioxin-6-yl)methanamine (0.51 g, 1.87 mmol, Example 1-1-4) in acetonitrile (10 mL) was added 2-chloro-5-iodo-3-nitropyridine (0.64 g, 2.25 mmol) and diisopropylethylamine (0.60 g, 4.68 mmol). The resulting bright yellow mixture was heated to reflux. After 5 h, the mixture was allowed to cool to room temperature and was diluted with water (40 mL). The mixture was extracted with ethyl acetate (3×25 mL). The combined organic extracts were washed with brine (30 mL), dried over magnesium sulfate, filtered, and concentrated. Chromatographic purification of the crude product (CombiFlash, 40 g silica gel column, 0-33% ethyl acetate/hexanes elute) afforded 0.81 g (84%) of 5-iodo-N-((2-(4-methoxyphenyl)-2,3-dihydrobenzo[b][1,4]dioxin-6-yl)methyl)-3-nitropyridin-2-amine as a yellow solid.

Example 1-2-2: Preparation of 5-iodo-$N^2$-((2-(4-methoxyphenyl)-2,3-dihydrobenzo[b][1,4]dioxin-6-yl)methyl)pyridine-2,3-diamine To a stirred solution of was added 5-iodo-N-((2-(4-methoxyphenyl)-2,3-dihydrobenzo[b][1,4]dioxin-6-yl)methyl)-3-nitropyridin-2-amine (0.81 g, 1.57 mmol) in acetic acid (15 mL) was added iron powder (0.61 g, 10.96 mmol). The mixture was heated to 100° C., and as the mixture warmed, the initial bright yellow color gradually darkened to gray-brown. After 45 min, the gray-brown suspension was allowed to cool to room temperature and was diluted with ethyl acetate (50 mL). The resulting suspension was filtered through Celite with the aid of additional ethyl acetate (30 mL). The filtrate was washed with brine (1×25 mL) and 1N sodium hydroxide solution (3×25 mL). The organic phase was dried over magnesium sulfate, filtered, and concentrated to provide 0.77 g (100%) of 5-iodo-$N^2$-((2-(4-methoxyphenyl)-2,3-dihydrobenzo[b][1,4]dioxin-6-yl)methyl)pyridine-2,3-diamine as a brown solid.

Example 1-2-3: Preparation of 6-iodo-3-((2-(4-methoxyphenyl)-2,3-dihydrobenzo[b][1,4]dioxin-6-yl)methyl)-3H-imidazo[4,5-b]pyridine To a stirred suspension of 5-iodo-$N^2$-((2-(4-methoxyphenyl)-2,3-dihydrobenzo[b][1,4]dioxin-6-yl)methyl)pyridine- 2,3-diamine (0.77 mg, 1.57 mmol) in ethanol (15 mL) was added triethyl orthoformate (0.70 g, 4.70 mmol), and p-toluenesulfonic acid monohydrate (0.014 g, 0.078 mmol). The mixture was heated to reflux. After 30 min, the brown solution was allowed to cool to room temperature. The mixture was diluted with water (40 mL) and extracted with dichloromethane (2×30 mL). The combined organic phases were washed with brine (30 mL), dried over magnesium sulfate, filtered, and concentrated. Chromatographic purification of the crude product (CombiFlash, 40 g silica gel column, 1-5% 2M ammonia in methanol/dichloromethane elute) afforded 0.54 g (70%) of 6-iodo-3-((2-(4-methoxyphenyl)-2,3-dihydrobenzo [b][1,4]dioxin-6-yl)methyl)-3H-imidazo[4,5-b]pyridine as a tan solid.

Example 1-2-4: Preparation of 4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine To a stirred solution of 6-iodo-3-((2-(4-methoxyphenyl)-2,3-dihydrobenzo[b][1,4]dioxin-6-yl)methyl)-3H-imidazo[4,5-b]pyridine (0.10 g, 0.20 mmol), in piperidine (3.5 mL) was added 2-methylbut-3-yn-2-amine (0.021 g, 0.24 mmol), copper(I) iodide (0.008 g, 0.040 mmol), and bis(triphenylphosphine)palladium(II) chloride (0.014 g, 0.020 mmol). The mixture was heated to 100° C. in the microwave reactor. After 30 min, the reaction mixture was diluted with 5N ammonium hydroxide solution (30 mL) and extracted with dichloromethane (3×25 mL). The combined organic phases were dried over magnesium sulfate, filtered, and concentrated. Chromatographic purification of the crude product (CombiFlash, 40 g silica gel column, 1-5% 2M ammonia in methanol/dichloromethane elute) afforded 0.060 g (66%) of 4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine as an off-white solid: $^1$H NMR (400 MHz, CDCl$_3$) δ 8.46 (d, J=1.8 Hz, 1H), 8.07 (d, J=1.8 Hz, 1H), 8.02 (s, 1H), 7.34-7.30 (m, 2H), 6.96-6.92 (m, 3H), 6.89 (d, J=2.0 Hz, 1H), 6.83 (dd, J=8.3, 2.1 Hz, 1H), 5.36 (s, 2H), 5.04 (dd, J=8.9, 2.3 Hz, 1H), 4.29 (dd, J=11.5, 2.4 Hz, 1H), 3.99 (dd, J=11.5, 9.0 Hz, 1H), 3.82 (s, 3H), 1.77 (br s, 2H), 1.53 (s, 6H) ppm; (M+1)=455.

Example 1-2-5: Chiral separation of 4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine The racemic 4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine was subjected to SFC preparative purification (21.2×250 mm LUX-3 column, 50% methanol/0.2% diethylamine modifier, 45 g/min flow rate, 100 bar pressure, sample concentration 20 mg/mL) to afford the individual enantiomers (absolute configuration not assigned).

Example 1-3: Synthesis of 3-((2-(4-methoxyphenyl)-2,3-dihydrobenzo[b][1,4]dioxin-6-yl)methyl)-6-(4-methylpiperazin-1-yl)-3H-imidazo[4,5-b]pyridine To a stirred solution of 6-iodo-3-((2-(4-methoxyphenyl)-2,3-dihydrobenzo[b][1,4]dioxin-6-yl)methyl)-3H-imidazo[4,5-b]pyridine (0.19 g, 0.38 mmol, Example 1-2-3) in dimethyl sulfoxide (3.5 mL) was added 1-methylpiperazine (0.046 g, 0.46 mmol), L-proline (0.011 g, 0.091 mmol), potassium carbonate (0.18 g, 1.33 mmol), and copper(I) iodide (0.009 g, 0.047 mmol). The resulting light yellow suspension was heated to 150° C. After 16 h, the mixture was allowed to cool to room temperature and was diluted with 3N ammonium hydroxide solution (15 mL). The mixture was extracted with dichloromethane (3×20 mL). The combined organic phases were washed with water (2×15 mL) and brine (20 mL), dried over magnesium sulfate, filtered, and concentrated. Chromatographic purification of the crude product (CombiFlash, 12 g silica gel column, 1-10% methanol/dichloromethane elute) afforded 0.048 g (27%) of 3-((2-(4-methoxyphenyl)-2,3-dihydrobenzo[b][1,4]dioxin-6-yl)methyl)-6-(4-methylpiperazin-1-yl)-3H-imidazo[4,5-b]pyridine as an off-white solid: $^1$H NMR (400 MHz, CDCl$_3$) δ 8.26 (d, J=2.5 Hz, 1H), 7.95 (s, 1H), 7.63 (d, J=2.5 Hz, 1H), 7.33-7.29 (m, 2H), 6.79-7.00 (m, 5H), 5.33 (s, 2H), 5.03 (dd, J=9.0, 2.4 Hz, 1H), 4.29 (dd, J=11.5, 2.4 Hz, 1H), 3.99 (dd, J=11.5, 9.0 Hz, 1H), 3.82 (s, 3H), 3.19-3.33 (m, 4H), 2.57-2.70 (m, 4H), 2.38 (s, 3H) ppm (M+1)=472.

Example 1-4: Synthesis of 3-((2-(4-methoxyphenyl)-2,3-dihydrobenzo[b][1,4]dioxin-6-yl)methyl)-6-(1-methyl-1H-pyrazol-4-yl)-3H-imidazo[4,5-b]pyridine To a stirred solution of 6-iodo-3-((2-(4-methoxyphenyl)-2,3-dihydrobenzo[b][1,4]dioxin-6-yl)methyl)-3H-imidazo[4,5-b]pyridine (0.15 g, 0.30 mmol) in 1,2-dimethoxyethane (3 mL) and water (0.3 mL) was added 1-methyl-4-(4,4,5,5-tetramethyl-1,3,2-dioxaborolan-2-yl)-1H-pyrazole (0.076 g, 0.36 mmol), cesium carbonate (0.30 g, 0.91 mmol), tetrakis(triphenylphosphine)palladium(0) (0.035 g, 0.030 mmol). The resulting mixture was heated to 100° C. After 7 h, the mixture was allowed to cool room temperature and was diluted with ethyl acetate. The mixture was filtered through Celite, and the filtrate was concentrated. Chromatographic purification of the crude product (CombiFlash, silica gel column, 90% ethyl acetate/heptane elute) afforded a beige oil which crystallized on standing. The beige solid was treated with acetonitrile and water, and the resulting precipitate was isolated by filtration to provide 0.050 g (37%) of 3-((2-(4-methoxyphenyl)-2,3-dihydrobenzo[b][1,4]dioxin-6-yl)methyl)-6-(1-methyl-1H-pyrazol-4-yl)-3H-imidazo[4,5-b]pyridine as a white solid: $^1$H NMR (400 MHz, DMSO-d$_6$) δ 8.65 (d, J=1.9 Hz, 1H), 8.56 (s, 1H), 8.29-8.19 (m, 2H), 7.97 (d, J=0.9 Hz, 1H), 7.41-7.30 (m, 2H), 7.02-6.93 (m, 3H), 6.90 (d, J=1.2 Hz, 2H), 5.39 (s, 2H), 5.12 (dd, J=8.5, 2.4 Hz, 1H), 4.33 (dd, J=11.6, 2.5 Hz, 1H), 4.04 (dd, J=11.6, 8.5 Hz, 1H), 3.88 (s, 3H), 3.75 (s, 3H).

Example 1-5: Synthesis of 4-(3-((2-(6-methoxypyridin-3-yl)-2,3-dihydrobenzo[b][1,4]dioxin-6-yl)methyl)-3H-imidazo[4,5-b]pyridin-6-yl)- 2-methylbut-3-yn-2-amine Example 1-5-1: Preparation of 4-iodo-3-(2-(6-methoxypyridin-3-yl)-2-oxoethoxy)benzamide To a stirred solution of 3-hydroxy-4-iodobenzamide (1.36 g, 5.16 mmol) in N,N-dimethylformamide (20 mL) was added potassium carbonate (1.95 g, 14.08 mmol) and 2-bromo-1-(6-methoxypyridin-3-yl)ethanone (1.08 g, 4.69 mmol). The resulting reaction mixture was heated to 80° C. After 2 h, the mixture was allowed to cool to room temperature and was diluted with water (100 mL). The mixture was extracted with dichloromethane (2×40 mL). The combined organic extracts were washed with water (40 mL) and brine (40 mL), dried over magnesium sulfate, filtered, and concentrated. Chromatographic purification of the crude product (CombiFlash, silica gel column, 0-100% ethyl acetate/heptane elute) afforded 0.89 g, (46%) of 4-iodo-3-(2-(6-methoxypyridin-3-yl)-2-oxoethoxy)benzamide as a tan solid.

Example 1-5-2: Preparation of 3-(2-hydroxy-2-(6-methoxypyridin-3-yl)ethoxy)-4-iodobenzamide To a stirred solution of 4-iodo-3-(2-(6-methoxypyridin-3-yl)-2-oxoethoxy)benzamide (0.89 g, 2.15 mmol) in tetrahydrofuran (20 mL) and water (5 mL) was added sodium borohydride (0.16 g, 4.30 mmol). The resulting mixture was allowed to stir at room temperature After 16 h, the mixture was quenched with a saturated ammonium chloride solution (30 mL). The mixture was extracted with ethyl acetate (3×25 mL). The combined organic phases were washed with brine (30 mL), dried over magnesium sulfate, filtered, and concentrated to provide 0.89 g (100%) of 3-(2-hydroxy-2-(6-methoxypyridin-3-yl)ethoxy)-4-iodobenzamide as an off-white solid.

Example 1-5-3: Preparation of 2-(6-methoxypyridin-3-yl)-2,3-dihydrobenzo[b][1,4]dioxine-6-carboxamide To a stirred solution of 3-(2-hydroxy-2-(6-methoxypyridin-3-yl)ethoxy)-4-iodobenzamide (0.93 g, 2.24 mmol) in N,N-dimethylformamide (15 mL) was added sodium hydride (60% dispersion, 0.27 g, 6.71 mmol). The reaction was allowed to stir at room temperature for 15 min, and then copper(I) iodide (0.43 g, 2.24 mmol) was added. The mixture was heated to 80° C. After 3 h, the mixture allowed to cool to room temperature and was diluted with water (75 mL). The mixture was extracted with dichloromethane (3×25 mL). The combined organic phases were washed with brine (50 mL), dried over magnesium sulfate, filtered, and concentrated. Chromatographic purification of the crude product (CombiFlash, 40 g silica gel column, 1-10% methanol/dichloromethane elute) afforded 0.40 g (63%) of 2-(6-methoxypyridin-3-yl)-2,3-dihydrobenzo[b][1,4]dioxine-6-carboxamide as a tan solid.

Example 1-5-4: Preparation of (2-(6-methoxypyridin-3-yl)-2,3-dihydrobenzo[b][1,4]dioxin-6-yl)methanamine To a stirred solution of 2-(6-methoxypyridin-3-yl)-2,3-dihydrobenzo[b][1,4]dioxine-6-carboxamide (0.40 g, 1.40 mmol) in tetrahydrofuran (10 mL) was added 1.0 M borane-tetrahydrofuran complex (5.6 mL, 5.60 mmol). The mixture was heated to reflux. After 2 h, the mixture was cooled to 0° C. Methanol (5 mL) was added slowly to quench the reaction, and the resulting mixture was heated to reflux. After 1 h, the mixture was allowed to cool to room temperature and was concentrated. The residue was dissolved in tetrahydrofuran (20 mL) and 1N hydrochloric acid solution (10 mL). The resulting mixture was heated to reflux. After 2 h, the mixture was allowed to cool to room temperature, and the pH of the mixture was adjusted to ~7 by the addition of 1N sodium hydroxide solution. The neutral mixture was extracted with dichloromethane (3×25 mL). The combined organic phases were washed with brine (40 mL), dried over magnesium sulfate, filtered, and concentrated to afford 0.38 g (100%) of (2-(6-methoxypyridin-3-yl)-2,3-dihydrobenzo[b][1,4]dioxin-6-yl)methanamine as an oil.

Example 1-5-5: Preparation of 5-iodo-N-((2-(6-methoxypyridin-3-yl)-2,3-dihydrobenzo[b][1,4]dioxin-6-yl)methyl)-3-nitropyridin-2-amine To a stirred solution of (2-(6-methoxypyridin-3-yl)-2,3-dihydrobenzo[b][1,4]dioxin-6-yl)methanamine (0.38 g, 1.40 mmol) in acetonitrile (10 mL) was added 2-chloro-5-iodo-3-nitropyridine (0.48 g, 1.67 mmol) and diisopropylethylamine (0.54 g, 4.19 mmol). The resulting yellow mixture was heated to reflux. After 4 h, the mixture was allowed to cool to room temperature and was diluted with water (40 mL). The mixture was extracted with ethyl acetate (3×25 mL). The combined organic phases were washed with brine (40 mL), dried over magnesium sulfate, filtered, and concentrated. Chromatographic purification of the crude product (CombiFlash, 40 g silica gel column, 0-33% ethyl acetate/hexanes elute) afforded 0.35 g (48%) of 5-iodo-N-((2-(6-methoxypyridin-3-yl)-2,3-dihydrobenzo[b][1,4]dioxin-6-yl)methyl)-3-nitropyridin-2-amine as a yellow solid.

Example 1-5-6: Preparation of 5-iodo-$N^2$-((2-(6-methoxypyridin-3-yl)-2,3-dihydrobenzo[b][1,4]dioxin-6-yl)methyl)pyridine-2,3-diamine To a stirred suspension of 5-iodo-N-((2-(6-methoxypyridin-3-yl)-2,3-dihydrobenzo[b][1,4]dioxin-6-yl)methyl)-3-nitropyridin-2-amine (0.35 g, 0.67 mmol) in acetic acid (8 mL) was added iron powder (0.26 g, 4.71 mmol). The mixture was heated to 100° C., and as the mixture warmed, the initial bright yellow color gradually darkened to gray-brown. After 45 min, the gray-brown suspension was allowed to cool to room temperature and was diluted with ethyl acetate (50 mL). The resulting suspension was filtered through Celite with the aid of additional ethyl acetate (25 mL). The filtrate was washed with brine (1×25 mL) and IN sodium hydroxide solution (3×25 mL). The organic phase was dried over magnesium sulfate, filtered, and concentrated to provide 0.30 g (91%) of 5-iodo-$N^2$-((2-(6-methoxypyridin-3-yl)-2,3-dihydrobenzo[b][1,4]dioxin-6-yl)methyl)pyridine-2,3-diamine as an orange solid.

Example 1-5-7: Preparation of 6-iodo-3-((2-(6-methoxypyridin-3-yl)-2,3-dihydrobenzo[b][1,4]dioxin-6-yl)methyl)-3H-imidazo[4,5-b]pyridine To a stirred suspension of 5-iodo-$N^2$-((2-(6-methoxypyridin-3-yl)-2,3-dihydrobenzo[b][1,4]dioxin-6-yl)methyl)pyridine-2,3-diamine (0.300 g, 0.61 mmol) in ethanol (10 mL) was added triethyl orthoformate (0.27 g, 1.84 mmol) and p-toluenesulfonic acid monohydrate (0.006 g, 0.031 mmol). The resulting mixture was heated to reflux. After 30 min, the brown solution was allowed to cool to room temperature and was diluted with water (40 mL). The mixture was extracted with dichloromethane (3×25 mL). The combined organic extracts were washed with brine (30 mL), dried over magnesium sulfate, filtered, and concentrated. Chromatographic purification of the crude product (CombiFlash, 40 g silica gel column, 1-5% 2M ammonia in methanol/dichloromethane elute) afforded 0.30 g (98%) of 6-iodo-3-((2-(6- methoxypyridin-3-yl)-2,3-dihydrobenzo[b][1,4]dioxin-6-yl) methyl)-3H-imidazo[4,5-b]pyridine as a tan solid.

Example 1-5-8: Preparation of 4-(3-((2-(6-methoxy-pyridin-3-yl)-2,3-dihydrobenzo[b][1,4]dioxin-6-yl) methyl)-3H-imidazo[4,5-b]pyridin-6-yl)-2-methyl-but-3-yn-2-amine To a stirred solution of 6-iodo-3-((2-(6-methoxypyridin-3-yl)-2,3-dihydrobenzo[b][1,4]dioxin-6-yl)methyl)-3H-imidazo[4,5-b]pyridine (0.22 g, 0.45 mmol) in piperidine (3.5 mL) was added 2-methylbut-3-yn-2-amine (0.047 g, 0.53 mmol), copper(I) iodide (0.017 mg, 0.089 mmol), and bis(triphenylphosphine)palladium(II) chloride (0.031 mg, 0.044 mmol). The mixture was heated to 100° C. in the microwave reactor. After 30 min, the reaction mixture was diluted with 5N ammonium hydroxide solution (30 mL) and extracted with dichloromethane (3×25 mL). The combined organic phases were dried over magnesium sulfate, filtered, and concentrated. Chromatographic purification of the crude product (CombiFlash, 12 g silica gel column, 1-5% 2M ammonia in methanol/dichloromethane elute) afforded 0.16 g (79%) of 4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine, also known as GENZ-882706 and RA03546849, as an off-white solid:: $^1$H NMR (400 MHz, CDCl$_3$) δ 8.46 (d, J=1.8 Hz, 1H), 8.19 (d, J=2.4 Hz, 1H), 8.07 (d, J=1.8 Hz, 1H), 8.03 (s, 1H), 7.59 (dd, J=8.6, 2.5 Hz, 1H), 6.87-6.96 (m, 2H), 6.84 (dd, J=8.3, 2.1 Hz, 1H), 6.79 (d, J=8.6 Hz, 1H), 5.36 (s, 2H), 5.07 (dd, J=8.7, 2.3 Hz, 1H), 4.30 (dd, J=11.6, 2.3 Hz, 1H), 4.02 (dd, J=11.6, 8.7 Hz, 1H), 3.95 (s, 3H), 1.80 (br s, 2H), 1.53 (s, 6H) ppm; (M+1)=456.

Example 1-5-9: Chiral separation of 4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine The racemic 4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine was subjected to SFC preparative purification (21.2×250 mm Chiralcel OJ column, 25% ethanol/0.2% diethylamine modifier, 75 g/min flow rate) to afford the individual enantiomers.

Example 1-6: Synthesis of 3-((2-(6-methoxypyridin-3-yl)-2,3-dihydrobenzo[b][1,4]dioxin-6-yl)methyl)-6-(4-methylpiperazin-1-yl)-3H-imidazo[4,5-b]pyridine The title compound was prepared from 3-((2-(6-methoxy-pyridin-3-yl)-2,3-dihydrobenzo[b][1,4]dioxin-6-yl)methyl)-6-(4-methylpiperazin-1-yl)-3H-imidazo[4,5-b]pyridine (Example 1-5-7) and 1-methylpiperazine as described in Example 1-3: $^1$H NMR (400 MHz, CDCl$_3$) δ 8.26 (d, J=2.5 Hz, 1H), 8.19 (d, J=2.4 Hz, 1H), 7.95 (s, 1H), 7.63 (d, J=2.4 Hz, 1H), 7.59 (dd, J=8.6, 2.5 Hz, 1H), 6.87-6.95 (m, 2H), 6.84 (dd, J=8.3, 2.1 Hz, 1H), 6.79 (d, J=8.6 Hz, 1H), 5.33 (s, 2H), 5.07 (dd, J=8.8, 2.3 Hz, 1H), 4.29 (dd, J=11.6, 2.3 Hz, 1H), 4.02 (dd, J=11.6, 8.8 Hz, 1H), 3.95 (s, 3H), 3.14-3.30 (m, 4H), 2.60-2.70 (m, 4H), 2.38 (s, 3H) ppm; (M+1)=473.

Example 1-7: Synthesis of 3-((2-(6-methoxypyridin-3-yl)-2,3-dihydrobenzo[b][1,4]dioxin-6-yl) methyl)-3H-imidazo[4,5-b]pyridine-6-carbonitrile A solution of 6-iodo-3-((2-(6-methoxypyridin-3-yl)-2,3-dihydrobenzo[b][1,4]dioxin-6-yl)methyl)-3H-imidazo[4,5-b]pyridine (0.10 g, 0.20 mmol, Example 1-5-7) in N,N-dimethylformamide (3 mL) was degassed using nitrogen. The mixture was treated with tetrakis(triphenylphosphine) palladium(0) (0.023 g, 0.019 mmol) and zinc cyanide (0.014 g, 0.12 mmol) and was heated to 100° C. in a sealed vessel. After 3 hours, the mixture was allowed to cool to room temperature. The mixture was diluted with ethyl acetate and water, and the phases were separated. The aqueous phase was extracted with ethyl acetate. The combined organic phase were washed with brine and concentrated. Chromatographic purification of the crude product (CombiFlash, silica gel column, 70% ethyl acetate/hexanes elute) followed by trituration of the isolated material with acetone/hexanes afforded 0.054 g (68%) of 3-((2-(6-methoxypyridin-3-yl)-2,3-dihydrobenzo[b][1,4]dioxin-6-yl)methyl)-3H-imidazo[4,5-b]pyridine-6-carbonitrile as a white solid: $^1$H NMR (400 MHz, DMSO-d$_6$) δ 8.91-8.76 (m, 2H), 8.71 (d, J=1.8 Hz, 1H), 8.24 (d, J=2.3 Hz, 1H), 7.76 (dd, J=8.6, 2.5 Hz, 1H), 7.00 (t, J=1.2 Hz, 1H), 6.96-6.78 (m, 3H), 5.44 (s, 2H), 5.21 (dd, J=8.4, 2.4 Hz, 1H), 4.37 (dd, J=11.6, 2.5 Hz, 1H), 4.14 (dd, J=11.6, 8.4 Hz, 1H), 3.84 (s, 3H).

Example 1-8: Synthesis of 6-(azetidin-1-yl)-3-((2-(6-methoxypyridin-3-yl)-2,3-dihydrobenzo[b][1,4] dioxin-6-yl)methyl)-3H-imidazo[4,5-b]pyridine To a stirred solution of 6-iodo-3-((2-(6-methoxypyridin-3-yl)-2,3-dihydrobenzo[b][1,4]dioxin-6-yl)methyl)-3H-imidazo[4,5-b]pyridine (0.11 g, 0.22 mmol, Example 1-5-7) in 1,2-dimethoxyethane (3 mL) was added palladium(II) acetate (0.003 mg, 0.013 mmol) and (R)-1-[(S$_P$)-2-(dicyclohexylphosphino)ferrocenyl]ethyldicyclohexylphosphine (0.007 g, 0.012 mmol). The resulting yellow solution was treated with azetidine (0.025 g, 0.44 mmol) and solid sodium t-butoxide (0.042 g, 0.44 mmol). The mixture was heated to 100° C. in a sealed vessel. After 20 hours, the mixture was allowed to cool to room temperature and was concentrated. Chromatographic purification of the crude product (Combi-Flash, silica gel column, 0-5% methanol/dichloromethane elute) afforded 0.043 g (46%) of 6-(azetidin-1-yl)-3-((2-(6-methoxypyridin-3-yl)-2,3-dihydrobenzo[b][1,4]dioxin-6-yl) methyl)-3H-imidazo[4,5-b]pyridine as a white solid: $^1$H NMR (400 MHz, DMSO-d$_6$) δ 8.39 (s, 1H), 8.24 (d, J=2.5 Hz, 1H), 7.75 (dd, J=8.6, 2.5 Hz, 1H), 7.68 (d, J=2.5 Hz, 1H), 7.06 (d, J=2.5 Hz, 1H), 7.00-6.76 (m, 4H), 5.30 (s, 2H), 5.20 (dd, J=8.4, 2.5 Hz, 1H), 4.36 (dd, J=11.5, 2.5 Hz, 1H), 4.13 (dd, J=11.5, 8.4 Hz, 1H), 3.92-3.74 (m, 4H), 3.32 (s, 3H), 2.37-2.27 (m, 2H) ppm; (M+1)=430.

Example 1-9: Synthesis of 6-cyclopropyl-3-((2-(6-methoxypyridin-3-yl)-2,3-dihydrobenzo[b][1,4]dioxin-6-yl)methyl)-3H-imidazo[4,5-b]pyridine To a mixture of 6-iodo-3-((2-(6-methoxypyridin-3-yl)-2,3-dihydrobenzo[b][1,4]dioxin-6-yl)methyl)-3H-imidazo[4,5-b]pyridine (0.11 g, 0.21 mmol, Example 1-5-7), [1,1'-bis(diphenylphosphino)ferrocene]palladium(II) chloride (0.016 g, 0.021 mmol), cesium carbonate (0.21 g, 0.66 mmol) and cyclopropylboronic acid (0.028 g, 0.33 mmol) was added 1,2-dimethoxyethane (3 mL) and water (0.3 mL). The resulting mixture was heated to 100° C. in a sealed vessel. After 4 hours, additional portions of the catalyst and boronic acid were added, and the mixture was stirred. After a total of 7 h, the mixture was allowed to cool to room temperature and was diluted with ethyl acetate. The mixture was filtered through a short pad of silica gel and Celite, and the residue was concentrated. Chromatographic purification of the crude product (CombiFlash, silica gel column, 0-5% methanol/dichloromethane elute) followed by preparative HPLC (10-90% acetonitrile/0.1% trifluoroacetic acid in water) afforded 0.012 g (10%) of 6-cyclopropyl-3-((2-(6-methoxypyridin-3-yl)-2,3-dihydrobenzo[b][1,4]dioxin-6-yl)methyl)-3H-imidazo[4,5-b]pyridine (trifluoroacetate salt) as a white solid: $^1$H NMR (400 MHz, DMSO-$d_6$) δ 8.80 (s, 1H), 8.33 (d, J=2.0 Hz, 1H), 8.24 (d, J=2.4 Hz, 1H), 7.76 (dd, J=8.5, 2.4 Hz, 2H), 7.00-6.98 (m, 1H), 6.92-6.90 (m, 2H), 6.86 (d, J=8.5 Hz, 1H), 5.41 (s, 2H), 5.21 (dd, J=8.3, 2.5 Hz, 1H), 4.37 (dd, J=11.6, 2.5 Hz, 1H), 4.14 (dd, J=11.6, 8.3 Hz, 1H), 3.85 (s, 3H), 2.16-2.06 (m, 1H), 1.05-0.96 (m, 2H), 0.83-0.75 (m, 2H) ppm; (M+1)=415.

Example 1-10: Synthesis of 4-(3-((2-(6-methoxypyridin-3-yl)-2,3-dihydrobenzo[b][1,4]dioxin-6-yl)methyl)-3H-imidazo[4,5-b]pyridin-6-yl)morpholine To a stirred solution of 6-iodo-3-((2-(6-methoxypyridin-3-yl)-2,3-dihydrobenzo[b][1,4]dioxin-6-yl)methyl)-3H-imidazo[4,5-b]pyridine (0.23 g, 0.45 mmol, Example 1-5-7) in 1,4-dioxane (3 mL) was added morpholine (0.062 g, 0.70 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (0.012 g, 0.013 mmol), 2-dicyclohexylphosphino-2',6'-di-i-propoxy-1,1'-biphenyl (0.006 g, 0.013 mmol), and sodium t-butoxide (62.38 mg, 629.64 μmol). The vessel was sealed, and the contents were degassed under vacuum/backfilled with nitrogen (×3). The mixture was then heated to 110° C. After 16 h, the mixture was allowed to cool to room temperature and was diluted with water (50 mL). The mixture was extracted with ethyl acetate (3×30 mL). The combined organic phases were washed with brine (25 mL), dried over magnesium sulfate, filtered, and concentrated. Chromatographic purification of the crude product (CombiFlash, 24 g silica gel gold column, 0-5% methanol/dichloromethane elute) 0.066 g (32%) of 4-(3-((2-(6-methoxypyridin-3-yl)-2,3-dihydrobenzo[b][1,4]dioxin-6-yl)methyl)-3H-imidazo[4,5-b]pyridin-6-yl)morpholine as a white solid: $^1$H NMR (400 MHz, CDCl$_3$) δ 8.24 (d, J=2.5 Hz, 1H), 8.21-8.17 (m, 1H), 7.96 (s, 1H), 7.61 (d, J=2.5 Hz, 1H), 7.59 (dd, J=8.6, 2.5 Hz, 1H), 6.93-6.82 (m, 3H), 6.79 (d, J=8.6 Hz, 1H), 5.34 (s, 2H), 5.07 (dd, J=8.8, 2.5 Hz, 1H), 4.30 (dd, J=11.6, 2.5 Hz, 1H), 4.02 (dd, J=11.6, 8.8 Hz, 1H), 3.95 (s, 3H), 3.93-3.90 (m, 4H), 3.20-3.14 (m, 4H) ppm; (M+1)=460.

Example 1-11: Synthesis of 6-methoxy-3-((2-(6-methoxypyridin-3-yl)-2,3-dihydrobenzo[b][1,4]dioxin-6-yl)methyl)-3H-imidazo[4,5-b]pyridine To a stirred solution of 6-iodo-3-((2-(6-methoxypyridin-3-yl)-2,3-dihydrobenzo[b][1,4]dioxin-6-yl)methyl)-3H-imidazo[4,5-b]pyridine (0.26 g, 0.52 mmol, Example 1-5-7) in methanol (3.0 mL) was added copper(I) iodide (0.010 g, 0.052 mmol), 1,10-phenanthroline (0.019 g, 0.10 mmol), and cesium carbonate (0.34 g, 1.05 mmol). The mixture was heated to 110° C. in a sealed vessel. After 20 h, the mixture was allowed to cool to room temperature and was dilute with 5 N ammonium hydroxide solution (50 mL) and dichloromethane (50 mL). The phases were separated, and the aqueous phase was extracted with dichloromethane (2×30 mL). The combined organic phases were dried over magnesium sulfate, filtered, and concentrated. Chromatographic purification of the crude product (CombiFlash, 24 g silica gel gold column, 0-5% methanol/dichloromethane elute) afforded 0.17 g of a white solid (contaminated with 1,10-phenanthroline). The material was dissolved in dichloromethane (30 mL) and washed with 1N hydrochloric acid solution (2×30 mL). The combined aqueous phases were made basic with 1N sodium hydroxide solution (~60 mL), and the resulting milky white mixture was extracted with diethyl ether (3×15 mL). The combined organic phases were dried over magnesium sulfate, filtered, and concentrated to provide a colorless oil. The material was re-dissolved in diethyl ether (15 mL) and sonicated to induce precipitation. The solids were isolated by filtration and dried to provide 0.090 g (43%) of 6-methoxy-3-((2-(6-methoxypyridin-3-yl)-2,3-dihydrobenzo[b][1,4]dioxin-6-yl)methyl)-3H-imidazo[4,5-b]pyridine as a white solid: $^1$H NMR (400 MHz, CDCl$_3$) δ 8.21 (d, J=2.6 Hz, 1H), 8.19 (d, J=2.4 Hz, 1H), 7.97 (s, 1H), 7.61-7.58 (m, 2H), 6.93-6.88 (m, 2H), 6.84 (dd, J=8.3, 2.2 Hz, 1H), 6.79 (d, J=8.6 Hz, 1H), 5.35 (s, 2H), 5.07 (dd, J=8.8, 2.5 Hz, 1H), 4.30 (dd, J=11.6, 2.5 Hz, 1H), 4.02 (dd, J=11.6, 8.8 Hz, 1H), 3.95 (s, 3H), 3.90 (s, 3H) ppm: (M+1)=405.

Example 1-12: Synthesis of 4-(3-((2-(4-methoxyphenyl)-3-methyl-2,3-dihydrobenzo[b][1,4]dioxin-6-yl)methyl)-3H-imidazo[4,5-b]pyridin-6-yl)-2-methylbut-3-yn-2-amine Example 1-12-1: Preparation of t-butyl (4-(benzyloxy)-3-hydroxybenzyl)carbamate A stirred solution of 3-hydroxy-4-benzyloxybenzaldehyde (4.05 g, 16.86 mmol) and t-butyl carbamate (3.02 g, 25.29 mmol) in acetonitrile (100 mL) was cooled to 0° C. while triethylsilane (5.94 g, 50.57 mmol) and trifluoroacetic acid (3.88 g, 33.71 mmol) were added. The resulting yellow solution was allowed to stir at 0° C. for 15 min, and then the mixture was allowed to warm to room temperature. After 3 h, additional portions of t-butyl carbamate (1.00 g), triethylsilane (5.94 g) and trifluoroacetic acid (3.88 g) were added, and the mixture was allowed to stir at room temperature. After 20 h, the mixture was concentrated, and the residue was diluted with saturated sodium bicarbonate solution (150 mL). The mixture was extracted with diethyl ether (3×75 mL). The combined organic phases were washed with 1N sodium hydroxide solution (2×50 mL), 1N hydrochloric acid solution (2×50 mL), and brine (50 mL). The organic phase was dried over magnesium sulfate, filtered, and concentrated. Chromatographic purification of the crude product (CombiFlash, 120 g silica gel gold column, 0-10% ethyl acetate/dichloromethane elute) provided a white solid. Trituration of this material with heptane afforded 2.25 g (41%) of t-butyl 4-(benzyloxy)-3-hydroxybenzylcarbamate as a white solid.

Example 1-12-2: Preparation of t-butyl (4-(benzyloxy)-3-((1-(4-methoxyphenyl)-1-oxopropan-2-yl)oxy)benzyl)carbamate To a stirred solution of t-butyl 4-(benzyloxy)-3-hydroxybenzylcarbamate (1.25 g, 3.79 mmol) in acetonitrile (40 mL) was added cesium carbonate (1.86 g, 5.69 mmol) and 2-bromo-1-(4-methoxyphenyl)propan-1-one (0.97 g, 3.79 mmol). After 2 h, the mixture was diluted with water (100 mL) and extracted with ethyl acetate (3×50 mL). The combined organic phases were dried over magnesium sulfate, filtered, and concentrated. Chromatographic purification of the crude product (CombiFlash, 40 g silica gel column, 10-30% ethyl acetate/heptane elute) afforded 1.35 g (72%) of t-butyl 4-(benzyloxy)-3-((1-(4-methoxyphenyl)-1-oxopropan-2-yl)oxy)benzylcarbamate as a white solid.

Example 1-12-3: Preparation of t-butyl (4-hydroxy-3-((1-hydroxy-1-(4-methoxyphenyl)propan-2-yl)oxy)benzyl)carbamate To a stirred solution of t-butyl 4-(benzyloxy)-3-((1-(4-methoxyphenyl)-1-oxopropan-2-yl)oxy)benzylcarbamate (1.35 g, 2.75 mmol) in tetrahydrofuran (30 mL) was added 10% palladium on carbon (wet) (0.89 g, 0.84 mmol). The mixture was degassed under vacuum/backfilled with nitrogen (×3). After a final evacuation, the atmosphere was replaced with hydrogen via a balloon. The reaction mixture was allowed to stir at room temperature. After 1 h, the vessel was evacuated, and the atmosphere replaced with nitrogen. The mixture was filtered through Celite with the aid of tetrahydrofuran (50 mL). The filtrate was diluted with methanol (10 mL), and the yellow solution was treated with sodium borohydride (0.13 g, 3.43 mmol) (gas evolution and mild exotherm noted). After 90 min, the mixture was treated with water (2 mL) and was concentrated. The residue was dissolved in ethyl acetate (75 mL) and washed with saturated sodium bicarbonate solution (75 mL). The organic phase was dried over magnesium sulfate, filtered, and concentrated to provide 1.18 g (>100%) of t-butyl 4-hydroxy-3-((1-hydroxy-1-(4-methoxyphenyl)propan-2-yl)oxy)benzylcarbamate as a colorless oil.

Example 1-12-4: Preparation of t-butyl ((2-(4-methoxyphenyl)-3-methyl-2,3-dihydrobenzo[b][1,4]dioxin-6-yl)methyl)carbamate To a stirred solution of t-butyl 4-hydroxy-3-((1-hydroxy-1-(4-methoxyphenyl)propan-2-yl)oxy)benzylcarbamate (1.11 g, 2.75 mmol) and triphenylphosphine (0.98 g, 3.71 mmol) in tetrahydrofuran (30 mL) was added a solution of bis(2-methoxyethyl) azodicarboxylate (0.90 g, 3.71 mmol) in tetrahydrofuran (10 mL) over 3 min. The resulting yellow solution was heated to reflux. After 3 h, the mixture was allowed to cool to room temperature and was diluted with ethyl acetate (75 mL). The organic phase washed with water (2×50 mL), 1N hydrochloric acid solution (50 mL), 1N sodium hydroxide solution (50 mL), and brine (50 mL). The organic phase was dried over magnesium sulfate, filtered, and concentrated. Chromatographic purification of the crude product (CombiFlash, 40 g silica gel gold column, 10-25% ethyl acetate/heptane elute) afforded 0.50 g (47%) of t-butyl ((2-(4-methoxyphenyl)-3-methyl-2,3-dihydrobenzo[b][1,4]dioxin-6-yl)methyl)carbamate as a white solid.

Example 1-12-5: Preparation of (2-(4-methoxyphenyl)-3-methyl-2,3-dihydrobenzo[b][1,4]dioxin-6-yl)methanamine To a stirred solution of t-butyl ((2-(4-methoxyphenyl)-3-methyl-2,3-dihydrobenzo[b][1,4]dioxin-6-yl)methyl)carbamate (0.50 g, 1.30 mmol) in dichloromethane (10 mL) was added trifluoroacetic acid (5.0 mL, 64.64 mmol). After 30 min, the solution was concentrated, and the residue was dissolved in 5N ammonium hydroxide solution (20 mL). The basic mixture was extracted with dichloromethane (2×30 mL). The combined organic phases were dried over magnesium sulfate, filtered, and concentrated to provide 0.36 g (97%) of (2-(4-methoxyphenyl)-3-methyl-2,3-dihydrobenzo[b][1,4]dioxin-6-yl)methanamine as a colorless oil.

Example 1-12-6: Preparation of 4-(3-((2-(4-methoxyphenyl)-3-methyl-2,3-dihydrobenzo[b][1,4]dioxin-6-yl)methyl)-3H-imidazo[4,5-b]pyridin-6-yl)-2-methylbut-3-yn-2-amine The title compound was prepared in four steps from (2-(4-methoxyphenyl)-3-methyl-2,3-dihydrobenzo[b][1,4]dioxin-6-yl)methanamine as described in Example 1-5-5 through Example 1-5-8: $^1$H NMR (400 MHz, Chloroform-d) δ 8.46 (d, J=1.9 Hz, 1H), 8.07 (d, J=1.9 Hz, 1H), 8.02 (s, 1H), 7.29-7.24 (m, 2H), 6.96-6.80 (m, 5H), 5.36 (s, 2H), 4.57 (d, J=8.0 Hz, 1H), 4.08 (dq, J=8.0, 6.4 Hz, 1H), 3.82 (s, 3H), 1.53 (s, 6H), 1.14 (d, J=6.4 Hz, 3H) ppm: (M+1)=469.

Example 1-13: Synthesis of 6-methoxy-3-((2-(6-methoxypyridin-3-yl)-3-methyl-2,3-dihydrobenzo[b][1,4]dioxin-6-yl)methyl)-3H-imidazo[4,5-b]pyridine Example 1-13-1: Preparation of (2-(6-methoxypyridin-3-yl)-3-methyl-2,3-dihydrobenzo[b][1,4]dioxin-6-yl)methanamine The title compound was prepared in four steps from 2-bromo-1-(6-methoxypyridin-3-yl)propan-1-one as described in Example 1-12-2 through Example 1-12-5.

Example 1-13-2: Preparation of 6-iodo-3-((2-(6-methoxypyridin-3-yl)-3-methyl-2,3-dihydrobenzo[b][1,4]dioxin-6-yl)methyl)-3H-imidazo[4,5-b]pyridine The title compound was prepared in three steps from (2-(6-methoxypyridin-3-yl)-3-methyl-2,3-dihydrobenzo[b][1,4]dioxin-6-yl)methanamine and 2-chloro-5-iodo-3-nitropyridine as described in Example 1-5-5 through Example 1-5-7.

Example 1-13-3: Preparation of 6-methoxy-3-((2-(6-methoxypyridin-3-yl)-3-methyl-2,3-dihydrobenzo[b][1,4]dioxin-6-yl)methyl)-3H-imidazo[4,5-b]pyridine The title compound was prepared from 6-iodo-3-((2-(6-methoxypyridin-3-yl)-3-methyl-2,3-dihydrobenzo[b][1,4]dioxin-6-yl)methyl)-3H-imidazo[4,5-b]pyridine and methanol as described in Example 1-11: (55:45 trans/cis) $^1$H NMR (400 MHz, Chloroform-d) δ 8.23-8.20 (m, 1H), 8.16-8.12 (m, 1H), 8.00-7.96 (m, 1H), 7.60-7.57 (m, 1H), 7.57-7.53 (m, 1H), 6.93-6.72 (m, 4H), 5.35 (s, 2H), 5.12 (d, J=2.6 Hz, 1H, cis isomer), 4.60 (d, J=8.0 Hz, 1H, trans isomer), 4.51-4.43 (m, 1H, cis isomer), 4.13-4.04 (m, 1H, trans isomer), 3.99-3.88 (m, 9H), 1.17 (d, J=6.3 Hz, 3H, trans isomer), 1.12 (d, J=6.6 Hz, 3H, cis isomer) ppm; (M+1)=419.

Example 1-14: Synthesis of 4-(3-((2-(2,4-dichlorophenyl)-2,3-dihydrobenzo[b][1,4]dioxin-6-yl)methyl)-3H-imidazo[4,5-b]pyridin-6-yl)-2-methylbut-3-yn-2-amine Example 1-14-1: Preparation of 3-(2-(2,4-dichlorophenyl)-2-oxoethoxy)-4-fluorobenzonitrile To a stirred and cooled (0° C.) suspension of 4-fluoro-3-hydroxybenzonitrile (5.00 g, 36.47 mmol) and potassium carbonate (10.08 g, 72.93 mmol) in N,N-dimethylformamide (80 mL) was added dropwise a solution of 2-bromo-1-(2,4-dichlorophenyl)ethanone (9.77 g, 36.47 mmol) in N,N-dimethylformamide (10 mL) over 3 min. After 15 min, the cooling bath was removed, and the mixture was allowed to warm to room temperature. After 90 min, the mixture was re-cooled to 0° C. while water was added to induce precipitation. The solids were isolated by filtration, washed with water followed by hexanes, and dried to provide 11.80 g (97%) of 3-(2-(2,4-dichlorophenyl)-2-oxoethoxy)-4-fluorobenzonitrile as a beige solid.

Example 1-14-2: Preparation of 3-(2-(2,4-dichlorophenyl)-2-hydroxyethoxy)-4-fluorobenzonitrile Methanol (80 mL) was cooled to 0° C. while sodium borohydride (2.45 g, 64.76 mmol) was added slowly. After the addition was complete, the mixture was stirred for 15 min at 0° C. before 3-(2-(2,4-dichlorophenyl)-2-oxoethoxy)-4-fluorobenzonitrile (7.00 g, 21.60 mmol) was added slowly. A precipitate formed near the end of the addition, so an additional portion of methanol was added (70 mL). The resulting suspension was allowed to warm to room temperature. After 1 h, the mixture was re-cooled to 0° C. before 0.1N hydrochloric acid solution (20 mL) was added. The mixture was extracted using dichloromethane, and the combined organic phases were concentrated. The crude solid was triturated with dichloromethane, filtered, and then washed with hexanes. A second trituration with dichloromethane/wash with hexanes afforded 5.90 g (84%) of 3-(2-(2,4-dichlorophenyl)-2-hydroxyethoxy)-4-fluorobenzonitrile as an off-white solid.

Example 1-14-3: Preparation of 2-(2,4-dichlorophenyl)-2,3-dihydrobenzo[b][1,4]dioxine-6-carbonitrile A stirred suspension of potassium carbonate (6.25 g, 45.22 mmol) and 3-(2-(2,4-dichlorophenyl)-2-hydroxyethoxy)-4-fluorobenzonitrile (5.90 g, 18.09 mmol) in N,N-dimethylformamide (60 mL) was heated to 80° C. After 24 h, the mixture was allowed to cool to room temperature while water and ethyl acetate were added. The phases were separated, and the aqueous phase was extracted with ethyl acetate. The combined organic phases were washed with brine, dried over magnesium sulfate, filtered, and concentrated. The crude material was triturated with methanol and filtered to provide 2.75 g of a white solid. The filtrate was concentrated, and the residue was purified (CombiFlash, silica gel column, 10-20% ethyl acetate/heptane elute) to afford an additional 0.73 g of a white solid. A total of 3.48 g (63%) of 2-(2,4-dichlorophenyl)-2,3-dihydrobenzo[b][1,4]dioxine-6-carbonitrile was obtained.

Example 1-14-4: Preparation of (2-(2,4-dichlorophenyl)-2,3-dihydrobenzo[b][1,4]dioxin-6-yl)methanamine To a stirred and cooled (0° C.) solution of 2-(2,4-dichlorophenyl)-2,3-dihydrobenzo[b][1,4]dioxine-6-carbonitrile (3.48 g, 11.37 mmol) in tetrahydrofuran (60 mL) was added 2.4M lithium aluminum hydride solution in ether (9.5 mL, 22.80 mmol) via syringe. The mixture was allowed to stir at 0° C. After 30 min, the cooling bath was removed, and the mixture was allowed to warm to room temperature. After 4 hours, the mixture was re-cooled to 0° C. and diluted with Et$_2$O. The mixture was quenched by the slow addition of water (0.87 mL), 1N sodium hydroxide solution (0.87 mL), and water (2.6 mL). The mixture was stirred at 0° C. for 1 hour. The resulting white suspension was filtered through Celite, and the filter cake was washed with ethyl acetate. The filtrate was concentrated to provide 3.53 g (93%) of (2-(2,4-dichlorophenyl)-2,3-dihydrobenzo[b][1,4]dioxin-6-yl)methanamine as a colorless oil that crystallized on standing.

Example 1-14-5: Preparation of 4-(3-((2-(2,4-dichlorophenyl)-2,3-dihydrobenzo[b][1,4]dioxin-6-yl)methyl)-3H-imidazo[4,5-b]pyridin-6-yl)-2-methylbut-3-yn-2-amine The title compound was prepared in four steps from (2-(2,4-dichlorophenyl)-2,3-dihydrobenzo[b][1,4]dioxin-6-yl)methanamine, 2-chloro-5-iodo-3-nitropyridine, and 2-methylbut-3-yn-2-amine as described in Example 1-5-5 through Example 1-5-8: $^1$H NMR (400 MHz, DMSO-d$_6$) δ 8.72 (s, 1H), 8.58 (s, 2H), 8.48 (d, J=1.8 Hz, 1H), 8.20 (d, J=1.9 Hz, 1H), 7.73 (d, J=1.6 Hz, 1H), 7.53 (d, J=2.0 Hz, 2H), 7.10-6.81 (m, 3H), 5.42 (q, J=2.6 Hz, 3H), 4.44 (dd, J=11.7, 2.4 Hz, 1H), 4.01 (dd, J=11.7, 8.2 Hz, 1H), 3.61-3.31 (m, 1H), 1.65 (s, 4H) ppm; (M+1)=493.

Example 1-15: Synthesis of 2,2,2-trifluoro-N-((6-((6-(1-methyl-1H-pyrazol-4-yl)-3H-imidazo[4,5-b]pyridin-3-yl)methyl)-2,3-dihydrobenzo[b][1,4]dioxin-2-yl)methyl)acetamide Example 1-15-1: Preparation of 6-(hydroxymethyl)-2,3-dihydrobenzo[b][1,4]dioxine-2-carbonitrile The title compound was prepared from 6-formyl-2,3-dihydrobenzo[b][1,4]dioxine-2-carbonitrile as described in Example 1-14-2.

Example 1-15-2: Preparation of 6-((6-bromo-3H-imidazo[4,5-b]pyridin-3-yl)methyl)-2,3-dihydrobenzo[b][1,4]dioxine-2-carbonitrile To a stirred solution of 6-(hydroxymethyl)-2,3-dihydrobenzo[b][1,4]dioxine-2-carbonitrile (1.16 g, 6.06 mmol) in toluene (17 mL) was added 2-(tributylphosphoranylidene)acetonitrile (1.46 g, 6.06 mmol). The mixture was stirred at room temperature. After 10 min, 6-bromo-3H-imidazo[4,5-b]pyridine (1.00 g, 5.05 mmol) was added to the mixture, and the resulting mixture was heated to 90° C. After 6 h, the mixture was allowed to cool to room temperature and was concentrated. Chromatographic purification of the crude product (CombiFlash, silica gel column, 80% ethyl acetate/hexanes elute) afforded 0.82 g (44%) of 6-((6-bromo-3H-imidazo[4,5-b]pyridin-3-yl)methyl)-2,3-dihydrobenzo[b][1,4]dioxine-2-carbonitrile as an off-white foam.

Example 1-15-3: Preparation of 6-((6-(1-methyl-1H-pyrazol-4-yl)-3H-imidazo[4,5-b]pyridin-3-yl)methyl)-2,3-dihydrobenzo[b][1,4]dioxine-2-carbonitrile The title compound was prepared from 6-((6-bromo-3H-imidazo[4,5-b]pyridin-3-yl)methyl)-2,3-dihydrobenzo[b][1,4]dioxine-2-carbonitrile and 1-methyl-4-(4,4,5,5-tetramethyl-1,3,2-dioxaborolan-2-yl)-1H-pyrazole as described in Example 1-4.

Example 1-15-4: (6-((6-(1-methyl-1H-pyrazol-4-yl)-3H-imidazo[4,5-b]pyridin-3-yl)methyl)-2,3-dihydrobenzo[b][1,4]dioxin-2-yl)methanamine The title compound was prepared from 6-((6-(1-methyl-1H-pyrazol-4-yl)-3H-imidazo[4,5-b]pyridin-3-yl)methyl)-2,3-dihydrobenzo[b][1,4]dioxine-2-carbonitrile as described in Example 1-14-4.

Example 1-15-5: Preparation of 2,2,2-trifluoro-N-((6-((6-(1-methyl-1H-pyrazol-4-yl)-3H-imidazo[4,5-b]pyridin-3-yl)methyl)-2,3-dihydrobenzo[b][1,4]dioxin-2-yl)methyl)acetamide To a stirred and cooled (0° C.) solution of (6-((6-(1-methyl-1H-pyrazol-4-yl)-3H-imidazo[4,5-b]pyridin-3-yl)methyl)-2,3-dihydrobenzo[b][1,4]dioxin-2-yl)methanamine (0.030 g, 0.079 mmol) in dichloromethane (2 mL) was added triethylamine (0.022 mL, 0.15 mmol) followed by trifluoroacetic anhydride (0.007 mL, 0.079 mmol). The mixture was stirred at 0° C. After 15 min, the cooling bath was removed, and the mixture was allowed to warm to room temperature. After 1 h, the mixture was diluted with dichloromethane (10 mL) and saturated sodium bicarbonate solution. The phases were separated, and the aqueous phase was extracted with dichloromethane. The combined organic phases were dried over magnesium sulfate, filtered and concentrated. Chromatographic purification of the crude product (CombiFlash, silica gel column, 5% methanol/dichloromethane elute) afforded 0.038 g (8%) of 2,2,2-trifluoro-N-((6-((6-(1-methyl-1H-pyrazol-4-yl)-3H-imidazo[4,5-b]pyridin-3-yl)methyl)-2,3-dihydrobenzo[b][1,4]dioxin-2-yl)methyl)acetamide as a white solid: $^1$H NMR (400 MHz, DMSO-$d_6$) δ 9.67 (s, 1H), 8.63 (d, J=1.9 Hz, 1H), 8.53 (s, 1H), 8.30-8.17 (m, 2H), 7.96 (s, 1H), 7.00-6.77 (m, 3H), 5.36 (s, 2H), 4.38-4.20 (m, 2H), 3.94 (dd, J=11.6, 6.6 Hz, 1H), 3.87 (s, 3H), 3.45 (d, J=5.2 Hz, 2H) ppm; (M+1)=473.

Example 1-16: Synthesis of 6-(3-methoxyazetidin-1-yl)-3-((2-(6-methoxypyridin-3-yl)-2,3-dihydrobenzo[b][1,4]dioxin-6-yl)methyl)-3H-imidazo[4,5-b]pyridine The title compound was prepared from 6-iodo-3-((2-(6-methoxypyridin-3-yl)-2,3-dihydrobenzo[b][1,4]dioxin-6-yl)methyl)-3H-imidazo[4,5-b]pyridine (Example 1-5-7) and 3-methoxyazetidine hydrochloride as described in Example 1-10: $^1$H NMR (400 MHz, CDCl$_3$) δ 8.19 (d, J=2.5 Hz, 1H), 7.91 (s, 1H), 7.78 (d, J=2.5 Hz, 1H), 7.59 (dd, J=8.6, 2.5 Hz, 1H), 7.15 (d, J=2.5 Hz, 1H), 6.95-6.76 (m, 4H), 5.31 (s, 2H), 5.07 (dd, J=8.8, 2.5 Hz, 1H), 4.43-4.35 (m, 1H), 4.29 (dd, J=11.6, 2.5 Hz, 1H), 4.22-4.15 (m, 2H), 4.02 (dd, J=11.6, 8.8 Hz, 1H), 3.95 (s, 3H), 3.79-3.73 (m, 2H), 3.36 (s, 3H) ppm; (M+1)=460.

Example 1-17: Synthesis of 2-methyl-4-(3-((2-(1-methyl-1H-pyrazol-4-yl)-2,3-dihydrobenzo[b][1,4]dioxin-6-yl)methyl)-3H-imidazo[4,5-b]pyridin-6-yl)but-3-yn-2-amine The title compound was prepared in 8 steps from 3-hydroxy-4-iodobenzamide, 2-bromo-1-(1-methyl-1H-pyrazol-4-yl)ethan-1-one, 2-chloro-5-iodo-3-nitropyridine, and 2-methylbut-3-yn-2-amine as described in Example 1-5-1 through Example 1-5-8: $^1$H NMR (400 MHz, Chloroform-d) δ 8.45 (d, J=1.8 Hz, 1H), 8.07 (d, J=1.8 Hz, 1H), 8.01 (s, 1H), 7.52 (d, J=0.8 Hz, 1H), 7.44 (s, 1H), 6.90-6.78 (m, 3H), 5.35 (s, 2H), 5.14 (dd, J=7.9, 2.4 Hz, 1H), 4.32 (dd, J=11.4, 2.5 Hz, 1H), 4.09 (dd, J=11.4, 8.0 Hz, 1H), 3.90 (s, 3H), 1.53 (s, 6H); (M+H)=429.

Example 1-18: Synthesis of 4-(3-(1-(2-(6-methoxypyridin-3-yl)-2,3-dihydrobenzo[b][1,4]dioxin-6-yl)ethyl)-3H-imidazo[4,5-b]pyridin-6-yl)-2-methylbut-3-yn-2-amine

Example 1-18-1: Preparation of methyl 4-(benzyloxy)-3-(2-(6-methoxypyridin-3-yl)-2-oxoethoxy)benzoate To a stirred solution of methyl 4-(benzyloxy)-3-hydroxybenzoate (3.37 g, 13.05 mmol) in N,N-dimethylformamide (20 mL) was added potassium carbonate (2.71 g, 19.57 mmol) and 2-bromo-1-(6-methoxypyridin-3-yl)ethanone (3.00 g, 13.05 mmol). The reaction was allowed to stir at room temperature. After 16 h, the mixture was diluted with ethyl acetate and water. The phases were separated, and the aqueous phase extracted with ethyl acetate. The combined organic phases were washed with water and brine, dried over magnesium sulfate, filtered, and concentrated. Chromatographic purification of the crude product (CombiFlash, silica gel column, 0-50% ethyl acetate/heptane elute) afforded 3.81 g (72%) of methyl 4-(benzyloxy)-3-(2-(6-methoxypyridin-3-yl)-2-oxoethoxy)benzoate as a white solid.

Example 1-18-2: Preparation of methyl 4-(benzyloxy)-3-(2-hydroxy-2-(6-methoxypyridin-3-yl)ethoxy)benzoate The title compound was prepared from methyl 4-(benzyloxy)-3-(2-(6-methoxypyridin-3-yl)-2-oxoethoxy)benzoate as described in Example 1-14-2.

Example 1-18-3: Preparation of methyl 4-hydroxy-3-(2-hydroxy-2-(6-methoxypyridin-3-yl)ethoxy)benzoate To a stirred solution of methyl 4-(benzyloxy)-3-(2-hydroxy-2-(6-methoxypyridin-3-yl)ethoxy)benzoate (3.53 g, 8.62 mmol) was added 10% palladium on carbon (0.92 g, 0.86 mmol). The mixture was degassed under vacuum/backfilled with nitrogen (×3). After a final evacuation, the atmosphere was replaced with hydrogen via a balloon. The reaction mixture was heated to 65° C. After 16 h, the mixture was allowed to cool to room temperature, the vessel was evacuated, and the atmosphere replaced with nitrogen. The mixture was filtered through Celite, and filtrate was concentrated to afford 2.39 g (87%) of methyl 4-hydroxy-3-(2-hydroxy-2-(6-methoxypyridin-3-yl)ethoxy)benzoate as a white solid.

Example 1-18-4: Preparation of methyl 2-(6-methoxypyridin-3-yl)-2,3-dihydrobenzo[b][1,4]dioxine-6-carboxylate The title compound was prepared from methyl 4-hydroxy-3-(2-hydroxy-2-(6-methoxypyridin-3-yl)ethoxy)benzoate as described in Example 1-12-4.

Example 1-18-5: Preparation of 2-(6-methoxypyridin-3-yl)-2,3-dihydrobenzo[b][1,4]dioxine-6-carboxylic acid To a stirred solution of methyl 2-(6-methoxypyridin-3-yl)-2,3-dihydrobenzo[b][1,4]dioxine-6-carboxylate (1.69 g, 5.61 mmol) in 1:4 water/methanol (25 mL) was added lithium hydroxide (1.41 g, 56.10 mmol). The reaction was allowed to stir at room temperature. After 16 h, the mixture was concentrated, and the residue was dissolved in water. The pH was adjusted to ~5 with concentrated hydrochloric acid solution, resulting in the formation of a precipitate. The mixture was filtered, and the filter cake was washed with water and dried to provide 1.56 g (97%) of 2-(6-methoxypyridin-3-yl)-2,3-dihydrobenzo[b][1,4]dioxine-6-carboxylic acid as a white solid.

Example 1-18-6: Preparation of N-methoxy-2-(6-methoxypyridin-3-yl)-N-methyl-2,3-dihydrobenzo[b][1,4]dioxine-6-carboxamide To a stirred solution of 2-(6-methoxypyridin-3-yl)-2,3-dihydrobenzo[b][1,4]dioxine-6-carboxylic acid (1.56 g, 5.43 mmol) in N,N-dimethylformamide (15 mL) was added 1-[bis(dimethylamino)methylene]-1H-1,2,3-triazolo[4,5-b]pyridinium 3-oxid hexafluorophosphate (4.26 g, 10.86 mmol), N,O-dimethylhydroxylamine hydrochloride (1.08 g, 10.86 mmol) and N,N-diisopropylethylamine (3.86 mL, 21.70 mmol). The mixture was allowed to stir at room temperature. After 5 min, the mixture was diluted with ethyl acetate and water. The phases were separated, and the aqueous phase was extracted with ethyl acetate (3×50 mL). The combined organic phases were washed with water (3×40 mL) and brine, dried over magnesium sulfate, filtered, and concentrated to provide 1.51 g (84%) of N-methoxy-2-(6-methoxypyridin-3-yl)-N-methyl-2,3-dihydrobenzo[b][1,4]dioxine-6-carboxamide the desired material as a colorless semisolid.

Example 1-18-7: Preparation of 1-(2-(6-methoxypyridin-3-yl)-2,3-dihydrobenzo[b][1,4]dioxin-6-yl)ethan-1-one To a stirred and cooled (0° C.) solution of N-methoxy-2-(6-methoxypyridin-3-yl)-N-methyl-2,3-dihydrobenzo[b][1,4]dioxine-6-carboxamide (1.51 g, 4.57 mmol) in tetrahydrofuran (40 mL) was added 3.0M methylmagnesium bromide in ether solution (3.0 mL, 9.00 mmol). The mixture was stirred at 0° C. After 30 min, the mixture was quenched with water and diluted with ethyl acetate. The phases were separated, and the organic phase was washed with brine, dried over magnesium sulfate, filtered, and concentrated to provide 1.16 g (87%) of 1-(2-(6-methoxypyridin-3-yl)-2,3-dihydrobenzo[b][1,4]dioxin-6-yl)ethan-1-one as a white solid.

Example 1-18-8: Preparation of (E/Z)-1-(2-(6-methoxypyridin-3-yl)-2,3-dihydrobenzo[b][1,4]dioxin-6-yl)ethan-1-one oxime To a stirred solution of 1-(2-(6-methoxypyridin-3-yl)-2,3-dihydrobenzo[b][1,4]dioxin-6-yl)ethanone (1.16 g, 4.07 mmol) in methanol (10 mL) was added sodium acetate (1.67 g, 20.33 mmol) and hydroxylamine hydrochloride (0.30 g, 4.97 mmol). The mixture was heated to 60° C. After 2 h, the solution was allowed to cool to room temperature and was concentrated. The residue was diluted with water resulting in the formation of a precipitate. The solids were isolated by filtration, and the filter cake was dried to afford 1.16 g (95%) of (E/Z)-1-(2-(6-methoxypyridin-3-yl)-2,3-dihydrobenzo[b][1,4]dioxin-6-yl)ethan-1-one oxime as a white solid.

Example 1-18-9: Preparation of 1-(2-(6-methoxypyridin-3-yl)-2,3-dihydrobenzo[b][1,4]dioxin-6-yl)ethan-1-amine To a stirred solution of (E/Z)-1-(2-(6-methoxypyridin-3-yl)-2,3-dihydrobenzo[b][1,4]dioxin-6-yl)ethanone oxime (1.16 g, 3.86 mmol) in glacial acetic acid (20 mL) was added zinc powder (3.03 g, 46.4 mmol). The reaction was heated to 40° C. After 2 h, the mixture was allowed to cool to room temperature and diluted with ethyl acetate and water. The phases were separated (organic phase discarded), and the aqueous phase was neutralized with 1N sodium hydroxide solution. The neutral aqueous phase was extracted with ethyl acetate (2×50 mL). The combined organic phases were dried over magnesium sulfate, filtered, and concentrated to provide 0.29 g (26%) of 1-(2-(6-methoxypyridin-3-yl)-2,3-dihydrobenzo[b][1,4]dioxin-6-yl)ethan-1-amine as a brown oil.

Example 1-18-10: Preparation of 4-(3-(1-(2-(6-methoxypyridin-3-yl)-2,3-dihydrobenzo[b][1,4]dioxin-6-yl)ethyl)-3H-imidazo[4,5-b]pyridin-6-yl)-2-methylbut-3-yn-2-amine The title compound was prepared in four steps from 1-(2-(6-methoxypyridin-3-yl)-2,3-dihydrobenzo[b][1,4]dioxin-6-yl)ethan-1-amine, 2-chloro-5-iodo-3-nitropyridine, and 2-methylbut-3-yn-2-amine as described in Example 1-5-5 through Example 1-5-8: $^1$H NMR (400 MHz, Chloroform-d) δ 8.43 (d, J=1.8 Hz, 1H), 8.20 (d, J=2.4 Hz, 1H), 8.08-8.02 (m, 2H), 7.59 (dd, J=8.6, 2.5 Hz, 1H), 6.96-6.83 (m, 3H), 6.79 (d, J=8.6 Hz, 1H), 5.97 (q, J=7.1 Hz, 1H), 5.08 (dt, J=8.8, 2.0 Hz, 1H), 4.31 (dd, J=11.6, 2.5 Hz, 1H), 4.03 (ddd, J=11.6, 8.8, 0.9 Hz, 1H), 3.95 (s, 3H), 1.96 (d, J=7.1 Hz, 3H), 1.53 (s, 6H), 1.33-1.17 (m, 2H), 0.92-0.84 (m, 1H); (M+H)=470.

Example 1-19: Synthesis of 3-((2-(4-(difluoromethoxy)phenyl)-2,3-dihydrobenzo[b][1,4]dioxin-6-yl)methyl)-3H-imidazo[4,5-b]pyridine Example 1-19-1: Preparation of 2-(benzyloxy)-4-((6-iodo-3H-imidazo[4,5-b]pyridin-3-yl)methyl)phenol The title compound was prepared in three steps from 5-(aminomethyl)-2-(benzyloxy)phenol and 2-chloro-3-nitropyridine as described in Example 1-2-1 through Example 1-2-3.

Example 1-19-2: Preparation of 2-(2-(benzyloxy)-4-((6-iodo-3H-imidazo[4,5-b]pyridin-3-yl)methyl)phenoxy)-1-(4-(difluoromethoxy)phenyl)ethan-1-one The title compound was prepared from 2-(benzyloxy)-4-((6-iodo-3H-imidazo[4,5-b]pyridin-3-yl)methyl)phenol and 2-bromo-1-(4-(difluoromethoxy)phenyl)ethan-1-one as described in Example 1-1-1.

Example 1-19-3: Preparation of 2-(4-((3H-imidazo[4,5-b]pyridin-3-yl)methyl)-2-(benzyloxy)phenoxy)-1-(4-(difluoromethoxy)phenyl)ethan-1-ol To a stirred solution of 2-(2-(benzyloxy)-5-((6-iodo-3H-imidazo[4,5-b]pyridin-3-yl)methyl)phenoxy)-1-(4-(difluoromethoxy)phenyl)ethanone (0.45 g, 0.70 mmol) in tetrahydrofuran (15 mL) was added 2.0M lithium aluminum hydride solution in tetrahydrofuran (0.44 mL, 0.88 mmol) dropwise. After 25 min, the mixture was diluted with ether (50 mL) and quenched by the addition of 5 drops of water and 3 drops of 50% sodium hydroxide solution. The mixture was stirred at room temperature for 15 min and was then dried over magnesium sulfate, filtered, and concentrated to provide 0.37 g (>100%) of 2-(4-((3H-imidazo[4,5-b]pyridin-3-yl)methyl)-2-(benzyloxy)phenoxy)-1-(4-(difluoromethoxy)phenyl)ethan-1-ol as an orange oil.

Example 1-19-4: Preparation of 3-((2-(4-(difluoromethoxy)phenyl)-2,3-dihydrobenzo[b][1,4]dioxin-6-yl)methyl)-3H-imidazo[4,5-b]pyridine To a stirred solution of 2-(4-((3H-imidazo[4,5-b]pyridin-3-yl)methyl)-2-(benzyloxy)phenoxy)-1-(4-(difluoromethoxy)phenyl)ethan-1-ol (0.32 g, 0.62 mmol) in acetic acid (5 mL) was added 37 wt. % hydrochloric acid solution (5 mL). The resulting mixture was heated to 70° C. After 20 min, the mixture was allowed to cool to room temperature and was diluted with water. The mixture was adjusted to pH ~6 by the addition of 2N sodium hydroxide solution, then it was extracted with ethyl acetate. The organic phase was separated and washed with water and brine. The organic phase was dried over magnesium sulfate, filtered, and concentrated to provide a crude mixture, which contained the title compound and uncyclized intermediates. The crude mixture was dissolved in 1,4-dioxane (25 mL) and was treated with resin-bound triphenylphosphine (0.43 g, 1.30 mmol), N,N-diisopropylethylamine (1.0 mL, 5.85 mmol), and carbon tetrachloride (0.30 mL, 3.11 mmol). The mixture was heated to 120° C. After 16 h, the mixture was allowed to cool to room temperature and was filtered with the aid of dichloromethane. The filtrate was concentrated. Chromatographic purification of the crude product (Biotage, 12 g silica gel column, 0-10% methanol/dichloromethane elute) afforded a partially purified product that was further subjected to HPLC purification to provide 0.006 g (2%) of 3-((2-(4-(difluoromethoxy)phenyl)-2,3-dihydrobenzo[b][1,4]dioxin-6-yl)methyl)-3H-imidazo[4,5-b]pyridine as an oil: $^1$H NMR (400 MHz, CDCl$_3$) δ 8.46 (dd, J=4.8, 1.3 Hz, 1H), 8.15-8.03 (m, 2H), 7.41 (d, J=8.6 Hz, 2H), 7.32-7.23 (m, 1H), 7.21-7.13 (m, 2H), 6.98-6.82 (m, 3H), 6.52 (t, J=73.6 Hz, 1H), 5.41 (s, 2H), 5.10 (dd, J=8.8, 2.4 Hz, 1H), 4.32 (dd, J=11.6, 2.4 Hz, 1H), 3.98 (dd, J=11.6, 8.8 Hz, 1H) ppm; (M+1)=410.

Example 1-20: Synthesis of 6-(1,3-dimethyl-1H-pyrazol-4-yl)-3-((2-(2-fluoro-4-methoxyphenyl)-2,3-dihydrobenzo[b][1,4]dioxin-6-yl)methyl)-3H-imidazo[4,5-b]pyridine Example 1-20-1: Preparation of 2-(benzyloxy)-4-((6-(1,3-dimethyl-1H-pyrazol-4-yl)-3H-imidazo[4,5-b]pyridin-3-yl)methyl)phenol The title compound was prepared from 2-(benzyloxy)-4-((6-iodo-3H-imidazo[4,5-b]pyridin-3-yl)methyl)phenol (Example 1-19-1) and 1,3-dimethyl-4-(4,4,5,5-tetramethyl-1,3,2-dioxaborolan-2-yl)-1H-pyrazole as described in Example 1-4.

Example 1-20-2: Preparation of 2-(2-(benzyloxy)-4-((6-(1,3-dimethyl-1H-pyrazol-4-yl)-3H-imidazo[4,5-b]pyridin-3-yl)methyl)phenoxy)-1-(2-fluoro-4-methoxyphenyl)ethan-1-one The title compound was prepared from 2-(benzyloxy)-4-((6-(1,3-dimethyl-1H-pyrazol-4-yl)-3H-imidazo[4,5-b]pyridin-3-yl)methyl)phenol and 2-bromo-1-(2-fluoro-4-methoxyphenyl)ethan-1-one as described in Example 1-1-1.

Example 1-20-3: Preparation of 2-(2-(benzyloxy)-4-((6-(1,3-dimethyl-1H-pyrazol-4-yl)-3H-imidazo[4,5-b]pyridin-3-yl)methyl)phenoxy)-1-(2-fluoro-4-methoxyphenyl)ethan-1-ol The title compound was prepared from 2-(2-(benzyloxy)-4-((6-(1,3-dimethyl-1H-pyrazol-4-yl)-3H-imidazo[4,5-b]pyridin-3-yl)methyl)phenoxy)-1-(2-fluoro-4-methoxyphenyl)ethan-1-one as described in Example 1-5-2.

Example 1-20-4: Preparation of 6-(1,3-dimethyl-1H-pyrazol-4-yl)-3-((2-(2-fluoro-4-methoxyphenyl)-2,3-dihydrobenzo[b][1,4]dioxin-6-yl)methyl)-3H-imidazo[4,5-b]pyridine To a stirred solution of 2-(2-(benzyloxy)-4-((6-(1,3-dimethyl-1H-pyrazol-4-yl)-3H-imidazo[4,5-b]pyridin-3-yl)methyl)phenoxy)-1-(2-fluoro-4-methoxyphenyl)ethan-1-ol (0.14 g, 0.24 mmol) in methanol (4 mL) was slowly added 48% aqueous hydrobromic acid solution (8 mL). The reaction was heated to 50° C. After 25 min, the mixture was diluted with (50 mL) and dichloromethane (50 mL). The biphasic mixture neutralized by the addition of solid sodium bicarbonate (resulting pH ~7-8). The organic phase was separated. The aqueous phase was extracted with chloroform. The combined organic phases were dried over sodium sulfate, filtered, and concentrated. Chromatographic purification of the crude product (Biotage, 12 g silica gel column, 0-10% methanol/dichloromethane elute) afforded 0.055 g (47%) of 6-(1,3-dimethyl-1H-pyrazol-4-yl)-3-((2-(2-fluoro-4-methoxyphenyl)-2,3-dihydrobenzo[b][1,4]dioxin-6-yl)methyl)-3H-imidazo[4,5-b]pyridine as a white solid: $^1$H NMR (400 MHz, CDCl$_3$) δ 8.46 (d, J=1.9 Hz, 1H), 8.09-8.02 (m, 2H), 7.47 (s, 1H), 7.37-7.33 (m, 1H), 6.98-6.91 (m, 2H), 6.87 (dd, J=8.3, 2.1 Hz, 1H), 6.78-6.70 (m, 1H), 6.67-6.63 (m, 1H), 5.39 (s, 2H), 5.35 (dd, J=8.7, 2.4 Hz, 1H), 4.35 (dd, J=11.4, 2.4 Hz, 1H), 4.00 (dd, J=11.4, 8.7 Hz, 1H), 3.91 (s, 3H), 3.80 (s, 3H), 2.41 (s, 3H) ppm; (M+1)=486.

Example 1-21: Synthesis of 6-bromo-3-((2-(6-methoxypyridin-3-yl)-2,3-dihydrobenzo[b][1,4]dioxin-6-yl)methyl)pyrazolo[1,5-a]pyrimidine Example 1-21-1: Preparation of 5-bromo-2-((4-methoxybenzyl)oxy)phenol To a stirred solution of 5-bromo-2-((4-methoxybenzyl)oxy)benzaldehyde (1.00 g, 3.11 mmol) in dichloromethane (30 mL) was added 3-chloroperoxybenzoic acid (1.40 g, 6.23 mmol). After 16 h, the mixture was partitioned between dichloromethane and saturated sodium metabisulfite solution. The phases were separated, and the organic phase was washed with water and brine, dried over magnesium sulfate, filtered, and concentrated. The crude product was dissolved in methanol (20 mL) and 1M sodium hydroxide solution (1 mL) was added. The mixture turned yellow immediately. After 30 min, the reaction mixture was partitioned between water and ethyl acetate. 1M hydrochloric acid solution (2 mL) was added, and the phases were separated. The organic phase was washed with water and brine, dried over magnesium sulfate, filtered, and to provide 0.94 g (98%) of 5-bromo-2-((4-methoxybenzyl)oxy)phenol as a yellow liquid.

Example 1-21-2: Preparation of 2-(5-bromo-2-((4-methoxybenzyl)oxy)phenoxy)-1-(6-methoxypyridin-3-yl)ethan-1-one The title compound was prepared from 5-bromo-2-((4-methoxybenzyl)oxy)phenol as described in Example 1-18-1.

Example 1-21-3: Preparation of 2-(5-bromo-2-hydroxyphenoxy)-1-(6-methoxypyridin-3-yl)ethan-1-one To a stirred solution of 2-(5-bromo-2-((4-methoxybenzyl)oxy)phenoxy)-1-(6-methoxypyridin-3-yl)ethanone (1.00 g, 2.18 mmol) in dichloromethane (10 mL) was added trifluoroacetic acid (5 mL). The mixture was allowed to stir at room temperature. After 30 min, the reaction mixture was concentrated, and the residue was partitioned between dichloromethane and saturated sodium bicarbonate solution. The phases were separated, and the organic phase was washed with water and brine, dried over magnesium sulfate, filtered, and concentrated. Chromatographic purification of the crude product (CombiFlash, silica gel column, 0-50% ethyl acetate/dichloromethane elute) afforded 0.68 g (91%) of 2-(5-bromo-2-hydroxyphenoxy)-1-(6-methoxypyridin-3-yl)ethanone as a light yellow gum.

Example 1-21-4: Preparation of 5-(6-bromo-2,3-dihydrobenzo[b][1,4]dioxin-2-yl)-2-methoxypyridine The title compound was prepared in two steps from 2-(5-bromo-2-hydroxyphenoxy)-1-(6-methoxypyridin-3-yl)ethanone using similar procedures to those described in Example 1-14-2 (ketone reduction) and Example 1-12-4 (cyclization).

Example 1-21-5: Preparation of (2-(6-methoxypyridin-3-yl)-2,3-dihydrobenzo[b][1,4]dioxin-6-yl)boronic acid To a stirred and cooled (−78° C.) solution of 5-(6-bromo-2,3-dihydrobenzo[b][1,4]dioxin-2-yl)-2-methoxypyridine (100.0 mg, 310.4 μmol) in tetrahydrofuran (5 mL) was added 2.5M n-butyllithium solution in hexane (0.19 mL, 0.47 mmol). The resulting mixture was allowed to stir at −78° C. After 5 min, triisopropyl borate (0.22 mL, 0.93 mmol) was added. The mixture was allowed to slowly warm to room temperature. After 30 min, water was added, and the mixture was further diluted with ethyl acetate. The two phases were separated, and the organic phase was washed with brine, dried over magnesium sulfate, filtered, and concentrated. Chromatographic purification of the crude product (CombiFlash, silica gel column, 0-20% methanol/ethyl acetate elute) afforded 0.053 g (60%) of (2-(6-methoxypyridin-3-yl)-2,3-dihydrobenzo[b][1,4]dioxin-6-yl)boronic acid as a white solid.

Example 1-21-6: Preparation of 6-bromopyrazolo[1,5-a]pyrimidine-3-carbaldehyde To a stirred and cooled (0° C.) solution of 6-bromopyrazolo[1,5-a]pyrimidine (9.00 g, 43.13 mmol) in N,N-dimethylformamide (90 mL) was added phosphorous oxychloride (20.06 g, 129.53 mmol) dropwise over a 3 min period. After 30 min, the cooling bath was removed, and the mixture was allowed to warm to room temperature. After 16 h, the mixture was quenched by the slow addition of saturated sodium carbonate solution. The resulting basic mixture was extracted with dichloromethane (×3). The combined organic phases were washed with water and brine, dried over magnesium sulfate, filtered, and concentrated. The residue was suspended in dichloromethane and heptane, and the solid material was collected by filtration and dried to provide 7.10 g (73%) of 6-bromopyrazolo[1,5-a]pyrimidine-3-carbaldehyde as a yellow solid.

Example 1-21-7: Preparation of (E/Z)-N'-((6-bromopyrazolo[1,5-a]pyrimidin-3-yl)methylene)-4-methylbenzenesulfonohydrazide To a stirred solution of 6-bromopyrazolo[1,5-a]pyrimidine-3-carbaldehyde (7.10 g, 31.6 mmol) in 1,4-dioxane (200 mL) was added 4-methylbenzenesulfonylhydrazide (6.10 g, 31.6 mmol). The resulting mixture was heated to 100° C. After 2 h, the mixture was allowed to cool to room temperature and was concentrated. The residue was suspended in ethyl acetate/hexanes, and the solids were isolated by filtration and dried to provide 12.50 g (99%) of (E/Z)-N'-((6-bromopyrazolo[1,5-a]pyrimidin-3-yl)methylene)-4-methylbenzenesulfonohydrazide as an orange solid.

Example 1-21-8: Preparation of 6-bromo-3-((2-(6-methoxypyridin-3-yl)-2,3-dihydrobenzo[b][1,4]dioxin-6-yl)methyl)pyrazolo[1,5-a]pyrimidine To a stirred solution of (2-(6-methoxypyridin-3-yl)-2,3-dihydrobenzo[b][1,4]dioxin-6-yl)boronic acid (0.050 g, 0.17 mmol), in 1,4-dioxane (10 mL) was added N'-((6-bromopyrazolo[1,5-a]pyrimidin-3-yl)methylene)-4-methylbenzenesulfonohydrazide (0.069 mg, 0.17 mmol), and potassium carbonate (0.048 g, 0.34 mmol). The resulting mixture was heated to 100° C. After 16 h, the mixture was allowed to cool to room temperature and was filtered. The filtrate was concentrated. Chromatographic purification of the crude product (CombiFlash, silica gel column, 0-50% ethyl acetate/hexanes elute) afforded 0.028 g (36%) of 6-bromo-3-((2-(6-methoxypyridin-3-yl)-2,3-dihydrobenzo[b][1,4]dioxin-6-yl)methyl)pyrazolo[1,5-a]pyrimidine as a beige solid: $^1$H NMR (400 MHz, CDCl$_3$) δ 8.76 (d, J=2.2 Hz, 1H), 8.43 (d, J=2.2 Hz, 1H), 8.20 (d, J=2.5 Hz, 1H), 7.92 (s, 1H), 7.61 (ddd, J=8.7, 6.4, 2.5 Hz, 1H), 6.90-6.75 (m, 4H), 5.05 (td, J=9.2, 2.4 Hz, 1H), 4.29 (dt, J=11.5, 2.8 Hz, 1H), 4.10-3.92 (m, 6H) ppm; (M+1)=453.

Example 1-22: Synthesis of 3-((2-(6-methoxypyridin-3-yl)-2,3-dihydrobenzo[b][1,4]dioxin-6-yl)methyl)pyrazolo[1,5-a]pyridine

Example 1-22-1: Preparation of (2-(6-methoxypyridin-3-yl)-2,3-dihydrobenzo[b][1,4]dioxin-6-yl)(pyrazolo[1,5-a]pyridin-3-yl)methanol To a stirred and cooled (−78 °C.) solution of 5-(6-bromo-2,3-dihydrobenzo[b][1,4]dioxin-2-yl)-2-methoxypyridine (0.21 g, 0.66 mmol, Example 1-21-4) in tetrahydrofuran (3 mL) was added 2.5M n-butyllithium solution in hexane (0.29 mL, 0.73 mmol). After 5 min, pyrazolo[1,5-a]pyridine-3-carbaldehyde (0.097 g, 0.66 mmol) in tetrahydrofuran (1 mL) was added. After 30 min, the mixture was quenched by the addition of saturated ammonium chloride solution, and the mixture was allowed to warm to room temperature. The mixture was partitioned between water and ethyl acetate. The two phases were separated, and the organic phase was washed with brine, dried over magnesium sulfate, filtered, and concentrated. Chromatographic purification of the crude product (CombiFlash, silica gel column, ethyl acetate/dichloromethane elute) afforded 0.068 g (26%) of (2-(6-methoxypyridin-3-yl)-2,3-dihydrobenzo[b][1,4]dioxin-6-yl)(pyrazolo[1,5-a]pyridin-3-yl)methanol as a beige solid.

Example 1-22-2: Preparation of 3-((2-(6-methoxypyridin-3-yl)-2,3-dihydrobenzo[b][1,4]dioxin-6-yl)methyl)pyrazolo[1,5-a]pyridine A stirred solution of (2-(6-methoxypyridin-3-yl)-2,3-dihydrobenzo[b][1,4]dioxin-6-yl)(pyrazolo[1,5-a]pyridin-3-yl)methanol (0.065 g, 0.17 mmol) in trifluoroacetic acid (3 mL) was added triethylsilane (0.082 mL, 0.50 mmol). The mixture was allowed to stir at room temperature. After 30 min, the mixture was partitioned between dichloromethane and saturated sodium bicarbonate solution. Additional solid sodium bicarbonate was added until the mixture was neutralized. The phases were separated, and the organic phase was washed with saturated sodium bicarbonate solution, water, and brine, dried over magnesium sulfate, filtered, and concentrated. Chromatographic purification of the crude product (CombiFlash, silica gel column, 0-50% ethyl acetate/dichloromethane elute) afforded 0.047 g (76%) of 3-((2-(6-methoxypyridin-3-yl)-2,3-dihydrobenzo[b][1,4]dioxin-6-yl)methyl)pyrazolo[1,5-a]pyridine as a colorless sticky gum: $^1$H NMR (400 MHz, CDCl$_3$) δ 8.42 (dt, J=7.0, 1.1 Hz, 1H), 8.20 (d, J=2.5 Hz, 1H), 7.80 (s, 1H), 7.61 (dd, J=8.6, 2.5 Hz, 1H), 7.36 (dt, J=8.9, 1.3 Hz, 1H), 7.02 (ddd, J=8.9, 6.6, 1.1 Hz, 1H), 6.87 (d, J=8.2 Hz, 1H), 6.82-6.66 (m, 4H), 5.07 (dd, J=8.8, 2.4 Hz, 1H), 4.28 (dd, J=11.5, 2.4 Hz, 1H), 4.07-3.96 (m, 3H), 3.95 (s, 3H) ppm; (M+1)=374.

Example 1-23: Synthesis of 4-(3-((2-(6-methoxypyridin-3-yl)-2,3-dihydrobenzo[b][1,4]dioxin-6-yl)methyl)imidazo[1,2-b]pyridazin-7-yl)-2-methylbut-3-yn-2-amine Example 1-23-1: Preparation of 2-(6-methoxypyridin-3-yl)-2,3-dihydrobenzo[b][1,4]dioxine-6-carbaldehyde To a stirred and cooled (−78 °C.) solution of 5-(6-bromo-2,3-dihydrobenzo[b][1,4]dioxin-2-yl)-2-methoxypyridine (0.13 g, 0.40 mmol) in tetrahydrofuran (5 mL) was added 2.7M n-butyllithium solution in hexane (0.30 ml, 0.81 mmol). The resulting mixture was allowed to stir −78 °C. After 15 min, N,N-dimethylformamide (0.094 ml, 1.21 mmol) was added, and the mixture was allowed to stir at −78° C. After 30 min, the cooling bath was removed, and the mixture was allowed to warm to room temperature. After 30 min, the mixture was quenched by the addition of saturated ammonium chloride solution (5 mL). The mixture was extracted with diethyl ether/ethyl acetate (1:1, 2×50 mL), and the combined organic phases were washed with brine (10 mL), dried over magnesium sulfate, filtered and concentrated to provide 0.10 g (91%) of 2-(6-methoxypyridin-3-yl)-2,3-dihydrobenzo[b][1,4]dioxine-6-carbaldehyde as an oil.

Example 1-23-2: Preparation of 3-bromo-7-chloroimidazo[1,2-b]pyridazine

To a stirred and cooled (0° C.) solution of 7-chloroimidazo[1,2-b]pyridazine (7.30 g, 47.54 mmol) in N,N-dimethylformamide (100 mL) was added N-bromosuccinimide (8.55 g, 47.54 mmol). The mixture was allowed to stir at 0° C. After 1 h, the mixture was allowed to warm to room temperature. After 30 min, the mixture was diluted with water and ethyl acetate. The phases were separated, and the aqueous phase was extracted with ethyl acetate. The combined organic phases were washed with brine, dried over sodium sulfate, filtered, and concentrated. Chromatographic purification of the crude product (Biotage, silica gel column, 5-40% ethyl acetate/dichloromethane elute) afforded 5.32 g (48%) of 3-bromo-7-chloroimidazo[1,2-b]pyridazine as a light yellow solid.

Example 1-23-3: Preparation of (7-chloroimidazo[1,2-b]pyridazin-3-yl)(2-(6-methoxypyridin-3-yl)-2,3-dihydrobenzo[b][1,4]dioxin-6-yl)methanol To a stirred solution of 3-bromo-7-chloroimidazo[1,2-b]pyridazine (0.11 g, 0.46 mmol) in tetrahydrofuran (3 mL) was added 3M ethylmagnesium bromide solution in ether (0.18 mL, 0.55 mmol). A moderate exotherm was noted upon addition, and the resulting dark suspension was allowed to stir at room temperature. After 15 min, a solution of 2-(6-methoxypyridin-3-yl)-2,3-dihydrobenzo[b][1,4]dioxine-6-carbaldehyde (0.10 g, 0.37 mmol, Example 1-23-1) in tetrahydrofuran (2 mL) was added to the reaction mixture via cannula. After 80 min, the mixture was heated to −50° C. After 15 min, the mixture was allowed to cool to room temperature and was quenched by the addition of saturated ammonium chloride solution (0.020 mL). The mixture was concentrated. Chromatographic purification of the crude product (Biotage, 12 g silica gel column, 0-10% methanol/dichloromethane elute) afforded 0.025 g (16%) of (7-chloroimidazo[1,2-b]pyridazin-3-yl)(2-(6-methoxypyridin-3-yl)-2,3-dihydrobenzo[b][1,4]dioxin-6-yl)methanol as an oil.

Example 1-23-4: Preparation of 7-chloro-3-((2-(6-methoxypyridin-3-yl)-2,3-dihydrobenzo[b][1,4]dioxin-6-yl)methyl)imidazo[1,2-b]pyridazine The title compound was prepared from of (7-chloroimidazo[1,2-b]pyridazin-3-yl)(2-(6-methoxypyridin-3-yl)-2,3-dihydrobenzo[b][1,4]dioxin-6-yl)methanol as described in Example 1-22-2.

Example 1-23-5: Preparation of 4-(3-((2-(6-methoxypyridin-3-yl)-2,3-dihydrobenzo[b][1,4]dioxin-6-yl)methypimidazo[1,2-b]pyridazin-7-yl)-2-methylbut-3-yn-2-amine A suspension of 7-chloro-3-((2-(6-methoxypyridin-3-yl)-2,3-dihydrobenzo[b][1,4]dioxin-6-yl)methyl)imidazo[1,2-b]pyridazine (0.020 g, 0.049 mmol) and cesium carbonate (0.048 g, 0.15 mmol) in acetonitrile (5 mL) was degassed under nitrogen for 2 min. The mixture was treated with bis(acetonitrile)palladium(II) chloride (0.002 g, 0.007 mmol), 2-(dicyclohexylphosphino)-2',4',6'-triisopropylbiphenyl (0.007 g, 0.015 mmol) and 2-methylbut-3-yn-2-amine (0.041 g, 0.49 mmol). The mixture was again degassed under nitrogen for 2 min. The mixture was then heated to 105° C. in a sealed vessel. After 45 min, the mixture was allowed to cool to room temperature and was concentrated. Chromatographic purification of the crude product (Biotage, 12 g silica gel column, 0-10% methanol/dichloromethane elute) afforded 0.011 g (49%) of 4-(3-((2-(6-methoxypyridin-3-yl)-2,3-dihydrobenzo[b][1,4]dioxin-6-yl)methyl)imidazo[1,2-b]pyridazin-7-yl)-2-methylbut-3-yn-2-amine as a solid: $^1$H NMR (400 MHz, CDCl$_3$) δ 8.26 (d, J=2.0 Hz, 1H), 8.20 (d, J=2.4 Hz, 1H), 7.89 (d, J=2.0 Hz, 1H), 7.61 (dd, J=8.6, 2.5 Hz, 1H), 7.57 (s, 1H), 6.91-6.84 (m, 2H), 6.84-6.76 (m, 2H), 5.07 (dd, J=8.8, 2.4 Hz, 1H), 4.29 (dd, J=11.5, 2.4 Hz, 1H), 4.25 (s, 2H), 4.03 (dd, J=11.5, 8.8 Hz, 1H), 3.95 (s, 3H), 1.53 (s, 6H) ppm; (M+1)=456.

Example 1-24: Synthesis of N-ethyl-4-((2-(6-methoxypyridin-3-yl)-2,3-dihydrobenzo[b][1,4]dioxin-6-yl)methyl)picolinamide Example 1-24-1: Preparation of 4-(chloromethyl)-N-ethylpicolinamide hydrochloride To a stirred solution of N-ethyl-4-(hydroxymethyl)picolinamide (0.20 g, 1.11 mmol) in dichloromethane (3 mL) was added thionyl chloride (0.24 mL, 3.33 mmol). The resulting mixture was allowed to stir at room temperature. After 3 h, the mixture was concentrated, and the residue was suspended in diethyl ether (20 mL)/1M hydrochloric acid in diethyl ether (1 mL). After 1 h, the mixture was concentrated to provide 0.25 g (96%) of 4-(chloromethyl)-N-ethylpicolinamide hydrochloride as a white solid.

Example 1-24-2: Preparation of 2-methoxy-5-(6-(4,4,5,5-tetramethyl-1,3,2-dioxaborolan-2-yl)-2,3-dihydrobenzo[b][1,4]dioxin-2-yl)pyridine To a stirred solution of 5-(6-bromo-2,3-dihydrobenzo[b][1,4]dioxin-2-yl)-2-methoxypyridine (0.29 g, 0.90 mmol, Example 1-21-4) in 1,4-dioxane (5 mL) was added [1,1'-bis(diphenylphosphino)ferrocene]palladium(II) chloride dichloromethane adduct (0.10 g, 0.13 mmol), bis(pinacolato)diboron (0.47 g, 1.82 mmol) and potassium acetate (0.29 g, 2.93 mmol). The mixture was flushed with nitrogen, the vessel was sealed, and the mixture was heated to 100° C. After 2 h, the mixture was allowed to cool to room temperature and was diluted with ethyl acetate. The mixture was filtered through a short plug of silica gel, and the filtrate was concentrated. Chromatographic purification of the crude product (CombiFlash, 12 g silica gel column, 0-25% ethyl acetate/heptane elute) afforded 0.38 g (>100%) of 2-methoxy-5-(6-(4,4,5,5-tetramethyl-1,3,2-dioxaborolan-2-yl)-2,3-dihydrobenzo[b][1,4]dioxin-2-yl)pyridine as a white solid (contaminated with pinacolborane).

Example 1-24-3: Preparation of N-ethyl-4-((2-(6-methoxypyridin-3-yl)-2,3-dihydrobenzo[b][1,4]dioxin-6-yl)methyl)picolinamide To a mixture 4-(chloromethyl)-N-ethylpicolinamide hydrochloride (0.13 g, 0.53 mmol), $2^{ND}$ generation XPhos precatalyst (0.035 g, 0.044 mmol), and potassium phosphate tribasic (0.39 g, 1.76 mmol) was added a solution of 2-methoxy-5-(6-(4,4,5,5-tetramethyl-1,3,2-dioxaborolan-2-yl)-2,3-dihydrobenzo[b][1,4]dioxin-2-yl)pyridine (0.27 g, 0.44 mmol) in tetrahydrofuran (2 mL) and water (2 mL). The vessel was sealed and the mixture was heated to 80° C. After 17 h, the mixture was allowed to cool to room temperature and was diluted with ethyl acetate (3 mL). The phases were separated and the aqueous phase was extracted with ethyl acetate (2×3 mL). The combined organic phases were dried over sodium sulfate, filtered, and concentrated. Chromatographic purification of the crude product (CombiFlash, 12 g silica gel column, 0-30% ethyl acetate/heptane elute) afforded an impure oil. This material was further purified by reverse phase HPLC (10-90% acetonitrile/0.1% trifluoroacetic acid in water) to provide 0.025 g (14%) of N-ethyl-4-((2-(6-methoxypyridin-3-yl)-2,3-dihydrobenzo[b][1,4]dioxin-6-yl)methyl)picolinamide as a sticky colorless solid. $^{1}$H NMR (400 MHz, CDCl$_3$) δ 8.42 (dd, J=4.9, 0.8 Hz, 1H), 8.21 (d, J=2.5 Hz, 1H), 8.05 (dd, J=1.8, 0.9 Hz, 1H), 8.00 (s, 1H), 7.61 (dd, J=8.6, 2.5 Hz, 1H), 7.22 (dd, J=5.0, 1.8 Hz, 1H), 6.88 (d, J=8.2 Hz, 1H), 6.83-6.76 (m, 2H) 6.69 (dd, J=8.2, 2.1 Hz, 1H), 5.08 (dd, J=8.8, 2.5 Hz, 1H), 4.30 (dd, J=11.5, 2.5 Hz, 1H), 4.03 (dd, J=11.5, 8.8 Hz, 1H), 3.95 (s, 3H), 3.94 (s, 2H), 3.50 (qd, J=7.3, 5.9 Hz, 2H), 1.26 (t, J=7.3 Hz, 3H) ppm; (M+1)=406.

Example 1-25: Synthesis of 4-((2-(6-methoxypyridin-3-yl)-2,3-dihydrobenzo[b][1,4]dioxin-6-yl)methyl)picolinamide Example 1-25-1: Preparation of 4-((2-(6-methoxypyridin-3-yl)-2,3-dihydrobenzo[b][1,4]dioxin-6-yl)methyl)picolinonitrile The title compound was prepared from 4-(chloromethyl)picolinonitrile and 2-methoxy-5-(6-(4,4,5,5-tetramethyl-1,3,2-dioxaborolan-2-yl)-2,3-dihydrobenzo[b][1,4]dioxin-2-yl)pyridine (Example 1-24-2) as described in Example 1-24-3.

Example 1-25-2: Preparation of 4-((2-(6-methoxypyridin-3-yl)-2,3-dihydrobenzo[b][1,4]dioxin-6-yl)methyl)picolinamide To a stirred solution of 4-((2-(6-methoxypyridin-3-yl)-2,3-dihydrobenzo[b][1,4]dioxin-6-yl)methyl)picolinonitrile (0.030 g, 0.083 mmol) and (E/Z)-acetaldehyde oxime (0.050 g, 0.85 mmol) in toluene (3 mL) was added chlorotris(triphenylphosphine)rhodium(I) (0.015 g, 0.016 mmol). The mixture was heated to 100° C. After 2 h, the mixture was allowed to cool to room temperature and was concentrated. Chromatographic purification of the crude product (CombiFlash, 4 g silica gel column, 0-100% ethyl acetate/heptane elute) afforded 0.024 g (76%) of 4-((2-(6-methoxypyridin-3-yl)-2,3-dihydrobenzo[b][1,4]dioxin-6-yl)methyl)picolinamide as a white solid: $^{1}$H NMR (400 MHz, DMSO-d6) δ 8.51 (dd, J=5.0, 0.7 Hz, 1H), 8.27 (d, J=2.4 Hz, 1H), 8.14-8.02 (m, 1H), 7.86 (dd, J=1.7, 0.8 Hz, 1H), 7.79 (dd, J=8.6, 2.5 Hz, 1H), 7.65-7.58 (m, 1H), 7.46 (dd, J=5.0, 1.7 Hz, 1H), 6.93-6.83 (m, 3H), 6.77 (dd, J=8.3, 2.1 Hz, 1H), 5.22 (dd, J=8.5, 2.4 Hz, 1H), 4.38 (dd, J=11.5, 2.5 Hz, 1H), 4.16 (dd, J=11.5, 8.5 Hz, 1H), 3.97 (s, 2H), 3.86 (s, 3H) ppm; (M+1)=378.

Example 1-26: Synthesis of 4-((2-(6-methoxypyridin-3-yl)-2,3-dihydrobenzo[b][1,4]dioxin-6-yl)methyl)-N-methylpicolinamide To a stirred solution of 4-((2-(6-methoxypyridin-3-yl)-2,3-dihydrobenzo[b][1,4]dioxin-6-yl)methyl)picolinonitrile (0.050 g, 0.14 mmol, Example 1-25-1) in 1,4-dioxane (2 mL) was added potassium trimethylsilanoate (0.040 g, 0.28 mmol). The resulting mixture was heated to 80° C. After 3 h, the mixture was treated with iodomethane (0.18 mL, 0.35 mmol), and the mixture was allowed to stir at 80° C. After 75 min, the mixture was allowed to cool to room temperature and was diluted with water. The mixture was extracted with ethyl acetate (3×2 mL). The combined organic phases were concentrated.

Chromatographic purification of the crude product (CombiFlash, 4 g silica gel column, 0-100% ethyl acetate/heptane elute) afforded a crude oil. Further purification by reverse phase HPLC (water/acetonitrile 10-90% elute, 15 mL/min)

followed by salt formation with 1.0M hydrogen chloride in diethyl ether provided 0.028 g (47%) of 4-((2-(6-methoxy-pyridin-3-yl)-2,3-dihydrobenzo[b][1,4]dioxin-6-yl)methyl)-N-methylpicolinamide as a light yellow solid:
1H NMR (400 MHz, DMSO-d6) δ 8.96-8.66 (m, 1H), 8.52 (d, J=4.3 Hz, 1H), 8.26 (s, 1H), 7.91 (s, 1H), 7.79 (d, J=7.9 Hz, 1H), 7.56-7.42 (m, 1H), 6.87 (m, 3H), 6.77 (d, J=7.7 Hz, 1H), 5.21 (d, J=7.6 Hz, 1H), 4.37 (d, J=11.1 Hz, 1H), 4.15 (t, J=9.6 Hz, 1H), 3.98 (s, 2H), 3.85 (s, 3H), 2.80 (d, J=4.2 Hz, 3H) ppm; (M+1)=392.

Example 1-27: Synthesis of 2-(1-methyl-1H-pyrazol-4-yl)-4-((2-(4-(trifluoromethyl)phenyl)-2,3-dihydrobenzo[b][1,4]dioxin-6-yl)methyl)pyridine 2,2,2-trifluoroacetate Example 1-27-1: Preparation of 2-(2,5-dibromophenoxy)-1-(4-(trifluoromethyl)phenyl)ethan-1-ol The title compound was prepared in two steps from 2,5-dibromophenol and 2-bromo-1-(4-(trifluoromethyl)phenyl)ethanone as described in Example 1-1-1 (alkylation) and Example 1-1-2 (ketone reduction).

Example 1-27-2: Preparation of 6-bromo-2-(4-(trifluoromethyl)phenyl)-2,3-dihydrobenzo[b][1,4]dioxine To a stirred solution of 2-(2,5-dibromophenoxy)-1-(4-(trifluoromethyl)phenyl)ethanol (4.17 g, 9.48 mmol) in degassed toluene (100 mL) was added copper(I) iodide (0.54 g, 2.84 mmol), cesium carbonate (3.40 g, 10.42 mmol), and N,N'-dimethylethylenediamine (0.52 mL, 4.74 mmol). The resulting mixture was heated to reflux. After 20 h, additional portions of copper(I) iodide and N,N'-dimethylethylenediamine were added to the mixture. After 48 h, the mixture was allowed to cool to room temperature and was concentrated. The residue was partitioned between 1M potassium bisulfate solution (100 mL) and ethyl acetate (100 mL). The phases were separated, and the aqueous phase was extracted with ethyl acetate (2×100 mL). The combined organic phases were dried over sodium sulfate, filtered, and concentrated. Chromatographic purification of the crude product (CombiFlash, 40 g silica gel column, 0-10% ethyl acetate/heptane elute) afforded 1.57 g (46%) of 6-bromo-2-(4-(trifluoromethyl)phenyl)-2,3-dihydrobenzo[b][1,4]dioxine as a white solid.

Example 1-27-3: Preparation of 4,4,5,5-tetramethyl-2-(2-(4-(trifluoromethyl)phenyl)-2,3-dihydrobenzo[b][1,4]dioxin-6-yl)-1,3,2-dioxaborolane The title compound was prepared from 6-bromo-2-(4-(trifluoromethyl)phenyl)-2,3-dihydrobenzo[b][1,4]dioxine as described in Example 1-24-2.

Example 1-27-4: Preparation of methyl 2-(1-methyl-1H-pyrazol-4-yl)isonicotinate

To a stirred solution of methyl 2-chloroisonicotinate (1.26 g, 7.12 mmol) in tetrahydrofuran (20 mL) and water (15 mL) was added 1-methyl-4-(4,4,5,5-tetramethyl-1,3,2-dioxaborolan-2-yl)-1H-pyrazole (1.72 g, 7.84 mmol), $2^{nd}$ generation XPhos precatalyst (0.11 g, 0.14 mmol), and potassium phosphate tribasic (4.63 g, 21.37 mmol). The mixture was degassed under vacuum/backfilled with nitrogen (×3), and then it was allowed to stir at room temperature. After 1 h, the yellow solution was diluted with water (75 mL). The mixture was extracted with ethyl acetate (3×75 mL). The combined organic phases were dried over magnesium sulfate, filtered, and concentrated. Chromatographic purification of the crude product (CombiFlash, 24 g silica gel gold column, 1-5% methanol/dichloromethane elute) afforded 1.28 g (83%) of methyl 2-(1-methyl-1H-pyrazol-4-yl)isonicotinate a white solid.

Example 1-27-5: Preparation of (2-(1-methyl-1H-pyrazol-4-yl)pyridin-4-yl)methanol To a stirred and cooled (0° C.) solution of methyl 2-(1-methyl-1H-pyrazol-4-yl)isonicotinate (1.28 g, 5.89 mmol) in tetrahydrofuran (40 mL) was added lithium aluminum hydride (0.23 g, 6.19 mmol) (gas evolution noted). The resulting mixture was allowed to stir at 0° C. After 30 min, the reaction mixture was treated with water (0.25 mL), 1N sodium hydroxide solution (0.25 mL), and water (0.75 mL). The resulting mixture was allowed to stir at room temperature for 15 min. The mixture was then treated with magnesium sulfate and filtered through Celite with the aid of ethyl acetate (100 mL). The filtrate was concentrated to provide 1.01 g (91%) of (2-(1-methyl-1H-pyrazol-4-yl)pyridin-4-yl)methanol as a colorless oil.

Example 1-27-6: Preparation of 4-(chloromethyl)-2-(1-methyl-1H-pyrazol-4-yl)pyridine hydrochloride To a stirred solution of (2-(1-methyl-1H-pyrazol-4-yl)pyridin-4-yl)methanol (0.19 g, 0.98 mmol) in dichloromethane (10 mL) was added thionyl chloride (0.50 mL, 6.85 mmol), resulting in the formation of a milky white suspension. After 2.5 h, the mixture was concentrated to provide 0.25 g (>100%) of 4-(chloromethyl)-2-(1-methyl-1H-pyrazol-4-yl)pyridine hydrochloride as a light yellow solid.

Example 1-27-7: Preparation of 2-(1-methyl-1H-pyrazol-4-yl)-4-((2-(4-(trifluoromethyl)phenyl)-2,3-dihydrobenzo[b][1,4]dioxin-6-yl)methyl)pyridine 2,2,2-trifluoroacetate The title compound was prepared from 4,4,5,5-tetramethyl-2-(2-(4-(trifluoromethyl)phenyl)-2,3-dihydrobenzo[b][1,4]dioxin-6-yl)-1,3,2-dioxaborolane (Example 1-27-3) and 4-(chloromethyl)-2-(1-methyl-1H-pyrazol-4-yl)pyridine hydrochloride (Example 1-27-6) as described in Example 1-24-3: $^1$H NMR (400 MHz, DMSO-d6) δ 8.50 (d, J=5.6 Hz, 1H), 8.45 (s, 1H), 8.14 (s, 1H), 7.92 (s, 1H), 7.80 (d, J=8.2 Hz, 2H), 7.70 (d, J=8.2 Hz, 2H), 7.40-7.28 (m, 1H), 7.01-6.91 (m, 2H), 6.86 (dd, J=8.2, 2.1 Hz, 1H), 5.38 (dd, J=7.9, 2.4 Hz, 1H), 4.47 (dd, J=11.6, 2.4 Hz, 1H), 4.10 (dd, J=11.6, 7.9 Hz, 1H), 3.99 (s, 2H), 3.92 (s, 3H) ppm; (M+1)=452.

Example 1-28: Synthesis of 5-((2-(6-methoxypyridin-3-yl)-2,3-dihydrobenzo[b][1,4]dioxin-6-yl)methyl)pyrimidine-2,4-diamine Example 1-28-1: Preparation of 4-iodo-3-(2-(6-methoxypyridin-3-yl)-2-oxoethoxy)benzaldehyde The title compound was prepared from 3-hydroxy-4-iodobenzaldehyde and 2-bromo-1-(6-methoxypyridin-3-yl)ethan-1-one as described in Example 1-1-1.

Example 1-28-2: Preparation of 2-(5-(5,5-dimethyl-1,3-dioxan-2-yl)-2-iodophenoxy)-1-(6-methoxypyridin-3-yl)ethan-1-one To a stirred solution of 4-iodo-3-(2-(6-methoxypyridin-3-yl)-2-oxoethoxy)benzaldehyde (0.50 g, 1.26 mmol) and 2,2-dimethylpropane-1,3-diol (0.15 g, 1.38 mmol) in toluene (10 mL) was added Amberlyst-15 (0.050 g). The resulting mixture was heated to 110° C. After 16 h, the mixture was allowed to cool to room temperature and was washed with brine (3×10 mL), dried over sodium sulfate, filtered and concentrated to provide 0.61 g (99%) of 2-(5-(5,5-dimethyl-1,3-dioxan-2-yl)-2-iodophenoxy)-1-(6-methoxypyridin-3-yl)ethan-1-one as a colorless oil.

Example 1-28-3: Preparation of 2-(5-(5,5-dimethyl-1,3-dioxan-2-yl)-2-iodophenoxy)-1-(6-methoxypyridin-3-yl)ethan-1-ol The title compound was prepared from 2-(5-(5,5-dimethyl-1,3-dioxan-2-yl)-2-iodophenoxy)-1-(6-methoxypyridin-3-yl)ethan-1-one as described in Example 1-1-2.

Example 1-28-4: Preparation of 5-(6-(5,5-dimethyl-1,3-dioxan-2-yl)-2,3-dihydrobenzo[b][1,4]dioxin-2-yl)-2-methoxypyridine To a stirred suspension of 2-(5-(5,5-dimethyl-1,3-dioxan-2-yl)-2-iodophenoxy)-1-(6-methoxypyridin-3-yl)ethan-1-ol (0.44 g, 0.91 mmol), [1,1'-binaphthalene]-2,2'-diol (0.060 g, 0.20 mmol), and cesium carbonate (0.65 g, 2.00 mmol) in acetonitrile (10 mL) was added copper(I) iodide (0.040 g, 0.20 mmol). The mixture was degassed under vacuum/backfilled with nitrogen (×3), and then it was heated to 110° C. After 12 h, the mixture was allowed to cool to room temperature and was concentrated. Chromatographic purification of the crude product (silica gel column, 25% ethyl acetate/petroleum ether elute) provided 0.16 g (49%) of 5-(6-(5,5-dimethyl-1,3-dioxan-2-yl)-2,3-dihydrobenzo[b][1,4]dioxin-2-yl)-2-methoxypyridine as a white solid.

Example 1-28-5: Preparation of 2-(6-methoxypyridin-3-yl)-2,3-dihydrobenzo[b][1,4]dioxine-6-carbaldehyde To a stirred solution of 5-(6-(5,5-dimethyl-1,3-dioxan-2-yl)-2,3-dihydrobenzo[b][1,4]dioxin-2-yl)-2-methoxypyridine (0.16 g, 0.45 mmol) in dichloromethane (4 mL) was added trifluoroacetic acid (0.4 mL). After 3 h, the mixture was diluted with dichloromethane and neutralized with saturated sodium bicarbonate solution (pH=7-8). The phases were separated, and the organic phase was extracted with extracted dichloromethane (3×15 mL). The combined organic phases were washed with brine (15 mL), dried over sodium sulfate, filtered, and concentrated. Chromatographic purification of the crude product (silica gel column, 25% ethyl acetate/petroleum ether elute) provided 0.12 g (90%) of 2-(6-methoxypyridin-3-yl)-2,3-dihydrobenzo[b][1,4]dioxine-6-carbaldehyde as a light yellow solid.

Example 1-28-6: Preparation of (E/Z)-2-((2-(6-methoxypyridin-3-yl)-2,3-dihydrobenzo[b][1,4]dioxin-6-yl)methyl)-3-(phenylamino)acrylonitrile To a stirred solution of 2-(6-methoxypyridin-3-yl)-2,3-dihydrobenzo[b][1,4]dioxine-6-carbaldehyde (0.17 g, 0.62 mmol) and 3-(phenylamino)propanenitrile (0.10 g, 0.69 mmol) in dimethylsulfoxide was added sodium methoxide (0.038 g, 0.69 mmol). The mixture was heated to 95° C. After 1 h, the mixture was allowed to cool to room temperature and diluted with water (20 mL). The mixture was extracted with dichloromethane (3×60 mL). The combined organic phases were washed with brine (2×50 mL), dried over sodium sulfate, filtered, and concentrated. Chromatographic purification of the crude product (silica gel column, 50% ethyl acetate/petroleum ether elute) provided 0.10 g (40%) of (E/Z)-2-((2-(6-methoxypyridin-3-yl)-2,3-dihydrobenzo[b][1,4]dioxin-6-yl)methyl)-3-(phenylamino)acrylonitrile as a yellow solid.

Example 1-28-7: Preparation of 5-((2-(6-methoxypyridin-3-yl)-2,3-dihydrobenzo[b][1,4]dioxin-6-yl)methyl)pyrimidine-2,4-diamine To a stirred solution of guanidine hydrochloride (0.064 g, 0.67 mmol) in ethanol (2 mL) was added potassium tert-butoxide (0.081 g, 0.72 mmol) After 30 min, (E/Z)-2-((2-(6-methoxypyridin-3-yl)-2,3-dihydrobenzo[b][1,4]dioxin-6-yl)methyl)-3-(phenylamino)acrylonitrile (0.080 g, 0.20 mmol) was added, and resulting mixture was heated to 70° C. After 48 h, the mixture was allowed to cool to room temperature and was concentrated. The residue was dissolved in dichloromethane (20 mL) and was washed with brine, dried over sodium sulfate, filtered, and concentrated. Purification of the crude product via preparative HPLC afforded 0.031 g (39%) of 5-((2-(6-methoxypyridin-3-yl)-2,3-dihydrobenzo[b][1,4]dioxin-6-yl)methyl)pyrimidine-2,4-diamine as a white solid: $^1$H NMR (500 MHz, CDCl$_3$) δ 8.23 (d, J=2.5 Hz, 1H), 7.81 (s, 1H), 7.66-7.62 (m, 1H), 6.91 (d, J=8.0 Hz, 1H), 6.82 (d, J=8.5 Hz, 1H), 6.77 (s, 1H), 6.76-6.72 (m, 1H), 5.12-5.08 (m, 1H), 4.69 (s, 2H), 4.55 (s, 2H), 4.35-4.31 (m, 1H), 4.08-4.04 (m, 1H), 3.98 (s, 3H), 3.65 (s, 2H) ppm; (M+1)=366.

Example 1-29: Synthesis of 4-(3-((8-fluoro-2-(4-(trifluoromethyl)phenyl)-2,3-dihydrobenzo[b][1,4]dioxin-6-yl)methyl)-3H-imidazo[4,5-b]pyridin-6-yl)-2-methylbut-3-yn-2-amine

Example 1-29-1: Preparation of 8-fluoro-2-(4-(trifluoromethyl)phenyl)-2,3-dihydrobenzo[b][1,4]dioxine-6-carbonitrile The title compound was prepared in three steps from 3,4-difluoro-5-hydroxybenzonitrile and 2-bromo-1-(4-(trifluoromethyl)phenyl)ethan-1-one as described in Example 1-14-1 through Example 1-14-3.

Example 1-29-2: Preparation of tent-butyl ((8-fluoro-2-(4-(trifluoromethyl)phenyl)-2,3-dihydrobenzo[b][1,4]dioxin-6-yl)methyl)carbamate To a stirred and cooled (0° C.) solution of 8-fluoro-2-(4-(trifluoromethyl)phenyl)-2,3-dihydrobenzo[b][1,4]dioxine-6-carbonitrile (0.40 g, 1.24 mmol) in methanol (20 mL) was added di-t-butyl dicarbonate (0.54 g, 2.46 mmol), nickel(II) chloride hexahydrate (0.029 g, 0.12 mmol) and sodium borohydride (0.33 g, 8.66 mmol). The resulting black mixture was allowed to warm to room temperature. After 16 h, the mixture was diluted with water and extracted with ethyl acetate. The phases were separated, and the organic phase was washed saturated sodium bicarbonate solution and brine, dried over magnesium sulfate, filtered, and concentrated. Chromatographic purification of the crude product (CombiFlash, silica gel column, 0-100% ethyl acetate/dichloromethane elute) afforded 0.50g (95%) of tert-butyl ((8-fluoro-2-(4-(trifluoromethyl)phenyl)-2,3-dihydrobenzo[b][1,4]dioxin-6-yl)methyl)carbamate as a white solid.

Example 1-29-3: Preparation of (8-fluoro-2-(4-(trifluoromethyl)phenyl)-2,3-dihydrobenzo[b][1,4]dioxin-6-yl)methanamine hydrochloride To a stirred solution of tert-butyl ((8-fluoro-2-(4-(trifluoromethyl)phenyl)-2,3-dihydrobenzo[b][1,4]dioxin-6-yl)methyl)carbamate (0.50 g, 1.17 mmol) in dichloromethane (20 mL) was added 4N hydrogen chloride in dioxane solution (20 mL). The reaction mixture was allowed to stir at room temperature. After 2 h, the mixture was concentrated to provide 0.42 g (99%) of (8-fluoro-2-(4-(trifluoromethyl)phenyl)-2,3-dihydrobenzo[b][1,4]dioxin-6-yl)methanamine hydrochloride.

Example 1-29-4: Preparation of 3-((8-fluoro-2-(4-(trifluoromethyl)phenyl)-2,3-dihydrobenzo[b][1,4]dioxin-6-yl)methyl)-6-iodo-3H-imidazo[4,5-b]pyridine The title compound was prepared in three steps from (8-fluoro-2-(4-(trifluoromethyl)phenyl)-2,3-dihydrobenzo[b][1,4]dioxin-6-yl)methanamine hydrochloride and 2-chloro-5-iodo-3-nitropyridine as described in Example 1-5-5 through Example 1-5-7.

Example 1-29-5: Preparation of 4-(3-((8-fluoro-2-(4-(trifluoromethyl)phenyl)-2,3-dihydrobenzo[b][1,4]dioxin-6-yl)methyl)-3H-imidazo[4,5-b]pyridin-6-yl)-2-methylbut-3-yn-2-amine The title compound was prepared from 3-((8-fluoro-2-(4-(trifluoromethyl)phenyl)-2,3-dihydrobenzo[b][1,4]dioxin-6-yl)methyl)-6-iodo-3H-imidazo[4,5-b]pyridine and 2-methylbut-3-yn-amine as described Example 1-5-8: $^1$H NMR (400 MHz, DMSO-$d_6$) δ 8.68 (s, 1H), 8.44 (d, J=1.8 Hz, 1H), 8.13 (d, J=1.8 Hz, 1H), 7.80 (d, J=8.2 Hz, 2H), 7.69 (d, J=8.1 Hz, 2H), 6.94 (dd, J=11.2, 2.0 Hz, 1H), 6.83 (t, J=1.7 Hz, 1H), 5.45-5.41 (m, 3H), 4.52 (dd, J=11.8, 2.5 Hz, 1H), 4.19 (dd, J=11.8, 7.8 Hz, 1H), 1.47 (s, 6H) ppm; (M+1)=511.

Example 1-30: Synthesis of 3-((8-fluoro-2-(4-(trifluoromethyl)phenyl)-2,3-dihydrobenzo[b][1,4]dioxin-6-yl)methyl)-6-(4-methylpiperazin-1-yl)-3H-imidazo[4,5-b]pyridine 2,2,2-trifluoroacetate The title compound was prepared from 3-((8-fluoro-2-(4-(trifluoromethyl)phenyl)-2,3-dihydrobenzo[b][1,4]dioxin-6-yl)methyl)-6-iodo-3H-imidazo[4,5-b]pyridine and 1-methylpiperazine as described in Example 1-3: $^1$H NMR (400 MHz, DMSO-$d_6$) δ 9.37 (s, 1H), 8.55 (d, J=2.6 Hz, 1H), 7.86-7.75 (m, 3H), 7.71 (d, J=8.2 Hz, 2H), 7.05 (dd, J=11.0, 2.1 Hz, 1H), 6.96-6.92 (m, 1H), 5.54 (s, 2H), 5.46 (dd, J=7.6, 2.4 Hz, 1H), 4.55 (dd, J=11.8, 2.4 Hz, 1H), 4.33-4.17 (m, 1H), 3.97-3.93 (m, 2H), 3.62-3.58 (m, 2H), 3.30-3.26 (m, 2H), 3.18-3.14 (m, 2H), 2.92 (s, 3H) ppm; (M+1)=528.

Example 1-31: Synthesis of 3-((8-fluoro-2-(4-(trifluoromethyl)phenyl)-2,3-dihydrobenzo[b][1,4]dioxin-6-yl)methyl)-6-(piperidin-3-ylethynyl)-3H-imidazo[4,5-b]pyridine hydrochloride The title compound was prepared from 3-((8-fluoro-2-(4-(trifluoromethyl)phenyl)-2,3-dihydrobenzo[b][1,4]dioxin-6-yl)methyl)-6-iodo-3H-imidazo[4,5-b]pyridine (Example 1-29-4) and 3-ethynylpiperidine as described in Example 1-5-8: $^1$H NMR (400 MHz, DMSO-$d_6$) δ 9.72-9.57 (m, 1H), 9.39-9.16 (m, 2H), 8.61 (d, J=1.4 Hz, 1H), 8.33 (s, 1H), 7.81 (d, J=8.1 Hz, 2H), 7.71 (d, J=8.0 Hz, 2H), 7.02 (dd, J=11.2, 2.0 Hz, 1H), 6.92 (d, J=2.1 Hz, 1H), 5.57-5.43 (m, 3H), 4.55 (dd, J=11.7, 2.4 Hz, 1H), 4.21 (dd, J=11.7, 7.8 Hz, 1H), 3.75-3.64 (m, 1H), 3.55-3.45 (m, 1H), 3.43-3.33 (m, 1H), 3.31-3.10 (m, 1H), 3.09-2.89 (m, 1H), 2.11-1.64 (m, 4H) ppm; (M+1)=537.

Example 1-32: Synthesis of 3-((8-fluoro-2-(4-(trifluoromethyl)phenyl)-2,3-dihydrobenzo[b][1,4]dioxin-6-yl)methyl)-6-(1-methyl-1H-pyrazol-4-yl)-3H-imidazo[4,5-b]pyridine 2,2,2-trifluoroacetate The title compound was prepared from 3-((8-fluoro-2-(4-(trifluoromethyl)phenyl)-2,3-dihydrobenzo[b][1,4]dioxin-6-yl)methyl)-6-iodo-3H-imidazo[4,5-b]pyridine (Example 1-29-4) and 1-methyl-4-(4,4,5,5-tetramethyl-1,3,2-dioxaborolan-2-yl)-1H-pyrazole as described in Example 1-4: $^1$H NMR (400 MHz, DMSO-$d_6$) δ 8.99 (s, 1H), 8.78 (d, J=1.9 Hz, 1H), 8.34 (d, J=1.9 Hz, 1H), 8.30 (s, 1H), 8.03 (s, 1H), 7.81 (d, J=8.1 Hz, 2H), 7.70 (d, J=8.1 Hz, 2H), 7.02 (dd, J=11.1, 2.0 Hz, 1H), 6.95-6.82 (m, 1H), 5.47 (d, J=8.3 Hz, 3H), 4.54 (dd, J=11.8, 2.5 Hz, 1H), 4.20 (dd, J=11.8, 8.0 Hz, 1H), 3.90 (s, 3H) ppm; (M+1)=510.

Example 1-33: Synthesis of 3-((8-fluoro-2-(6-methoxypyridin-3-yl)-5-methyl-2,3-dihydrobenzo[b][1,4]dioxin-6-yl)methyl)-6-iodo-3H-imidazo[4,5-b]pyridine

Example 1-33-1: Preparation of 2-bromo-4,5-difluoro-3-hydroxybenzonitrile

To a stirred solution of 3,4-difluoro-5-hydroxybenzonitrile (6.53 g, 42.10 mmol) in acetic acid (75 mL), was added bromine (3.36 g, 21.05 mmol) over a period of 3 h. After the addition was complete, the mixture was diluted with water and extracted with dichloromethane. The phases were separated, and the organic phase was washed with brine, dried over magnesium sulfate, filtered, and concentrated. Chromatographic purification of the crude product (CombiFlash, silica gel column, 1% 7N ammonia in methanol/dichloromethane elute) afforded 3.52 g of a mixture of 2-bromo-4,5-difluoro-3-hydroxybenzonitrile and 2,6-dibromo-3,4-difluoro-5-hydroxybenzonitrile. This mixture was used on the next step without further purification.

Example 1-33-2: Preparation of 4,5-difluoro-3-hydroxy-2-methylbenzonitrile

To a stirred solution of 2-bromo-4,5-difluoro-3-hydroxybenzonitrile and 2,6-dibromo-3,4-difluoro-5-hydroxybenzonitrile (4.23 g crude material, ~40% 2-bromo-4,5-difluoro-3-hydroxybenzonitrile/~54% of 2,6-dibromo-3,4-difluoro-5-hydroxybenzonitrile) in tetrahydrofuran (100 mL) was added bis(trimethylalluminum)-1,4-diazabicyclo[2.2.2]octane adduct (4.63 g, 11.08 mmol), dicyclohexyl [2',4',6'-tris(1-methylethyl)[1,1'-biphenyl]-2-yl]-phosphine (0.52 g, 1.08 mmol), and tris(dibenzylideneacetone)dipalladium(0) (0.50 g, 0.54 mmol). The mixture was heated reflux. After 4 h, the mixture was cooled to 0° C. and was quenched by the addition of 1N hydrochloric acid solution. The mixture was extracted with dichloromethane, and the phases were separated. The organic phase was washed with brine, dried over magnesium sulfate, filtered, and concentrated. The residue was purified by prep-HPLC to afford 1.40 g (46%) of 4,5-difluoro-3-hydroxy-2-methylbenzonitrile as a white solid. In addition, 0.68 g (21%) of 3,4-difluoro-5-hydroxy-2,6-dimethylbenzonitrile was obtained, also as a white solid.

Example 1-33-3: Preparation of (8-fluoro-2-(6-methoxypyridin-3-yl)-5-methyl-2,3-dihydrobenzo[b][1,4]dioxin-6-yl)methanamine The title compound was prepared in four steps from 4,5-difluoro-3-hydroxy-2-methylbenzonitrile and 2-bromo-1-(6-methoxypyridin-3-yl)ethan-1-one as described in Example 1-14-1 through Example 1-14-4.

Example 1-33-4: Preparation of 3-((8-fluoro-2-(6-methoxypyridin-3-yl)-5-methyl-2,3-dihydrobenzo[b][1,4]dioxin-6-yl)methyl)-6-iodo-3H-imidazo[4,5-b]pyridine The title compound was prepared in three steps from (8-fluoro-2-(6-methoxypyridin-3-yl)-5-methyl-2,3-dihydrobenzo[b][1,4]dioxin-6-yl)methanamine and 2-chloro-5-iodo-3-nitropyridine as described in Example 1-5-5 through Example 1-5-7:. $^1$H NMR (400 MHz, DMSO-$d_6$) δ 8.61 (d, J=1.7 Hz, 1H), 8.53-8.46 (m, 2H), 8.29 (d, J=2.4 Hz, 1H), 8.14 (s, 1H), 7.81 (dd, J=8.7, 2.5 Hz, 1H), 6.90 (d, J=8.7 Hz, 1H), 5.43 (s, 2H), 5.30 (dd, J=8.4, 2.5 Hz, 1H), 4.53 (dd, J=11.5, 2.5 Hz, 1H), 4.23 (dd, J=11.7, 8.4 Hz, 1H), 3.87 (s, 3H), 2.12 (s, 3H) ppm; (M+1)=547.

Example 1-34: Synthesis of 6-cyclopropyl-3-((8-fluoro-2-(6-methoxypyridin-3-yl)-5-methyl-2,3-dihydrobenzo[b][1,4]dioxin-6-yl)methyl)-3H-imidazo[4,5-b]pyridine 2,2,2-trifluoroacetate The title compound was prepared from 3-((8-fluoro-2-(6-methoxypyridin-3-yl)-5-methyl-2,3-dihydrobenzo[b][1,4]dioxin-6-yl)methyl)-6-iodo-3H-imidazo[4,5-b]pyridine (Example 1-33-4) and cyclopropylboronic acid was described in Example 1-9: $^1$H NMR (400 MHz, DMSO-$d_6$) δ 9.04-8.48 (m, 2H), 8.45 (s, 1H), 8.30 (d, J=2.5 Hz, 1H), 7.81 (dd, J=8.6, 2.4 Hz, 1H), 6.90 (d, J=8.6 Hz, 1H), 6.79 (d, J=11.4 Hz, 1H), 5.55 (s, 2H), 5.29 (dd, J=8.4, 2.4 Hz, 1H), 4.68-4.39 (m, 1H), 4.27 (dd, J=11.7, 8.4 Hz, 1H), 3.88 (s, 3H), 2.25-2.10 (m, 4H), 1.10-1.02 (m, 2H), 0.88-0.78 (m, 2H) ppm; (M+1)=447.

Example 1-35: Synthesis of 4-(3-((8-fluoro-2-(6-methoxypyridin-3-yl)-5-methyl-2,3-dihydrobenzo[b][1,4]dioxin-6-yl)methyl)-3H-imidazo[4,5-b]pyridin-6-yl)-2-methylbut-3-yn-2-amine The title compound was prepared from 3-((8-fluoro-2-(6-methoxypyridin-3-yl)-5-methyl-2,3-dihydrobenzo[b][1,4]dioxin-6-yl)methyl)-6-iodo-3H-imidazo[4,5-b]pyridine (Example 1-33-4) and 2-methylbut-3-yn-2-amine as described Example 1-5-8: $^1$H NMR (400 MHz, DMSO-$d_6$) δ 8.55 (s, 1H), 8.45 (d, J=1.8 Hz, 1H), 8.31-8.27 (m, 1H), 8.15 (d, J=1.8 Hz, 1H), 7.80 (dd, J=8.7, 2.5 Hz, 1H), 6.89 (d, J=8.7 Hz, 1H), 6.66 (dd, J=11.4, 4.9 Hz, 1H), 5.46 (s, 2H), 5.28 (dd, J=8.4, 2.5 Hz, 1H), 4.55 (dd, J=11.7, 2.5 Hz, 1H), 4.26 (dd, J=11.7, 8.4 Hz, 1H), 3.87 (s, 3H), 2.19 (s, 3H), 1.55 (s, 6H) ppm; (M+1)=488.

Example 1-36: Synthesis of 3-((8-fluoro-2-(6-methoxypyridin-3-yl)-5-methyl-2,3-dihydrobenzo[b][1,4]dioxin-6-yl)methyl)-6-(1-methyl-1H-pyrazol-4-yl)-3H-imidazo[4,5-b]pyridine The title compound was prepared from 3-((8-fluoro-2-(6-methoxypyridin-3-yl)-5-methyl-2,3-dihydrobenzo[b][1,4]dioxin-6-yl)methyl)-6-iodo-3H-imidazo[4,5-b]pyridine (Example 1-33-4) and 1-methyl-4-(4,4,5,5-tetramethyl-1,3,2-dioxaborolan-2-yl)-1H-pyrazole as described in Example 1-4: δ 8.66 (d, J=2.0 Hz, 1H), 8.46 (s, 1H), 8.29 (d, J=2.0 Hz, 2H), 8.24 (s, 1H), 7.99 (d, J=0.8 Hz, 1H), 7.83-7.80 (m, 1H), 6.90 (dd, J=8.5, 3.0 Hz, 1H), 6.68 (dd, J=11.5, 4.5 Hz, 1H), 5.45 (s, 2H), 5.28 (dd, J=8.5, 2.5 Hz, 1H), 4.55 (dd, J=11.7, 2.5 Hz, 1H), 4.26 (dd, J=11.7, 8.5 Hz, 1H), 3.90 (s, 3H), 3.87 (s, 3H), 2.22 (s, 3H) ppm; (M+1)=487.

Example 1-37: Synthesis of 3-((5-cyclopropyl-8-fluoro-2-(6-methoxypyridin-3-yl)-2,3-dihydrobenzo[b][1,4]dioxin-6-yl)methyl)-6-(1-methyl-1H-pyrazol-4-yl)-3H-imidazo[4,5-b]pyridine

Example 1-37-1: Preparation of 5-bromo-8-fluoro-2-(6-methoxypyridin-3-yl)-2,3-dihydrobenzo[b][1,4]dioxine-6-carbonitrile The title compound was prepared in three steps from 2-bromo-4,5-difluoro-3-hydroxybenzonitrile (Example 1-33-1) and 2-bromo-1-(6-methoxypyridin-3-yl)ethan-1-one as described in Example 1-14-1 through Example 1-14-3.

Example 1-37-2: Preparation of 5-cyclopropyl-8-fluoro-2-(6-methoxypyridin-3-yl)-2,3-dihydrobenzo[b][1,4]dioxine-6-carbonitrile To a stirred solution of 5-bromo-8-fluoro-2-(6-methoxypyridin-3-yl)-2,3-dihydrobenzo[b][1,4]dioxine-6-carbonitrile (0.79 g, 2.15 mmol) in tetrahydrofuran (4 mL) was added tetrakis(triphenylphosphine)palladium(0) (0.050 g, 0.043 mmol). The mixture was allowed to stir at room temperature. After 5 min, a solution of 0.5M cyclopropylzinc bromide in tetrahydrofuran (20.1 mL, 10.05 mmol) was added. The mixture was heated at 80° C. in a sealed vessel. After 2 h, the mixture was allowed to cool to room temperature. The mixture was quenched by the addition on 1N hydrochloric acid solution. The mixture was extracted with dichloromethane, and the phases were separated. The organic phase was washed with brine, dried over magnesium sulfate, filtered, and concentrated. Chromatographic purification of the crude product (CombiFlash, silica gel column, 0-100% ethyl acetate/dichloromethane elute) afforded 0.95 g of 5-cyclopropyl-8-fluoro-2-(6-methoxypyridin-3-yl)-2,3-dihydrobenzo[b][1,4]dioxine-6-carbonitrile (~85% purity) as a light yellow solid.

Example 1-37-3: Preparation of (5-cyclopropyl-8-fluoro-2-(6-methoxypyridin-3-yl)-2,3-dihydrobenzo[b][1,4]dioxin-6-yl)methanamine The title compound was prepared from 5-cyclopropyl-8-fluoro-2-(6-methoxypyridin-3-yl)-2,3-dihydrobenzo[b][1,4]dioxine-6-carbonitrile as described in Example 1-14-4.

Example 1-37-4: Preparation of 3-((5-cyclopropyl-8-fluoro-2-(6-methoxypyridin-3-yl)-2,3-dihydrobenzo[b][1,4]dioxin-6-yl)methyl)-6-iodo-3H-imidazo[4,5-b]pyridine The title compound was prepared in three steps from (5-cyclopropyl-8-fluoro-2-(6-methoxypyridin-3-yl)-2,3-dihydrobenzo[b][1,4]dioxin-6-yl)methanamine and 2-chloro-5-iodo-3-nitropyridine as described in Example 1-5-5 through Example 1-5-7.

Example 1-37-5: Preparation of 3-((5-cyclopropyl-8-fluoro-2-(6-methoxypyridin-3-yl)-2,3-dihydrobenzo[b][1,4]dioxin-6-yl)methyl)-6-(1-methyl-1H-pyrazol-4-yl)-3H-imidazo[4,5-b]pyridine The title compound was prepared from 3-((5-cyclopropyl-8-fluoro-2-(6-methoxypyridin-3-yl)-2,3-dihydrobenzo[b][1,4]dioxin-6-yl)methyl)-6-iodo-3H-imidazo[4,5-b]pyridine and 1-methyl-4-(4,4,5,5-tetramethyl-1,3,2-dioxaborolan-2-yl)-1H-pyrazole as described in Example 1-4: $^1$H NMR (400 MHz, DMSO-$d_6$) δ 8.56-8.52 (m, 1H), 8.40 (s, 1H), 8.29-8.10 (m, 3H), 7.90 (s, 1H), 7.81-7.67 (m, 1H), 6.87-6.77 (m, 1H), 6.41-6.30 (m, 1H), 5.62-5.49 (m, 2H), 5.25-5.16 (m, 1H), 4.49-4.39 (m, 1H), 4.12-3.97 (m ,1H), 3.84-3.76 (m, 6H), 1.63-1.53 (m, 1H), 0.97-0.81 (m, 2H), 0.79-0.60 (m, 2H) ppm; (M+1)=559.

Example 1-38: Synthesis of 4-(3-((8-fluoro-2-(6-methoxypyridin-3-yl)-5,7-dimethyl-2,3-dihydrobenzo[b][1,4]dioxin-6-yl)methyl)-3H-imidazo[4,5-b]pyridin-6-yl)-2-methylbut-3-yn-2-amine 2,2,2-trifluoroacetate

Example 1-38-1: (8-fluoro-2-(6-methoxypyridin-3-yl)-5,7-dimethyl-2,3-dihydrobenzo[b][1,4]dioxin-6-yl)methanamine The title compound was prepared in four steps from 3,4-difluoro-5-hydroxy-2,6-dimethylbenzonitrile (Example 1-32-2) and 2-bromo-1-(6-methoxypyridin-3-yl)ethan-1-one as described in Example 1-14-1 through Example 1-14-4.

Example 1-38-2: Preparation of 4-(3-((8-fluoro-2-(6-methoxypyridin-3-yl)-5,7-dimethyl-2,3-dihydrobenzo[b][1,4]dioxin-6-yl)methyl)-3H-imidazo[4,5-b]pyridin-6-yl)-2-methylbut-3-yn-2-amine 2,2,2-trifluoroacetate The title compound was prepared in four steps from (8-fluoro-2-(6-methoxypyridin-3-yl)-5,7-dimethyl-2,3-dihydrobenzo[b][1,4]dioxin-6-yl)methanamine, 2-chloro-5-iodo-3-nitropyridine, and 2-methylbut-3-yn-2-amine as described in Example 1-5-5 through Example 1-5-8: $^1$H NMR (400 MHz, DMSO-$d_6$) δ 8.62 (br s, 2H), 8.52 (d, J=1.8 Hz, 1H), 8.30 (d, J=2.4 Hz, 1H), 8.28-8.16 (m, 2H), 7.81 (dd, J=8.6, 2.5 Hz, 1H), 6.91 (d, J=8.6 Hz, 1H), 5.46 (s, 2H), 5.30 (dd, J=8.3, 2.4 Hz, 1H), 4.53 (dd, J=11.7, 2.5 Hz, 1H), 4.24 (dd, J=11.7, 8.3 Hz, 1H), 3.87 (s, 3H), 2.20 (s, 3H), 2.13 (s, 3H), 1.67 (s, 6H) ppm; (M+1)=502.

Example 1-39: Synthesis of 4-(3-((8-fluoro-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine

Example 1-39-1: Preparation of (8-fluoro-2-(6-methoxypyridin-3-yl)-2,3-dihydrobenzo[b][1,4]dioxin-6-yl)methanamine The title compound was prepared in four steps from 3,4-difluoro-5-hydroxybenzonitrile and 2-bromo-1-(6-methoxypyridin-3-yl)ethan-1-one as described in Example 1-14-1 through Example 1-14-4.

Example 1-39-2: Preparation of 3-((8-fluoro-2-(6-methoxypyridin-3-yl)-2,3-dihydrobenzo[b][1,4]dioxin-6-yl)methyl)-6-iodo-3H-imidazo[4,5-b]pyridine The title compound was prepared in three steps from (8-fluoro-2-(6-methoxypyridin-3-yl)-2,3-dihydrobenzo[b][1,4]dioxin-6-yl)methanamine and 2-chloro-5-iodo-3-nitropyridine as described in Example 1-5-5 through Example 1-5-7.

Example 1-39-3: Preparation of 4-(3-((8-fluoro-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine The title compound was prepared from 3-((8-fluoro-2-(6-methoxypyridin-3-yl)-2,3-dihydrobenzo[b][1,4]dioxin-6-yl)methyl)-6-iodo-3H-imidazo[4,5-b]pyridine and 2-methylbut-3-yn-2-amine as described in Example 1-5-8: $^1$H NMR (400 MHz, CDCl$_3$) δ 8.46 (d, J=1.8 Hz, 1H), 8.20 (d, J=2.4 Hz, 1H), 8.08 (d, J=1.8 Hz, 1H), 8.05 (s, 1H), 7.60 (dd, J=8.6, 2.4 Hz, 1H), 6.79 (d, J=8.6 Hz, 1H), 6.64-6.75 (m, 2H), 5.34 (s, 2H), 5.10 (dd, J=8.6, 2.3 Hz, 1H), 4.34 (dd, J=11.7, 2.3 Hz, 1H), 4.07 (dd, J=11.7, 8.6 Hz, 1H), 3.94 (s, 3H), 1.75 (bs, 2H), and 1.53 (s, 6H) ppm; (M+1)=457.

Example 1-40: Synthesis of 3-((8-fluoro-2-(6-methoxypyridin-3-yl)-2,3-dihydrobenzo[b][1,4]dioxin-6-yl)methyl)-6-(piperidin-3-ylethynyl)-3H-imidazo[4,5-b]pyridine The title compound was prepared from 3-((8-fluoro-2-(6-methoxypyridin-3-yl)-2,3-dihydrobenzo[b][1,4]dioxin-6-yl)methyl)-6-iodo-3H-imidazo[4,5-b]pyridine (Example 1-39-2) and 3-ethynylpiperidine as described in Example 1-5-8: $^1$H NMR (400 MHz, CDCl$_3$) δ 8.47 (d, J=1.8 Hz, 1H), 8.20 (d, J=2.4 Hz, 1H), 8.10 (d, J=1.8 Hz, 1H), 8.04 (s, 1H), 7.60 (dd, J=8.6, 2.5 Hz, 1H), 6.79 (d, J=8.6 Hz, 1H), 6.63-6.73 (m, 2H), 5.34 (s, 2H), 5.09 (dd, J=8.7, 2.5 Hz, 1H), 4.34 (dd, J=11.7, 2.5 Hz, 1H), 4.06 (dd, J=11.7, 8.7 Hz, 1H), 3.94 (s, 3H), 3.21-3.19 (m, 1H), 2.61-2.98 (m, 4H), 2.08-2.04 (m, 1H), 1.77-1.73 (m, 3H), and 1.57-1.42 (m, 1H) ppm; (M+1)= 500.

Example 1-41: Synthesis of 4-(3-((8-fluoro-2-(6-methoxypyridin-3-yl)-2,3-dihydrobenzo[b][1,4]dioxin-6-yl)methyl)-3H-imidazo[4,5-b]pyridin-6-yl)morpholine The title compound was prepared from 3-((8-fluoro-2-(6-methoxypyridin-3-yl)-2,3-dihydrobenzo[b][1,4]dioxin-6-yl)methyl)-6-iodo-3H-imidazo[4,5-b]pyridine (Example 1-39-2) and morpholine as described in Example 1-10: $^1$H NMR (400 MHz, CDCl$_3$) δ 8.24 (d, J=2.5 Hz, 1H), 8.22-8.19 (m, 1H), 7.97 (s, 1H), 7.63-7.58 (m, 2H), 6.79 (dd, J=8.5, 0.7 Hz, 1H), 6.71-6.66 (m, 2H), 5.32 (s, 2H), 5.09 (dd, J=8.6, 2.5 Hz, 1H), 4.34 (dd, J=11.7, 2.5 Hz, 1H), 4.06 (dd, J=11.7, 8.6 Hz, 1H), 3.95 (s, 3H), 3.94-3.90 (m, 4H), 3.21-3.13 (m, 4H) ppm; (M+1)=488.

Example 1-42: Synthesis of 3-((8-fluoro-2-(6-methoxypyridin-3-yl)-2,3-dihydrobenzo[b][1,4]dioxin-6-yl)methyl)-6-(2-methyl-1H-imidazol-1-yl)-3H-imidazo[4,5-b]pyridine To a stirred suspension of 3-((8-fluoro-2-(6-methoxypyridin-3-yl)-2,3-dihydrobenzo[b][1,4]dioxin-6-yl)methyl)-6- iodo-3H-imidazo[4,5-b]pyridine (0.19 g, 0.36 mmol) in dimethylsulfoxide (1 mL) was added 2-methylimidazole (0.037 g, 0.45 mmol), copper(I) oxide (0.002 g, 0.018 mmol), 4,7-dimethoxy-1,10-phenanthroline (0.013 g, 0.054 mmol), cesium carbonate (0.16 g, 0.50 mmol), and poly (ethylene glycol) (0.10 g). The vessel was sealed, and the contents degassed under vacuum/backfilled with nitrogen (×3). The red-brown suspension was heated to 110° C. After 18 h, the mixture was allowed to cool to room temperature and was diluted with water (40 mL). The mixture was extracted with dichloromethane (3×25 mL). The combined organic phases were dried over magnesium sulfate, filtered, and concentrated. Chromatographic purification of the crude product (CombiFlash, 12 g silica gel gold column, 0-5% 2M ammonia in methanol/dichloromethane elute) provided 0.095 g of an impure white solid. A second chromatographic purification (CombiFlash, 12 g silica gel gold column, 0-5% methanol/dichloromethane elute) afforded 0.072 g of 3-((8-fluoro-2-(6-methoxypyridin-3-yl)-2,3-dihydrobenzo[b][1,4]dioxin-6-yl)methyl)-6-(2-methyl-1H-imidazol-1-yl)-3H-imidazo[4,5-b]pyridine, also known as RA10813949, as a white solid: $^1$H NMR (400 MHz, CDCl$_3$) δ 8.41 (d, J=2.1 Hz, 1H), 8.23-8.16 (m, 2H), 8.03 (s, 1H), 7.61 (dd, J=8.5, 2.4 Hz, 1H), 7.08 (d, J=12.5 Hz, 2H), 6.85-6.71 (m, 3H), 5.41 (s, 2H), 5.16-5.08 (m, 1H), 4.37 (dd, J=11.8, 2.4 Hz, 1H), 4.09 (dd, J=11.8, 8.6 Hz, 1H), 3.95 (s, 3H), and 2.38 (s, 3H) ppm; (M+1)=473.

Example 1-43: Synthesis of 3-((8-fluoro-2-(6-methoxypyridin-3-yl)-2,3-dihydrobenzo[b][1,4]dioxin-6-yl)methyl)-7-methoxyimidazo[1,2-a]pyridine Example 1-43-1: Preparation of 5-(6-bromo-8-fluoro-2,3-dihydrobenzo[b][1,4]dioxin-2-yl)-2-methoxypyridine The title compound was prepared in five steps from 5-bromo-3-fluoro-2-((4-methoxybenzyl)oxy)benzaldehyde and 2-bromo-1-(6-methoxypyridin-3-yl)ethan-1-one as described in Example 1-21-1 through Example 1-21-4.

Example 1-43-2: Preparation of 3-((8-fluoro-2-(6-methoxypyridin-3-yl)-2,3-dihydrobenzo[b][1,4]dioxin-6-yl)methyl)-7-methoxyimidazo[1,2- a]pyridine The title compound was prepared in two steps from 5-(6-bromo-8-fluoro-2,3-dihydrobenzo[b][1,4]dioxin-2-yl)-2-methoxypyridine and 7-methoxyimidazo[1,2-a]pyridine-3-carbaldehyde as described in Example 1-22-1 through Example 1-22-2: $^1$H NMR (400 MHz, CDCl$_3$) δ 8.24-8.18 (m, 1H), 7.66-7.52 (m, 2H), 7.35 (s, 1H), 6.91 (s, 1H), 6.79 (d, J=8.6 Hz, 2H), 6.64-6.44 (m, 2H), 5.09 (d, J=8.3 Hz, 1H), 4.37-4.29 (m, 1H), 4.08 (m, 1H), 3.95 (d, J=5.3 Hz, 3H), and 3.85 (s, 3H) ppm; (M+1)=422.

Example 1-44: Synthesis of 6-bromo-3-((8-fluoro-2-(6-methoxypyridin-3-yl)-2,3-dihydrobenzo[b][1,4]dioxin-6-yl)methyl)pyrazolo[1,5-a]pyrimidine (RA10848871)

Example 1-44-1: Preparation of (8-fluoro-2-(6-methoxypyridin-3-yl)-2,3-dihydrobenzo[b][1,4]dioxin-6-yl)boronic acid The title compound was prepared from 5-(6-bromo-8-fluoro-2,3-dihydrobenzo[b][1,4]dioxin-2-yl)-2-methoxypyridine (Example 1-43-1) as described in Example 1-21-5.

Example 1-44-2: Preparation of 6-bromo-3-((8-fluoro-2-(6-methoxypyridin-3-yl)-2,3-dihydrobenzo[b][1,4]dioxin-6-yl)methyl)pyrazolo[1,5-a]pyrimidine The title compound was prepared from (8-fluoro-2-(6-methoxypyridin-3-yl)-2,3-dihydrobenzo[b][1,4]dioxin-6-yl) boronic acid and (E/Z)-N'-((6-bromopyrazolo[1,5-a]pyrimidin-3-yl)methylene)-4-methylbenzenesulfonohydrazide (Example 1-21-7) as described in Example 1-21-8; $^1$H NMR (400 MHz, CDCl$_3$) δ 8.77 (d, J=2.2 Hz, 1H), 8.44 (d, J=2.2 Hz, 1H), 8.21 (d, J=2.5 Hz, 1H), 7.93 (s, 1H), 7.63 (dd, J=8.7, 2.5 Hz, 1H), 6.80 (d, J=8.6 Hz, 1H), 6.68-6.60 (m, 2H), 5.09 (dd, J=8.5, 2.4 Hz, 1H), 4.32 (dd, J=11.8, 2.5 Hz, 1H), 4.11-4.01 (m, 3H), 3.96 (s, 3H); (M+1)=471.

Example 1-45: Synthesis of 3-((8-fluoro-2-(6-methoxypyridin-3-yl)-2,3-dihydrobenzo[b][1,4]dioxin-6-yl)methyl)-6-methoxypyrazolo[1,5-a]pyrimidine The title compound was prepared from 6-bromo-3-((8-fluoro-2-(6-methoxypyridin-3-yl)-2,3-dihydrobenzo[b][1,4]dioxin-6-yl)methyl)pyrazolo[1,5-a]pyrimidine and methanol as described in Example 1-11 with slight modification. The reaction was conducted by heating to 130° C. in a microwave reactor for 30 min rather than conventional heating to 110° C. for 20 h; $^1$H NMR (400 MHz, CDCl$_3$) δ 8.35 (d, J=2.7 Hz, 1H), 8.20 (dd, J=8.0, 2.6 Hz, 2H), 7.83 (s, 1H), 7.63 (dd, J=8.7, 2.5 Hz, 1H), 6.80 (d, J=8.6 Hz, 1H), 6.70-6.61 (m, 2H), 5.09 (dd, J=8.6, 2.4 Hz, 1H), 4.32 (dd, J=11.6, 2.4 Hz, 1H), 4.11-4.01 (m, 3H), 3.96 (s, 3H), and 3.88 (s, 3H) ppm; (M+1)=423.

Example 1-46: Synthesis of 3-((8-fluoro-2-(6-methoxypyridin-3-yl)-2,3-dihydrobenzo[b][1,4]dioxin-6-yl)methyl)pyrazolo[1,5-a]pyrimidine The title compound was isolated as a by-product from Example 1-44-3; $^1$H NMR (400 MHz, CDCl$_3$) δ 8.64 (dd, J=7.1, 1.8 Hz, 1H), 8.47 (dd, J=4.0, 1.8 Hz, 1H), 8.21 (d, J=2.5 Hz, 1H), 7.97 (s, 1H), 7.62 (dd, J=8.6, 2.5 Hz, 1H), 6.83-6.75 (m, 2H), 6.67 (dd, J=8.9, 2.0 Hz, 2H), 5.09 (dd, J=8.8, 2.4 Hz, 1H), 4.32 (dd, J=11.6, 2.5 Hz, 1H), 4.11-4.01 (m, 3H), 3.94 (s, 3H) ppm; (M+1)=393.

Example 1-47: Synthesis of 7-chloro-3-((8-fluoro-2-(6-methoxypyridin-3-yl)-2,3-dihydrobenzo[b][1,4]dioxin-6-yl)methyl)imidazo[1,2-b]pyridazine (RA10872685)

Example 1-47-1: Preparation of 8-fluoro-2-(6-methoxypyridin-3-yl)-2,3-dihydrobenzo[b][1,4]dioxine-6-carbaldehyde The title compound was prepared from 5-(6-bromo-8-fluoro-2,3-dihydrobenzo[b][1,4]dioxin-2-yl)-2-methoxypyridine (Example 1-43-1) as described in Example 1-23-1.

Example 1-47-2: Preparation of 7-chloro-3-((8-fluoro-2-(6-methoxypyridin-3-yl)-2,3-dihydrobenzo[b][1,4]dioxin-6-yl)methyl)imidazo[1,2-b]pyridazine The title compound was prepared in two steps from 8-fluoro-2-(6-methoxypyridin-3-yl)-2,3-dihydrobenzo[b][1,4]dioxine-6-carbaldehyde and 3-bromo-7-chloroimidazo[1,2-b]pyridazine (Example 1-23-2) as described in Example 1-23-3 through Example 1-24-4; ¹H NMR (400 MHz, CDCl₃) δ 8.29 (d, J=2.4 Hz, 1H), 8.21 (dt, J=2.5, 0.7 Hz, 1H), 7.93 (d, J=2.4 Hz, 1H), 7.66-7.56 (m, 2H), 6.79 (dd, J=8.6, 0.7 Hz, 1H), 6.70-6.62 (m, 2H), 5.10 (dd, J=8.7, 2.4 Hz, 1H), 4.33 (dd, J=11.7, 2.4 Hz, 1H), 4.21 (d, J=0.8 Hz, 2H), 4.07 (dd, J=11.7, 8.7 Hz, 1H), 3.95 (s, 3H) ppm; (M+1)=427.

Example 1-48: Synthesis of 3-((8-fluoro-2-(6-methoxypyridin-3-yl)-2,3-dihydrobenzo[b][1,4]dioxin-6-yl)methyl)-6-(3-methoxyazetidin-1-yl)pyrazolo[1,5-a]pyridine

Example 1-48-1: Preparation of (E/Z)-N'-((6-bromopyrazolo[1,5-a]pyridin-3-yl)methylene)-4-methylbenzenesulfonohydrazide The title compound was prepared from 6-bromopyrazolo[1,5-a]pyridine-3-carbaldehyde as described in Example 1-21-7.

Example 1-48-2: Preparation of 6-bromo-3-((8-fluoro-2-(6-methoxypyridin-3-yl)-2,3-dihydrobenzo[13][1,4]dioxin-6-yl)methyl)pyrazolo[1,5-a]pyridine The title compound was prepared from (8-fluoro-2-(6-methoxypyridin-3-yl)-2,3-dihydrobenzo[b][1,4]dioxin-6-yl)boronic acid (Example 1-44-1) and (E/Z)-N'-((6-bromopyrazolo[1,5-a]pyridin-3-yl)methylene)-4-methylbenzenesulfonohydrazide as described in Example 1-21-8.

Example 1-48-3: Preparation of 3-((8-fluoro-2-(6-methoxypyridin-3-yl)-2,3-dihydrobenzo[b][1,4]dioxin-6-yl)methyl)-6-(3-methoxyazetidin-1-yl)pyrazolo[1,5-a]pyridine The title compound was prepared from 6-bromo-3-((8-fluoro-2-(6-methoxypyridin-3-y1)-2,3-dihydrobenzo[b][1,4]dioxin-6-yl)methyl)pyrazolo[1,5-a]pyridine and 3-methoxyazetidine hydrochloride as described in Example 1-10; ¹H NMR (400 MHz, CDCl₃) δ 8.21 (d, J=2.5 Hz, 1H), 7.67-7.58 (m, 3H), 7.19 (dd, J=9.4, 0.8 Hz, 1H), 6.79 (dd, J=8.6, 0.7 Hz, 1H), 6.62-6.53 (m, 3H), 5.09 (dd, J=8.7, 2.4 Hz, 1H), 4.40-4.28 (m, 2H), 4.13-4.01 (m, 3H), 3.96-3.92 (m, 5H), 3.71-3.63 (m, 2H), 3.34 (s, 3H); (M+1)=477.

Example 1-49: Preparation of 4-((8-fluoro-2-(4-(trifluoromethyl)phenyl)-2,3-dihydrobenzo[b][1,4]dioxin-6-yl)methyl)-2-(1-methyl-1H-pyrazol-4-yl)pyridine

Example 1-49-1: Preparation of 2-(8-fluoro-2-(4-(trifluoromethyl)phenyl)-2,3-dihydrobenzo[b][1,4]dioxin-6-yl)-5,5-dimethyl-1,3,2-dioxaborinane To a nitrogen-flushed mixture of 8-fluoro-2-(4-(trifluoromethyl)phenyl)-2,3-dihydrobenzo[b][1,4]dioxine-6-carbonitrile (0.13 mg, 0.41 mmol, Example 1-29-1), 1,4-diazabicyclo[2.2.2]octane (0.047 g, 0.41 mmol), bis(neopentyl glycolato)diboron (0.19 g, 0.82 mmol), chloro(1,5-cyclooctadiene)rhodium(I) dimer (0.010 g, 0.021 mmol), 4,5-bis(diphenylphosphino)-9,9-dimethylxanthene (0.048 g, 0.082 mmol) was added toluene (0.50 mL). The resulting orange solution was heated at 100° C. After 15 h, the mixture was allowed to cool to room temperature and was diluted with ethyl acetate (3 mL) and water (2 mL). The phases were separated, and the aqueous phase was extracted with ethyl acetate (3×3 mL). The combined organic phases were dried over sodium sulfate and concentrated. Chromatographic purification of the crude product (CombiFlash, 4 g silica gel column deactivated with triethylamine, 2-100% ethyl acetate/heptane elute) provided 0.098 g (58%) of 2-(8-fluoro-2-(4-(trifluoromethyl)phenyl)-2,3-dihydrobenzo[b][1,4]dioxin-6-yl)-5,5-dimethyl-1,3,2-dioxaborinane as an off-white solid.

Example 1-49-2: Preparation of 4-((8-fluoro-2-(4-(trifluoromethyl)phenyl)-2,3-dihydrobenzo[b][1,4]dioxin-6-yl)methyl)-2-(1-methyl-1H-pyrazol-4-yl)pyridine The title compound was prepared from 2-(8-fluoro-2-(4-(trifluoromethyl)phenyl)-2,3-dihydrobenzo[b][1,4]dioxin-6-yl)-5,5-dimethyl-1,3,2-dioxaborinane and 4-(chloromethyl)-2-(1-methyl-1H-pyrazol-4-yl)pyridine hydrochloride (Example 1-27-6) as described in Example 1-24-3: 1H NMR (400 MHz, DMSO-d6) δ 8.38 (d, J=5.1 Hz, 1H), 8.24 (s, 1H), 7.96 (s, 1H), 7.81 (d, J=8.1 Hz, 2H), 7.71 (d, J=8.1 Hz, 2H), 7.56 (s, 1H), 7.03 (dd, J=5.1, 1.6 Hz, 1H), 6.84 (dd, J=11.4, 2.1 Hz, 1H), 6.75 (d, J=2.0 Hz, 1H), 5.44 (dd, J=7.9, 2.5 Hz, 1H), 4.52 (dd, J=11.6, 2.5 Hz, 1H), 4.19 (dd, J=11.6, 7.90 Hz, 1H), 3.88 (s, 3H), and 3.85 (s, 2H) ppm; (M+1)= 470.

Example 1-50: Synthesis of 3-((8-fluoro-2-(4-(trifluoromethyl)phenyl)-2,3-dihydrobenzo[b][1,4]dioxin-6-yl)methyl)-5-(1-methyl-1H-pyrazol-4-yl)pyridine

Example 1-50-1: Preparation of methyl 5-(1-methyl-1H-pyrazol-4-yl)nicotinate To stirred solution of methyl 5-(4,4,5,5-tetramethyl-1,3,2-dioxaborolan-2-yl)nicotinate (1.00 g, 3.80 mmol) in 1,4-dioxane (10 mL)/water (0.50 mL) was added 4-bromo-1-methyl-1H-pyrazole (0.61 g, 3.80 mmol), tetrakis(triphenylphosphine)palladium(0) (0.22 g, 0.19 mmol), and cesium carbonate (2.48 g, 7.60 mmol). The mixture was heated to 100° C. After 2.5 h, the mixture was allowed to cool to room temperature and was diluted with ethyl acetate (50 mL). The mixture was washed with water (10 mL). The phases were separated, and the aqueous phase was extracted with dichloromethane (3×20 mL). The combined organic phases were dried over sodium sulfate, filtered, and concentrated. The oil was chromatographed on silica gel (40 g) eluted with a gradient of heptane and EtOAc (0-100%) at 50 mL/min over 20 min then flushed with 20% 2N ammonia in methanol in DCM (50 mL) to remove the product. Chromatographic purification of the crude product (CombiFlash, 12 g silica gel column, 0-10% 2M ammonia in methanol/dichloromethane elute) provided 0.42 g (50%) of methyl 5-(1-methyl-1H-pyrazol-4-yl)nicotinate as a white solid.

Example 1-50-2: Preparation of 3-(chloromethyl)-5-(1-methyl-1H-pyrazol-4-yl)pyridine hydrochloride The title compound was prepared in two steps from methyl 5-(1-methyl-1H-pyrazol-4-yl)nicotinate as described in Example 1-27-5 through Example 1-27-6.

Example 1-50-3: Preparation of 3-((8-fluoro-2-(4-(trifluoromethyl)phenyl)-2,3-dihydrobenzo[b][1,4]dioxin-6-yl)methyl)-5-(1-methyl-1H-pyrazol-4-yl)pyridine The title compound was prepared from 3-(chloromethyl)-5-(1-methyl-1H-pyrazol-4-yl)pyridine hydrochloride and 2-(8-fluoro-2-(4-(trifluoromethyl)phenyl)-2,3-dihydrobenzo[b][1,4]dioxin-6-yl)-5,5-dimethyl-1,3,2-dioxaborinane (Example 1-49-1) as described in Example 1-24-3: $^1$H NMR (400 MHz, DMSO-d6) δ 8.67 (d, J=2.1 Hz, 1H), 8.32 (d, J=2.0 Hz, 1H), 8.23 (s, 1H), 7.94 (s, 1H), 7.87-7.83 (m, 1H), 7.81 (d, J=8.2 Hz, 2H), 7.70 (d, J=8.2 cHz, 2H), 6.84 (dd, J=11.4, 2.0 Hz, 1H), 6.77-6.73 (m, 1H), 5.43 (dd, J=8.0, 2.4 Hz, 1H), 4.52 (dd, J=11.7, 2.4 Hz, 1H), 4.19 (dd, J=11.7, 8.0 Hz, 1H), and 3.89-3.85 (m, 5H) ppm; (M+1)=470.

Example 1-51: Synthesis of 3-((8-fluoro-2-(4-(trifluoromethyl)phenyl)-2,3-dihydrobenzo[b][1,4]dioxin-6-yl)methyl)-5-(1-methyl-1H-pyrazol-3-yl)pyridine (RA08464874)

Example 1-51-1: Preparation of 3-(chloromethyl)-5-(1-methyl-1H-pyrazol-3-yl)pyridine hydrochloride The title compound was prepared in three steps from 3-bromo-1-methyl-1H-pyrazole and 5-(4,4,5,5-tetramethyl-1,3,2-dioxaborolan-2-yl)nicotinate as described in Example 1-50-1 through Example 1-50-2.

Example 1-51-2: Preparation of 3-((8-fluoro-2-(4-(trifluoromethyl)phenyl)-2,3-dihydrobenzo[b][1,4]dioxin-6-yl)methyl)-5-(1-methyl-1H-pyrazol-3-yl)pyridine The title compound was prepared from 3-(chloromethyl)-5-(1-methyl-1H-pyrazol-3-yl)pyridine hydrochloride and 2-(8-fluoro-2-(4-(trifluoromethyl)phenyl)-2,3-dihydrobenzo[b][1,4]dioxin-6-yl)-5,5-dimethyl-1,3,2-dioxaborinane (Example 1-49-1) as described in Example 1-24-3: $^1$H NMR (400 MHz, CDCl$_3$) δ 8.86 (d, J=2.1 Hz, 1H), 8.39 (d, J=2.2 Hz, 1H), 7.93 (dd, J=2.4, 1.7 Hz, 1H), 7.73-7.64 (m, 2H), 7.61-7.53 (m, 2H), 7.41 (d, J=2.3 Hz, 1H), 6.66-6.54 (m, 3H), 5.20 (dd, J=8.6, 2.4 Hz, 1H), 4.39 (dd, J=11.7, 2.4 Hz, 1H), 4.03 (dd, J=11.7, 8.6 Hz, 1H), 3.97 (s, 3H), 3.91 (s, 2H) ppm; (M+1)=470.

Example 1-52: Synthesis of 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine Example 1-52-1: Preparation of methyl 4-(benzyloxy)-3-methoxy-5-(2-(6-methoxypyridin-3-yl)-2-oxoethoxy)benzoate To stirred solution of methyl 4-(benzyloxy)-3-hydroxy-5-methoxybenzoate (16.48 g, 57.16 mmol) in acetonitrile (150 mL) was added cesium carbonate (23.30 g, 71.45 mmol). The mixture was treated with 2-bromo-1-(6-methoxypyridin-3-yl)ethanone (13.15 g, 57.16 mmol) and allowed to stir at room temperature. After 1 h, the mixture was diluted with water (500 mL), resulting in the formation of a precipitate. The solids were isolated by filtration and washed with water (150 mL). The moist filter cake was dissolved in dichloromethane (250 mL). The solution was washed with brine (50 mL), dried over magnesium sulfate, filtered, and concentrated to provide 25.60 g (>100%) of methyl 4-(benzyloxy)-3-methoxy-5-(2-(6-methoxypyridin-3-yl)-2-oxoethoxy)benzoate as a yellow solid.

Example 1-52-2: Preparation of methyl 4-hydroxy-3-(2-hydroxy-2-(6-methoxypyridin-3-yl)ethoxy)-5-methoxybenzoate To a stirred solution of methyl 4-(benzyloxy)-3-methoxy-5-(2-(6-methoxypyridin-3-yl)-2-oxoethoxy)benzoate (25.00 g, 57.15 mmol) in tetrahydrofuran (200 mL) was added 10% palladium on carbon (wet) (5.00 g, 4.70 mmol). The mixture was degassed under vacuum/backfilled with nitrogen (×3). After a final evacuation, the atmosphere was replaced with hydrogen via a balloon. The mixture was allowed to stir at room temperature. After 1 h, an additional portion of catalyst (5.00 g) was added. After 5 h, the vessel was evacuated, and the atmosphere replaced with nitrogen. The mixture was filtered through Celite with the aid of tetrahydrofuran (50 mL). The filtrate was diluted with methanol (10 mL). The resulting yellow solution was cooled to 0° C. while sodium borohydride (2.97 g, 76.93 mmol) was added (gas evolution noted). After 15 min, the mixture was treated with 1N hydrochloric acid solution (2 mL) and was concentrated. The residue was dissolved in ethyl acetate (100 mL) and washed with saturated sodium bicarbonate solution (75 mL) and brine (75 mL). The organic phase was dried over magnesium sulfate, filtered, and concentrated to provide 18.77 g (94%) of methyl 4-hydroxy-3-(2-hydroxy-2-(6-methoxypyridin-3-yl)ethoxy)-5-methoxybenzoate as a white foamy solid.

Example 1-52-3: Preparation of methyl 8-methoxy-2-(6-methoxypyridin-3-yl)-2,3-dihydrobenzo[b][1,4]dioxine-6-carboxylate To a stirred solution of methyl 4-hydroxy-3-(2-hydroxy-2-(6-methoxypyridin-3-yl)ethoxy)-5-methoxybenzoate (18.77 g, 53.73 mmol) in acetonitrile (150 mL) was added triphenylphosphine resin (27.00 g, 81.00 mmol) and triethylamine (16.48 g, 161.19 mmol). The suspension was treated with carbon tetrachloride (41.37 g, 268.65 mmol) and was heated to reflux. After 15 h, the mixture was allowed to cool to room temperature and was filtered through Celite with the aid of ethyl acetate (300 mL). The filtrate was washed with water (150 mL), saturated sodium bicarbonate solution (100 mL), and brine (100 mL). The organic phase was dried over magnesium sulfate, filtered, and concentrated to provide 16.44 g (92%) of methyl 8-methoxy-2-(6-methoxypyridin-3-yl)-2,3-dihydrobenzo[b][1,4]dioxine-6-carboxylate as a brown oil.

Example 1-52-4: Preparation of (8-methoxy-2-(6-methoxypyridin-3-yl)-2,3-dihydrobenzo[b][1,4]dioxin-6-yl)methanol To a stirred and cooled (0° C.) solution of methyl 8-methoxy-2-(6-methoxypyridin-3-yl)-2,3-dihydrobenzo[b][1,4]dioxine-6-carboxylate (16.44 g, 49.62 mmol) in tetrahydrofuran (200 mL) was added lithium aluminum hydride (2.40 g, 60.07 mmol) in several portions over 3 min (significant evolution of gas noted). The resulting gray-brown mixture was allowed to stir at 0° C. After 20 min, the mixture was quenched by the slow addition of water (2.4 mL), 1N sodium hydroxide solution (2.4 mL), and water (7.2 mL). The resulting mixture was allowed to stir at 0° C. for 15 min, and then magnesium sulfate was added. The mixture was filtered through Celite, and the filter cake was washed with ethyl acetate (300 mL). The filtrate was concentrated to provide 13.50 g (90%) of (8-methoxy-2-(6-methoxypyridin-3-yl)-2,3-dihydrobenzo[b][1,4]dioxin-6-yl)methanol as a sticky brown foam.

Example 1-52-5: Preparation of 5-(6-(azidomethyl)-8-methoxy-2,3-dihydrobenzo[b][1,4]dioxin-2-yl)-2-methoxypyridine To a stirred solution of (8-methoxy-2-(6-methoxypyridin-3-yl)-2,3-dihydrobenzo[b][1,4]dioxin-6-yl)methanol (13.50 g, 44.51 mmol), in tetrahydrofuran (200 mL) was added diphenylphosphoryl azide (17.15 g, 62.31 mmol). The mixture was treated with 1,8-diazabicyclo[5.4.0]undec-7-ene (10.84 g, 71.21 mmol) and was heated to reflux. After 45 min, the brown mixture was allowed to cool to room temperature and was diluted with ethyl acetate (200 mL). The solution was washed with water (150 mL), saturated sodium bicarbonate solution (150 mL), and brine (150 mL). The organic phase was dried over magnesium sulfate, filtered, and concentrated. Chromatographic purification of the crude product (CombiFlash, 220 g silica gel gold column, 15-30% ethyl acetate/heptane elute) afforded 12.00 g (82%) of 5-(6-(azidomethyl)-8-methoxy-2,3-dihydrobenzo[b][1,4]dioxin-2-yl)-2-methoxypyridine as a white solid.

Example 1-52-6: Preparation of (8-methoxy-2-(6-methoxypyridin-3-yl)-2,3-dihydrobenzo[b][1,4]dioxin-6-yl)methanamine To a stirred solution of 5-(6-(azidomethyl)-8-methoxy-2,3-dihydrobenzo[b][1,4]dioxin-2-yl)-2-methoxypyridine (12.00 g, 36.55 mmol) in tetrahydrofuran (100 mL) and water (20 mL) was added triphenylphosphine resin (20.00 g, 60.00 mmol). The orange suspension was heated to reflux. After 1 h, the mixture was allowed to cool to room temperature and was filtered through Celite with the aid of ethyl acetate (150 mL). The filtrate was washed with water (50 mL), dried over magnesium sulfate, filtered, and concentrated to provide 10.19 g (92%) of (8-methoxy-2-(6-methoxypyridin-3-yl)-2,3-dihydrobenzo[b][1,4]dioxin-6-yl)methanamine as an off-white waxy solid.

Example 1-52-7: Preparation of 5-iodo-N-((8-methoxy-2-(6-methoxypyridin-3-yl)-2,3-dihydrobenzo[b][1,4]dioxin-6-yl)methyl)-3-nitropyridin-2-amine To a stirred solution of 2-chloro-5-iodo-3-nitropyridine (4.40 g, 15.00 mmol) in acetonitrile (150 mL) was added (8-methoxy-2-(6-methoxypyridin-3-yl)-2,3-dihydrobenzo[b][1,4]dioxin-6-yl)methanamine (4.20 g, 13.89 mmol) and N,N-diisopropylethylamine (2.72 g, 20.84 mmol). The yellow mixture was heated to reflux and stirred. After 15 h, the mixture was allowed to cool to room temperature and was diluted with water (200 mL), resulting in the formation of a precipitate. The solids were isolated by filtration and washed with water (150 mL). The moist filter cake was dissolved in dichloromethane (150 mL). The solution was dried over magnesium sulfate, filtered, and concentrated to provide 7.64 g (99%) of 5-iodo-N-((8-methoxy-2-(6-methoxypyridin-3-yl)-2,3-dihydrobenzo[b][1,4]dioxin-6-yl)methyl)-3-nitropyridin-2-amine as an orange solid.

Example 1-52-8: Preparation of 5-iodo-$N^2$-((8-methoxy-2-(6-methoxypyridin-3-yl)-2,3-dihydrobenzo[b][1,4]dioxin-6-yl)methyl)pyridine-2,3-diamine To a stirred suspension of 5-iodo-N-((8-methoxy-2-(6-methoxypyridin-3-yl)-2,3-dihydrobenzo[b][1,4]dioxin-6-yl)methyl)-3-nitropyridin-2-amine (1.70 g, 3.09 mmol) in acetic acid (30 mL) was added iron powder (0.86 g, 15.45 mmol). The mixture was heated to 125° C. As the mixture warmed, the yellow color faded and a gray suspension formed. After 15 min, the mixture was allowed to cool to room temperature and was diluted with ethyl acetate (150 mL). The suspension was filtered through Celite with the aid of ethyl acetate (100 mL). The filtrate was washed with water (2×30 mL) and then with concentrated ammonium hydroxide solution (2×75 mL). The organic phase was dried over magnesium sulfate, filtered, and concentrated to provide 1.51 g (94%) of 5-iodo-$N^2$-((8-methoxy-2-(6-methoxypyridin-3-yl)-2,3-dihydrobenzo[b][1,4]dioxin-6-yl)methyl)pyridine-2,3-diamine as a brown solid.

Example 1-52-9: Preparation of 6-iodo-3-((8-methoxy-2-(6-methoxypyridin-3-yl)-2,3-dihydrobenzo[b][1,4]dioxin-6-yl)methyl)-3H-imidazo[4,5-b]pyridine To a stirred suspension of 5-iodo-$N^2$-((8-methoxy-2-(6-methoxypyridin-3-yl)-2,3-dihydrobenzo[b][1,4]dioxin-6-yl)methyl)pyridine-2,3-diamine (1.51 g, 2.90 mmol) in ethanol (30 mL) was added triethyl orthoformate (2.67 g, 17.68 mmol), and p-toluenesulfonic acid monohydrate (0.050 g, 0.26 mmol). The mixture was heated to reflux, and the solids gradually dissolved. After 30 min, the mixture was allowed to cool to room temperature, resulting in the formation of a precipitate. The mixture was filtered, and the filter cake was washed with diethyl ether (30 mL) and dried to provide 1.12 g (73%) of 6-iodo-3-((8-methoxy-2-(6-methoxypyridin-3-yl)-2,3-dihydrobenzo[b][1,4]dioxin-6-yl)methyl)-3H-imidazo[4,5-b] as a gray solid.

Example 1-52-10: Preparation of 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] and 2-methylbut-3-yn-2-amine as described in Example 1-5-8: $^1$H NMR (400 MHz, CDCl$_3$) δ 8.46 (d, J=1.8 Hz, 1H), 8.20 (d, J=2.5 Hz, 1H), 8.08 (d, J=1.8 Hz, 1H), 8.04 (s, 1H), 7.61 (dd, J=8.6, 2.5 Hz, 1H), 6.77 (d, J=8.6 Hz, 1H), 6.54-6.51 (m, 2H), 5.35 (s, 2H), 5.09 (dd, J=8.4, 2.4 Hz, 1H), 4.30 (dd, J=11.6, 2.4 Hz, 1H), 4.06 (dd, J=11.6, 8.4 Hz, 1H), 3.94 (s, 3H), 3.80 (s, 3H), 1.53 (s, 6H) ppm; (M+1)=486.

Example 1-52-11: Chiral separation of 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine The racemic 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine was subjected to HPLC preparative purification (21.2×250 mm Chiralpak AD-H column, 60% ethanol/40% heptane with 0.5% diethylamine modifier, 9 mL/min flow rate) to afford the individual enantiomers.

Example 1-53: Synthesis of 3-((8-methoxy-2-(6-methoxypyridin-3-yl)-2,3-dihydrobenzo[b][1,4]dioxin-6-yl)methyl)-6-(1-methyl-1H-pyrazol-4-yl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 1-methyl-4-(4,4,5,5-tetramethyl-1,3,2-dioxaborolan-2-yl)-1H-pyrazole as described in Example 1-4: $^1$H NMR (400 MHz, CDCl$_3$) δ 8.58 (d, J=1.9 Hz, 1H), 8.20 (d, J=2.4 Hz, 1H), 8.12 (d, J=1.9 Hz, 1H), 8.04 (s, 1H), 7.81 (d, J=0.9 Hz, 1H), 7.67 (d, J=0.9 Hz, 1H), 7.61 (dd, J=8.5, 2.4 Hz, 1H), 6.77 (d, J=8.5 Hz, 1H), 6.56-6.54 (m, 2H), 5.37 (s, 2H), 5.09 (dd, J=8.4, 2.5 Hz, 1H), 4.30 (dd, J=11.6, 2.5 Hz, 1H), 4.07 (dd, J=11.6, 8.4 Hz, 1H), 3.99 (s, 3H), 3.94 (s, 3H), 3.81 (s, 3H) ppm; (M+1)=485.

Example 1-54: Synthesis of 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)morpholine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and morpholine as described in Example 1-10: $^1$H NMR (400 MHz, CDCl$_3$) δ 8.25 (d, J=2.5 Hz, 1H), 8.20 (d, J=2.5 Hz, 1H), 7.97 (s, 1H), 7.64-7.57 (m, 2H), 6.77 (dd, J=8.6, 0.7 Hz, 1H), 6.52 (s, 2H), 5.32 (s, 2H), 5.09 (dd, J=8.4, 2.5 Hz, 1H), 4.30 (dd, J=11.6, 2.5 Hz, 1H), 4.06 (dd, J=11.6, 8.4 Hz, 1H), 3.96-3.88 (m, 7H), 3.80 (s, 3H), 3.21-3.12 (m, 4H) ppm; (M+1)=490.

Example 1-55: Synthesis of 6-cyclopropyl-3-((8-methoxy-2-(6-methoxypyridin-3-yl)-2,3-dihydrobenzo[b][1,4]dioxin-6-yl)methyl)-3H-imidazo[4,5-b]pyridine To a stirred solution of 6-iodo-3-((8-methoxy-2-(6-methoxypyridin-3-yl)-2,3-dihydrobenzo[b][1,4]dioxin-6-yl)methyl)-3H-imidazo[4,5-b]pyridine (0.19 g, 0.36 mmol, Example 1-52-9) in toluene (5 mL) and water (1 mL) was added cyclopropylboronic acid (0.078 g, 0.91 mmol), tricyclohexylphosphine (0.010 g, 0.036 mmol), and potassium phosphate tribasic (0.26 g, 1.20 mmol). The mixture was treated with palladium(II) acetate (0.004 g, 0.018 mmol) and was degassed under vacuum/backfilled with nitrogen (×3). The mixture was heated to reflux. After 18 h, the yellow mixture was allowed to cool to room temperature and was diluted with ethyl acetate (50 mL) and water (50 mL). The phases were separated, and the organic phase washed with brine (50 mL), dried over magnesium sulfate, filtered, and concentrated. Chromatographic purification of the crude product (CombiFlash, 12 g silica gel column, 0-5% methanol/dichloromethane elute) afforded 0.097 g of 6-cyclopropyl-3-((8-methoxy-2-(6-methoxypyridin-3-yl)-2,3-dihydrobenzo[b][1,4]dioxin-6-yl)methyl)-3H-imidazo[4,5-b]pyridine as an off-white solid: $^1$H NMR (400 MHz, CDCl3) δ 8.31 (d, J=2.0 Hz, 1H), 8.20 (d, J=2.5 Hz, 1H), 7.98 (s, 1H), 7.71 (d, J=2.0 Hz, 1H), 7.61 (dd, J=8.6, 2.5 Hz, 1H), 6.81-6.74 (m, 1H), 6.52 (s, 2H), 5.34 (s, 2H), 5.09 (dd, J=8.4, 2.5 Hz, 1H), 4.29 (dd, J=11.6, 2.5 Hz, 1H), 4.06 (dd, J=11.6, 8.4 Hz, 1H), 3.93 (s, 3H), 3.80 (s, 3H), 2.11-2.03 (m, 1H), 1.08-1.00 (m, 2H), 0.79-0.72 (m, 2H) ppm; (M+1)=445.

Example 1-56: Synthesis of 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-ol The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 2-methylbut-3-yn-2-ol as described in Example 1-5-8: $^1$H NMR (400 MHz, CDCl$_3$) δ 8.52 (s, 1H), 8.38-8.12 (m, 3H), 7.61 (dd, J=8.6, 2.4 Hz, 1H), 6.77 (d, J=8.6 Hz, 1H), 6.55-6.51 (m, 2H), 5.35 (s, 2H), 5.09 (dd, J=8.4, 2.4 Hz, 1H), 4.30 (dd, J=11.6, 2.4 Hz, 1H), 4.06 (dd, J=11.6, 8.4 Hz, 1H), 3.94 (s, 3H), 3.80 (s, 3H), 1.66 (s, 6H) ppm: (M+1)=487.

Example 1-57: Synthesis of 6-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-oxa-6-azaspiro[3.3]heptane The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 2-oxa-6-azaspiro[3.3]heptane as described in Example 1-10: $^1$H NMR (400 MHz, CDCl$_3$) δ 8.20 (d, J=2.5 Hz, 1H), 7.95 (s, 1H), 7.76 (d, J=2.5 Hz, 1H), 7.60 (dd, J=8.7, 2.5 Hz, 1H), 7.14 (d, J=2.5 Hz, 1H), 6.77 (dd, J=8.7, 0.7 Hz, 1H), 6.51 (s, 2H), 5.30 (s, 2H), 5.08 (dd, J=8.3, 2.4 Hz, 1H), 4.87 (s, 4H), 4.29 (dd, J=11.6, 2.5 Hz, 1H), 4.10 (s, 4H), 4.06 (dd, J=11.6, 8.4 Hz, 1H), 3.93 (s, 3H), 3.79 (s, 3H) ppm; (M+1)=502.

Example 1-58: Synthesis of 3-((8-methoxy-2-(6-methoxypyridin-3-yl)-2,3-dihydrobenzo[b][1,4]dioxin-6-yl)methyl)-6-(3-methoxyprop-1-yn-1-yl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 3-methoxyprop-1-yne as described in Example 1-5-8: $^1$H NMR (400 MHz, DMSO-d6) δ 8.72 (br s, 1H), 8.50 (s, 1H), 8.25-8.23 (m, 2H), 7.74 (dd, J=8.6, 2.4 Hz, 1H), 6.91-6.81 (m, 1H), 6.75 (d, J=1.8 Hz, 1H), 6.53 (d, J=1.8 Hz, 1H), 5.38 (s, 2H), 5.15 (dd, J=8.2, 2.4 Hz, 1H), 4.41-4.27 (m, 3H), 4.13 (dd, J=11.5, 8.3 Hz, 1H), 3.85 (s, 3H), 3.72 (s, 3H), 3.36 (s, 3H) ppm; (M+1)=473.

Example 1-59: Synthesis of 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)isoxazole The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 4-(4,4,5,5-tetramethyl-1,3,2-dioxaborolan-2-yl)isoxazole as described in Example 1-55: $^1$H NMR (400 MHz, DMSO-d6) δ 9.54 (s, 1H), 9.28 (s, 1H), 8.79 (d, J=1.9 Hz, 1H), 8.64 (s, 1H), 8.47 (d, J=1.9 Hz, 1H), 8.23 (d, J=2.5 Hz, 1H), 7.74 (dd, J=8.7, 2.5 Hz, 1H), 6.86 (d, J=8.7 Hz, 1H), 6.78 (d, J=1.9 Hz, 1H), 6.55 (d, J=1.9 Hz, 1H), 5.40 (s, 2H), 5.15 (dd, J=8.2, 2.5 Hz, 1H), 4.34 (dd, J=11.6, 2.5 Hz, 1H), 4.20-4.06 (m, 1H), 3.85 (s, 3H), 3.73 (s, 3H) ppm; (M+1)=472.

Example 1-60: Synthesis of 6-methoxy-3-((8-methoxy-2-(6-methoxypyridin-3-yl)-2,3-dihydrobenzo[b][1,4]dioxin-6-yl)methyl)-3H-imidazo[4,5-b]pyridine The title compound, also known as RA10651967, was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and methanol as described in Example 1-11: $^1$H NMR (400 MHz, CDCl$_3$) δ 8.23-8.19 (m, 2H), 7.98 (s, 1H), 7.64-7.57 (m, 2H), 6.77 (dd, J=8.5, 0.7 Hz, 1H), 6.53-6.52 (m, 2H), 5.33 (s, 2H), 5.09 (dd, J=8.4, 2.5 Hz, 1H), 4.30 (dd, J=11.6, 2.5 Hz, 1H), 4.06 (dd, J=11.6, 8.4 Hz, 1H), 3.94 (s, 3H), 3.91 (s, 3H), 3.80 (s, 3H) ppm; (M+1)= 435.

Example 1-60-1: Chiral separation of 6-methoxy-3-((8-methoxy-2-(6-methoxypyridin-3-yl)-2,3-dihydrobenzo[b][1,4]dioxin-6-yl)methyl)-3H-imidazo[4,5-b]pyridine The racemic 6-methoxy-3-((8-methoxy-2-(6-methoxypyridin-3-yl)-2,3-dihydrobenzo[b][1,4]dioxin-6-yl)methyl)-3H-imidazo[4,5-b]pyridine was subjected to SFC preparative purification (21.2×250 mm IA column, 30% ethanol/0.1% diethylamine modifier, 75 g/min flow rate) to afford the individual enantiomers. (S)-6-methoxy-3-((8-methoxy-2-(6-methoxypyridin-3-yl)-2,3-dihydrobenzo[b][1,4]dioxin-6-yl)methyl)-3H-imidazo[4,5-b]pyridine is also known as RA10846843.

Example 1-61: Synthesis of 3-((8-methoxy-2-(6-methoxypyridin-3-yl)-2,3-dihydrobenzo[b][1,4]dioxin-6-yl)methyl)-6-(3-methoxyazetidin-1-yl)-3H-imidazo[4,5-b]pyridine The title compound, also known as RA10680889, was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 3-methoxyazetidine hydrochloride as described in Example 1-10: $^1$H NMR (400 MHz, CDCl$_3$) δ 8.20 (d, J=2.4 Hz, 1H), 7.92 (s, 1H), 7.78 (d, J=2.4 Hz, 1H), 7.61 (dd, J=8.6, 2.5 Hz, 1H), 7.15 (d, J=2.5 Hz, 1H), 6.77 (d, J=8.6 Hz, 1H), 6.55-6.48 (m, 2H), 5.29 (s, 2H), 5.09 (dd, J=8.4, 2.5 Hz, 1H), 4.45-4.35 (m, 1H), 4.29 (dd, J=11.6, 2.5 Hz, 1H), 4.24-4.15 (m, 2H), 4.06 (dd, J=11.6, 8.4 Hz, 1H), 3.94 (s, 3H), 3.82-3.73 (m, 5H), 3.36 (s, 3H); (M+H)=490.

Example 1-62: Synthesis of 6-(azetidin-1-yl)-3-((8-methoxy-2-(6-methoxypyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and azetidine as described in Example 1-10: $^1$H NMR (400 MHz, CDCl$_3$) δ 8.21 (d, J=2.4 Hz, 1H), 8.03 (s, 1H), 7.79 (d, J=2.4 Hz, 1H), 7.61 (dd, J=8.6, 2.5 Hz, 1H), 7.13 (d, J=2.5 Hz, 1H), 6.82-6.73 (m, 1H), 6.58-6.48 (m, 2H), 5.32 (s, 2H), 5.10 (dd, J=8.4, 2.5 Hz, 1H), 4.31 (dd, J=11.6, 2.5 Hz, 1H), 4.07 (dd, J=11.6, 8.4 Hz, 1H), 3.98-3.95 (m, 4H), 3.94 (s, 3H), 3.81 (s, 3H), 2.47-2.44 (m, 2H) ppm; (M+1)=460.

Example 1-63: Synthesis of 2-((3-((8-methoxy-2-(6-methoxypyridin-3-yl)-2,3-dihydrobenzo[b][1,4]dioxin-6-yl)methyl)-3H-imidazo[4,5-b]pyridin-6-yl)oxy)-N,N-dimethylethan-1-amine To 2-(dimethylamino)ethanol (2 mL) was added 60% sodium hydride dispersion (0.18 g, 4.53 mmol). The mixture was stirred at room temperature. After 10 min, the mixture was diluted with N,N-dimethylformamide (2 mL) and copper(I) iodide (0.065 g, 0.34 mmol) and 6-iodo-3-((8-methoxy-2-(6-methoxypyridin-3-yl)-2,3-dihydrobenzo[b][1,4]dioxin-6-yl)methyl)-3H-imidazo[4,5-b]pyridine (0.12 g, 0.23 mmol) were added. The mixture was heated to 90° C. in a sealed vessel. After 2 h, the mixture was allowed to cool to room temperature and was diluted with water (50 mL). The pH of the mixture was adjusted to ~3, and the acidic mixture was extracted with ethyl acetate (×2). The organic phases were discarded. The aqueous phase was made basic and was extracted with chloroform (×3). The combined organic phases were washed with water, dried over sodium sulfate, filtered, and concentrated. Chromatographic purification of the crude product (Biotage, 12 g silica gel column, 0-10% methanol/dichloromethane elute) provided 0.032 g (24%) of 2-((3-((8-methoxy-2-(6-methoxypyridin-3-yl)-2,3-dihydrobenzo[b][1,4]dioxin-6-yl)methyl)-3H-imidazo[4,5-b]pyridin-6-yl)oxy)-N,N-dimethylethan-1-amine as a colorless oil: $^1$H NMR (400 MHz, CDCl3) δ 8.24 (d, J=2.5 Hz, 1H), 8.20 (d, J=2.3 Hz, 1H), 7.98 (s, 1H), 7.63-7.58 (m, 2H), 6.77 (dd, J=8.5, 0.8 Hz, 1H), 6.55-6.52 (m, 2H), 5.32 (s, 2H), 5.09 (dd, J=8.4, 2.5 Hz, 1H), 4.30 (dd, J=11.6, 2.5 Hz, 1H), 4.15 (t, J=5.6 Hz, 2H), 4.10-4.01 (m, 1H), 3.93 (s, 3H), 3.80 (s, 3H), 2.79 (t, J=5.6 Hz, 2H), 2.37 (s, 6H) ppm; (M+1)=492.

Example 1-64: Synthesis of 3-((8-methoxy-2-(6-methoxypyridin-3-yl)-2,3-dihydrobenzo[b][1,4]dioxin-6-yl)methyl)-6-(oxetan-3-yloxy)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and oxetan-3-ol as described in Example 1-11: $^1$H NMR (400 MHz, CDCl$_3$) δ 8.26-8.18 (m, 3H), 7.61 (dd, J=8.7, 2.5 Hz, 1H), 7.34 (d, J=2.5 Hz, 1H), 6.78 (d, J=8.7 Hz, 1H), 6.61-6.53 (m, 2H), 5.37 (s, 2H), 5.33-5.23 (m, 1H), 5.10 (dd, J=8.4, 2.5 Hz, 1H), 5.06-4.99 (m, 2H), 4.81 (dd, J=7.5, 5.1 Hz, 2H), 4.32 (dd, J=11.6, 2.5 Hz, 1H), 4.08 (dd, J=11.6, 8.4 Hz, 1H), 3.94 (s, 3H), 3.82 (s, 3H) ppm; (M+1)=477.

Example 1-65: Synthesis of 3-((8-methoxy-2-(6-methoxypyridin-3-yl)-2,3-dihydrobenzo[b][1,4]dioxin-6-yl)methyl)-N,N-dimethyl-3H-imidazo[4,5-b]pyridin-6-amine To stirred suspension of 6-iodo-3-((8-methoxy-2-(6-methoxypyridin-3-yl)-2,3-dihydrobenzo[b][1,4]dioxin-6-yl)methyl)-3H-imidazo[4,5-b]pyridine (0.12 g, 0.23 mmol, Example 1-52-9) in dimethylamine (2.2 mL) was added 2-(di-tert-butylphosphino)biphenyl (0.014 g, 0.045 mmol), tris(dibenzylideneacetone)dipalladium(0) (0.011 g, 0.011 mmol) and sodium tert-butoxide (0.044 g, 0.045 mmol). The mixture was heated to 90° C. in a microwave reactor. After 30 min, the mixture was allowed to cool to room temperature and was concentrated. Chromatographic purification of the crude product (Biotage, 12 g silica gel column, 0-10% methanol/dichlormethane elute) provided 0.041 g (41%) of 3-((8-methoxy-2-(6-methoxypyridin-3-yl)-2,3-dihydrobenzo[b][1,4]dioxin-6-yl)methyl)-N,N-dimethyl-3H-imidazo[4,5-b]pyridin-6-amine as a white solid: $^1$H NMR (400 MHz, CDCl$_3$) δ 8.24-8.16 (m, 1H), 8.13 (d, J=2.6 Hz, 1H), 7.93 (s, 1H), 7.61 (dd, J=8.6, 2.5 Hz, 1H), 7.45 (d, J=2.6 Hz, 1H), 6.77 (d, J=8.6, 0.7 Hz, 1H), 6.55-6.50 (m, 2H), 5.30 (s, 2H), 5.09 (dd, J=8.4, 2.5 Hz, 1H), 4.29 (dd, J=11.6, 2.5 Hz, 1H), 4.06 (dd, J=11.6, 8.4 Hz, 1H), 3.93 (s, 3H), 3.80 (s, 3H), 2.99 (s, 6H) ppm; (M+1)=448.

Example 1-66: Synthesis of 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-3-methylazetidin-3-ol The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 3-methylazetidin-3-ol hydrochloride as described in Example 1-10: $^1$H NMR (400 MHz, acetone-d6) δ 8.28 (dt, J=2.5, 0.7 Hz, 1H), 8.23 (s, 1H), 7.80-7.72 (m, 2H), 7.07 (d, J=2.5 Hz, 1H), 6.84-6.79 (m, 1H), 6.79 (d, J=2.0 Hz, 1H), 6.57 (d, J=2.0 Hz, 1H), 5.36 (s, 2H), 5.14 (dd, J=8.4, 2.5 Hz, 1H), 4.38 (dd, J=11.5, 2.5 Hz, 1H), 4.10 (dd, J=11.5, 8.4 Hz, 1H), 3.92 (d, J=7.6 Hz, 2H), 3.90 (s, 3H), 3.77 (s, 3H), 3.74 (d, J=7.2 Hz, 2H), 1.59 (s, 3H) ppm; (M+1)=490.

Example 1-67: Synthesis of 3-((8-methoxy-2-(6-methoxypyridin-3-yl)-2,3-dihydrobenzo[b][1,4]dioxin-6-yl)methyl)-6-(1H-1,2,4-triazol-1-yl)-3H-imidazo[4,5-b]pyridine To a stirred suspension of 6-iodo-3-((8-methoxy-2-(6-methoxypyridin-3-yl)-2,3-dihydrobenzo[b][1,4]dioxin-6-yl)methyl)-3H-imidazo[4,5-b]pyridine (0.12 g, 0.23 mmol, Example 1-52-9) in N,N-dimethylformamide (4 mL) was added potassium carbonate (0.095 g, 0.68 mmol), copper(I) iodide (0.016 g, 0.084 mmol), N,N'-dimethyl-1,2-cyclohexanediamine (0.026 g, 0.18 mmol), and 1H-1,2,4-triazole (0.16 g, 2.26 mmol). The mixture was degassed under vacuum/backfilled with nitrogen (×3). The mixture heated to 135° C. in a sealed vessel. After 3 h, the mixture was allowed to cool to room temperature and was diluted with water (40 mL). The pH was adjusted to ~7, and the mixture was extracted with chloroform (×2). The combined organic phases were washed with 1N ammonium hydroxide solution (×2), dried over magnesium sulfate, filtered, and concentrated. The residue was subjected to reverse phase chromatography (Biotage, 50 g C18 column, water/acetonitrile/0.1% formic acid elute). The fractions containing the desired product was combined and concentrated to remove the organic solvent. The remaining aqueous solution was extracted with chloroform (×3). The combined organic phases were dried over sodium sulfate, filtered, and concentrated. Chromatographic purification of this material (Biotage, 12 g silica gel column, 0-10% methanol/dichloromethane elute) provided 0.020 g (19%) of 3-((8-methoxy-2-(6-methoxypyridin-3-yl)-2,3-dihydrobenzo[b][1,4]dioxin-6-yl)methyl)-6-(1H-1,2,4-triazol-1-yl)-3H-imidazo[4,5-b]pyridine as a white solid: $^1$H NMR (400 MHz, CDCl$_3$) δ 8.81 (d, J=2.3 Hz, 1H), 8.58 (s, 1H), 8.35 (d, J=2.3 Hz, 1H), 8.23-8.14 (m, 3H), 7.62 (dd, J=8.6, 2.5 Hz, 1H), 6.78 (dd, J=8.6, 0.7 Hz, 1H), 6.62-6.51 (m, 2H), 5.41 (s, 2H), 5.10 (dd, J=8.4, 2.5 Hz, 1H), 4.32 (dd, J=11.6, 2.5 Hz, 1H), 4.08 (dd, J=11.6, 8.4 Hz, 1H), 3.94 (s, 3H), 3.83 (s, 3H) ppm; (M+1)=472.

Example 1-68: Synthesis of 3-((8-methoxy-2-(6-methoxypyridin-3-yl)-2,3-dihydrobenzo[b][1,4]dioxin-6-yl)methyl)-6-(1H-pyrazol-1-yl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 1H-pyrazole as described in Example 1-67: $^1$H NMR (400 MHz, DMSO-d6) δ 8.94 (d, J=2.3 Hz, 1H), 8.69 (s, 1H), 8.58 (dd, J=2.5, 0.6 Hz, 1H), 8.51 (d, J=2.3 Hz, 1H), 8.23 (d, J=2.4 Hz, 1H), 7.80 (d, J=1.7 Hz, 1H), 7.75 (dd, J=8.6, 2.4 Hz, 1H), 6.90-6.84 (m, 1H), 6.78 (d, J=1.9 Hz, 1H), 6.62-6.48 (m, 2H), 5.41 (s, 2H), 5.15 (dd, J=8.3, 2.5 Hz, 1H), 4.35 (dd, J=11.5, 2.5 Hz, 1H), 4.14 (dd, J=11.5, 8.3 Hz, 1H), 3.85 (s, 3H), 3.73 (s, 3H) ppm; (M+1)=471.

Example 1-69: Synthesis of 6-(1H-imidazol-1-yl)-3-((8-methoxy-2-(6-methoxypyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 1H-imidazole as described in Example 1-67: $^1$H NMR (400 MHz, DMSO-d6) δ 8.74-8.72 (m, 2H), 8.43 (d, J=2.4 Hz, 1H), 8.29 (t, J=1.1 Hz, 1H), 8.23 (d, J=2.4 Hz, 1H), 7.82 (t, J=1.3 Hz, 1H), 7.75 (dd, J=8.7, 2.4 Hz, 1H), 7.14 (t, J=1.1 Hz, 1H), 6.92-6.82 (m, 1H), 6.79 (d, J=1.9 Hz, 1H), 6.55 (d, J=1.9 Hz, 1H), 5.42 (s, 2H), 5.15 (dd, J=8.3, 2.5 Hz, 1H), 4.35 (dd, J=11.5, 2.5 Hz, 1H), 4.14 (dd, J=11.5, 8.3 Hz, 1H), 3.85 (s, 3H), 3.74 (s, 3H) ppm; (M+1)=471.

Example 1-70: Synthesis of 3-((8-methoxy-2-(6-methoxypyridin-3-yl)-2,3-dihydrobenzo[b][1,4]dioxin-6-yl)methyl)-6-(2-methyl-1H-imidazol-1-yl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 2-methyl-1H-imidazole as described in Example 1-67: $^1$H NMR (400 MHz, CDCl$_3$) δ 8.41 (d, J=2.2 Hz, 1H), 8.24-8.13 (m, 2H), 8.03 (d, J=2.2 Hz, 1H), 7.61 (dd, J=8.6, 2.5 Hz, 1H), 7.12-7.06 (m, 2H), 6.78 (dd, J=8.6, 0.7 Hz, 1H), 6.60-6.56 (m, 2H), 5.41 (s, 2H), 5.11 (dd, J=8.3, 2.5 Hz, 1H), 4.32 (dd, J=11.6, 2.5 Hz, 1H), 4.08 (dd, J=11.6, 8.4 Hz, 1H), 3.94 (s, 3H), 3.84 (s, 3H), 2.39 (s, 3H) ppm; (M+1)=485.

Example 1-71: Synthesis of 6-(2,4-dimethyl-1H-imidazol-1-yl)-3-((8-methoxy-2-(6-methoxypyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methoxypyridin-3-yl)-2,3-dihydrobenzo [b][1,4]dioxin-6-yl)methyl)-3H-imidazo[4,5-b] (Example 1-52-9) and 2,4-dimethyl-1H-imidazole as described in Example 1-67: $^1$H NMR (400 MHz, CDCl$_3$) δ 8.39 (d, J=2.2 Hz, 1H), 8.24-8.19 (m, 1H), 8.16 (s, 1H), 8.00 (d, J=2.2 Hz, 1H), 7.61 (dd, J=8.6, 2.5 Hz, 1H), 6.85-6.72 (m, 2H), 6.59-6.57 (m, 2H), 5.40 (s, 2H), 5.10 (dd, J=8.4, 2.5 Hz, 1H), 4.32 (dd, J=11.6, 2.5 Hz, 1H), 4.08 (dd, J=11.6, 8.4 Hz, 1H), 3.94 (s, 3H), 3.84 (s, 3H), 2.34 (s, 3H), 2.27 (s, 3H) ppm; (M+1)=499.

Example 1-72: Synthesis of 3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine

Example 1-72-1: Preparation of tert-butyl 3-((3-((8-methoxy-2-(6-methoxypyridin-3-yl)-2,3-dihydrobenzo[b][1,4]dioxin-6-yl)methyl)-3H-imidazo[4,5-b]pyridin-6-yl)oxy)azetidine-1-carboxylate The title compound was prepared from 6-iodo-3-((8-methoxy-2-(6-methoxypyridin-3-yl)-2,3-dihydrobenzo [b]

[1,4]dioxin-6-yl)methyl)-3H-imidazo[4,5-b] (Example 1-52-9) and tert-butyl 3-hydroxyazetidine-1-carboxylate as described in Example 1-11.

Example 1-72-2: Preparation of 3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine To a stirred solution of tert-butyl 3-((3-((8-methoxy-2-(6-methoxypyridin-3-yl)-2,3-dihydrobenzo[b][1,4]dioxin-6-yl)methyl)-3H-imidazo[4,5-b]pyridin-6-yl)oxy)azetidine-1-carboxylate (0.81 g, 1.41 mmol) in dichloromethane (20 mL) was added trifluoroacetic acid (10 mL). The resulting golden yellow solution was allowed to stir at room temperature. After 1 h, the mixture was concentrated, and the residue was dissolved in dichloromethane (50 mL). The solution was washed with saturated sodium carbonate solution (50 mL) and brine (50 mL). The organic phase was dried over magnesium sulfate, filtered, and concentrated. The crude material was dissolved in dichloromethane (20 mL) and was treated with 37% formaldehyde solution in water (0.52 mL, 7.04 mmol) and sodium triacetoxyborohydride (0.77 g, 3.52 mmol). A minor exotherm was noted upon addition. The mixture was allowed to stir at room temperature. After 15 h, the mixture was diluted with saturated sodium carbonate solution (50 mL) and dichloromethane (50 mL). The phases were separated, and the aqueous phase was extracted with dichloromethane (30 mL). The combined organic phases were dried over magnesium sulfate, filtered, and concentrated. Chromatographic purification of the crude product (CombiFlash, 40 g silica gel gold column, 0-5% 2M ammonia in methanol/dichloromethane elute) afforded 0.20 g (29%) of 3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine, also known as RA10848270, as an off-white solid: $^1$H NMR (400 MHz, CDCl$_3$) δ 8.23-8.17 (m, 1H), 8.14 (d, J=2.6 Hz, 1H), 7.98 (s, 1H), 7.61 (dd, J=8.6, 2.5 Hz, 1H), 7.41 (d, J=2.6 Hz, 1H), 6.77 (dd, J=8.6, 0.7 Hz, 1H), 6.53- 6.51 (m, 2H), 5.32 (s, 2H), 5.09 (dd, J=8.4, 2.5 Hz, 1H), 4.83-4.75 (m, 1H), 4.30 (dd, J=11.6, 2.5 Hz, 1H), 4.06 (dd, J=11.6, 8.4 Hz, 1H), 3.94 (s, 3H), 3.89-3.83 (m, 2H), 3.80 (s, 3H), 3.22-3.12 (m, 2H), 2.43 (s, 3H) ppm; (M+1)=490.

Example 1-73: Synthesis of 3-((8-methoxy-2-(6-methoxypyridin-3-yl)-2,3-dihydrobenzo[b][1,4]dioxin-6-yl)methyl)-6-methyl-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 2,4,6-trimethyl-1,3,5,2,4,6-trioxatriborinane as described in Example 1-55: $^1$H NMR (400 MHz, CDCl$_3$) δ 8.29-8.24 (m, 1H), 8.20 (d, J=2.5 Hz, 1H), 7.99 (s, 1H), 7.88 (dd, J=1.9, 0.8 Hz, 1H), 7.61 (dd, J=8.6, 2.5 Hz, 1H), 6.77 (dd, J=8.6, 0.8 Hz, 1H), 6.54-6.52 (m, 2H), 5.34 (s, 2H), 5.09 (dd, J=8.4, 2.5 Hz, 1H), 4.30 (dd, J=11.6, 2.5 Hz, 1H), 4.06 (dd, J=11.6, 8.4 Hz, 1H), 3.94 (s, 3H), 3.80 (s, 3H), 2.49 (s, 3H) ppm; (M+1)=419.

Example 1-74: Synthesis of 3-((8-methoxy-2-(6-methoxypyridin-3-yl)-2,3-dihydrobenzo[b][1,4]dioxin-6-yl)methyl)-N-methyl-3H-imidazo[4,5-b]pyridin-6-amine To a stirred suspension of 6-iodo-3-((8-methoxy-2-(6-methoxypyridin-3-yl)-2,3-dihydrobenzo[b][1,4]dioxin-6-yl)methyl)-3H-imidazo[4,5-b]pyridine (0.20 g, 0.38 mmol, Example 1-52-9) in 1,4-dioxane (5 mL) was added tert-butyl-N-methylcarbamate (0.10 g, 0.75 mmol), tris(dibenzylideneacetone)dipalladium(0) (0.018 g, 0.019 mmol), 4,5-bis(diphenylphosphino)-9,9-dimethylxanthene (0.044 g, 0.075 mmol) and cesium carbonate (0.18 g, 0.57 mmol). The mixture was degassed under vacuum/backfilled with nitrogen (×3). The mixture was then heated to 115° C. After 18 h, the mixture was allowed to cool to room temperature and was concentrated. Chromatographic purification of the crude product (Biotage, 12 g silica gel column, ethyl acetate/heptane elute) provided semi-pure material. This material was dissolved in dichloromethane (10 mL) and was treated with trifluoroacetic acid (6 mL). The mixture was allowed to stir at room temperature. After 15 min, the mixture was concentrated. The residue was dissolved in methanol and was neutralized by the addition of solid potassium carbonate. The mixture was filtered and concentrated. Chromatographic purification of the crude product (Biotage, 12 g silica gel column, 0-8% methanol/ethyl acetate elute) provided 0.020 g (12%) of 3-((8-methoxy-2-(6-methoxypyridin-3-yl)-2,3-dihydrobenzo[b][1,4]dioxin-6-yl)methyl)-N-methyl-3H-imidazo[4,5-b]pyridin-6-amine as a light yellow solid: $^1$H NMR (400 MHz, CDCl$_3$) δ 8.22-8.18 (m, 1H), 7.95 (d, J=2.5 Hz, 1H), 7.92 (s, 1H), 7.61 (dd, J=8.6, 2.5 Hz, 1H), 7.28 (d, J=2.5 Hz, 1H), 6.77 (dd, J=8.5, 0.7 Hz, 1H), 6.54-6.48 (m, 2H), 5.30 (s, 2H), 5.09 (dd, J=8.4, 2.5 Hz, 1H), 4.29 (dd, J=11.6, 2.5 Hz, 1H), 4.06 (dd, J=11.6, 8.4 Hz, 1H), 3.93 (s, 3H), 3.79 (s, 3H), 2.91 (s, 3H) ppm; (M+1)=434.

Example 1-75: Synthesis of 6-(1,3-dimethyl-1H-pyrazol-4-yl)-3-((8-methoxy-2-(6-methoxypyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 1,3-dimethyl-4-(4,4,5,5-tetramethyl-1,3,2-dioxaborolan-2-yl)-1H-pyrazole as described in Example 1-55: $^1$H NMR (400 MHz, CDCl$_3$) δ 8.52 (d, J=1.9 Hz, 1H), 8.24-8.15 (m, 2H), 8.10 (d, J=1.9 Hz, 1H), 7.62 (dd, J=8.6, 2.5 Hz, 1H), 7.49 (s, 1H), 6.82-6.73 (m, 1H), 6.59-6.57 (m, 2H), 5.40 (s, 2H), 5.10 (dd, J=8.4, 2.5 Hz, 1H), 4.31 (dd, J=11.6, 2.5 Hz, 1H), 4.08 (dd, J=11.6, 8.4 Hz, 1H), 3.94 (s, 3H), 3.92 (s, 3H), 3.83 (s, 3H), 2.42 (s, 3H) ppm; (M+1)=499.

Example 1-76: Synthesis of 6-(6-fluoropyridin-3-yl)-3-((8-methoxy-2-(6-methoxypyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and (6-fluoropyridin-3-yl)boronic acid as described in Example 1-55: $^1$H NMR (400 MHz, CDCl$_3$) δ 8.65 (d, J=2.0 Hz, 1H), 8.50-8.46 (m, 1H), 8.28-8.23 (m, 2H), 8.22-8.18 (m, 1H), 8.05-8.00 (m, 1H), 7.61 (dd, J=8.6, 2.5 Hz, 1H), 7.10-7.07 (m, 1H), 6.81-6.75 (m, 1H), 6.59-6.57 (m, 2H), 5.43 (s, 2H), 5.10 (dd, J=8.4, 2.5 Hz, 1H), 4.32 (dd, J=11.6, 2.5 Hz, 1H), 4.08 (dd, J=11.6, 8.4 Hz, 1H), 3.94 (s, 3H), 3.83 (s, 3H) ppm; (M+1)=500.

Example 1-77: Synthesis of 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)azetidin-3-ol The title compound was prepared from 6-iodo-3-((8-methoxy-2-(6-methoxypyridin-3-yl)-2,3-dihydrobenzo[b]

[1,4]dioxin-6-yl)methyl)-3H-imidazo[4,5-b] (Example 1-52-9) and azetidin-3-ol hydrochloride as described in Example 1-10: $^1$H NMR (400 MHz, CD$_3$OD) δ 8.28 (s, 1H), 8.20 (d, J=2.5 Hz, 1H), 7.81-7.70 (m, 2H), 7.14 (d, J=2.5 Hz, 1H), 6.82 (d, J=8.6 Hz, 1H), 6.67 (d, J=2.0 Hz, 1H), 6.51 (d, J=2.0 Hz, 1H), 5.35 (s, 2H), 5.11 (dd, J=8.2, 2.5 Hz, 1H), 4.76-4.67 (m, 1H), 4.34 (dd, J=11.6, 2.5 Hz, 1H), 4.26-4.22 (m, 2H), 4.06 (dd, J=11.6, 8.2 Hz, 1H), 3.91 (s, 3H), 3.78 (s, 3H), 3.71-3.63 (m, 2H) ppm; (M+1)=476.

Example 1-78: Synthesis of 3-((8-methoxy-2-(6-methoxypyridin-3-yl)-2,3-dihydrobenzo[b][1,4]dioxin-6-yl)methyl)-6-(4-methylpiperazin-1-yl)-3H-imidazo[4,5-b]pyridine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 1-methylpiperazine as described in Example 1-10: $^1$H NMR (400 MHz, CD$_3$OD) δ 8.33 (s, 1H), 8.27 (d, J=2.5 Hz, 1H), 8.19 (d, J=2.5 Hz, 1H), 7.73 (dd, J=8.7, 2.5 Hz, 1H), 7.64 (d, J=2.5 Hz, 1H), 6.82 (dd, J=8.7, 0.7 Hz, 1H), 6.68 (d, J=2.0 Hz, 1H), 6.53 (d, J=2.0 Hz, 1H), 5.37 (s, 2H), 5.10 (dd, J=8.3, 2.5 Hz, 1H), 4.33 (dd, J=11.5, 2.5 Hz, 1H), 4.06 (dd, J=11.5, 8.3 Hz, 1H), 3.90 (s, 3H), 3.78 (s, 3H), 3.27-3.21 (m, 4H), 2.71-2.64 (m, 4H), 2.37 (s, 3H) ppm; (M+1)=503.

Example 1-79: Synthesis of 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-3-methylazetidin-3-amine The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b] (Example 1-52-9) and 3-methylazetidin-3-amine hydrochloride as described in Example 1-10: $^1$H NMR (400 MHz, CD$_3$OD) δ 8.29 (s, 1H), 8.19 (d, J=2.4 Hz, 1H), 7.81-7.69 (m, 2H), 7.14 (d, J=2.4 Hz, 1H), 6.82 (dd, J=8.6, 0.7 Hz, 1H), 6.67 (d, J=2.0 Hz, 1H), 6.50 (d, J=2.0 Hz, 1H), 5.35 (s, 2H), 5.10 (dd, J=8.3, 2.5 Hz, 1H), 4.33 (dd, J=11.5, 2.5 Hz, 1H), 4.06 (dd, J=11.5, 8.3 Hz, 1H), 3.90 (s, 3H), 3.90-3.87 (m, 2H), 3.78 (s, 3H), 3.74-3.70 (m, 2H), 1.56 (s, 3H) ppm; (M+1)=489.

Example 1-80: Synthesis of 6-(3-fluoroazetidin-1-yl)-3-((8-methoxy-2-(6-methoxypyridin-3-yl)-2,3-dihydrobenzo[b][1,4]dioxin-6-yl)methyl)-3H-imidazo[4,5-b]pyridine To a stirred and cooled (0° C.) suspension of 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)azetidin-3-ol (0.050 g, 0.11 mmol, Example 1-77) in dichloromethane (3 mL) was added bis(2-methoxyethyl)aminosulfur trifluoride (0.029 g, 0.13 mmol). The resulting red mixture was allowed to stir at 0° C. After 40 min, the cooling bath was removed, and the mixture was allowed to warm to room temperature. After 30 min, the mixture was re-cooled to 0° C., and an additional portion of bis(2-methoxyethyl)aminosulfur trifluoride (0.029 g, 0.13 mmol) was added. After 10 min, the cooling bath was removed, and the mixture was allowed to warm to room temperature. After 15 min, the mixture was diluted with dichloromethane and was washed with saturated sodium bicarbonate solution. The organic phase dried over magnesium sulfate, filtered, and concentrated.

Chromatographic purification of the crude product (Biotage, 12 g silica gel column, ethyl acetate/heptane followed by 0-5% methanol/ethyl acetate elute) provided a partially purified material. Two additional chromatographic purifications afforded 0.007 g (14%) of 6-(3-fluoroazetidin-1-yl)-3-((8-methoxy-2-(6-methoxypyridin-3-yl)-2,3-dihydrobenzo[b][1,4]dioxin-6-yl)methyl)-3H-imidazo[4,5-b]pyridine as a white solid: $^1$H NMR (400 MHz, CDCl$_3$) δ 8.24-8.15 (m, 1H), 8.00 (s, 1H), 7.80 (d, J=2.5 Hz, 1H), 7.61 (dd, J=8.6, 2.5 Hz, 1H), 7.18 (d, J=2.5 Hz, 1H), 6.77 (dd, J=8.6, 0.7 Hz, 1H), 6.57-6.48 (m, 2H), 5.56-5.40 (m, 1H), 5.31 (s, 2H), 5.09 (dd, J=8.4, 2.4 Hz, 1H), 4.37-4.19 (m, 3H), 4.11-4.02 (m, 2H), 4.02-3.96 (m, 1H), 3.94 (s, 3H), 3.80 (s, 3H) ppm; (M+1)=478.

Example 1-81: Synthesis of 6-fluoro-3-((8-methoxy-2-(6-methoxypyridin-3-yl)-2,3-dihydrobenzo[b][1,4]dioxin-6-yl)methyl)-3H-imidazo[4,5-b]pyridine The title compound was prepared in three steps from (8-methoxy-2-(6-methoxypyridin-3-yl)-2,3-dihydrobenzo[b][1,4]dioxin-6-yl)methanamine (Example 1-52-6) and 2-chloro-5-fluoro-3-nitropyridine as described in Example 1-52-7 through Example 1-52-9: $^1$H NMR (400 MHz, CDCl$_3$) δ 8.36-8.31 (m, 1H), 8.21-8.19 (m, 1H), 8.07 (s, 1H), 7.80 (dd, J=8.7, 2.6 Hz, 1H), 7.61 (dd, J=8.6, 2.6 Hz, 1H), 6.77 (dd, J=8.6, 0.7 Hz, 1H), 6.56-6.50 (m, 2H), 5.34 (s, 2H), 5.09 (dd, J=8.4, 2.5 Hz, 1H), 4.31 (dd, J=11.6, 2.5 Hz, 1H), 4.07 (dd, J=11.6, 8.4 Hz, 1H), 3.94 (s, 3H), 3.81 (s, 3H) ppm; (M+1)=423.

Example 1-82: Synthesis of 3-((8-methoxy-2-(6-methoxypyridin-3-yl)-2,3-dihydrobenzo[b][1,4]dioxin-6-yl)methyl)-3H-imidazo[4,5-b]pyridine The title compound was prepared in three steps from (8-methoxy-2-(6-methoxypyridin-3-yl)-2,3-dihydrobenzo[b][1,4]dioxin-6-yl)methanamine (Example 1-52-6) and 2-chloro-3-nitropyridine as described in Example 1-52-7 through Example 1-52-9: $^1$H NMR (400 MHz, CDCl$_3$) δ 8.45 (dd, J=4.8, 1.4 Hz, 1H), 8.20 (d, J=2.5 Hz, 1H), 8.10 (dd, J=8.1, 1.4 Hz, 1H), 8.05 (s, 1H), 7.61 (dd, J=8.6, 2.5 Hz, 1H), 7.29-7.26 (m, 1H), 6.80-6.74 (m, 1H), 6.56-6.54 (m, 2H), 5.38 (s, 2H), 5.09 (dd, J=8.4, 2.5 Hz, 1H), 4.30 (dd, J=11.6, 2.5 Hz, 1H), 4.06 (dd, J=11.6, 8.4 Hz, 1H), 3.94 (s, 3H), 3.80 (s, 3H) ppm; (M+1)=.

Example 1-83: Synthesis of azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone Example 1-83-1: Preparation of methyl 3-((8-methoxy-2-(6-methoxypyridin-3-yl)-2,3-dihydrobenzo[b][1,4]dioxin-6-yl)methyl)-3H-imidazo[4,5-b]pyridine-6-carboxylate The title compound was prepared in three steps from (8-methoxy-2-(6-methoxypyridin-3-yl)-2,3-dihydrobenzo[b][1,4]dioxin-6-yl)methanamine (Example 1-52-6) and methyl 6-chloro-5-nitronicotinate as described in Example 1-52-7 through Example 1-52-9.

Example 1-83-2: Preparation of 3-((8-methoxy-2-(6-methoxypyridin-3-yl)-2,3-dihydrobenzo[b][1,4]dioxin-6-yl)methyl)-3H-imidazo[4,5-b]pyridine-6-carboxylic acid To a stirred solution of methyl 3-((8-methoxy-2-(6-methoxypyridin-3-yl)-2,3-dihydrobenzo[b][1,4]dioxin-6-yl)

methyl)-3H-imidazo[4,5-b]pyridine-6-carboxylate (0.20 g, 0.43 mmol) in 1:1:1 methanol/tetrahydrofuran/water (15 mL) was added lithium hydroxide (0.070 g, 2.92 mmol). The mixture was allowed to stir at room temperature. After 1 h, the mixture was treated with 2N hydrochloric acid solution (1.6 mL) and water (15 mL). The acidic mixture was extracted with ethyl acetate (×3). The combined organic phases were washed with brine, dried over magnesium sulfate, filtered, and concentrated to provide 0.15 g (77%) of 3-((8-methoxy-2-(6-methoxypyridin-3-yl)-2,3-dihydrobenzo[b][1,4]dioxin-6-yl)methyl)-3H-imidazo[4,5-b]pyridine-6-carboxylic acid as a white solid.

Example 1-83-3: Preparation of azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone To a stirred solution of 3-((8-methoxy-2-(6-methoxypyridin-3-yl)-2,3-dihydrobenzo[b][1,4]dioxin-6-yl)methyl)-3H-imidazo[4,5-b]pyridine-6-carboxylic acid (0.15 g, 0.33 mmol) in dichloromethane (10 mL) was added 2-(1H-benzo[d][1,2,3]triazol-1-yl)-1,1,3,3-tetramethylisouronium tetrafluoroborate (0.13 g, 0.40 mmol), N,N-diisopropylethylamine (0.13 g, 1.00 mmol) and azetidine (0.029 g, 0.50 mmol). The mixture was allowed to stir at room temperature. After 25 min, the mixture was concentrated. Chromatographic purification of the crude product (Biotage, 12 g silica gel column, 0-10% methanol/dichloromethane elute) provided a partially purified material. This material was dissolved in ethyl acetate and was washed with water (3×30 mL). The organic phase was dried over magnesium sulfate, filtered, and concentrated to provide 0.050 g (31%) of azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone, also known as RA10600053, as a white solid: $^1$H NMR (400 MHz, CDCl$_3$) δ 8.80 (d, J=1.9 Hz, 1H), 8.32 (d, J=1.9 Hz, 1H), 8.20 (d, J=2.4 Hz, 1H), 8.11 (s, 1H), 7.61 (dd, J=8.6, 2.5 Hz, 1H), 6.78 (dd, J=8.5, 0.7 Hz, 1H), 6.55-6.53 (m, 2H), 5.38 (s, 2H), 5.09 (dd, J=8.4, 2.4 Hz, 1H), 4.44-4.26 (m, 5H), 4.07 (dd, J=11.6, 8.4 Hz, 1H), 3.94 (s, 3H), 3.81 (s, 3H), 2.46-2.33 (m, 2H) ppm; (M+1)=488.

Example 1-83-4: Chiral separation of azetidin-1-yl (3-((8-methoxy-2-(6-methoxypyridin-3-yl)-2,3-dihydrobenzo[b][1,4]dioxin-6-yl)methyl)-3H- imidazo[4,5-b]pyridin-6-yl)methanone The racemic 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine was subjected to HPLC preparative purification (21.2×250 mm Lux Cellulose-3 column, 80% ethanol/20% heptane with 0.1% diethylamine modifier, 7 mL/min flow rate) to afford the individual enantiomers.

Example 1-84: Synthesis of (3-((8-methoxy-2-(6-methoxypyridin-3-yl)-2,3-dihydrobenzo[b][1,4]dioxin-6-yl)methyl)-3H-imidazo[4,5-b]pyridin-6-yl)methanol The title compound was prepared from methyl 3-((8-methoxy-2-(6-methoxypyridin-3-yl)-2,3-dihydrobenzo[b][1,4]dioxin-6-yl)methyl)-3H-imidazo[4,5-b]pyridine-6-carboxylate (Example 1-83-1) as described in Example 1-52-4: $^1$H NMR (400 MHz, CDCl$_3$) δ 8.46 (d, J=1.8 Hz, 1H), 8.20 (d, J=2.5 Hz, 1H), 8.10 (d, J=1.8 Hz, 1H), 8.05 (s, 1H), 7.61 (dd, J=8.7, 2.5 Hz, 1H), 6.80-6.75 (m, 1H), 6.54-6.52 (m, 2H), 5.37 (s, 2H), 5.09 (dd, J=8.4, 2.5 Hz, 1H), 4.87 (d, J=5.5 Hz, 2H), 4.30 (dd, J=11.6, 2.5 Hz, 1H), 4.06 (dd, J=11.6, 8.4 Hz, 1H), 3.93 (s, 3H), 3.80 (s, 3H), 1.96 (t, J=5.5 Hz, 1H) ppm; (M+1)=435.

Example 1-85: Synthesis of 3-((8-methoxy-2-(6-methoxypyridin-3-yl)-2,3-dihydrobenzo[b][1,4]dioxin-6-yl)methyl)-6-(methoxymethyl)-3H-imidazo[4,5-b]pyridine To a stirred solution of (3-((8-methoxy-2-(6-methoxypyridin-3-yl)-2,3-dihydrobenzo[b][1,4]dioxin-6-yl)methyl)-3H-imidazo[4,5-b]pyridin-6-yl)methanol (0.31 g, 0.72 mmol) and N,N-dimethylformamide (10 mL) was added 60% sodium hydride dispersion (0.063 g, 1.59 mmol). The resulting yellow mixture was allowed to stir at room temperature. After 15 min, the mixture was treated with iodomethane (0.26 g, 1.80 mmol), and the resulting mixture was allowed to stir. After 45 min, the mixture was diluted with water (50 mL) and extracted with diethyl ether (3×30 mL). The combined organic phases were dried over magnesium sulfate, filtered, and concentrated. Chromatographic purification of the crude product (CombiFlash, 24 g silica gel gold column, 0-5% methanol/dichloromethane elute) afforded 0.22 g (67%) of 3-((8-methoxy-2-(6-methoxypyridin-3-yl)-2,3-dihydrobenzo[b][1,4]dioxin-6-yl)methyl)-6-(methoxymethyl)-3H-imidazo[4,5-b]pyridine as a white solid: $^1$H NMR (400 MHz, CDCl$_3$) δ 8.43 (d, J=1.8 Hz, 1H), 8.20 (d, J=2.5 Hz, 1H), 8.07 (d, J=1.8 Hz, 1H), 8.05 (s, 1H), 7.61 (dd, J=8.6, 2.5 Hz, 1H), 6.77 (d, J=8.6 Hz, 1H), 6.54-6.52 (m, 2H), 5.37 (s, 2H), 5.09 (dd, J=8.4, 2.5 Hz, 1H), 4.61 (s, 2H), 4.30 (dd, J=11.6, 2.5 Hz, 1H), 4.06 (dd, J=11.6, 8.4 Hz, 1H), 3.93 (s, 3H), 3.80 (s, 3H), 3.43 (s, 3H) ppm; (M+1)=449.

Example 1-86: Synthesis of 6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine Example 1-86-1: Preparation of 6-(methylthio)-5-nitronicotinic acid To a stirred solution of methyl 6-(methylthio)-5-nitronicotinate (14.25 g, 62.44 mmol), in tetrahydrofuran (200 mL) and water (50 mL) was added lithium hydroxide monohydrate (4.25 g, 99.26 mmol). The resulting orange solution was allowed to stir at room temperature. After 45 min, the mixture was concentrated to remove tetrahydrofuran, and the residual solution was treated with 1N hydrochloric acid solution (100 mL). The resulting suspension was filtered, and the filter cake was washed with water (300 mL). The moist solids were suspended in ethyl acetate (300 mL) and methanol (150 mL), and the mixture was concentrated to provide 12.54 g (94%) of 6-(methylthio)-5-nitronicotinic acid as a bright yellow solid.

Example 1-86-2: Preparation of (6-(methylthio)-5-nitropyridin-3-yl)methanol

To a stirred solution of 6-(methylthio)-5-nitronicotinic acid (2.53 g, 11.81 mmol) in tetrahydrofuran (100 mL) was added 1.0M borane-tetrahydrofuran complex (29.5 mL, 29.53 mmol) (via syringe over ~5 min). The resulting mixture was heated to ~50° C. and stirred. After 25 min, the mixture was cooled to 0° C. while methanol (10 mL) was added. The mixture was allowed to stir for 10 min, and then it was concentrated onto silica gel. Chromatographic purification of the crude product (CombiFlash, 80 g silica gel gold column, 50% ethyl acetate/heptane to 100% ethyl acetate elute) afforded 0.95 g (40%) of (6-(methylthio)-5-nitropyridin-3-yl)methanol as a bright yellow solid.

Example 1-86-3: Preparation of 6-(methylthio)-5-nitronicotinaldehyde

To a stirred solution of (6-(methylthio)-5-nitropyridin-3-yl)methanol (1.76 g, 8.79 mmol) in dichloromethane (50 mL) was added manganese(IV) oxide(5.39 g, 52.74 mmol). The resulting black suspension was allowed to stir at room temperature. After 22 h, the mixture was filtered through Celite with the aid of chloroform (200 mL). The filtrate was concentrated to provide 1.23 g (71%) of 6-(methylthio)-5-nitronicotinaldehyde as a yellow solid.

Example 1-86-4: Preparation of 5-(difluoromethyl)-2-(methylthio)-3-nitropyridine To a stirred and cooled (0° C.) solution of 6-(methylthio)-5-nitronicotinaldehyde (1.23 g, 6.21 mmol) in dichloromethane (100 mL) was added bis(2-methoxyethyl)aminosulfur trifluoride (6.86 g, 31.03 mmol) (via syringe over ~1 min). The resulting mixture was allowed to slowly warm to room temperature. After 4 h, the mixture was diluted with dichloromethane (50 mL)/saturated potassium carbonate solution (50 mL) and allowed to stir at room temperature. After 10 min, the phases were separated, and the aqueous phase was extracted with dichloromethane (30 mL). The combined organic phases were dried over magnesium sulfate, filtered, and concentrated to provide 1.28 g (94%) of 5-(difluoromethyl)-2-(methylthio)-3-nitropyridine as a yellow solid.

Example 1-86-5: Preparation of 5-(difluoromethyl)-2-(methylsulfonyl)-3-nitropyridine To a stirred solution of 5-(difluoromethyl)-2-(methylthio)-3-nitropyridine (1.28 g, 5.81 mmol) and dichloromethane (100 mL) was added 3-chloroperoxybenzoic acid (10.42 g, 46.50 mmol). The resulting yellow solution was allowed to stir at room temperature. After 6 h, the cloudy yellow suspension was diluted with saturated sodium thiosulfate solution (50 mL), and the biphasic mixture was allowed to stir at room temperature. After 10 min, the mixture was further diluted with dichloromethane (100 mL) and water (60 mL). The phases were separated, and the organic phase was washed with saturated potassium carbonate solution (2×50 mL). The organic phase was separated and dried over magnesium sulfate, filtered, and concentrated to provide 1.23 g (84%) of 5-(difluoromethyl)-2-(methylsulfonyl)-3-nitropyridine as a yellow solid.

Example 1-86-6: Preparation of 6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine The title compound, also known as RA10940752, was prepared in three steps from (8-methoxy-2-(6-methoxypyridin-3-yl)-2,3-dihydrobenzo[b][1,4]dioxin-6-yl)methanamine (Example 1-52-6) and 5-(difluoromethyl)-2-(methylsulfonyl)-3-nitropyridine as described in Example 1-52-7 through Example 1-52-9: $^1$H NMR (400 MHz, CDCl$_3$) δ 8.60 (s, 1H), 8.24 (s, 1H), 8.20 (d, J=2.5 Hz, 1H), 8.14 (s, 1H), 7.61 (dd, J=8.6, 2.4 Hz, 1H), 7.03-6.71 (m, 2H), 6.56-6.52 (m, 2H), 5.39 (s, 2H), 5.09 (dd, J=8.5, 2.5 Hz, 1H), 4.31 (dd, J=11.6, 2.5 Hz, 1H), 4.07 (dd, J=11.6, 8.5 Hz, 1H), 3.94 (s, 3H), 3.81 (s, 3H) ppm; (M+1)=455.

Example 1-86-7: Chiral separation of 6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine The racemic 6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine was subjected to SFC preparative purification (30×250 mm IA column, 45% ethanol/0.1% diethylamine modifier, 60 g/min flow rate) to afford the individual enantiomers.

Example 1-87: Synthesis of 6-methoxy-3-((8-methoxy-2-(6-methoxypyridin-3-yl)-2,3-dihydrobenzo[b][1,4]dioxin-6-yl)methyl)-2-methyl-3H-imidazo[4,5-b]pyridine

Example 1-87-1: Preparation of 5-methoxy-N$^2$-((8-methoxy-2-(6-methoxypyridin-3-yl)-2,3-dihydrobenzo[b][1,4]dioxin-6-yl)methyl)pyridine-2,3-diamine The title compound was prepared in two steps from (8-methoxy-2-(6-methoxypyridin-3-yl)-2,3-dihydrobenzo[b][1,4]dioxin-6-yl)methanamine (Example 1-52-6) and 2-chloro-5-methoxy-3-nitropyridine as described in Example 1-52-7 through Example 1-52-8 (note: displacement reaction described in Example 1-52-7 was conducted in refluxing 1-butanol instead of acetonitrile).

Example 1-87-2: Preparation of 6-methoxy-3-((8-methoxy-2-(6-methoxypyridin-3-yl)-2,3-dihydrobenzo[b][1,4]dioxin-6-yl)methyl)-2-methyl-3H-imidazo[4,5-b]pyridine The title compound was prepared from 5-methoxy-N$^2$-((8-methoxy-2-(6-methoxypyridin-3-yl)-2,3-dihydrobenzo[b][1,4]dioxin-6-yl)methyl)pyridine-2,3-diamine and triethyl orthoacetate as described in Example 1-52-9: $^1$H NMR (400 MHz, CDCl$_3$) δ 8.19 (d, J=2.5 Hz, 1H), 8.11 (d, J=2.6 Hz, 1H), 7.60 (dd, J=8.6, 2.5 Hz, 1H), 7.50 (d, J=2.6 Hz, 1H), 6.77 (d, J=8.6 Hz, 1H), 6.44 (d, J=1.9 Hz, 1H), 6.34 (d, J=1.9 Hz, 1H), 5.33 (s, 2H), 5.07 (dd, J=8.4, 2.4 Hz, 1H), 4.27 (dd, J=11.6, 2.4 Hz, 1H), 4.04 (dd, J=11.6, 8.4 Hz, 1H), 3.93 (s, 3H), 3.90 (s, 3H), 3.76 (s, 3H), 2.56 (s, 3H) ppm; (M+1)=455.

Example 1-88: Synthesis of 6-(azetidin-3-yl)-3-((8-methoxy-2-(6-methoxypyridin-3-yl)-2,3-dihydrobenzo[b][1,4]dioxin-6-yl)methyl)-3H-imidazo[4,5-b]pyridine 2,2,2-trifluoroacetate

Example 1-88-1: Preparation of (3-((8-methoxy-2-(6-methoxypyridin-3-yl)-2,3-dihydrobenzo[b][1,4]dioxin-6-yl)methyl)-3H-imidazo[4,5-b]pyridin-6-yl)boronic acid The title compound was prepared from 6-iodo-3-((8-methoxy-2-(6-methoxypyridin-3-yl)-2,3-dihydrobenzo[b][1,4]dioxin-6-yl)methyl)-3H-imidazo[4,5-b]pyridine (Example 1-52-9) and bis(pinacolato)diboron as described in Example 1-24-2 (isolated as ~1:1 mixture of boronic acid and corresponding pinacol ester).

Example 1-88-2: Preparation of 6-(azetidin-3-yl)-3-((8-methoxy-2-(6-methoxypyridin-3-yl)-2,3-dihydrobenzo[b][1,4]dioxin-6-yl)methyl)-3H-imidazo[4,5-b]pyridine 2,2,2-trifluoroacetate The title compound was prepared from (3-((8-methoxy-2-(6-methoxypyridin-3-yl)-2,3-dihydrobenzo[b][1,4]dioxin-6-yl)methyl)-3H-imidazo[4,5-b]pyridin-6-yl)boronic acid and tert-butyl 3-(2-tosylhydrazono)azetidine-1-carboxylate as described in Example 1-21-8. The product of this reaction was de-protected with trifluoroacetic acid as described in Example 1-12-5: $^1$H NMR (400 MHz, CD$_3$OD) δ 8.59 (s, 1H), 8.46 (d, J=2.0 Hz, 1H), 8.23-8.19 (m, 2H), 7.73 (dd, J=8.6, 2.5 Hz, 1H), 6.83 (d, J=8.6 Hz, 1H), 6.72 (d, J=2.0 Hz, 1H), 6.55 (d, J=2.0 Hz, 1H), 5.45 (s, 2H), 5.11 (dd, J=8.1, 2.4 Hz, 1H), 4.51-4.40 (m, 2H), 4.40-4.28 (m, 4H), 4.15-4.00 (m, 1H), 3.91 (s, 3H), 3.79 (s, 3H) ppm; (M+1)=460.

Example 1-89: Synthesis of 5,6-dimethoxy-1-((8-methoxy-2-(6-methoxypyridin-3-yl)-2,3-dihydrobenzo[b][1,4]dioxin-6-yl)methyl)-1H-benzo[d]imidazole To a stirred solution of (8-methoxy-2-(6-methoxypyridin-3-yl)-2,3-dihydrobenzo[b][1,4]dioxin-6-yl)methanol (0.028 g, 0.092 mmol, Example 1-52-4) in toluene (3 mL) was added 5,6-dimethoxy-1H-benzo[d]imidazole (0.019 g, 0.10 mmol). The mixture was treated with cyanomethylenetributylphosphorane (0.047 g, 0.18 mol). The resulting mixture was allowed to stir at room temperature. After 1.5 h, the mixture was warmed to 75° C. After 1 h of heating, the mixture was allowed to cool to room temperature and was quenched by the addition of 2 drops of saturated sodium bicarbonate solution. The mixture was then concentrated. Chromatographic purification of the crude product (Biotage, 12 g silica gel column, 0-10% methanol/ethyl acetate elute) afforded a partially purified product. This material was triturated with 2% diethyl ether in heptane (×2). The solid was then dissolved in 10% methanol in dichloromethane, and the solution was filtered and concentrated to provide 0.021 g (49%) of 5,6-dimethoxy-1-((8-methoxy-2-(6-methoxypyridin-3-yl)-2,3-dihydrobenzo[b][1,4]dioxin-6-yl)methyl)-1H-benzo[d]imidazole as a white solid: $^1$H NMR (400 MHz, CDCl$_3$) δ 8.22-8.20 (m, 1H), 7.82 (s, 1H), 7.62 (dd, J=8.6, 2.5 Hz, 1H), 7.30 (s, 1H), 6.78 (dd, J=8.6, 0.7 Hz, 1H), 6.76 (s, 1H), 6.44 (d, J=2.0 Hz, 1H), 6.34 (d, J=2.0 Hz, 1H), 5.21 (s, 2H), 5.10 (dd, J=8.4, 2.4 Hz, 1H), 4.31 (dd, J=11.6, 2.4 Hz, 1H), 4.08 (dd, J=11.6, 8.4 Hz, 1H), 3.94 (s, 3H), 3.94 (s, 3H), 3.89 (s, 3H), 3.77 (s, 3H) ppm; (M+1)=464.

Example 1-90: Synthesis of 6-(1H-imidazol-2-yl)-3-((8-methoxy-2-(6-methoxypyridin-3-yl)-2,3-dihydrobenzo[b][1,4]dioxin-6-yl)methyl)-3H-imidazo[4,5-b]pyridine formate

Example 1-90-1: Preparation of 3-((8-methoxy-2-(6-methoxypyridin-3-yl)-2,3-dihydrobenzo[b][1,4]dioxin-6-yl)methyl)-3H-imidazo[4,5-b]pyridine-6-carbaldehyde The title compound was prepared from (3-((8-methoxy-2-(6-methoxypyridin-3-yl)-2,3-dihydrobenzo[b][1,4]dioxin-6-yl)methyl)-3H-imidazo[4,5-b]pyridin-6-yl)methanol (Example 1-84) as described in Example 1-86-3.

Example 1-90-2: Preparation of 6-(1H-imidazol-2-yl)-3-((8-methoxy-2-(6-methoxypyridin-3-yl)-2,3-dihydrobenzo[b][1,4]dioxin-6-yl)methyl)-3H-imidazo[4,5-b]pyridine formate To a stirred suspension of 3-((8-methoxy-2-(6-methoxypyridin-3-yl)-2,3-dihydrobenzo[b][1,4]dioxin-6-yl)methyl)-3H-imidazo[4,5-b]pyridine-6-carbaldehyde (0.040 g, 0.093 mmol) in 1-methyl-2-pyrrolidinone (2 mL) was added ammonium acetate (0.072 g, 0.93 mmol), and 40% glyoxal solution in water (0.053 mL, 0.46 mmol). The mixture heated to 120° C. in a sealed vessel. After 16 h, the dark red mixture was allowed to cool to room temperature. Chromatographic purification of the crude reaction mixture (Biotage, 50 g C18 column, 0-60% water/methanol/0.1% formic acid elute) provided 0.008 g (14%) of 6-(1H-imidazol-2-yl)-3-((8-methoxy-2-(6-methoxypyridin-3-yl)-2,3-dihydrobenzo[b][1,4]dioxin-6-yl)methyl)-3H-imidazo[4,5-b]pyridine formate as a white solid: $^1$H NMR (400 MHz, CD$_3$OD) δ 8.99 (d, J=1.8 Hz, 1H), 8.55-8.47 (m, 2H), 8.19 (d, J=2.4 Hz, 1H), 7.72 (dd, J=8.6, 2.5 Hz, 1H), 7.24-7.22 (m, 2H), 6.81 (d, J=8.6 Hz, 1H), 6.74 (d, J=1.9 Hz, 1H), 6.60 (d, J=1.9 Hz, 1H), 5.45 (s, 2H), 5.10 (dd, J=8.3, 2.4 Hz, 1H), 4.33 (dd, J=11.6, 2.4 Hz, 1H), 4.05 (dd, J=11.6, 8.3 Hz, 1H), 3.90 (s, 3H), 3.79 (s, 3H) ppm; (M+1)=471.

Example 1-91: Synthesis of 3-((8-methoxy-2-(6-methoxypyridin-3-yl)-2,3-dihydrobenzo[b][1,4]dioxin-6-yl)methyl)-6-(4-methyl-1H-imidazol-2-yl)-3H-imidazo[4,5-b]pyridine The title compound was prepared from 3-((8-methoxy-2-(6-methoxypyridin-3-yl)-2,3-dihydrobenzo[b][1,4]dioxin-6-yl)methyl)-3H-imidazo[4,5-b]pyridine-6-carbaldehyde (Example 1-90-1) and 2-oxopropanal as described in Example 1-90-2: $^1$H NMR (400 MHz, CDCl$_3$)δ 9.08 (d, J=1.7 Hz, 1H), 8.55-8.50 (m, 1H), 8.18 (d, J=2.5 Hz, 1H), 8.03 (s, 1H), 7.59 (dd, J=8.6, 2.5 Hz, 1H), 6.87 (s, 1H), 6.80-6.72 (m, 1H), 6.61-6.51 (m, 2H), 5.34 (s, 2H), 5.06 (dd, J=8.4, 2.5 Hz, 1H), 4.28 (dd, J=11.6, 2.5 Hz, 1H), 4.04 (dd, J=11.6, 8.4 Hz, 1H), 3.93 (s, 3H), 3.78 (s, 3H), 2.30 (s, 3H) ppm; (M+1)=485.

Example 1-92: Synthesis of 3-((8-methoxy-2-(6-methoxypyridin-3-yl)-3-methyl-2,3-dihydrobenzo[b][1,4]dioxin-6-yl)methyl)-3H-imidazo[4,5-b]pyridine

Example 1-92-1: Preparation of methyl 4-hydroxy-3-((1-hydroxy-1-(6-methoxypyridin-3-yl)propan-2-yl)oxy)-5-methoxybenzoate The title compound was prepared in two steps from methyl 4-(benzyloxy)-3-hydroxy-5-methoxybenzoate and 2-bromo-1-(6-methoxypyridin-3-yl)propan-1-one as described in Example 1-52-1 through Example 1-52-2.

Example 1-92-2: Preparation of methyl 8-methoxy-2-(6-methoxypyridin-3-yl)-3-methyl-2,3-dihydrobenzo[b][1,4]dioxine-6-carboxylate To a stirred and cooled (0° C.) solution of 4-hydroxy-3-((1-hydroxy-1-(6-methoxypyridin-3-yl)propan-2-yl)oxy)-5-methoxybenzoate (9.11 g, 25.07 mmol) and triphenylphosphine (9.30 g, 35.10 mmol) in tetrahydrofuran (100 mL) was added a solution of bis(2-methoxyethyl)azodicarboxylate (8.56 g, 35.10 mmol) in tetrahydrofuran (30 mL) over 5 min. After 1 h, the mixture was concentrated. Chromatographic purification of the crude product (Combiflash, 330 g silica gel column, 5-50% ethyl acetate/heptane elute) provided 3.68 g (43%) of methyl 8-methoxy-2-(6-methoxypyridin-3-yl)-3-methyl-2,3-dihydrobenzo[b][1,4]dioxine-6-carboxylate as a white solid.

Example 1-92-3: Preparation of (8-methoxy-2-(6-methoxypyridin-3-yl)-3-methyl-2,3-dihydrobenzo[b][1,4]dioxin-6-yl)methanamine The title compound was prepared in three steps from methyl 8-methoxy-2-(6-methoxypyridin-3-yl)-3-methyl-2,3-dihydrobenzo[b][1,4]dioxine-6-carboxylate as described in Example 1-52-4 through Example 1-52-6.

Example 1-92-4: Preparation of 3-((8-methoxy-2-(6-methoxypyridin-3-yl)-3-methyl-2,3-dihydrobenzo[b][1,4]dioxin-6-yl)methyl)-3H-imidazo[4,5-b]pyridine The title compound was prepared in three steps from (8-methoxy-2-(6-methoxypyridin-3-yl)-3-methyl-2,3-dihydrobenzo[b][1,4]dioxin-6-yl)methanamine and 2-chloro-3-nitropyridine as described in Example 1-52-7 through Example 1-52-9: $^1$H NMR (400 MHz, CDCl3) δ 8.48-8.42 (m, 1H), 8.19-8.02 (m, 3H), 7.60-7.50 (m, 1H), 7.31-7.23 (m, 1H), 6.78 (d, J=8.7 Hz, 0.4H), 6.72 (d, J=8.7 Hz, 0.6H), 6.58-6.52 (m, 2H), 5.39 (d, J=2.5 Hz, 2H), 5.15 (d, J=2.6 Hz, 1H), 4.62 (d, J=7.8 Hz, 0.4H), 4.51-4.43 (m, 0.6H), 4.16-4.07 (m, 1H), 3.96-3.90 (m, 3H), 3.81-3.77 (m, 3H), 1.19-1.12 (m, 3H) ppm (as a mixture of diastereomers); (M+1)=419.

Example 1-92-5: Chiral separation of 3-((8-methoxy-2-(6-methoxypyridin-3-yl)-3-methyl-2,3-dihydrobenzo[b][1,4]dioxin-6-yl)methyl)-3H-imidazo[4,5-b]pyridine The title compound was separated into its individual diastereomers by chiral chromatography.
Separation #1
  Column: Whelk-O1 21×250 mm
  Mobile phase: 50% ethanol in $CO_2$, 0.1% diethylamine, 70 mL/min
  This operation afforded diastereomer A (peak 1) and diastereomer B (peak 4) as pure fractions (absolute configurations unknown) and a mixture of the two remaining diastereomers (peaks 2 and 3).
Diastereomer A: $^1$H NMR (400 MHz, CDCl$_3$) δ 8.45 (dd, J=4.8, 1.5 Hz, 1H), 8.13 (d, J=2.4 Hz, 1H), 8.10 (dd, J=8.1, 1.5 Hz, 1H), 8.07 (s, 1H), 7.55 (dd, J=8.6, 2.4 Hz, 1H), 7.30-7.27 (m, 1H), 6.72 (d, J=8.6 Hz, 1H), 6.55 (d, J=2.0 Hz, 1H), 6.53 (d, J=2.0 Hz, 1H), 5.39 (s, 2H), 5.15 (d, J=2.7 Hz, 1H), 4.47 (qd, J=6.6, 2.7 Hz, 1H), 3.92 (s, 3H), 3.80 (s, 3H), 1.14 (d, J=6.6 Hz, 3H) ppm.
Diastereomer B, also known as RA10947016: $^1$H NMR (400 MHz, CDCl$_3$) δ 8.45 (dd, J=4.8, 1.5 Hz, 1H), 8.16 (d, J=2.5 Hz, 1H), 8.09 (dd, J=8.0, 1.5 Hz, 1H), 8.04 (s, 1H), 7.56 (dd, J=8.6, 2.5 Hz, 1H), 7.29-7.26 (m, 1H), 6.78 (d, J=8.6 Hz, 1H), 6.54-6.52 (m, 2H), 5.38 (s, 2H), 4.62 (d, J=7.8 Hz, 1H), 4.11 (dq, J=7.8, 6.3 Hz, 1H), 3.94 (s, 3H), 3.79 (s, 3H), 1.17 (d, J=6.3 Hz, 3H) ppm.

The remaining mixture of diastereomers (peaks 2 and 3) from the first separation were subjected to a second chromatography:
Separation #2
  Column: AD-H 21×250 mm
  Mobile phase: 25% methanol in $CO_2$, 0.5% diethylamine 45 mL/min
  This operation afforded diastereomer C (peak 1) and diastereomer D (peak 2) as pure fractions (absolute configurations unknown)
Diastereomer C: $^1$H NMR (400 MHz, CDCl$_3$) δ 8.45 (dd, J=4.8, 1.5 Hz, 1H), 8.13 (d, J=2.4 Hz, 1H), 8.10 (dd, J=8.1, 1.5 Hz, 1H), 8.07 (s, 1H), 7.55 (dd, J=8.6, 2.4 Hz, 1H), 7.30-7.26 (m, 1H), 6.72 (d, J=8.6 Hz, 1H), 6.55 (d, J=2.0 Hz, 1H), 6.53 (d, J=2.0 Hz, 1H), 5.39 (s, 2H), 5.15 (d, J=2.7 Hz, 1H), 4.47 (qd, J=6.6, 2.7 Hz, 1H), 3.92 (s, 3H), 3.80 (s, 3H), 1.14 (d, J=6.6 Hz, 3H) ppm.
Diastereomer D: $^1$H NMR (400 MHz, CDCl$_3$) δ 8.45 (dd, J=4.8, 1.5 Hz, 1H), 8.16 (d, J=2.4 Hz, 1H), 8.10 (dd, J=8.1, 1.5 Hz, 1H), 8.05 (s, 1H), 7.56 (dd, J=8.7, 2.4 Hz, 1H), 7.29-7.26 (m, 1H), 6.78 (d, J=8.6 Hz, 1H), 6.54-6.52 (m, 2H), 5.38 (s, 2H), 4.62 (d, J=7.8 Hz, 1H), 4.11 (dq, J=7.8, 6.3 Hz, 1H), 3.94 (s, 3H), 3.79 (s, 3H), 1.17 (d, J=6.3 Hz, 3H) ppm.

Example 1-93: Synthesis of 6-methoxy-3-((8-methoxy-2-(6-methoxypyridin-3-yl)-3-methyl-2,3-dihydrobenzo[b][1,4]dioxin-6-yl)methyl)-3H-imidazo[4,5-b]pyridine Example 1-93-1: Preparation of 6-iodo-3-((8-methoxy-2-(6-methoxypyridin-3-yl)-3-methyl-2,3-dihydrobenzo[b][1,4]dioxin-6-yl)methyl)-3H-imidazo[4,5-b]pyridine The title compound was prepared in three steps from (8-methoxy-2-(6-methoxypyridin-3-yl)-3-methyl-2,3-dihydrobenzo[b][1,4]dioxin-6-yl)methanamine (Example 1-92-3) and 2-chloro-5-iodo-3-nitropyridine as described in Example 1-52-7 through Example 1-52-9.

Example 1-93-2: Preparation of 6-methoxy-3-((8-methoxy-2-(6-methoxypyridin-3-yl)-3-methyl-2,3-dihydrobenzo[b][1,4]dioxin-6-yl)methyl)-3H-imidazo[4,5-b]pyridine The title compound was prepared from 6-iodo-3-((8-methoxy-2-(6-methoxypyridin-3-yl)-3-methyl-2,3-dihydrobenzo[b][1,4]dioxin-6-yl)methyl)-3H-imidazo[4,5-b]pyridine and methanol as described in Example 1-11: $^1$H NMR (400 MHz, CDCl$_3$) δ 8.23-8.20 (m, 1H), 8.17-8.11 (m, 1H), 8.00-7.96 (m, 1H), 7.62-7.52 (m, 2H), 6.80-6.75 (m, 1H), 6.54-6.49 (m, 2H), 5.34-5.32 (m, 2H), 5.16-5.14 (m, 0.3H, cis-diastereomers), 4.61 (d, J=7.8 Hz, 1H, trans-diastereomers), 4.50-4.43 (m, 0.3H, cis-diastereomers), 4.15-4.07 (m, 1H), 3.96-3.89 (m, 6H), 3.81-3.76 (m, 3H), 1.18-1.12 (m, 3H) ppm (as a mixture of diastereomers); (M+1)=449.

Example 1-93-3: Chiral separation of 6-methoxy-3-((8-methoxy-2-(6-methoxypyridin-3-yl)-3-methyl-2,3-dihydrobenzo[b][1,4]dioxin-6-yl)methyl)-3H-imidazo[4,5-b]pyridine The title compound was separated into its individual diastereomers by chiral chromatography.

Separation #1
 Column: Whelk-O1 21×250 mm
 Mobile phase: 60% Ethanol in $CO_2$, 0.1% diethylamine, 55 mL/min This operation afforded diastereomer A (peak 1) and diastereomer B (peak 4) as pure fractions (absolute configurations unknown) and a mixture of the two remaining diastereomers (peaks 2 and 3).

Diastereomer A: $^1$H NMR (400 MHz, $CDCl_3$) δ 8.22 (d, J=2.6 Hz, 1H), 8.14-8.12 (m, 1H), 8.00 (s, 1H), 7.60 (d, J=2.6 Hz, 1H), 7.54 (dd, J=8.7, 2.5 Hz, 1H), 6.72 (dd, J=8.7, 0.7 Hz, 1H), 6.53 (d, J=2.0 Hz, 1H), 6.51 (d, J=2.0 Hz, 1H), 5.34 (s, 2H), 5.15 (d, J=2.6 Hz, 1H), 4.47 (qd, J=6.6, 2.6 Hz, 1H), 3.92 (s, 3H), 3.91 (s, 3H), 3.80 (s, 3H), 1.14 (d, J=6.6 Hz, 3H) ppm.

Diastereomer B: $^1$H NMR (400 MHz, $CDCl_3$) δ 8.21 (d, J=2.6 Hz, 1H), 8.16 (d, J=2.4 Hz, 1H), 7.98 (s, 1H), 7.59 (d, J=2.6 Hz, 1H), 7.56 (dd, J=8.6, 2.4 Hz, 1H), 6.78 (dd, J=8.6, 0.7 Hz, 1H), 6.53-6.51 (m, 2H), 5.33 (s, 2H), 4.61 (d, J=7.8 Hz, 1H), 4.11 (dq, J=7.8, 6.5 Hz, 1H), 3.94 (s, 3H), 3.91 (s, 3H), 3.79 (s, 3H), 1.17 (d, J=6.5 Hz, 3H) ppm.

The remaining mixture of diastereomers (peaks 2 and 3) from the first separation were subjected to a second chromatography:

Separation #2
 Column: AD-H 21×250 mm
 Mobile phase: 25% methanol in $CO_2$, 0.5% diethylamine 45 mL/min This operation afforded diastereomer C (peak 1) and diastereomer D (peak 2) as pure fractions (absolute configurations unknown):

Diastereomer C: $^1$H NMR (400 MHz, $CDCl_3$) δ 8.22 (d, J=2.6 Hz, 1H), 8.14-8.12 (m, 1H), 8.00 (s, 1H), 7.60 (d, J=2.6 Hz, 1H), 7.54 (dd, J=8.7, 2.5 Hz, 1H), 6.72 (dd, J=8.7, 0.7 Hz, 1H), 6.53 (d, J=2.0 Hz, 1H), 6.51 (d, J=2.0 Hz, 1H), 5.34 (s, 2H), 5.15 (d, J=2.6 Hz, 1H), 4.47 (qd, J=6.6, 2.6 Hz, 1H), 3.92 (s, 3H), 3.91 (s, 3H), 3.80 (s, 3H), 1.14 (d, J=6.6 Hz, 3H) ppm.

Diastereomer D: $^1$H NMR (400 MHz, $CDCl_3$) δ 8.21 (d, J=2.6 Hz, 1H), 8.16 (d, J=2.4 Hz, 1H), 7.98 (s, 1H), 7.59 (d, J=2.6 Hz, 1H), 7.56 (dd, J=8.6, 2.4 Hz, 1H), 6.78 (dd, J=8.6, 0.7 Hz, 1H), 6.53-6.51 (m, 2H), 5.33 (s, 2H), 4.61 (d, J=7.8 Hz, 1H), 4.11 (dq, J=7.8, 6.5 Hz, 1H), 3.94 (s, 3H), 3.91 (s, 3H), 3.79 (s, 3H), 1.17 (d, J=6.5 Hz, 3H) ppm.

Example 1-94: Synthesis of 4-(3-((8-methoxy-2-(6-methoxypyridin-3-yl)-2-methyl-2,3-dihydrobenzo[b][1,4]dioxin-6-yl)methyl)-3H-imidazo[4,5-b]pyridin-6-yl)-2-methylbut-3-yn-2-amine

Example 1-94-1: Preparation of methyl 4-(benzyloxy)-3-(2-hydroxy-2-(6-methoxypyridin-3-yl)propoxy)-5-methoxybenzoate To a stirred and cooled (−78° C.) solution of methyl 4-(benzyloxy)-3-methoxy-5-(2-(6-methoxypyridin-3-yl)-2-oxoethoxy)benzoate (0.31 g, 0.70 mmol, Example 1-52-1) in tetrahydrofuran (5 mL) was added 3.0M methylmagnesium bromide solution in diethyl ether (0.29 mL, 0.87 mmol). The mixture was allowed to stir at −78° C. After 20 min, an additional portion of 3.0M methylmagnesium bromide solution in diethyl ether (0.10 mL, 0.30 mmol) was added to the mixture. After 55 min, the cold mixture was quenched by the addition of saturated ammonium chloride solution (5 mL). The mixture was allowed to warm to room temperature and was further diluted with water (5 mL). The mixture was extracted with ethyl acetate (×2). The combined organic phases were dried over magnesium sulfate, filtered, and concentrated. Chromatographic purification of the crude product (Biotage, 12 g silica gel column, ethyl acetate/heptane elute) provided an impure product (contaminated with starting ketone). This material was used in the subsequent reaction.

Example 1-94-2: Preparation of methyl 4-hydroxy-3-(2-hydroxy-2-(6-methoxypyridin-3-yl)propoxy)-5-methoxybenzoate To a stirred solution of impure methyl 4-(benzyloxy)-3-(2-hydroxy-2-(6-methoxypyridin-3-yl)propoxy)-5-methoxybenzoate (0.57 g, 0.75 mmol) in methanol (30 mL) was added 10% palladium on carbon (wet) (0.33 g, 0.31 mmol). The mixture was degassed under vacuum/backfilled with nitrogen (×3). After a final evacuation, the atmosphere was replaced with hydrogen via a balloon. The reaction mixture was allowed to stir at room temperature. After 1 h, the vessel was evacuated, and the atmosphere replaced with nitrogen. The mixture was filtered through Celite with the aid of methanol and dichloromethane. The filtrate was concentrated to provide 0.55 g of methyl 4-hydroxy-3-(2-hydroxy-2-(6-methoxypyridin-3-yl)propoxy)-5-methoxybenzoate (~33% pure) as an oil.

Example 1-94-3: Preparation of (8-methoxy-2-(6-methoxypyridin-3-yl)-2-methyl-2,3-dihydrobenzo[b][1,4]dioxin-6-yl)methanamine The title compound was prepared in four steps from methyl 4-hydroxy-3-(2-hydroxy-2-(6-methoxypyridin-3-yl)propoxy)-5-methoxybenzoate as described in Example 1-52-3 through Example 1-52-6.

Example 1-94-4: Preparation of 6-iodo-3-((8-methoxy-2-(6-methoxypyridin-3-yl)-2-methyl-2,3-dihydrobenzo[b][1,4]dioxin-6-yl)methyl)-3H-imidazo[4,5-b]pyridine The title compound was prepared in three steps from (8-methoxy-2-(6-methoxypyridin-3-yl)-2-methyl-2,3-dihydrobenzo [b][1,4]dioxin-6-yl)methanamine and 2-chloro-5-iodo-3-nitropyridine as described in Example 1-52-7 through Example 1-57-9.

Example 1-94-5: Preparation of 4-(3-((8-methoxy-2-(6-methoxypyridin-3-yl)-2-methyl-2,3-dihydrobenzo[b][1,4]dioxin-6-yl)methyl)-3H-imidazo[4,5-b]pyridin-6-yl)-2-methylbut-3-yn-2-amine The title compound was prepared from 6-iodo-3-((8-methoxy-2-(6-methoxypyridin-3-yl)-2-methyl-2,3-dihydrobenzo[b][1,4]dioxin-6-yl)methyl)-3H-imidazo[4,5-b]pyridine and 2-methylbut-3-yn-2-amine as described in Example 1-5-8.

Example 1-94-6: Chiral separation of 4-(3-((8-methoxy-2-(6-methoxypyridin-3-yl)-2-methyl-2,3-dihydrobenzo[b][1,4]dioxin-6-yl)methyl)-3H-imidazo[4,5-b]pyridin-6-yl)-2-methylbut-3-yn-2-amine $^1$H NMR (400 MHz, $CDCl_3$) δ 8.44 (d, J=1.7 Hz, 1H), 8.22 (dd, J=2.6, 0.8 Hz, 1H), 8.07 (d, J=1.7 Hz, 1H), 8.01 (d, J=6.7 Hz, 1H), 7.62 (dd, J=8.7, 2.6 Hz, 1H), 6.71 (dd, J=8.7, 0.8 Hz, 1H), 6.50 (d, J=2.0 Hz, 1H), 6.41 (d, J=2.0 Hz, 1H), 5.30 (s, 2H), 4.32 (d, J=11.5 Hz, 1H), 4.05 (d, J=11.5 Hz, 1H), 3.90 (s, 3H), 3.83 (s, 3H), 1.64 (s, 3H), 1.53 (s, 6H) ppm; (M+1)=500.

Example 1-95: Synthesis of 7-((8-methoxy-2-(6-methoxypyridin-3-yl)-2,3-dihydrobenzo[b][1,4]dioxin-6-yl)methyl)-7H-imidazo[4,5-c]pyridazine

Example 1-95-1: Preparation of (E/Z)-N-((8-methoxy-2-(6-methoxypyridin-3-yl)-2,3-dihydrobenzo[b][1,4]dioxin-6-yl)methyl)-1-(methylthio)-2-nitroethen-1-amine To a stirred solution of (8-methoxy-2-(6-methoxypyridin-3-yl)-2,3-dihydrobenzo[b][1,4]dioxin-6-yl)methanamine (0.73 g, 2.42 mmol, Example 1-52-6) in ethanol (40 mL) was added 1,1-bis(methylthio)-2-nitroethylene (0.63 g, 3.63 mmol). The light brown solution was heated to reflux and stirred. After 19 h, the mixture was allowed to cool to room temperature, resulting in a precipitate. The mixture was filtered, and the filter cake was washed with ethanol (10 mL) and dried to provide 0.83 g (82%) of (E/Z)-N-((8-methoxy-2-(6-methoxypyridin-3-yl)-2,3-dihydrobenzo[b][1,4]dioxin-6-yl)methyl)-1-(methylthio)-2-nitroethenamine as a tan solid.

Example 1-95-2: Preparation of (E/Z)-N-((8-methoxy-2-(6-methoxypyridin-3-yl)-2,3-dihydrobenzo[b][1,4]dioxin-6-yl)methyl)-2-nitroacetohydrazonamide To a stirred suspension of (E/Z)-N-((8-methoxy-2-(6-methoxypyridin-3-yl)-2,3-dihydrobenzo[b][1,4]dioxin-6-yl)methyl)-1-(methylthio)-2-nitroethenamine (0.83 g, 1.98 mmol) in ethanol (15 mL) was added hydrazine hydrate (0.39 g, 7.92 mmol). The mixture was heated to reflux. After 2.5 h, the tan suspension was allowed to cool to room temperature and was filtered. The filter cake was washed with a small amount of ethanol (15 mL) and dried to provide 0.62 g (78%) of (E/Z)-N-((8-methoxy-2-(6-methoxypyridin-3-yl)-2,3-dihydrobenzo[b][1,4]dioxin-6-yl)methyl)-2-nitroacetohydrazonamide as a tan solid.

Example 1-95-3: Preparation of N-((8-methoxy-2-(6-methoxypyridin-3-yl)-2,3-dihydrobenzo[b][1,4]dioxin-6-yl)methyl)-4-nitropyridazin-3-amine To a stirred solution of 40% glyoxal in water (0.22 g, 1.53 mmol) and sodium carbonate (0.20 g, 1.84 mmol) in 2:1:1 water/ethanol/tetrahydrofuran (40 mL) was added (E/Z)-N-((8-methoxy-2-(6-methoxypyridin-3-yl)-2,3-dihydrobenzo[b][1,4]dioxin-6-yl)methyl)-2-nitroacetohydrazonamide (0.62 g, 1.53 mmol) in portions over ~3 min. The resulting yellow mixture was allowed to stir at room temperature. After 17 h, the mixture was concentrated to remove the organic solvent. The residue was diluted with water (20 mL) and was extracted with ethyl acetate (3×20 mL). The combined organic phases were dried over magnesium sulfate, filtered, and concentrated. Chromatographic purification of the crude product (CombiFlash, 40 g silica gel gold column, 30-75% ethyl acetate/heptane elute) afforded 0.39 g (59%) of N-((8-methoxy-2-(6-methoxypyridin-3-yl)-2,3-dihydrobenzo[b][1,4]dioxin-6-yl)methyl)-4-nitropyridazin-3-amine as an orange solid.

Example 1-95-4: Preparation of $N^3$-((8-methoxy-2-(6-methoxypyridin-3-yl)-2,3-dihydrobenzo[b][1,4]dioxin-6-yl)methyl)pyridazine-3,4-diamine The title compound was prepared from N-((8-methoxy-2-(6-methoxypyridin-3-yl)-2,3-dihydrobenzo[b][1,4]dioxin-6-yl)methyl)-4-nitropyridazin-3-amine as described in Example 1-52-8.

Example 1-95-5: Preparation of 7-((8-methoxy-2-(6-methoxypyridin-3-yl)-2,3-dihydrobenzo[b][1,4]dioxin-6-yl)methyl)-7H-imidazo[4,5-c]pyridazine To a stirred solution of $N^3$-((8-methoxy-2-(6-methoxypyridin-3-yl)-2,3-dihydrobenzo[b][1,4]dioxin-6-yl)methyl)pyridazine-3,4-diamine (0.36 g, 0.91 mmol) in N,N-dimethylformamide (5 mL) was added triethyl orthoformate (7.13 g, 47.14 mmol). The mixture was heated to 150° C. After 30 min, the light brown solution was allowed to cool to room temperature and was concentrated. Chromatographic purification of the crude product (CombiFlash, 24 g silica gel gold column, 0-5% methanol/dichloromethane elute) afforded 0.22 g (58%) of 9-((8-methoxy-2-(6-methoxypyridin-3-yl)-2,3-dihydrobenzo[b][1,4]dioxin-6-yl)methyl)-9H-imidazo[4,5-c]pyridazine as a white solid: $^1$H NMR (400 MHz, CDCl$_3$) δ 9.18 (d, J=5.6 Hz, 1H), 8.22-8.20 (m, 2H), 7.86 (d, J=5.6 Hz, 1H), 7.61 (dd, J=8.6, 2.5 Hz, 1H), 6.78 (dd, J=8.6, 0.7 Hz, 1H), 6.65-6.63 (m, 2H), 5.54 (s, 2H), 5.10 (dd, J=8.4, 2.5 Hz, 1H), 4.32 (dd, J=11.6, 2.5 Hz, 1H), 4.08 (dd, J=11.6, 8.4 Hz, 1H), 3.94 (s, 3H), 3.82 (s, 3H) ppm; (M+1)=406.

Example 1-96: Synthesis of 6-bromo-3-((8-methoxy-2-(6-methoxypyridin-3-yl)-2,3-dihydrobenzo[b][1,4]dioxin-6-yl)methyl)pyrazolo[1,5-a]pyrimidine

Example 1-96-1: Preparation of 5-bromo-3-methoxy-2-((4-methoxybenzyl)oxy)benzaldehyde To a stirred solution of 5-bromo-2-hydroxy-3-methoxybenzaldehyde (5.00 g, 21.64 mmol), potassium iodide (0.50 g, 3.01 mmol), and potassium carbonate (4.53 g, 32.46 mmol) in N,N-dimethylformamide (30 mL) was added 4-methoxybenzyl chloride (3.63 g, 22.72 mmol). The mixture was allowed to stir at room temperature. After 3 the mixture was partitioned between water and ethyl acetate. The phases were separated, and the organic phase was washed with water and brine, dried over magnesium sulfate, filtered, and concentrated. The residue was recrystallized from dichloromethane/hexanes to provide 6.20 g (81%) of 5-bromo-3-methoxy-2-((4-methoxybenzyl)oxy)benzaldehyde as a white crystalline solid.

Example 1-96-2: Preparation of 5-(6-bromo-8-methoxy-2,3-dihydrobenzo[b][1,4]dioxin-2-yl)-2-methoxypyridine The title compound was prepared in four steps from 5-bromo-3-methoxy-2-((4-methoxybenzyl)oxy)benzaldehyde and 2-bromo-1-(6-methoxypyridin-3-yl)ethanone as described in Example 1-21-1 through Example 1-21-4.

Example 1-96-3: Preparation of (8-methoxy-2-(6-methoxypyridin-3-yl)-2,3-dihydrobenzo[b][1,4]dioxin-6-yl)boronic acid The title compound was prepared from 5-(6-bromo-8-methoxy-2,3-dihydrobenzo[b][1,4]dioxin-2-yl)-2-methoxypyridine as described in Example 1-21-5.

Example 1-96-4: Preparation of (6-bromopyrazolo[1,5-a]pyrimidin-3-yl)(8-methoxy-2-(6-methoxypyridin-3-yl)-2,3-dihydrobenzo[b][1,4]dioxin-6-yl)methanol The title compound was prepared from (8-methoxy-2-(6-methoxypyridin-3-yl)-2,3-dihydrobenzo[b][1,4]dioxin-6-yl)boronic acid and (E/Z)-N-((6-bromopyrazolo[1,5-a]pyrimidin-3-yl)methylene)-4-methylbenzenesulfonohydrazide (Example 1-21-7) as described in Example 1-21-8.

Example 1-96-5: Preparation of 6-bromo-3-((8-methoxy-2-(6-methoxypyridin-3-yl)-2,3-dihydrobenzo[b][1,4]dioxin-6-yl)methyl)pyrazolo[1,5-a]pyrimidine The title compound was prepared from (6-bromopyrazolo[1,5-a]pyrimidin-3-yl)(8-methoxy-2-(6-methoxypyridin-3-yl)-2,3-dihydrobenzo[b][1,4]dioxin-6-yl)methanol as described in Example 1-22-2: $^1$H NMR (400 MHz, CDCl$_3$) δ 8.77 (d, J=2.2 Hz, 1H), 8.43 (d, J=2.2 Hz, 1H), 8.20 (d, J=2.5 Hz, 1H), 7.94 (s, 1H), 7.62 (dd, J=8.6, 2.5 Hz, 1H), 6.77 (d, J=8.6 Hz, 1H), 6.50-6.48 (m, 2H), 5.08 (dd, J=8.3, 2.5 Hz, 1H), 4.28 (dd, J=11.5, 2.5 Hz, 1H), 4.11-4.01 (m, 3H), 3.93 (s, 3H), 3.82 (s, 3H) ppm; (M+1)=483.

Example 1-97: Synthesis of 3-((8-methoxy-2-(6-methoxypyridin-3-yl)-2,3-dihydrobenzo[b][1,4]dioxin-6-yl)methyl)pyrazolo[1,5-a]pyrimidine To a stirred solution of 6-bromo-3-((8-methoxy-2-(6-methoxypyridin-3-yl)-2,3-dihydrobenzo[b][1,4]dioxin-6-yl)methyl)pyrazolo[1,5-a]pyrimidine (0.073 g, 0.15 mmol, Example 1-96-4) in 1,4-dioxane (5 ml) was added triethylamine (0.021 mL, 0.15 mmol), formic acid (0.007 mL, 0.15 mmol) and tetrakis(triphenylphosphine)palladium(0) (0.018 g, 0.015 mmol). The resulting mixture was heated to 100° C. After 16 h, the mixture was allowed to cool to room temperature and was filtered through Celite. The filtrate was partitioned between water and ethyl acetate. The phases were separated, and the aqueous phase was extracted with ethyl acetate. The combined organic phases were washed with brine, dried over magnesium sulfate, filtered, and concentrated. Chromatographic purification of the crude product (CombiFlash, 12 g silica gel column, 0-5% methanol/dichloromethane elute) afforded 0.030 g (49%) of 3-((8-methoxy-2-(6-methoxypyridin-3-yl)-2,3-dihydrobenzo[b][1,4]dioxin-6-yl)methyl)pyrazolo[1,5-a]pyrimidine as an off-white solid: $^1$H NMR (400 MHz, CDCl$_3$) δ 8.63 (dd, J=7.0, 1.8 Hz, 1H), 8.46 (dd, J=4.0, 1.8 Hz, 1H), 8.20 (d, J=2.4 Hz, 1H), 7.97 (s, 1H), 7.62 (dd, J=8.6, 2.5 Hz, 1H), 6.69-6.88 (m, 2H), 6.61-6.47 (m, 2H), 5.08 (dd, J=8.4, 2.3 Hz, 1H), 4.28 (dd, J=11.5, 2.4 Hz, 1H), 4.17-4.01 (m, 3H), 3.93 (s, 3H), 3.82 (s, 3H) ppm; (M+1)=405.

Example 1-98: Synthesis of 3-((8-methoxy-2-(6-methoxypyridin-3-yl)-2,3-dihydrobenzo[b][1,4]dioxin-6-yl)methyl)-6-(3-methoxyazetidin-1-yl)pyrazolo[1,5-a]pyrimidine The title compound was prepared from 6-bromo-3-((8-methoxy-2-(6-methoxypyridin-3-yl)-2,3-dihydrobenzo[b][1,4]dioxin-6-yl)methyl)pyrazolo[1,5-a]pyrimidine (Example 1-96-4) and 3-methoxyazetidine hydrochloride as described in Example 1-10: $^1$H NMR (400 MHz, CDCl$_3$) 8.20 (d, J=2.4 Hz, 1H), 8.07 (d, J=2.6 Hz, 1H), 7.84-7.73 (m, 2H), 7.62 (dd, J=8.6, 2.4 Hz, 1H), 6.82-6.71 (m, 1H), 6.62-6.45 (m, 2H), 5.08 (dd, J=8.4, 2.2 Hz, 1H), 4.46-4.34 (m, 1H), 4.32-4.23 (m, 1H), 4.22-3.99 (m, 5H), 3.93 (s, 3H), 3.82 (s, 3H), 3.75 (dd, J=8.0, 4.7 Hz, 2H), 3.36 (s, 3H) ppm; (M+1)=490.

Example 1-99: Synthesis of 4-(3-((8-methoxy-2-(6-methoxypyridin-3-yl)-2,3-dihydrobenzo[b][1,4]dioxin-6-yl)methyl)pyrazolo[1,5-a]pyrimidin-6-yl)morpholine The title compound was prepared from 6-bromo-3-((8-methoxy-2-(6-methoxypyridin-3-yl)-2,3-dihydrobenzo[b][1,4]dioxin-6-yl)methyl)pyrazolo[1,5-a]pyrimidine (Example 1-96-4) and morpholine as described in Example 1-10: $^1$H NMR (400 MHz, CDCl$_3$) 8.42 (d, J=2.6 Hz, 1H), 8.20 (d, J=2.4 Hz, 1H), 8.08 (d, J=2.6 Hz, 1H), 7.83 (s, 1H), 7.62 (dd, J=8.6, 2.5 Hz, 1H), 6.76 (d, J=8.6 Hz, 1H), 6.57-6.45 (m, 2H), 5.08 (dd, J=8.3, 2.3 Hz, 1H), 4.27 (dd, J=11.5, 2.4 Hz, 1H), 4.17-4.00 (m, 3H), 3.95-3.88 (m, 6H), 3.83-3.80 (m, 4H), 3.10 (dd, J=5.6, 3.8 Hz, 4H) ppm; (M+1)=490.

Example 1-100: Synthesis of 6-methoxy-3-((8-methoxy-2-(6-methoxypyridin-3-yl)-2,3-dihydrobenzo[b][1,4]dioxin-6-yl)methyl)pyrazolo[1,5-a]pyrimidine To a stirred suspension of 6-bromo-3-((8-methoxy-2-(6-methoxypyridin-3-yl)-2,3-dihydrobenzo[b][1,4]dioxin-6-yl)methyl)pyrazolo[1,5-a]pyrimidine (0.090 g, 0.19 mmol, Example 1-96-4) in toluene (0.5 mL) was added methanol (0.075 mL, 1.86 mmol), cesium carbonate (0.12 g, 0.37 mmol), and [(2-di-tert-butylphosphino-3-methoxy-6-methyl-2',4',6'-triisopropyl-1,1'-biphenyl)-2-(2-aminobiphenyl)]palladium(II) methanesulfonate. The mixture was degassed with nitrogen, and then it was heated at 100° C. in a sealed vessel. After 5 h, the mixture was allowed to cool to room temperature. The mixture was filtered through Celite, and the filtrate was concentrated. Chromatographic purification of the crude product (CombiFlash, 12 g silica gel column, 0-4% methanol/dichloromethane elute) afforded 0.043 g (53%) of 6-methoxy-3-((8-methoxy-2-(6-methoxypyridin-3-yl)-2,3-dihydrobenzo[b][1,4]dioxin-6-yl)methyl)pyrazolo[1,5-a]pyrimidine as an amber oil: $^1$H NMR (400 MHz, CDCl$_3$) δ 8.35 (d, J=2.7 Hz, 1H), 8.20 (d, J=2.4 Hz, 1H), 8.18 (d, J=2.7 Hz, 1H), 7.84 (s, 1H), 7.62 (dd, J=8.7, 2.4 Hz, 1H), 6.77 (d, J=8.7 Hz, 1H), 6.52 (d, J=1.9 Hz, 1H), 6.50 (d, J=1.9 Hz, 1H), 5.08 (dd, J=8.4, 2.4 Hz, 1H), 4.28 (dd, J=11.5, 2.4 Hz, 1H), 4.09-4.02 (m, 3H), 3.93 (s, 3H), 3.87 (s, 3H), 3.82 (s, 3H) ppm: (M+1)=435.

Example 1-101: Synthesis of 3-((8-methoxy-2-(6-methoxypyridin-3-yl)-2,3-dihydrobenzo[b][1,4]dioxin-6-yl)methyl)-6-((1-methylazetidin-3-yl)oxy)pyrazolo[1,5-a]pyrimidine

Example 1-101-1: Preparation of tert-butyl 3-((3-((8-methoxy-2-(6-methoxypyridin-3-yl)-2,3-dihydrobenzo[b][1,4]dioxin-6-yl)methyl)pyrazolo[1,5-a]pyrimidin-6-yl)oxy)azetidine-1-carboxylate The title compound was prepared from 6-bromo-3-((8-methoxy-2-(6-methoxypyridin-3-yl)-2,3-dihydrobenzo[b]

[1,4]dioxin-6-yl)methyl)pyrazolo[1,5-a]pyrimidine (Example 1-96-4) and tert-butyl 3-hydroxyazetidine-1-carboxylate as described in Example 1-100.

Example 1-101-2: Preparation of 3-((8-methoxy-2-(6-methoxypyridin-3-yl)-2,3-dihydrobenzo[b][1,4]dioxin-6-yl)methyl)-6-((1-methylazetidin-3-yl)oxy)pyrazolo[1,5-a]pyrimidine The title compound was prepared from tert-butyl 3-((3-((8-methoxy-2-(6-methoxypyridin-3-yl)-2,3-dihydrobenzo[b][1,4]dioxin-6-yl)methyl)pyrazolo[1,5-a]pyrimidin-6-yl)oxy)azetidine-1-carboxylate as described in Example 1-72-2: $^1$H NMR (400 MHz, CDCl$_3$) δ 8.32 (d, J=2.7 Hz, 1H), 8.20 (d, J=2.5 Hz, 1H), 7.98 (d, J=2.7 Hz, 1H), 7.84 (s, 1H), 7.62 (dd, J=8.6, 2.5 Hz, 1H), 6.76 (d, J=8.6 Hz, 1H), 6.51 (d, J=2.0 Hz, 1H), 6.49 (d, J=2.0 Hz, 1H), 5.08 (dd, J=8.4, 2.5 Hz, 1H), 4.74-4.68 (m, 1H), 4.27 (dd, J=11.5, 2.5 Hz, 1H), 4.09-4.02 (m, 3H), 3.93 (s, 3H), 3.86-3.80 (m, 5H), 3.24-3.17 (m, 2H), 2.43 (s, 3H) ppm; (M+1)=490.

Example 1-102: Synthesis of 7-chloro-3-((8-methoxy-2-(6-methoxypyridin-3-yl)-2,3-dihydrobenzo[b][1,4]dioxin-6-yl)methyl)imidazo[1,2-b]pyridazine Example 1-102-1: Preparation of 8-methoxy-2-(6-methoxypyridin-3-yl)-2,3-dihydrobenzo[b][1,4]dioxine-6-carbaldehyde To a stirred solution of (8-methoxy-2-(6-methoxypyridin-3-yl)-2,3-dihydrobenzo[b][1,4]dioxin-6-yl)methanol (2.30 g, 7.58 mmol, Example 1-52-4) in dichloromethane (50 mL) was added Dess-Martin periodinane (3.46 g, 7.91 mmol). The mixture was allowed to stir at room temperature. After 30 min, the mixture was partitioned between saturated sodium bicarbonate solution and dichloromethane. The phases were separated, and the organic phase was washed with saturated sodium bicarbonate solution (×2), water and brine, dried over magnesium sulfate, filtered, and concentrated. Chromatographic purification of the crude product (CombiFlash, silica gel column, 50% ethyl acetate/hexanes to 100% ethyl acetate elute) afforded 1.85 g (93%) of 8-methoxy-2-(6-methoxypyridin-3-yl)-2,3-dihydrobenzo[b][1,4]dioxine-6-carbaldehyde as a white solid.

Example 1-102-2: Preparation of 7-chloro-3-((8-methoxy-2-(6-methoxypyridin-3-yl)-2,3-dihydrobenzo[b][1,4]dioxin-6-yl)methyl)imidazo[1,2-b]pyridazine The title compound was prepared in two steps from 8-methoxy-2-(6-methoxypyridin-3-yl)-2,3-dihydrobenzo[b][1,4]dioxine-6-carbaldehyde and 3-bromo-7-chloroimidazo[1,2-b]pyridazine (Example 1-23-2) as described in Example 1-23-3 through Example 1-23-4: $^1$H NMR (400 MHz, CDCl$_3$) δ 8.31 (d, J=2.3 Hz, 1H), 8.21 (d, J=2.4 Hz, 1H), 7.96 (d, J=2.4 Hz, 1H), 7.66-7.55 (m, 2H), 6.77 (dd, J=8.5, 0.7 Hz, 1H), 6.50-6.48 (m, 2H), 5.09 (dd, J=8.4, 2.4 Hz, 1H), 4.33-4.20 (m, 3H), 4.07 (dd, J=11.5, 8.4 Hz, 1H), 3.94 (s, 3H), 3.82 (s, 3H) ppm; (M+1)=439.

Example 1-103: Synthesis of 4-(3-((8-methoxy-2-(6-methoxypyridin-3-yl)-2,3-dihydrobenzo[b][1,4]dioxin-6-yl)methypimidazo[1,2-b]pyridazin-7-yl)-2-methylbut-3-yn-2-amine The title compound was prepared from 7-chloro-3-((8-methoxy-2-(6-methoxypyridin-3-yl)-2,3-dihydrobenzo[b][1,4]dioxin-6-yl)methyl)imidazo[1,2-b]pyridazine (Example 1-102-2) and 2-methylbut-3-yn-2-amine as described in Example 1-5-8: $^1$H NMR (400 MHz, CDCl$_3$) δ 8.27 (d, J=2.0 Hz, 1H), 8.24-8.18 (m, 1H), 7.90 (d, J=2.0 Hz, 1H), 7.66-7.56 (m, 2H), 6.77 (dd, J=8.6, 0.8 Hz, 1H), 6.53-6.47 (m, 2H), 5.09 (dd, J=8.4, 2.4 Hz, 1H), 4.33-4.21 (m, 3H), 4.07 (dd, J=11.5, 8.4 Hz, 1H), 3.94 (s, 3H), 3.82 (s, 3H), 1.53 (s, 6H) ppm; (M+1)=486.

Example 1-104: Synthesis of 4-(3-((8-methoxy-2-(6-methoxypyridin-3-yl)-2,3-dihydrobenzo[b][1,4]dioxin-6-yl)methypimidazo[1,2-b]pyridazin-7-yl)morpholine To a stirred suspension of 7-chloro-3-((8-methoxy-2-(6-methoxypyridin-3-yl)-2,3-dihydrobenzo[b][1,4]dioxin-6-yl)methyl)imidazo[1,2-b]pyridazine (0.10 g, 0.23 mmol, Example 1-102-2) in degassed toluene (3 mL) was added palladium(II) acetate (0.013 g, 0.057 mmol), 2-(dicyclohexylphosphino)-2',4',6'-triisopropylbiphenyl (0.050 g, 0.10 mmol), morpholine (0.071 mL, 0.80 mmol), and 5.0 M potassium hydroxide solution (0.5 mL, 2.50 mmol). The mixture was heated to 120° C. in a microwave reactor. After 5 h, the mixture was partitioned between water and toluene. The phases were separated, and the organic phase was washed with brine, dried over magnesium sulfate, filtered, and concentrated. Chromatographic purification of the crude product (CombiFlash, silica gel column, 0-100% ethyl acetate/methanol/ammonium hydroxide (85/10/5)/ethyl acetate elute) afforded a beige powder. This powder was triturated with hexanes, and the solid was isolated by filtration and dried to provide 0.061 g (54%) of 4-(3-((8-methoxy-2-(6-methoxypyridin-3-yl)-2,3-dihydrobenzo[b][1,4]dioxin-6-yl)methyl)imidazo[1,2-b]pyridazin-7-yl)morpholine as a beige solid: $^1$H NMR (400 MHz, CDCl$_3$) δ 8.26-8.18 (m, 2H), 7.62 (dd, J=8.6, 2.5 Hz, 1H), 7.37 (s, 1H), 7.08 (d, J=2.8 Hz, 1H), 6.77 (dd, J=8.5, 0.7 Hz, 1H), 6.50-6.48 (m, 2H), 5.08 (dd, J=8.4, 2.4 Hz, 1H), 4.28 (dd, J=11.5, 2.5 Hz, 1H), 4.18 (s, 2H), 4.06 (dd, J=11.5, 8.4 Hz, 1H), 3.94 (s, 3H), 3.93-3.86 (m, 4H), 3.82 (s, 3H), 3.24-3.17 (m, 4H) ppm; (M+1)=490.

Example 1-105: Synthesis of 3-((8-methoxy-2-(6-methoxypyridin-3-yl)-2,3-dihydrobenzo[b][1,4]dioxin-6-yl)methyl)-7-(3-methoxyazetidin-1-yl)imidazo[1,2-b]pyridazine The title compound, also known as RA10813661, was prepared from 7-chloro-3-((8-methoxy-2-(6-methoxypyridin-3-yl)-2,3-dihydrobenzo[b][1,4]dioxin-6-yl)methyl)imidazo[1,2-b]pyridazine (Example 1-102-2) and 3-methoxyazetidine hydrochloride as described in Example 1-104: $^1$H NMR (400 MHz, CDCl$_3$) δ 8.21 (d, J=2.4 Hz, 1H), 7.85 (d, J=2.7 Hz, 1H), 7.62 (dd, J=8.6, 2.5 Hz, 1H), 7.31 (s, 1H), 6.77 (d, J=8.5 Hz, 1H), 6.68 (d, J=2.7 Hz, 1H), 6.52-6.44 (m, 2H), 5.09 (dd, J=8.4, 2.4 Hz, 1H), 4.40 (tt, J=6.1, 4.3 Hz, 1H), 4.33-4.13 (m, 5H), 4.06 (dd, J=11.5, 8.4 Hz, 1H), 3.94 (s, 3H), 3.90-3.79 (m, 5H), 3.36 (s, 3H) ppm; (M+1)=490.

Example 1-106: Synthesis of 3-((8-methoxy-2-(6-methoxypyridin-3-yl)-2,3-dihydrobenzo[b][1,4]dioxin-6-yl)methyl)imidazo[1,2-a]pyridine Example 1-106-1: Preparation of imidazo[1,2-a]pyridin-3-yl(8-methoxy-2-(6-methoxypyridin-3-yl)-2,3-dihydrobenzo[b][1,4]dioxin-6-yl)methanol To a stirred solution of 3-bromoimidazo[1,2-a]pyridine (0.080 g, 0.39 mmol) in tetrahydrofuran (4 mL) was added 3.0M ethylmagnesium bromide solution in diethyl ether (0.13 mL, 0.39 mmol) dropwise via syringe. After 50 min, the light yellow suspension was treated with a solution of 8-methoxy-2-(6-methoxypyridin-3-yl)-2,3-dihydrobenzo[b][1,4]dioxine-6-carbaldehyde (0.10 g, 0.33 mmol, Example 1-102-1) in tetrahydrofuran (4 mL) (added via cannula). The resulting light green solution was allowed to stir at room temperature. After 3.5 h, the mixture was quenched by the addition of saturated ammonium chloride solution (0.25 mL), and the mixture was concentrated. Chromatographic purification of the crude product (Biotage, 12 g silica gel column, 0-10% methanol/dichloromethane elute) afforded 0.085 g (61%) of imidazo[1,2-a]pyridin-3-yl(8-methoxy-2-(6-methoxypyridin-3-yl)-2,3-dihydrobenzo[b][1,4]dioxin-6-yl)methanol as a white solid.

Example 1-106-2: Preparation of 3-((8-methoxy-2-(6-methoxypyridin-3-yl)-2,3-dihydrobenzo[b][1,4]dioxin-6-yl)methyl)imidazo[1,2-a]pyridine The title compound was prepared from imidazo[1,2-a]pyridin-3-yl(8-methoxy-2-(6-methoxypyridin-3-yl)-2,3-dihydrobenzo[b][1,4]dioxin-6-yl)methanol as described in Example 1-22-2: $^1$H NMR (400 MHz, CDCl$_3$) δ 8.21 (d, J=2.5 Hz, 1H), 8.11 (d, J=9.1 Hz, 1H), 7.97 (d, J=6.9 Hz, 1H), 7.64-7.60 (m, 2H), 7.54-7.49 (m, 1H), 7.10-7.04 (m, 1H), 6.78 (dd, J=8.6, 0.7 Hz, 1H), 6.43 (d, J=2.0 Hz, 1H), 6.35 (d, J=2.0 Hz, 1H), 5.10 (dd, J=8.5, 2.5 Hz, 1H), 4.31 (dd, J=11.6, 2.5 Hz, 1H), 4.20 (s, 2H), 4.08 (dd, J=11.6, 8.5 Hz, 1H), 3.94 (s, 3H), 3.79 (s, 3H) ppm; (M+1)=404.

Example 1-107: Synthesis of 3-((8-methoxy-2-(6-methoxypyridin-3-yl)-2,3-dihydrobenzo[b][1,4]dioxin-6-yl)methyl)imidazo[1,2-b]pyridazine The title compound was prepared in two steps from 8-methoxy-2-(6-methoxypyridin-3-yl)-2,3-dihydrobenzo[b][1,4]dioxine-6-carbaldehyde (Example 1-102-1) and 3-bromoimidazo[1,2-b]pyridazine as described in Example 1-106-1 through Example 1-106-2: $^1$H NMR (400 MHz, CDCl$_3$) δ 8.36 (dd, J=4.4, 1.6 Hz, 1H), 8.21 (dt, J=2.5, 0.7 Hz, 1H), 8.00 (dd, J=9.2, 1.6 Hz, 1H), 7.62 (dd, J=8.6, 2.5 Hz, 1H), 7.58 (s, 1H), 7.04 (dd, J=9.2, 4.4 Hz, 1H), 6.77 (dd, J=8.6, 0.7 Hz, 1H), 6.53-6.50 (m, 2H), 5.09 (dd, J=8.5, 2.4 Hz, 1H), 4.33-4.23 (m, 3H), 4.07 (dd, J=11.5, 8.5 Hz, 1H), 3.94 (s, 3H), 3.82 (s, 3H) ppm; (M+1)=405.

Example 1-108: Synthesis of 7-methoxy-3-((8-methoxy-2-(6-methoxypyridin-3-yl)-2,3-dihydrobenzo[b][1,4]dioxin-6-yl)methyl)imidazo[1,2-a]pyridine Example 1-108-1: Preparation of (8-methoxy-2-(6-methoxypyridin-3-yl)-2,3-dihydrobenzo[b][1,4]dioxin-6-yl)(7-methoxyimidazo[1,2-a]pyridin-3-yl)methanol To a stirred and cooled (−78° C.) solution of 5-(6-bromo-8-methoxy-2,3-dihydrobenzo[b][1,4]dioxin-2-yl)-2-methoxypyridine (0.20 g, 0.57 mmol, Example 1-96-2) in tetrahydrofuran (5 mL) was added 1.6M n-butyllithium solution in hexanes (0.43 mL, 0.68 mmol). After 5 min, a solution of 7-methoxyimidazo[1,2-a]pyridine-3-carbaldehyde (0.10 g, 0.57 µmol) in tetrahydrofuran (2 mL) was added. After 30 min, saturated ammonium chloride solution was added, and the mixture was allowed to warm to room temperature. The mixture was partitioned between water and ethyl acetate. The product was insoluble in either organic or aqueous layer (product settled between the phases). The organic phase (including the insoluble product) was washed with brine and concentrated. The residue was suspended in a small amount of ethyl acetate, and a white solid was collected by filtration. The solid was suspended in dichloromethane and concentrated to dryness to yield 0.050 g (20%) of (8-methoxy-2-(6-methoxypyridin-3-yl)-2,3-dihydrobenzo[b][1,4]dioxin-6-yl)(7-methoxyimidazo[1,2-a]pyridin-3-yl)methanol as a white solid.

Example 1-108-2: Preparation of 7-methoxy-3-((8-methoxy-2-(6-methoxypyridin-3-yl)-2,3-dihydrobenzo[b][1,4]dioxin-6-yl)methyl)imidazo[1,2-a]pyridine The title compound was prepared from (8-methoxy-2-(6-methoxypyridin-3-yl)-2,3-dihydrobenzo[b][1,4]dioxin-6-yl)(7-methoxyimidazo[1,2-a]pyridin-3-yl)methanol as described in Example 1-22-2: $^1$H NMR (400 MHz, CDCl$_3$) δ 8.21 (d, J=2.5 Hz, 1H), 7.66-7.56 (m, 2H), 7.36 (s, 1H), 6.92 (d, J=2.5 Hz, 1H), 6.77 (d, J=8.6 Hz, 1H), 6.51-6.39 (m, 2H), 6.34 (d, J=2.1 Hz, 1H), 5.09 (dd, J=8.5, 2.5 Hz, 1H), 4.29 (dd, J=11.6, 2.5 Hz, 1H), 4.13-4.02 (m, 3H), 3.94 (s, 3H), 3.85 (s, 3H), 3.77 (s, 3H) ppm; (M+1)=434.

Example 1-109: Synthesis of 3-((8-methoxy-2-(6-methoxypyridin-3-yl)-2,3-dihydrobenzo[b][1,4]dioxin-6-yl)methyl)-1H-pyrrolo[2,3-b]pyridine Example 1-109-1: Preparation of 5-(6-(bromomethyl)-8-methoxy-2,3-dihydrobenzo[b][1,4]dioxin-2-yl)-2-methoxypyridine To a stirred solution of (8-methoxy-2-(6-methoxypyridin-3-yl)-2,3-dihydrobenzo[b][1,4]dioxin-6-yl)methanol (0.30 g, 0.99 mmol, Example 1-52-4) in tetrahydrofuran (25 mL) was added triphenylphosphine resin (0.78 g, 2.34 mmol). The mixture was treated with carbon tetrabromide (0.33 g, 0.99 mmol). The mixture was then heated to 80° C. After 2 h, the mixture was allowed to cool to room temperature and was filtered through Celite with the aid of dichloromethane. The filtrate was concentrated to provide a crude oil that was used immediately in the next reaction.

Example 1-109-2: Preparation of 3-((8-methoxy-2-(6-methoxypyridin-3-yl)-2,3-dihydrobenzo[b][1,4]dioxin-6-yl)methyl)-1H-pyrrolo[2,3-b]pyridine The title compound was prepared from 5-(6-(bromomethyl)-8-methoxy-2,3-dihydrobenzo[b][1,4]dioxin-2-yl)-2-methoxypyridine and tert-butyl 3-(4,4,5,5-tetramethyl-1,3,2-dioxaborolan-2-yl)-1H-pyrrolo[2,3-b]pyridine-1-carboxylate as described in Example 1-55. The product of this reaction was de-protected with trifluoroacetic acid as described in Example 1-12-5: $^1$H NMR (400 MHz, CDCl$_3$) δ 8.71 (br s, 1H), 8.28 (d, J=3.2 Hz, 1H), 8.21 (d, J=2.2 Hz, 1H), 7.80 (d, J=7.8 Hz, 1H), 7.67-7.58 (m, 1H), 7.09 (d, J=2.2 Hz, 1H), 7.06-7.01 (m, 1H), 6.77 (d, J=8.6 Hz, 1H), 6.49 (d, J=2.1 Hz, 1H), 6.45 (d, J=2.1 Hz, 1H), 5.09 (dd, J=8.6, 2.3 Hz, 1H), 4.29 (dd, J=11.5, 2.3 Hz, 1H), 4.11-3.99 (m, 3H), 3.94 (s, 3H), 3.80 (s, 3H) ppm; (M+1)=404.

Example 1-110: Synthesis of 3-((2-(6-cyclopropylpyridin-3-yl)-8-methoxy-2,3-dihydrobenzo[b][1,4]dioxin-6-yl)methyl)-3H-imidazo[4,5-b]pyridine

Example 1-110-1: Preparation of 1-(6-cyclopropylpyridin-3-yl)ethan-1-one

The title compound was prepared from 1-(6-bromopyridin-3-yl)ethan-1-one and cyclopropylboronic acid as described in Example 1-55.

Example 1-110-2: Preparation of 2-bromo-1-(6-cyclopropylpyridin-3-yl)ethan-1-one To a stirred solution of 33% hydrobromic acid in acetic acid (20 mL) was added 1-(6-cyclopropylpyridin-3-yl)ethanone (3.75 g, 23.26 mmol). The yellow suspension was allowed to stir at room temperature. After 20 min, the mixture was treated with a solution of bromine (4.48 g, 27.92 mmol) in chloroform (20 mL) (added dropwise over 60 min). The resulting yellow-orange suspension was allowed to stir at room temperature. After 30 min (120 min total reaction time), the mixture was diluted with ethyl acetate (150 mL) and water (150 mL). The acidic biphasic mixture was neutralized by the slow addition of solid sodium bicarbonate. Once the pH was ~7, the phases were separated. The aqueous phase was extracted with ethyl acetate (75 mL). The combined organic phases were washed with saturated sodium thiosulfate solution (75 mL), dried over magnesium sulfate, filtered, and concentrated. Chromatographic purification of the crude product (CombiFlash, 120 g silica gel gold column, 10-20% ethyl acetate/heptane elute) afforded 4.16 g (75%) of 2-bromo-1-(6-cyclopropylpyridin-3-yl)ethanone as a red-brown oil that solidified on standing.

Example 1-110-3: Preparation of methyl 2-(6-cyclopropylpyridin-3-yl)-8-methoxy-2,3-dihydrobenzo[b][1,4]dioxine-6-carboxylate (A) and methyl 8-methoxy-2-(6-propylpyridin-3-yl)-2,3-dihydrobenzo[b][1,4]dioxine-6-carboxylate (B)

The title compound was prepared in three steps from methyl 4-(benzyloxy)-3-hydroxy-5-methoxybenzoate and 2-bromo-1-(6-cyclopropylpyridin-3-yl)ethanone as described in Example 1-52-1 through Example 1-52-3. The n-propyl analog was also isolated from this sequence.

Example 1-110-4: Preparation of (2-(6-cyclopropylpyridin-3-yl)-8-methoxy-2,3-dihydrobenzo[b][1,4]dioxin-6-yl)methanamine The title compound was prepared in three steps from methyl 2-(6-cyclopropylpyridin-3-yl)-8-methoxy-2,3-dihydrobenzo[b][1,4]dioxine-6-carboxylate as described in Example 1-52-4 through Example 1-52-6.

Example 1-110-5: Preparation of 3-((2-(6-cyclopropylpyridin-3-yl)-8-methoxy-2,3-dihydrobenzo[b][1,4]dioxin-6-yl)methyl)-3H-imidazo[4,5-b]pyridine The title compound, also known as RA10607080, was prepared in three steps from (2-(6-cyclopropylpyridin-3-yl)-8-methoxy-2,3-dihydrobenzo[b][1,4]dioxin-6-yl)methanamine (Example 1-110-4) and 2-chloro-3-nitropyridine as described in Example 1-52-7 through Example 1-52-9: $^1$H NMR (400 MHz, CDCl$_3$) δ 8.46 (d, J=2.3 Hz, 1H), 8.44 (dd, J=4.8, 1.5 Hz, 1H), 8.09 (dd, J=8.0, 1.5 Hz, 1H), 8.04 (s, 1H), 7.59-7.55 (m, 1H), 7.29-7.25 (m, 1H), 7.16 (dd, J=8.2, 0.8 Hz, 1H), 6.56-6.52 (m, 2H), 5.37 (s, 2H), 5.11 (dd, J=8.3, 2.5 Hz, 1H), 4.31 (dd, J=11.6, 2.5 Hz, 1H), 4.06 (dd, J=11.6, 8.3 Hz, 1H), 3.80 (s, 3H) 2.09-1.97 (m, 1H), 1.05-0.95 (m, 4H) ppm; (M+1)=415.

Example 1-111: Synthesis of 1-((2-(6-cyclopropylpyridin-3-yl)-8-methoxy-2,3-dihydrobenzo[b][1,4]dioxin-6-yl)methyl)-1H-benzo[d]imidazole The title compound was prepared in three steps from (2-(6-cyclopropylpyridin-3-yl)-8-methoxy-2,3-dihydrobenzo[b][1,4]dioxin-6-yl)methanamine (Example 1-110-4) and 1-fluoro-2-nitrobenzene as described in Example 1-52-7 through Example 1-52-9: $^1$H NMR (400 MHz, CDCl$_3$) δ 8.46 (d, J=2.3 Hz, 1H), 7.94 (s, 1H), 7.87-7.79 (m, 1H), 7.62-7.54 (m, 1H), 7.35-7.30 (m, 1H), 7.30-7.25 (m, 2H), 7.18-7.14 (m, 1H), 6.45 (d, J=2.0 Hz, 1H), 6.35 (d, J=2.0 Hz, 1H), 5.25 (s, 2H), 5.11 (dd, J=8.4, 2.5 Hz, 1H), 4.31 (dd, J=11.6, 2.5 Hz, 1H), 4.06 (dd, J=11.6, 8.4 Hz, 1H), 3.77 (s, 3H), 2.08-1.99 (m, 5.6 Hz, 1H), 1.06-0.96 (m, 4H) ppm; (M+1)=414.

Example 1-112: Synthesis of 3-((2-(6-cyclopropylpyridin-3-yl)-8-methoxy-2,3-dihydrobenzo[b][1,4]dioxin-6-yl)methyl)-5-methyl-3H-imidazo[4,5-b]pyridine The title compound was prepared in three steps from (2-(6-cyclopropylpyridin-3-yl)-8-methoxy-2,3-dihydrobenzo[b][1,4] dioxin-6-yl)methanamine (Example 1-110-4) and 2-chloro-6-methyl-3-nitropyridine as described in Example 1-52-7 through Example 1-52-9: $^1$H NMR (400 MHz, CDCl$_3$) δ 8.47 (d, J=2.4 Hz, 1H), 7.97-7.92 (m, 2H), 7.58 (dd, J=8.1, 2.4 Hz, 1H), 7.16 (dd, J=8.2, 0.8 Hz, 1H), 7.12 (d, J=8.2 Hz, 1H), 6.58 (d, J=2.0 Hz, 1H), 6.55 (d, J=2.0 Hz, 1H), 5.33 (s, 2H), 5.11 (dd, J=8.3, 2.5 Hz, 1H), 4.31 (dd, J=11.5, 2.5 Hz, 1H), 4.07 (dd, J=11.6, 8.3 Hz, 1H), 3.81 (s, 3H), 2.68 (s, 3H), 2.07-1.99 (m, 1H), 1.05-0.97 (m, 4H) ppm; (M+1)=429.

Example 1-113: Synthesis of 1-((2-(6-cyclopropylpyridin-3-yl)-8-methoxy-2,3-dihydrobenzo[b][1,4]dioxin-6-yl)methyl)-1H-imidazo[4,5-c]pyridine The title compound was prepared in three steps from (2-(6-cyclopropylpyridin-3-yl)-8-methoxy-2,3-dihydrobenzo[b][1,4]dioxin-6-yl)methanamine (Example 1-110-4) and 4-chloro-3-nitropyridine as described in Example 1-52-7 through Example 1-52-9: $^1$H NMR (400 MHz, Chloroform-d) δ 9.15 (s, 1H), 8.47 (d, J=2.3 Hz, 1H), 8.43 (d, J=5.6 Hz, 1H), 7.99 (s, 1H), 7.58 (dd, J=8.2, 2.3 Hz, 1H), 7.28 (dd, J=5.6, 0.8 Hz, 1H), 7.17 (dd, J=8.2, 0.8 Hz, 1H), 6.44 (d, J=2.0 Hz, 1H), 6.34 (d, J=2.0 Hz, 1H), 5.26 (s, 2H), 5.12 (dd, J=8.3, 2.5 Hz, 1H), 4.33 (dd, J=11.6, 2.5 Hz, 1H), 4.07 (dd, J=11.6, 8.3 Hz, 1H), 3.78 (s, 3H), 2.08-2.00 (m, 1H), 1.05-0.98 (m, 4H) ppm; (M+1)=415.

Example 1-114: Synthesis of 3-((2-(6-cyclopropylpyridin-3-yl)-8-methoxy-2,3-dihydrobenzo[b][1,4]dioxin-6-yl)methyl)imidazo[1,2-a]pyrazine

Example 1-114-1: Preparation of 2-(6-cyclopropylpyridin-3-yl)-8-methoxy-2,3-dihydrobenzo[b][1,4]dioxine-6-carboxylic acid The title compound was prepared from 2-(6-cyclopropylpyridin-3-yl)-8-methoxy-2,3-dihydrobenzo[b][1,4]dioxine-6-carboxylate (Example 1-110-3A) as described in Example 1-18-5.

Example 1-114-2: Preparation of 2-bromo-1-(2-(6-cyclopropylpyridin-3-yl)-8-methoxy-2,3-dihydrobenzo[b][1,4]dioxin-6-yl)ethan-1-one To a stirred suspension of 2-(6-cyclopropylpyridin-3-yl)-8-methoxy-2,3-dihydrobenzo[b][1,4]dioxine-6-carboxylic acid (0.48 g, 1.45 mmol) in dichloromethane (20 mL) and N,N-dimethylformamide (0.050 mL) was added oxalyl chloride (0.30 mL, 3.51 mmol). The solids dissolved and rapid gas evolution was noted. The mixture was allowed to stir at room temperature. After 90 min, the solution was concentrated to provide 0.55 g of 2-(6-cyclopropylpyridin-3-yl)-8-methoxy-2,3-dihydrobenzo[b][1,4]dioxine-6-carbonyl chloride hydrochloride as a white solid. This material was suspended in 1:1 tetrahydrofuran/acetonitrile (20 mL) and was added dropwise over 10 min to a stirred and cooled (0° C.) mixture of 2.0M (trimethylsilyl)diazomethane solution in diethyl ether (9.0 mL, 18.00 mmol) and tetrahydrofuran (15 mL). The resulting yellow mixture was allowed to stir at 0° C. After 1 h, the ice bath was removed, and the yellow mixture was allowed to warm to room temperature. After 19 h, the mixture was re-cooled to 0° C. while 48% hydrobromic acid in water (6.0 mL, 53.40 mmol) added dropwise over 5 min (vigorous gas evolution noted upon addition). After 10 min, the mixture was diluted with water (50 mL), and the pH was adjusted to ~8 by the addition of solid sodium bicarbonate. The phases were separated, and the basic mixture was extracted with ethyl acetate (40 mL). The combined organic phases were washed with brine (30 mL), dried over magnesium sulfate, filtered, and concentrated. Chromatographic purification of the crude product (CombiFlash, 24 g silica gel gold column, 20-50% ethyl acetate/heptane elute) afforded 0.32 g (56%) of 2-bromo-1-(2-(6-cyclopropylpyridin-3-yl)-8-methoxy-2,3-dihydrobenzo[b][1,4]dioxin-6-yl)ethanone as a white solid.

Example 1-114-3: Preparation of (2-(6-cyclopropylpyridin-3-yl)-8-methoxy-2,3-dihydrobenzo[b][1,4]dioxin-6-yl)(imidazo[1,2-a]pyrazin-3-yl)methanone To a stirred solution of 2-bromo-1-(2-(6-cyclopropylpyridin-3-yl)-8-methoxy-2,3-dihydrobenzo[b][1,4]dioxin-6-yl)ethanone (0.32 mg, 0.80 mmol) in acetonitrile (25 mL) was added (E)-N,N-dimethyl-N'-(pyrazin-2-yl)formimidamide (0.18 g, 1.17 mmol) The yellow solution was heated to reflux. After 42 h, the mixture was allowed to cool to room temperature and was concentrated. Chromatographic purification of the crude product (CombiFlash, 24 g silica gel gold column, 0-5% 2M ammonia in methanol/dichloromethane elute) afforded 0.096 g (28%) of (2-(6-cyclopropylpyridin-3-yl)-8-methoxy-2,3-dihydrobenzo[b][1,4]dioxin-6-yl)(imidazo[1,2-a]pyrazin-3-yl)methanone as a tan solid.

Example 1-114-4: Preparation of 3-((2-(6-cyclopropylpyridin-3-yl)-8-methoxy-2,3-dihydrobenzo[b][1,4]dioxin-6-yl)methyl)imidazo[1,2-a]pyrazine To a stirred and cooled (0° C.) solution of (2-(6-cyclopropylpyridin-3-yl)-8-methoxy-2,3-dihydrobenzo[b][1,4]dioxin-6-yl)(imidazo[1,2-a]pyrazin-3-yl)methanone (0.096 g, 0.22 mmol) in methanol (10 mL) was added sodium borohydride (0.025 g, 0.65 mmol). After 30 min, the mixture was treated with 1N hydrochloric acid solution (1 mL) and concentrated. The residue was dissolved in trifluoroacetic acid (5 mL) and was treated with triethylsilane (0.079 g, 0.67 mmol). The resulting yellow mixture was allowed to stir at room temperature. After 30 min, an additional portion of triethylsilane (0.47 g) was added, and the reaction was allowed to stir. After 2 h, the mixture was concentrated, and the residue was partitioned between chloroform (20 mL) and saturated sodium bicarbonate solution (20 mL). The phases were separated, and the aqueous phase was extracted with chloroform (2×20 mL). The combined organic phases were washed with brine, dried over magnesium sulfate, filtered, and concentrated. Chromatographic purification of the crude product (CombiFlash, 12 g silica gel gold column, 0-5% 2M ammonia in methanol/dichloromethane elute) afforded 0.015 g (16%) of 3-((2-(6-cyclopropylpyridin-3-yl)-8-methoxy-2,3-dihydrobenzo[b][1,4]dioxin-6-yl)methyl)imidazo[1,2-a]pyrazine as a yellow oil: $^1$H NMR (400 MHz, CDCl$_3$) δ 9.09 (d, J=1.5 Hz, 1H), 8.47 (d, J=2.4 Hz, 1H), 7.83 (d, J=4.6 Hz, 1H), 7.75 (dd, J=4.6, 1.5 Hz, 1H), 7.68 (s, 1H), 7.58 (dd, J=8.2, 2.4 Hz, 1H), 7.16 (dd, J=8.2 Hz, 1H), 6.39 (d, J=2.0 Hz, 1H), 6.33 (d, J=2.0 Hz, 1H), 5.11 (dd, J=8.4, 2.5 Hz, 1H), 4.31 (dd, J=11.6, 2.5 Hz, 1H), 4.19 (s, 2H), 4.07 (dd, J=11.6, 8.4 Hz, 1H), 3.78 (s, 3H), 2.07-2.00 (m, 1H), 1.06-0.94 (m, 5H) ppm; (M+1)=415.

Example 1-115: Synthesis of 9-((2-(6-cyclopropylpyridin-3-yl)-8-methoxy-2,3-dihydrobenzo[b][1,4]dioxin-6-yl)methyl)-9H-purine

Example 1-115-1: Preparation of (2-(6-cyclopropylpyridin-3-yl)-8-methoxy-2,3-dihydrobenzo[b][1,4]dioxin-6-yl)methanol The title compound was prepared from methyl 2-(6-cyclopropylpyridin-3-yl)-8-methoxy-2,3-dihydrobenzo[b][1,4]dioxine-6-carboxylate (Example 1-110-3A) as described in Example 1-52-4.

Example 1-115-2: Preparation of 9-((2-(6-cyclopropylpyridin-3-yl)-8-methoxy-2,3-dihydrobenzo[b][1,4]dioxin-6-yl)methyl)-9H-purine To a stirred solution of (2-(6-cyclopropylpyridin-3-yl)-8-methoxy-2,3-dihydrobenzo[b][1,4]dioxin-6-yl)methanol (0.28 g, 0.89 mmol), 9H-purine (0.11 g, 0.89 mmol), and triphenylphosphine (0.33 g, 1.25 mmol) in tetrahydrofuran (15 mL) was added a solution of (E)-bis(2-methoxyethyl)diazene-1,2-dicarboxylate (0.29 g, 1.25 mmol) in tetrahydrofuran (5 mL). The resulting yellow mixture was allowed to stir at room temperature. After 3 h, the mixture was diluted with ethyl acetate (50 mL). The organic phase washed with water (50 mL) and brine (50 mL). The organic phase was dried over magnesium sulfate, filtered, and concentrated. Chromatographic purification of the crude product (CombiFlash, 24 g silica gel gold column, 100% heptane to 5% methanol/dichloromethane elute) provided an impure white solid. A second chromatographic purification (CombiFlash, 24 g silica gel gold column, 0-5% methanol/dichloromethane elute) afforded 0.075 g (20%) of 9-((2-(6-cyclopropylpyridin-3-yl)-8-methoxy-2,3-dihydrobenzo[b][1,4]dioxin-6-yl)methyl)-9H-purine as a white solid: $^1$H NMR (400 MHz, Chloroform-d) δ 9.17 (s, 1H), 9.04 (s, 1H), 8.46 (d, J=2.2 Hz, 1H), 8.08 (s, 1H), 7.57 (dd, J=8.1, 2.2 Hz, 1H), 7.16 (d, J=8.1 Hz, 1H), 6.55 (d, J=2.0 Hz, 1H), 6.53 (d, J=2.0 Hz, 1H), 5.35 (s, 2H), 5.11 (dd, J=8.3, 2.5 Hz, 1H), 4.32 (dd, J=11.6, 2.5 Hz, 1H), 4.07 (dd, J=11.6, 8.3 Hz, 1H), 3.82 (s, 3H), 2.07-2.00 (m, 1H), 1.04-0.98 (m, 4H) ppm; (M+1)=416.

Example 1-116: Synthesis of 3-((2-(6-cyclopropylpyridin-3-yl)-8-methoxy-2,3-dihydrobenzo[b][1,4]dioxin-6-yl)methyl)-6-((1-methylazetidin-3-yl)oxy)-3H-imidazo[4,5-b]pyridine

Example 1-116-1: Preparation of 3-((2-(6-cyclopropylpyridin-3-yl)-8-methoxy-2,3-dihydrobenzo[b][1,4]dioxin-6-yl)methyl)-6-iodo-3H-imidazo[4,5-b]pyridine The title compound was prepared in three steps from (2-(6-cyclopropylpyridin-3-yl)-8-methoxy-2,3-dihydrobenzo[b][1,4]dioxin-6-yl)methanamine (Example 1-110-4) and 2-chloro-5-iodo-3-nitropyridine as described in Example 1-52-7 through Example 1-52-9.

Example 1-116-2: Preparation of 3-((2-(6-cyclopropylpyridin-3-yl)-8-methoxy-2,3-dihydrobenzo[b][1,4]dioxin-6-yl)methyl)-6-((1-methylazetidin-3-yl)oxy)-3H-imidazo[4,5-b]pyridine The title compound was prepared in two steps from 3-((2-(6-cyclopropylpyridin-3-yl)-8-methoxy-2,3-dihydrobenzo[b][1,4]dioxin-6-yl)methyl)-6-iodo-3H-imidazo[4,5-b]pyridine and tert-butyl 3-hydroxyazetidine-1-carboxylate as described in Example 1-72-1 through Example 1-72-2: $^1$H NMR (400 MHz, CDCl$_3$) δ 8.46 (d, J=2.4 Hz, 1H), 8.14 (d, J=2.6 Hz, 1H), 7.98 (s, 1H), 7.57 (dd, J=8.1, 2.4 Hz, 1H), 7.41 (d, J=2.6 Hz, 1H), 7.16 (d, J=8.1 Hz, 1H), 6.55-6.49 (m, 2H), 5.32 (s, 2H), 5.10 (dd, J=8.3, 2.4 Hz, 1H), 4.84-4.75 (m, 1H), 4.31 (dd, J=11.6, 2.5 Hz, 1H), 4.06 (dd, J=11.6, 8.3 Hz, 1H), 3.92-3.83 (m, 2H), 3.80 (s, 3H), 3.23-3.11 (m, 2H), 2.43 (s, 3H), 2.06-1.99 (m, 1H), 1.04-0.95 (m, 4H) ppm; (M+1)=500.

Example 1-117: Synthesis of (3-((2-(6-cyclopropylpyridin-3-yl)-8-methoxy-2,3-dihydrobenzo[b][1,4]dioxin-6-yl)methyl)-3H-imidazo[4,5-b]pyridin-6-yl)methanol

Example 1-117-1: Preparation of methyl 3-((2-(6-cyclopropylpyridin-3-yl)-8-methoxy-2,3-dihydrobenzo[b][1,4]dioxin-6-yl)methyl)-3H-imidazo[4,5-b]pyridine-6-carboxylate The title compound was prepared in three steps from (2-(6-cyclopropylpyridin-3-yl)-8-methoxy-2,3-dihydrobenzo[b][1,4]dioxin-6-yl)methanamine (Example 1-110-4) and methyl 6-chloro-5-nitronicotinate as described in Example 1-52-7 through Example 1-52-9.

Example 1-117-2: Preparation of (3-((2-(6-cyclopropylpyridin-3-yl)-8-methoxy-2,3-dihydrobenzo[b][1,4]dioxin-6-yl)methyl)-3H-imidazo[4,5-b]pyridin-6-yl)methanol The title compound was prepared from methyl 3-((2-(6-cyclopropylpyridin-3-yl)-8-methoxy-2,3-dihydrobenzo[b][1,4]dioxin-6-yl)methyl)-3H-imidazo[4,5-b]pyridine-6-carboxylate as described in Example 1-52-4: $^1$H NMR (400 MHz, CDCl$_3$) δ 8.48-8.43 (m, 2H), 8.09 (d, J=1.9 Hz, 1H), 8.05 (s, 1H), 7.57 (dd, J=8.1, 2.4 Hz, 1H), 7.15 (d, J=8.1 Hz, 1H), 6.55-6.50 (m, 2H), 5.36 (s, 2H), 5.10 (dd, J=8.3, 2.5 Hz, 1H), 4.86 (s, 2H), 4.30 (dd, J=11.6, 2.5 Hz, 1H), 4.05 (dd, J=11.6, 8.3 Hz, 1H), 3.80 (s, 3H), 2.19 (br s, 1H), 2.09-1.98 (m, 1H), 1.05-0.95 (m, 4H) ppm; (M+1)=445.

Example 1-118: Synthesis of 4-(3-((8-methoxy-2-(6-methylpyridin-3-yl)-2,3-dihydrobenzo[b][1,4]dioxin-6-yl)methyl)-3H-imidazo[4,5-b]pyridin-6-yl)-2-methylbut-3-yn-2-amine

Example 1-118-1: Preparation of 6-iodo-3-((8-methoxy-2-(6-methylpyridin-3-yl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-methylpyridin-3-yl)ethan-1-one, and 2-chloro-5-iodo-3-nitropyridine as described in Example 1-52-1 through Example 1-52-9.

Example 1-118-2: Preparation of 4-(3-((8-methoxy-2-(6-methylpyridin-3-yl)-2,3-dihydrobenzo[b][1,4]dioxin-6-yl)methyl)-3H-imidazo[4,5-b]pyridin-6-yl)-2-methylbut-3-yn-2-amine The title compound was prepared from 6-iodo-3-((8-methoxy-2-(6-methylpyridin-3-yl)-2,3-dihydrobenzo[b][1,4]dioxin-6-yl)methyl)-3H-imidazo[4,5-b]pyridine and 2-methylbut-3-yn-2-amine as described in Example 1-5-8: $^1$H NMR (400 MHz, CDCl$_3$) δ 8.53 (d, J=2.3 Hz, 1H), 8.46 (d, J=1.8 Hz, 1H), 8.11-8.01 (m, 2H), 7.63 (dd, J=8.0, 2.4 Hz, 1H), 7.19 (d, J=8.0 Hz, 1H), 6.55-6.51 (m, 2H), 5.34 (s, 2H), 5.14 (dd, J=8.4, 2.4 Hz, 1H), 4.33 (dd, J=11.7, 2.4 Hz, 1H), 4.06 (dd, J=11.7, 8.4 Hz, 1H), 3.81 (s, 3H), 2.57 (s, 3H), 1.56 (s, 6H) ppm; (M+1)=470.

Example 1-119: Synthesis of 3-((8-methoxy-2-(6-methylpyridin-3-yl)-2,3-dihydrobenzo[b][1,4]dioxin-6-yl)methyl)-6-(2-methyl-1H-imidazol-1-yl)-3H-imidazo[4,5-b]pyridine hydrochloride The title compound was prepared from 6-iodo-3-((8-methoxy-2-(6-methylpyridin-3-yl)-2,3-dihydrobenzo[b][1,4]dioxin-6-yl)methyl)-3H-imidazo[4,5-b]pyridine (Example 118-1-1) and 2-methyl-1H-imidazole as described in Example 1-67: $^1$H NMR (400 MHz, DMSO-d$_6$) δ 8.88 (s, 1H), 8.76-8.70 (m, 1H), 8.65 (d, J=2.0 Hz, 1H), 8.51 (d, J=2.3 Hz, 1H), 8.27 (d, J=8.5 Hz, 1H), 7.93 (d, J=2.0 Hz, 1H), 7.84-7.74 (m, 2H), 6.86 (d, J=1.8 Hz, 1H), 6.57 (d, J=1.8 Hz, 1H), 5.47 (s, 2H), 5.39 (d, J=7.5 Hz, 1H), 4.50-4.42 (m, 1H), 4.20 (dd, J=11.6, 7.8 Hz, 1H), 3.78 (s, 3H), 2.67 (s, 3H), 2.55 (s, 3H) ppm; (M+1)=469.

Example 1-120: Synthesis of 6-methoxy-3-((8-methoxy-2-(6-methylpyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methylpyridin-3-yl)-2,3-dihydrobenzo[b][1,4]dioxin-6-yl)methyl)-3H-imidazo[4,5-b]pyridine (Example 118-1-1) and methanol as described in Example 1-11:

¹H NMR (400 MHz, CDCl₃) δ 8.54 (s, 1H), 8.22 (s, 1H), 8.10 (s, 1H), 7.70-7.60 (m, 2H), 7.21 (d, J=8.0 Hz, 1H), 6.55-6.51 (m, 2H), 5.34 (s, 2H), 5.17-5.13 (m, 1H), 4.33 (dd, J=11.6, 2.3 Hz, 1H), 4.07 (dd, J=11.6, 8.1 Hz, 1H), 3.91 (s, 3H), 3.81 (s, 3H), 2.59 (s, 3H) ppm; (M+1)=419.

Example 1-120-1: Chiral separation of 6-methoxy-3-((8-methoxy-2-(6-methylpyridin-3-yl)-2,3-dihydrobenzo[b][1,4]dioxin-6-yl)methyl)-3H-imidazo[4,5-b]pyridine Example 1-121: Synthesis of 3-((8-methoxy-2-(6-methylpyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methylpyridin-3-yl)-2,3-dihydrobenzo[b][1,4]dioxin-6-yl)methyl)-3H-imidazo[4,5-b]pyridine (Example 118-1-1) as described in Example 1-97: ¹H NMR (400 MHz, CDCl₃) δ 8.54 (s, 1H), 8.48-8.42 (m, 1H), 8.13-8.09 (m, 2H), 7.63 (dd, J=8.1, 2.3 Hz, 1H), 7.31-7.24 (m, 1H), 7.19 (d, J=8.0 Hz, 1H), 6.57-6.53 (m, 2H), 5.38 (s, 2H), 5.14 (dd, J=8.3, 2.5 Hz, 1H), 4.33 (dd, J=11.6, 2.5 Hz, 1H), 4.07 (dd, J=11.6, 8.3 Hz, 1H), 3.81 (s, 3H), 2.57 (s, 3H) ppm; (M+1)=389.

Example 1-122: Synthesis of 3-((8-methoxy-2-(6-methylpyridin-3-yl)-2,3-dihydrobenzo[b][1,4]dioxin-6-yl)methyl)-6-(3-methoxyazetidin-1-yl)-3H-imidazo[4,5-b]pyridine The title compound was prepared from 6-iodo-3-((8-methoxy-2-(6-methylpyridin-3-yl)-2,3-dihydrobenzo[b][1,4]dioxin-6-yl)methyl)-3H-imidazo[4,5-b]pyridine (Example 118-1-1) and 3-methoxyazetidine hydrochloride as described in Example 1-10: ¹H NMR (400 MHz, Chloroform-d) δ 8.53 (d, J=2.3 Hz, 1H), 7.92 (s, 1H), 7.78 (d, J=2.5 Hz, 1H), 7.63 (dd, J=8.0, 2.3 Hz, 1H), 7.22-7.12 (m, 2H), 6.54-6.50 (m, 2H), 5.30 (s, 2H), 5.13 (dd, J=8.3, 2.4 Hz, 1H), 4.45-4.28 (m, 2H), 4.22-4.18 (m, 2H), 4.06 (dd, J=11.6, 8.3 Hz, 1H), 3.83-3.72 (m, 5H), 3.36 (s, 3H), 2.57 (s, 3H) ppm; (M+1)=474.

Example 1-123: Synthesis of 1-(3-((8-methoxy-2-(6-methylpyridin-3-yl)-2,3-dihydrobenzo[b][1,4]dioxin-6-yl)methyl)-3H-imidazo[4,5-b]pyridin-6-yl)azetidin-3-ol The title compound was prepared from 6-iodo-3-((8-methoxy-2-(6-methylpyridin-3-yl)-2,3-dihydrobenzo [b][1,4]dioxin-6-yl)methyl)-3H-imidazo[4,5-b]pyridine (Example 118-1-1) and 3-hydroxyazetidine hydrochloride as described in Example 1-10: ¹H NMR (400 MHz, CDCl₃) δ 8.53 (d, J=2.4 Hz, 1H), 7.93 (s, 1H), 7.78 (d, J=2.5 Hz, 1H), 7.63 (dd, J=8.1, 2.4 Hz, 1H), 7.19 (d, J=8.0 Hz, 1H), 7.15 (d, J=2.5 Hz, 1H), 6.54-6.50 (m, 2H), 5.30 (s, 2H), 5.13 (dd, J=8.3, 2.4 Hz, 1H), 4.83 (d, J=5.7 Hz, 1H), 4.32 (dd, J=11.6, 2.4 Hz, 1H), 4.29-4.23 (m, 2H), 4.06 (dd, J=11.6, 8.3 Hz, 1H), 3.80 (s, 3H), 3.76-3.72 (m, 2H), 2.57 (s, 3H) ppm; (M+H)=460.

Example 1-124: Synthesis of 3-((8-methoxy-2-(6-methylpyridin-3-yl)-2,3-dihydrobenzo[b][1,4]dioxin-6-yl)methyl)-7-(3-methoxyazetidin-1-yl)imidazo[1,2-b]pyridazine Example 1-124-1: Preparation of (8-methoxy-2-(6-methylpyridin-3-yl)-2,3-dihydrobenzo[b][1,4]dioxin-6-yl)methanol The title compound was prepared in four steps from methyl 4-(benzyloxy)-3-hydroxy-5-methoxybenzoate and 2-bromo-1-(6-methylpyridin-3-yl)ethan-1-one as described in Example 1-52-1 through Example 1-52-4.

Example 1-124-2: Preparation of 8-methoxy-2-(6-methylpyridin-3-yl)-2,3-dihydrobenzo[b][1,4]dioxine-6-carbaldehyde The title compound was prepared from (8-methoxy-2-(6-methylpyridin-3-yl)-2,3-dihydrobenzo[b][1,4]dioxin-6-yl)methanol as described in Example 1-102-1.

Example 1-124-3: Preparation of 7-chloro-3-((8-methoxy-2-(6-methylpyridin-3-yl)-2,3-dihydrobenzo[b][1,4]dioxin-6-yl)methyl)imidazo[1,2-b]pyridazine The title compound was prepared in two steps from 8-methoxy-2-(6-methylpyridin-3-yl)-2,3-dihydrobenzo[b][1,4]dioxine-6-carbaldehyde and 3-bromo-7-chloroimidazo[1,2-b]pyridazine (Example 1-23-2) as described in Example 1-23-3 through Example 1-23-4.

Example 1-124-4: Preparation of 3-((8-methoxy-2-(6-methylpyridin-3-yl)-2,3-dihydrobenzo[b][1,4]dioxin-6-yl)methyl)-7-(3-methoxyazetidin-1-yl)imidazo[1,2-b]pyridazine The title compound, also known as RA10854918, was prepared from 7-chloro-3-((8-methoxy-2-(6-methylpyridin-3-yl)-2,3-dihydrobenzo[b][1,4]dioxin-6-yl)methyl)imidazo[1,2-b]pyridazine (Example 1-102-2) and 3-methoxyazetidine hydrochloride as described in Example 1-104: ¹H NMR (400 MHz, CDCl₃) δ 8.54 (d, J=2.2 Hz, 1H), 7.83 (d, J=2.7 Hz, 1H), 7.64 (dd, J=8.0, 2.2 Hz, 1H), 7.32 (s, 1H), 7.18 (d, J=8.0 Hz, 1H), 6.63 (d, J=2.7 Hz, 1H), 6.55-6.46 (m, 2H), 5.13 (dd, J=8.3, 2.4 Hz, 1H), 4.44-4.24 (m, 2H), 4.24-4.14 (m, 4H), 4.06 (dd, J=11.5, 8.3 Hz, 1H), 3.87-3.79 (m, 5H), 3.36 (s, 3H), 2.57 (s, 3H) ppm; (M+1)=474.

Example 1-125: Synthesis of 3-((8-methoxy-2-(6-propylpyridin-3-yl)-2,3-dihydrobenzo[13][1,4]dioxin-6-yl)methyl)-3H-imidazo[4,5-b]pyridine The title compound was prepared in six steps from methyl 8-methoxy-2-(6-propylpyridin-3-yl)-2,3-dihydrobenzo[b][1,4]dioxine-6-carboxylate (Example 1-110-3B) and 2-chloro-3-nitropyridine as described in Example 1-52-4 through Example 1-52-9: ¹H NMR (400 MHz, CDCl₃) δ 8.56 (d, J=2.3 Hz, 1H), 8.45 (dd, J=4.8, 1.5 Hz, 1H), 8.09 (dd, J=8.1, 1.5 Hz, 1H), 8.05 (s, 1H), 7.64 (dd, J=8.0, 2.3 Hz, 1H), 7.27 (dd, J=8.1, 4.8 Hz, 3H), 7.18 (d, J=8.0 Hz, 1H), 6.56-6.54 (m, 2H), 5.38 (s, 2H), 5.13 (dd, J=8.5, 2.5 Hz, 1H), 4.33 (dd, J=11.6, 2.5 Hz, 1H), 4.07 (dd, J=11.6, 8.4 Hz, 1H), 3.81 (s, 3H), 2.82-2.73 (m, 2H), 1.80-1.68 (m, 2H), 0.96 (t, J=7.3 Hz, 3H) ppm; (M+1)=417.

Example 1-126: Synthesis of 3-((2-(6-ethylpyridin-3-yl)-8-methoxy-2,3-dihydrobenzo[b][1,4]dioxin-6-yl)methyl)-3H-imidazo[4,5-b]pyridine Example 1-126-1: Preparation of 2-bromo-1-(6-ethylpyridin-3-yl)ethan-1-one The title compound was prepared from 1-(6-ethylpyridin-3-yl)ethan-1-one and bromine as described in Example 1-110-2.

Example 1-126-2: Preparation of (2-(6-ethylpyridin-3-yl)-8-methoxy-2,3-dihydrobenzo[b][1,4]dioxin-6-yl)methanamine The title compound was prepared in six steps from methyl 4-(benzyloxy)-3-hydroxy-5-methoxybenzoate and 2-bromo-1-(6-ethylpyridin-3-yl)ethan-1-one as described in Example 1-52-1 through Example 1-52-6.

Example 1-126-3: Preparation of 3-((2-(6-ethylpyridin-3-yl)-8-methoxy-2,3-dihydrobenzo[b][1,4]dioxin-6-yl)methyl)-3H-imidazo[4,5-b]pyridine The title compound was prepared in three steps from (2-(6-ethylpyridin-3-yl)-8-methoxy-2,3-dihydrobenzo[b][1,4]dioxin-6-yl)methanamine and 2-chloro-3-nitropyridine as described in Example 1-52-7 through Example 1-52-9: $^1$H NMR (400 MHz, CDCl$_3$) 8.56 (d, J=2.2 Hz, 1H), 8.45 (dd, J=4.8, 1.4 Hz, 1H), 8.10 (dd, J=8.0, 1.4 Hz, 1H), 8.05 (s, 1H), 7.66 (dd, J=8.1, 2.3 Hz, 1H), 7.33-7.24 (m, 1H), 7.20 (d, J=8.1 Hz, 1H), 6.56-6.54 (m, 2H), 5.38 (s, 2H), 5.14 (dd, J=8.3, 2.5 Hz, 1H), 4.33 (dd, J=11.6, 2.5 Hz, 1H), 4.08 (dd, J=11.6, 8.3 Hz, 1H), 3.81 (s, 3H), 2.84 (q, J=7.6 Hz, 2H), 1.30 (t, J=7.6 Hz, 3H) ppm; (M+1)=403.

Example 1-127: Synthesis of 4-(3-((2-(6-ethylpyridin-3-yl)-8-methoxy-2,3-dihydrobenzo[b][1,4]dioxin-6-yl)methyl)-3H-imidazo[4,5-b]pyridin-6-yl)morpholine

Example 1-127-1: Preparation of 3-((2-(6-ethylpyridin-3-yl)-8-methoxy-2,3-dihydrobenzo[b][1,4]dioxin-6-yl)methyl)-6-iodo-3H-imidazo[4,5-b]pyridine The title compound was prepared in three steps from (2-(6-ethylpyridin-3-yl)-8-methoxy-2,3-dihydrobenzo[b][1,4]dioxin-6-yl)methanamine and 2-chloro-5-iodo-3-nitropyridine as described in Example 1-52-7 through Example 1-52-9.

Example 1-127-2: Preparation of 4-(3-((2-(6-ethylpyridin-3-yl)-8-methoxy-2,3-dihydrobenzo[b][1,4]dioxin-6-yl)methyl)-3H-imidazo[4,5-b]pyridin-6-yl)morpholine The title compound was prepared from 3-((2-(6-ethylpyridin-3-yl)-8-methoxy-2,3-dihydrobenzo[b][1,4]dioxin-6-yl)methyl)-6-iodo-3H-imidazo[4,5-b]pyridine and morpholine as described in Example 1-10: $^1$H NMR (400 MHz, CDCl$_3$) δ 8.56 (d, J=2.2 Hz, 1H), 8.25 (d, J=2.5 Hz, 1H), 7.97 (s, 1H), 7.79-7.54 (m, 2H), 7.20 (d, J=8.1 Hz, 1H), 6.54-6.52 (m, 2H), 5.31 (s, 2H), 5.14 (dd, J=8.3, 2.4 Hz, 1H), 4.33 (dd, J=11.6, 2.4 Hz, 1H), 4.07 (dd, J=11.6, 8.3 Hz, 1H), 4.00-3.88 (m, 4H), 3.81 (s, 3H), 3.20-3.16 (m, 4H), 2.83 (q, J=7.6 Hz, 2H), 1.30 (t, J=7.6 Hz, 3H); (M+1)=488.

Example 1-128: Synthesis of 3-((2-(6-ethylpyridin-3-yl)-8-methoxy-2,3-dihydrobenzo[b][1,4]dioxin-6-yl)methyl)-6-((1-methylazetidin-3-yl)oxy)-3H-imidazo[4,5-b]pyridine The title compound was prepared two steps from 3-((2-(6-ethylpyridin-3-yl)-8-methoxy-2,3-dihydrobenzo[b][1,4]dioxin-6-yl)methyl)-6-iodo-3H-imidazo[4,5-b]pyridine (Example 1-127-1) and tert-butyl 3-hydroxyazetidine-1-carboxylate as described in Example 1-72-1 through Example 1-72-2: $^1$H NMR (400 MHz, CDCl$_3$ δ 8.55 (d, J=1.7 Hz, 1H), 8.14 (d, J=2.5 Hz, 1H), 7.98 (s, 1H), 7.65 (dd, J=8.0, 2.1 Hz, 1H), 7.40 (d, J=2.5 Hz, 1H), 7.20 (d, J=8.1 Hz, 1H), 6.54-6.52 (m, 2H), 5.31 (s, 2H), 5.15-5.11 (m, 1H), 4.86-4.74 (m, 1H), 4.33 (dd, J=11.6, 2.4 Hz, 1H), 4.07 (dd, J=11.6, 8.3 Hz, 1H), 3.99-3.73 (m, 5H), 3.18 (dd, J=8.0, 6.2 Hz, 2H), 2.83 (q, J=7.6 Hz, 2H), 2.43 (s, 3H), 1.29 (t, J=7.6 Hz, 3H); (M+1)=488.

Example 1-129: Synthesis of 3-((2-(6-ethylpyridin-3-yl)-8-methoxy-2,3-dihydrobenzo[b][1,4]dioxin-6-yl)methyl)-6-methoxy-3H-imidazo[4,5-b]pyridine The title compound was prepared in three steps from (2-(6-ethylpyridin-3-yl)-8-methoxy-2,3-dihydrobenzo[b][1,4]dioxin-6-yl)methanamine and 2-chloro-5-methoxy-3-nitropyridine as described in Example 1-52-7 through Example 1-52-9: $^1$H NMR (400 MHz, CDCl$_3$) δ 8.57-8.55 (m, 1H), 8.21 (d, J=2.6 Hz, 1H), 7.98 (s, 1H), 7.69-7.63 (m, 1H), 7.59 (d, J=2.6 Hz, 1H), 7.20 (d, J=8.0 Hz, 1H), 6.54-6.52 (m, 2H), 5.33 (s, 2H), 4.33 (dd, J=11.6, 2.4 Hz, 1H), 4.11-4.04 (m, 2H), 3.91 (s, 3H), 3.81 (s, 3H), 2.84 (q, J=7.6 Hz, 2H), 1.30 (t, J=7.6 Hz, 3H); (M+1)=433.

Example 1-130: Synthesis of 3-((2-(6-ethylpyridin-3-yl)-8-methoxy-2,3-dihydrobenzo[b][1,4]dioxin-6-yl)methyl)-6-methoxypyrazolo[1,5-a]pyrimidine

Example 1-130-1: Preparation of (2-(6-ethylpyridin-3-yl)-8-methoxy-2,3-dihydrobenzo[b][1,4]dioxin-6-yl)boronic acid The title compound was prepared in five steps from 5-bromo-2-((4-methoxybenzyl)oxy)phenol (Example 1-21-1) and 2-bromo-1-(6-ethylpyridin-3-yl)ethan-1-one (Example 1-126-1) as described in Example 1-21-2 through Example 1-21-5.

Example 1-130-2: Preparation of 6-bromo-3-((2-(6-ethylpyridin-3-yl)-8-methoxy-2,3-dihydrobenzo[13][1,4]dioxin-6-yl)methyl)pyrazolo[1,5-a]pyrimidine The title compound was prepared from (2-(6-ethylpyridin-3-yl)-8-methoxy-2,3-dihydrobenzo[b][1,4]dioxin-6-yl)boronic acid and (E/Z)-N'-((6-bromopyrazolo[1,5-a]pyrimidin-3-yl)methylene)-4-methylbenzenesulfonohydrazide (Example 1-21-7) as described in Example 1-21-8.

Example 1-130-3: Preparation of 3-((2-(6-ethylpyridin-3-yl)-8-methoxy-2,3-dihydrobenzo[b][1,4]dioxin-6-yl)methyl)-6-methoxypyrazolo[1,5-a]pyrimidine The title compound was prepared from 6-bromo-3-((2-(6-ethylpyridin-3-yl)-8-methoxy-2,3-dihydrobenzo[b][1,4]dioxin-6-yl)methyl)pyrazolo[1,5-a]pyrimidine and methanol as described in Example 1-100: $^1$H NMR (400 MHz, CDCl$_3$) δ 8.56 (d, J=2.4 Hz, 1H), 8.35 (d, J=2.7 Hz, 1H), 8.18 (d, J=2.7 Hz, 1H), 7.84 (s, 1H), 7.66 (dd, J=8.0, 2.4 Hz, 1H), 7.19 (d, J=8.0 Hz, 1H), 6.52 (d, J=1.9 Hz, 1H), 6.50 (d, J=1.9 Hz, 1H), 5.13 (dd, J=8.3, 2.5 Hz, 1H), 4.31 (dd, J=11.5, 2.5 Hz, 1H), 4.11-4.03 (m, 3H), 3.87 (s, 3H), 3.82 (s, 3H), 2.83 (q, J=7.6 Hz, 2H), 1.29 (t, J=7.6 Hz, 3H) ppm; (M+1)=433.

Example 1-131: Synthesis of 3-((2-(6-ethylpyridin-3-yl)-8-methoxy-2,3-dihydrobenzo[b][1,4]dioxin-6-yl)methyl)-6-(3-methoxyazetidin-1-yl)pyrazolo[1,5-a]pyrimidine The title compound was prepared from 6-bromo-3-((2-(6-ethylpyridin-3-yl)-8-methoxy-2,3-dihydrobenzo[b][1,4]

dioxin-6-yl)methyl)pyrazolo[1,5-a]pyrimidine (Example 1-130-2) and 3-methoxyazetidine hydrochloride as described in Example 1-10: $^1$H NMR (400 MHz, CDCl$_3$) δ 8.56 (d, J=2.4 Hz, 1H), 8.07 (d, J=2.6 Hz, 1H), 7.79 (d, J=2.6 Hz, 1H), 7.77 (s, 1H), 7.66 (dd, J=8.1, 2.4 Hz, 1H), 7.19 (d, J=8.1 Hz, 1H), 6.52 (d, J=2.0 Hz, 1H), 6.50 (d, J=2.0 Hz, 1H), 5.12 (dd, J=8.4, 2.5 Hz, 1H), 4.45-4.36 (m, 1H), 4.31 (dd, J=11.5, 2.5 Hz, 1H), 4.21-4.14 (m, 2H), 4.11-4.03 (m, 3H), 3.82 (s, 3H), 3.78-3.73 (m, 2H), 3.36 (s, 3H), 2.83 (q, J=7.6 Hz, 2H), 1.29 (t, J=7.6 Hz, 3H) ppm; (M+1)=488.

Example 1-132: Synthesis of 3-((8-methoxy-2-(6-methylpyridin-3-yl)-2,3-dihydrobenzo[b][1,4]dioxin-6-yl)methyl)-6-(trifluoromethyl)-3H-imidazo[4,5-b]pyridine The title compound was prepared in nine steps from methyl 4-(benzyloxy)-3-hydroxy-5-methoxybenzoate, 2-bromo-1-(6-methylpyridin-3-yl)ethan-1-one, and 2-chloro-3-nitro-5-(trifluoromethyl)pyridine as described in Example 1-52-1 through Example 1-52-9: $^1$H NMR (400 MHz, CDCl$_3$) δ 8.74 (s, 1H), 8.55 (s, 1H), 8.35 (s, 1H), 8.20 (s, 1H), 7.65 (d, J=8.2 Hz, 1H), 7.21 (d, J=8.2 Hz, 1H), 6.58-6.56 (m, 2H), 5.42 (s, 2H), 5.17-5.15 (m, 1H), 4.37-4.33 (m, 1H), 4.11-4.06 (m, 1H), 3.84 (s, 3H), 2.59 (s, 3H) ppm; (M+1)=457.

Example 1-133: Synthesis of 3-((2-(4,6-dimethylpyridin-3-yl)-8-methoxy-2,3-dihydrobenzo[b][1,4]dioxin-6-yl)methyl)-6-methoxy-3H-imidazo[4,5-b]pyridine Example 1-133-1: Preparation of 4,6-dimethylnicotinoyl chloride hydrochloride A stirred suspension of 4,6-dimethylnicotinic acid (4.32 g, 28.58 mmol) in thionyl chloride (30 mL) was heated to reflux. After 30 min, the mixture was allowed to cool to room temperature and was concentrated to afford 5.89 g (100%) of 4,6-dimethylnicotinoyl chloride hydrochloride as a brown solid.

Example 1-133-2: Preparation of 2-bromo-1-(4,6-dimethylpyridin-3-yl)ethan-1-one

To a stirred and cooled (0° C.) solution of 4,6-dimethylnicotinoyl chloride hydrochloride (5.89 g, 28.58 mmol) in acetonitrile (50 mL) at was added 2.0 M trimethylsilyldiazomethane solution (in hexanes) (57.2 mL, 144.33 mmol) dropwise over 30 minutes. After the addition was complete, the mixture was allowed to warm to room temperature. After 3 h, the mixture was treated with aqueous 48% hydrobromic acid solution (10 mL). After 30 min, the mixture was diluted with ethyl acetate, and the mixture was neutralized by the addition of solid sodium bicarbonate. The phases were separated, and the organic phase was washed with brine, dried over magnesium sulfate, filtered and concentrated. Chromatographic purification of the crude product (Combi-Flash, silica gel column, 15-70% ethyl acetate/heptane elute) provided 1.35 g (21%) of 2-bromo-1-(4,6-dimethylpyridin-3-yl)ethan-1-one as a beige solid.

Example 1-133-3: Preparation of 3-((2-(4,6-dimethylpyridin-3-yl)-8-methoxy-2,3-dihydrobenzo[b][1,4]dioxin-6-yl)methyl)-6-iodo-3H-imidazo[4,5-b]pyridine The title compound was prepared in nine steps from methyl 4-(benzyloxy)-3-hydroxy-5-methoxybenzoate, 2-bromo-1-(4,6-dimethylpyridin-3-yl)ethan-1-one, and 2-chloro-5-iodo-3-nitropyridine as described in Example 1-52-1 through Example 1-52-9.

Example 1-133-4: Preparation of 3-((2-(4,6-dimethylpyridin-3-yl)-8-methoxy-2,3-dihydrobenzo[b][1,4]dioxin-6-yl)methyl)-6-methoxy-3H-imidazo[4,5-b]pyridine The title compound was prepared from 3-((2-(4,6-dimethylpyridin-3-yl)-8-methoxy-2,3-dihydrobenzo[b][1,4]dioxin-6-yl)methyl)-6-iodo-3H-imidazo[4,5-b]pyridine and methanol as described in Example 1-11: $^1$H NMR (400 MHz, CDCl$_3$) δ 8.49 (s, 1H), 8.22 (d, J=2.6 Hz, 1H), 8.02 (s, 1H), 7.61 (d, J=2.6 Hz, 1H), 7.00 (s, 1H), 6.56-6.53 (m, 2H), 5.34 (s, 2H), 5.32-5.22 (m, 1H), 4.31 (dd, J=11.7, 2.4 Hz, 1H), 4.08 (dd, J=11.7, 8.7 Hz, 1H), 3.90 (s, 3H), 3.80 (s, 3H), 2.53 (s, 3H), 2.37 (s, 3H) ppm; (M+1)=433.

Example 1-134: Synthesis of 3-((2-(4,6-dimethylpyridin-3-yl)-8-methoxy-2,3-dihydrobenzo[b][1,4]dioxin-6-yl)methyl)-6-(3-methoxyazetidin-1-yl)-3H-imidazo[4,5-b]pyridine The title compound was prepared from 3-((2-(4,6-dimethylpyridin-3-yl)-8-methoxy-2,3-dihydrobenzo[b][1,4]dioxin-6-yl)methyl)-6-iodo-3H-imidazo[4,5-b]pyridine and 3-methoxyazetidine hydrochloride as described in Example 1-10: $^1$H NMR (400 MHz, CDCl$_3$) δ 8.48 (s, 1H), 7.93 (s, 1H), 7.78 (d, J=2.5 Hz, 1H), 7.15 (d, J=2.5 Hz, 1H), 6.98 (s, 1H), 6.54 (d, J=2.0 Hz, 1H), 6.52 (d, J=2.0 Hz, 1H), 5.27 (dd, J=9.0, 2.4 Hz, 1H), 4.43-4.36 (m, 1H), 4.30 (dd, J=11.7, 2.4 Hz, 1H), 4.23-4.16 (m, 2H), 4.08 (dd, J=11.7, 8.8 Hz, 1H), 3.83-3.72 (m, 4H), 3.36 (s, 3H), 2.51 (s, 3H), 2.35 (s, 3H) ppm; (M+1)=488.

Example 1-135: Synthesis of 4-(3-((8-methoxy-2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine Example 1-135-1: Preparation of 6-iodo-3-((8-methoxy-2-(4-methoxyphenyl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(4-methoxyphenyl)ethan-1-one, and 2-chloro-5-iodo-3-nitropyridine as described in Example 1-52-1 through Example 1-52-9.

Example 1-135-2: Preparation of 4-(3-((8-methoxy-2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine The title compound was prepared from 6-iodo-3-((8-methoxy-2-(4-methoxyphenyl)-2,3-dihydrobenzo[b][1,4]dioxin-6-yl)methyl)-3H-imidazo[4,5-b]pyridine and 2-methylbut-3-yn-2-amine as described in Example 1-5-8: $^1$H NMR (400 MHz, CDCl$_3$) δ 8.46 (d, J=1.8 Hz, 1H), 8.08 (d, J=1.8 Hz, 1H), 8.04 (s, 1H), 7.36-7.28 (m, 2H), 6.96-6.86 (m, 2H), 6.53 (d, J=2.0 Hz, 1H), 6.52 (d, J=2.0 Hz, 1H), 5.34 (s, 2H), 5.05 (dd, J=8.7, 2.4 Hz, 1H), 4.29 (dd, J=11.6, 2.4 Hz, 1H), 4.02 (dd, J=11.6, 8.7 Hz, 1H), 3.81 (s, 3H), 3.80 (s, 3H), 1.66 (br s, 2H), 1.54 (s, 6H) ppm; (M+1)=485.

Example 1-136: Synthesis of 3-((8-methoxy-2-(4-methoxyphenyl)-2,3-dihydrobenzo[b][1,4]dioxin-6-yl)methyl)-6-(1-methyl-1H-imidazol-4-yl)-3H-imidazo[4,5-b]pyridine The title compound was prepared from 6-iodo-3-((8-methoxy-2-(4-methoxyphenyl)-2,3-dihydrobenzo[b][1,4]dioxin-6-yl)methyl)-3H-imidazo[4,5-b]pyridine and 1-methyl-4-(4,4,5,5-tetramethyl-1,3,2-dioxaborolan-2-yl)-1H-imidazole as described in Example 1-55: $^1$H NMR (400 MHz, CDCl$_3$) δ 8.49 (d, J=1.8 Hz, 1H), 8.15-8.06 (m, 2H), 7.68 (s, 1H), 7.37-7.28 (m, 2H), 7.20 (s, 1H), 6.95-6.88 (m, 2H), 6.57-6.55 (m, 2H), 5.40 (s, 2H), 5.06 (dd, J=8.8, 2.5 Hz, 1H), 4.30 (dd, J=11.6, 2.5 Hz, 1H), 4.03 (dd, J=11.6, 8.6 Hz, 1H), 3.83 (s, 3H), 3.81 (s, 3H), 3.70 (s, 3H) ppm; (M+1)=484.

Example 1-137: Synthesis of 6-bromo-3-((2-(4-(difluoromethoxy)phenyl)-8-methoxy-2,3-dihydrobenzo[b][1,4]dioxin-6-yl)methyl)-3H-imidazo[4,5-b]pyridine hydrochloride

Example 1-137-1: Preparation of (2-(4-(difluoromethoxy)phenyl)-8-methoxy-2,3-dihydrobenzo[b][1,4]dioxin-6-yl)methanol The title compound was prepared in four steps from methyl 4-(benzyloxy)-3-hydroxy-5-methoxybenzoate and 2-bromo-1-(4-(difluoromethoxy)phenyl)ethan-1-one as described in Example 1-52-1 through Example 1-52-4.

Example 1-137-2: Preparation of 6-bromo-3-((2-(4-(difluoromethoxy)phenyl)-8-methoxy-2,3-dihydrobenzo[13][1,4]dioxin-6-yl)methyl)-3H-imidazo[4,5-b]pyridine hydrochloride To a stirred solution of 6-bromo-1H-imidazo[4,5-b]pyridine (0.67 g, 3.38 mmol) and (2-(4-(difluoromethoxy)phenyl)-8-methoxy-2,3-dihydrobenzo[b][1,4]dioxin-6-yl)methanol (1.00 g, 2.96 mmol) in toluene (30 mL) was added cyanomethylenetributylphosphorane (1.13 g, 4.43 mmol). The resulting mixture was allowed to stir at room temperature. After 1.5 h, the mixture was warmed to 60° C. and stirring was continued. After 2.5 h, the mixture was allowed to cool to room temperature and was concentrated. Chromatographic purification of the crude product (Biotage, 40 g silica gel column, 0-10% methanol/dichloromethane elute) provided 0.55 g (36%) of 6-bromo-3-((2-(4-(difluoromethoxy)phenyl)-8-methoxy-2,3-dihydrobenzo[b][1,4]dioxin-6-yl)methyl)-3H-imidazo[4,5-b]pyridine as a white solid. A small portion of this material was treated with excess 4M hydrogen chloride in 1,4-dioxane to provide 6-bromo-3-((2-(4-(difluoromethoxy)phenyl)-8-methoxy-2,3-dihydrobenzo[b][1,4]dioxin-6-yl)methyl)-3H-imidazo[4,5-b]pyridine hydrochloride as a white solid: $^1$H NMR (400 MHz, CD3OD) δ 9.45 (s, 1H), 8.82 (d, J=2.0 Hz, 1H), 8.51 (d, J=2.0 Hz, 1H), 7.50-7.46 (m, 2H), 7.21-7.14 (m, 2H), 7.03-6.63 (m, 3H), 5.58 (s, 2H), 5.13 (dd, J=8.3, 2.5 Hz, 1H), 4.38 (dd, J=11.6, 2.5 Hz, 1H), 4.02 (dd, J=11.6, 8.3 Hz, 1H), 3.83 (s, 3H) ppm; (M+1)=518.

Example 1-138: Synthesis of 3-((2-(4-(difluoromethoxy)phenyl)-8-methoxy-2,3-dihydrobenzo[b][1,4]dioxin-6-yl)methyl)-3H-imidazo[4,5-b]pyridine hydrochloride To a stirred solution of 6-bromo-3-((2-(4-(difluoromethoxy)phenyl)-8-methoxy-2,3-dihydrobenzo[b][1,4]dioxin-6-yl)methyl)-3H-imidazo[4,5-b]pyridine (0.050 g, 0.096 mmol) in methanol (10 mL) was added 10% palladium on carbon (0.070 g). The suspension was degassed and back filled with nitrogen (×3). The mixture was degassed again, and hydrogen was added via a ballon. After 40 min, the mixture was filtered through Celite with the aid of dichloromethane. The filtrate was concentrated, dissolved into dichloromethane, and re- filtered through a 0.1 □m TF filter. The filtrate was treated with excess 4M hydrogen chloride in 1,4-dioxane. The mixture was concentrated, and the residue was suspended in ethyl acetate. The suspension was concentrated, and the residue was re-suspended into ethyl acetate/diethyl ether (~1/5). The liquid phase was decanted, and the solids were washed with diethyl ether and dried to provide 0.020 g (44%) of 3-((2-(4-(difluoromethoxy)phenyl)-8-methoxy-2,3-dihydrobenzo[b][1,4]dioxin-6-yl)methyl)-3H-imidazo[4,5-b]pyridine hydrochloride as a white solid: $^1$H NMR (400 MHz, CD$_3$OD) δ 9.49 (s, 1H), 8.75 (dd, J=4.8, 1.3 Hz, 1H), 8.29 (dd, J=8.3, 1.3 Hz, 1H), 7.68 (dd, J=8.3, 4.8 Hz, 1H), 7.52-7.44 (m, 2H), 7.22-7.12 (m, 2H), 7.03-6.63 (m, 3H), 5.62 (s, 2H), 5.13 (dd, J=8.3, 2.4 Hz, 1H), 4.38 (dd, J=11.6, 2.5 Hz, 1H), 4.02 (dd, J=11.6, 8.3 Hz, 1H), 3.83 (s, 3H) ppm; (M+1)=440.

Example 1-139: Synthesis of 4-(3-((2-(4-(difluoromethoxy)phenyl)-8-methoxy-2,3-dihydrobenzo[b][1,4]dioxin-6-yl)methyl)-3H-imidazo[4,5-b]pyridin-6-yl)-2-methylbut-3-yn-2-amine The title compound was prepared from 6-bromo-3-((2-(4-(difluoromethoxy)phenyl)-8-methoxy-2,3-dihydrobenzo[b][1,4]dioxin-6-yl)methyl)-3H-imidazo[4,5-b]pyridine (Example 1-137-2) and 2-methylbut-3-yn-2-amine as described in Example 1-5-8: $^1$H NMR (400 MHz, CDCl$_3$) δ 8.46 (d, J=1.8 Hz, 1H), 8.10 (d, J=1.8 Hz, 1H), 8.06 (s, 1H), 7.41 (d, J=8.6 Hz, 2H), 7.15 (d, J=8.6 Hz, 2H), 6.74-6.25 (m, 3H), 5.34 (s, 2H), 5.10 (dd, J=8.5, 2.4 Hz, 1H), 4.32 (dd, J=11.6, 2.4 Hz, 1H), 4.01 (dd, J=11.6, 8.5 Hz, 1H), 3.81 (s, 3H), 1.56 (s, 6H) ppm; (M+1)=522.

Example 1-140: Synthesis of 1-(3-((2-(4-(difluoromethoxy)phenyl)-8-methoxy-2,3-dihydrobenzo[b][1,4]dioxin-6-yl)methyl)-3H-imidazo[4,5-b]pyridin-6-yl)-N,N-dimethylazetidin-3-amine The title compound was prepared from 6-bromo-3-((2-(4-(difluoromethoxy)phenyl)-8-methoxy-2,3-dihydrobenzo[b][1,4]dioxin-6-yl)methyl)-3H-imidazo[4,5 -b]pyridine (Example 1-137-2) and N,N-dimethylazetidin-3-amine hydrobromide as described in Example 1-65: $^1$H NMR (400 MHz, CDCl$_3$) δ 7.92 (s, 1H), 7.78 (d, J=2.5 Hz, 1H), 7.46-7.37 (m, 2H), 7.18-7.09 (m, 3H), 6.74-6.27 (m, 3H), 5.29 (s, 2H), 5.10 (dd, J=8.5, 2.4 Hz, 1H), 4.31 (dd, J=11.6, 2.4 Hz, 1H), 4.13-3.97 (m, 4H), 3.80 (s, 3H), 3.74-3.68 (m, 2H), 2.23 (s, 6H) ppm; (M+1)=538.

Example 1-141: Synthesis of 3-((2-(4-(difluoromethoxy)phenyl)-8-methoxy-2,3-dihydrobenzo[b][1,4]dioxin-6-yl)methyl)-N-methyl-3H-imidazo[4,5-b]pyridin-6-amine The title compound was prepared from 6-bromo-3-((2-(4-(difluoromethoxy)phenyl)-8-methoxy-2,3-dihydrobenzo[b][1,4]dioxin-6-yl)methyl)-3H-imidazo[4,5-b]pyridine (Example 1-137-2) and methylamine as described in Example 1-65: $^1$H NMR (400 MHz, CDCl$_3$) δ 7.95 (d, J=2.5 Hz, 1H), 7.94-7.90 (m, 1H), 7.45-7.38 (m, 2H), 7.28 (d, J=2.5 Hz, 1H), 7.18-7.13 (m, 2H), 6.71-6.30 (m, 3H), 5.30 (s, 2H), 5.10 (dd, J=8.5, 2.4 Hz, 1H), 4.31 (dd, J=11.6, 2.4 Hz, 1H), 4.01 (dd, J=11.6, 8.5 Hz, 1H), 3.81 (s, 3H), 2.91 (s, 3H) ppm; (M+1)=469.

Example 1-142: Synthesis of 7-chloro-3-((2-(4-(difluoromethoxy)phenyl)-8-methoxy-2,3-dihydrobenzo[b][1,4]dioxin-6-yl)methyl)imidazo[1,2-b]pyridazine

Example 1-142-1: Preparation of 2-(4-(difluoromethoxy)phenyl)-8-methoxy-2,3-dihydrobenzo[b][1,4]dioxine-6-carbaldehyde The title compound was prepared from (2-(4-(difluoromethoxy)phenyl)-8-methoxy-2,3-dihydrobenzo[b][1,4]dioxin-6-yl)methanol and manganese(IV) oxide as described in Example 1-86-3.

Example 1-142-2: Preparation of (7-chloroimidazo[1,2-b]pyridazin-3-yl)(2-(4-(difluoromethoxy)phenyl)-8-methoxy-2,3-dihydrobenzo[b][1,4]dioxin-6-yl)methanol The title compound was prepared from 3-bromo-7-chloroimidazo[1,2-b]pyridazine (Example 1-23-2) and 2-(4-(difluoromethoxy)phenyl)-8-methoxy-2,3-dihydrobenzo[b][1,4]dioxine-6-carbaldehyde as described in Example 1-23-3.

Example 1-142-3: Preparation of 7-chloro-3-((2-(4-(difluoromethoxy)phenyl)-8-methoxy-2,3-dihydrobenzo[b][1,4]dioxin-6-yl)methyl)imidazo[1,2-b]pyridazine The title compound was prepared from (7-chloroimidazo[1,2-b]pyridazin-3-yl)(2-(4-(difluoromethoxy)phenyl)-8-methoxy-2,3-dihydrobenzo[b][1,4]dioxin-6-yl)methanol as described in Example 1-22-2: $^1$H NMR (400 MHz, CDCl$_3$) δ 8.35 (d, J=2.3 Hz, 1H), 8.07 (d, J=2.4 Hz, 1H), 7.58 (s, 1H), 7.43 (d, J=8.6 Hz, 2H), 7.15 (d, J=8.6 Hz, 2H), 6.69-6.32 (m, 3H), 5.11 (dd, J=8.5, 2.4 Hz, 1H), 4.31 (dd, J=11.6, 2.4 Hz, 1H), 4.23 (s, 2H), 4.02 (dd, J=11.6, 8.5 Hz, 1H), 3.84 (s, 3H) ppm; (M+1)=474.

Example 1-143: Synthesis of 1-(3-((2-(4-(difluoromethoxy)phenyl)-8-methoxy-2,3-dihydrobenzo[b][1,4]dioxin-6-yl)methypimidazo[1,2-b]pyridazin-7-yl)-3-methylazetidin-3-ol The title compound was prepared from 7-chloro-3-((2-(4-(difluoromethoxy)phenyl)-8-methoxy-2,3-dihydrobenzo[b][1,4]dioxin-6-yl)methyl)imidazo[1,2-b]pyridazine and 3-methylazetidin-3-ol hydrochloride as described in Example 1-104: $^1$H NMR (400 MHz, CDCl$_3$) δ 7.73 (d, J=2.8 Hz, 1H), 7.44-7.42 (m, 2H), 7.17-7.12 (m, 2H), 6.69-6.31 (m, 5H), 5.09 (dd, J=8.5, 2.4 Hz, 1H), 4.30 (dd, J=11.5, 2.4 Hz, 1H), 4.12 (s, 2H), 4.04-3.93 (m, 4H), 3.91-3.86 (m, 2H), 3.82 (s, 3H), 1.64 (s, 3H) ppm; (M+1)=525.

Example 1-144: Synthesis of 3-((2-(4-(difluoromethoxy)phenyl)-8-methoxy-2,3-dihydrobenzo[b][1,4]dioxin-6-yl)methyl)imidazo[1,2-b]pyridazine (RA10878158)

The title compound was isolated as a side product from Example 1-143: $^1$H NMR (400 MHz, CDCl$_3$) δ 8.34 (dd, J=4.4, 1.6 Hz, 1H), 7.94 (dd, J=9.1, 1.6 Hz, 1H), 7.58 (s, 1H), 7.42 (d, J=8.6 Hz, 2H), 7.20-7.09 (m, 2H), 7.01 (dd, J=9.1, 4.4 Hz, 1H), 6.69-6.32 (m, 3H), 5.10 (dd, J=8.5, 2.4 Hz, 1H), 4.30 (dd, J=11.5, 2.4 Hz, 1H), 4.27 (s, 2H), 4.01 (dd, J=11.5, 8.5 Hz, 1H), 3.83 (s, 3H) ppm; (M+1)=440.

Example 1-145: Synthesis of 7-chloro-3-((2-(4-(difluoromethoxy)phenyl)-8-methoxy-2,3-dihydrobenzo[b][1,4]dioxin-6-yl)(methoxy)methyl)imidazo[1,2-b]pyridazine To a stirred solution of (7-chloroimidazo[1,2-b]pyridazin-3-yl)(2-(4-(difluoromethoxy)phenyl)-8-methoxy-2,3-dihydrobenzo[b][1,4]dioxin-6-yl)methanol (0.010 g, 0.020 mmol, Example 1-142-3) in dichloromethane (3 mL) was added deoxo-fluor (0.007 g, 0.031 mmol). The resulting mixture was allowed to stir at room temperature. After 2 h, the mixture was quenched by the addition of methanol (0.5 mL). After 15 min, four drops of 2N potassium hydroxide solution were added, and the mixture was allowed to stir at room temperature overnight. The phases were separated, and the organic phase was dried over magnesium sulfate, filtered, and concentrated. Chromatographic purification of the crude product (Biotage, 4 g silica gel column, 0-10% methanol/dichloromethane elute) provided 0.003 g (29%) of 7-chloro-3-((2-(4-(difluoromethoxy)phenyl)-8-methoxy-2,3-dihydrobenzo[b][1,4]dioxin-6-yl)(methoxy)methyl)imidazo[1,2-b]pyridazine as a yellow film: $^1$H NMR (400 MHz, CDCl$_3$) δ 8.36 (d, J=2.3 Hz, 1H), 8.03 (d, J=2.4 Hz, 1H), 7.59 (s, 1H), 7.48-7.39 (m, 2H), 7.16 (d, J=8.5 Hz, 2H), 6.72-6.33 (m, 3H), 5.72 (s, 1H), 5.17-5.10 (m, 1H), 4.34 (dd, J=11.6, 2.5 Hz, 1H), 4.08-4.04 (m, 1H), 3.87 (s, 3H), 3.47 (s, 3H) ppm; (M+1)=504.

Example 1-146: Synthesis of 4-(3-((2-(4-(difluoromethoxy)phenyl)-8-methoxy-2,3-dihydrobenzo[b][1,4]dioxin-6-yl)methypimidazo[1,2-b]pyridazin-7-yl)-2-methylbut-3-yn-2-amine The title compound was prepared from 7-chloro-3-((2-(4-(difluoromethoxy)phenyl)-8-methoxy-2,3-dihydrobenzo[b][1,4]dioxin-6-yl)methyl)imidazo[1,2-b]pyridazine (Example 1-142-3) and 2-methylbut-3-yn-2-amine as described in Example 1-23-5: $^1$H NMR (400 MHz, CDCl$_3$) δ 8.27 (d, J=2.0 Hz, 1H), 7.90 (d, J=2.0 Hz, 1H), 7.58 (s, 1H), 7.43 (d, J=8.6 Hz, 2H), 7.20-7.10 (m, 2H), 6.69-6.32 (m, 3H), 5.10 (dd, J=8.5, 2.4 Hz, 1H), 4.31 (dd, J=11.6, 2.4 Hz, 1H), 4.24 (s, 2H), 4.01 (dd, J=11.6, 8.5 Hz, 1H), 3.83 (s, 3H), 1.53 (s, 6H) ppm; (M+1)=521.

Example 1-147: Synthesis of 4-(3-((8-methoxy-2-(pyridin-3-yl)-2,3-dihydrobenzo[b][1,4]dioxin-6-yl)methyl)-3H-imidazo[4,5-b]pyridin-6-yl)-2-methylbut-3-yn-2-amine

Example 1-147-1: Preparation of 6-iodo-3-((8-methoxy-2-(pyridin-3-yl)-2,3-dihydrobenzo[b][1,4]dioxin-6-yl)methyl)-3H-imidazo[4,5-b]pyridine The title compound was prepared in nine steps methyl 4-(benzyloxy)-3-hydroxy-5-methoxybenzoate, 2-bromo-1-(pyridin-3-yl)ethan-1-one, and 2-chloro-5-iodo-3-nitropyridine as described in Example 1-52-1 through Example 1-52-9.

Example 1-147-2: Preparation of 4-(3-((8-methoxy-2-(pyridin-3-yl)-2,3-dihydrobenzo[b][1,4]dioxin-6-yl)methyl)-3H-imidazo[4,5-b]pyridin-6-yl)-2-methylbut-3-yn-2-amine The title compound was prepared from 6-iodo-3-((8-methoxy-2-(pyridin-3-yl)-2,3-dihydrobenzo[b][1,4]dioxin-6-yl)methyl)-3H-imidazo[4,5-b]pyridine and 2-methylbut-3-yn-2-amine as described in Example 1-5-8: $^1$H NMR (400 MHz, CDCl$_3$) δ 8.69-8.66 (m, 1H), 8.62 (dd, J=4.8, 1.7 Hz, 1H), 8.46 (d, J=1.8 Hz, 1H), 8.08 (d, J=1.8 Hz, 1H), 8.04 (s, 1H), 7.77-7.73 (m, 1H), 7.37-7.31 (m, 1H), 6.55-6.53 (m, 2H), 5.35 (s, 2H), 5.18 (d, J=8.2, 2.5 Hz, 1H), 4.36 (dd, J=11.6, 2.5 Hz, 1H), 4.07 (dd, J=11.6, 8.2 Hz, 1H), 3.81 (s, 3H), 1.73 (br s, 2H), 1.53 (s, 6H) ppm; (M+1)=456.

Example 1-148: Synthesis of 6-(1H-imidazol-1-yl)-3-((8-methoxy-2-(pyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(pyridin-3-yl)-2,3-dihydrobenzo[b][1,4]dioxin-6-yl)methyl)-3H-imidazo[4,5-b]pyridine (Example 1-147-1) and 1H-imidazole as described in Example 1-67: $^1$H NMR (400 MHz, CDCl$_3$) δ 8.68 (d, J=2.2 Hz, 1H), 8.63 (dd, J=4.8, 1.7 Hz, 1H), 8.54 (d, J=2.3 Hz, 1H), 8.17 (s, 1H), 8.09 (d, J=2.3 Hz, 1H), 7.87-7.85 (m, 1H), 7.78-7.72 (m, 1H), 7.37-7.32 (m, 1H), 7.32-7.30 (m, 1H), 7.29-7.27 (m, 1H), 6.59-6.55 (m, 2H), 5.41 (s, 2H), 5.19 (dd, J=8.2, 2.5 Hz, 1H), 4.37 (dd, J=11.6, 2.5 Hz, 1H), 4.09 (dd, J=11.6, 8.2 Hz, 1H), 3.85 (s, 3H) ppm; (M+1)=441.

Example 1-149: Synthesis of 4-(3-((8-methoxy-2-(2-methylthiazol-4-yl)-2,3-dihydrobenzo[b][1,4]dioxin-6-yl)methyl)-3H-imidazo[4,5-b]pyridin-6-yl)-2-methylbut-3-yn-2-amine

Example 1-149-1: Preparation of 4-(6-((6-iodo-3H-imidazo[4,5-b]pyridin-3-yl)methyl)-8-methoxy-2,3-dihydrobenzo[b][1,4]dioxin-2-yl)-2-methylthiazole The title compound was prepared in nine steps methyl 4-(benzyloxy)-3-hydroxy-5-methoxybenzoate, 2-bromo-1-(2-methylthiazol-4-yl)ethan-1-one, and 2-chloro-5-iodo-3-nitropyridine as described in Example 1-52-1 through Example 1-52-9.

Example 1-149-2: Preparation of 4-(3-((8-methoxy-2-(2-methylthiazol-4-yl)-2,3-dihydrobenzo[b][1,4]dioxin-6-yl)methyl)-3H-imidazo[4,5-b]pyridin-6-yl)-2-methylbut-3-yn-2-amine The title compound was prepared from 4-(6-((6-iodo-3H-imidazo[4,5-b]pyridin-3-yl)methyl)-8-methoxy-2,3-dihydrobenzo[b][1,4]dioxin-2-yl)-2-methylthiazole and 2-methylbut-3-yn-2-amine as described in Example 1-5-8: $^1$H NMR (400 MHz, CDCl$_3$) δ 8.46 (d, J=1.8 Hz, 1H), 8.08 (d, J=1.8 Hz, 1H), 8.02 (s, 1H), 7.20 (d, J=1.0 Hz, 1H), 6.52-6.50 (m, 2H), 5.38-5.30 (m, 3H), 4.49 (dd, J=11.4, 2.5 Hz, 1H), 4.28 (dd, J=11.4, 7.0 Hz, 1H), 3.81 (s, 3H), 2.70 (s, 3H), 1.56 (s, 6H) ppm; (M+1)=476.

Example 1-150: Synthesis of 4-(6-((6-(3-(1H-imidazol-1-yl)prop-1-yn-1-yl)-3H-imidazo[4,5-b]pyridin-3-yl)methyl)-8-methoxy-2,3-dihydrobenzo[b][1,4]dioxin-2-yl)-2-methylthiazole The title compound was prepared from 4-(6-((6-iodo-3H-imidazo[4,5-b]pyridin-3-yl)methyl)-8-methoxy-2,3-dihydrobenzo[b][1,4]dioxin-2-yl)-2-methylthiazole (Example 1-149-1) and 1-(prop-2-yn-1-yl)-1H-imidazole as described in Example 1-5-8: $^1$H NMR (400 MHz, CDCl$_3$) δ 8.51 (d, J=1.8 Hz, 1H), 8.14 (d, J=1.8 Hz, 1H), 8.07 (s, 1H), 7.77 (s, 1H), 7.20 (dd, J=1.0 Hz, 1H), 7.16-7.14 (m, 2H), 6.55-6.48 (m, 2H), 5.38-5.30 (m, 3H), 5.04 (s, 2H), 4.49 (dd, J=11.4, 2.5 Hz, 1H), 4.28 (dd, J=11.4, 7.1 Hz, 1H), 3.82 (s, 3H), 2.70 (s, 3H) ppm; (M+1)=499.

Example 1-151: Synthesis of 4-(3-((8-methoxy-2-(2-methylthiazol-4-yl)-2,3-dihydrobenzo[b][1,4]dioxin-6-yl)methyl)-3H-imidazo[4,5-b]pyridin-6-yl)morpholine The title compound was prepared from 4-(6-((6-iodo-3H-imidazo[4,5-b]pyridin-3-yl)methyl)-8-methoxy-2,3-dihydrobenzo[b][1,4]dioxin-2-yl)-2-methylthiazole (Example 1-149-1) and morpholine as described in Example 1-10: $^1$H NMR (400 MHz, CDCl$_3$) δ 8.28 (d, J=2.5 Hz, 1H), 8.06 (s, 1H), 7.63 (d, J=2.5 Hz, 1H), 7.20 (s, 1H), 6.55-6.48 (m, 2H), 5.38-5.27 (m, 3H), 4.49 (dd, J=11.4, 2.5 Hz, 1H), 4.29 (dd, J=11.4, 7.1 Hz, 1H), 3.96-3.88 (m, 4H), 3.83 (s, 3H), 3.23-3.15 (m, 4H), 2.70 (s, 3H) ppm; (M+1)=480.

Example 1-152: Synthesis of 4-(6-((3H-imidazo[4,5-b]pyridin-3-yl)methyl)-8-methoxy-2,3-dihydrobenzo[b][1,4]dioxin-2-yl)-2-cyclopropylthiazole

Example 1-152-1: Preparation of 2-bromo-1-(2-cyclopropylthiazol-4-yl)ethan-1-one The title compound was prepared from 2-cyclopropylthiazole-4-carbonyl chloride as described in Example 1-133-2.

Example 1-152-2: Preparation of 4-(6-((3H-imidazo[4,5-b]pyridin-3-yl)methyl)-8-methoxy-2,3-dihydrobenzo[b][1,4]dioxin-2-yl)-2-cyclopropylthiazole The title compound was prepared in nine steps from methyl 4-(benzyloxy)-3-hydroxy-5-methoxybenzoate, 2-bromo-1-(2-cyclopropylthiazol-4-yl)ethan-1-one, and 2-chloro-5-iodo-3-nitropyridine as described in Example 1-52-1 through Example 1-52-9: $^1$H NMR (400 MHz, CDCl$_3$) δ 8.44 (dd, J=4.8, 1.5 Hz, 1H), 8.12-8.01 (m, 2H), 7.26 (dd, J=8.1, 4.7 Hz, 1H), 7.10 (s, 1H), 6.56-6.48 (m, 2H), 5.39-5.27 (m, 3H), 4.47 (dd, J=11.4, 2.5 Hz, 1H), 4.26 (dd, J=11.4, 7.0 Hz, 1H), 3.82 (s, 3H), 2.33-2.24 (m, 1H), 1.32-0.96 (m, 4H) ppm; (M+1)=421.

Example 1-153: Synthesis of 4-(3-((2-(2-cyclopropylthiazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine

Example 1-153-1: Preparation of 2-cyclopropyl-4-(6-((6-iodo-3H-imidazo[4,5-b]pyridin-3-yl)methyl)-8-methoxy-2,3-dihydrobenzo[b][1,4]dioxin-2-yl)thiazole The title compound was prepared in nine steps from methyl 4-(benzyloxy)-3-hydroxy-5-methoxybenzoate, 2-bromo-1-(2-cyclopropylthiazol-4-yl)ethan-1-one (Example 1-152-1), and 2-chloro-5-iodo-3-nitropyridine as described in Example 1-52-1 through Example 1-52-9.

Example 1-153-2: Preparation of 4-(3-((2-(2-cyclopropylthiazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine The title compound was prepared from 2-cyclopropyl-4-(6-((6-iodo-3H-imidazo[4,5-b]pyridin-3-yl)methyl)-8-methoxy-2,3-dihydrobenzo[b][1,4]dioxin-2-yl)thiazole and 2-methylbut-3-yn-2-amine as described in Example 1-5-8: $^1$H NMR (400 MHz, CDCl$_3$) δ 8.46 (d, J=1.8 Hz, 1H), 8.10-8.00 (m, 2H), 7.13-7.08 (m, 1H), 6.54-6.47 (m, 2H), 5.35-5.27 (m, 3H), 4.48 (dd, J=11.4, 2.5 Hz, 1H), 4.26 (dd, J=11.4, 7.1 Hz, 1H), 3.81 (s, 3H), 2.33-2.24 (m, 1H), 1.53 (s, 6H), 1.17-1.05 (m, 2H), 1.08-0.96 (m, 2H) ppm; (M+1)=502.

Example 1-154: Synthesis of 2-cyclopropyl-4-(8-methoxy-6-((6-methoxy-3H-imidazo[4,5-b]pyridin-3-yl)methyl)-2,3-dihydrobenzo[b][1,4]dioxin-2-yl)thiazole The title compound was prepared from 2-cyclopropyl-4-(6-((6-iodo-3H-imidazo[4,5-b]pyridin-3-yl)methyl)-8-methoxy-2,3-dihydrobenzo[b][1,4]dioxin-2-yl)thiazole (Example 1-153-1) and methanol as described in Example 1-11: $^1$H NMR (400 MHz, CDCl$_3$) δ 8.20 (d, J=2.6 Hz, 1H), 7.97 (s, 1H), 7.59 (d, J=2.6 Hz, 1H), 7.10 (s, 1H), 6.55-6.47 (m, 2H), 5.39-5.27 (m, 3H), 4.47 (dd, J=11.4, 2.5 Hz, 1H), 4.25 (dd, J=11.4, 7.0 Hz, 1H), 3.91 (s, 3H), 3.82 (s, 3H), 2.33-2.24 (m, 1H), 1.17-0.93 (m, 4H) ppm; (M+1)=451.

Example 1-155: Synthesis of 4-(3-((2-(2,5-dimethylthiazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine

Example 1-155-1: Preparation of 2-bromo-1-(2,5-dimethylthiazol-4-yl)ethan-1-one The title compound was prepared in two steps from 2,5-dimethylthiazole-4-carboxylic acid as described in Example 1-133-1 through Example 1-133-2.

Example 1-155-2: Preparation of 4-(6-((6-iodo-3H-imidazo[4,5-b]pyridin-3-yl)methyl)-8-methoxy-2,3-dihydrobenzo[b][1,4]dioxin-2-yl)-2,5-dimethylthiazole The title compound was prepared in nine steps from methyl 4-(benzyloxy)-3-hydroxy-5-methoxybenzoate, 2-bromo-1-(2,5-dimethylthiazol-4-yl)ethan-1-one, and 2-chloro-5-iodo-3-nitropyridine as described in Example 1-52-1 through Example 1-52-9.

Example 1-155-3: Preparation of 4-(3-((2-(2,5-dimethylthiazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine The title compound was prepared from 4-(6-((6-iodo-3H-imidazo[4,5-b]pyridin-3-yl)methyl)-8-methoxy-2,3-dihydrobenzo[b][1,4]dioxin-2-yl)-2,5-dimethylthiazole and 2-methylbut-3-yn-2-amine as described in Example 1-5-8: $^1$H NMR (400 MHz, CDCl$_3$) δ 8.45 (d, J=1.7 Hz, 1H), 8.18-8.06 (m, 2H), 6.53 (d, J=2.0 Hz, 1H), 6.50 (d, J=2.0 Hz, 1H), 5.34 (s, 2H), 5.18 (dd, J=8.8, 2.5 Hz, 1H), 4.44 (dd, J=11.6, 8.8 Hz, 1H), 4.34 (dd, J=11.6, 2.5 Hz, 1H), 3.78 (s, 3H), 2.61 (s, 3H), 2.45 (s, 3H), 1.60 (s, 6H) ppm; (M+1)=490.

Example 1-156: Synthesis of 4-(3-((8-methoxy-2-(2-methyloxazol-4-yl)-2,3-dihydrobenzo[b][1,4]dioxin-6-yl)methyl)-3H-imidazo[4,5-b]pyridin-6-yl)-2-methylbut-3-yn-2-amine

Example 1-156-1: Preparation of 2-bromo-1-(2-methyloxazol-4-yl)ethan-1-one

The title compound was prepared in two steps from 2-methyloxazole-4-carboxylic acid as described in Example 1-133-1 through Example 1-133-2.

Example 1-156-2: Preparation of 4-(6-((6-iodo-3H-imidazo[4,5-b]pyridin-3-yl)methyl)-8-methoxy-2,3-dihydrobenzo[b][1,4]dioxin-2-yl)-2-methyloxazole The title compound was prepared in nine steps from methyl 4-(benzyloxy)-3-hydroxy-5-methoxybenzoate, 2-bromo-1-(2-methyloxazol-4-yl)ethan-1-one, and 2-chloro-5-iodo-3-nitropyridine as described in Example 1-52-1 through Example 1-52-9.

Example 1-156-3: Preparation of 4-(3-((8-methoxy-2-(2-methyloxazol-4-yl)-2,3-dihydrobenzo[b][1,4]dioxin-6-yl)methyl)-3H-imidazo[4,5-b]pyridin-6-yl)-2-methylbut-3-yn-2-amine The title compound was prepared from 4-(6-((6-iodo-3H-imidazo[4,5-b]pyridin-3-yl)methyl)-8-methoxy-2,3-dihydrobenzo[b][1,4]dioxin-2-yl)-2-methyloxazole and 2-methylbut-3-yn-2-amine as described in Example 1-5-8: $^1$H NMR (400 MHz, CDCl$_3$) δ 8.46 (d, J=1.8 Hz, 1H), 8.07 (d, J=1.8 Hz, 1H), 8.02 (s, 1H), 7.58 (s, 1H), 6.53-6.47 (m, 2H), 5.33 (s, 2H), 5.19 (dd, J=6.9, 2.5, 1H), 4.40 (dd, J=11.5, 2.5 Hz, 1H), 4.29 (dd, J=11.5, 6.9 Hz, 1H), 3.79 (s, 3H), 2.44 (s, 3H), 1.53 (s, 6H) ppm; (M+1)=460.

Example 1-157: Synthesis of 4-(3-((2-(2,5-dimethyloxazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine

Example 1-157-1: Preparation of 2-bromo-1-(2,5-dimethyloxazol-4-yl)ethan-1-one The title compound was prepared in two steps from 2,5-dimethyloxazole-4-carboxylic acid as described in Example 1-133-1 through Example 1-133-2.

Example 1-157-2: Preparation of 4-(6-((6-iodo-3H-imidazo[4,5-b]pyridin-3-yl)methyl)-8-methoxy-2,3-dihydrobenzo[b][1,4]dioxin-2-yl)-2,5-dimethyloxazole The title compound was prepared in nine steps from methyl 4-(benzyloxy)-3-hydroxy-5-methoxybenzoate, 2-bromo-1-(2,5-dimethyloxazol-4-yl)ethan-1-one, and 2-chloro-5-iodo-3-nitropyridine as described in Example 1-52-1 through Example 1-52-9.

Example 1-157-3: Preparation of 4-(3-((2-(2,5-dimethyloxazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine The title compound was prepared from 4-(6-((6-iodo-3H-imidazo[4,5-b]pyridin-3-yl)methyl)-8-methoxy-2,3-dihydrobenzo[b][1,4]dioxin-2-yl)-2,5-dimethyloxazole and 2-methylbut-3-yn-2-amine as described in Example 1-5-8: $^1$H NMR (400 MHz, CDCl$_3$) δ 8.46 (d, J=1.8 Hz, 1H), 8.10-8.00 (m, 2H), 6.54-6.46 (m, 2H), 5.33 (s, 2H), 5.05 (dd, J=7.9, 2.9 Hz, 1H), 4.42-4.27 (m, 2H), 3.78 (s, 3H), 2.38 (s, 3H), 2.31 (s, 3H), 1.53 (s, 6H) ppm; (M+1)=473.

Example 1-158: Synthesis of 3-((8-methoxy-2-(6-(2-methoxyethoxy)pyridin-3-yl)-2,3-dihydrobenzo[b][1,4]dioxin-6-yl)methyl)-3H-imidazo[4,5-b]pyridine

Example 1-158-1: Preparation of 2-bromo-1-(6-(2-methoxyethoxy)pyridin-3-yl)ethan-1-one The title compound was prepared from 1-(6-(2-methoxyethoxy)pyridin-3-yl)ethan-1-one as described in Example 1-110-2.

Example 1-158-2: Preparation of 3-((8-methoxy-2-(6-(2-methoxyethoxy)pyridin-3-yl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-(2-methoxyethoxy)pyridin-3-yl)ethan-1-one, and 2-chloro-3-nitropyridine as described in Example 1-52-1 through Example 1-52-9: $^1$H NMR (400 MHz, CDCl$_3$) δ 8.44 (dd, J=4.8, 1.4 Hz, 1H), 8.17 (d, J=2.4 Hz, 1H), 8.09 (dd, J=8.0, 1.4 Hz, 1H), 8.05 (s, 1H), 7.61 (dd, J=8.6, 2.5 Hz, 1H), 7.32-7.23 (m, 1H), 6.83 (d, J=8.6 Hz, 1H), 6.55-6.53 (m, 2H), 5.37 (s, 2H), 5.08 (dd, J=8.4, 2.4 Hz, 1H), 4.52-4.43 (m, 2H), 4.30 (dd, J=11.6, 2.4 Hz, 1H), 4.06 (dd, J=11.6, 8.4 Hz, 1H), 3.80 (s, 3H), 3.76-3.71 (m, 2H), 3.43 (s, 3H) ppm; (M+1)=449.

Example 1-159: Synthesis of 4-(3-((8-methoxy-2-(6-(2-methoxyethoxy)pyridin-3-yl)-2,3-dihydrobenzo[b][1,4]dioxin-6-yl)methyl)-3H-imidazo[4,5-b]pyridin-6-yl)-2-methylbut-3-yn-2-amine

Example 1-159-1: Preparation of 6-iodo-3-((8-methoxy-2-(6-(2-methoxyethoxy)pyridin-3-yl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-(2-methoxyethoxy)pyridin-3-yl)ethan-1-one (Example 1-158-1), and 2-chloro-5-iodo-3-nitropyridine as described in Example 1-52-1 through Example 1-52-9.

Example 1-159-2: Preparation of 4-(3-((8-methoxy-2-(6-(2-methoxyethoxy)pyridin-3-yl)-2,3-dihydrobenzo[b][1,4]dioxin-6-yl)methyl)-3H-imidazo[4,5-b]pyridin-6-yl)-2-methylbut-3-yn-2-amine The title compound was prepared from 6-iodo-3-((8-methoxy-2-(6-(2-methoxyethoxy)pyridin-3-yl)-2,3-dihydrorobenzo[b][1,4]dioxin-6-yl)methyl)-3H-imidazo[4,5-b]pyridine and 2-methylbut-3-yn-2-amine as described in Example 1-5-8: $^1$H NMR (400 MHz, CDCl$_3$) δ 8.46 (d, J=1.8 Hz, 1H), 8.17 (d, J=2.4 Hz, 1H), 8.12-7.99 (m, 2H), 7.61 (dd, J=8.6, 2.5 Hz, 1H), 6.83 (d, J=8.6 Hz, 1H), 6.54-6.52 (m, 2H), 5.34 (s, 2H), 5.08 (dd, J=8.4, 2.5 Hz, 1H), 4.55-4.42 (m, 2H), 4.30 (dd, J=11.6, 2.5 Hz, 1H), 4.06 (dd, J=11.6, 8.4 Hz, 1H), 3.80 (s, 3H), 3.79-3.64 (m, 2H), 3.43 (s, 3H), 1.67 (bs, 2H), 1.53 (s, 6H) ppm; (M+1)=530.

Example 1-160: Synthesis of 3-((8-methoxy-2-(6-(2-methoxyethoxy)pyridin-3-yl)-2,3-dihydrobenzo[b][1,4]dioxin-6-yl)methyl)-6-(1-methyl-1H-imidazol-4-yl)-3H-imidazo[4,5-b]pyridine The title compound was prepared from 6-iodo-3-((8-methoxy-2-(6-(2-methoxyethoxy)pyridin-3-yl)-2,3-dihydrobenzo[b][1,4]dioxin-6-yl)methyl)-3H-imidazo[4,5-b]pyridine and 1-methyl-4-(4,4,5,5-tetramethyl-1,3,2-dioxaborolan-2-yl)-1H-imidazole as described in Example 1-55: $^1$H NMR (400 MHz, CDCl$_3$) δ 8.49 (d, J=1.9 Hz, 1H), 8.18 (d, J=2.4 Hz, 1H), 8.15-8.05 (m, 2H), 7.69-7.53 (m, 2H), 7.18 (s, 1H), 6.84 (d, J=8.6 Hz, 1H), 6.58-6.56 (m, 2H), 5.40 (s, 2H), 5.09 (dd, J=8.4, 2.5 Hz, 1H), 4.57-4.42 (m, 2H), 4.31 (dd, J=11.6, 2.5 Hz, 1H), 4.07 (dd, J=11.6, 8.4 Hz, 1H), 3.83 (s, 3H), 3.81-3.62 (m, 5H), 3.43 (s, 3H) ppm; (M+1)=529.

Example 1-161: Synthesis of 6-methoxy-3-((8-methoxy-2-(6-(2-methoxyethoxy)pyridin-3-yl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-(2-methoxyethoxy)pyridin-3-yl)ethan-1-one (Example 1-158-1), and 2-chloro-5-methoxy-3-nitropyridine as described in Example 1-52-1 through Example 1-52-9: $^1$H NMR (400 MHz, CDCl$_3$) δ 8.21 (d, J=2.6 Hz, 1H), 8.17 (t, J=2.6 Hz, 1H), 7.98 (s, 1H), 7.67-7.53 (m, 2H), 6.89-6.76 (m, 1H), 6.54-6.52 (m, 2H), 5.33 (s, 2H), 5.08 (dd, J=8.4, 2.4 Hz, 1H), 4.51-4.42 (m, 2H), 4.29 (dd, J=11.6, 2.4 Hz, 1H), 4.05 (dd, J=11.6, 8.4 Hz, 1H), 3.91 (s, 3H), 3.80 (s, 3H), 3.76-3.66 (m, 2H), 3.43 (s, 3H) ppm; (M+1)=479.

Example 1-162: Synthesis of 3-((2-(6-ethoxypyridin-3-yl)-8-methoxy-2,3-dihydrobenzo[b][1,4]dioxin-6-yl)methyl)-3H-imidazo[4,5-b]pyridine

Example 1-162-1: Preparation of 2-bromo-1-(6-ethoxypyridin-3-yl)ethan-1-one

The title compound was prepared in two steps from 6-ethoxynicotinic acid as described in Example 1-133-1 through Example 1-133-2.

Example 1-162-2: Preparation of 3-((2-(6-ethoxypyridin-3-yl)-8-methoxy-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-ethoxypyridin-3-yl)ethan-1-one, and 2-chloro-3-nitropyridine as described in Example 1-52-1 through Example 1-52-9: $^1$H NMR (400 MHz, CDCl$_3$) δ 8.44 (dd, J=4.8, 1.4 Hz, 1H), 8.19-8.16 (m, 1H), 8.09 (dd, J=8.0, 1.4 Hz, 1H), 8.04 (s, 1H), 7.60 (dd, J=8.6, 2.5 Hz, 1H), 7.27 (dd, J=8.0, 4.8 Hz, 1H), 6.77-6.72 (m, 1H), 6.55-6.53 (m, 2H), 5.38 (s, 2H), 5.08 (dd, J=8.5, 2.5 Hz, 1H), 4.36 (q, J=7.1 Hz, 2H), 4.30 (dd, J=11.6, 2.5 Hz, 1H), 4.06 (dd, J=11.6, 8.5 Hz, 1H), 3.80 (s, 3H), 1.38 (t, J=7.1 Hz, 3H) ppm; (M+1)=419.

Example 1-163: Synthesis of 3-((2-(6-ethoxypyridin-3-yl)-8-methoxy-2,3-dihydrobenzo[b][1,4]dioxin-6-yl)methyl)-6-methoxy-3H-imidazo[4,5-b]pyridine The title compound was prepared in nine steps from methyl 4-(benzyloxy)-3-hydroxy-5-methoxybenzoate, 2-bromo-1-(6-ethoxypyridin-3-yl)ethan-1-one (Example 1-162-1), and 2-chloro-5-methoxy-3-nitropyridine as described in Example 1-52-1 through Example 1-52-9: $^1$H NMR (400 MHz, CDCl$_3$) δ 8.21 (d, J=2.4 Hz, 1H), 8.18 (d, J=2.4 Hz, 1H), 7.98 (s, 1H), 7.64-7.56 (m, 2H), 6.74 (d, J=8.6 Hz, 1H), 6.54-6.52 (m, 2H), 5.33 (s, 2H), 5.08 (dd, J=8.4, 2.5 Hz, 1H), 4.36 (q, J=7.1 Hz, 2H), 4.30 (dd, J=11.6, 2.5 Hz, 1H), 4.06 (dd, J=11.6, 8.4 Hz, 1H), 3.91 (s, 3H), 3.80 (s, 3H), 1.38 (t, J=7.1 Hz, 3H) ppm; (M+1)=449.

Example 1-164: Synthesis of (3-((2-(6-ethoxypyridin-3-yl)-8-methoxy-2,3-dihydrobenzo[b][1,4]dioxin-6-yl)methyl)-3H-imidazo[4,5-b]pyridin-6-yl)methanol

Example 1-164-1: Preparation of methyl 3-((2-(6-ethoxypyridin-3-yl)-8-methoxy-2,3-dihydrobenzo[b][1,4]dioxin-6-yl)methyl)-3H-imidazo[4,5-b]pyridine-6-carboxylate The title compound was prepared in nine steps from methyl 4-(benzyloxy)-3-hydroxy-5-methoxybenzoate, 2-bromo-1-(6-ethoxypyridin-3-yl)ethan-1-one (Example 1-162-1), and methyl 6-chloro-5-nitronicotinate as described in Example 1-52-1 through Example 1-52-9.

Example 1-164-2: Preparation of (3-((2-(6-ethoxypyridin-3-yl)-8-methoxy-2,3-dihydrobenzo[b][1,4]dioxin-6-yl)methyl)-3H-imidazo[4,5-b]pyridin-6-yl)methanol The title compound was prepared from 3-((2-(6-ethoxypyridin-3-yl)-8-methoxy-2,3-dihydrobenzo[b][1,4]dioxin-6-yl)methyl)-3H-imidazo[4,5-b]pyridine-6-carboxylate as described in Example 1-117-1: $^1$H NMR (400 MHz, CDCl$_3$) δ 8.46 (s, 1H), 8.18 (d, J=2.4 Hz, 1H), 8.13-8.02 (m, 2H), 7.64-7.54 (m, 1H), 6.75 (d, J=8.5 Hz, 1H), 6.57-6.50 (m, 2H), 5.37 (s, 2H), 5.07 (dd, J=8.5, 2.5 Hz, 1H), 4.87 (s, 2H), 4.42-4.26 (m, 3H), 4.06 (dd, J=11.6, 8.5 Hz, 1H), 3.80 (s, 3H), 1.38 (t, J=7.0 Hz, 3H) ppm; (M+1)=449.

Example 1-165: Synthesis of 3-((2-(6-ethoxypyridin-3-yl)-8-methoxy-2,3-dihydrobenzo[b][1,4]dioxin-6-yl)methyl)-1H-pyrrolo[2,3-b]pyridine

Example 1-165-1: Preparation of (2-(6-ethoxypyridin-3-yl)-8-methoxy-2,3-dihydrobenzo[b][1,4]dioxin-6-yl)methanol The title compound was prepared in four steps from methyl 4-(benzyloxy)-3-hydroxy-5-methoxybenzoate and 2-bromo-1-(6-ethoxypyridin-3-yl)ethan-1-one (Example 1-162-1) as described in Example 1-52-1 through Example 1-52-4.

Example 1-165-2: Preparation of 5-(6-(bromomethyl)-8-methoxy-2,3-dihydrobenzo[b][1,4]dioxin-2-yl)-2-ethoxypyridine The title compound was prepared from (2-(6-ethoxypyridin-3-yl)-8-methoxy-2,3-dihydrobenzo[b][1,4]dioxin-6-yl)methanol and carbon tetrabromide as described in Example 1-109-1.

Example 1-165-3: Preparation of 3-((2-(6-ethoxypyridin-3-yl)-8-methoxy-2,3-dihydrobenzo[b][1,4]dioxin-6-yl)methyl)-1H-pyrrolo[2,3-b]pyridine The title compound was prepared from 5-(6-(bromomethyl)-8-methoxy-2,3-dihydrobenzo[b][1,4]dioxin-2-yl)-2-ethoxypyridine and tert-butyl 3-(4,4,5,5-tetramethyl-1,3,2-dioxaborolan-2-yl)-1H-pyrrolo[2,3-b]pyridine-1-carboxylate as described in Example 1-55. The product of this reaction was de-protected with trifluoroacetic acid as described in Example 1-12-5: $^1$H NMR (400 MHz, CDCl$_3$) δ 9.41 (s, 1H), 8.32-8.26 (m, 1H), 8.19 (d, J=2.6 Hz, 1H), 7.81 (d, J=7.9 Hz, 1H), 7.62 (dd, J=8.7, 2.6 Hz, 1H), 7.11 (s, 1H), 7.04 (dd, J=7.9, 4.6 Hz, 1H), 6.75 (d, J=8.7 Hz, 1H), 6.52-6.42 (m, 2H), 5.12-5.04 (m, 1H), 4.36 (q, J=7.1 Hz, 2H), 4.28 (dd, J=11.6, 2.5 Hz, 1H), 4.07 (dd, J=11.6, 8.5 Hz, 1H), 4.01 (s, 2H), 3.80 (s, 3H), 1.39 (t, J=7.1 Hz, 3H) ppm; (M+1)=418.

Example 1-166: Synthesis of 3-((2-(6-(difluoromethoxy)pyridin-3-yl)-8-methoxy-2,3-dihydrobenzo[b][1,4]dioxin-6-yl)methyl)-6-methoxy-3H-imidazo[4,5-b]pyridine The title compound was prepared in nine steps from methyl 4-(benzyloxy)-3-hydroxy-5-methoxybenzoate, 2-bromo-1-(6-(difluoromethoxy)pyridin-3-yl)ethan-1-one, and 2-chloro-5-methoxy-3-nitropyridine as described in Example 1-52-1 through Example 1-52-9: $^1$H NMR (400 MHz, CDCl$_3$) δ 8.28-8.17 (m, 2H), 8.00 (s, 1H), 7.78 (dd, J=8.5, 2.4 Hz, 1H), 7.66-7.24 (m, 2H), 6.94 (dd, J=8.5, 0.7 Hz, 1H), 6.58-6.49 (m, 2H), 5.33 (s, 2H), 5.15 (dd, J=8.1, 2.5 Hz, 1H), 4.32 (dd, J=11.6, 2.5 Hz, 1H), 4.06 (dd, J=11.6, 8.1 Hz, 1H), 3.91 (s, 3H), 3.81 (s, 3H) ppm; (M+1)=471.

Example 1-167: Synthesis of 1-(3-((2-(6-(difluoromethoxy)pyridin-3-yl)-8-methoxy-2,3-dihydrobenzo[b][1,4]dioxin-6-yl)methyl)-3H-imidazo[4,5-b]pyridin-6-yl)-3-methylazetidin-3-ol

Example 1-167-1: Preparation of 3-((2-(6-(difluoromethoxy)pyridin-3-yl)-8-methoxy-2,3-dihydrobenzo[b][1,4]dioxin-6-yl)methyl)-6-iodo-3H-imidazo[4,5-b]pyridine The title compound was prepared in nine steps from methyl 4-(benzyloxy)-3-hydroxy-5-methoxybenzoate, 2-bromo-1-(6-(difluoromethoxy)pyridin-3-yl)ethan-1-one, and 2-chloro-5-iodo-3-nitropyridine as described in Example 1-52-1 through Example 1-52-9.

Example 1-167-2: Preparation of 1-(3-((2-(6-(difluoromethoxy)pyridin-3-yl)-8-methoxy-2,3-dihydrobenzo[b][1,4]dioxin-6-yl)methyl)-3H-imidazo[4,5-b]pyridin-6-yl)-3-methylazetidin-3-ol The title compound was prepared from 3-((2-(6-(difluoromethoxy)pyridin-3-yl)-8-methoxy-2,3-dihydrobenzo[b]

[1,4]dioxin-6-yl)methyl)-6-iodo-3H-imidazo[4,5-b]pyridine and 3-methylazetidin-3-ol hydrochloride as described in Example 1-10: $^1$H NMR (400 MHz, CDCl$_3$) δ 8.24 (d, J=2.5 Hz, 1H), 7.92 (s, 1H), 7.78 (dd, J=8.6, 2.5 Hz, 1H), 7.73 (d, J=2.5 Hz, 1H), 7.46 (t, J=73 Hz, 1H), 7.11 (d, J=2.5 Hz, 1H), 6.93 (dd, J=8.4, 0.7 Hz, 1H), 6.55-6.47 (m, 2H), 5.28 (s, 2H), 5.14 (dd, J=8.1, 2.4 Hz, 1H), 4.32 (dd, J=11.6, 2.4 Hz, 1H), 4.05 (dd, J=11.6, 8.1 Hz, 1H), 3.96-3.88 (m, 2H), 3.80-3.77 (m, 5H), 1.64 (s, 3H) ppm; (M+1)=526.

Example 1-168: Synthesis of 3-((2-(6-(difluoromethoxy)pyridin-3-yl)-8-methoxy-2,3-dihydrobenzo[b][1,4]dioxin-6-yl)methyl)-3H-imidazo[4,5-b]pyridine To a stirred solution of 3-((2-(6-(difluoromethoxy)pyridin-3-yl)-8-methoxy-2,3-dihydrobenzo[b][1,4]dioxin-6-yl)methyl)-6-iodo-3H-imidazo[4,5-b]pyridine (0.14 g, 0.25 mmol) in tetrahydrofuran (15 mL) was added 2.0M lithium aluminum hydride solution in tetrahydrofuran (0.32 mL, 0.64 mmol). After 5 min, the mixture was quenched by the addition of water (5 drops) and 50% sodium hydroxide solution (3 drops). The mixture was diluted with dichloromethane, and the resulting solution was dried over sodium sulfate, filtered, and concentrated. Chromatographic purification of the crude product (Biotage, 12 g silica gel column, 0-30% methanol/ethyl acetate elute) provided 0.064 g (59%) of 3-((2-(6-(difluoromethoxy)pyridin-3-yl)-8-methoxy-2,3-dihydrobenzo [b][1,4]dioxin-6-yl)methyl)-3H-imidazo[4,5-b]pyridine as a white solid: $^1$H NMR (400 MHz, CDCl$_3$) δ 8.44 (dd, J=4.8, 1.4 Hz, 1H), 8.24 (d, J=2.5 Hz, 1H), 8.10 (dd, J=8.1, 1.4 Hz, 1H), 8.06 (s, 1H), 7.78 (dd, J=8.5, 2.5 Hz, 1H), 7.67-7.28 (m, 1H), 7.27-7.22 (m, 1H), 6.94 (dd, J=8.5, 0.7 Hz, 1H), 6.59-6.50 (m, 2H), 5.38 (s, 2H), 5.15 (dd, J=8.1, 2.4 Hz, 1H), 4.33 (dd, J=11.6, 2.4 Hz, 1H), 4.06 (dd, J=11.6, 8.1 Hz, 1H), 3.81 (s, 3H) ppm; (M+1)=441.

Example 1-169: Synthesis of 3-((8-methoxy-2,3-dihydrobenzo[b][1,4]dioxin-6-yl)methyl)-6-(1-(piperidin-4-yl)-1H-pyrazol-4-yl)-3H-imidazo[4,5-b]pyridine

Example 1-169-1: Preparation of 6-iodo-3-((8-methoxy-2,3-dihydrobenzo[b][1,4]dioxin-6-yl)methyl)-3H-imidazo[4,5-b]pyridine The title compound was prepared three steps from (8-methoxy-2,3-dihydrobenzo[b][1,4]dioxin-6-yl)methanamine and 2-chloro-5-iodo-3-nitropyridine as described in Example 1-52-7 and Example 1-52-9.

Example 1-169-2: Preparation of tert-butyl 4-(4-(3-((8-methoxy-2,3-dihydrobenzo[b][1,4]dioxin-6-yl)methyl)-3H-imidazo[4,5-b]pyridin-6-yl)-1H-pyrazol-1-yl)piperidine-1-carboxylate The title compound was prepared from 6-iodo-3-((8-methoxy-2,3-dihydrobenzo[b][1,4]dioxin-6-yl)methyl)-3H-imidazo[4,5-b]pyridine and (1-(1-(tert-butoxycarbonyl)piperidin-4-yl)-1H-pyrazol-4-yl)boronic acid as described in Example 1-4.

Example 1-169-3: Preparation of 3-((8-methoxy-2,3-dihydrobenzo[b][1,4]dioxin-6-yl)methyl)-6-(1-(piperidin-4-yl)-1H-pyrazol-4-yl)-3H-imidazo[4,5-b]pyridine To a stirred solution of tert-butyl 4-(4-(3-((8-methoxy-2,3-dihydrobenzo[b][1,4]dioxi-6-yl)methyl)-3H-imidazo[4,5-b]pyridin-6-yl)-1H-pyrazol-1-yl)piperidine-1-carboxylate (0.12 g, 0.21 mmol) in 1,4-dioxane (2 mL) was added 4.0M hydrogen chloride in 1,4-dioxane (2.0 mL, 8.00 mmol). The mixture was allowed to stir at room temperature. After 1 h, the mixture was partitioned between ethyl acetate and water. The aqueous phase was washed with ethyl acetate. The aqueous phase was neutralized with saturated sodium bicarbonate solution, and then it was extracted with a 1:5 mixture of isopropanol/chloroform. The organic phase was washed with brine, dried over magnesium sulfate, filtered, and concentrated to provide 0.073 g (77%) of the 3-((8-methoxy-2,3-dihydrobenzo[b][1,4]dioxin-6-yl)methyl)-6-(1-(piperidin-4-yl)-1H-pyrazol-4-yl)-3H-imidazo[4,5-b] pyridine as a white solid: $^1$H NMR (400 MHz, CDCl$_3$) δ 8.58 (d, J=1.9 Hz, 1H), 8.12 (d, J=2.0 Hz, 1H), 8.02 (s, 1H), 7.82 (d, J=0.8 Hz, 1H), 7.73 (d, J=0.8 Hz, 1H), 6.54-6.47 (m, 2H), 5.34 (s, 2H), 4.35-4.20 (m, 4H), 4.05-3.98 (m, 1H), 3.82 (s, 3H), 3.33-3.24 (m, 2H), 2.86-2.75 (m, 2H), 2.28-2.18 (m, 2H), 2.05-1.97 (m, 2H) ppm; (M+1)=447.

Example 1-170: Synthesis of 3-((8-methoxy-2-methyl-2,3-dihydrobenzo[b][1,4]dioxin-6-yl)methyl)-6-(1-(piperidin-4-yl)-1H-pyrazol-4-yl)-3H-imidazo[4,5-b]pyridine

Example 1-170-1: Preparation of 6-iodo-3-((8-methoxy-2-methyl-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, chloroacetone, and 2-chloro-5-iodo-3-nitropyridine as described in Example 1-52-1 through Example 1-52-9.

Example 1-170-2: Preparation of 3-((8-methoxy-2-methyl-2,3-dihydrobenzo[b][1,4]dioxin-6-yl)methyl)-6-(1-(piperidin-4-yl)-1H-pyrazol-4-yl)-3H-imidazo[4,5-b]pyridine The title compound was prepared in two steps from 6-iodo-3-((8-methoxy-2-methyl-2,3-dihydrobenzo[b][1,4] dioxin-6-yl)methyl)-3H-imidazo[4,5-b]pyridine and (1-(1-(tert-butoxycarbonyl)piperidin-4-yl)-1H-pyrazol-4-yl)boronic acid as described in Example 1-169-2 through Example 1-169-3: $^1$H NMR (400 MHz, CDCl$_3$) δ 8.58 (d, J=2.0 Hz, 1H), 8.12 (d, J=2.0 Hz, 1H), 8.02 (s, 1H), 7.82 (s, 1H), 7.74 (s, 1H), 6.51-6.49 (m, 2H), 5.34 (s, 2H), 4.36-4.07 (m, 3H), 3.86-3.75 (m, 4H), 3.35-3.25 (m, 2H), 2.88-2.76 (m, 2H), 2.28-2.20 (m, 2H), 2.04-1.92 (m, 2H), 1.41 (d, J=6.4 Hz, 3H) ppm; (M+1)=461.

Example 1-171: Synthesis of 3-((8-methoxy-2-methyl-2,3-dihydrobenzo[b][1,4]dioxin-6-yl)methyl)-6-(pyridin-3-yl)-3H-imidazo[4,5-b]pyridine formate The title compound was prepared from 6-iodo-3-((8-methoxy-2-methyl-2,3-dihydrobenzo[b][1,4]dioxin-6-yl)methyl)-3H-imidazo[4,5-b]pyridine (Example 1-170-1) and 3-(4,4,5,5-tetramethyl-1,3,2-dioxaborolan-2-yl)pyridine as described in Example 1-55: $^1$H NMR (400 MHz, CD$_3$OD) δ 8.88 (dd, J=2.4, 0.9 Hz, 1H), 8.71 (d, J=2.0 Hz, 1H), 8.57 (dd, J=4.9, 1.5 Hz, 1H), 8.51 (s, 1H), 8.32 (d, J=2.0 Hz, 1H), 8.20-8.14 (m, 1H), 8.09 (s, 1H), 7.59-7.53 (m, 1H), 6.68 (d, J=2.0 Hz, 1H), 6.52 (d, J=2.0 Hz, 1H), 5.41 (s, 2H), 4.23-4.10 (m, 2H), 3.78 (s, 3H), 3.76-3.69 (m, 1H), 1.31 (d, J=6.4 Hz, 3H) ppm; (M+1)=389.

Example 1-172: Synthesis of 3-((8-methoxy-2-methyl-2,3-dihydrobenzo[b][1,4]dioxin-6-yl)methyl)-6-(1-methyl-1H-pyrazol-4-yl)-3H-imidazo[4,5-b]pyridine formate The title compound was prepared from 6-iodo-3-((8-methoxy-2-methyl-2,3-dihydrobenzo[b][1,4]dioxin-6-yl)methyl)-3H-imidazo[4,5-b]pyridine (Example 1-170-1) and 1-methyl-4-(4,4,5,5-tetramethyl-1,3,2-dioxaborolan-2-yl)-1H-pyrazole as described in Example 1-55: $^1$H NMR (400 MHz, CD$_3$OD) δ 8.61 (d, J=1.9 Hz, 1H), 8.39 (s, 1H), 8.15 (d, J=1.9 Hz, 1H), 8.03 (d, J=0.8 Hz, 1H), 7.89 (d, J=0.8 Hz, 1H), 6.65 (d, J=1.9 Hz, 1H), 6.49 (d, J=1.9 Hz, 1H), 5.35 (s, 2H), 4.22-4.09 (m, 2H), 3.94 (s, 3H), 3.76 (s, 3H), 3.74-3.68 (m, 1H), 1.30 (d, J=6.4 Hz, 3H) ppm; (M+1)=392.

Example 1-173: Synthesis of 3-((2-cyclopropyl-8-methoxy-2,3-dihydrobenzo[b][1,4]dioxin-6-yl)methyl)-6-(1-(piperidin-4-yl)-1H-pyrazol-4-yl)-3H-imidazo[4,5-b]pyridine Example 1-173-1: Preparation of 3-((2-cyclopropyl-8-methoxy-2,3-dihydrobenzo[b][1,4]dioxin-6-yl)methyl)-6-iodo-3H-imidazo[4,5-b]pyridine The title compound was prepared in nine steps from methyl 4-(benzyloxy)-3-hydroxy-5-methoxybenzoate, 2-bromo-1-cyclopropylethan-1-one, and 2-chloro-5-iodo-3-nitropyridine as described in Example 1-52-1 through Example 1-52-9.

Example 1-173-2: Preparation of 3-((2-cyclopropyl-8-methoxy-2,3-dihydrobenzo[b][1,4]dioxin-6-yl)methyl)-6-(1-(piperidin-4-yl)-1H-pyrazol-4-yl)-3H-imidazo[4,5-b]pyridine The title compound was prepared from 3-((2-cyclopropyl-8-methoxy-2,3-dihydrobenzo[b][1,4]dioxin-6-yl)methyl)-6-iodo-3H-imidazo[4,5-b]pyridine and (1-(1-(tert-butoxycarbonyl)piperidin-4-yl)-1H-pyrazol-4-yl)boronic acid as described in Example 1-169-2 and Example 1-169-3: $^1$H NMR (400 MHz, CDCl$_3$) δ 8.57 (d, J=1.9 Hz, 1H), 8.11 (d, J=2.0 Hz, 1H), 8.01 (s, 1H), 7.82 (d, J=0.8 Hz, 1H), 7.74 (d, J=0.8 Hz, 1H), 6.51-6.49 (m, 2H), 5.34 (s, 2H), 4.35-4.25 (m, 2H), 4.00 (dd, J=11.3, 7.7 Hz, 1H), 3.82 (s, 3H), 3.42-3.35 (m, 1H), 3.34-3.27 (m, 2H), 2.89-2.77 (m, 2H), 2.30-2.20 (m, 2H), 2.05-1.93 (m, 2H), 1.10-1.00 (m, 1H), 0.78-0.68 (m, 1H), 0.68-0.58 (m, 1H), 0.41-0.31 (m, 1H) ppm; (M+1)=487.

Example 1-174: Synthesis of 3-((2-cyclopropyl-8-methoxy-2,3-dihydrobenzo[b][1,4]dioxin-6-yl)methyl)-6-(1-methyl-1H-imidazol-4-yl)-3H-imidazo[4,5-b]pyridine The title compound was prepared from 3-((2-cyclopropyl-8-methoxy-2,3-dihydrobenzo[b][1,4]dioxin-6-yl)methyl)-6-iodo-3H-imidazo[4,5-b]pyridine (Example 1-173-1) and 1-methyl-4-(4,4,5,5-tetramethyl-1,3,2-dioxaborolan-2-yl)-1H-imidazole as described in Example 1-55: $^1$H NMR (400 MHz, CDCl$_3$) δ 8.48 (d, J=1.9 Hz, 1H), 8.12-8.05 (m, 2H), 7.59 (s, 1H), 7.21-7.14 (m, 1H), 6.56-6.48 (m, 2H), 5.37 (s, 2H), 4.29 (dd, J=11.4, 2.3 Hz, 1H), 4.01 (dd, J=11.4, 7.7 Hz, 1H), 3.84 (s, 3H), 3.68 (s, 3H), 3.45-3.35 (m, 1H), 1.33-1.22 (m, 1H), 1.10-1.02 (m, 1H), 0.80-0.56 (m, 3H), 0.40-0.32 (m, 1H) ppm; (M+1)=418.

Example 1-75: Synthesis of 4-(3-((2-cyclopropyl-8-methoxy-2,3-dihydrobenzo[b][1,4]dioxin-6-yl)methyl)-3H-imidazo[4,5-b]pyridin-6-yl)-2-methyl-but-3-yn-2-amine The title compound was prepared from 3-((2-cyclopropyl-8-methoxy-2,3-dihydrobenzo[b][1,4]dioxin-6-yl)methyl)-6-iodo-3H-imidazo[4,5-b]pyridine (Example 1-173-1) and 2-methylbut-3-yn-2-amine as described in Example 1-5-8: $^1$H NMR (400 MHz, Chloroform-d) δ 8.45 (d, J=1.8 Hz, 1H), 8.07 (d, J=1.8 Hz, 1H), 8.01 (s, 1H), 6.50-6.46 (m, 2H), 5.31 (s, 2H), 4.29 (dd, J=11.3, 2.3 Hz, 1H), 4.00 (dd, J=11.3, 7.7 Hz, 1H), 3.81 (s, 3H), 3.44-3.35 (m, 1H), 1.53 (s, 6H), 1.10-1.00 (m, 1H), 0.77-0.68 (m, 1H), 0.69-0.56 (m, 2H), 0.41-0.29 (m, 1H) ppm; (M+1)=419.

Example 1-176: Synthesis of 3-((2-isopropyl-8-methoxy-2,3-dihydrobenzo[b][1,4]dioxin-6-yl)methyl)-6-(1-methyl-1H-pyrazol-4-yl)-3H-imidazo[4,5-b]pyridine formate Example 1-176-1: Preparation of 6-iodo-3-((2-isopropyl-8-methoxy-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 1-bromo-3-methylbutan-2-one, and 2-chloro-5-iodo-3-nitropyridine as described in Example 1-52-1 through Example 1-52-9.

Example 1-176-2: Preparation of 3-((2-isopropyl-8-methoxy-2,3-dihydrobenzo[b][1,4]dioxin-6-yl)methyl)-6-(1-methyl-1H-pyrazol-4-yl)-3H-imidazo[4,5-b]pyridine formate The title compound was prepared from 6-iodo-3-((2-isopropyl-8-methoxy-2,3-dihydrobenzo[b][1,4]dioxin-6-yl)methyl)-3H-imidazo[4,5-b]pyridine and 1-methyl-4-(4,4,5,5-tetramethyl-1,3,2-dioxaborolan-2-yl)-1H-pyrazole as described in Example 1-55: $^1$H NMR (400 MHz, CD$_3$OD) δ 8.60 (d, J=1.8 Hz, 1H), 8.38 (s, 1H), 8.14 (d, J=1.8 Hz, 1H), 8.02 (s, 1H), 7.88 (d, J=0.9 Hz, 1H), 6.64 (d, J=1.9 Hz, 1H), 6.48 (d, J=1.9 Hz, 1H), 5.34 (s, 2H), 4.22 (dd, J=11.4, 2.1 Hz, 1H), 3.94 (s, 3H), 3.86 (dd, J=11.4, 7.6 Hz, 1H), 3.77 (s, 3H), 3.72-3.67 (m, 1H), 1.94-1.83 (m, 1H), 1.04 (d, J=6.7 Hz, 3H), 0.97 (d, J=6.8 Hz, 3H) ppm; (M+1)=420.

Example 1-177: Synthesis of 4-(3-((2-isopropyl-8-methoxy-2,3-dihydrobenzo[b][1,4]dioxin-6-yl)methyl)-3H-imidazo[4,5-b]pyridin-6-yl)-3,5-dimethylisoxazole The title compound was prepared from 6-iodo-3-((2-isopropyl-8-methoxy-2,3-dihydrobenzo[b][1,4]dioxin-6-yl)methyl)-3H-imidazo[4,5-b]pyridine (Example 1-176-1) and 3,5-dimethyl-4-(4,4,5,5-tetramethyl-1,3,2-dioxaborolan-2-yl)isoxazole as described in Example 1-55: $^1$H NMR (400 MHz, CDCl$_3$) δ 8.33 (d, J=1.9 Hz, 1H), 8.09 (s, 1H), 7.97 (d, J=1.9 Hz, 1H), 6.54-6.50 (m, 2H), 5.37 (s, 2H), 4.26 (dd, J=11.3, 2.2 Hz, 1H), 3.98 (dd, J=11.3, 7.2 Hz, 1H), 3.83 (s, 3H), 3.87-3.75 (m, 1H), 2.44 (s, 3H), 2.30 (s, 3H), 2.09-1.91 (m, 1H), 1.11 (d, J=6.8 Hz, 3H), 1.01 (d, J=6.8 Hz, 3H) ppm; (M+1)=435.

Example 1-178: Synthesis of 3-((2-cyclopropyl-8-methoxy-3-methyl-2,3-dihydrobenzo[b][1,4]dioxin-6-yl)methyl)-6-(1-methyl-1H-pyrazol-4-yl)-3H-imidazo[4,5-b]pyridine Example 1-178-1: Preparation of 3-((2-cyclopropyl-8-methoxy-3-methyl-2,3-dihydrobenzo[b][1,4]dioxin-6-yl)methyl)-6-iodo-3H-imidazo[4,5-b]pyridine The title compound was prepared in nine steps from methyl 4-(benzyloxy)-3-hydroxy-5-methoxybenzoate, 2-bromo-1-cyclopropylpropan-1-one, and 2-chloro-5-iodo-3-nitropyridine as described in Example 1-52-1 through Example 1-52-9.

Example 1-178-2: Preparation of 3-((2-cyclopropyl-8-methoxy-3-methyl-2,3-dihydrobenzo[b][1,4]dioxin-6-yl)methyl)-6-(1-methyl-1H-pyrazol-4-yl)-3H-imidazo[4,5-b]pyridine The title compound was prepared from 3-((2-cyclopropyl-8-methoxy-3-methyl-2,3-dihydrobenzo[b][1,4]dioxin-6-yl)methyl)-6-iodo-3H-imidazo[4,5-b]pyridine and 1-methyl-4-(4,4,5,5-tetramethyl-1,3,2-dioxaborolan-2-yl)-1H-pyrazole as described in Example 1-55.

Example 1-178-3: Chiral separation of 3-((2-cyclopropyl-8-methoxy-3-methyl-2,3-dihydrobenzo[b][1,4]dioxin-6-yl)methyl)-6-(1-methyl-1H-pyrazol-4-yl)-3H-imidazo[4,5-b]pyridine The title compound was separated into its individual diastereomers by chiral chromatography.
Separation #1
Column: Whelk-O1 21×250 mm
Mobile phase: 60% Ethanol in CO$_2$, 0.1% diethylamine, 55 mL/min
This operation afforded diastereomer A (peak 3) and diastereomer B (peak 4) as pure fractions (absolute configurations unknown) and a mixture of the two remaining diastereomers (peaks 1 and 2)
Diastereomer A: $^1$H NMR (600 MHz, CDCl$_3$) δ 8.57 (d, J=2.0 Hz, 1H), 8.11 (d, J=2.0 Hz, 1H), 8.01 (s, 1H), 7.80 (s, 1H), 7.67 (s, 1H), 6.52-6.46 (m, 2H), 5.33 (s, 2H), 4.10-4.05 (m, 1H), 3.99 (s, 3H), 3.81 (s, 3H), 3.01 (dd, J=9.1, 7.1 Hz, 1H), 1.43 (d, J=6.4 Hz, 3H), 1.04-0.96 (m, 1H), 0.77-0.65 (m, 2H), 0.65-0.59 (m, 1H), 0.50-0.43 (m, 1H) ppm; (M+1)=432.
Diastereomer B: $^1$H NMR (600 MHz, CDCl$_3$) δ 8.57 (d, J=1.9 Hz, 1H), 8.11 (d, J=1.9 Hz, 1H), 8.02 (s, 1H), 7.80 (d, J=0.9 Hz, 1H), 7.67 (d, J=0.9 Hz, 1H), 6.51-6.47 (m, 2H), 5.34 (s, 2H), 4.34 (qd, J=6.6, 2.2 Hz, 1H), 3.99 (s, 3H), 3.83 (s, 3H), 3.33 (dd, J=9.6, 2.2 Hz, 1H), 1.39 (d, J=6.6 Hz, 3H), 1.08-1.02 (m, 1H), 0.70-0.60 (m, 2H), 0.60-0.53 (m, 1H), 0.37-0.30 (m, 1H) ppm; (M+1)=432.
The remaining mixture of diastereomers (peaks 2 and 3) from the first separation were subjected to a second chromatography:
Separation #2
Column: AD-H 21×250 mm
Mobile phase: 25% methanol in CO$_2$, 0.5% diethylamine 45 mL/min
This operation afforded diastereomer C (peak 1) and diastereomer D (peak 2) as pure fractions (absolute configurations unknown)
Diastereomer C: $^1$H NMR (600 MHz, CDCl$_3$) δ 8.57 (d, J=2.0 Hz, 1H), 8.11 (d, J=2.0 Hz, 1H), 8.01 (s, 1H), 7.80 (s, 1H), 7.67 (s, 1H), 6.52-6.46 (m, 2H), 5.33 (s, 2H), 4.10-4.05 (m, 1H), 3.99 (s, 3H), 3.81 (s, 3H), 3.01 (dd, J=9.1, 7.1 Hz, 1H), 1.43 (d, J=6.4 Hz, 3H), 1.04-0.96 (m, 1H), 0.77-0.65 (m, 2H), 0.65-0.59 (m, 1H), 0.50-0.43 (m, 1H) ppm; (M+1)=432.
Diastereomer D: $^1$H NMR (600 MHz, CDCl$_3$) δ 8.57 (d, J=1.9 Hz, 1H), 8.11 (d, J=1.9 Hz, 1H), 8.02 (s, 1H), 7.80 (d, J=0.9 Hz, 1H), 7.67 (d, J=0.9 Hz, 1H), 6.51-6.47 (m, 2H), 5.34 (s, 2H), 4.34 (qd, J=6.6, 2.2 Hz, 1H), 3.99 (s, 3H), 3.83 (s, 3H), 3.33 (dd, J=9.6, 2.2 Hz, 1H), 1.39 (d, J=6.6 Hz, 3H), 1.08-1.02 (m, 1H), 0.70-0.60 (m, 2H), 0.60-0.53 (m, 1H), 0.37-0.30 (m, 1H) ppm; (M+1)=432.

Example 1-179: Synthesis of 3-((2-(6-(difluoromethyl)pyridin-3-yl)-8-methoxy-2,3-dihydrobenzo[b][1,4]dioxin-6-yl)methyl)-3H-imidazo[4,5-b]pyridine Example 1-179-1: Preparation of 2-bromo-1-(6-(difluoromethyl)pyridin-3-yl)ethan-1-one The title compound was prepared from 1-(6-(difluoromethyl)pyridin-3-yl)ethan-1-one as described in Example 1-110-2.

Example 1-179-2: Preparation of 3-((2-(6-(difluoromethyl)pyridin-3-yl)-8-methoxy-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-(difluoromethyl)pyridin-3-yl)ethan-1-one, and 2-chloro-3-nitropyridine as described in Example 1-52-1 through Example 1-52-9: $^1$H NMR (400 MHz, CDCl$_3$) δ 8.71 (d, J=2.0 Hz, 1H), 8.45 (dd, J=4.8, 1.5 Hz, 1H), 8.10 (dd, J=8.0, 1.5 Hz, 1H), 8.05 (s, 1H), 7.92 (dd, J=8.1, 2.2 Hz, 1H), 7.68 (d, J=8.1 Hz, 1H), 7.30-7.24 (m, 1H), 6.65 (t, J=55 Hz, 1H), 6.57 (d, J=2.0 Hz, 1H), 6.55 (d, J=2.0 Hz, 1H), 5.39 (s, 2H), 5.28-5.22 (m, 1H), 4.38 (dd, J=11.6, 2.5 Hz, 1H), 4.09 (dd, J=11.6, 7.9 Hz, 1H), 3.82 (s, 3H) ppm; (M+1)=425.

Example 1-180: Synthesis of 3-((2-(2-cyclopropylpyrimidin-5-yl)-8-methoxy-2,3-dihydrobenzo[b][1,4]dioxin-6-yl)methyl)-3H-imidazo[4,5-b]pyridine Example 1-180-1: Preparation of 2-bromo-1-(2-cyclopropylpyrimidin-5-yl)ethan-1-one The title compound was prepared in two steps from 2-cyclopropylpyrimidine-5-carboxylic acid as described in Example 1-133-1 through Example 1-133-2.

Example 1-180-2: Preparation of 3-((2-(2-cyclopropylpyrimidin-5-yl)-8-methoxy-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(2-cyclopropylpyrimidin-5-yl)ethan-1-one, and 2-chloro-3-nitropyridine as described in Example 1-52-1 through Example 1-52-9: $^1$H NMR (400 MHz, CDCl$_3$) δ

8.61-8.57 (m, 2H), 8.44 (dd, J=4.8, 1.5 Hz, 1H), 8.09 (dd, J=8.0, 1.5 Hz, 1H), 8.04 (s, 1H), 7.29-7.25 (m, 1H), 6.55 (d, J=2.0 Hz, 1H), 6.54 (d, J=2.0 Hz, 1H), 5.38 (s, 2H), 5.13 (dd, J=7.8, 2.5 Hz, 1H), 4.34 (dd, J=11.6, 2.5 Hz, 1H), 4.13 (dd, J=11.6, 7.8 Hz, 1H), 3.80 (s, 3H), 2.30-2.22 (m, 1H), 1.17-1.05 (m, 4H) ppm; (M+1)=416.

Example 1-181: Synthesis of 3-((8-methoxy-2-(6-methoxy-2-methylpyridin-3-yl)-2,3-dihydrobenzo[b][1,4]dioxin-6-yl)methyl)-3H-imidazo[4,5-b]pyridine Example 1-181-1: Preparation of 2-bromo-1-(6-methoxy-2-methylpyridin-3-yl)ethan-1-one The title compound was prepared in two steps from 6-methoxy-2-methylnicotinic acid as described in Example 1-133-1 through Example 1-133-2.

Example 1-181-2: Preparation of 6-iodo-3-((8-methoxy-2-(6-methoxy-2-methylpyridin-3-yl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-methoxy-2-methylpyridin-3-yl)ethan-1-one, and 2-chloro-5-iodo-3-nitropyridine as described in Example 1-52-1 through Example 1-52-9.

Example 1-181-3: Preparation of 3-((8-methoxy-2-(6-methoxy-2-methylpyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methoxy-2-methylpyridin-3-yl)-2,3-dihydrobenzo[b][1,4]dioxin-6-yl)methyl)-3H-imidazo[4,5-b]pyridine as described in Example 1-97: $^1$H NMR (400 MHz, CDCl$_3$) δ 8.45 (dd, J=4.8, 1.5 Hz, 1H), 8.10 (dd, J=8.0, 1.5 Hz, 1H), 8.05 (s, 1H), 7.61 (d, J=8.5 Hz, 1H), 7.27 (dd, J=8.0, 4.8 Hz, 1H), 6.62 (d, J=8.5 Hz, 1H), 6.56 (d, J=2.0 Hz, 1H), 6.55 (d, J=2.0 Hz, 1H), 5.39 (s, 2H), 5.24 (dd, J=8.9, 2.4 Hz, 1H), 4.28 (dd, J=11.7, 2.4 Hz, 1H), 3.98-3.89 (m, 4H), 3.80 (s, 3H), 2.50 (s, 3H) ppm; (M+1)=419.

Example 1-182: Synthesis of 3-((8-methoxy-2-(6-methoxy-2-methylpyridin-3-yl)-2,3-dihydrobenzo[b][1,4]dioxin-6-yl)methyl)-6-(3-methoxyazetidin-1-yl)-3H-imidazo[4,5-b]pyridine The title compound was prepared from 6-iodo-3-((8-methoxy-2-(6-methoxy-2-methylpyridin-3-yl)-2,3-dihydrobenzo[b][1,4]dioxin-6-yl)methyl)-3H-imidazo[4,5-b]pyridine (Example 1-181-2) and 3-methoxyazetidine hydrochloride as described in Example 1-10: $^1$H NMR (400 MHz, CDCl$_3$) δ 7.93 (s, 1H), 7.78 (d, J=2.5 Hz, 1H), 7.60 (d, J=8.5 Hz, 1H), 7.16 (d, J=2.5 Hz, 1H), 6.62 (d, J=8.5 Hz, 1H), 6.54 (d, J=2.0 Hz, 1H), 6.51 (d, J=2.0 Hz, 1H), 5.30 (s, 2H), 5.23 (dd, J=8.9, 2.4 Hz, 1H), 4.43-4.36 (m, 1H), 4.27 (dd, J=11.7, 2.4 Hz, 1H), 4.23-4.16 (m, 2H), 3.97-3.88 (m, 4H), 3.79 (s, 3H), 3.79-3.74 (m, 2H), 3.36 (s, 3H), 2.50 (s, 3H) ppm; (M+1)=504.

Example 1-183: Synthesis of 6-methoxy-3-((8-methoxy-2-(6-methoxy-2-methylpyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methoxy-2-methylpyridin-3-yl)-2,3-dihydrobenzo[b][1,4]dioxin-6-yl)methyl)-3H-imidazo[4,5-b]pyridine (Example 1-181-2) and methanol as described in Example 1-11: $^1$H NMR (400 MHz, CDCl$_3$) δ 8.21 (d, J=2.6 Hz, 1H), 7.99 (s, 1H), 7.63-7.58 (m, 2H), 6.62 (d, J=8.5 Hz, 1H), 6.54 (d, J=2.0 Hz, 1H), 6.53 (d, J=2.0 Hz, 1H), 5.34 (s, 2H), 5.23 (dd, J=8.9, 2.4 Hz, 1H), 4.27 (dd, J=11.6, 2.4 Hz, 1H), 3.97-3.88 (m, 7H), 3.80 (s, 3H), 2.50 (s, 3H) ppm; (M+1)=449.

Example 1-184: Synthesis of 3-((8-methoxy-2-(6-methoxy-2-methylpyridin-3-yl)-2,3-dihydrobenzo[b][1,4]dioxin-6-yl)methyl)-7-(3-methoxyazetidin-1-yl)imidazo[1,2-b]pyridazine Example 1-184-1: Preparation of (8-methoxy-2-(6-methoxy-2-methylpyridin-3-yl)-2,3-dihydrobenzo[b][1,4]dioxin-6-yl)methanol The title compound was prepared in four steps from methyl 4-(benzyloxy)-3-hydroxy-5-methoxybenzoate and 2-bromo-1-(6-methoxy-2-methylpyridin-3-yl)ethan-1-one as described in Example 1-52-1 through Example 1-52-4.

Example 1-184-2: Preparation of 8-methoxy-2-(6-methoxy-2-methylpyridin-3-yl)-2,3-dihydrobenzo[b][1,4]dioxine-6-carbaldehyde To a stirred solution of (8-methoxy-2-(6-methoxy-2-methylpyridin-3-yl)-2,3-dihydrobenzo[b][1,4]dioxin-6-yl)methanol (0.68 g, 2.13 mmol) in dichloromethane (30 mL) was added Dess-Martin periodinane (0.93 g, 2.13 mmol). After 30 min, the mixture was partitioned between saturated sodium bicarbonate solution and dichloromethane. The phases were separated, and the organic phase was washed with saturated sodium bicarbonate solution, water, and brine. The organic phases was dried over magnesium sulfate, filtered, and concentrated. Chromatographic purification of the crude product (CombiFlash, silica gel column, 0-50% ethyl acetate/heptane elute) provided 0.66 g (98%) of 8-methoxy-2-(6-methoxy-2-methylpyridin-3-yl)-2,3-dihydrobenzo[b][1,4]dioxine-6-carbaldehyde as a white solid.

Example 1-184-3: Preparation of 7-chloro-3-((8-methoxy-2-(6-methoxy-2-methylpyridin-3-yl)-2,3-dihydrobenzo[b][1,4]dioxin-6-yl)methyl)imidazo[1,2-b]pyridazine The title compound was prepared in two steps from 3-bromo-7-chloroimidazo[1,2-b]pyridazine (Example 1-23-2) and 8-methoxy-2-(6-methoxy-2-methylpyridin-3-yl)-2,3-dihydrobenzo[b][1,4]dioxine-6-carbaldehyde as described in Example 1-23-1 (step 1) and Example 1-22-2 (step 2).

Example 1-184-4: Preparation of 3-((8-methoxy-2-(6-methoxy-2-methylpyridin-3-yl)-2,3-dihydrobenzo[b][1,4]dioxin-6-yl)methyl)-7-(3-methoxyazetidin-1-yl)imidazo[1,2-b]pyridazine The title compound was prepared from 7-chloro-3-((8-methoxy-2-(6-methoxy-2-methylpyridin-3-yl)-2,3-dihydrobenzo[b][1,4]dioxin-6-yl)methyl)imidazo[1,2-b]pyridazine and 3-methoxyazetidine hydrochloride as described in Example 1-104: $^1$H NMR (400 MHz, CDCl$_3$) δ 7.91-7.87 (m, 1H), 7.62 (d, J=8.5 Hz, 1H), 7.31-7.24 (m, 1H), 6.80-6.75 (m, 1H), 6.63 (d, J=8.5 Hz, 1H), 6.50 (d, J=2.0 Hz, 1H), 6.46 (d, J=2.0 Hz, 1H), 5.26-5.20 (m, 1H), 4.45-4.37 (m, 1H), 4.30-4.22 (m, 3H), 4.17-4.13 (m, 2H), 3.95-3.88 (m, 6H), 3.82 (s, 3H), 3.37 (s, 3H), 2.50 (s, 3H) ppm; (M+1)=504.

Example 1-185: Synthesis of 3-((2-(2,6-dimethoxypyridin-3-yl)-8-methoxy-2,3-dihydrobenzo[b][1,4]dioxin-6-yl)methyl)-3H-imidazo[4,5-b]pyridine

Example 1-185-1: Preparation of 2-bromo-1-(2,6-dimethoxypyridin-3-yl)ethan-1-one The title compound was prepared in two steps from 2,6-dimethoxynicotinic acid as described in Example 1-133-1 through Example 1-133-2.

Example 1-185-2: Preparation of 3-((2-(2,6-dimethoxypyridin-3-yl)-8-methoxy-2,3-dihydrobenzo[b][1,4]dioxin-6-yl)methyl)-6-iodo-3H-imidazo[4,5-b]pyridine The title compound was prepared in nine steps from methyl 4-(benzyloxy)-3-hydroxy-5-methoxybenzoate, 2-bromo-1-(2,6-dimethoxypyridin-3-yl)ethan-1-one, and 2-chloro-5-iodo-3-nitropyridine as described in Example 1-52-1 through Example 1-52-9.

Example 1-185-3: Preparation of 3-((2-(2,6-dimethoxypyridin-3-yl)-8-methoxy-2,3-dihydrobenzo[b][1,4]dioxin-6-yl)methyl)-3H-imidazo[4,5-b]pyridine The title compound was prepared from 3-((2-(2,6-dimethoxypyridin-3-yl)-8-methoxy-2,3-dihydrobenzo[b][1,4]dioxin-6-yl)methyl)-6-iodo-3H-imidazo[4,5-b]pyridine as described in Example 1-97: $^1$H NMR (400 MHz, CDCl$_3$) δ 8.45 (dd, J=4.9, 2.0 Hz, 1H), 8.09 (dd, J=8.0, 2.0 Hz, 1H), 8.04 (s, 1H), 7.61 (d, J=8.2 Hz, 1H), 7.30-7.24 (m, 1H), 6.56-6.51 (m, 2H), 6.34 (d, J=8.2 Hz, 1H), 5.40-5.32 (m, 3H), 4.39-4.31 (m, 1H), 3.94 (s, 3H), 3.91 (s, 3H), 3.81 (s, 3H) ppm; (M+1)=435.

Example 1-186: Synthesis of 3-((2-(2,6-dimethoxypyridin-3-yl)-8-methoxy-2,3-dihydrobenzo[b][1,4]dioxin-6-yl)methyl)-6-methoxy-3H-imidazo[4,5-b]pyridine The title compound was prepared from 3-((2-(2,6-dimethoxypyridin-3-yl)-8-methoxy-2,3-dihydrobenzo[b][1,4]dioxin-6-yl)methyl)-6-iodo-3H-imidazo[4,5-b]pyridine (Example 1-185-2) and methanol as described in Example 1-11: $^1$H NMR (400 MHz, CDCl$_3$) δ 8.23-8.19 (m, 1H), 7.98 (s, 1H), 7.64-7.56 (m, 2H), 6.55-6.50 (m, 2H), 6.33 (dd, J=8.1, 1.8 Hz, 1H), 5.38-5.29 (m, 3H), 4.38-4.30 (m, 1H), 3.96-3.89 (m, 10H), 3.81 (s, 3H) ppm; (M+1)=465.

Example 1-187: Synthesis of 3-((2-(2,6-dimethoxypyridin-3-yl)-8-methoxy-2,3-dihydrobenzo[b][1,4]dioxin-6-yl)methyl)-6-(3-methoxyazetidin-1-yl)-3H-imidazo[4,5-b]pyridine The title compound was prepared from 3-((2-(2,6-dimethoxypyridin-3-yl)-8-methoxy-2,3-dihydrobenzo[b][1,4]dioxin-6-yl)methyl)-6-iodo-3H-imidazo[4,5-b]pyridine (Example 1-185-2) and 3-methoxyazetidine hydrochloride as described in Example 1-10: $^1$H NMR (400 MHz, CDCl$_3$) δ 7.92 (s, 1H), 7.78 (d, J=2.5 Hz, 1H), 7.61 (d, J=8.1 Hz, 1H), 7.15 (d, J=2.5 Hz, 1H), 6.54-6.47 (m, 2H), 6.34 (d, J=8.3 Hz, 1H), 5.38-5.32 (m, 1H), 5.29 (s, 2H), 4.45-4.30 (m, 3H), 4.20 (t, J=6.9 Hz, 2H), 3.94 (s, 3H), 3.91 (s, 3H), 3.82-3.72 (m, 5H), 3.36 (s, 3H) ppm; (M+1)=520.

Example 1-188: Synthesis of 3-((8-methoxy-2-(6-(trifluoromethyl)pyridin-3-yl)-2,3-dihydrobenzo[b][1,4]dioxin-6-yl)methyl)-3H-imidazo[4,5-b]pyridine The title compound, also known as RA10982908, was prepared in nine steps from methyl 4-(benzyloxy)-3-hydroxy-5-methoxybenzoate, 2-bromo-1-(6-(trifluoromethyl)pyridin-3-yl)ethan-1-one, and 2-chloro-3-nitropyridine as described in Example 1-52-1 through Example 1-52-9: $^1$H NMR (400 MHz, CDCl$_3$) δ 8.78 (dd, J=2.3, 0.9 Hz, 1H), 8.45 (dd, J=4.8, 1.5 Hz, 1H), 8.10 (dd, J=8.0, 1.5 Hz, 1H), 8.05 (s, 1H), 7.99-7.93 (m, 1H), 7.73 (dd, J=8.1, 0.9 Hz, 1H), 7.30-7.26 (m, 1H), 6.57 (d, J=2.0 Hz, 1H), 6.55 (d, J=2.0 Hz, 1H), 5.39 (s, 2H), 5.29 (dd, J=7.8, 2.5 Hz, 1H), 4.40 (dd, J=11.7, 2.5 Hz, 1H), 4.10 (dd, J=11.7, 7.8 Hz, 1H), 3.82 (s, 3H) ppm; (M+1)=443.

Example 1-188-1: Chiral separation of 3-((8-methoxy-2-(6-(trifluoromethyl)pyridin-3-yl)-2,3-dihydrobenzo[b][1,4]dioxin-6-yl)methyl)-3H-imidazo[4,5-b]pyridine The racemic 3-((8-methoxy-2-(6-(trifluoromethyl)pyridin-3-yl)-2,3-dihydrobenzo[b][1,4]dioxin-6-yl)methyl)-3H-imidazo[4,5-b]pyridine was subjected to SFC preparative purification (30×250 mm Chiralpak IC column, 35% ethanol/0.1% diethylamine modifier, 65 g/min flow rate) to afford the individual enantiomers.

Example 1-189: Synthesis of 6-methoxy-3-((8-methoxy-2-(6-methoxy-4-methylpyridin-3-yl)-2,3-dihydrobenzo[b][1,4]dioxin-6-yl)methyl)-3H-imidazo[4,5-b]pyridine

Example 1-189-1: Preparation of 2-bromo-1-(6-methoxy-4-methylpyridin-3-yl)ethan-1-one The title compound was prepared in two steps from 6-methoxy-4-methylnicotinic acid as described in Example 1-133-1 through Example 1-133-2.

Example 1-189-2: Preparation of 6-iodo-3-((8-methoxy-2-(6-methoxy-4-methylpyridin-3-yl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-methoxy-4-methylpyridin-3-yl)ethan-1-one, and 2-chloro-5-iodo-3-nitropyridine as described in Example 1-52-1 through Example 1-52-9.

Example 1-189-3: Preparation of 6-methoxy-3-((8-methoxy-2-(6-methoxy-4-methylpyridin-3-yl)-2,3-dihydrobenzo[b][1,4]dioxin-6-yl)methyl)-3H-imidazo[4,5-b]pyridine The title compound was prepared from 6-iodo-3-((8-methoxy-2-(6-methoxy-4-methylpyridin-3-yl)-2,3-dihydrobenzo[b][1,4]dioxin-6-yl)methyl)-3H-imidazo[4,5-b]pyridine and methanol as described in Example 1-11: $^1$H NMR (400 MHz, CDCl$_3$) δ 8.21 (d, J=2.7 Hz, 1H), 8.16 (s, 1H), 7.99 (s, 1H), 7.59 (d, J=2.7 Hz, 1H), 6.57 (s, 1H), 6.55 (d, J=2.0 Hz, 1H), 6.53 (d, J=2.1 Hz, 1H), 5.33 (s, 2H), 5.22

(dd, J=8.7, 2.4 Hz, 1H), 4.31 (dd, J=11.7, 2.4 Hz, 1H), 4.08 (dd, J=11.7, 8.7 Hz, 1H), 3.91 (s, 6H), 3.80 (s, 3H), 2.34 (s, 3H) ppm; (M+1)=449.

Example 1-190: Synthesis of 3-((8-methoxy-2-(6-methoxy-4-methylpyridin-3-yl)-2,3-dihydrobenzo [b][1,4] dioxin-6-yl)methyl)-3H-imidazo[4,5-b]pyridine The title compound was prepared from 6-iodo-3-((8-methoxy-2-(6-methoxy-4-methylpyridin-3-yl)-2,3 -dihydrobenzo [b][1,4]dioxin-6-yl)methyl)-3H-imidazo[4,5-b] pyridine as described in Example 1-97: $^1$H NMR (400 MHz, CDCl$_3$) δ 8.48-8.42 (m, 1H), 8.16 (s, 1H), 8.10 (d, J=8.1 Hz, 1H), 8.05 (s, 1H), 7.30-7.24 (m, 1H), 6.60-6.52 (m, 3H), 5.38 (s, 2H), 5.26-5.19 (m, 1H), 4.32 (dd, J=11.6, 2.5 Hz, 1H), 4.09 (dd, J=11.6, 8.8 Hz, 1H), 3.91 (s, 3H), 3.80 (s, 3H), 2.34 (s, 3H) ppm; (M+1)=419.

Example 1-191: Synthesis of 5-(6-((3H-imidazo[4,5-b]pyridin-3-yl)methyl)-8-methoxy-2,3-dihydrobenzo[b][1,4]dioxin-2-yl)-N,N-diethylpyridin-2-amine Example 1-191-1: Preparation of 2-bromo-1-(6-(diethylamino)pyridin-3-yl)ethan-1-one The title compound was prepared from 1-(6-(diethylamino)pyridin-3-yl)ethan-1-one and bromine as described in Example 1-110-2.

Example 1-191-2: Preparation of 5-(6-((3H-imidazo[4,5-b]pyridin-3-yl)methyl)-8-methoxy-2,3-dihydrobenzo[b][1,4]dioxin-2-yl)-N,N-diethylpyridin-2-amine The title compound was prepared in nine steps from methyl 4-(benzyloxy)-3-hydroxy-5-methoxybenzoate, 2-bromo-1-(6-(diethylamino)pyridin-3-yl)ethan-1-one, and 2-chloro-3-nitropyridine as described in Example 1-52-1 through Example 1-52-9: $^1$H NMR (400 MHz, CDCl$_3$) δ 8.44 (dd, J=4.8, 1.4 Hz, 1H), 8.19-8.00 (m, 3H), 7.42 (dd, J=8.9, 2.5 Hz, 1H), 7.31-7.23 (m, 1H), 6.60-6.41 (m, 3H), 5.37 (s, 2H), 4.97 (dd, J=8.6, 2.4 Hz, 1H), 4.27 (dd, J=11.5, 2.4 Hz, 1H), 4.08 (dd, J=11.5, 8.6 Hz, 1H), 3.79 (s, 3H), 3.51 (q, J=7.1 Hz, 4H), 1.16 (t, J=7.0 Hz, 6H) ppm; (M+1)=446.

Example 1-192: Synthesis of 4-(5-(6-((3H-imidazo[4,5-b]pyridin-3-yl)methyl)-8-methoxy-2,3-dihydrobenzo[13][1,4]dioxin-2-yl)pyridin-2-yl)morpholine The title compound was prepared in nine steps from methyl 4-(benzyloxy)-3-hydroxy-5-methoxybenzoate, 2-bromo-1-(6-morpholinopyridin-3-yl)ethan-1-one, and 2-chloro-3-nitropyridine as described in Example 1-52-1 through Example 1-52-9: $^1$H NMR (400 MHz, CDCl$_3$) δ 8.44 (dd, J=4.8, 1.4 Hz, 1H), 8.22 (d, J=2.5 Hz, 1H), 8.13-8.00 (m, 2H), 7.53 (dd, J=8.8, 2.5 Hz, 1H), 7.33-7.22 (m, 1H), 6.64 (d, J=8.8 Hz, 1H), 6.60-6.50 (m, 2H), 5.37 (s, 2H), 5.04 (dd, J=8.4, 2.5 Hz, 1H), 4.28 (dd, J=11.6, 2.5 Hz, 1H), 4.07 (dd, J=11.6, 8.4 Hz, 1H), 3.87-3.75 (m, 7H), 3.54-3.50 (m, 4H) ppm; (M+1)=460.

Example 1-193: Synthesis of 3-((8-methoxy-2-(1-methyl-1H-pyrazol-4-yl)-2,3-dihydrobenzo[b][1,4] dioxin-6-yl)methyl)-3H-imidazo[4,5-b]pyridine Example 1-193-1: Preparation of methyl 4-(benzyloxy)-3-methoxy-5-((4-methoxybenzyl)oxy)benzoate To a stirred suspension of methyl 4-(benzyloxy)-3-hydroxy-5-methoxybenzoate (26.00 g, 90.20 mmol) and potassium carbonate (18.70 g, 135.30 mmol) in acetonitrile (200 mL) was added p-methoxybenzyl chloride (21.20 g, 135.3 mmol). The resulting mixture was heated to 85° C. After 20 h, the mixture was allowed to cool to room temperature and was concentrated. The residue was purified by silica gel chromatography (0-25% ethyl acetate/petroleum ether elute) to afford 34.00 g (92%) of methyl 4-(benzyloxy)-3-methoxy-5-((4-methoxybenzyl)oxy)benzoate as a white solid.

Example 1-193-2: Preparation of 4-(benzyloxy)-3-methoxy-5-((4-methoxybenzyl)oxy)benzoic acid The title compound was prepared from methyl 4-(benzyloxy)-3-methoxy-5-((4-methoxybenzyl)oxy)benzoate as described in Example 1-86-1.

Example 1-193-3: Preparation of 4-(benzyloxy)-3-methoxy-5-((4-methoxybenzyl)oxy)benzamide To a stirred suspension of 4-(benzyloxy)-3-methoxy-5-((4-methoxybenzyl)oxy)benzoic acid (20.00 g, 50.70 mmol), ammonium chloride (13.60 g, 250.0 mmol), and 1-[bis(dimethylamino)methylene]-1H-1,2,3-triazolo[4,5-b]pyridinium 3-oxid hexafluorophosphate (28.90 g, 760.0 mmol) in N,N-dimethylformamide (200 mL) was added TEA (20.9 mL, 150.0 mmol). The resulting mixture was heated to 50° C. After 20 h, the mixture was allowed to cool to room temperature and was poured into water (3.0 L). The precipitate that formed was filtered and washed with water (3×500 mL). The solid was dissolved in ethyl acetate (2.0 L) and washed with brine (1×500 mL), dried over sodium sulfate, filtered and concentrated to afford 12.00 g (60%) of 4-(benzyloxy)-3-methoxy-5-((4-methoxybenzyl)oxy)benzamide as an off-white solid.

Example 1-193-4: Preparation of (4-(benzyloxy)-3-methoxy-5-((4-methoxybenzyl)oxy)phenyl)methanamine To a stirred and cooled (0° C.) solution of 4-(benzyloxy)-3-methoxy-5-((4-methoxybenzyl)oxy)benzamide (9.00 g, 22.90 mmol) in tetrahydrofuran (150 mL) was added dropwise over 15 min a 1.0M solution of lithium aluminide hydride in tetrahydrofuran (60.0 mL, 60.00 mmol). The resulting mixture heated to reflux. After 20 h, the mixture was cooled to 0° C. and was slowly quenched by the addition of water (2.3 mL), 15% aqueous sodium hydroxide solution (2.3 mL) and water (6.9 mL). The mixture was allowed to stir at room temperature. After 1 h, the mixture was filtered, and the filtrate was concentrated to afford 7.00 g (81%) of (4-(benzyloxy)-3-methoxy-5-((4-methoxybenzyl)oxy)phenyl)methanamine as light yellow oil.

Example 1-193-5: Preparation of N-(4-(benzyloxy)-3-methoxy-5-((4-methoxybenzyl)oxy)benzyl)-3-nitropyridin-2-amine The title compound was prepared from (4-(benzyloxy)-3-methoxy-5-((4-methoxybenzyl)oxy)phenyl)methanamine and 2-chloro-3-nitropyridine as described in Example 1-52-7.

Example 1-193-6: Preparation of N$^2$-(4-(benzyloxy)-3-methoxy-5-((4-methoxybenzyl)oxy)benzyl) pyridine-2,3-diamine To a stirred and cooled (0° C.) solution of N-(4-(benzyloxy)-3-methoxy-5-((4-methoxybenzyl)oxy)benzyl)-3-nitropyridin-2-amine (7.90 g, 15.70 mmol) and ammonium chloride (8.40 g, 157.0 mmol) in 1:1:1 mixture of tetrahydrofuran/methanol/water (150 mL) was added zinc powder (10.20 g, 157.0 mmol). The resulting mixture was allowed to stirred at 0° C. After 3 h, the mixture was filtered. The filtrate was extracted with dichloromethane (3×100 mL). The combined organic phases were washed with brine (2×50 mL), dried over sodium sulfate, filtered and concentrated to afford 6.10 g of (82%) of $N^2$-(4-(benzyloxy)-3-methoxy-5-((4-methoxybenzyl)oxy)benzyl)pyridine-2,3-diamine as dark-brown oil.

Example 1-193-7: Preparation of 3-(4-(benzyloxy)-3-methoxy-5-((4-methoxybenzyl)oxy)benzyl)-3H-imidazo[4,5-b]pyridine To a stirred solution of $N^2$-(4-(benzyloxy)-3-methoxy-5-((4-methoxybenzyl)oxy)benzyl)pyridine-2,3-diamine (6.10 g, 12.95 mmol) and triethyl orthoformate (10 mL) in N,N-dimethylformamide (40 mL) was added 4-methylbenzenesulfonic acid (1.50 g, 8.70 mmol). After 20 h, the mixture was diluted with water (300 mL), and extracted with ethyl acetate (3×150 mL). The combined organic phases were washed with brine (2×50 mL), dried over sodium sulfate, filtered, and concentrated. The crude product was purified by silica gel chromatography (0 to 100% ethyl acetate/petroleum ether elute) to afford 5.60 g (90%) of 3-(4-(benzyloxy)-3-methoxy-5-((4-methoxybenzyl)oxy)benzyl)-3H-imidazo[4,5-b]pyridine as dark-brown oil.

Example 1-193-8: Preparation of 5-((3H-imidazo[4,5-b]pyridin-3-yl)methyl)-2-(benzyloxy)-3-methoxyphenol A stirred solution of 3-(4-(benzyloxy)-3-methoxy-5-((4-methoxybenzyl)oxy)benzyl)-3H-imidazo[4,5-b]pyridine (4.98 g, 10.34 mmol) in acetic acid (5 mL) was heated to 110° C. After 16 h, the mixture was allowed to cool to room temperature and was concentrated. The residue was dissolved in dichloromethane, and the resulting solution was washed with saturated sodium bicarbonate solution (2×) and brine. The organic phase was dried over magnesium sulfate, filtered, and concentrated. Chromatographic purification of the crude product (CombiFlash, silica gel column, 0-5% methanol/ethyl acetate elute) provided 3.00 g (80%) of 5-((3H-imidazo[4,5-b]pyridin-3-yl)methyl)-2-(benzyloxy)-3-methoxyphenol as a beige foam.

Example 1-193-9: Preparation of 3-((8-methoxy-2-(1-methyl-1H-pyrazol-4-yl)-2,3-dihydrobenzo[b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol and 2-bromo-1-(1-methyl-1H-pyrazol-4-yl)ethan-1-one as described in Example 1-52-1 through Example 1-52-3: $^1$H NMR (400 MHz, DMSO-$d_6$) δ 8.58 (s, 1H), 8.38 (dd, J=4.8, 1.2 Hz, 1H), 8.07 (dd, J=8.0, 1.2 Hz, 1H), 7.76 (s, 1H), 7.47 (s, 1H), 7.28 (d, J=8.0 Hz, 1H), 6.72 (d, J=1.8 Hz, 1H), 6.48 (d, J=1.8 Hz, 1H), 5.36 (s, 2H), 5.10-5.07 (m, 1H), 4.29-4.26 (m, 1H), 4.11-4.06 (m, 1H), 3.80 (s, 3H), 3.68 (s, 3H) ppm; (M+1)=378.

Example 1-194: Synthesis of 3-((2-(1-cyclobutyl-1H-pyrazol-4-yl)-8-methoxy-2,3-dihydrobenzo[b][1,4]dioxin-6-yl)methyl)-3H-imidazo[4,5-b]pyridine

Example 1-194-1: Preparation of 2-bromo-1-(1-cyclobutyl-1H-pyrazol-4-yl)ethan-1-one To a stirred solution of 1-(1-cyclobutyl-1H-pyrazol-4-yl)ethan-1-one (1.00 g, 6.10 mmol) in 4:1 dichloromethane/ethanol (10 mL) was added pyridinium tribromide (1.95 g, 6.10 mmol). After 3 h, the mixture was diluted with water (20 mL) and was extracted with ethyl acetate (3×30 mL). The combined organic phases were washed with brine (50 mL), dried over sodium sulfate, filtered, and concentrated. The crude product was purified by silica gel chromatography (petroleum ether/ethyl acetate=10/1) to afford 0.89 g (60%) of 2-bromo-1-(1-cyclobutyl-1H-pyrazol-4-yl)ethan-1-one as yellow oil.

Example 1-194-2: Preparation of 3-((2-(1-cyclobutyl-1H-pyrazol-4-yl)-8-methoxy-2,3-dihydrobenzo[b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(1-cyclobutyl-1H-pyrazol-4-yl)ethan-1-one as described in Example 1-52-1 through Example 1-52-3: $^1$H NMR (500 MHz, DMSO-$d_6$) δ 8.58 (s, 1H), 8.40 (dd, J=5.0, 1.5 Hz, 1H), 8.10 (dd, J=8.5, 1.5 Hz, 1H), 7.91 (s, 1H), 7.54 (s, 1H), 7.29 (dd, J=8.5, 5.0 Hz, 1H), 6.73 (d, J=1.7 Hz, 1H), 6.50 (d, J=1.7 Hz, 1H), 5.37 (s, 2H), 5.09-5.07 (m, 1H), 4.84-4.77 (m, 1H), 4.32-4.29 (m, 1H), 4.13-4.09 (m, 1H), 3.69 (s, 3H), 2.45-2.31 (m, 4H), 1.79-1.71 (m, 2H) ppm; (M+1)=418.

Example 1-195: Synthesis of 3-((2-(1-isopropyl-1H-pyrazol-4-yl)-8-methoxy-2,3-dihydrobenzo[b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(1-isopropyl-1H-pyrazol-4-yl)ethan-1-one as described in Example 1-52-1 through Example 1-52-3: $^1$H NMR (500 MHz, DMSO-$d_6$) δ 8.60 (s, 1H), 8.40 (dd, J=5.0, 1.5 Hz, 1H), 8.10 (dd, J=8.5, 1.5 Hz, 1H), 7.89 (s, 1H), 7.51 (s, 1H), 7.32-7.29 (m, 1H), 6.74 (d, J=2.0 Hz, 1H), 6.51 (d, J=2.0 Hz, 1H), 5.38 (s, 2H), 5.08-5.06 (m, 1H), 4.46 (sept, J=6.5 Hz, 1H), 4.33-4.30 (m, 1H), 4.14-4.10 (m, 1H), 3.70 (s, 3H), 1.39 (d, J=6.5 Hz, 6H) ppm; (M+1)=406.

Example 1-196: Synthesis of 3-((8-methoxy-2-(6-(methoxymethyl)pyridin-3-yl)-2,3-dihydrobenzo[b][1,4]dioxin-6-yl)methyl)-3H-imidazo[4,5-b]pyridine

Example 1-196-1: Preparation of 2-bromo-1-(6-(methoxymethyl)pyridin-3-yl)ethan-1-one To a stirred solution of 5-bromo-2-(methoxymethyl)pyridine (2.60 g, 12.90 mmol) and tributyl(1-ethoxyvinyl)stannane (5.20 g, 14.40 mmol) in 1,4-dioxane (30 mL) was added (1,1'-bis(diphenylphosphino)ferrocene)palladium(II) chloride (0.87 g, 1.19 mmol). The resulting mixture was heated to 100° C. After 4 h, the mixture was allowed to cool to room temperature and was concentrated to afford a light brown oil. This material was dissolved in 9:1 tetrahydrofuran/water (20 mL) and cooled to 0° C. N-Bromosuccinimide (1.80 g, 10.10 mmol) was added. The resulting mixture was allowed to stir at 0° C. After 2 h, the mixture was diluted with water (60 mL) and extracted with ethyl acetate (3×100 mL). The combined organic phases were washed with brine (100 mL), dried over sodium sulfate, filtered, and concentrated. The crude product was purified by silica gel chromatography (5:1 petroleum ether/ethyl acetate) to afford 2.30 g, (70%) of 2-bromo-1-(6-(methoxymethyl)pyridin-3-yl)ethan-1-one as a light brown solid.

Example 1-196-2: Preparation of 3-((8-methoxy-2-(6-(methoxymethyl)pyridin-3-yl)-2,3-dihydrobenzo [b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(6-(methoxymethyl)pyridin-3-yl)ethan-1-one as described in Example 1-52-1 through Example 1-52-3: $^1$H NMR (500 MHz, DMSO-d$_6$) δ 8.61 (s, 1H), 8.58 (d, J=1.5 Hz, 1H), 8.40 (dd, J=5.0, 1.5 Hz, 1H), 8.10 (dd, J=8.0, 1.0 Hz, 1H), 7.85 (dd, J=8.0, 2.5 Hz, 1H), 7.46 (d, J=8.0 Hz, 1H), 7.30 (dd, J=8.0, 5.0 Hz, 1H), 6.79 (d, J=1.7 Hz, 1H), 6.53 (d, J=1.7 Hz, 1H), 5.39 (s, 2H), 5.26-5.24 (m, 1H), 4.51 (s, 2H), 4.42-4.39 (m, 1H), 4.17-4.12 (m, 1H), 3.74 (s, 3H), 3.36 (s, 3H) ppm; (M+1)=419.

Example 1-197: Synthesis of 3-((8-methoxy-2-(5-methoxypyrazin-2-yl)-2,3-dihydrobenzo[b][1,4]dioxin-6-yl)methyl)-3H-imidazo[4,5-b]pyridine Example 1-197-1: Preparation of 2-bromo-1-(5-methoxypyrazin-2-yl)ethan-1-one The title compound was prepared from 2-bromo-5-methoxypyrazine, tributyl(1-ethoxyvinyl)stannane, and N-bromosuccinimide as described in Example 1-196-1.

Example 1-197-2: Preparation of 3-((8-methoxy-2-(5-methoxypyrazin-2-yl)-2,3-dihydrobenzo[b][1,4] dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(5-methoxypyrazin-2-yl)ethan-1-one as described in Example 1-52-1 through Example 1-52-3: $^1$H NMR (400 MHz, DMSO-d$_6$) δ 8.59 (s, 1H), 8.38 (dd, J=4.8, 1.2 Hz, 1H), 8.32 (d, J=1.2 Hz, 1H), 8.26 (s, 1H), 8.09 (dd, J=8.0, 1.2 Hz, 1H), 7.28 (dd, J=8.0, 4.8 Hz, 1H), 6.77 (d, J=1.8 Hz, 1H), 6.48 (d, J=1.8 Hz, 1H), 5.37 (s, 2H), 5.29-5.26 (m, 1H), 4.44-4.40 (m, 1H), 4.32-4.27 (m, 1H), 3.90 (s, 3H), 3.73 (s, 3H) ppm; (M+1)=406.

Example 1-198: Synthesis of 3-((8-methoxy-2-(2-methoxypyrimidin-5-yl)-2,3-dihydrobenzo[b][1,4] dioxin-6-yl)methyl)-3H-imidazo[4,5-b]pyridine Example 1-198-1: Preparation of 2-bromo-1-(2-methoxypyrimidin-5-yl)ethan-1-one The title compound was prepared from 5-bromo-2-methoxypyrimidine, tributyl(1-ethoxyvinyl)stannane, and N-bromosuccinimide as described in Example 1-196-1.

Example 1-198-2: Preparation of 3-((8-methoxy-2-(2-methoxypyrimidin-5-yl)-2,3-dihydrobenzo[b][1, 4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(2-methoxypyrimidin-5-yl)ethan-1-one as described in Example 1-52-1 through Example 1-52-3: $^1$H NMR (500 MHz, DMSO-d$_6$) δ 8.66 (s, 2H), 8.60 (s, 1H), 8.40 (dd, J=5.0, 1.5 Hz, 1H), 8.10 (dd, J=7.5, 1.5 Hz, 1H), 7.30 (dd, J=7.5, 5.0 Hz, 1H), 6.78 (d, J=2.0 Hz, 1H), 6.52 (d, J=2.0 Hz, 1H), 5.39 (s, 2H), 5.23-5.21 (m, 1H), 4.41-4.37 (m, 1H), 4.25-4.20 (m, 1H), 3.92 (s, 3H), 3.73 (s, 3H) ppm; (M+1)= 406.

Example 1-199: Synthesis of 3-((2-(6-(1,1-difluoroethyl)pyridin-3-yl)-8-methoxy-2,3-dihydrobenzo[b] [1,4]dioxin-6-yl)methyl)-3H-imidazo[4,5-b]pyridine Example 1-199-1: Preparation of 6-(1,1-difluoroethyl)nicotinonitrile To a stirred solution of 6-acetylnicotinonitrile (3.28 g, 22.44 mmol) in toluene (25 mL) was added bis(2-methoxyethyl)aminosulfur trifluoride (19.86 g, 89.77 mmol). The mixture was heated to 45° C. After 24 h, the mixture was cooled to 0° C. and was quenched by the slow addition of saturated sodium bicarbonate solution until the mixture reached a pH ~7. Ethyl acetate was added, and the phases were separated. The organic phase was washed with water and brine, dried over magnesium sulfate, filtered, and concentrated. Chromatographic purification of the crude product (CombiFlash, silica gel column, 0-10% ethyl acetate/heptane elute) provided 3.09 g (82%) of 6-(1,1-difluoroethyl)nicotinonitrile as a yellow oil.

Example 1-199-2: Preparation of 1-(6-(1,1-difluoroethyl)pyridin-3-yl)ethan-1-one To a stirred and cooled (0° C.) of 6-(1,1-difluoroethyl) nicotinonitrile (3.23 g, 19.21 mmol) and copper(I) bromide (0.10 g, 0.70 mmol) in tetrahydrofuran (10 mL) was added 3.0M methylmagnesium bromide solution in diethyl ether (19.2 mL, 57.63 mmol). After 15 min, the mixture was allowed to warm to room temperature. After 30 min, the mixture was re-cooled to 0° C. while saturated ammonium chloride solution was added. The mixture was further diluted with ethyl acetate and water. The phases were separated, and the organic phase was washed with brine, dried over magnesium sulfate, filtered, and concentrated. Chromatographic purification of the crude product (CombiFlash, silica gel column, 0-30% ethyl acetate/heptane elute) provided 1.72 g (48%) of 1-(6-(1,1-difluoroethyl)pyridin-3-yl)ethan-1-one (1.72 g, 9.29 mmol, 48.4% yield) as a yellow oil.

Example 1-199-3: Preparation of 2-bromo-1-(6-(1, 1-difluoroethyl)pyridin-3-yl)ethan-1-one The title compound was prepared from 1-(6-(1,1-difluoroethyl)pyridin-3-yl)ethan-1-one and bromine as described in Example 1-110-2.

Example 1-199-4: Preparation of 3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine The title compound, also known as RA10963700, was prepared in three steps from 5-((3H-imidazo [4,5-b]pyridin-3-yl)methyl)-2-(benzyloxy)-3-methoxyphenol (Example 1-193-8) and 2-bromo-1-(6-(1,1-difluoroethyl)pyridin-3-yl) ethan-1-one as described in Example 1-52-1 through Example 1-52-3: $^1$H NMR (500 MHz, DMSO-d$_6$) δ 8.74 (s, 1H), 8.61 (s, 1H), 8.40 (dd, J=5.0, 1.5 Hz, 1H), 8.10 (dd, J=8.0, 1.5 Hz, 1H), 8.02 (dd, J=8.0, 2.5 Hz, 1H), 7.77 (d, J=8.0 Hz, 1H), 7.31 (d, J=8.0, 5.0 Hz, 1H), 6.80 (d, J=2.0 Hz, 1H), 6.53 (d, J=2.0 Hz, 1H), 5.40 (s, 2H), 5.38-5.35 (m, 1H), 4.47-4.44 (m, 1H), 4.21-4.17 (m, 1H), 3.75 (s, 3H), 2.00 (t, J=19.5 Hz, 3H) ppm; (M+1)=439.

Example 1-199-5: Chiral separation of 3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine The racemic 3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine was subjected to SFC preparative purification (21.2×250 mm Chiralpak AD-H column, 19% ethanol/0.1% diethylamine modifier, 48 g/min flow rate) to afford the individual enantiomers.

Example 1-200: Synthesis of 5-(6-((3H-imidazo[4,5-b]pyridin-3-yl)methyl)-8-methoxy-2,3-dihydrobenzo[b][1,4]dioxin-2-yl)furo[2,3-b]pyridine Example 1-200-1: Preparation of 2-bromo-1-(2-(trimethylsilyl)furo[2,3-b]pyridin-5-yl)ethan-1-one The title compound was prepared from 5-bromo-2-(trimethylsilyl)furo[2,3-b]pyridine, tributyl(1-ethoxyvinyl)stannane, and N-bromosuccinimide as described in Example 1-196-1.

Example 1-200-2: Preparation of 5-(6-((3H-imidazo[4,5-b]pyridin-3-yl)methyl)-8-methoxy-2,3-dihydrobenzo[b][1,4]dioxin-2-yl)furo[2,3-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(2-(trimethylsilyl)furo[2,3-b]pyridin-5-yl)ethan-1-one as described in Example 1-52-1 through Example 1-52-3: $^1$H NMR (500 MHz, DMSO-d$_6$) δ 8.61 (s, 1H), 8.41-8.39 (m, 2H), 8.19 (d, J=2.0 Hz, 1H), 8.16 (d, J=2.5 Hz, 1H), 8.10 (dd, J=8.0, 1.5 Hz, 1H), 7.30 (dd, J=8.0, 4.5 Hz, 1H), 7.07 (d, J=2.5 Hz, 1H), 6.79 (d, J=2.0 Hz, 1H), 6.55 (d, J=2.0 Hz, 1H), 5.40 (s, 2H), 5.35-5.33 (m, 1H), 4.45-4.42 (m, 1H), 4.20-4.16 (m, 1H), 3.73 (s, 3H) ppm; (M+1)=415.

Example 1-201: Synthesis of 5-(6-((3H-imidazo[4,5-b]pyridin-3-yl)methyl)-8-methoxy-2,3-dihydrobenzo[b][1,4]dioxin-2-yl)-2,3-dihydrofuro[2,3-b]pyridine The title compound was isolated as a by-product of the synthesis of Example 1-200: $^1$H NMR (500 MHz, DMSO-d$_6$) δ 8.61 (s, 1H), 8.40 (dd, J=5.0, 1.5 Hz, 1H), 8.10 (dd, J=8.0, 1.5 Hz, 1H), 7.97 (s, 1H), 7.66 (s, 1H), 7.30 (dd, J=8.0, 5.0 Hz, 1H), 6.77 (d, J=2.0 Hz, 1H), 6.53 (d, J=2.0 Hz, 1H), 5.39 (s, 2H), 5.10-5.07 (m, 1H), 4.58 (t, J=8.5 Hz, 2H), 4.34-4.30 (m, 1H), 4.13-4.08 (m, 1H), 3.72 (s, 3H), 3.26-3.21 (m, 2H) ppm; (M+1)=417.

Example 1-202: Synthesis of 3-((2-(1-(cyclopropylmethyl)-1H-pyrazol-4-yl)-8-methoxy-2,3-dihydrobenzo[b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(1-(cyclopropylmethyl)-1H-pyrazol-4-yl)ethan-1-one as described in Example 1-52-1 through Example 1-52-3: $^1$H NMR (500 MHz, DMSO-d$_6$) δ 8.59 (s, 1H), 8.40 (dd, J=5.0, 1.5 Hz, 1H), 8.10 (dd, J=8.0, 1.5 Hz, 1H), 7.87 (s, 1H), 7.50 (s, 1H), 7.31 (dd, J=8.0, 5.0 Hz, 1H), 6.73 (d, J=1.5 Hz, 1H), 6.50 (d, J=1.5 Hz, 1H), 5.37 (s, 2H), 5.11-5.08 (m, 1H), 4.33-4.30 (m, 1H), 4.14-4.10 (m, 1H), 3.94 (d, J=7.0 Hz, 2H), 3.70 (s, 3H), 1.23-1.18 (m, 1H), 0.52-0.49 (m, 2H), 0.35-0.32 (m, 2H) ppm; (M+1)=418.

Example 1-203: Synthesis of 3-((2-(4,4-difluorocyclohexyl)-8-methoxy-2,3-dihydrobenzo[b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(4,4-difluorocyclohexyl)ethan-1-one as described in Example 1-52-1 through Example 1-52-3: $^1$H NMR (400 MHz, DMSO-d$_6$) δ 8.59 (s, 1H), 8.39 (dd, J=4.8, 1.2 Hz, 1H), 8.09 (dd, J=8.0, 1.2 Hz, 1H), 7.30 (dd, J=8.0, 4.8 Hz, 1H), 6.73 (d, J=1.6 Hz, 1H), 6.46 (d, J=1.6 Hz, 1H), 5.36 (s, 2H), 4.28-4.24 (m, 1H), 3.94-3.90 (m, 2H), 3.73 (s, 3H), 2.08-1.95 (m, 3H), 1.75-1.73 (m, 4H), 1.38-1.34 (m, 2H) ppm; (M+1)=416.

Example 1-204: Synthesis of 3-((8-methoxy-2-(1-(2-methoxyethyl)-1H-pyrazol-4-yl)-2,3-dihydrobenzo[b][1,4]dioxin-6-yl)methyl)-3H-imidazo[4,5-b]pyridine Example 1-204-1: Preparation of 2-bromo-1-(1-(2-methoxyethyl)-1H-pyrazol-4-yl)ethan-1-one The title compound was prepared from 1-(1-(2-methoxyethyl)-1H-pyrazol-4-yl)ethan-1-one and pyridinium tribromide as described in Example 1-194-1.

Example 1-204-2: Preparation of 3-((8-methoxy-2-(1-(2-methoxyethyl)-1H-pyrazol-4-yl)-2,3-dihydrobenzo[b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(1-(2-methoxyethyl)-1H-pyrazol-4-yl)ethan-1-one as described in Example 1-52-1 through Example 1-52-3: $^1$H NMR (500 MHz, DMSO-d$_6$) δ 8.59 (s, 1H), 8.40 (dd, J=4.5, 1.5 Hz, 1H), 8.11 (dd, J=8.5, 1.5 Hz, 1H), 7.81 (s, 1H), 7.51 (s, 1H), 7.30 (dd, J=8.5, 4.5 Hz, 1H), 6.73 (d, J=1.5 Hz, 1H), 6.50 (d, J=1.5 Hz, 1H), 5.37 (s, 2H), 5.11-5.09 (m, 1H), 4.32-4.29 (m, 1H), 4.23 (t, J=5.0 Hz, 2H), 4.14-4.10 (m, 1H), 3.70 (s, 3H), 3.66 (t, J=5.0 Hz, 2H), 3.21 (s, 3H) ppm; (M+1)=422.

Example 1-205: Synthesis of 3-((2-butyl-8-methoxy-2,3-dihydrobenzo[b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 1-bromohexan-2-one as described in Example 1-52-1 through Example 1-52-3: $^1$H NMR (400 MHz, CDCl$_3$) δ 8.46 (d, J=4.8 Hz, 1H), 8.11 (d, J=8.0 Hz, 1H), 8.04 (s, 1H), 7.30-7.26 (m, 1H), 6.51 (s, 1H), 6.50 (s, 1H), 5.37 (s, 2H), 4.25 (dd, J=11.2, 1.6 Hz, 1H), 4.16-4.10 (m, 1H), 3.92-3.86 (m, 1H), 3.82 (s, 3H), 1.86-1.78 (m, 1H), 1.67-1.34 (m, 5H), 0.96 (t, J=7.2 Hz, 3H) ppm; (M+1)=354.

Example 1-206: Synthesis of 6-methoxy-3-((8-methoxy-2-(1-methyl-1H-pyrazol-4-yl)-2,3-dihydrobenzo[b][1,4]dioxin-6-yl)methyl)-3H-imidazo[4,5-b]pyridine

Example 1-206-1: Preparation of 2-(benzyloxy)-3-methoxy-5-((6-methoxy-3H-imidazo[4,5-b]pyridin-3-yl)methyl)phenol The title compound was prepared in four steps from (4-(benzyloxy)-3-methoxy-5-((4-methoxybenzyl)oxy)phenyl)methanamine (Example 1-193-4) and 2-chloro-5-methoxy-3-nitropyridine as described as described in Example 1-193-5 through Example 1-193-8.

Example 1-206-2: Preparation of 6-methoxy-3-((8-methoxy-2-(1-methyl-1H-pyrazol-4-yl)-2,3-dihydrobenzo[b][1,4]dioxin-6-yl)methyl)-3H-imidazo[4,5-b]pyridine The title compound was prepared in three steps from 2-(benzyloxy)-3-methoxy-5-((6-methoxy-3H-imidazo[4,5-b]pyridin-3-yl)methyl)phenol and 2-bromo-1-(1-methyl-1H-pyrazol-4-yl)ethan-1-one as described in Example 1-52-1 through Example 1-52-3: $^1$H NMR (500 MHz, CD$_3$OD) δ 8.41-8.37 (m, 1H), 8.18 (d, J=2.0 Hz, 1H), 7.70 (s, 1H), 7.65 (s, 1H), 7.55 (s, 1H), 6.68 (d, J=2.0 Hz, 1H), 6.53 (d, J=2.0 Hz, 1H), 5.38 (s, 2H), 5.16-5.13 (m, 1H), 4.35-4.31 (m, 1H), 4.14-4.10 (m, 1H), 3.93 (s, 3H), 3.88 (s, 3H), 3.78 (s, 3H) ppm; (M+1)=408.

Example 1-207: Synthesis of 3-((2-(1,5-dimethyl-1H-pyrazol-4-yl)-8-methoxy-2,3-dihydrobenzo[b][1,4]dioxin-6-yl)methyl)-6-methoxy-3H-imidazo[4,5-b]pyridine The title compound was prepared in three steps from 2-(benzyloxy)-3-methoxy-5-((6-methoxy-3H-imidazo[4,5-b]pyridin-3-yl)methyl)phenol (Example 1-206-1) and 2-bromo-1-(1,5-dimethyl-1H-pyrazol-4-yl)ethan-1-one as described in Example 1-52-1 through Example 1-52-3: $^1$H NMR (400 MHz, DMSO-d$_6$) δ 8.51 (s, 1H), 8.15 (d, J=2.4 Hz,1H), 7.72 (d, J=2.4 Hz, 1H), 7.36 (s, 1H), 6.70 (d, J=1.2 Hz 1H), 6.49 (d, J=1.2 Hz, 1H), 5.33 (s, 2H), 5.05-5.02 (m, 1H), 4.26-4.23 (m, 1H), 4.19-4.13 (m, 1H), 3.85 (s, 3H), 3.71 (s, 3H), 3.69 (s, 3H), 2.25 (s, 3H) ppm; (M+1)=422.

Example 1-208: Synthesis of 3-((2-(1,3-dimethyl-1H-pyrazol-4-yl)-8-methoxy-2,3-dihydrobenzo[b][1,4]dioxin-6-yl)methyl)-6-methoxy-3H-imidazo[4,5-b]pyridine The title compound was prepared in three steps from 2-(benzyloxy)-3-methoxy-5-((6-methoxy-3H-imidazo[4,5-b]pyridin-3-yl)methyl)phenol (Example 1-206-1) and 2-bromo-1-(1,3-dimethyl-1H-pyrazol-4-yl)ethan-1-one as described in Example 1-52-1 through Example 1-52-3: $^1$H NMR (500 MHz, DMSO-d$_6$) δ 8.51 (s, 1H), 8.15 (d, J=2.5 Hz, 1H), 7.72 (d, J=2.5 Hz, 1H), 7.64 (s, 1H), 6.71 (d, J=1.5 Hz, 1H), 6.49 (d, J=1.5 Hz, 1H), 5.33 (s, 2H), 5.05-5.03 (m, 1H), 4.30-4.27 (m, 1H), 4.10-4.05 (m, 1H), 3.85 (s, 3H), 3.72 (s, 3H), 3.69 (s, 3H), 2.15 (s, 3H) ppm; (M+1)=422.

Example 1-209: Synthesis of 3-((2-(1-(cyclopropylmethyl)-1H-pyrazol-4-yl)-8-methoxy-2,3-dihydrobenzo[b][1,4]dioxin-6-yl)methyl)-6-methoxy-3H-imidazo[4,5-b]pyridine The title compound was prepared in three steps from 2-(benzyloxy)-3-methoxy-5-((6-methoxy-3H-imidazo[4,5-b]pyridin-3-yl)methyl)phenol (Example 1-206-1) and 2-bromo-1-(1-(cyclopropylmethyl)-1H-pyrazol-4-yl)ethan-1-one as described in Example 1-52-1 through Example 1-52-3: $^1$H NMR (500 MHz, DMSO-d$_6$) δ 8.51 (s, 1H), 8.15 (d, J=2.5 Hz, 1H), 7.88 (s, 1H), 7.72 (d, J=2.5 Hz, 1H), 7.50 (s, 1H), 6.71 (d, J=1.5 Hz, 1H), 6.48 (d, J=1.5 Hz, 1H), 5.33 (s, 2H), 5.11-5.09 (m, 1H), 4.33-4.30 (m, 1H), 4.15-4.11 (m, 1H), 3.94 (d, J=7.0 Hz, 2H), 3.86 (s, 3H), 3.70 (s, 3H), 1.24-1.18 (m, 1H), 0.52-0.49 (m, 2H), 0.36-0.33 (m, 2H) ppm; (M+1)=448.

Example 1-210: Synthesis of 3-((2-(1-cyclobutyl-1H-pyrazol-4-yl)-8-methoxy-2,3-dihydrobenzo[b][1,4]dioxin-6-yl)methyl)-6-methoxy-3H-imidazo[4,5-b]pyridine The title compound was prepared in three steps from 2-(benzyloxy)-3-methoxy-5-((6-methoxy-3H-imidazo[4,5-b]pyridin-3-yl)methyl)phenol (Example 1-206-1) and 2-bromo-1-(1-cyclobutyl-1H-pyrazol-4-yl)ethan-1-one (Example 1-194-1) as described in Example 1-52-1 through Example 1-52-3: $^1$H NMR (500 MHz, DMSO-d$_6$) δ 8.50 (s, 1H), 8.15 (d, J=2.5 Hz, 1H), 7.91 (s, 1H), 7.72 (d, J=2.5 Hz, 1H), 7.54 (s, 1H), 6.70 (d, J=1.5 Hz, 1H), 6.47 (d, J=1.5 Hz, 1H), 5.32 (s, 2H), 5.09-5.07 (m, 1H), 4.83-4.79 (m, 1H), 4.32-4.29 (m, 1H), 4.13-4.09 (m, 1H), 3.85 (s, 3H), 3.69 (s, 3H), 2.45-2.39 (m, 2H), 2.37-2.31 (m, 2H), 1.79-1.73 (m, 2H) ppm; (M+1)=448.

Example 1-211: Synthesis of 6-methoxy-3-((8-methoxy-2-(6-(methoxymethyl)pyridin-3-yl)-2,3-dihydrobenzo[b][1,4]dioxin-6-yl)methyl)-3H-imidazo[4,5-b]pyridine The title compound was prepared in three steps from 2-(benzyloxy)-3-methoxy-5-((6-methoxy-3H-imidazo[4,5-b]pyridin-3-yl)methyl)phenol (Example 1-206-1) and 2-bromo-1-(6-(methoxymethyl)pyridin-3-yl)ethan-1-one (Example 1-196-1) as described in Example 1-52-1 through Example 1-52-3: $^1$H NMR (500 MHz, DMSO-d$_6$) δ 8.59 (d, J=2.0 Hz, 1H), 8.52 (s, 1H), 8.15 (d, J=2.5 Hz, 1H), 7.85 (dd, J=8.0, 2.0 Hz, 1H), 7.73 (d, J=2.5 Hz, 1H), 7.46 (d, J=8.0 Hz, 1H), 6.76 (d, J=2.0 Hz, 1H), 6.50 (d, J=2.0 Hz, 1H), 5.35 (s, 2H), 5.25 (dd, J=8.0, 2.5 Hz, 1H), 4.51 (s, 2H), 4.41 (dd, J=11.5, 2.5 Hz, 1H), 4.15 (dd, J=11.5, 8.0 Hz, 1H), 3.85 (s, 3H), 3.74 (s, 3H), 3.36 (s, 3H) ppm; (M+1)=449.

Example 1-212: Synthesis of 3-((2-butyl-8-methoxy-2,3-dihydrobenzo[b][1,4]dioxin-6-yl)methyl)-6-methoxy-3H-imidazo[4,5-b]pyridine The title compound was prepared in three steps from 2-(benzyloxy)-3-methoxy-5-((6-methoxy-3H-imidazo[4,5-b]pyridin-3-yl)methyl)phenol (Example 1-206-1) and 1-bromohexan-2-one as described in Example 1-52-1 through Example 1-52-3: $^1$H NMR (400 MHz, CDCl$_3$) δ 8.22 (d, J=2.6 Hz, 1H), 7.98 (s, 1H), 7.60 (d, J=2.6 Hz, 1H), 6.50 (d, J=1.8 Hz, 1H), 6.48 (d, J=1.8 Hz, 1H), 5.32 (s, 2H), 4.23 (dd, J=11.2, 2.0 Hz, 1H), 4.16-4.09 (m, 1H), 3.92 (s, 3H), 3.91-3.86 (m, 1H), 3.82 (s, 3H), 1.85-1.79 (m, 1H), 1.65-1.36 (m, 5H), 0.93 (t, J=7.2 Hz, 3H) ppm; (M+1)=384.

Example 1-213: Synthesis of 6-(azetidin-1-yl)-3-((8-methoxy-2-(1-methyl-1H-pyrazol-4-yl)-2,3-dihydrobenzo[b][1,4]dioxin-6-yl)methyl)-3H-imidazo[4,5-b]pyridine Example 1-213-1: Preparation of 2-(benzyloxy)-5-((6-bromo-3H-imidazo[4,5-b]pyridin-3-yl)methyl)-3-methoxyphenol The title compound was prepared in four steps from (4-(benzyloxy)-3-methoxy-5-((4-methoxybenzyl)oxy)phenyl)methanamine (Example 1-193-4) and 5-bromo-2-chloro-3-nitropyridine as described in Example 1-193-5 through Example 1-193-8.

Example 1-213-2: Preparation of 2-(2-(benzyloxy)-5-((6-bromo-3H-imidazo[4,5-b]pyridin-3-yl)methyl)-3-methoxyphenoxy)-1-(1-methyl-1H-pyrazol-4-yl)ethan-1-one The title compound was prepared from 2-(benzyloxy)-5-((6-bromo-3H-imidazo[4,5-b]pyridin-3-yl)methyl)-3-methoxyphenol and 2-bromo-1-(1-methyl-1H-pyrazol-4-yl)ethan-1-one as described in Example 1-52-1.

Example 1-213-3: Preparation of 2-(2-(benzyloxy)-5-((6-bromo-3H-imidazo[4,5-b]pyridin-3-yl)methyl)-3-methoxyphenoxy)-1-(1-methyl-1H-pyrazol-4-yl)ethan-1-ol The title compound was prepared from 2-(2-(benzyloxy)-5-((6-bromo-3H-imidazo[4,5-b]pyridin-3-yl)methyl)-3-methoxyphenoxy)-1-(1-methyl-1H-pyrazol-4-yl)ethan-1-one as described in Example 1-14-2.

Example 1-213-4: Preparation of 6-bromo-3-((8-methoxy-2-(1-methyl-1H-pyrazol-4-yl)-2,3-dihydrobenzo[b][1,4]dioxin-6-yl)methyl)-3H-imidazo[4,5-b]pyridine A stirred suspension of 2-(2-(benzyloxy)-5-((6-bromo-3H-imidazo[4,5-b]pyridin-3-yl)methyl)-3-methoxyphenoxy)-1-(1-methyl-1H-pyrazol-4-yl)ethan-1-ol (1.30 g, 2.30 mmol) in 6M hydrochloric acid solution (20 mL) was heated to reflux. After 2 h, the mixture was allowed to cool to room temperature and was diluted with water. The acidic solution was neutralized by the addition of solid potassium carbonate. The neutral mixture was extracted with ethyl acetate (×3). The combine organic phases were washed with brine, dried over sodium sulfate, filtered, and concentrated. The crude product was purified by silica gel chromatography (1:1 petroleum ether/ethyl acetate) to afford 0.80 g, (76%) of 6-bromo-3-((8-methoxy-2-(1-methyl-1H-pyrazol-4-yl)-2,3-dihydrobenzo[b][1,4]dioxin-6-yl)methyl)-3H-imidazo[4,5-b]pyridine as a tan solid.

Example 1-213-5: Preparation of 6-(azetidin-1-yl)-3-((8-methoxy-2-(1-methyl-1H-pyrazol-4-yl)-2,3-dihydrobenzo[b][1,4]dioxin-6-yl)methyl)-3H-imidazo[4,5-b]pyridine The title compound was prepared from 6-bromo-3-((8-methoxy-2-(1-methyl-1H-pyrazol-4-yl)-2,3-dihydrobenzo[b][1,4]dioxin-6-yl)methyl)-3H-imidazo[4,5-b]pyridine and azetidine as described in Example 1-10: $^1$H NMR (500 MHz, CDCl$_3$) δ 7.93 (s, 1H), 7.77 (d, J=2.5 Hz, 1H), 7.54 (s, 1H), 7.47 (s, 1H), 7.14 (d, J=2.5 Hz, 1H), 6.51 (s, 1H), 6.50 (s, 1H), 5.30 (s, 2H), 5.18 (dd, J=8.0, 2.5 Hz, 1H), 4.32 (dd, J=11.5, 2.5 Hz, 1H), 4.16 (dd, J=11.5, 8.0 Hz, 1H), 3.99-3.95 (m, 4H), 3.89 (s, 3H), 3.79 (s, 3H), 2.48-2.42 (m, 2H) ppm; (M+1)=433.

Example 1-214: Synthesis of 3-((8-methoxy-2-(1-methyl-1H-pyrazol-4-yl)-2,3-dihydrobenzo[b][1,4]dioxin-6-yl)methyl)-6-(3-methoxyazetidin-1-yl)-3H-imidazo[4,5-b]pyridine The title compound was prepared from 6-bromo-3-((8-methoxy-2-(1-methyl-1H-pyrazol-4-yl)-2,3-dihydrobenzo[b][1,4]dioxin-6-yl)methyl)-3H-imidazo[4,5-b]pyridine (Example 1-213-4) and 3-methoxyazetidine hydrochloride as described in Example 1-10: $^1$H NMR (500 MHz, CDCl$_3$) δ 7.94 (s, 1H), 7.80 (d, J=2.5 Hz, 1H), 7.55 (s, 1H), 7.48 (s, 1H), 7.17 (d, J=2.5 Hz, 1H), 6.52 (d, J=2.0 Hz, 1H), 6.50 (d, J=2.0 Hz, 1H), 5.31 (s, 2H), 5.20-5.17 (m, 1H), 4.44-4.40 (m, 1H), 4.33 (dd, J=11.5, 2.0 Hz, 1H), 4.24-4.20 (m, 2H), 4.17 (dd, J=11.5, 7.5 Hz, 1H), 3.89 (s, 3H), 3.80 (s, 3H), 3.79-3.77 (m, 2H), 3.38 (s, 3H) ppm; (M+1)=463.

Example 1-215: Synthesis of 6-cyclopropyl-3-((8-methoxy-2-(1-methyl-1H-pyrazol-4-yl)-2,3-dihydrobenzo[b][1,4]dioxin-6-yl)methyl)-3H-imidazo[4,5-b]pyridine The title compound was prepared from 6-bromo-3-((8-methoxy-2-(1-methyl-1H-pyrazol-4-yl)-2,3-dihydrobenzo[b][1,4]dioxin-6-yl)methyl)-3H-imidazo[4,5-b]pyridine (Example 1-213-4) and cyclopropylboronic acid as described in Example 1-9: $^1$H NMR (500 MHz, CDCl$_3$) δ 8.32 (d, J=2.0 Hz, 1H), 8.00 (s, 1H), 7.72 (d, J=2.0 Hz, 1H), 7.55 (s, 1H), 7.48 (s, 1H), 6.54-6.50 (m, 2H), 5.35 (s, 2H), 5.19 (dd, J=7.5, 2.5 Hz, 1H), 4.32 (dd, J=11.5, 2.5 Hz, 1H), 4.17-4.12 (m, 1H), 3.89 (s, 3H), 3.80 (s, 3H), 2.10-2.06 (m, 1H), 1.08-1.03 (m, 2H), 0.79-0.75 (m, 2H) ppm; (M+1)=418.

Example 1-216: Synthesis of 6-cyclopropyl-3-((8-methoxy-2-(6-(methoxymethyl)pyridin-3-yl)-2,3-dihydrobenzo[b][1,4]dioxin-6-yl)methyl)-3H-imidazo[4,5-b]pyridine Example 1-216-1: Preparation of 6-bromo-3-((8-methoxy-2-(6-(methoxymethyl)pyridin-3-yl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-(methoxymethyl)pyridin-3-yl)ethan-1-one (Example 1-196-1), and 5-bromo-2-chloro-3-nitropyridine as described in Example 1-52-1 through Example 1-52-9.

Example 1-216-2: Preparation of 6-cyclopropyl-3-((8-methoxy-2-(6-(methoxymethyl)pyridin-3-yl)-2,3-dihydrobenzo[b][1,4]dioxin-6-yl)methyl)-3H-imidazo[4,5-b]pyridine The title compound was prepared from 6-bromo-3-((8-methoxy-2-(6-(methoxymethyl)pyridin-3-yl)-2,3-dihydrobenzo[b][1,4]dioxin-6-yl)methyl)-3H-imidazo[4,5-b]pyridine and cyclopropylboronic acid as described in Example 1-9: $^1$H NMR (500 MHz, CDCl$_3$) δ 8.61 (d, J=1.5 Hz, 1H), 8.32 (d, J=1.5 Hz, 1H), 8.01 (s, 1H), 7.78 (dd, J=8.5, 1.5 Hz, 1H), 7.72 (d, J=1.5 Hz, 1H), 7.48 (d, J=8.0 Hz, 1H), 6.55 (s, 1H), 6.53 (s, 1H), 5.36 (s, 2H), 5.19 (d, J=8.0, 2.0 Hz, 1H), 4.61 (s, 2H), 4.35 (d, J=11.5, 2.0 Hz, 1H), 4.08 (dd, J=11.5, 8.0 Hz, 1H), 3.82 (s, 3H), 3.48 (s, 3H), 2.10-2.06 (m, 1H), 1.07-1.04 (m, 2H), 0.78-0.75 (m, 2H) ppm; (M+1)=459.

Example 1-217: Synthesis of 6-(difluoromethyl)-3-((8-methoxy-2-(6-(methoxymethyl)pyridin-3-yl)-2,3-dihydrobenzo[b][1,4]dioxin-6-yl)methyl)-3H-imidazo[4,5-b]pyridine The title compound was prepared in nine steps from methyl 4-(benzyloxy)-3-hydroxy-5-methoxybenzoate, 2-bromo-1-(6-(methoxymethyl)pyridin-3-yl)ethan-1-one (Example 1-196-1), and 5-(difluoromethyl)-2-(methylsulfonyl)-3-nitropyridine (Example 1-86-5) as described in Example 1-52-1 through Example 1-52-9: $^1$H NMR (400 MHz, CDCl$_3$) δ 8.64-8.60 (m, 2H), 8.26 (s, 1H), 8.16 (s, 1H), 7.78 (dd, J=8.0, 1.6 Hz, 1H), 7.49 (d, J=8.0 Hz, 1H), 6.89 (t, J=56 Hz, 1H), 6.59-6.55 (m, 2H), 5.42 (s, 2H), 5.21-5.19 (m, 1H), 4.61 (s, 2H), 4.39-4.35 (m, 1H), 4.12-4.07 (m, 1H), 3.84 (s, 3H), 3.49 (s, 3H) ppm; (M+1)=469.

Example 1-218: Synthesis of (3-((2-(1-cyclobutyl-1H-pyrazol-4-yl)-8-methoxy-2,3-dihydrobenzo[b][1,4]dioxin-6-yl)methyl)-3H-imidazo[4,5-b]pyridin-6-yl)methanol Example 1-218-1: Preparation of 6-bromo-3-((2-(1-cyclobutyl-1H-pyrazol-4-yl)-8-methoxy-2,3-dihydrobenzo[b][1,4]dioxin-6-yl)methyl)-3H-imidazo[4,5-b]pyridine The title compound was prepared in three steps from 2-(benzyloxy)-5-((6-bromo-3H-imidazo[4,5-b]pyridin-3-yl)methyl)-3-methoxyphenol (Example 1-213-1) and 2-bromo-1-(1-cyclobutyl-1H-pyrazol-4-yl)ethan-1-one (Example 1-194-1) as described in Example 1-213-2 through Example 1-213-4.

Example 1-218-2: Preparation of methyl 3-((2-(1-cyclobutyl-1H-pyrazol-4-yl)-8-methoxy-2,3-dihydrobenzo[b][1,4]dioxin-6-yl)methyl)-3H- imidazo[4,5-b]pyridine-6-carboxylate To a stirred suspension of 6-bromo-3-((2-(1-cyclobutyl-1H-pyrazol-4-yl)-8-methoxy-2,3-dihydrobenzo[b][1,4]dioxin-6-yl)methyl)-3H-imidazo[4,5-b]pyridine (0.23 g, 0.46 mmol), 4,5-bis(diphenylphosphino)-9,9-dimethylxanthene (0.027 g, 0.046 mmol), and triethylamine (0.47 g, 4.63 mmol) in 1:1 methanol/N,N-dimethylformamide (10 mL) was added palladium(II) acetate (0.010 g, 0.046 mmol). The mixture was evacuated, and the atmosphere was replaced with carbon monoxide (1 atm via balloon). The mixture was heated to 65° C. After 48 h, the mixture was allowed to cool to room temperature and was concentrated. The crude product was purified by silica gel chromatography (8% methanol/dichloromethane elute) to afford 0.10 g (45%) of methyl 3-((2-(1-cyclobutyl-1H-pyrazol-4-yl)-8-methoxy-2,3-dihydrobenzo[b][1,4]dioxin-6-yl)methyl)-3H-imidazo[4,5-b]pyridine-6-carboxylate as a light yellow solid.

Example 1-218-3: Preparation of (3-((2-(1-cyclobutyl-1H-pyrazol-4-yl)-8-methoxy-2,3-dihydrobenzo[b][1,4]dioxin-6-yl)methyl)-3H-imidazo[4,5-b]pyridin-6-yl)methanol The title compound was prepared from methyl 3-((2-(1-cyclobutyl-1H-pyrazol-4-yl)-8-methoxy-2,3-dihydrobenzo[b][1,4]dioxin-6-yl)methyl)-3H-imidazo[4,5-b]pyridine-6-carboxylate as described in Example 1-52-4: $^1$H NMR (400 MHz, CDCl$_3$) δ 8.45 (d, J=1.6 Hz, 1H), 8.09 (d, J=1.6 Hz, 1H), 8.05 (s, 1H), 7.57 (s, 1H), 7.55 (s, 1H), 6.53-6.51 (m, 2H), 5.36 (s, 2H), 5.17 (dd, J=7.6, 2.4 Hz, 1H), 4.86 (s, 2H), 4.75-4.72 (m, 1H), 4.32 (dd, J=11.2, 2.4 Hz, 1H), 4.14 (dd, J=11.2, 7.6 Hz, 1H), 3.80 (s, 3H), 2.56-2.42 (m, 4H), 1.91-1.79 (m, 3H) ppm; (M+1)=448.

Example 1-219: Synthesis of 3-((8-methoxy-2-(6-methylpyridin-3-yl)-2,3-dihydrobenzo[b][1,4]dioxin-6-yl)methyl)-6-(trifluoromethyl)-3H-imidazo[4,5-b]pyridine Example 1-219-1: Preparation of 2-(benzyloxy)-3-methoxy-5-((6-(trifluoromethyl)-3H-imidazo[4,5-b]pyridin-3-yl)methyl)phenol The title compound was prepared in four steps from (4-(benzyloxy)-3-methoxy-5-((4-methoxybenzyl)oxy)phenyl)methanamine (Example 1-193-4) and 2-chloro-3-nitro-5-(trifluoromethyl)pyridine as described in Example 1-193-5 through Example 1-193-8.

Example 1-219-2: Preparation of 3-((8-methoxy-2-(6-methylpyridin-3-yl)-2,3-dihydrobenzo[b][1,4]dioxin-6-yl)methyl)-6-(trifluoromethyl)-3H-imidazo[4,5-b]pyridine The title compound was prepared in three steps from 2-(benzyloxy)-3-methoxy-5-((6-(trifluoromethyl)-3H-imidazo[4,5-b]pyridin-3-yl)methyl)phenol and 2-bromo-1-(6-methylpyridin-3-yl)ethan-1-one as described in Example 1-52-1 through Example 1-52-3: $^1$H NMR (400 MHz, CDCl$_3$) δ 8.74 (s, 1H), 8.55 (s, 1H), 8.35 (s, 1H), 8.20 (s, 1H), 7.65 (d, J=8.2 Hz, 1H), 7.21 (d, J=8.2 Hz, 1H), 6.58-6.56 (m, 2H), 5.42 (s, 2H), 5.17-5.15 (m, 1H), 4.37-4.33 (m, 1H), 4.11-4.06 (m, 1H), 3.84 (s, 3H), 2.59 (s, 3H) ppm; (M+1)=457.

Example 1-220: Synthesis of 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)azetidin-2-one To a stirred suspension of 6-iodo-3-((8-methoxy-2-(6-methoxypyridin-3-yl)-2,3-dihydrobenzo[b][1,4]dioxin-6-yl)methyl)-3H-imidazo[4,5-b]pyridine (0.068 g, 0.13 mmol, Example 1-52-9), cesium carbonate (0.17 g, 0.52 mmol), bis(diphenylphosphino)-9,9-dimethylxanthene (0.016 g, 0.027 mmol), and azetidin-2-one (0.026 g, 0.37 mmol) in 1,4-dioxane (10 mL) was added tris(dibenzylideneacetone)dipalladium(0) (0.016 g, 0.017 mmol. The mixture was degassed under vacuum/backfilled with nitrogen (×3). The mixture was heated to 105° C. in a sealed vessel. After 1 h, the mixture was allowed to cool to room temperature and was concentrated. Chromatographic purification of the crude product (Biotage, 12 g silica gel column, 0-100% ethyl acetate/heptane followed by 0-10% methanol/ethyl acetate elute) provided 0.017 g (28%) of 1-(3-((8-methoxy-2-(6- methoxypyridin-3-yl)-2,3-dihydrobenzo[b][1,4]dioxin-6-yl)methyl)-3H-imidazo[4,5-b]pyridin-6-yl)azetidin-2-one as a tan solid: $^1$H NMR (400 MHz, CDCl$_3$) δ 8.68-8.66 (m, 1H), 8.24-8.16 (m, 1H), 8.05 (d, J=1.4 Hz, 1H), 8.01 (d, J=2.1 Hz, 1H), 7.63-7.59 (m, 1H), 6.77 (dd, J=8.7, 1.4 Hz, 1H), 6.55-6.53 (m, 2H), 5.34 (s, 2H), 5.11-5.07 (m, 1H), 4.32-4.28 (m, 1H), 4.11-4.02 (m, 1H), 3.94 (s, 3H), 3.80 (s, 3H), 3.76-3.72 (m, 2H), 3.23-3.19 (m, 2H) ppm; (M+1)=474.

Example 1-221: Synthesis of 7-((8-methoxy-2-(6-methoxypyridin-3-yl)-2,3-dihydrobenzo[b][1,4]dioxin-6-yl)methyl)-5H-pyrrolo[2,3-b]pyrazine Example 1-221-1: Preparation of 7-bromo-5-((2-(trimethylsilyl)ethoxy)methyl)-5H-pyrrolo[2,3-b]pyrazine To a stirred and cooled (0° C.) suspension of 7-bromo-5H-pyrrolo[2,3-b]pyrazine (0.75 g, 3.64 mmol) in N,N-dimethylformamide (15 mL) was added 60% sodium hydride dispersion (0.18 g, 4.54 mmol). After 15 min, the mixture was treated with 2-(trimethylsilyl)ethoxymethyl chloride (0.73 g, 4.36 mmol). The resulting cloudy mixture was allowed to warm to room temperature. After 2 h, the mixture was diluted with water (15 mL). The mixture was then extracted with 1:3 ethyl acetate/ether (×2). The combined organic phases were washed with water, dried over magnesium sulfate, filtered, and concentrated. The residue was suspended in diethyl ether and was sonicated. The liquid phase was decanted, and the process repeated. The combined liquid phases were concentrated to provide 1.10 g (92%) of 7-bromo-5-((2-(trimethylsilyl)ethoxy)methyl)-5H-pyrrolo[2,3-b]pyrazine as a brown oil.

Example 1-221-2: Preparation of 7-((8-methoxy-2-(6-methoxypyridin-3-yl)-2,3-dihydrobenzo[b][1,4]dioxin-6-yl)methyl)-5H-pyrrolo[2,3-b]pyrazine The title compound was prepared in two steps from 7-bromo-5-((2-(trimethylsilyl)ethoxy)methyl)-5H-pyrrolo[2,3-b]pyrazine and 8-methoxy-2-(6-methoxypyridin-3-yl)-2,3-dihydrobenzo[b][1,4]dioxine-6-carbaldehyde (Example 1-102-1) as described in Example 1-23-3 through Example 1-23-4: $^1$H NMR (400 MHz, CDCl$_3$) δ 9.65 (s, 1H), 8.48 (d, J=2.5 Hz, 1H), 8.25 (d, J=2.5 Hz, 1H), 8.21 (d, J=2.5 Hz, 1H), 7.62 (dd, J=8.6, 2.5 Hz, 1H), 7.39-7.32 (m, 1H), 6.76 (d, J=8.6 Hz, 1H), 6.60 (d, J=1.9 Hz, 1H), 6.54 (d, J=1.9 Hz, 1H), 5.09 (dd, J=8.4, 2.4 Hz, 1H), 4.28 (dd, J=11.5, 2.4 Hz, 1H), 4.13 (s, 2H), 4.06 (dd, J=11.5, 8.4 Hz, 1H), 3.93 (s, 3H), 3.82 (s, 3H) ppm; (M+1)=405.

Example 1-222: Synthesis of 4-((8-methoxy-2-(6-methoxypyridin-3-yl)-2,3-dihydrobenzo[b][1,4]dioxin-6-yl)methyl)-1H-pyrrolo[2,3-b]pyridine Example 1-222-1: Preparation of (8-methoxy-2-(6-methoxypyridin-3-yl)-2,3-dihydrobenzo[b][1,4]dioxin-6-yl)(1H-pyrrolo[2,3-b]pyridin-4-yl)methanol To a stirred and cooled (−78° C.) solution of 4-bromo-1H-pyrrolo[2,3-b]pyridine (0.25 g, 1.28 mmol) in tetrahydrofuran (5 mL) was added dropwise via syringe a 2.7 M n-butyllithium solution in hexanes (0.49 mL, 1.34 mmol). After 30 min, the mixture was treated with a 1.7 M tert-butyllithium solution in heptane (0.75 mL, 1.28 mmol). After 15 min, the mixture was treated with a solution of 8-methoxy-2-(6-methoxypyridin-3-yl)-2,3-dihydrobenzo[b][1,4]dioxine-6-carbaldehyde (0.35 g, 1.16 mmol, Example 1-102-1) in tetrahydrofuran (3 mL). After 15 min, the mixture was allowed to warm to room temperature and stir. After 10 min at room temperature, the mixture was quenched by the addition of saturated ammonium chloride solution (0.2 mL). The mixture was concentrated, and the residue was partitioned between dichloromethane and water (pH adjusted to ~7-8). The phases were separated, and the organic phase was washed with water. The organic phase was dried over sodium sulfate, filtered, and concentrated to afford crude (8-methoxy-2-(6-methoxypyridin-3-yl)-2,3-dihydrobenzo[b][1,4]dioxin-6-yl)(1H-pyrrolo[2,3-b]pyridin-4-yl)methanol as an oil.

Example 1-222-2: Preparation of 4-((8-methoxy-2-(6-methoxypyridin-3-yl)-2,3-dihydrobenzo[b][1,4]dioxin-6-yl)methyl)-1H-pyrrolo[2,3-b]pyridine The title compound was prepared from (8-methoxy-2-(6-methoxypyridin-3-yl)-2,3-dihydrobenzo[b][1,4]dioxin-6-yl)(1H-pyrrolo[2,3-b]pyridin-4-yl)methanol as described in Example 1-22-2: $^1$H NMR (400 MHz, CDCl$_3$) δ 10.00 (s, 1H), 8.21 (d, J=2.4 Hz, 1H), 8.19 (d, J=5.2 Hz, 1H), 7.62 (dd, J=8.6, 2.5 Hz, 1H), 7.35 (d, J=3.6 Hz, 1H), 6.96 (d, J=5.2 Hz, 1H), 6.78 (d, J=8.6 Hz, 1H), 6.59 (d, J=3.6 Hz, 1H), 6.47 (d, J=1.9 Hz, 1H), 6.41 (d, J=1.9 Hz, 1H), 5.10 (dd, J=8.5, 2.4 Hz, 1H), 4.30 (dd, J=11.5, 2.4 Hz, 1H), 4.20 (s, 2H), 4.07 (dd, J=11.5, 8.5 Hz, 1H), 3.94 (s, 3H), 3.80 (s, 3H) ppm; (M+1)=404.

Example 1-223: Synthesis of 4-(3-((2-(6-methoxypyridin-3-yl)chroman-6-yl)methyl)-3H-imidazo[4,5-b]pyridin-6-yl)-2-methylbut-3-yn-2-amine Example 1-223-1: Preparation of (E)-1-(5-bromo-2-hydroxyphenyl)-3-(6-methoxypyridin-3-yl)prop-2-en-1-one To a stirred solution of 1-(5-bromo-2-hydroxyphenyl)ethanone (22.35 g, 103.91 mmol) in ethanol (225 mL) was added 6-methoxynicotinaldehyde (15.00 g, 109.38 mmol). The resulting homogeneous solution was treated with a solution of potassium hydroxide (13.50 g, 240.64 mmol) in water (75 mL) (added dropwise over 5 min). The mixture was allowed to stir. After 16 h, the mixture was poured into water (400 mL) and was neutralized to pH ~7 with slow addition of 3N hydrochloric acid solution. The resulting suspension was filtered, and the solids were re-suspended in water (400 mL) and re-filtered. The solid was dried in a vacuum dessicator followed by azeotroping with toluene to provide 27.70 g (76%) of (E)-1-(5-bromo-2-hydroxyphenyl)-3-(6-methoxypyridin-3-yl)prop-2-en-1-one as a yellow solid.

Example 1-223-2: Preparation of 6-bromo-2-(6-methoxypyridin-3-yl)chroman-4-one

To a stirred suspension of (E)-1-(5-bromo-2-hydroxyphenyl)-3-(6-methoxypyridin-3-yl)prop-2-en-1-one (27.70 g, 82.89 mmol) in ethanol (500 mL) was added sodium acetate (51.00 g, 621.7 mmol). To this mixture was added water (12.5 mL), and the resulting yellow suspension was heated to reflux. After 16 h, an additional portion of sodium acetate (10.0 g) was added, and heating was continued for 1 h. The mixture was then allowed to cool to room temperature and then it was concentrated to ~300 mL total volume. The mixture was extracted with dichloromethane (2×250 mL).

The combined organic phases were washed with brine, dried over sodium sulfate, and concentrated. The crude yellow solid was triturated in diethyl ether (150 mL), and the suspension refluxed for 30 min to provide 13 g of product (~80% purity). This material was refluxed in ethanol (150 mL) for 20 minutes, and the suspension was allowed to stand overnight. The mixture was cooled in an ice bath, and the solids were isolated by filtration. The filter cake was washed with ethanol, and the solids were dried to provide 12.10 g (44%) of 6-bromo-2-(6-methoxypyridin-3-yl)chroman-4-one as a yellow solid.

Example 1-223-3: Preparation of 5-(6-bromochroman-2-yl)-2-methoxypyridine

The title compound was prepared from of 6-bromo-2-(6-methoxypyridin-3-yl)chroman-4-one as described in Example 1-22-2 (note: reaction conducted at reflux for 20 h).

Example 1-223-4: Preparation of 2-methoxy-5-(6-vinylchroman-2-yl)pyridine

To a stirred suspension of 5-(6-bromochroman-2-yl)-2-methoxypyridine (1.60 g, 5.00 mmol), potassium vinyltrifluoroborate (0.85 g, 6.00 mmol), triphenylphosphine (0.13 g, 0.50 mmol), cesium carbonate (4.88 g, 14.99 mmol) in 10:1 tetrahydrofuran/water (30 mL) was added palladium (II) chloride (0.044 g, 0.25 mmol). The suspension was degassed under vacuum/backfilled with nitrogen (×3) and then it was heated at 100° C. After 16 h, the mixture was allowed to cool to room temperature and was partitioned between water (30 mL) and dichloromethane (100 mL). The organic phase was washed with water and brine, dried over sodium sulfate and concentrated. Chromatographic purification of the crude product (CombiFlash, 40 g silica gel gold column, 10-20% ethyl acetate/hexanes elute) afforded 0.79 g (59%) of 2-methoxy-5-(6-vinylchroman-2-yl)pyridine as a white solid.

Example 1-223-5: Preparation of 2-(6-methoxypyridin-3-yl)chromane-6-carbaldehyde To a stirred solution of 2-methoxy-5-(6-vinylchroman-2-yl)pyridine (0.79 g, 2.96 mmol), tetrahydrofuran (20 mL) and water (6.7 mL, 2.96 mmol) was added 4% wt/wt osmium tetroxide solution in water (0.36 mL, 0.059 mmol), resulting in the formation of a light brown solution. Sodium periodate (1.58 g, 7.39 mmol) was added in one portion and a mild exotherm was noted. The thick mixture was allowed to stir at room temperature for 1 hr. The mixture was treated with sodium sulfite (1.75 g) and was allowed to stir at room temperature for 15 min. A thick viscous material formed on the bottom of the flask, and the clear liquid was decanted off and filtered through Celite. The pad was washed with ethyl acetate (75 mL). The filtrate was diluted with water (15 mL), and the phases were separated. The organic phase was washed with 1N sodium hydroxide solution (50 mL), dried over magnesium sulfate, filtered, and concentrated to provide 0.79 g (99%) of 2-(6-methoxypyridin-3-yl)chroman-6-carbaldehyde as a viscous light amber oil.

Example 1-223-6: Preparation of (2-(6-methoxypyridin-3-yl)chroman-6-yl)methanamine The title compound was prepared in two steps from 2-(6-methoxypyridin-3-yl)chroman-6-carbaldehyde and hydroxylamine hydrochloride as described in Example 1-18-8 through Example 1-18-9.

Example 1-223-7: Preparation of 4-(3-((2-(6-methoxypyridin-3-yl)chroman-6-yl)methyl)-3H-imidazo[4,5-b]pyridin-6-yl)-2-methylbut-3-yn-2-amine The title compound was prepared in four steps from (2-(6-methoxypyridin-3-yl)chroman-6-yl)methanamine, 2-chloro-5-iodo-3-nitropyridine, and 2-methylbut-3-yn-2-amine as described in Example 1-52-7 through Example 1-2-10: $^1$H NMR (400 MHz, CDCl$_3$) δ 8.46 (d, J=1.8 Hz, 1H), 8.18 (d, J=2.5 Hz, 1H), 8.08 (d, J=1.8 Hz, 1H), 8.03 (s, 1H), 7.62 (dd, J=8.6, 2.5 Hz, 1H), 7.14-6.99 (m, 2H), 6.84 (d, J=8.3 Hz, 1H), 6.77 (d, J=8.6 Hz, 1H), 5.36 (s, 2H), 5.01 (dd, J=10.3, 2.4 Hz, 1H), 3.94 (s, 3H), 3.01-2.88 (m, 1H), 2.80-2.70 (m, 1H), 2.24-1.82 (m, 4H), 1.53 (s, 6H) ppm; (M+1)=454.

Example 1-224: Synthesis of 4-(3-((8-methoxy-2-(4-methoxyphenyl)chroman-6-yl)methyl)-3H-imidazo[4,5-b]pyridin-6-yl)-2-methylbut-3-yn-2-amine Example 1-224-1: Preparation of (E)-3-(5-bromo-2-hydroxy-3-methoxyphenyl)-1-(4-methoxyphenyl)prop-2-en-1-one To a mechanically stirred suspension of 5-bromo-2-hydroxy-3-methoxybenzaldehyde (10.00 g, 42.42 mmol) and 4'-methoxyacetophenone (6.00 g, 39.55 mmol) in ethanol (150 mL) was added 10M sodium hydroxide solution (13.8 mL, 138.44 mmol). The resulting thick mixture was heated to reflux (a color change to orange-red was observed as the mixture warmed). Additional portions (~0.5 g) of the aldehyde were added at 1 h and 2 h. After 3 h, mixture was allowed to cool to room temperature and was diluted with water (~500 mL). The basic suspension was treated with concentrated hydrochloric acid solution (~12 mL, resulting solution pH ~3). The mixture was allowed to stir at room temperature. After 1 h, the mixture was filtered, and the filter cake was washed with water and air-dried to provide a brown solid. Trituration of the crude solid with hot ethanol (100 mL) afforded 10.25 g (71%) of (E)-3-(5-bromo-2-hydroxy-3-methoxyphenyl)-1-(4-methoxyphenyl)prop-2-en-1-one as a yellow solid.

Example 1-224-2: Preparation of 3-(5-bromo-2-hydroxy-3-methoxyphenyl)-1-(4-methoxyphenyl)propan-1-one To a stirred suspension of (E)-3-(5-bromo-2-hydroxy-3-methoxyphenyl)-1-(4-methoxyphenyl)prop-2-en-1-one (9.19 g, 25.30 mmol), ammonium chloride (27.07 g, 506.1 mmol) in tetrahydrofuran (25 mL), ethanol (15 mL), and water (5 mL) was added zinc dust (6.62 g, 101.21 mmol). The resulting mixture was allowed to stir at room temperature (the color of the mixture gradually changed to green-gray as the mixture was stirred). After 10 min, the gray suspension was filtered through Celite, and the filter cake was washed with ethanol (100 mL). The filtrate was concentrated, and the residue partitioned between water (150 mL) and ethyl acetate (100 mL). The phases were separated, and the aqueous phase extracted with ethyl acetate (2×100 mL). The combined organic phases dried over magnesium sulfate, filtered, and concentrated. Chromatographic purification of the crude product (CombiFlash, 80 g silica gel gold column, 20-40% ethyl acetate/heptane elute,) afforded 3.41 g (37%) of 3-(5-bromo-2-hydroxy-3-methoxyphenyl)-1-(4-methoxyphenyl)propan-1-one as a light yellow solid.

Example 1-224-3: Preparation of 4-bromo-2-(3-hydroxy-3-(4-methoxyphenyl)propyl)-6-methoxyphenol The title compound was prepared from 3-(5-bromo-2-hydroxy-3-methoxyphenyl)-1-(4-methoxyphenyl)propan-1-one as described in Example 1-14-2.

Example 1-224-4: Preparation of 6-bromo-8-methoxy-2-(4-methoxyphenyl)chromane

A stirred solution of 4-bromo-2-(3-hydroxy-3-(4-methoxyphenyl)propyl)-6-methoxyphenol (3.43 g, 9.34 mmol) in acetic acid (25 mL) was heated to 110° C. After 45 min, the mixture was allowed to cool to room temperature and was diluted with water (30 mL). The mixture was made basic by the addition of concentrated ammonium hydroxide solution (20 mL). The mixture was extracted with dichloromethane (3×50 mL). The combined organic phases were dried over magnesium sulfate, filtered, and concentrated. Chromatographic purification of the crude product (Combi-Flash, 220 g silica gel gold column, 10-25% ethyl acetate/heptane elute) afforded 2.41 g (74%) of 6-bromo-8-methoxy-2-(4-methoxyphenyl)chromane as a white solid.

Example 1-224-5: Preparation of (8-methoxy-2-(4-methoxyphenyl)chroman-6-yl)methanamine The title compound was prepared in four steps from 6-bromo-8-methoxy-2-(4-methoxyphenyl)chromane, potassium vinyltrifluoroborate, and hydroxylamine hydrochloride as described in Example 1-223-4 through Example 1-223-6.

Example 1-224-6: Preparation of 4-(3-((8-methoxy-2-(4-methoxyphenyl)chroman-6-yl)methyl)-3H-imidazo[4,5-b]pyridin-6-yl)-2-methylbut-3-yn-2-amine The title compound was prepared in four steps from (8-methoxy-2-(4-methoxyphenyl)chroman-6-yl)methanamine, 2-chloro-5-iodo-3-nitropyridine, and 2-methylbut-3-yn-2-amine as described in Example 1-52-7 through Example 1-52-10: $^1$H NMR (400 MHz, CDCl$_3$) δ 8.47 (d, J=1.8 Hz, 1H), 8.08 (d, J=1.8 Hz, 1H), 8.02 (s, 1H), 7.33-7.29 (m, 2H), 6.92-6.85 (m, 2H), 6.73 (d, J=2.0 Hz, 1H), 6.63 (d, J=2.0 Hz, 1H), 5.34 (s, 2H), 5.10 (dd, J=9.2, 2.7 Hz, 1H), 3.80 (s, 3H), 3.79 (s, 3H), 2.94-2.83 (m, 1H), 2.75-2.65 (m, 1H), 2.24-2.01 (m, 2H), 1.58 (br s, 2H), 1.53 (s, 6H) ppm; (M+1)=483.

Example 1-225: Synthesis of 6-fluoro-3-((8-methoxy-2-(6-methoxypyridin-3-yl)chroman-6-yl)methyl)-3H-imidazo[4,5-b]pyridine Example 1-225-1: Preparation of (E)-3-(5-bromo-2-hydroxy-3-methoxyphenyl)-1-(6-methoxypyridin-3-yl)prop-2-en-1-one The title compound was prepared from 5-bromo-2-hydroxy-3-methoxybenzaldehyde and 1-(6-methoxypyridin-3-yl)ethan-1-one as described in Example 1-224-1.

Example 1-225-2: Preparation of 4-bromo-2-(3-hydroxy-3-(6-methoxypyridin-3-yl)propyl)-6-methoxyphenol To a stirred and cooled (0° C.) solution of (E)-3-(5-bromo-2-hydroxy-3-methoxyphenyl)-1-(6-methoxypyridin-3-yl)prop-2-en-1-one (10.00 g, 27.50 mmol) in tetrahydrofuran (100 mL) was added cobalt(II) chloride hexahydrate (6.56 g, 27.50 mmol). After 30 min, sodium borohydride (6.25 g, 165 mmol) was added portionwise. The resulting mixture was allowed to slowly warm to room temperature. After 2 h, the mixture was quenched with water. The mixture was extracted with ethyl acetate (2×100 mL). The combined organic phases were dried over sodium sulfate, filtered, and concentrated. The residue was purified by silica gel chromatography (3:1 petroleum ether/ethyl acetate elute) to provide 5.80 g (57%) of 4-bromo-2-(3-hydroxy-3-(6-methoxypyridin-3-yl)propyl)-6-methoxyphenol as a yellow solid.

Example 1-225-3: Preparation of 5-(6-bromo-8-methoxychroman-2-yl)-2-methoxypyridine The title compound was prepared from 4-bromo-2-(3-hydroxy-3-(6-methoxypyridin-3-yl)propyl)-6-methoxyphenol as described in Example 1-12-4.

Example 1-225-4: Preparation of 8-methoxy-2-(6-methoxypyridin-3-yl)chromane-6-carbonitrile A mixture of palladium(II)acetate (0.23 g, 1.00 mmol) and sodium carbonate (1.06 g, 10.00 mmol) in 10:1 1-methyl-2-pyrrolidinone and propan-2-ol (22 mL) was stirred at room temperature under an air atmosphere. After 30 min, the mixture was treated with potassium hexacyanoferrate(II) trihydrate (2.10 g, 5.00 mmol) and 5-(6-bromo-8-methoxychroman-2-yl)-2-methoxypyridine (3.50 g, 10.00 mmol), and the resulting mixture was heated to 140° C. After 16 h, the mixture was allowed to cool to room temperature and was filtered through Celite. The filtrate was diluted with water (40 mL) and extracted with ethyl acetate (2×60 mL). The combined organic phases were dried over sodium sulfate, filtered, and concentrated. The residue was purified by silica gel chromatography (1:1 petroleum ether/ethyl acetate elute) to afford 1.48 g (50%) of 8-methoxy-2-(6-methoxypyridin-3-yl)chromane-6-carbonitrile (1.48 g, 50%) as a white solid.

Example 1-225-5: Preparation of (8-methoxy-2-(6-methoxypyridin-3-yl)chroman-6-yl)methanamine To a stirred suspension of 8-methoxy-2-(6-methoxypyridin-3-yl)chromane-6-carbonitrile (1.50 g, 5.10 mmol), and concentrated hydrochloric acid solution (0.5 mL) in methanol (20 mL) was added 10% palladium on carbon (0.20 g). The mixture was degassed under vacuum/backfilled with nitrogen (×3). The atmosphere was replaced with hydrogen (via balloon), and the mixture was allowed to stir at room temperature. After 20 h, the mixture was filtered through Celite, and the filtrate was concentrated to afford 1.50 g (99%) of (8-methoxy-2-(6-methoxypyridin-3-yl)chroman-6-yl)methanamine as a white solid.

Example 1-225-6: Preparation of 6-fluoro-3-((8-methoxy-2-(6-methoxypyridin-3-yl)chroman-6-yl)methyl)-3H-imidazo[4,5-b]pyridine The title compound was prepared in three steps from (8-methoxy-2-(6-methoxypyridin-3-yl)chroman-6-yl)methanamine and 2-chloro-5-fluoro-3-nitropyridine, as described in Example 1-52-7 through Example 1-52-9: $^1$H NMR (400 MHz, DMSO-d$_6$) δ 8.68 (s, 1H), 8.44 (s, 1H), 8.20-8.18 (m, 1H), 8.08 (dd, J=8.8, 2.4 Hz, 1H), 7.73 (dd, J=8.8, 2.4 Hz, 1H), 6.94 (s, 1H), 6.86-6.82 (m, 1H), 6.69 (s, 1H), 5.38 (s, 2H), 5.04-5.00 (m, 1H), 3.85 (s, 3H), 3.69 (s, 3H), 2.88-2.84 (m, 1H), 2.67-2.63 (m, 1H), 2.07-1.99 (m, 2H) ppm; (M+1)=421.

Example 1-226: Synthesis of 4-(3-((8-methoxy-2-(6-methoxypyridin-3-yl)chroman-6-yl)methyl)-3H-imidazo[4,5-b]pyridin-6-yl)-2-methylbut-3-yn-2-amine Example 1-226-1: Preparation of 6-iodo-3-((8-methoxy-2-(6-methoxypyridin-3-yl)chroman-6-yl)methyl)-3H-imidazo[4,5-b]pyridine The title compound was prepared in three steps from (8-methoxy-2-(6-methoxypyridin-3-yl)chroman-6-yl)methanamine (Example 1-225-5) and 2-chloro-5-iodo-3-nitropyridine as described in Example 1-52-7 through Example 1-52-9.

Example 1-226-2: Preparation of 4-(3-((8-methoxy-2-(6-methoxypyridin-3-yl)chroman-6-yl)methyl)-3H-imidazo[4,5-b]pyridin-6-yl)-2-methylbut-3-yn-2-amine The title compound was prepared from 6-iodo-3-((8-methoxy-2-(6-methoxypyridin-3-yl)chroman-6-yl)methyl)-3H-imidazo[4,5-b]pyridine and 2-methylbut-3-yn-2-amine as described in Example 1-52-10: $^1$H NMR (500 MHz, DMSO-$d_6$) δ 8.63 (s, 1H), 8.39 (d, J=1.5 Hz, 1H), 8.19 (d, J=2.0 Hz, 1H), 8.05 (d, J=1.5 Hz, 1H), 7.74-7.71 (m, 1H), 6.94 (d, J=2.0 Hz, 1H), 6.84 (d, J=8.5 Hz, 1H), 6.68 (d, J=2.0 Hz, 1H), 5.36 (s, 2H), 5.03-5.01 (m, 1H), 3.84 (s, 3H), 3.68 (s, 3H), 2.90-2.84 (m, 1H), 2.67-2.62 (m, 1H), 2.16 (br s, 2H), 2.10-2.06 (m, 1H), 2.02-1.97 (m, 1H), 1.14 (s, 6H) ppm; (M+1)=484.

Example 1-227: Synthesis of 4-(3-((8-methoxy-2-(6-methoxypyridin-3-yl)chroman-6-yl)methyl)-3H-imidazo[4,5-b]pyridin-6-yl)morpholine The title compound was prepared from 6-iodo-3-((8-methoxy-2-(6-methoxypyridin-3-yl)chroman-6-yl)methyl)-3H-imidazo[4,5-b]pyridine (Example 1-226-1) and morpholine as described in Example 1-10: $^1$H NMR (500 MHz, DMSO-$d_6$) δ 8.45 (s, 1H), 8.24 (d, J=2.5 Hz, 1H), 8.19 (d, J=2.5 Hz, 1H), 7.73 (dd, J=8.5, 2.5 Hz, 1H), 7.62 (d, J=2.5 Hz, 1H), 6.93 (d, J=2.0 Hz, 1H), 6.84 (d, J=8.5 Hz, 1H), 6.66 (d, J=2.0 Hz, 1H), 5.32 (s, 2H), 5.02 (dd, J=10.0, 2.5 Hz, 1H), 3.85 (s, 3H), 3.80-3.76 (m, 4H), 3.69 (s, 3H), 3.15-3.11 (m, 4H), 2.88-2.85 (m, 1H), 2.67-2.62 (m, 1H), 2.09-1.98 (m, 2H) ppm; (M+1)=488.

Example 1-228: Synthesis of 3-((8-methoxy-2-(6-methoxypyridin-3-yl)chroman-6-yl)methyl)-6-(2-methyl-1H-imidazol-1-yl)-3H-imidazo[4,5-b]pyridine The title compound was prepared from 6-iodo-3-((8-methoxy-2-(6-methoxypyridin-3-yl)chroman-6-yl)methyl)-3H-imidazo[4,5-b]pyridine (Example 1-226-1) and 2-methyl-1H-imidazole as described in Example 1-42: $^1$H NMR (400 MHz, CD$_3$OD) δ 8.63 (s, 1H), 8.51 (d, J=2.4 Hz, 1H), 8.18-8.16 (m, 2H), 7.77-7.73 (m, 1H), 7.28 (s, 1H), 7.04 (s, 1H), 6.99 (s, 1H), 6.82 (d, J=8.0 Hz, 1H), 6.81 (s, 1H), 5.50 (s, 2H), 5.08-5.05 (m, 1H), 3.92 (s, 3H), 3.79 (s, 3H), 2.97-2.92 (m, 1H), 2.76-2.72 (m, 1H), 2.35 (s, 3H), 2.21-2.16 (m, 1H), 2.08-2.03 (m, 1H) ppm; (M+1)=483.

Example 1-229: Synthesis of 3-((8-methoxy-2-(6-methoxypyridin-3-yl)chroman-6-yl)methyl)-3H-imidazo[4,5-b]pyridine The title compound was prepared in three steps from (8-methoxy-2-(6-methoxypyridin-3-yl)chroman-6-yl)methanamine (Example 1-225-5) and 2-chloro-3-nitropyridine as described in Example 1-52-7 through Example 1-52-9: $^1$H NMR (400 MHz, DMSO-$d_6$) δ 8.59 (s, 1H), 8.40 (d, J=4.4 Hz, 1H), 8.19 (s, 1H), 8.09 (d, J=8.0 Hz, 1H), 7.73 (d, J=8.4 Hz, 1H), 7.32-7.28 (m, 1H), 6.96 (s, 1H), 6.84 (d, J=8.4 Hz, 1H), 6.69 (s, 1H), 5.38 (s, 2H), 5.04-5.01 (m, 1H), 3.85 (s, 3H), 3.69 (s, 3H), 2.90-2.84 (m, 1H), 2.66-2.63 (m, 1H), 2.07-1.98 (m, 2H) ppm; (M+1)=403.

Example 1-230: Synthesis of 4-(3-((8-methoxy-2-(6-methoxypyridin-3-yl)chroman-6-yl)methyl)pyrazolo[1,5-a]pyrimidin-6-yl)-2-methylbut-3-yn-2-amine Example 1-230-1: Preparation of 2-methoxy-5-(8-methoxy-6-(4,4,5,5-tetramethyl-1,3,2-dioxaborolan-2-yl)chroman-2-yl)pyridine To a stirred solution of 5-(6-bromo-8-methoxychroman-2-yl)-2-methoxypyridine (1.00 g, 2.86 mmol, Example 1-225-3), 4,4,4',4',5,5,5',5'-octamethyl-2,2'-bi(1,3,2-dioxaborolane) (0.80 g, 3.15 mmol), and potassium acetate (0.84 g, 8.60 mmol) in 1,4-dioxane (10 mL) was added [1,1'-bis(diphenylphosphino)ferrocene]dichloropalladium(II) (0.11 g, 0.14 mmol). The mixture was heated to 100° C. After 5 h, the mixture was allowed to cool to room temperature and was filtered. The filtrate was diluted with water (15 mL) and extracted with ethyl acetate (3×20 mL). The combined organic phases were washed with brine (30 mL), dried over sodium sulfate, filtered, and concentrated. The residue was purified by silica gel chromatography (10:1 petroleum ether/ethyl acetate elute) to afford 1.00 g(88%) of 2-methoxy-5-(8-methoxy-6-(4,4,5,5-tetramethyl-1,3,2-dioxaborolan-2-yl)chroman-2-yl)pyridine (1.0 g, 88%) as yellow oil.

Example 1-230-2: Preparation of (8-methoxy-2-(6-methoxypyridin-3-yl)chroman-6-yl)boronic acid To a stirred solution of 2-methoxy-5-(8-methoxy-6-(4,4,5,5-tetramethyl-1,3,2-dioxaborolan-2-yl)chroman-2-yl)pyridine (1.70 g, 4.28 mmol) in 4:1 tetrahydrofuran/water (25 mL) was added sodium periodate (1.83 g, 8.56 mmol). The resulting mixture was allowed to stir at room temperature. After 16 h, the mixture was treated with 1.0M hydrochloric acid solution HCl (10 mL), and the mixture was extracted with ethyl acetate (3×30 mL). The combined organic phases were washed with brine (50 mL), dried over sodium sulfate, filtered, and concentrated. The residue was purified by silica gel chromatography (2% methanol in dichloromethane elute) to afford 1.10 g (81%) of (8-methoxy-2-(6-methoxypyridin-3-yl)chroman-6-yl)boronic acid as a white solid.

Example 1-230-3: Preparation of 6-bromo-3-((8-methoxy-2-(6-methoxypyridin-3-yl)chroman-6-yl)methyl)pyrazolo[1,5-a]pyrimidine The title compound was prepared from (E/Z)-N'-((6-bromopyrazolo[1,5-a]pyrimidin-3-yl)methylene)-4-methylbenzenesulfonohydrazide (Example 1-21-7) and (8-methoxy-2-(6-methoxypyridin-3-yl)chroman-6-yl)boronic acid as described in Example 1-21-8.

Example 1-230-4: Preparation of 4-(3-((8-methoxy-2-(6-methoxypyridin-3-yl)chroman-6-yl)methyp-pyrazolo[1,5-a]pyrimidin-6-yl)-2-methylbut-3-yn-2-amine The title compound was prepared from 6-bromo-3-((8-methoxy-2-(6-methoxypyridin-3-yl)chroman-6-yl)methyl)pyrazolo[1,5-a]pyrimidine and 2-methylbut-3-yn-2-amine as described in Example 1-23-5: $^1$H NMR (500 MHz, CD$_3$OD) δ 8.93 (s, 1H), 8.46 (s, 1H), 8.18 (s, 1H), 8.03 (s, 1H), 7.78-7.76 (m, 1H), 6.83-6.78 (m, 2H), 6.62 (s, 1H), 5.05-5.04 (m, 1H), 4.05 (s, 2H), 3.92 (s, 3H), 3.77 (s, 3H), 2.97-2.92 (m, 1H), 2.74-2.69 (m, 1H), 2.19-2.16 (m, 1H), 2.08-2.02 (m, 1H), 1.49 (s, 6H) ppm; (M+1)=484.

Example 1-231: Synthesis of 4-(3-((8-methoxy-2-(6-methoxypyridin-3-yl)chroman-6-yl)methyl)pyrazolo[1,5-a]pyrimidin-6-yl)morpholine The title compound was prepared from 6-bromo-3-((8-methoxy-2-(6-methoxypyridin-3-yl)chroman-6-yl)methyl)pyrazolo[1,5-a]pyrimidine (Example 1-230-3) and morpholine as described in Example 1-10: $^1$H NMR (500 MHz, DMSO-d$_6$) δ 8.64 (d, J=2.5 Hz, 1H), 8.44 (d, J=2.5 Hz, 1H), 8.20 (d, J=2.5 Hz, 1H), 7.91 (s, 1H), 7.75 (dd, J=8.5, 2.5 Hz, 1H), 6.85 (d, J=8.5 Hz, 1H), 6.76 (s, 1H), 6.55 (s, 1H), 5.01-4.99 (m, 1H), 3.95 (s, 2H), 3.86 (s, 3H), 3.80-3.76 (m, 4H), 3.67 (s, 3H), 3.14-3.10 (m, 4H), 2.88-2.85 (m, 1H), 2.65-2.62 (m, 1H), 2.08-2.01 (m, 2H) ppm; (M+1)=488.

Example 1-232: Synthesis of 3-((8-methoxy-2-(6-methoxypyridin-3-yl)chroman-6-yl)methyl)-6-(2-methyl-1H-imidazol-1-yl)pyrazolo[1,5-a]pyrimidine The title compound was prepared from 6-bromo-3-((8-methoxy-2-(6-methoxypyridin-3-yl)chroman-6-yl)methyl)pyrazolo[1,5-a]pyrimidine (Example 1-230-3) and 2-methyl-1H-imidazole as described in Example 1-42: $^1$H NMR (400 MHz, CD$_3$OD) δ 9.22 (d, J=2.0 Hz, 1H), 8.59 (d, J=2.0 Hz, 1H), 8.18 (d, J=2.0 Hz, 1H), 8.15 (s, 1H), 7.77 (dd, J=8.4, 2.0 Hz, 1H), 7.32 (d, J=1.2 Hz, 1H), 7.05 (d, J=1.2 Hz, 1H), 6.83-6.81 (m, 2H), 6.66 (s, 1H), 5.06-5.03 (m, 1H), 4.11 (s, 2H), 3.92 (s, 3H), 3.78 (s, 3H), 2.95-2.91 (m, 1H), 2.74-2.69 (m, 1H), 2.41 (s, 3H), 2.21-2.16 (m, 1H), 2.08-2.03 (m, 1H) ppm; (M+1)=483.

Example 1-233: Synthesis of 4-(3-((8-methoxy-2-(6-methoxypyridin-3-yl)chroman-6-yl)methyl)pyrazolo[1,5-a]pyridin-6-yl)-2-methylbut-3-yn-2-amine Example 1-233-1: Preparation of (E/Z)-N'-((6-bromopyrazolo[1,5-a]pyridin-3-yl)methylene)-4-methylbenzenesulfonohydrazide The title compound was prepared from 6-bromopyrazolo[1,5-a]pyridine-3-carbaldehyde and 4-methylbenzenesulfonylhydrazide as described in Example 1-21-7.

Example 1-233-2: Preparation of (6-bromopyrazolo[1,5-a]pyridin-3-yl)(8-methoxy-2-(6-methoxypyridin-3-yl)chroman-6-yl)methanol The title compound was prepared from (E/Z)-N-((6-bromopyrazolo[1,5-a]pyridin-3-yl)methylene)-4-methylbenzenesulfonohydrazide and (8-methoxy-2-(6-methoxypyridin-3-yl)chroman-6-yl)boronic acid (Example 1-230-2) as described in Example 1-21-8 (note: in this case, the hydroxy-containing compound was isolated rather than the methylene-containing compound).

Example 1-233-3: Preparation of 6-bromo-3-((8-methoxy-2-(6-methoxypyridin-3-yl)chroman-6-yl)methyl)pyrazolo[1,5-a]pyridine The title compound was prepared from (6-bromopyrazolo[1,5-a]pyridin-3-yl)(8-methoxy-2-(6-methoxypyridin-3-yl)chroman-6-yl)methanol as described in Example 1-22-2.

Example 1-233-4: Preparation of 4-(3-((8-methoxy-2-(6-methoxypyridin-3-yl)chroman-6-yl)methyp-pyrazolo[1,5-a]pyridin-6-yl)-2-methylbut-3-yn-2-amine The title compound was prepared from 6-bromo-3-((8-methoxy-2-(6-methoxypyridin-3-yl)chroman-6-yl)methyl)pyrazolo[1,5-a]pyridine and 2-methylbut-3-yn-2-amine as described in Example 1-23-5: $^1$H NMR (500 MHz, CDCl$_3$) δ 8.48 (s, 1H), 8.19 (d, J=2.0 Hz, 1H), 7.81 (s, 1H), 7.66 (dd, J=8.5, 2.0 Hz, 1H), 7.25 (d, J=9.0 Hz, 1H), 6.99 (d, J=9.0 Hz, 1H), 6.75 (d, J=8.5 Hz, 1H), 6.58 (s, 1H), 6.51 (s, 1H), 5.11-5.08 (m, 1H), 3.99 (s, 2H), 3.93 (s, 3H), 3.78 (s, 3H), 2.94-2.87 (m, 1H), 2.73-2.68 (m, 1H), 2.19-2.07 (m, 2H), 1.51 (s, 6H) ppm; (M+1)=483.

Example 1-234: Synthesis of 4-(3-((8-methoxy-2-(6-methoxypyridin-3-yl)chroman-6-yl)methyl)pyrazolo[1,5-a]pyridin-6-yl)morpholine The title compound was prepared from 6-bromo-3-((8-methoxy-2-(6-methoxypyridin-3-yl)chroman-6-yl)methyl)pyrazolo[1,5-a]pyridine (Example 1-233-3) and morpholine as described in Example 1-10: $^1$H NMR (500 MHz, CDCl$_3$) δ 8.19 (d, J=2.0 Hz, 1H), 7.93 (s, 1H), 7.70 (s, 1H), 7.66 (dd, J=8.5, 2.5 Hz, 1H), 7.23 (d, J=9.5 Hz, 1H), 6.93 (dd, J=9.5, 2.0 Hz, 1H), 6.75 (d, J=8.5 Hz, 1H), 6.60 (s, 1H), 6.52 (s, 1H), 5.10-5.07 (m, 1H), 3.97 (s, 2H), 3.93 (s, 3H), 3.90-3.86 (m, 4H), 3.78 (s, 3H), 3.08-3.04 (m, 4H), 2.94-2.87 (m, 1H), 2.73-2.67 (m, 1H), 2.18-2.06 (m, 2H) ppm; (M+1)=487.

Example 1-235: Synthesis of 3-((8-methoxy-2-(6-methoxypyridin-3-yl)chroman-6-y1)methyl)-6-(2-methyl-1H-imidazol-1-yl)pyrazolo[1,5-a]pyridine The title compound was prepared from 6-bromo-3-((8-methoxy-2-(6-methoxypyridin-3-yl)chroman-6-yl)methyl)pyrazolo[1,5-a]pyridine (Example 1-233-3) and 2-methyl-1H-imidazole as described in Example 1-42: $^1$H NMR (500 MHz, CDCl$_3$) δ 8.49 (s, 1H), 8.19 (d, J=2.5 Hz, 1H), 7.92 (s, 1H), 7.66 (dd, J=8.5, 2.5 Hz, 1H), 7.44 (d, J=9.5 Hz, 1H), 7.06 (s, 1H), 7.01 (s, 1H), 7.00 (dd, J=9.5, 2.0 Hz, 1H), 6.76 (d, J=8.5 Hz, 1H), 6.62 (s, 1H), 6.56 (s, 1H), 5.12-5.09 (m, 1H), 4.04 (s, 2H), 3.93 (s, 3H), 3.80 (s, 3H), 2.96-2.89 (m, 1H), 2.75-2.70 (m, 1H), 2.39 (s, 3H), 2.22-2.07 (m, 2H) ppm; (M+1)=482.

Example 1-236: Synthesis of 4-(3-((8-methoxy-2-(6-methoxypyridin-3-yl)chroman-6-yl)methyl)imidazo[1,2-b]pyridazin-7-yl)-2-methylbut-3-yn-2-amine

Example 1-236-1: Preparation of 7-chloroimidazo[1,2-b]pyridazine-3-carbaldehyde The title compound was prepared in two steps from 3-bromo-7-chloroimidazo[1,2-b]pyridazine and potassium vinyltrifluoroborate as describe in Example 1-223-4 through Example 1-223-5.

Example 1-236-2: Preparation of (E/Z)-N'-((7-chloroimidazo[1,2-b]pyridazin-3-yl)methylene)-4-methylbenzenesulfonohydrazide The title compound was prepared from 7-chloroimidazo[1,2-b]pyridazine-3-carbaldehyde and 4-methylbenzenesulfonylhydrazide as described in Example 1-21-7.

Example 1-236-3: Preparation of 7-chloro-3-((8-methoxy-2-(6-methoxypyridin-3-yl)chroman-6-yl)methyl)imidazo[1,2-b]pyridazine The title compound was prepared from (E/Z)-N-((7-chloroimidazo[1,2-b]pyridazin-3-yl)methylene)-4-methylbenzenesulfonohydrazide and (8-methoxy-2-(6-methoxypyridin-3-yl)chroman-6-yl)boronic acid (Example 1-230-2) as described in Example 1-21-8.

Example 1-236-4: Preparation of 4-(3-((8-methoxy-2-(6-methoxypyridin-3-yl)chroman-6-yl)methyl)imidazo[1,2-b]pyridazin-7-yl)-2-methylbut-3-yn-2-amine The title compound was prepared from 7-chloro-3-((8-methoxy-2-(6-methoxypyridin-3-yl)chroman-6-yl)methyl)imidazo[1,2-b]pyridazine and 2-methylbut-3-yn-2-amine as described in Example 1-23-5: $^1$H NMR (500 MHz, CDCl$_3$) δ 8.29 (s, 1H), 8.20 (d, J=2.0 Hz, 1H), 7.92 (s, 1H), 7.66 (dd, J=8.5, 2.0 Hz, 1H), 7.58 (s, 1H), 6.76 (d, J=8.5 Hz, 1H), 6.73 (s, 1H), 6.61 (s, 1H), 5.13-5.10 (m, 1H), 4.25 (s, 2H), 3.94 (s, 3H), 3.82 (s, 3H), 2.95-2.90 (m, 1H), 2.76-2.71 (m, 1H), 2.20-2.09 (m, 2H), 1.54 (s, 6H) ppm; (M+1)=484.

Example 1-237: Synthesis of 4-(3-((8-methoxy-2-(6-methoxypyridin-3-yl)chroman-6-yl)methyl)imidazo[1,2-b]pyridazin-7-yl)morpholine The title compound was prepared from 7-chloro-3-((8-methoxy-2-(6-methoxypyridin-3-yl)chroman-6-yl)methyl)imidazo[1,2-b]pyridazine (Example 1-236-3) and morpholine as described in Example 1-10: $^1$H NMR (500 MHz, CDCl$_3$) δ 8.24 (s, 1H), 8.20 (d, J=2.5 Hz, 1H), 7.66 (dd, J=9.0, 2.5 Hz, 1H), 7.38 (s, 1H), 7.08 (s, 1H), 6.76 (d, J=9.0 Hz, 1H), 6.72 (s, 1H), 6.61 (s, 1H), 5.12-5.10 (m, 1H), 4.20 (s, 2H), 3.95 (s, 3H), 3.93-3.89 (m, 4H), 3.82 (s, 3H), 3.24-3.20 (m, 4H), 2.95-2.89 (m, 1H), 2.77-2.68 (m, 1H), 2.21-2.03 (m, 2H) ppm; (M+1)=488.

Example 1-238: Synthesis of 4-(3-((8-fluoro-2-(6-methoxypyridin-3-yl)chroman-6-yl)methyl)-3H-imidazo[4,5-b]pyridin-6-yl)-2-methylbut-3-yn-2-amine

Example 1-238-1: Preparation of (8-fluoro-2-(6-methoxypyridin-3-yl)chroman-6-yl)methanamine The title compound was prepared in five steps from 5-bromo-3-fluoro-2-hydroxybenzaldehyde and 1-(6-methoxypyridin-3-yl)ethan-1-one as described in Example 1-225-1 through Example 1-225-5.

Example 1-238-2: Preparation of 4-(3-((8-fluoro-2-(6-methoxypyridin-3-yl)chroman-6-yl)methyl)-3H-imidazo[4,5-b]pyridin-6-yl)-2-methylbut-3-yn-2-amine The title compound was prepared in four steps from (8-fluoro-2-(6-methoxypyridin-3-yl)chroman-6-yl)methanamine, 2-chloro-5-iodo-3-nitropyridine, and 2-methylbut-3-yn-2-amine as described in Example 1-52-7 through Example 1-52-10: $^1$H NMR (500 MHz, CDCl$_3$) δ 8.48 (d, J=1.5 Hz, 1H), 8.20 (d, J=2.5 Hz, 1H), 8.10 (d, J=1.5 Hz, 1H), 8.06 (s, 1H), 7.66 (dd, J=8.5, 2.5 Hz, 1H), 6.97-6.93 (m, 1H), 6.82 (s, 1H), 6.79 (d, J=8.5 Hz, 1H), 5.36 (s, 2H), 5.10-5.07 (m, 1H), 3.96 (s, 3H), 3.00-2.96 (m, 1H), 2.82-2.78 (m, 1H), 2.22-2.20 (m, 1H), 2.13-2.10 (m, 1H), 1.78-1.75 (br s, 2H), 1.55 (s, 6H) ppm; (M+1)=472.

Example 1-239: Synthesis of 4-(3-((8-methoxy-2-(6-methylpyridin-3-yl)chroman-6-yl)methyl)-3H-imidazo[4,5-b]pyridin-6-yl)-2-methylbut-3-yn-2-amine

Example 1-239-1: Preparation of (8-methoxy-2-(6-methylpyridin-3-yl)chroman-6-yl)methanamine The title compound was prepared in five steps from 5-bromo-2-hydroxy-3-methoxybenzaldehyde and 1-(6-methylpyridin-3-yl)ethan-1-one as described in Example 1-225-1 through Example 1-225-5.

Example 1-239-2: Preparation of 6-iodo-3-((8-methoxy-2-(6-methylpyridin-3-yl)chroman-6-yl)methyl)-3H-imidazo[4,5-b]pyridine The title compound was prepared in three steps from (8-methoxy-2-(6-methylpyridin-3-yl)chroman-6-yl)methanamine and 2-chloro-5-iodo-3-nitropyridine as described in Example 1-52-7 through Example 1-52-9.

Example 1-239-3: Preparation of 4-(3-((8-methoxy-2-(6-methylpyridin-3-yl)chroman-6-yl)methyl)-3H-imidazo[4,5-b]pyridin-6-yl)-2-methylbut-3-yn-2-amine The title compound was prepared from 6-iodo-3-((8-methoxy-2-(6-methylpyridin-3-yl)chroman-6-yl)methyl)-3H-imidazo[4,5-b]pyridine and 2-methylbut-3-yn-2-amine as described in Example 1-5-8: $^1$H NMR (500 MHz, DMSO-d$_6$) δ 8.64-8.62 (m, 1H), 8.49 (s, 1H), 8.40 (s, 1H), 8.09-8.07 (m, 1H), 7.69-7.67 (m, 1H), 7.28-7.26 (m, 1H), 6.95 (s, 1H), 6.69 (s, 1H), 5.38 (s, 2H), 5.09-5.05 (m, 1H), 3.70 (s, 3H), 2.91-2.85 (m, 1H), 2.65-2.62 (m, 1H), 2.47 (s, 3H), 2.13-2.10 (m, 1H), 2.01-1.97 (m, 1H), 1.14 (s, 6H) ppm; (M+1)=468.

Example 1-240: Synthesis of 4-(3-((8-methoxy-2-(6-methylpyridin-3-yl)chroman-6-yl)methyl)-3H-imidazo[4,5-b]pyridin-6-yl)morpholine The title compound was prepared from 6-iodo-3-((8-methoxy-2-(6-methylpyridin-3-yl)chroman-6-yl)methyl)-3H-imidazo[4,5-b]pyridine (Example 1-239-2) and morpholine as described in Example 1-10: $^1$H NMR (500 MHz, DMSO-d$_6$) δ 8.47-8.45 (m, 2H), 8.24 (d, J=2.0 Hz, 1H), 7.68

(dd, J=8.5, 2.0 Hz, 1H), 7.62 (d, J=2.0 Hz, 1H), 7.26 (d, J=8.5 Hz, 1H), 6.94 (s, 1H), 6.66 (s, 1H), 5.32 (s, 2H), 5.08-5.06 (m, 1H), 3.80-3.76 (m, 4H), 3.70 (s, 3H), 3.15-3.11 (m, 4H), 2.88-2.85 (m, 1H), 2.65-2.61 (m, 1H), 2.47 (s, 3H), 2.12-2.09 (m, 1H), 2.00-1.97 (m, 1H) ppm; (M+1)=472.

Example 1-241: Synthesis of 3-((8-methoxy-2-(6-methylpyridin-3-yl)chroman-6-yl)methyl)-6-(2-methyl-1H-imidazol-1-yl)-3H-imidazo[4,5-b]pyridine The title compound was prepared from 6-iodo-3-((8-methoxy-2-(6-methylpyridin-3-yl)chroman-6-yl)methyl)-3H-imidazo[4,5-b]pyridine (Example 1-239-2) and 2-methyl-1H-imidazole as described in Example 1-42: $^1$H NMR (500 MHz, CD$_3$OD) δ 8.65 (s, 1H), 8.52 (s, 1H), 8.48 (s, 1H), 8.18 (s, 1H), 7.80 (d, J=7.5 Hz, 1H), 7.33-7.00 (m, 3H), 6.99 (s, 1H), 6.82 (s, 1H), 5.50 (s, 2H), 5.16-5.12 (m, 1H), 3.81 (s, 3H), 2.99-2.94 (m, 1H), 2.76-2.70 (m, 1H), 2.55 (s, 3H), 2.33 (s, 3H), 2.25-2.22 (m, 1H), 2.06-2.02 (m, 1H) ppm; (M+1)=467.

Example 1-242: Synthesis of 6-cyclopropyl-3-((8-methoxy-2-(6-methylpyridin-3-yl)chroman-6-yl)methyl)-3H-imidazo[4,5-b]pyridine The title compound was prepared from 6-iodo-3-((8-methoxy-2-(6-methylpyridin-3-yl)chroman-6-yl)methyl)-3H-imidazo[4,5-b]pyridine (Example 1-239-2) and cyclopropylboronic acid as described in Example 1-9: $^1$H NMR (500 MHz, CDCl$_3$) δ 8.53-8.51 (m, 1H), 8.33-8.31 (m, 1H), 7.99 (s, 1H), 7.73-7.71 (m, 1H), 7.65 (dd, J=8.0, 2.5 Hz, 1H), 7.16 (d, J=8.0 Hz, 1H), 6.76 (d, J=1.5 Hz, 1H), 6.63 (d, J=1.5 Hz, 1H), 5.35 (s, 2H), 5.17-5.15 (m, 1H), 3.81 (s, 3H), 2.95-2.87 (m, 1H), 2.73-2.68 (m, 1H), 2.56 (s, 3H), 2.24-2.19 (m, 1H), 2.13-2.09 (m, 2H), 1.07-1.03 (m, 2H), 0.78-0.74 (m, 2H) ppm; (M+1)=427.

Example 1-243: Synthesis of 4-(3-((2-(6-ethylpyridin-3-yl)-8-methoxychroman-6-yl)methyl)-3H-imidazo[4,5-b]pyridin-6-yl)-2-methylbut-3-yn-2-amine Example 1-243-1: Preparation of (2-(6-ethylpyridin-3-yl)-8-methoxychroman-6-yl)methanamine The title compound was prepared in five steps from 5-bromo-2-hydroxy-3-methoxybenzaldehyde and 1-(6-ethylpyridin-3-yl)ethan-1-one as described in Example 1-225-1 through Example 1-225-5.

Example 1-243-2: Preparation of 3-((2-(6-ethylpyridin-3-yl)-8-methoxychroman-6-yl)methyl)-6-iodo-3H-imidazo[4,5-b]pyridine The title compound was prepared in three steps from (2-(6-ethylpyridin-3-yl)-8-methoxychroman-6-yl)methanamine and 2-chloro-5-iodo-3-nitropyridine as described in Example 1-52-7 through Example 1-52-9.

Example 1-243-3: Preparation of 4-(3-((2-(6-ethylpyridin-3-yl)-8-methoxychroman-6-yl)methyl)-3H-imidazo[4,5-b]pyridin-6-yl)-2-methylbut-3-yn-2-amine The title compound was prepared from 3-((2-(6-ethylpyridin-3-yl)-8-methoxychroman-6-yl)methyl)-6-iodo-3H-imidazo[4,5-b]pyridine and 2-methylbut-3-yn-2-amine as described in Example 1-52-10: $^1$H NMR (500 MHz, DMSO-d$_6$) δ 8.64 (s, 1H), 8.50 (d, J=2.5 Hz, 1H), 8.40 (d, J=1.5 Hz, 1H), 8.06 (d, J=1.5 Hz, 1H), 7.71 (dd, J=8.0, 2.5 Hz, 1H), 7.29 (d, J=8.0 Hz, 1H), 6.95 (d, J=2.0 Hz, 1H), 6.69 (d, J=2.0 Hz, 1H), 5.37 (s, 2H), 5.09-5.06 (m, 1H), 3.70 (s, 3H), 2.93-2.86 (m, 1H), 2.76 (q, J=7.5 Hz, 2H), 2.68-2.61 (m, 1H), 2.16-1.96 (m, 4H), 1.41 (s, 6H), 1.22 (t, J=7.5 Hz, 3H) ppm; (M+1)=482.

Example 1-244: Synthesis of 4-(3-((2-(6-ethylpyridin-3-yl)-8-methoxychroman-6-yl)methyl)-3H-imidazo[4,5-b]pyridin-6-yl)morpholine The title compound was prepared from 3-((2-(6-ethylpyridin-3-yl)-8-methoxychroman-6-yl)methyl)-6-iodo-3H-imidazo[4,5-b]pyridine (Example 1-243-2) and morpholine as described in Example 1-10: $^1$H NMR (500 MHz, DMSO-d$_6$) δ 8.50 (d, J=2.5 Hz, 1H), 8.46 (s, 1H), 8.25 (d, J=2.5 Hz, 1H), 7.70 (dd, J=8.0, 2.5 Hz, 1H), 7.63 (d, J=2.5 Hz, 1H), 7.27 (d, J=8.0 Hz, 1H), 6.94 (d, J=1.5 Hz, 1H), 6.67 (d, J=1.5 Hz, 1H), 5.32 (s, 2H), 5.08-5.06 (m, 1H), 3.80-3.76 (m, 4H), 3.70 (s, 3H), 3.15-3.11 (m, 4H), 2.92-2.85 (m, 1H), 2.75 (q, J=7.5 Hz, 2H), 2.66-2.61 (m, 1H), 2.14-2.08 (m, 1H), 2.03-1.95 (m, 1H), 1.22 (t, J=7.5 Hz, 3H) ppm; (M+1)=486.

Example 1-245: Synthesis of 3-((2-(6-ethylpyridin-3-yl)-8-methoxychroman-6-yl)methyl)-6-(2-methyl-1H-imidazol-1-yl)-3H-imidazo[4,5-b]pyridine The title compound was prepared from 3-((2-(6-ethylpyridin-3-yl)-8-methoxychroman-6-yl)methyl)-6-iodo-3H-imidazo[4,5-b]pyridine (Example 1-243-2) and 2-methyl-1H-imidazole as described in Example 1-42: $^1$H NMR (500 MHz, CD$_3$OD) δ 8.63 (s, 1H), 8.52-8.50 (m, 2H), 8.18 (d, J=2.5 Hz, 1H), 7.84 (dd, J=8.0, 2.0 Hz, 1H), 7.35 (d, J=8.0 Hz, 1H), 7.29 (s, 1H), 7.04 (s, 1H), 7.00 (d, J=1.5 Hz, 1H), 6.82 (d, J=1.5 Hz, 1H), 5.51 (s, 2H), 5.17-5.14 (m, 1H), 3.82 (s, 3H), 3.02-2.95 (m, 1H), 2.84 (q, J=7.5 Hz, 2H), 2.78-2.73 (m, 1H), 2.35 (s, 3H), 2.29-2.21 (m, 1H), 2.07-2.02 (m, 1H), 1.30 (t, J=7.5 Hz, 3H) ppm; (M+1)=481.

Example 1-246: Synthesis of 4-(3-((8-methoxy-2-(2-methylthiazol-4-yl)chroman-6-yl)methyl)-3H-imidazo[4,5-b]pyridin-6-yl)-2-methylbut-3-yn-2-amine Example 1-246-1: Preparation of (8-methoxy-2-(2-methylthiazol-4-yl)chroman-6-yl)methanamine The title compound was prepared in five steps from 5-bromo-2-hydroxy-3-methoxybenzaldehyde and 1-(2-methylthiazol-4-yl)ethan-1-one as described in Example 1-225-1 through Example 1-225-5.

Example 1-246-2: Preparation of 4-(6-((6-iodo-3H-imidazo[4,5-b]pyridin-3-yl)methyl)-8-methoxychroman-2-yl)-2-methylthiazole The title compound was prepared in three steps from (8-methoxy-2-(2-methylthiazol-4-yl)chroman-6-yl)methanamine and 2-chloro-5-iodo-3-nitropyridine as described in Example 1-52-7 through Example 1-52-9.

Example 1-246-3: Preparation of 4-(3-((8-methoxy-2-(2-methylthiazol-4-yl)chroman-6-yl)methyl)-3H-imidazo[4,5-b]pyridin-6-yl)-2-methylbut-3-yn-2-amine The title compound was prepared from 4-(6-((6-iodo-3H-imidazo[4,5-b]pyridin-3-yl)methyl)-8-methoxychroman-2-yl)-2-methylthiazole and 2-methylbut-3-yn-2-amine as described in Example 1-52-10: $^1$H NMR (500 MHz, CDCl$_3$) δ 8.48 (d, J=1.5 Hz, 1H), 8.09 (d, J=1.5 Hz, 1H), 8.04 (s, 1H), 7.10 (s, 1H), 6.75 (d, J=1.5 Hz, 1H), 6.63 (d , J=1.5 Hz, 1H), 5.38 (dd, J=8.0, 2.5 Hz, 1H), 5.35 (s, 2H), 3.83 (s, 3H), 2.83-2.80 (m, 1H), 2.72 (s, 3H), 2.67-2.63 (m, 1H), 2.39-2.36 (m, 1H), 2.26-2.24 (m, 1H), 1.55 (s, 6H) ppm; (M+1)=474.

Example 1-247: Synthesis of 4-(3-((8-methoxy-2-(2-methylthiazol-4-yl)chroman-6-yl)methyl)-3H-imidazo[4,5-b]pyridin-6-yl)morpholine The title compound was prepared from 4-(6-((6-iodo-3H-imidazo[4,5-b]pyridin-3-yl)methyl)-8-methoxychroman-2-yl)-2-methylthiazole (Example 1-246-2) and morpholine as described in Example 1-10: $^1$H NMR (500 MHz, CDCl$_3$) δ 8.28 (d, J=2.0 Hz, 1H), 7.98 (s, 1H), 7.64 (d, J=2.0 Hz, 1H), 7.10 (s, 1H), 6.75 (d, J=1.5 Hz, 1H), 6.63 (d, J=1.5 Hz, 1H), 5.38 (dd, J=8.0, 2.5 Hz, 1H), 5.33 (s, 2H), 3.96-3.92 (m, 4H), 3.84 (s, 3H), 3.21-3.17 (m, 4H), 2.87-2.81 (m, 1H), 2.72 (s, 3H), 2.67-2.61 (m, 1H), 2.39-2.34 (m, 1H), 2.27-2.22 (m, 1H) ppm; (M+1)=478.

Example 1-248: Synthesis of 2-methyl-4-(3-((4-methyl-2-(4-(trifluoromethyl)phenyl)-3,4-dihydro-2H-benzo[b][1,4]oxazin-6-yl)methyl)-3H-imidazo[4,5-b]pyridin-6-yl)but-3-yn-2-amine Example 1-248-1: Preparation of 6-bromo-2-(4-(trifluoromethyl)phenyl)-2H-benzo[b][1,4]oxazin-3(4H)-one To a stirred suspension of 2-amino-4-bromophenol (3.72 g, 19.81 mmol) and potassium carbonate (2.99 g, 21.61 mmol) in acetone (85 mL) was added methyl 2-bromo-2-(4-(trifluoromethyl)phenyl)acetate (5.35 g, 18.01 mmol). The mixture was heated to reflux. After 16 h, the mixture was allowed to cool to room temperature, and the volume was reduced by one-half. The remaining suspension was diluted with water (50 mL) and EtOAc (250 mL). The phases were separated, and the organic phase was washed with brine (3×40 mL), 1N hydrochloric acid solution (3×25 mL), and brine. The organic phase was dried over sodium sulfate, filtered, and concentrated. The solid was recrystallized from hot ethyl acetate, and the precipitate was isolated by filtration and washed with heptane. The mother liquor was concentrated, and the residue subjected to a second recrystallization from ethyl acetate. The two batches were combined to provide 4.02 g (60%) of 6-bromo-2-(4-(trifluoromethyl)phenyl)-2H-benzo[b][1,4]oxazin-3(4H)-one as a white solid.

Example 1-248-2: Preparation of 6-bromo-4-methyl-2-(4-(trifluoromethyl)phenyl)-2H-benzo[b][1,4]oxazin-3(4H)-one To a stirred solution of 6-bromo-2-(4-(trifluoromethyl)phenyl)-2H-benzo[b][1,4]oxazin-3(4H)-one (3.00 g, 8.06 mmol) in acetone (60 mL) was added potassium hydroxide (1.67 g, 29.83 mmol). The mixture was treated with a 2M iodomethane solution (6.05 ml, 12.09 mmol) (added via syringe over 5 minutes). The reaction was heated to 60° C. After 45 min, the mixture was filtered and the solid washed with acetone. The filtrate was concentrated. Chromatographic purification of the crude product (CombiFlash, 80 g silica gel gold column, 0-6% ethyl acetate/heptane elute) provided 2.42 g (78%) of 6-bromo-4-methyl-2-(4-(trifluoromethyl)phenyl)-2H-benzo[b][1,4]oxazin-3(4H)-one as a white solid.

Example 1-248-3: Preparation of 6-bromo-4-methyl-2-(4-(trifluoromethyl)phenyl)-3,4-dihydro-2H-benzo[b][1,4]oxazine To a stirred solution of 6-bromo-4-methyl-2-(4-(trifluoromethyl)phenyl)-2H-benzo[b][1,4]oxazin-3(4H)-one (3.13 g, 8.11 mmol) in tetrahydrofuran (100 mL) was added 2M borane dimethyl sulfide complex solution in tetrahydrofuran (16.2 mL, 32.42 mmol). The mixture was heated at 50° C. After 4 h, the mixture was allowed to cool to room temperature and stir overnight. After 16 h, the mixture was quenched by dropwise addition of methanol and was concentrated. The residue was re-dissolved in methanol (50 mL) and was concentrated (repeated three times). Chromatographic purification of the crude product (CombiFlash, 80 g silica gel gold column, 0-10% ethyl acetate/heptane elute) provided 2.90 g (96%) of 6-bromo-4-methyl-2-(4-(trifluoromethyl)phenyl)-3,4-dihydro-2H-benzo[b][1,4]oxazine as a white solid.

Example 1-248-4: Preparation of 4-methyl-2-(4-(trifluoromethyl)phenyl)-3,4-dihydro-2H-benzo[b][1,4]oxazine-6-carbonitrile To a stirred suspension of 6-bromo-4-methyl-2-(4-(trifluoromethyl)phenyl)-3,4-dihydro-2H-benzo[b][1,4]oxazine (2.00 g, 5.37 mmol) and zinc cyanide (0.64 g, 5.37 mmol) in degassed N,N-dimethylformamide (20 mL) was added tetrakis(triphenylphosphine)palladium(0) (0.31 g, 0.27 mmol). The mixture was heated to 80° C. in a sealed vessel. After 16 h, the mixture was allowed to cool to room temperature and diluted with water (75 mL). The resulting precipitate was isolated by filtration, was washed with water and heptane, and was dried under vacuum. Chromatographic purification of the crude product (CombiFlash, 40 g silica gel column, 0-20% ethyl acetate/heptane elute) provided 1.29 g (75%) of 4-methyl-2-(4-(trifluoromethyl)phenyl)-3,4-dihydro-2H-benzo[b][1,4]oxazine-6-carbonitrile (1.29 g, 4.05 mmol, 75.4% yield) as a light yellow solid.

Example 1-248-5: Preparation of tert-butyl ((4-methyl-2-(4-(trifluoromethyl)phenyl)-3,4-dihydro-2H-benzo[b][1,4]oxazin-6-yl)methyl)carbamate To a stirred suspension of 4-methyl-2-(4-(trifluoromethyl)phenyl)-3,4-dihydro-2H-benzo[b][1,4]oxazine-6-carbonitrile (1.19 g, 3.74 mmol) in methanol (80 mL) was added di-tert-butyl dicarbonate (1.63 g, 7.48 mmol) and nickel(II) chloride hexahydrate (0.089 g, 0.37 mmol). The mixture was cooled to 0° C. while sodium borohydride (0.99 g, 26.17 mmol) was added in small portions over 30 min. The resulting black mixture was allowed to warm to room temperature. After 4 h, the mixture was diluted with ethyl acetate (250 mL) and was washed with saturated sodium bicarbonate solution (2×75 mL) and brine. The organic phase was dried over sodium sulfate, filtered, and concentrated. The residue was suspended in dichloromethane (75 mL) and filtered through Celite with the aid of additional dichloromethane. Chromatographic purification of the crude product (CombiFlash, 40 g silica gel column, 10-30% ethyl acetate/heptane elute) provided 0.97 g (61%) of tert-butyl ((4-methyl-2-(4-(trifluoromethyl)phenyl)-3,4-dihydro-2H-benzo[b][1,4]oxazin-6-yl)methyl)carbamate as a white solid.

Example 1-248-6: Preparation of (4-methyl-2-(4-(trifluoromethyl)phenyl)-3,4-dihydro-2H-benzo[b][1,4]oxazin-6-yl)methanamine hydrochloride To a stirred solution of tert-butyl ((4-methyl-2-(4-(trifluoromethyl)phenyl)-3,4-dihydro-2H-benzo[b][1,4]oxazin-6-yl)methyl)carbamate (0.96 g, 2.27 mmol) in dichloromethane (20 mL) was added 4N hydrogen chloride in 1,4-dioxane (20 mL, 80.00 mmol). The mixture was stirred. After 1 h, the mixture was concentrated to provide 0.81 g (99%) of (4-methyl-2-(4-(trifluoromethyl)phenyl)-3,4-dihydro-2H-benzo[b][1,4]oxazin-6-yl)methanamine hydrochloride as a white solid.

Example 1-248-7: Preparation of 6-((6-iodo-3H-imidazo[4,5-b]pyridin-3-yl)methyl)-4-methyl-2-(4-(trifluoromethyl)phenyl)-3,4-dihydro-2H-benzo[b][1,4]oxazine The title compound was prepared in three steps from (4-methyl-2-(4-(trifluoromethyl)phenyl)-3,4-dihydro-2H-benzo[b][1,4]oxazin-6-yl)methanamine hydrochloride and 2-chloro-5-iodo-3-nitropyridine as described in Example 1-52-7 through Example 1-52-9.

Example 1-248-8: Preparation of 2-methyl-4-(3-((4-methyl-2-(4-(trifluoromethyl)phenyl)-3,4-dihydro-2H-benzo[b][1,4]oxazin-6-yl)methyl)-3H-imidazo[4,5-b]pyridin-6-yl)but-3-yn-2-amine The title compound was prepared from 6-((6-iodo-3H-imidazo[4,5-b]pyridin-3-yl)methyl)-4-methyl-2-(4-(trifluoromethyl)phenyl)-3,4-dihydro-2H-benzo[b][1,4]oxazine and 2-methylbut-3-yn-2-amine as described in Example 1-52-10: $^1$H NMR (400 MHz, DMSO-d6) δ 8.63 (s, 1H), 8.40 (d, J=1.7 Hz, 1H), 8.06 (d, J=1.7 Hz, 1H), 7.77 (d, J=8.2 Hz, 2H), 7.64 (d, J=8.2 Hz, 2H), 6.88 (d, J=2.0 Hz, 1H), 6.77 (d, J=8.0 Hz, 1H), 6.61 (dd, J=8.0, 2.0 Hz, 1H), 5.43-5.28 (m, 3H), 3.49 (dd, J=12.0, 2.7 Hz, 1H), 3.19 (dd, J=12.0, 7.9 Hz, 1H), 2.84 (s, 3H), 1.42 (s, 6H) ppm; (M+1)=506.

Example 1-249: Synthesis of 4-methyl-6-((6-(1-methyl-1H-pyrazol-4-yl)-3H-imidazo[4,5-b]pyridin-3-yl)methyl)-2-(4-(trifluoromethyl)phenyl)-3,4-dihydro-2H-benzo[b][1,4]oxazine The title compound was prepared from from 6-((6-iodo-3H-imidazo[4,5-b]pyridin-3-yl)methyl)-4-methyl-2-(4-(trifluoromethyl)phenyl)-3,4-dihydro-2H-benzo[b][1,4]oxazine and 1-methyl-4-(4,4,5,5-tetramethyl-1,3,2-dioxaborolan-2-yl)-1H-pyrazole as described in Example 1-4: $^1$H NMR (400 MHz, DMSO-d6) δ 8.65 (d, J=1.9 Hz, 1H), 8.56 (s, 1H), 8.30-8.18 (m, 2H), 7.98 (d, J=0.8 Hz, 1H), 7.77 (d, J=8.2 Hz, 2H), 7.64 (d, J=8.2 Hz, 2H), 6.90 (d, J=2.0 Hz, 1H), 6.77 (d, J=8.1 Hz, 1H), 6.63 (dd, J=8.1, 2.0 Hz, 1H), 5.42-5.29 (m, 3H), 3.89 (s, 3H), 3.49 (dd, J=12.0, 2.7 Hz, 1H), 3.19 (dd, J=12.0, 7.8 Hz, 1H), 2.85 (s, 3H) ppm; (M+1)=505.

Example 1-250: Synthesis of 6-bromo-3-((2-(6-methoxypyridin-3-yl)-2,3-dihydrobenzo[b][1,4]oxathiin-6-yl)methyl)-3H-imidazo[4,5-b]pyridine Example 1-250-1: Preparation of 2-((5-bromo-2-fluorophenyl)thio)-1-(6-methoxypyridin-3-yl)ethan-1-ol The title compound was prepared in two steps from 5-bromo-2-fluorobenzenethiol and 2-bromo-1-(6-methoxypyridin-3-yl)ethan-1-one as describe in Example 1-14-1 through Example 1-14-2.

Example 1-250-2: Preparation of 4-fluoro-3-((2-hydroxy-2-(6-methoxypyridin-3-yl)ethyl)thio)benzonitrile To a stirred suspension of 2-((5-bromo-2-fluorophenyl)thio)-1-(6-methoxypyridin-3-yl)ethan-1-ol (2.80 g, 7.81 mmol), zinc(II) cyanide (0.64 g, 5.47 mmol) in N,N-dimethylformamide (30 mL) was added tetrakis(triphenylphosphine)palladium(0). The mixture was heated to 90° C. After 4 h, the mixture was cooled to 0° C. and was quenched by the addition of 1N hydrochloric acid solution. The mixture was extracted with dichloromethane, and the phases were separated. The organic phase was washed with brine, dried over magnesium sulfate, filtered, and concentrated. Chromatographic purification of the crude product (CombiFlash, silica gel column, 0-100% ethyl acetate/hexanes elute) provided 2.35 g (99%) of 4-fluoro-3-((2-hydroxy-2-(6-methoxypyridin-3-yl)ethyl)thio)benzonitrile as a white solid.

Example 1-250-3: Preparation of 2-(6-methoxypyridin-3-yl)-2,3-dihydrobenzo[b][1,4]oxathiine-6-carbonitrile The title compound was prepared from 4-fluoro-3-((2-hydroxy-2-(6-methoxypyridin-3-yl)ethyl)thio)benzonitrile as described in Example 1-14-3.

Example 1-250-4: Preparation of 2-(6-methoxypyridin-3-yl)-2,3-dihydrobenzo[b][1,4]oxathiine-6-carbaldehyde To a stirred and cooled (0° C.) solution of 2-(6-methoxypyridin-3-yl)-2,3-dihydrobenzo[b][1,4]oxathiine-6-carbonitrile (1.30 g, 4.57 mmol) in tetrahydrofuran (30 mL) was added lithium aluminum hydride (0.26 g, 6.86 mmol). After 1 h, the mixture was quenched by the slow addition of water (1.4 mL), 15% sodium hydroxide solution (3.7 mL), and water (1.4 mL). The mixture was allowed to stir at 0° C. for another 30 min, and then magnesium sulfate was added. The mixture was filtered, the solids were washed with ethyl acetate, and the filtrate was concentrated. Chromatographic purification of the crude product (CombiFlash, silica gel column, 0-20% methanol/dichloromethane (+10% 7N ammonia in methanol) elute) provided 0.99 g (76%) of 2-(6-methoxypyridin-3-yl)-2,3-dihydrobenzo[b][1,4]oxathi-ine-6-carbaldehyde as a light yellow solid.

Example 1-250-5: Preparation of (2-(6-methoxy-pyridin-3-yl)-2,3-dihydrobenzo[b][1,4]oxathiin-6-yl) methanol The title compound was prepared from 2-(6-methoxypyridin-3-yl)-2,3-dihydrobenzo[b][1,4]oxathiine-6-carbaldehyde as described in Example 1-14-2.

Example 1-250-6: Preparation of 6-bromo-3-((2-(6-methoxypyridin-3-yl)-2,3-dihydrobenzo[b][1,4]oxathiin-6-yl)methyl)-3H-imidazo[4,5-b]pyridine To a stirred solution of (2-(6-methoxypyridin-3-yl)-2,3-dihydrobenzo[b][1,4]oxathiin-6-yl)methanol (0.18 g, 0.60 mmol) in toluene (10 mL) was added 2-(tributylphosphora-nylidene)acetonitrile (0.18 g, 0.75 mmol). After 5 min, the mixture treated with 6-bromo-3H-imidazo[4,5-b]pyridine (0.10 g, 0.51 mmol). The vessel was sealed, and the contents were heated to 100° C. After 1 h, the mixture was allowed to cool to room temperature and was concentrated. Chromatographic purification of the crude product (CombiFlash, silica gel column, 0-100% ethyl acetate/hexanes elute) provided 0.13 g (56%) of 6-bromo-3-((2-(6-methoxypyridin-3-yl)-2,3-dihydrobenzo[b][1,4]oxathiin-6-yl)methyl)-3H-imidazo[4,5-b]pyridine as off-white solid: $^1$H NMR (400 MHz, DMSO-$d_6$) δ 8.67 (s, 1H), 8.49 (d, J=2.1 Hz, 1H), 8.39 (d, J=2.1 Hz, 1H), 8.25 (d, J=2.4 Hz, 1H), 7.77 (dd, J=8.5, 2.4 Hz, 1H), 7.20 (d, J=2.2 Hz, 1H), 7.03 (dd, J=8.5, 2.2 Hz, 1H), 6.87-6.86 (m, 1H), 6.85-6.83 (m, 1H), 5.39 (s, 2H), 5.25 (dd, J=8.9, 2.3 Hz, 1H), 3.85 (s, 3H), 3.42-3.36 (m, 1H), 3.28 (dd, J=13.2, 2.3 Hz, 1H) ppm; (M+1)=469.

Example 1-251: Synthesis of 4-(3-((2-(6-methoxy-pyridin-3-yl)-2,3-dihydrobenzo[b][1,4]oxathiin-6-yl)methyl)-3H-imidazo[4,5-b]pyridin-6-yl)-2-methyl-but-3-yn-2-amine The title compound was prepared from 6-bromo-3-((2-(6-methoxypyridin-3-yl)-2,3-dihydrobenzo[b][1,4]oxathiin-6-yl)methyl)-3H-imidazo[4,5-b]pyridine (Example 1-250-6) and 2-methylbut-3-yn-2-amine as described in Example 1-5-8: $^1$H NMR (400 MHz, DMSO-$d_6$) δ 8.66 (s, 1H), 8.40 (d, J=1.8 Hz, 1H), 8.24 (d, J=2.4 Hz, 1H), 8.08 (d, J=1.8 Hz, 1H), 7.77 (dd, J=8.7, 2.4 Hz, 1H), 7.19 (d, J=2.1 Hz, 1H), 7.03 (dd, J=8.5, 2.1 Hz, 1H), 6.86 (d, J=1.3 Hz, 1H), 6.84 (d, J=1.3 Hz, 1H), 5.39 (s, 2H), 5.25 (dd, J=9.0, 2.3 Hz, 1H), 3.85 (s, 3H), 3.39-3.33 (m, 1H), 3.28 (dd, J=13.3, 2.3 Hz, 1H), 1.45 (s, 6H) ppm; (M+1)=472.

Example 1-252: Synthesis of 3-(3-methoxy-4-((6-methoxypyridin-3-yl)methoxy)benzyl)-6-(piperidin-3-ylethynyl)-3H-imidazo[4,5-b]pyridine Example 1-252-1: Preparation of tert-butyl (3-methoxy-4-((6-methoxypyridin-3-yl)methoxy) benzyl)carbamate To a stirred suspension of tert-butyl 4-hydroxy-3-methoxybenzylcarbamate (22.44 g, 88.59 mmol) and potassium carbonate (30.61 g, 221.5 mmol) in acetonitrile (250 mL), was added 5-(chloromethyl)-2-methoxypyridine hydrochloride (18.33 g, 94.46 mmol). The resulting mixture was heated to reflux. After 23 h, the light green suspension was allowed to cool to room temperature and was diluted with water (600 mL), resulting in the formation of a precipitate. The solids were isolated by filtration and washed with water. The moist solids were dissolved in dichloromethane (300 mL), and a small amount of water was removed. The organic phase was dried over magnesium sulfate, filtered, and concentrated to provide 31.92 g (96%) of tert-butyl 3-methoxy-4-((6-methoxypyridin-3-yl) methoxy)benzylcarbamate as an off white solid.

Example 1-252-2: Preparation of (3-methoxy-4-((6-methoxypyridin-3-yl)methoxy)phenyl)methanamine The title compound was prepared from tert-butyl 3-methoxy-4-((6-methoxypyridin-3-yl)methoxy)benzylcar-bamate as described in Example 1-12-5.

Example 1-252-3: Preparation of 6-iodo-3-(3-methoxy-4-((6-methoxypyridin-3-yl)methoxy)ben-zyl)-3H-imidazo[4,5-b]pyridine The title compound was prepared in three steps from (3-methoxy-4-((6-methoxypyridin-3-yl)methoxy)phenyl) methanamine and 2-chloro-5-iodo-3-nitropyridine as described in Example 1-52-7 through Example 1-52-9.

Example 1-252-4: Preparation of 3-(3-methoxy-4-((6-methoxypyridin-3-yl)methoxy)benzyl)-6-(piperidin-3-ylethynyl)-3H-imidazo[4,5-b]pyridine The title compound was prepared from 6-iodo-3-(3-methoxy-4-((6-methoxypyridin-3-yl)methoxy)benzyl)-3H-imidazo[4,5-b]pyridine and 3-ethynylpiperidine hydrochloride as described in Example 1-5-8: $^1$H NMR (400 MHz, DMSO-$d_6$) δ 8.64 (s, 1H), 8.42 (d, J=1.8 Hz, 1H), 8.21 (d, J=2.4 Hz, 1H), 8.11 (d, J=1.8 Hz, 1H), 7.74 (dd, J=8.5, 2.4 Hz, 1H), 7.12 (d, J=2.0 Hz, 1H), 7.01 (d, J=8.2 Hz, 1H), 6.86-6.81 (m, 2H), 5.41 (s, 2H), 4.97 (s, 2H), 3.84 (s, 3H), 3.72 (s, 3H), 3.26-3.16 (m, 2H), 3.09 (d, J=9.2 Hz, 1H), 2.86-2.76 (m, 1H), 2.70-2.58 (m, 2H), 2.05-1.95 (m, 1H), 1.67-1.50 (m, 2H), 1.45-1.33 (m, 1H) ppm; (M+1)=484.

Example 1-253: Synthesis of 3-(3-methoxy-4-((6-methoxypyridin-3-yl)methoxy)benzyl)-6-(pyrrolidin-3-ylethynyl)-3H-imidazo[4,5-b]pyridine The title compound was prepared from 6-iodo-3-(3-methoxy-4-((6-methoxypyridin-3-yl)methoxy)benzyl)-3H-imidazo[4,5-b]pyridine (Example 1-252-3) and 3-ethy-nylpyrrolidine hydrochloride as described in Example 1-5-8: $^1$H NMR (400 MHz, DMSO-$d_6$) δ 8.62 (s, 1H), 8.40 (d, J=1.9 Hz, 1H), 8.20 (dd, J=2.4 Hz, 1H), 8.09 (d, J=1.9 Hz, 1H), 7.73 (dd, J=8.5, 2.4 Hz, 1H), 7.11 (d, J=2.0 Hz, 1H), 7.00 (d, J=8.5 Hz, 1H), 6.85-6.83 (m, 1H), 6.83-6.81 (m, 1H), 5.40 (s, 2H), 4.97 (s, 2H), 3.84 (s, 3H), 3.71 (s, 3H), 3.31 (br s, 1H), 3.16 (dd, J=10.6, 7.2 Hz, 1H), 3.03-2.79 (m, 4H), 2.71 (dd, J=10.6, 7.2 Hz, 1H), 2.13-2.03 (m, 1H), 1.79-1.69 (m, 1H) ppm; (M+1)=470.

Example 1-254: Synthesis of 3-(3-methoxy-4-((6-methoxypyridin-3-yl)methoxy)benzyl)-6-(4-meth-ylpiperazin-1-yl)-3H-imidazo[4,5-b]pyridine The title compound, also known as RA08466682, was prepared from 6-iodo-3-(3-methoxy-4-((6-methoxypyridin-3-yl)methoxy)benzyl)-3H-imidazo[4,5-b]pyridine (Example 1-252-3) and 1-methylpiperazine as described in Example 1-3: $^1$H NMR (400 MHz, DMSO-$d_6$) δ 8.43 (s, 1H), 8.24-8.17 (m, 2H), 7.74 (dd, J=8.5, 2.4 Hz, 1H), 7.59 (d, J=2.4 Hz, 1H), 7.10 (d, J=2.0 Hz, 1H), 6.99 (d, J=8.3 Hz, 1H), 6.84-6.78 (m, 2H), 5.34 (s, 2H), 4.96 (s, 2H), 3.84 (s, 3H), 3.72 (s, 3H), 3.16-3.10 (m, 4H), 2.52-2.46 (m, 4H), 2.23 (s, 3H) ppm; (M+1)=475.

Example 1-255: Synthesis of 4-(3-(3-methoxy-4-((6-methylpyridin-3-yl)methoxy)benzyl)-3H-imidazo[4,5-b]pyridin-6-yl)-2-methylbut-3-yn-2-amine Example 1-255-1: Preparation of (3-methoxy-4-((6-methylpyridin-3-yl)methoxy)phenyl)methanamine The title compound was prepared in two steps from tert-butyl 4-hydroxy-3-methoxybenzylcarbamate and 5-(chloromethyl)-2-methylpyridine hydrochloride as described in Example 1-252-1 through Example 1-252-2.

Example 1-255-2: Preparation of 4-(3-(3-methoxy-4-((6-methylpyridin-3-yl)methoxy)benzyl)-3H-imidazo[4,5-b]pyridin-6-yl)-2-methylbut-3-yn-2-amine The title compound was prepared in four steps from (3-methoxy-4-((6-methylpyridin-3-yl)methoxy)phenyl)methanamine, 2-chloro-5-iodo-3-nitropyridine, and 2-methylbut-3-yn-2-amine as described in Example 1-52-7 through Example 1-52-10: $^1$H NMR (400 MHz, DMSO-d$_6$) δ 8.63 (s, 1H), 8.49-8.44 (m, 1H), 8.38 (d, J=1.8 Hz, 1H), 8.05 (d, J=1.8 Hz, 1H), 7.69 (dd, J=8.0, 2.2 Hz, 1H), 7.25 (d, J=8.0 Hz, 1H), 7.12 (d, J=2.2 Hz, 1H), 6.99 (d, J=8.2 Hz, 1H), 6.83 (dd, J=8.2, 2.0 Hz, 1H), 5.40 (s, 2H), 5.02 (s, 2H), 3.72 (s, 3H), 2.45 (s, 3H), 2.10 (br s, 2H), 1.40 (s, 6H) ppm; (M+1)=442.

Example 1-256: Synthesis of 4-(3-((5-ethoxy-6-((6-methylpyridin-3-yl)methoxy)pyridin-3-yl)methyl)-3H-imidazo[4,5-b]pyridin-6-yl)-2-methylbut-3-yn-2-amine Example 1-256-1: Preparation of 5-bromo-3-ethoxy-2-fluoropyridine To a stirred suspension of 5-bromo-2-fluoropyridin-3-ol (7.77 g, 40.47 mmol) and potassium carbonate (8.39 g, 60.71 mmol) in acetonitrile (75 mL) was added iodoethane (6.63 g, 42.50 mmol). The resulting mixture was heated to reflux. After 16 h, the tan mixture was allowed to cool to room temperature and was diluted with water (250 mL). The mixture was extracted with diethyl ether (2×75 mL). The combined organic phases were dried over magnesium sulfate, filtered, and concentrated to provide 8.31 g (93%) of 5-bromo-3-ethoxy-2-fluoropyridine as a tan solid.

Example 1-256-2: Preparation of 5-bromo-3-ethoxy-2-((6-methylpyridin-3-yl)methoxy)pyridine To a stirred solution of (6-methylpyridin-3-yl)methanol (2.37 g, 19.28 mmol) in dimethylsulfoxide (50 mL) was added 60% sodium hydride dispersion (0.81 g, 20.20 mmol) resulting in gas evolution and mild exotherm. The mixture was allowed to stir at room temperature. After 20 min, the yellow mixture was treated with 5-bromo-3-ethoxy-2-fluoropyridine (4.04 g, 18.36 mmol), resulting in a moderate exotherm. After 1.5 h, the brown mixture was treated with water (150 mL), resulting in the formation of a precipitate. The solids were isolated by filtration, washed with water (100 mL) and then hexanes (50 mL), and dried to provide 4.73 g (80%) of 5-bromo-3-ethoxy-2-((6-methylpyridin-3-yl)methoxy)pyridine as a tan solid.

Example 1-256 3: Preparation of tert-butyl ((5-ethoxy-6-((6-methylpyridin-3-yl)methoxy)pyridin-3-yl)methyl)carbamate To a stirred suspension of 5-bromo-3-ethoxy-2-((6-methylpyridin-3-yl)methoxy)pyridine (4.73 g, 14.64 mmol), potassium N-BOC-aminomethyltrifluoroborate (5.08 g, 21.00 mmol), and cesium carbonate (14.31 g, 43.91 mmol) in 4:1 toluene/water (50 mL) was added chloro(2-dicyclohexylphosphino-2',4',6'-triisopropyl-1,1'-biphenyl)[2-(2'-amino-1,1'-biphenyl)]palladium(II) (1.15 g, 1.46 mmol). The mixture was degassed under vacuum/backfilled with nitrogen (×3). The mixture was then heated to reflux. After 20 h, additional portions of the precatalyst (0.50 g) and borate salt (1.00 g) were added and heating continued. After 43 h, the black mixture was allowed to cool to room temperature and was diluted with ethyl acetate (100 mL) and water (50 mL). The phases were separated, and the organic phase washed with brine (50 mL), dried over magnesium sulfate, filtered, and concentrated to provide 7.07 g (>100%) of tert-butyl ((5-ethoxy-6-((6-methylpyridin-3-yl)methoxy)pyridin-3-yl)methyl)carbamate as an orange oil (contaminated with unreacted starting material).

Example 1-256-4: Preparation of (5-ethoxy-6-((6-methylpyridin-3-yl)methoxy)pyridin-3-yl)methanamine The title compound was prepared from tert-butyl ((5-ethoxy-6-((6-methylpyridin-3-yl)methoxy)pyridin-3-yl)methyl)carbamate as described in Example 1-12-5.

Example 1-256-5: Preparation of 4-(3-((5-ethoxy-6-((6-methylpyridin-3-yl)methoxy)pyridin-3-yl)methyl)-3H-imidazo[4,5-b]pyridin-6-yl)-2-methylbut-3-yn-2-amine The title compound was prepared in four steps from (5-ethoxy-6-((6-methylpyridin-3-yl)methoxy)pyridin-3-yl)methanamine, 2-chloro-5-iodo-3-nitropyridine, and 2-methylbut-3-yn-2-amine as described in Example 1-52-7 through Example 1-52-10: $^1$H NMR (400 MHz, DMSO-d$_6$) δ 8.65 (s, 1H), 8.49 (d, J=2.3 Hz, 1H), 8.39 (d, J=1.8 Hz, 1H), 8.05 (d, J=1.8 Hz, 1H), 7.76 (d, J=2.0 Hz, 1H), 7.70 (dd, J=7.9, 2.3 Hz, 1H), 7.44 (d, J=2.0 Hz, 1H), 7.23 (d, J=7.9 Hz, 1H), 5.42 (s, 2H), 5.32 (s, 2H), 4.00 (q, J=6.9 Hz, 2H), 2.44 (s, 3H), 2.11 (br s, 2H), 1.40 (s, 6H), 1.28 (t, J=6.9 Hz, 3H) ppm; (M+1)=457.

Example 1-257: Synthesis of 3-((5-ethoxy-6-((6-methylpyridin-3-yl)methoxy)pyridin-3-yl)methyl)pyrazolo[1,5-a]pyrimidine Example 1-257-1: Preparation of (5-ethoxy-6-((6-methylpyridin-3-yl)methoxy)pyridin-3-yl)boronic acid The title compound was prepared in two steps from 5-bromo-3-ethoxy-2-((6-methylpyridin-3-yl)methoxy)pyridine (Example 1-256-2) and 4,4,4',4',5,5,5',5'-octamethyl-2,2'-bi(1,3,2-dioxaborolane) as described in Example 1-230-1 through Example 1-230-2.

Example 1-257-2: Preparation of 6-bromo-3-((5-ethoxy-6-((6-methylpyridin-3-yl)methoxy)pyridin-3-yl)methyl)pyrazolo[1,5-a]pyrimidine The title compound was prepared from (5-ethoxy-6-((6-methylpyridin-3-yl)methoxy)pyridin-3-yl)boronic acid and (E/Z)-N'-((6-bromopyrazolo[1,5-a]pyrimidin-3-yl)methylene)-4-methylbenzenesulfonohydrazide (Example 1-21-7) as described in Example 1-21-8.

Example 1-257-3: Preparation of 3-((5-ethoxy-6-((6-methylpyridin-3-yl)methoxy)pyridin-3-yl)methyl)pyrazolo[1,5-a]pyrimidine The title compound was prepared from 6-bromo-3-((5-ethoxy-6-((6-methylpyridin-3-yl)methoxy)pyridin-3-yl)methyl)pyrazolo[1,5-a]pyrimidine as described in Example 1-97: $^1$H NMR (400 MHz, CDCl$_3$) δ 8.63 (dd, J=7.1, 1.8 Hz, 1H), 8.62-8.60 (m, 1H), 8.46 (dd, J=4.0, 1.8 Hz, 1H), 7.93 (s, 1H), 7.69 (dd, J=8.0, 2.3 Hz, 1H), 7.66-7.64 (m, 1H), 7.12 (d, J=8.0 Hz, 1H), 7.05 (d, J=2.0 Hz, 1H), 6.80 (dd, J=7.1, 4.0 Hz, 1H), 5.42 (s, 2H), 4.09 (s, 2H), 4.01 (q, J=7.0 Hz, 2H), 2.54 (s, 3H), 1.39 (t, J=7.0 Hz, 3H) ppm; (M+1)=376.

Example 1-258: Synthesis of 3-((5-ethoxy-6-((6-(trifluoromethyl)pyridin-3-yl)methoxy)pyridin-3-yl)methyl)-N,N-dimethylimidazo[1,2-b]pyridazine-7-carboxamide

Example 1-258-1: Preparation of 5-bromo-3-ethoxy-2-((6-(trifluoromethyl)pyridin-3-yl)methoxy)pyridine The title compound was prepared from 5-bromo-3-ethoxy-2-fluoropyridine (Example 1-256-1) and (6-(trifluoromethyl)pyridin-3-yl)methanol as described in Example 1-256-2.

Example 1-258-2: Preparation of 5-ethoxy-6-((6-(trifluoromethyl)pyridin-3-yl)methoxy)nicotinaldehyde The title compound was prepared in two steps from 5-bromo-3-ethoxy-2-((6-(trifluoromethyl)pyridin-3-yl)methoxy)pyridine and potassium vinyltrifluoroborate as described in Example 1-223-4 through Example 1-223-5.

Example 1-258-3: Preparation of 7-chloro-3-((5-ethoxy-6-((6-(trifluoromethyl)pyridin-3-yl)methoxy)pyridin-3-yl)methyl)imidazo[1,2-b]pyridazine The title compound was prepared in two steps from 3-bromo-7-chloroimidazo[1,2-b]pyridazine (Example 1-23-2) and 5-ethoxy-6-((6-(trifluoromethyl)pyridin-3-yl)methoxy)nicotinaldehyde as described in Example 1-23-3 through Example 1-23-4.

Example 1-258-4: Preparation of methyl 3-((5-ethoxy-6-((6-(trifluoromethyl)pyridin-3-yl)methoxy)pyridin-3-yl)methyl)imidazo[1,2-b]pyridazine-7-carboxylate To a stirred solution of 7-chloro-3-((5-ethoxy-6-((6-(trifluoromethyl)pyridin-3-yl)methoxy)pyridin-3-yl)methyl)imidazo[1,2-b]pyridazine (0.23 g, 0.50 mmol) and triethylamine (0.15 mg, 1.50 mmol) in 1:1 methanol/N,N-dimethylformamide DMF (20 mL) was added [1,1'-bis(diphenylphosphino)ferrocene]dichloropalladium(II) 0.044 g, 0.050 mmol). The mixture was evacuated, and the atmosphere was replaced with carbon monoxide (1 atm via balloon). The mixture was heated to 80° C. After 15 h, the mixture was allowed to cool to room temperature and was concentrated. The crude product was purified by silica gel chromatography (3% methanol/dichloromethane elute) to afford 0.15 g (61%) of methyl 3-((5-ethoxy-6-((6-(trifluoromethyl)pyridin-3-yl)methoxy)pyridin-3-yl)methyl)imidazo[1,2-b]pyridazine-7-carboxylate as a light yellow solid.

Example 1-258-5: Preparation of 3-((5-ethoxy-6-((6-(trifluoromethyl)pyridin-3-y1)methoxy)pyridin-3-yl)methyl)-N,N-dimethylimidazo[1,2-b]pyridazine-7-carboxamide The title compound was prepared in two steps from methyl 3-((5-ethoxy-6-((6-(trifluoromethyl)pyridin-3-yl)methoxy)pyridin-3-yl)methyl)imidazo[1,2-b]pyridazine-7-carboxylate and dimethylamine as described in Example 1-83-2 through Example 1-83-3: $^1$H NMR (400 MHz, DMSO-d$_6$) δ 8.83 (s, 1H), 8.61 (s, 1H), 8.23 (s, 1H), 8.10 (d, J=8.4 Hz, 1H), 7.92 (d, J=8.4 Hz, 1H), 7.72 (s, 1H), 7.62 (s, 1H), 7.35 (s, 1H), 5.50 (s, 2H), 4.28 (s, 2H), 4.05 (q, J=6.8 Hz, 2H), 3.03 (s, 6H), 1.31 (t, J=6.8 Hz, 3H) ppm; (M+1)= 501.

Example 1-259: Synthesis of 4-((6-((6-cyclopropylpyridin-3-yl)methoxy)-5-ethoxypyridin-3-yl)methyl)-N-methylpicolinamide

Example 1-259-1: Preparation of 5-bromo-2-((6-cyclopropylpyridin-3-yl)methoxy)-3-ethoxypyridine The title compound was prepared from 5-bromo-3-ethoxy-2-fluoropyridine (Example 1-256-1) and (6-cyclopropylpyridin-3-yl)methanol as described in Example 1-256-2.

Example 1-259-2: Preparation of 2-((6-cyclopropylpyridin-3-yl)methoxy)-3-ethoxy-5-(4,4,5,5-tetramethyl-1,3,2-dioxaborolan-2-yl)pyridine The title compound was prepared from -bromo-2-((6-cyclopropylpyridin-3-yl)methoxy)-3-ethoxypyridine and 4,4,4',4',5,5,5',5'-octamethyl-2,2'-bi(1,3,2-dioxaborolane) as described in Example 1-230-1.

Example 1-259-3: Preparation of methyl 4-(chloromethyl)picolinate hydrochloride The title compound was prepared from methyl 4-(hydroxymethyl)picolinate and thionyl chloride as described in Example 1-27-6.

Example 1-259-4: Preparation of methyl 4-((6-((6-cyclopropylpyridin-3-yl)methoxy)-5-ethoxypyridin-3-yl)methyl)picolinate The title compound was prepared from 2-((6-cyclopropylpyridin-3-yl)methoxy)-3-ethoxy-5-(4,4,5,5-tetramethyl-1,3,2-dioxaborolan-2-yl)pyridine and methyl 4-(chloromethyl)picolinate hydrochloride as described in Example 1-24-3.

Example 1-259-5: Preparation of 4-((6-((6-cyclopropylpyridin-3-yl)methoxy)-5-ethoxypyridin-3-yl)methyl)-N-methylpicolinamide To a stirred solution of methyl 4-((6-((6-cyclopropylpyridin-3-yl)methoxy)-5-ethoxypyridin-3-yl)methyl)picolinate (0.14 g, 0.33 mmol) in ethanol (6 mL) was added 33% wt/wt methylamine solution in ethanol (5.0 mL). The vessel was sealed, and the contents heated to 125° C. in the microwave. After 30 min, the mixture was concentrated. Chromatographic purification of the crude product (CombiFlash, 4 g silica gel column, 1-5% methanol/dichloromethane elute) afforded 0.12 g (86%) of 4-((6-((6-cyclopropylpyridin-3-yl)methoxy)-5-ethoxypyridin-3-yl)methyl)-N-methylpicolinamide as a waxy white solid: $^1$H NMR (400 MHz, CDCl$_3$) δ 8.56 (d, J=2.2 Hz, 1H), 8.42 (d, J=5.0 Hz, 1H), 8.09-8.05 (m, 1H), 8.01 (br s, 1H), 7.66 (dd, J=8.0, 2.2 Hz, 1H), 7.57 (d, J=1.9 Hz, 1H), 7.18 (dd, J=5.0, 1.7 Hz, 1H), 7.11 (d, J=8.0 Hz, 1H), 6.79 (d, J=1.9 Hz, 1H), 5.41 (s, 2H), 3.98 (q, J=7.0 Hz, 2H), 3.93 (s, 2H), 3.03 (d, J=5.1 Hz, 3H), 2.07-1.98 (m, 1H), 1.39 (t, J=7.0 Hz, 3H), 1.04-0.94 (m, 4H) ppm; (M+1)=419.

Example 1-260: Synthesis of 6-((3H-imidazo[4,5-b]pyridin-3-yl)methyl)-4-methoxy-2-((6-methoxypyridin-3-yl)methyl)benzo[d]oxazole

Example 1-260-1: Preparation of 2-amino-5-bromobenzene-1,3-diol

To a stirred and cooled (0° C.) suspension of 4-bromo-2,6-dimethoxyaniline (7.50 g, 32.30 mmol) in dichloromethane (100 mL) was added 1.0M boron tribromide solution in dichloromethane (96.9 mL, 96.9 mmol). After the addition was complete, the resulting mixture was allowed to warm to room temperature. After 1 h, the mixture was quenched into saturated aqueous sodium bicarbonate solution and was extracted with ethyl acetate (3×100 mL). The combined organic phases were washed with brine (100 mL), dried over sodium sulfate, filtered, and concentrated. Chromatographic purification of the crude product (silica gel column, 33% ethyl acetate/petroleum ether elute) afforded 5.50 g (83%) of 2-amino-5-bromobenzene-1,3-diol as a yellow solid.

Example 1-260-2: Preparation of N-(4-bromo-2,6-dihydroxyphenyl)-2-(6-methoxypyridin-3-yl)acetamide To a stirred solution of 2-amino-5-bromobenzene-1,3-diol (0.50 g, 2.45 mmol) and 2-(6-methoxypyridin-3-yl)acetic acid (0.41 g, 2.45 mmol) in N,N-dimethylformamide (5 mL) was added 1-[bis(dimethylamino)methylene]-1H-1,2,3-triazolo[4,5-b]pyridinium 3-oxid hexafluorophosphate (0.93 g, 2.45 mmol) and triethylamine (0.74 g, 7.35 mmol). The resulting mixture was allowed to stir at room temperature. After 3 h, the mixture was quenched with water (30 mL) and extracted with ethyl acetate (3×30 mL). The combined organic phase were washed with brine (20 mL), dried over anhydrous sodium sulfate, filtered, and concentrated. Chromatographic purification of the crude product (silica gel column, 25% ethyl acetate/petroleum ether elute) afforded 0.43 g (50%) of N-(4-bromo-2,6-dihydroxyphenyl)-2-(6-methoxypyridin-3-yl)acetamide as a white solid.

Example 1-260-3: Preparation of N-(4-bromo-2-hydroxy-6-methoxyphenyl)-2-(6-methoxypyridin-3-yl)acetamide To a stirred solution of N-(4-bromo-2,6-dihydroxyphenyl)-2-(6-methoxypyridin-3-yl)acetamide (0.43 g, 1.23 mmol) and potassium carbonate (0.17 g, 1.23 mmol) in acetonitrile (10 mL) was iodomethane (0.18 g, 1.23 mmol). The resulting mixture was allowed to stir at room temperature. After 16 h, the mixture was diluted with water (30 mL) and extracted with ethyl acetate (3×30 mL). The combined organic phases were dried over anhydrous sodium sulfate, filtered, and concentrated. Chromatographic purification of the crude product (silica gel column, 50% ethyl acetate/petroleum ether elute) afforded 0.38 g (85%) of N-(4-bromo-2-hydroxy-6-methoxyphenyl)-2-(6-methoxypyridin-3-yl)acetamide as a white solid.

Example 1-260-4: Preparation of 6-bromo-4-methoxy-2-((6-methoxypyridin-3-yl)methyl)benzo[d]oxazole To a solution of N-(4-bromo-2-hydroxy-6-methoxyphenyl)-2-(6-methoxypyridin-3-yl)acetamide (0.50 g, 1.37 mmol) and triphenylphosphine (0.72 g, 2.74 mmol) in tetrahydrofuran (5 mL) was added diethyl azodicarboxylate (0.48 g, 2.74 mmol). The resulting mixture was allowed to stir at room temperature. After 16 h, the mixture was concentrated. Chromatographic purification of the crude product (silica gel column, 20% ethyl acetate/petroleum ether elute) afforded 0.25 g (52%) of 6-bromo-4-methoxy-2-((6-methoxypyridin-3-yl)methyl)benzo[d]oxazole as a light yellow solid.

Example 1-260-5: Preparation of 4-methoxy-2-((6-methoxypyridin-3-yl)methyl)benzo[d]oxazole-6-carbonitrile To a stirred solution of 6-bromo-4-methoxy-2-((6-methoxypyridin-3-yl)methyl)benzo[d]oxazole (0.30 g, 0.86 mmol), Tris(dibenzylideneacetone)dipalladium (0.12 g, 0.13 mmol), and 1,1'-bis(diphenylphosphino)ferrocene (0.14 g, 0.26 mmol) in dimethylsulfoxide (5 mL) was added zinc(II) cyanide (0.061 g, 0.52 mmol). The resulting mixture was heated to 100° C. After 3 h, the mixture was allowed to cool to room temperature and was diluted with water (50 mL) and saturated ammonium bicarbonate solution (5 mL). The mixture was extracted with ethyl acetate (3×50 mL). The combined organic phase were dried over sodium sulfate, filtered, and concentrated. Chromatographic purification of the crude product (silica gel column, 20% ethyl acetate/petroleum ether elute) afforded 0.18 g (71%) of 4-methoxy-2-((6-methoxypyridin-3-yl)methyl)benzo[d]oxazole-6-carbonitrile as a light yellow solid.

Example 1-260-6: Preparation of (4-methoxy-2-((6-methoxypyridin-3-yl)methyl)benzo[d]oxazol-6-yl)methanamine To a stirred solution of 4-methoxy-2-((6-methoxypyridin-3-yl)methyl)benzo[d]oxazole-6-carbonitrile (0.22 g, 0.74 mmol) in 7.0M ammonia in methanol solution (6 mL) was added Raney nickel. The mixture was allowed to stir at room temperature under an atmosphere of hydrogen. After 2 h, the mixture was filtered and concentrated to provide 0.20 g (90%) of (4-methoxy-2-((6-methoxypyridin-3-yl)methyl)benzo[d]oxazol-6-yl)methanamine as a yellow solid.

Example 1-260-7: Preparation of 6-((3H-imidazo[4,5-b]pyridin-3-yl)methyl)-4-methoxy-2-((6-methoxypyridin-3-yl)methyl)benzo[d]oxazole The title compound was prepared in three steps from (4-methoxy-2-((6-methoxypyridin-3-yl)methyl)benzo[d]

oxazol-6-yl)methanamine and 2-chloro-3-nitropyridine as described in Example 1-52-7 through Example 1-52-9: $^1$H NMR (400 MHz, CDCl$_3$) δ 8.47-8.43 (m, 1H), 8.16 (d, J=2.0 Hz, 1H), 8.11 (dd, J=8.4, 2.0 Hz, 1H), 8.07 (s, 1H), 7.59-7.57 (m, 1H), 7.31-7.27 (m, 1H), 7.01 (s, 1H), 6.80 (s, 1H), 6.70 (d, J=8.4 Hz, 1H), 5.56 (s, 2H), 4.16 (s, 2H), 3.98 (s, 3H), 3.92 (s, 3H) ppm; (M+1)=402.

Example 1-261: Synthesis of 3-((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine Example 1-261-1: Preparation of 5-bromo-2-(2-fluoropropan-2-yl)pyridine To an stirred and cooled (0° C.) solution of 2-(5-bromopyridin-2-yl)propan-2-ol (3.00 g, 13.90 mmol) in dichloromethane (30 mL) was added diethylaminosulfur trifluoride (3.40 g, 21.10 mmol) dropwise. After 1 h, the mixture was quenched by the addition of saturated sodium bicarbonate solution and was extracted with ethyl acetate (30 mL×3). The combined organic phase were washed with brine (50 mL), dried over anhydrous sodium sulfate, filtered, concentrated. Chromatographic purification of the crude product (silica gel column, 10% ethyl acetate/petroleum ether elute) afforded 2.33 g (77%) of 5-bromo-2-(2-fluoropropan-2-yl)pyridine as yellow oil.

Example 1-261-2: Preparation of 2-bromo-1-(6-(2-fluoropropan-2-yl)pyridin-3-yl)ethan-1-one The title compound was prepared from bromo-2-(2-fluoropropan-2-yl)pyridine and tributyl(1-ethoxyvinyl)stannane as described in Example 1-196-1.

Example 1-261-3: Preparation of 3--((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine The title compound was prepared in three steps from 5-((3H-imidazo[4,5-b]pyridin-3-yl)methyl)-2-(benzyloxy)-3-methoxyphenol (Example 1-193-8) and 2-bromo-1-(6-(2-fluoropropan-2-yl)pyridin-3-yl)ethan-1-one as described in Example 1-52-1 through Example 1-52-3: $^1$H NMR (400 MHz, CDCl$_3$) δ 8.60 (s, 1H), 8.47 (d, J=4.8 Hz, 1H), 8.11 (d, J=8.0 Hz, 1H), 8.07 (s, 1H), 7.79-7.77 (m, 1H), 7.61 (d, J=8.0 Hz, 1H), 7.30-7.28 (m, 1H), 6.57 (s, 2H), 5.40 (s, 2H), 5.19 (dd, J=8.4, 2.4 Hz, 1H), 4.37 (dd, J=11.6, 2.4 Hz, 1H), 4.11 (dd, J=11.6, 8.4 Hz, 1H), 3.83 (s, 3H), 1.74-1.70 (m, 6H) ppm; (M+1)=435.

Example 1-262: Synthesis of 4-((6-((6-cyclopropylpyridin-3-yl)methoxy)-5-ethoxypyridin-3-yl)oxy)-N-methylpicolinamide Example 1-262-1: Preparation of 6-((6-cyclopropylpyridin-3-yl)methoxy)-5-ethoxypyridin-3-ol To a stirred solution of 2-((6-cyclopropylpyridin-3-yl)methoxy)-3-ethoxy-5-(4,4,5,5-tetramethyl-1,3,2-dioxaborolan-2-yl)pyridine (1.00 g, 2.52 mmol, Example 1-259-2) in tetrahydrofuran (20 mL) and water (20 mL) was added sodium perborate monohydrate (1.11 g, 11.10 mmol). The yellow reaction mixture was allowed to stir at room temperature. After 16 h, the suspension was diluted with saturated ammonium chloride solution (50 mL) and ethyl acetate (50 mL). The phases were separated, and the aqueous phase extracted with ethyl acetate (2×50 mL). The combined organic phases were dried over magnesium sulfate, filtered, and concentrated. The crude solid was suspended in dichloromethane (20 mL) and filtered. The filtercake was washed with dichloromethane (10 mL) and dried to provide 0.66 g (91%) of 6-((6-cyclopropylpyridin-3-yl)methoxy)-5-ethoxypyridin-3-ol as a white solid.

Example 1-262-2: Preparation of methyl 4-((6-((6-cyclopropylpyridin-3-yl)methoxy)-5-ethoxypyridin-3-yl)oxy)picolinate To a stirred solution of 6-((6-cyclopropylpyridin-3-yl)methoxy)-5-ethoxypyridin-3-ol (0.66 g, 2.30 mmol) in dimethylsulfoxide (10 mL) was added 60% sodium hydride dispersion (0.10 g, 2.53 mmol) (gas evolution noted upon addition). After 15 min, the mixture was treated with methyl 4-chloropyridine-2-carboxylate (0.42 g, 2.42 mmol) and was allowed to stir at room temperature. After 2 h, the temperature of the mixture was increased to 100° C. After a total of 5 h, the dark brown mixture was allowed to cool to room temperature and was diluted with saturated ammonium chloride solution (50 mL). The mixture was extracted with dichloromethane (3×25 mL). The combined organic phases were dried over magnesium sulfate, filtered, and concentrated. Chromatographic purification of the crude product (CombiFlash, 40 g silica gel gold column, 1-5% methanol/dichloromethane elute) afforded 0.35 g (36%) of methyl 4-((6-((6-cyclopropylpyridin-3-yl)methoxy)-5-ethoxypyridin-3-yl)oxy)picolinate as an orange oil.

Example 1-262-3: Preparation of 4-((6-((6-cyclopropylpyridin-3-yl)methoxy)-5-ethoxypyridin-3-yl)oxy)-N-methylpicolinamide To a stirred solution of methyl 4-((6-((6-cyclopropylpyridin-3-yl)methoxy)-5-ethoxypyridin-3-yl)oxy)picolinate (0.12 g, 0.28 mmol) and sodium cyanide (0.005 g, 0.10 mmol) in ethanol (7 mL) was added 33% methylamine solution in ethanol (7 mL, 56.00 mmol). The vessel was sealed, and the contents heated to 125° C. in the microwave. After 30 minutes, the mixture was concentrated. Chromatographic purification of the crude product (CombiFlash, 4 g silica gel column, 1-5% methanol/dichloromethane elute) afforded 0.069 g (59%) of 4-((6-((6-cyclopropylpyridin-3-yl)methoxy)-5-ethoxypyridin-3-yl)oxy)-N-methylpicolinamide as a yellow solid: $^1$H NMR (400 MHz, CDCl$_3$) δ 8.62-8.57 (m, 1H), 8.39 (d, J=5.6 Hz, 1H), 8.02-7.96 (m, 1H), 7.72-7.67 (m, 2H), 7.56 (d, J=2.3 Hz, 1H), 7.14 (dd, J=8.1, 0.9 Hz, 1H), 6.95 (dd, J=5.6, 2.5 Hz, 1H), 6.83 (d, J=2.5 Hz, 1H), 5.44 (s, 2H), 4.03 (q, J=7.0 Hz, 2H), 3.01 (d, J=5.1 Hz, 3H), 2.04 (m, 1H), 1.44 (t, J=7.0 Hz, 3H), 1.06-0.95 (m, 4H) ppm; (M+1)=421.

Example 1-263: Synthesis of 4-((6-((6-cyclopropylpyridin-3-yl)methoxy)-5-fluoropyridin-3-yl)oxy)-N-methylpicolinamide Example 1-263-1: Preparation of 5-bromo-2-((6-cyclopropylpyridin-3-yl)methoxy)-3-fluoropyridine The title compound was prepared from 5-bromo-2,3-difluoropyridine and (6-cyclopropylpyridin-3-yl)methanol as described in Example 1-256-2.

Example 1-263-2: Preparation of 2-((6-cyclopropylpyridin-3-yl)methoxy)-3-fluoro-5-(4,4,5,5-tetramethyl-1,3,2-dioxaborolan-2-yl)pyridine The title compound was prepared from 5-bromo-2-((6-cyclopropylpyridin-3-yl)methoxy)-3-fluoropyridine and 4,4,4',4',5,5,5',5'-octamethyl-2,2'-bi(1,3,2-dioxaborolane) as described in Example 1-230-1.

Example 1-263-3: Preparation of 4-((6-((6-cyclopropylpyridin-3-yl)methoxy)-5-fluoropyridin-3-yl)oxy)-N-methylpicolinamide The title compound was prepared in three steps from 2-((6-cyclopropylpyridin-3-yl)methoxy)-3-fluoro-5-(4,4,5,5-tetramethyl-1,3,2-dioxaborolan-2-yl)pyridine and methyl 4-chloropyridine-2-carboxylate as described in Example 1-262-1 through Example 1-262-3: $^1$H NMR (400 MHz, CDCl$_3$) δ 8.60-8.55 (m, 1H), 8.42 (d, J=5.6 Hz, 1H), 8.03-7.95 (m, 1H), 7.82 (d, J=2.6 Hz, 1H), 7.73-7.66 (m, 2H), 7.22-7.14 (m, 2H), 6.98 (dd, J=5.6, 2.6 Hz, 1H), 5.43 (s, 2H), 3.02 (d, J=5.1 Hz, 3H), 2.09-2.01 (m, 1H), 1.07-0.96 (m, 4H) ppm; (M+1)=395.

Example 2: In Vitro Studies

Example 2-1: c-FMS Activity

Reagents and consumables were purchased from Sigma Aldrich, Carna Biosciences, or Caliper Life Sciences. All assay reaction conditions for IC$_{50}$ determinations were within the linear range with respect to time and enzyme concentration. In a 384 well polypropylene plate, c-FMS (0.14 nM, Carna 08-155) was pre-incubated in a 100 mM Hepes-NaOH pH 7.5 buffer containing 0.01% Triton X-100, 10 mM MgCl$_2$, 0.1% BSA, 1 mM DTT, 10 μM sodium orthovanadate and 10 μM beta-glycerophosphate and compound with a concentration of 2.5% DMSO for 15 minutes at room temperature. The reaction was initiated with an equal volume of peptide substrate (Caliper Life Sciences catalog no. 760430) and ATP in the aforementioned buffer. The final concentrations in the reaction were 70 pM c-FMS, 1.5 μM peptide substrate and 500 μM ATP (ATP Km). The reaction was incubated at room temperature for 120 minutes and terminated with a buffer containing excess EDTA (100 mM Hepes-NaOH pH 7.5, 0.02% Brij, 0.1% CR-3, 0.36% DMSO and 100 mM EDTA). The plate was run for one cycle on a LabChip 3000 (Caliper Life Sciences, Hopkinton, Mass.) in an off-chip mobility shift type assay with an upstream voltage of −2250 volts, a downstream voltage of −500 volts and a vacuum pressure of −1.6 psi. The LabChip 3000 separates and measures the fluorescent signal of fluorescein labeled peptide substrate and fluorescein labeled peptide product present in each well. Results are expressed as percent conversion by measuring peak height for both the substrate and product and dividing the product peak height by the sum of peak heights for both substrate and product. On every plate 100% inhibition (with a saturating concentration of staurosporine) and 0% inhibition (substrate with enzyme and DMSO) controls were used to calculate percent inhibition of tested compounds and a Z' prime value.

Table 1 displays the c-FMS IC$_{50}$, the cellular receptor for colony stimulating factor-1 (CSF-1), for selected compounds.

Example 2-2: Phospho c-FMS Activity

Reagents and consumables were purchased from Sigma Aldrich, Gibco LifeTechnologies, BD Biosciences, Perkin Elmer, R&D Systems, Cell Signaling, Thermo Scientific (Pierce) and Santa Cruz Biotechnology. HEK293 cells overexpressing human cFMS (HEK293/hFMS) were cultured in RPMI media in T225 flasks and split twice a week. For the experiment, the cells were trypsinized, counted and diluted with serum-free Megacell media (Sigma Cat #M3817) to 600,000 cells/ml (30,000 cells/well). A serial dilution of test compounds was prepared by the Echo 555 (LABCYTE) using Echo LDV Plates, Cat #LP-0200; and 500 nl of each compound concentration was added to 96-well BD Biocoat poly-d-lysine plate (BD Cat #356640) in DMSO (0.5% final). 50 μL/well MegaCell serum-free media was then added to cover compounds before adding cells at 50 μL/well cells (30,000/well). The plates were spun down for 1 minute at 1000 rpm and then incubated on benchtop for 15-30 minutes; the plates were moved to a CO$_2$ incubator at 37° C. for overnight incubation. White 96-well Perkin Elmer OptiPlates (Cat #6005509) were pre-coated with 50 ng/well (100 μL/well) anti-cFMS/CSF-1R (C-20) (Santa Cruz Cat #sc-692) in PBS, sealed with a foil seal, spun down at 1000 rpm for one minute and incubated overnight at 4° C.

On the following day, the pre-coated OptiPlates plates were blocked with 200 μl/well 1% BSA in 1× PBST (PBS with 0.1% Triton-X) at room temperature for 2-3 hours. In parallel, 100 μL/well 2× hCSF1 (final 150 ng/ml) (R&D Systems, Cat #216-MC-025/CF) (or media as a negative control) was added to the HEK293/hFMS cells (BD culture plates) incubated overnight with compounds. On every plate 100% response (with CSF1 treatment) and 0% response (without CSF1) control columns were used to calculate percent inhibition of tested compounds and a Z' prime value. Plates were incubated at 37° C. for 10 minutes. Media/hCSF1 was aspirated off and cells were lysed with 100 μl/well pre-chilled lysis buffer made up with lysis buffer (Cell Signaling Cat #9803), protease/phosphatase inhibitors (Pierce Cat #78444), and PMSF (Sigma Cat #93482). Plates were shaken for 60 seconds; then, spun at 3200 rpm for 5 minutes at 4° C. and kept on ice. 90 μl of the lysate was transferred to the pre-coated/blocked OptiPlates. The plates were then spun at 1000 rpm for 60 seconds and incubated overnight at 4° C. sealed.

The next day lysates were removed from the plates; and plates were washed with 300 μL/well of 1× PBS 6 times using the Biotek washer. The remaining PBS on the plates was tapped out. 90 μL/well of 1:10,000 anti-phospho-Eu (Tyr 100) (Perkin Elmer Cat #AD0159) in 1% BSA in PBST was added to the plates; and plates were incubated for one hour at room temperature sealed. After one hour, the antibody was removed and plates were washed 6 times with 300 μL/well of PBST using the Biotek washer. 90 μL/well enhancement solution (Perkin Elmer Cat #4001-0010) was added next and the plates were sealed and shaken for 5 minutes. The signal was read immediately on the Perkin Elmer Envision for time-resolved fluorescence with excitation at 320 nm and emission at 615 nm.

The data were analyzed by Pipeline Pilot to calculate % Inhibition and IC$_{50}$ values; IC$_{50}$ values for phosphor c-FMS are provided for selected CSF-1R inhibitors in Table 1.

TABLE 1

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-1 | 4-(1-((2-(4-methoxyphenyl)-2,3-dihydrobenzo[b][1,4]dioxin-6-yl)methyl)-1H-benzo[d]imidazol-5-yl)-2-methylbut-3-yn-2-amine | 0.005 | 0.053 |
| Ex. 1-2 | 4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine | 0.006 | 0.02 |
| Ex. 1-2-enant A | (S)-4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine | 0.004 | 0.018 |
| Ex. 1-2-enant B | (R)-4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine | 0.004 | 0.016 |
| Ex. 1-3 | 3-((2-(4-methoxyphenyl)-2,3-dihydrobenzo[b][1,4]dioxin-6-yl)methyl)-6-(4-methylpiperazin-1-yl)-3H-imidazo[4,5-b]pyridine | 0.015 | 0.031 |
| Ex. 1-4 | 3-((2-(4-methoxyphenyl)-2,3-dihydrobenzo[b][1,4]dioxin-6-yl)methyl)-6-(1-methyl-1H-pyrazol-4-yl)-3H-imidazo[4,5-b]pyridine | 0.003 | 0.006 |
| Ex. 1-5 | 4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine | 0.014 | 0.055 |
| Ex. 1-5-enant A | (S)-4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine | 0.006 | 0.033 |
| Ex. 1-5-enant B | (R)-4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine | 0.016 | 0.061 |
| Ex. 1-6 | 3-((2-(6-methoxypyridin-3-yl)-2,3-dihydrobenzo[b][1,4]dioxin-6-yl)methyl)-6-(4-methylpiperazin-1-yl)-3H-imidazo[4,5-b]pyridine | 0.042 | 0.106 |
| Ex. 1-7 | 3-((2-(6-methoxypyridin-3-yl)-2,3-dihydrobenzo[b][1,4]dioxin-6-yl)methyl)-3H-imidazo[4,5-b]pyridine-6-carbonitrile | 0.762 | 0.757 |
| Ex. 1-8 | 6-(azetidin-1-yl)-3-((2-(6-methoxypyridin-3-yl)-2,3-dihydrobenzo[b][1,4]dioxin-6-yl)methyl)-3H-imidazo[4,5-b]pyridine | 0.1 | 0.076 |
| Ex. 1-9 | 6-cyclopropyl-3-((2-(6-methoxypyridin-3-yl)-2,3-dihydrobenzo[b][1,4]dioxin-6-yl)methyl)-3H-imidazo[4,5-b]pyridine | 0.116 | 0.108 |
| Ex. 1-10 | 4-(3-((2-(6-methoxypyridin-3-yl)-2,3-dihydrobenzo[b][1,4]dioxin-6-yl)methyl)-3H-imidazo[4,5-b]pyridin-6-yl)morpholine | 0.025 | 0.048 |
| Ex. 1-11 | 6-methoxy-3-((2-(6-methoxypyridin-3-yl)-2,3-dihydrobenzo[b][1,4]dioxin-6-yl)methyl)-3H-imidazo[4,5-b]pyridine | 0.081 | 0.106 |
| Ex. 1-12 | 4-(3-((2-(4-methoxyphenyl)-3-methyl-2,3-dihydrobenzo[b][1,4]dioxin-6-yl)methyl)-3H-imidazo[4,5-b]pyridin-6-yl)-2-methylbut-3-yn-2-amine | 0.006 | 0.017 |
| Ex. 1-13 | 6-methoxy-3-((2-(6-methoxypyridin-3-yl)-3-methyl-2,3-dihydrobenzo[b][1,4]dioxin-6-yl)methyl)-3H-imidazo[4,5-b]pyridine | 0.033 | 0.085 |
| Ex. 1-14 | 4-(3-((2-(2,4-dichlorophenyl)-2,3-dihydrobenzo[b][1,4]dioxin-6-yl)methyl)-3H-imidazo[4,5-b]pyridin-6-yl)-2-methylbut-3-yn-2-amine | 0.059 | 1.22 |
| Ex. 1-15 | 2,2,2-trifluoro-N-((6-((6-(1-methyl-1H-pyrazol-4-yl)-3H-imidazo[4,5-b]pyridin-3-yl)methyl)-2,3-dihydrobenzo[b][1,4]dioxin-2-yl)methyl)acetamide | 0.193 | 1.65 |
| Ex. 1-16 | 6-(3-methoxyazetidin-1-yl)-3-((2-(6-methoxypyridin-3-yl)-2,3-dihydrobenzo[b][1,4]dioxin-6-yl)methyl)-3H-imidazo[4,5-b]pyridine | 0.029 | 0.05 |
| Ex. 1-17 | 2-methyl-4-(3-((2-(1-methyl-1H-pyrazol-4-yl)-2,3-dihydrobenzo[b][1,4]dioxin-6-yl)methyl)-3H-imidazo[4,5-b]pyridin-6-yl)but-3-yn-2-amine | 0.292 | 0.428 |
| Ex. 1-18 | 4-(3-(1-(2-(6-methoxypyridin-3-yl)-2,3-dihydrobenzo[b][1,4]dioxin-6-yl)ethyl)-3H-imidazo[4,5-b]pyridin-6-yl)-2-methylbut-3-yn-2-amine | 0.625 | 0.79 |
| Ex. 1-19 | 3-((2-(4-(difluoromethoxy)phenyl)-2,3-dihydrobenzo[b][1,4]dioxin-6-yl)methyl)-3H-imidazo[4,5-b]pyridine | 0.116 | 0.224 |
| Ex. 1-20 | 6-(1,3-dimethyl-1H-pyrazol-4-yl)-3-((2-(2-fluoro-4-methoxyphenyl)-2,3-dihydrobenzo[b][1,4]dioxin-6-yl)methyl)-3H-imidazo[4,5-b]pyridine | 0.013 | 0.013 |
| Ex. 1-21 | 6-bromo-3-((2-(6-methoxypyridin-3-yl)-2,3-dihydrobenzo[b][1,4]dioxin-6-yl)methyl)pyrazolo[1,5-a]pyrimidine | 0.076 | 0.213 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-22 | 3-((2-(6-methoxypyridin-3-yl)-2,3-dihydrobenzo[b][1,4]dioxin-6-yl)methyl)pyrazolo[1,5-a]pyridine | 0.304 | 0.284 |
| Ex. 1-23 | 4-(3-((2-(6-methoxypyridin-3-yl)-2,3-dihydrobenzo[b][1,4]dioxin-6-yl)methyl)imidazo[1,2-b]pyridazin-7-yl)-2-methylbut-3-yn-2-amine | 0.004 | 0.032 |
| Ex. 1-24 | N-ethyl-4-((2-(6-methoxypyridin-3-yl)-2,3-dihydrobenzo[b][1,4]dioxin-6-yl)methyl)picolinamide | 1.06 | 1.01 |
| Ex. 1-25 | 4-((2-(6-methoxypyridin-3-yl)-2,3-dihydrobenzo[b][1,4]dioxin-6-yl)methyl)picolinamide | 1.61 | 0.929 |
| Ex. 1-26 | 4-((2-(6-methoxypyridin-3-yl)-2,3-dihydrobenzo[b][1,4]dioxin-6-yl)methyl)-N-methylpicolinamide | 0.593 | 0.565 |
| Ex. 1-27 | 2-(1-methyl-1H-pyrazol-4-yl)-4-((2-(4-(trifluoromethyl)phenyl)-2,3-dihydrobenzo[b][1,4]dioxin-6-yl)methyl)pyridine 2,2,2-trifluoroacetate | 0.021 | 0.031 |
| Ex. 1-28 | 5-((2-(6-methoxypyridin-3-yl)-2,3-dihydrobenzo[b][1,4]dioxin-6-yl)methyl)pyrimidine-2,4-diamine | 0.373 | 0.679 |
| Ex. 1-29 | 4-(3-((8-fluoro-2-(4-(trifluoromethyl)phenyl)-2,3-dihydrobenzo[b][1,4]dioxin-6-yl)methyl)-3H-imidazo[4,5-b]pyridin-6-yl)-2-methylbut-3-yn-2-amine | 0.007 | 0.064 |
| Ex. 1-30 | 3-((8-fluoro-2-(4-(trifluoromethyl)phenyl)-2,3-dihydrobenzo[b][1,4]dioxin-6-yl)methyl)-6-(4-methylpiperazin-1-yl)-3H-imidazo[4,5-b]pyridine | 0.014 | 0.033 |
| Ex. 1-31 | 3-((8-fluoro-2-(4-(trifluoromethyl)phenyl)-2,3-dihydrobenzo[b][1,4]dioxin-6-yl)methyl)-6-(piperidin-3-ylethynyl)-3H-imidazo[4,5-b]pyridine hydrochloride | 0.016 | 0.056 |
| Ex. 1-32 | 3-((8-fluoro-2-(4-(trifluoromethyl)phenyl)-2,3-dihydrobenzo[b][1,4]dioxin-6-yl)methyl)-6-(1-methyl-1H-pyrazol-4-yl)-3H-imidazo[4,5-b]pyridine 2,2,2-trifluoroacetate | 0.021 | 0.02 |
| Ex. 1-33 | 3-((8-fluoro-2-(6-methoxypyridin-3-yl)-5-methyl-2,3-dihydrobenzo[b][1,4]dioxin-6-yl)methyl)-6-iodo-3H-imidazo[4,5-b]pyridine | 0.809 | 0.641 |
| Ex. 1-34 | 6-cyclopropyl-3-((8-fluoro-2-(6-methoxypyridin-3-yl)-5-methyl-2,3-dihydrobenzo[b][1,4]dioxin-6-yl)methyl)-3H-imidazo[4,5-b]pyridine 2,2,2-trifluoroacetate | 0.474 | 0.921 |
| Ex. 1-35 | 4-(3-((8-fluoro-2-(6-methoxypyridin-3-yl)-5-methyl-2,3-dihydrobenzo[b][1,4]dioxin-6-yl)methyl)-3H-imidazo[4,5-b]pyridin-6-yl)-2-methylbut-3-yn-2-amine | 0.04 | 0.185 |
| Ex. 1-36 | 3-((8-fluoro-2-(6-methoxypyridin-3-yl)-5-methyl-2,3-dihydrobenzo[b][1,4]dioxin-6-yl)methyl)-6-(1-methyl-1H-pyrazol-4-yl)-3H-imidazo[4,5-b]pyridine | 0.026 | 0.037 |
| Ex. 1-37 | 3-((5-cyclopropyl-8-fluoro-2-(6-methoxypyridin-3-yl)-2,3-dihydrobenzo[b][1,4]dioxin-6-yl)methyl)-6-(1-methyl-1H-pyrazol-4-yl)-3H-imidazo[4,5-b]pyridine | 0.178 | 0.114 |
| Ex. 1-38 | 4-(3-((8-fluoro-2-(6-methoxypyridin-3-yl)-5,7-dimethyl-2,3-dihydrobenzo[b][1,4]dioxin-6-yl)methyl)-3H-imidazo[4,5-b]pyridin-6-yl)-2-methylbut-3-yn-2-amine 2,2,2-trifluoroacetate | 0.383 | 1.38 |
| Ex. 1-39 | 4-(3-((8-fluoro-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine | 0.012 | 0.058 |
| Ex. 1-40 | 3-((8-fluoro-2-(6-methoxypyridin-3-yl)-2,3-dihydrobenzo[b][1,4]dioxin-6-yl)methyl)-6-(piperidin-3-ylethynyl)-3H-imidazo[4,5-b]pyridine | 0.012 | 0.034 |
| Ex. 1-41 | 4-(3-((8-fluoro-2-(6-methoxypyridin-3-yl)-2,3-dihydrobenzo[b][1,4]dioxin-6-yl)methyl)-3H-imidazo[4,5-b]pyridin-6-yl)morpholine | 0.023 | 0.042 |
| Ex. 1-42 | 3-((8-fluoro-2-(6-methoxypyridin-3-yl)-2,3-dihydrobenzo[b][1,4]dioxin-6-yl)methyl)-6-(2-methyl-1H-imidazol-1-yl)-3H-imidazo[4,5-b]pyridine | 0.039 | 0.079 |
| Ex. 1-43 | 3-((8-fluoro-2-(6-methoxypyridin-3-yl)-2,3-dihydrobenzo[b][1,4]dioxin-6-yl)methyl)-7-methoxyimidazo[1,2-a]pyridine | 0.907 | 0.826 |
| Ex. 1-44 | 6-bromo-3-((8-fluoro-2-(6-methoxypyridin-3-yl)-2,3-dihydrobenzo[b][1,4]dioxin-6-yl)methyl)pyrazolo[1,5-a]pyrimidine | 0.061 | 0.122 |
| Ex. 1-45 | 3-((8-fluoro-2-(6-methoxypyridin-3-yl)-2,3-dihydrobenzo[b][1,4]dioxin-6-yl)methyl)-6-methoxypyrazolo[1,5-a]pyrimidine | 0.027 | 0.047 |
| Ex. 1-46 | 3-((8-fluoro-2-(6-methoxypyridin-3-yl)-2,3-dihydrobenzo[b][1,4]dioxin-6-yl)methyl)pyrazolo[1,5-a]pyrimidine | 0.097 | 0.107 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-47 | 7-chloro-3-((8-fluoro-2-(6-methoxypyridin-3-yl)-2,3-dihydrobenzo[b][1,4]dioxin-6-yl)methyl)imidazo[1,2-b]pyridazine | 0.142 | 0.241 |
| Ex. 1-48 | 3-((8-fluoro-2-(6-methoxypyridin-3-yl)-2,3-dihydrobenzo[b][1,4]dioxin-6-yl)methyl)-6-(3-methoxyazetidin-1-yl)pyrazolo[1,5-a]pyridine | 0.015 | |
| Ex. 1-49 | 4-((8-fluoro-2-(4-(trifluoromethyl)phenyl)-2,3-dihydrobenzo[b][1,4]dioxin-6-yl)methyl)-2-(1-methyl-1H-pyrazol-4-yl)pyridine | 0.026 | 0.031 |
| Ex. 1-50 | 3-((8-fluoro-2-(4-(trifluoromethyl)phenyl)-2,3-dihydrobenzo[b][1,4]dioxin-6-yl)methyl)-5-(1-methyl-1H-pyrazol-4-yl)pyridine | 0.069 | 0.158 |
| Ex. 1-51 | 3-((8-fluoro-2-(4-(trifluoromethyl)phenyl)-2,3-dihydrobenzo[b][1,4]dioxin-6-yl)methyl)-5-(1-methyl-1H-pyrazol-3-yl)pyridine | 0.076 | 0.177 |
| Ex. 1-52 | 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine | 0.01 | 0.018 |
| Ex. 1-52-enant A | (S)-4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine | 0.011 | 0.018 |
| Ex. 1-52-enant B | (R)-4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine | 0.032 | 0.054 |
| Ex. 1-53 | 3-((8-methoxy-2-(6-methoxypyridin-3-yl)-2,3-dihydrobenzo[b][1,4]dioxin-6-yl)methyl)-6-(1-methyl-1H-pyrazol-4-yl)-3H-imidazo[4,5-b]pyridine | 0.005 | 0.002 |
| Ex. 1-54 | 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)morpholine | 0.009 | 0.016 |
| Ex. 1-55 | 6-cyclopropyl-3-((8-methoxy-2-(6-methoxypyridin-3-yl)-2,3-dihydrobenzo[b][1,4]dioxin-6-yl)methyl)-3H-imidazo[4,5-b]pyridine | 0.013 | 0.039 |
| Ex. 1-56 | 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-ol | 0.015 | 0.012 |
| Ex. 1-57 | 6-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-oxa-6-azaspiro[3.3]heptane | 0.014 | 0.016 |
| Ex. 1-58 | 3-((8-methoxy-2-(6-methoxypyridin-3-yl)-2,3-dihydrobenzo[b][1,4]dioxin-6-yl)methyl)-6-(3-methoxyprop-1-yn-1-yl)-3H-imidazo[4,5-b]pyridine | 0.019 | 0.02 |
| Ex. 1-59 | 4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)isoxazole | 0.006 | 0.01 |
| Ex. 1-60 | 6-methoxy-3-((8-methoxy-2-(6-methoxypyridin-3-yl)-2,3-dihydrobenzo[b][1,4]dioxin-6-yl)methyl)-3H-imidazo[4,5-b]pyridine | 0.012 | 0.022 |
| Ex. 1-60-enant A | (S)-6-methoxy-3-((8-methoxy-2-(6-methoxypyridin-3-yl)-2,3-dihydrobenzo[b][1,4]dioxin-6-yl)methyl)-3H-imidazo[4,5-b]pyridine | 0.008 | 0.012 |
| Ex. 1-60-enant B | (R)-6-methoxy-3-((8-methoxy-2-(6-methoxypyridin-3-yl)-2,3-dihydrobenzo[b][1,4]dioxin-6-yl)methyl)-3H-imidazo[4,5-b]pyridine | 0.053 | 0.059 |
| Ex. 1-61 | 3-((8-methoxy-2-(6-methoxypyridin-3-yl)-2,3-dihydrobenzo[b][1,4]dioxin-6-yl)methyl)-6-(3-methoxyazetidin-1-yl)-3H-imidazo[4,5-b]pyridine | 0.016 | 0.012 |
| Ex. 1-62 | 6-(azetidin-1-yl)-3-((8-methoxy-2-(6-methoxypyridin-3-yl)-2,3-dihydrobenzo[b][1,4]dioxin-6-yl)methyl)-3H-imidazo[4,5-b]pyridine | 0.015 | 0.034 |
| Ex. 1-63 | 2-((3-((8-methoxy-2-(6-methoxypyridin-3-yl)-2,3-dihydrobenzo[b][1,4]dioxin-6-yl)methyl)-3H-imidazo[4,5-b]pyridin-6-yl)oxy)-N,N-dimethylethan-1-amine | 0.059 | 0.108 |
| Ex. 1-64 | 3-((8-methoxy-2-(6-methoxypyridin-3-yl)-2,3-dihydrobenzo[b][1,4]dioxin-6-yl)methyl)-6-(oxetan-3-yloxy)-3H-imidazo[4,5-b]pyridine | 0.016 | 0.025 |
| Ex. 1-65 | 3-((8-methoxy-2-(6-methoxypyridin-3-yl)-2,3-dihydrobenzo[b][1,4]dioxin-6-yl)methyl)-N,N-dimethyl-3H-imidazo[4,5-b]pyridin-6-amine | 0.018 | 0.024 |
| Ex. 1-66 | 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-3-methylazetidin-3-ol | 0.022 | 0.032 |
| Ex. 1-67 | 3-((8-methoxy-2-(6-methoxypyridin-3-yl)-2,3-dihydrobenzo[b][1,4]dioxin-6-yl)methyl)-6-(1H-1,2,4-triazol-1-yl)-3H-imidazo[4,5-b]pyridine | 0.032 | 0.051 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-68 | 3-((8-methoxy-2-(6-methoxypyridin-3-yl)-2,3-dihydrobenzo[b][1,4]dioxin-6-yl)methyl)-6-(1H-pyrazol-1-yl)-3H-imidazo[4,5-b]pyridine | 0.008 | 0.018 |
| Ex. 1-69 | 6-(1H-imidazol-1-yl)-3-((8-methoxy-2-(6-methoxypyridin-3-yl)-2,3-dihydrobenzo[b][1,4]dioxin-6-yl)methyl)-3H-imidazo[4,5-b]pyridine | 0.008 | 0.019 |
| Ex. 1-70 | 3-((8-methoxy-2-(6-methoxypyridin-3-yl)-2,3-dihydrobenzo[b][1,4]dioxin-6-yl)methyl)-6-(2-methyl-1H-imidazol-1-yl)-3H-imidazo[4,5-b]pyridine | 0.015 | 0.024 |
| Ex. 1-71 | 6-(2,4-dimethyl-1H-imidazol-1-yl)-3-((8-methoxy-2-(6-methoxypyridin-3-yl)-2,3-dihydrobenzo[b][1,4]dioxin-6-yl)methyl)-3H-imidazo[4,5-b]pyridine | 0.019 | 0.021 |
| Ex. 1-72 | 3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine | 0.031 | 0.061 |
| Ex. 1-73 | 3-((8-methoxy-2-(6-methoxypyridin-3-yl)-2,3-dihydrobenzo[b][1,4]dioxin-6-yl)methyl)-6-methyl-3H-imidazo[4,5-b]pyridine | 0.029 | 0.063 |
| Ex. 1-74 | 3-((8-methoxy-2-(6-methoxypyridin-3-yl)-2,3-dihydrobenzo[b][1,4]dioxin-6-yl)methyl)-N-methyl-3H-imidazo[4,5-b]pyridin-6-amine | 0.02 | 0.027 |
| Ex. 1-75 | 6-(1,3-dimethyl-1H-pyrazol-4-yl)-3-((8-methoxy-2-(6-methoxypyridin-3-yl)-2,3-dihydrobenzo[b][1,4]dioxin-6-yl)methyl)-3H-imidazo[4,5-b]pyridine | 0.005 | 0.002 |
| Ex. 1-76 | 6-(6-fluoropyridin-3-yl)-3-((8-methoxy-2-(6-methoxypyridin-3-yl)-2,3-dihydrobenzo[b][1,4]dioxin-6-yl)methyl)-3H-imidazo[4,5-b]pyridine | 0.009 | 0.012 |
| Ex. 1-77 | 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)azetidin-3-ol | 0.021 | 0.032 |
| Ex. 1-78 | 3-((8-methoxy-2-(6-methoxypyridin-3-yl)-2,3-dihydrobenzo[b][1,4]dioxin-6-yl)methyl)-6-(4-methylpiperazin-1-yl)-3H-imidazo[4,5-b]pyridine | 0.014 | 0.03 |
| Ex. 1-79 | 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-3-methylazetidin-3-amine | 0.03 | 0.062 |
| Ex. 1-80 | 6-(3-fluoroazetidin-1-yl)-3-((8-methoxy-2-(6-methoxypyridin-3-yl)-2,3-dihydrobenzo[b][1,4]dioxin-6-yl)methyl)-3H-imidazo[4,5-b]pyridine | 0.013 | 0.019 |
| Ex. 1-81 | 6-fluoro-3-((8-methoxy-2-(6-methoxypyridin-3-yl)-2,3-dihydrobenzo[b][1,4]dioxin-6-yl)methyl)-3H-imidazo[4,5-b]pyridine | 0.064 | 0.109 |
| Ex. 1-82 | 3-((8-methoxy-2-(6-methoxypyridin-3-yl)-2,3-dihydrobenzo[b][1,4]dioxin-6-yl)methyl)-3H-imidazo[4,5-b]pyridine | 0.08 | 0.095 |
| Ex. 1-83 | azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone | 0.013 | 0.01 |
| Ex. 1-83-enant A | (S)-azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone | 0.011 | 0.008 |
| Ex. 1-83-enant B | (R)-azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone | 0.031 | 0.038 |
| Ex. 1-84 | (3-((8-methoxy-2-(6-methoxypyridin-3-yl)-2,3-dihydrobenzo[b][1,4]dioxin-6-yl)methyl)-3H-imidazo[4,5-b]pyridin-6-yl)methanol | 0.069 | 0.094 |
| Ex. 1-85 | 3-((8-methoxy-2-(6-methoxypyridin-3-yl)-2,3-dihydrobenzo[b][1,4]dioxin-6-yl)methyl)-6-(methoxymethyl)-3H-imidazo[4,5-b]pyridine | 0.042 | 0.075 |
| Ex. 1-86 | 6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine | 0.022 | 0.045 |
| Ex. 1-86-enant A | (S)-6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine | 0.004 | 0.011 |
| Ex. 1-86-enant B | (R)-6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine | 0.069 | 0.157 |
| Ex. 1-87 | 6-methoxy-3-((8-methoxy-2-(6-methoxypyridin-3-yl)-2,3-dihydrobenzo[b][1,4]dioxin-6-yl)methyl)-2-methyl-3H-imidazo[4,5-b]pyridine | 2.78 | 2.13 |
| Ex. 1-88 | 6-(azetidin-3-yl)-3-((8-methoxy-2-(6-methoxypyridin-3-yl)-2,3-dihydrobenzo[b][1,4]dioxin-6-yl)methyl)-3H-imidazo[4,5-b]pyridine 2,2,2-trifluoroacetate | 0.251 | 0.773 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-89 | 5,6-dimethoxy-1-((8-methoxy-2-(6-methoxypyridin-3-yl)-2,3-dihydrobenzo[b][1,4]dioxin-6-yl)methyl)-1H-benzo[d]imidazole | 0.072 | 0.092 |
| Ex. 1-90 | 6-(1H-imidazol-2-yl)-3-((8-methoxy-2-(6-methoxypyridin-3-yl)-2,3-dihydrobenzo[b][1,4]dioxin-6-yl)methyl)-3H-imidazo[4,5-b]pyridine formate | 0.028 | 0.033 |
| Ex. 1-91 | 3-((8-methoxy-2-(6-methoxypyridin-3-yl)-2,3-dihydrobenzo[b][1,4]dioxin-6-yl)methyl)-6-(4-methyl-1H-imidazol-2-yl)-3H-imidazo[4,5-b]pyridine | 0.036 | 0.041 |
| Ex. 1-92 | 3-((8-methoxy-2-(6-methoxypyridin-3-yl)-3-methyl-2,3-dihydrobenzo[b][1,4]dioxin-6-yl)methyl)-3H-imidazo[4,5-b]pyridine | 0.041 | 0.055 |
| Ex. 1-92-diaster A | 3-(((2R,3S)-8-methoxy-2-(6-methoxypyridin-3-yl)-3-methyl-2,3-dihydrobenzo[b][1,4]dioxin-6-yl)methyl)-3H-imidazo[4,5-b]pyridine | 6.12 | 1.89 |
| Ex. 1-92-diasterB | 3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine | 0.014 | 0.014 |
| Ex. 1-92-diasterC | 3-(((2S,3R)-8-methoxy-2-(6-methoxypyridin-3-yl)-3-methyl-2,3-dihydrobenzo[b][1,4]dioxin-6-yl)methyl)-3H-imidazo[4,5-b]pyridine | 0.84 | 0.63 |
| Ex. 1-92-diasterD | 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine | 0.066 | 0.067 |
| Ex. 1-93 | 6-methoxy-3-((8-methoxy-2-(6-methoxypyridin-3-yl)-3-methyl-2,3-dihydrobenzo[b][1,4]dioxin-6-yl)methyl)-3H-imidazo[4,5-b]pyridine | 0.021 | 0.012 |
| Ex. 1-93-diasterA | 6-methoxy-3-(((2R,3S)-8-methoxy-2-(6-methoxypyridin-3-yl)-3-methyl-2,3-dihydrobenzo[b][1,4]dioxin-6-yl)methyl)-3H-imidazo[4,5-b]pyridine | 1.66 | 0.629 |
| Ex. 1-93-diasterB | | 0.015 | 0.005 |
| Ex. 1-93-diasterC | | 0.2 | 0.23 |
| Ex. 1-93-diasterD | | 0.045 | 0.017 |
| Ex. 1-94 | 4-(3-((8-methoxy-2-(6-methoxypyridin-3-yl)-2-methyl-2,3-dihydrobenzo[b][1,4]dioxin-6-yl)methyl)-3H-imidazo[4,5-b]pyridin-6-yl)-2-methylbut-3-yn-2-amine | n/d | n/d |
| Ex. 1-94-enant A | | 1.25 | 1.66 |
| Ex. 1-94-enant B | | 0.41 | 0.51 |
| Ex. 1-95 | 7-((8-methoxy-2-(6-methoxypyridin-3-yl)-2,3-dihydrobenzo[b][1,4]dioxin-6-yl)methyl)-7H-imidazo[4,5-c]pyridazine | 0.24 | 0.24 |
| Ex. 1-96 | 6-bromo-3-((8-methoxy-2-(6-methoxypyridin-3-yl)-2,3-dihydrobenzo[b][1,4]dioxin-6-yl)methyl)pyrazolo[1,5-a]pyrimidine | 0.006 | 0.035 |
| Ex. 1-97 | 3-((8-methoxy-2-(6-methoxypyridin-3-yl)-2,3-dihydrobenzo[b][1,4]dioxin-6-yl)methyl)pyrazolo[1,5-a]pyrimidine | 0.018 | 0.022 |
| Ex. 1-98 | 3-((8-methoxy-2-(6-methoxypyridin-3-yl)-2,3-dihydrobenzo[b][1,4]dioxin-6-yl)methyl)-6-(3-methoxyazetidin-1-yl)pyrazolo[1,5-a]pyrimidine | 0.004 | 0.004 |
| Ex. 1-99 | 4-(3-((8-methoxy-2-(6-methoxypyridin-3-yl)-2,3-dihydrobenzo[b][1,4]dioxin-6-yl)methyl)pyrazolo[1,5-a]pyrimidin-6-yl)morpholine | 0.003 | 0.006 |
| Ex. 1-100 | 6-methoxy-3-((8-methoxy-2-(6-methoxypyridin-3-yl)-2,3-dihydrobenzo[b][1,4]dioxin-6-yl)methyl)pyrazolo[1,5-a]pyrimidine | 0.003 | 0.009 |
| Ex. 1-101 | 3-((8-methoxy-2-(6-methoxypyridin-3-yl)-2,3-dihydrobenzo[b][1,4]dioxin-6-yl)methyl)-6-((1-methylazetidin-3-yl)oxy)pyrazolo[1,5-a]pyrimidine | 0.005 | 0.016 |
| Ex. 1-102 | 7-chloro-3-((8-methoxy-2-(6-methoxypyridin-3-yl)-2,3-dihydrobenzo[b][1,4]dioxin-6-yl)methyl)imidazo[1,2-b]pyridazine | 0.018 | 0.046 |
| Ex. 1-103 | 4-(3-((8-methoxy-2-(6-methoxypyridin-3-yl)-2,3-dihydrobenzo[b][1,4]dioxin-6-yl)methyl)imidazo[1,2-b]pyridazin-7-yl)-2-methylbut-3-yn-2-amine | 0.003 | 0.011 |
| Ex. 1-104 | 4-(3-((8-methoxy-2-(6-methoxypyridin-3-yl)-2,3-dihydrobenzo[b][1,4]dioxin-6-yl)methyl)imidazo[1,2-b]pyridazin-7-yl)morpholine | 0.003 | 0.008 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-105 | 3-((8-methoxy-2-(6-methoxypyridin-3-yl)-2,3-dihydrobenzo[b][1,4]dioxin-6-yl)methyl)-7-(3-methoxyazetidin-1-yl)imidazo[1,2-b]pyridazine | 0.005 | 0.014 |
| Ex. 1-106 | 3-((8-methoxy-2-(6-methoxypyridin-3-yl)-2,3-dihydrobenzo[b][1,4]dioxin-6-yl)methyl)imidazo[1,2-a]pyridine | 1.33 | 0.943 |
| Ex. 1-107 | 3-((8-methoxy-2-(6-methoxypyridin-3-yl)-2,3-dihydrobenzo[b][1,4]dioxin-6-yl)methyl)imidazo[1,2-b]pyridazine | 0.022 | 0.044 |
| Ex. 1-108 | 7-methoxy-3-((8-methoxy-2-(6-methoxypyridin-3-yl)-2,3-dihydrobenzo[b][1,4]dioxin-6-yl)methyl)imidazo[1,2-a]pyridine | 0.78 | 0.51 |
| Ex. 1-109 | 3-((8-methoxy-2-(6-methoxypyridin-3-yl)-2,3-dihydrobenzo[b][1,4]dioxin-6-yl)methyl)-1H-pyrrolo[2,3-b]pyridine | 0.003 | 0.01 |
| Ex. 1-110 | 3-((2-(6-cyclopropylpyridin-3-yl)-8-methoxy-2,3-dihydrobenzo[b][1,4]dioxin-6-yl)methyl)-3H-imidazo[4,5-b]pyridine | 0.011 | 0.03 |
| Ex. 1-111 | 1-((2-(6-cyclopropylpyridin-3-yl)-8-methoxy-2,3-dihydrobenzo[b][1,4]dioxin-6-yl)methyl)-1H-benzo[d]imidazole | 0.043 | 0.1 |
| Ex. 1-112 | 3-((2-(6-cyclopropylpyridin-3-yl)-8-methoxy-2,3-dihydrobenzo[b][1,4]dioxin-6-yl)methyl)-5-methyl-3H-imidazo[4,5-b]pyridine | 0.011 | 0.021 |
| Ex. 1-113 | 1-((2-(6-cyclopropylpyridin-3-yl)-8-methoxy-2,3-dihydrobenzo[b][1,4]dioxin-6-yl)methyl)-1H-imidazo[4,5-c]pyridine | 0.14 | 0.18 |
| Ex. 1-114 | 3-((2-(6-cyclopropylpyridin-3-yl)-8-methoxy-2,3-dihydrobenzo[b][1,4]dioxin-6-yl)methyl)imidazo[1,2-a]pyrazine | 0.15 | 0.17 |
| Ex. 1-115 | 9-((2-(6-cyclopropylpyridin-3-yl)-8-methoxy-2,3-dihydrobenzo[b][1,4]dioxin-6-yl)methyl)-9H-purine | 0.026 | 0.072 |
| Ex. 1-116 | 3-((2-(6-cyclopropylpyridin-3-yl)-8-methoxy-2,3-dihydrobenzo[b][1,4]dioxin-6-yl)methyl)-6-((1-methylazetidin-3-yl)oxy)-3H-imidazo[4,5-b]pyridine | 0.008 | 0.014 |
| Ex. 1-117 | (3-((2-(6-cyclopropylpyridin-3-yl)-8-methoxy-2,3-dihydrobenzo[b][1,4]dioxin-6-yl)methyl)-3H-imidazo[4,5-b]pyridin-6-yl)methanol | 0.013 | 0.031 |
| Ex. 1-118 | 4-(3-((8-methoxy-2-(6-methylpyridin-3-yl)-2,3-dihydrobenzo[b][1,4]dioxin-6-yl)methyl)-3H-imidazo[4,5-b]pyridin-6-yl)-2-methylbut-3-yn-2-amine | 0.024 | 0.05 |
| Ex. 1-119 | 3-((8-methoxy-2-(6-methylpyridin-3-yl)-2,3-dihydrobenzo[b][1,4]dioxin-6-yl)methyl)-6-(2-methyl-1H-imidazol-1-yl)-3H-imidazo[4,5-b]pyridine hydrochloride | 0.066 | 0.13 |
| Ex. 1-120 | 6-methoxy-3-((8-methoxy-2-(6-methylpyridin-3-yl)-2,3-dihydrobenzo[b][1,4]dioxin-6-yl)methyl)-3H-imidazo[4,5-b]pyridine | 0.063 | 0.065 |
| Ex. 1-120-enant A | | 0.026 | 0.04 |
| Ex. 1-120-enant B | | 0.14 | 0.16 |
| Ex. 1-121 | 3-((8-methoxy-2-(6-methylpyridin-3-yl)-2,3-dihydrobenzo[b][1,4]dioxin-6-yl)methyl)-3H-imidazo[4,5-b]pyridine | 0.31 | 0.23 |
| Ex. 1-122 | 3-((8-methoxy-2-(6-methylpyridin-3-yl)-2,3-dihydrobenzo[b][1,4]dioxin-6-yl)methyl)-6-(3-methoxyazetidin-1-yl)-3H-imidazo[4,5-b]pyridine | 0.027 | 0.032 |
| Ex. 1-123 | 1-(3-((8-methoxy-2-(6-methylpyridin-3-yl)-2,3-dihydrobenzo[b][1,4]dioxin-6-yl)methyl)-3H-imidazo[4,5-b]pyridin-6-yl)azetidin-3-ol | 0.046 | 0.07 |
| Ex. 1-124 | 3-((8-methoxy-2-(6-methylpyridin-3-yl)-2,3-dihydrobenzo[b][1,4]dioxin-6-yl)methyl)-7-(3-methoxyazetidin-1-yl)imidazo[1,2-b]pyridazine | 0.009 | 0.019 |
| Ex. 1-125 | 3-((8-methoxy-2-(6-propylpyridin-3-yl)-2,3-dihydrobenzo[b][1,4]dioxin-6-yl)methyl)-3H-imidazo[4,5-b]pyridine | 0.019 | 0.04 |
| Ex. 1-126 | 3-((2-(6-ethylpyridin-3-yl)-8-methoxy-2,3-dihydrobenzo[b][1,4]dioxin-6-yl)methyl)-3H-imidazo[4,5-b]pyridine | 0.034 | 0.066 |
| Ex. 1-127 | 4-(3-((2-(6-ethylpyridin-3-yl)-8-methoxy-2,3-dihydrobenzo[b][1,4]dioxin-6-yl)methyl)-3H-imidazo[4,5-b]pyridin-6-yl)morpholine | 0.013 | 0.01 |
| Ex. 1-128 | 3-((2-(6-ethylpyridin-3-yl)-8-methoxy-2,3-dihydrobenzo[b][1,4]dioxin-6-yl)methyl)-6-((1-methylazetidin-3-yl)oxy)-3H-imidazo[4,5-b]pyridine | 0.018 | 0.042 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-129 | 3-((2-(6-ethylpyridin-3-yl)-8-methoxy-2,3-dihydrobenzo[b][1,4]dioxin-6-yl)methyl)-6-methoxy-3H-imidazo[4,5-b]pyridine | 0.011 | 0.018 |
| Ex. 1-130 | 3-((2-(6-ethylpyridin-3-yl)-8-methoxy-2,3-dihydrobenzo[b][1,4]dioxin-6-yl)methyl)-6-methoxypyrazolo[1,5-a]pyrimidine | 0.003 | 0.005 |
| Ex. 1-131 | 3-((2-(6-ethylpyridin-3-yl)-8-methoxy-2,3-dihydrobenzo[b][1,4]dioxin-6-yl)methyl)-6-(3-methoxyazetidin-1-yl)pyrazolo[1,5-a]pyrimidine | 0.005 | 0.003 |
| Ex. 1-132 | 3-((8-methoxy-2-(6-methylpyridin-3-yl)-2,3-dihydrobenzo[b][1,4]dioxin-6-yl)methyl)-6-(trifluoromethyl)-3H-imidazo[4,5-b]pyridine | | |
| Ex. 1-133 | 3-((2-(4,6-dimethylpyridin-3-yl)-8-methoxy-2,3-dihydrobenzo[b][1,4]dioxin-6-yl)methyl)-6-methoxy-3H-imidazo[4,5-b]pyridine | 0.21 | 0.19 |
| Ex. 1-134 | 3-((2-(4,6-dimethylpyridin-3-yl)-8-methoxy-2,3-dihydrobenzo[b][1,4]dioxin-6-yl)methyl)-6-(3-methoxyazetidin-1-yl)-3H-imidazo[4,5-b]pyridine | 0.1 | 0.096 |
| Ex. 1-135 | 4-(3-((8-methoxy-2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine | 0.006 | 0.008 |
| Ex. 1-136 | 3-((8-methoxy-2-(4-methoxyphenyl)-2,3-dihydrobenzo[b][1,4]dioxin-6-yl)methyl)-6-(1-methyl-1H-imidazol-4-yl)-3H-imidazo[4,5-b]pyridine | 0.008 | 0.004 |
| Ex. 1-137 | 6-bromo-3-((2-(4-(difluoromethoxy)phenyl)-8-methoxy-2,3-dihydrobenzo[b][1,4]dioxin-6-yl)methyl)-3H-imidazo[4,5-b]pyridine hydrochloride | 0.028 | 0.026 |
| Ex. 1-138 | 3-((2-(4-(difluoromethoxy)phenyl)-8-methoxy-2,3-dihydrobenzo[b][1,4]dioxin-6-yl)methyl)-3H-imidazo[4,5-b]pyridine hydrochloride | 0.017 | 0.021 |
| Ex. 1-139 | 4-(3-((2-(4-(difluoromethoxy)phenyl)-8-methoxy-2,3-dihydrobenzo[b][1,4]dioxin-6-yl)methyl)-3H-imidazo[4,5-b]pyridin-6-yl)-2-methylbut-3-yn-2-amine | 0.007 | 0.016 |
| Ex. 1-140 | 1-(3-((2-(4-(difluoromethoxy)phenyl)-8-methoxy-2,3-dihydrobenzo[b][1,4]dioxin-6-yl)methyl)-3H-imidazo[4,5-b]pyridin-6-yl)-N,N-dimethylazetidin-3-amine | 0.019 | 0.011 |
| Ex. 1-141 | 3-((2-(4-(difluoromethoxy)phenyl)-8-methoxy-2,3-dihydrobenzo[b][1,4]dioxin-6-yl)methyl)-N-methyl-3H-imidazo[4,5-b]pyridin-6-amine | 0.027 | 0.011 |
| Ex. 1-142 | 7-chloro-3-((2-(4-(difluoromethoxy)phenyl)-8-methoxy-2,3-dihydrobenzo[b][1,4]dioxin-6-yl)methyl)imidazo[1,2-b]pyridazine | 0.012 | 0.044 |
| Ex. 1-143 | 1-(3-((2-(4-(difluoromethoxy)phenyl)-8-methoxy-2,3-dihydrobenzo[b][1,4]dioxin-6-yl)methyl)imidazo[1,2-b]pyridazin-7-yl)-3-methylazetidin-3-ol | 0.02 | 0.017 |
| Ex. 1-144 | 3-((2-(4-(difluoromethoxy)phenyl)-8-methoxy-2,3-dihydrobenzo[b][1,4]dioxin-6-yl)methyl)imidazo[1,2-b]pyridazine | 0.01 | 0.03 |
| Ex. 1-145 | 7-chloro-3-((2-(4-(difluoromethoxy)phenyl)-8-methoxy-2,3-dihydrobenzo[b][1,4]dioxin-6-yl)(methoxy)methyl)imidazo[1,2-b]pyridazine | 0.82 | 1.44 |
| Ex. 1-146 | 4-(3-((2-(4-(difluoromethoxy)phenyl)-8-methoxy-2,3-dihydrobenzo[b][1,4]dioxin-6-yl)methyl)imidazo[1,2-b]pyridazin-7-yl)-2-methylbut-3-yn-2-amine | 0.002 | 0.007 |
| Ex. 1-147 | 4-(3-((8-methoxy-2-(pyridin-3-yl)-2,3-dihydrobenzo[b][1,4]dioxin-6-yl)methyl)-3H-imidazo[4,5-b]pyridin-6-yl)-2-methylbut-3-yn-2-amine | 0.28 | 0.32 |
| Ex. 1-148 | 6-(1H-imidazol-1-yl)-3-((8-methoxy-2-(pyridin-3-yl)-2,3-dihydrobenzo[b][1,4]dioxin-6-yl)methyl)-3H-imidazo[4,5-b]pyridine | 0.51 | 0.42 |
| Ex. 1-149 | 4-(3-((8-methoxy-2-(2-methylthiazol-4-yl)-2,3-dihydrobenzo[b][1,4]dioxin-6-yl)methyl)-3H-imidazo[4,5-b]pyridin-6-yl)-2-methylbut-3-yn-2-amine | 0.064 | 0.11 |
| Ex. 1-150 | 4-(6-((6-(3-(1H-imidazol-1-yl)prop-1-yn-1-yl)-3H-imidazo[4,5-b]pyridin-3-yl)methyl)-8-methoxy-2,3-dihydrobenzo[b][1,4]dioxin-2-yl)-2-methylthiazole | 0.029 | 0.042 |
| Ex. 1-151 | 4-(3-((8-methoxy-2-(2-methylthiazol-4-yl)-2,3-dihydrobenzo[b][1,4]dioxin-6-yl)methyl)-3H-imidazo[4,5-b]pyridin-6-yl)morpholine | 0.077 | 0.087 |
| Ex. 1-152 | 4-(6-((3H-imidazo[4,5-b]pyridin-3-yl)methyl)-8-methoxy-2,3-dihydrobenzo[b][1,4]dioxin-2-yl)-2-cyclopropylthiazole | 0.037 | 0.059 |
| Ex. 1-153 | 4-(3-((2-(2-cyclopropylthiazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine | 0.015 | 0.014 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
| --- | --- | --- | --- |
| Ex. 1-154 | 2-cyclopropyl-4-(8-methoxy-6-((6-methoxy-3H-imidazo[4,5-b]pyridin-3-yl)methyl)-2,3-dihydrobenzo[b][1,4]dioxin-2-yl)thiazole | 0.02 | 0.018 |
| Ex. 1-155 | 4-(3-((2-(2,5-dimethylthiazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine | 0.59 | 0.44 |
| Ex. 1-156 | 4-(3-((8-methoxy-2-(2-methyloxazol-4-yl)-2,3-dihydrobenzo[b][1,4]dioxin-6-yl)methyl)-3H-imidazo[4,5-b]pyridin-6-yl)-2-methylbut-3-yn-2-amine | 0.46 | 0.48 |
| Ex. 1-157 | 4-(3-((2-(2,5-dimethyloxazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine | 1.08 | 0.62 |
| Ex. 1-158 | 3-((8-methoxy-2-(6-(2-methoxyethoxy)pyridin-3-yl)-2,3-dihydrobenzo[b][1,4]dioxin-6-yl)methyl)-3H-imidazo[4,5-b]pyridine | 0.49 | 0.38 |
| Ex. 1-159 | 4-(3-((8-methoxy-2-(6-(2-methoxyethoxy)pyridin-3-yl)-2,3-dihydrobenzo[b][1,4]dioxin-6-yl)methyl)-3H-imidazo[4,5-b]pyridin-6-yl)-2-methylbut-3-yn-2-amine | 0.029 | 0.061 |
| Ex. 1-160 | 3-((8-methoxy-2-(6-(2-methoxyethoxy)pyridin-3-yl)-2,3-dihydrobenzo[b][1,4]dioxin-6-yl)methyl)-6-(1-methyl-1H-imidazol-4-yl)-3H-imidazo[4,5-b]pyridine | 0.014 | 0.026 |
| Ex. 1-161 | 6-methoxy-3-((8-methoxy-2-(6-(2-methoxy ethoxy)pyridin-3-yl)-2,3-dihydrobenzo[b][1,4]dioxin-6-yl)methyl)-3H-imidazo[4,5-b]pyridine | 0.084 | 0.14 |
| Ex. 1-162 | 3-((2-(6-ethoxypyridin-3-yl)-8-methoxy-2,3-dihydrobenzo[b][1,4]dioxin-6-yl)methyl)-3H-imidazo[4,5-b]pyridine | 0.02 | 0.037 |
| Ex. 1-163 | 3-((2-(6-ethoxypyridin-3-yl)-8-methoxy-2,3-dihydrobenzo[b][1,4]dioxin-6-yl)methyl)-6-methoxy-3H-imidazo[4,5-b]pyridine | 0.007 | 0.013 |
| Ex. 1-164 | (3-((2-(6-ethoxypyridin-3-yl)-8-methoxy-2,3-dihydrobenzo[b][1,4]dioxin-6-yl)methyl)-3H-imidazo[4,5-b]pyridin-6-yl)methanol | 0.023 | 0.03 |
| Ex. 1-165 | 3-((2-(6-ethoxypyridin-3-yl)-8-methoxy-2,3-dihydrobenzo[b][1,4]dioxin-6-yl)methyl)-1H-pyrrolo[2,3-b]pyridine | 0.002 | 0.011 |
| Ex. 1-166 | 3-((2-(6-(difluoromethoxy)pyridin-3-yl)-8-methoxy-2,3-dihydrobenzo[b][1,4]dioxin-6-yl)methyl)-6-methoxy-3H-imidazo[4,5-b]pyridine | 0.017 | 0.019 |
| Ex. 1-167 | 1-(3-((2-(6-(difluoromethoxy)pyridin-3-yl)-8-methoxy-2,3-dihydrobenzo[b][1,4]dioxin-6-yl)methyl)-3H-imidazo[4,5-b]pyridin-6-yl)-3-methylazetidin-3-ol | 0.026 | 0.013 |
| Ex. 1-168 | 3-((2-(6-(difluoromethoxy)pyridin-3-yl)-8-methoxy-2,3-dihydrobenzo[b][1,4]dioxin-6-yl)methyl)-3H-imidazo[4,5-b]pyridine | 0.032 | 0.054 |
| Ex. 1-169 | 3-((8-methoxy-2,3-dihydrobenzo[b][1,4]dioxin-6-yl)methyl)-6-(1-(piperidin-4-yl)-1H-pyrazol-4-yl)-3H-imidazo[4,5-b]pyridine | 0.092 | 1.39 |
| Ex. 1-170 | 3-((8-methoxy-2-methyl-2,3-dihydrobenzo[b][1,4]dioxin-6-yl)methyl)-6-(1-(piperidin-4-yl)-1H-pyrazol-4-yl)-3H-imidazo[4,5-b]pyridine | 0.03 | 0.33 |
| Ex. 1-171 | 3-((8-methoxy-2-methyl-2,3-dihydrobenzo[b][1,4]dioxin-6-yl)methyl)-6-(pyridin-3-yl)-3H-imidazo[4,5-b]pyridine formate | 0.34 | 1.9 |
| Ex. 1-172 | 3-((8-methoxy-2-methyl-2,3-dihydrobenzo[b][1,4]dioxin-6-yl)methyl)-6-(1-methyl-1H-pyrazol-4-yl)-3H-imidazo[4,5-b]pyridine formate | 0.083 | 0.31 |
| Ex. 1-173 | 3-((2-cyclopropyl-8-methoxy-2,3-dihydrobenzo[b][1,4]dioxin-6-yl)methyl)-6-(1-(piperidin-4-yl)-1H-pyrazol-4-yl)-3H-imidazo[4,5-b]pyridine | 0.019 | 0.057 |
| Ex. 1-174 | 3-((2-cyclopropyl-8-methoxy-2,3-dihydrobenzo[b][1,4]dioxin-6-yl)methyl)-6-(1-methyl-1H-imidazol-4-yl)-3H-imidazo[4,5-b]pyridine | 0.18 | 0.51 |
| Ex. 1-175 | 4-(3-((2-cyclopropyl-8-methoxy-2,3-dihydrobenzo[b][1,4]dioxin-6-yl)methyl)-3H-imidazo[4,5-b]pyridin-6-yl)-2-methylbut-3-yn-2-amine | 0.62 | 1.51 |
| Ex. 1-176 | 3-((2-isopropyl-8-methoxy-2,3-dihydrobenzo[b][1,4]dioxin-6-yl)methyl)-6-(1-methyl-1H-pyrazol-4-yl)-3H-imidazo[4,5-b]pyridine formate | 0.1 | 0.25 |
| Ex. 1-177 | 4-(3-((2-isopropyl-8-methoxy-2,3-dihydrobenzo[b][1,4]dioxin-6-yl)methyl)-3H-imidazo[4,5-b]pyridin-6-yl)-3,5-dimethylisoxazole | 0.32 | 1.88 |
| Ex. 1-178 | 3-((2-cyclopropyl-8-methoxy-3-methyl-2,3-dihydrobenzo[b][1,4]dioxin-6-yl)methyl)-6-(1-methyl-1H-pyrazol-4-yl)-3H-imidazo[4,5-b]pyridine | n/a | n/a |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-178-diasterA | | 0.032 | 0.075 |
| Ex. 1-178-diasterB | | 1.09 | 0.85 |
| Ex. 1-178-diasterC | | 0.48 | 0.54 |
| Ex. 1-178-diasterD | | 0.36 | 0.93 |
| Ex. 1-179 | 3-((2-(6-(difluoromethyl)pyridin-3-yl)-8-methoxy-2,3-dihydrobenzo[b][1,4]dioxin-6-yl)methyl)-3H-imidazo[4,5-b]pyridine | 0.19 | 0.2 |
| Ex. 1-180 | 3-((2-(2-cyclopropylpyrimidin-5-yl)-8-methoxy-2,3-dihydrobenzo[b][1,4]dioxin-6-yl)methyl)-3H-imidazo[4,5-b]pyridine | 0.098 | 0.18 |
| Ex. 1-181 | 3-((8-methoxy-2-(6-methoxy-2-methylpyridin-3-yl)-2,3-dihydrobenzo[b][1,4]dioxin-6-yl)methyl)-3H-imidazo[4,5-b]pyridine | 0.12 | 0.17 |
| Ex. 1-182 | 3-((8-methoxy-2-(6-methoxy-2-methylpyridin-3-yl)-2,3-dihydrobenzo[b][1,4]dioxin-6-yl)methyl)-6-(3-methoxyazetidin-1-yl)-3H-imidazo[4,5-b]pyridine | 0.067 | 0.028 |
| Ex. 1-183 | 6-methoxy-3-((8-methoxy-2-(6-methoxy-2-methylpyridin-3-yl)-2,3-dihydrobenzo[b][1,4]dioxin-6-yl)methyl)-3H-imidazo[4,5-b]pyridine | 0.07 | 0.072 |
| Ex. 1-184 | 3-((8-methoxy-2-(6-methoxy-2-methylpyridin-3-yl)-2,3-dihydrobenzo[b][1,4]dioxin-6-yl)methyl)-7-(3-methoxyazetidin-1-yl)imidazo[1,2-b]pyridazine | 0.019 | 0.034 |
| Ex. 1-185 | 3-((2-(2,6-dimethoxypyridin-3-yl)-8-methoxy-2,3-dihydrobenzo[b][1,4]dioxin-6-yl)methyl)-3H-imidazo[4,5-b]pyridine | 0.04 | 0.077 |
| Ex. 1-186 | 3-((2-(2,6-dimethoxypyridin-3-yl)-8-methoxy-2,3-dihydrobenzo[b][1,4]dioxin-6-yl)methyl)-6-methoxy-3H-imidazo[4,5-b]pyridine | 0.028 | 0.046 |
| Ex. 1-187 | 3-((2-(2,6-dimethoxypyridin-3-yl)-8-methoxy-2,3-dihydrobenzo[b][1,4]dioxin-6-yl)methyl)-6-(3-methoxyazetidin-1-yl)-3H-imidazo[4,5-b]pyridine | 0.043 | 0.018 |
| Ex. 1-188 | 3-((8-methoxy-2-(6-(trifluoromethyl)pyridin-3-yl)-2,3-dihydrobenzo[b][1,4]dioxin-6-yl)methyl)-3H-imidazo[4,5-b]pyridine | 0.083 | 0.087 |
| Ex. 1-188-enant A | (S)-3-((8-methoxy-2-(6-(trifluoromethyl)pyridin-3-yl)-2,3-dihydrobenzo[b][1,4]dioxin-6-yl)methyl)-3H-imidazo[4,5-b]pyridine | 0.19 | 0.29 |
| Ex. 1-188-enant B | (R)-3-((8-methoxy-2-(6-(trifluoromethyl)pyridin-3-yl)-2,3-dihydrobenzo[b][1,4]dioxin-6-yl)methyl)-3H-imidazo[4,5-b]pyridine | 0.033 | 0.063 |
| Ex. 1-189 | 6-methoxy-3-((8-methoxy-2-(6-methoxy-4-methylpyridin-3-yl)-2,3-dihydrobenzo[b][1,4]dioxin-6-yl)methyl)-3H-imidazo[4,5-b]pyridine | 0.26 | 0.29 |
| Ex. 1-190 | 3-((8-methoxy-2-(6-methoxy-4-methylpyridin-3-yl)-2,3-dihydrobenzo[b][1,4]dioxin-6-yl)methyl)-3H-imidazo[4,5-b]pyridine | 0.91 | 1.24 |
| Ex. 1-191 | 5-(6-((3H-imidazo[4,5-b]pyridin-3-yl)methyl)-8-methoxy-2,3-dihydrobenzo[b][1,4]dioxin-2-yl)-N,N-diethylpyridin-2-amine | 0.019 | 0.023 |
| Ex. 1-192 | 4-(5-(6-((3H-imidazo[4,5-b]pyridin-3-yl)methyl)-8-methoxy-2,3-dihydrobenzo[b][1,4]dioxin-2-yl)pyridin-2-yl)morpholine | 0.16 | 0.47 |
| Ex. 1-193 | 3-((8-methoxy-2-(1-methyl-1H-pyrazol-4-yl)-2,3-dihydrobenzo[b][1,4]dioxin-6-yl)methyl)-3H-imidazo[4,5-b]pyridine | 3.26 | 1.77 |
| Ex. 1-194 | 3-((2-(1-cyclobutyl-1H-pyrazol-4-yl)-8-methoxy-2,3-dihydrobenzo[b][1,4]dioxin-6-yl)methyl)-3H-imidazo[4,5-b]pyridine | 0.024 | 0.04 |
| Ex. 1-195 | 3-((2-(1-isopropyl-1H-pyrazol-4-yl)-8-methoxy-2,3-dihydrobenzo[b][1,4]dioxin-6-yl)methyl)-3H-imidazo[4,5-b]pyridine | 0.032 | 0.067 |
| Ex. 1-196 | 3-((8-methoxy-2-(6-(methoxymethyl)pyridin-3-yl)-2,3-dihydrobenzo[b][1,4]dioxin-6-yl)methyl)-3H-imidazo[4,5-b]pyridine | 0.32 | 0.58 |
| Ex. 1-197 | 3-((8-methoxy-2-(5-methoxypyrazin-2-yl)-2,3-dihydrobenzo[b][1,4]dioxin-6-yl)methyl)-3H-imidazo[4,5-b]pyridine | 0.71 | 0.63 |
| Ex. 1-198 | 3-((8-methoxy-2-(2-methoxypyrimidin-5-yl)-2,3-dihydrobenzo[b][1,4]dioxin-6-yl)methyl)-3H-imidazo[4,5-b]pyridine | 1.69 | 1.3 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-199 | 3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine | 0.034 | 0.042 |
| Ex. 1-199-enant A | (R)-3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine | 0.013 | 0.02 |
| Ex. 1-199-enant B | (S)-3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine | 0.053 | 0.11 |
| Ex. 1-200 | 5-(6-((3H-imidazo[4,5-b]pyridin-3-yl)methyl)-8-methoxy-2,3-dihydrobenzo[b][1,4]dioxin-2-yl)furo[2,3-b]pyridine | 0.17 | 0.12 |
| Ex. 1-201 | 5-(6-((3H-imidazo[4,5-b]pyridin-3-yl)methyl)-8-methoxy-2,3-dihydrobenzo[b][1,4]dioxin-2-yl)-2,3-dihydrofuro[2,3-b]pyridine | 0.33 | 0.27 |
| Ex. 1-202 | 3-((2-(1-(cyclopropylmethyl)-1H-pyrazol-4-yl)-8-methoxy-2,3-dihydrobenzo[b][1,4]dioxin-6-yl)methyl)-3H-imidazo[4,5-b]pyridine | 0.097 | 0.15 |
| Ex. 1-203 | 3-((2-(4,4-difluorocyclohexyl)-8-methoxy-2,3-dihydrobenzo[b][1,4]dioxin-6-yl)methyl)-3H-imidazo[4,5-b]pyridine | 1.08 | 0.74 |
| Ex. 1-204 | 3-((8-methoxy-2-(1-(2-methoxyethyl)-1H-pyrazol-4-yl)-2,3-dihydrobenzo[b][1,4]dioxin-6-yl)methyl)-3H-imidazo[4,5-b]pyridine | 0.82 | 0.95 |
| Ex. 1-205 | 3-((2-butyl-8-methoxy-2,3-dihydrobenzo[b][1,4]dioxin-6-yl)methyl)-3H-imidazo[4,5-b]pyridine | 0.29 | 0.059 |
| Ex. 1-206 | 6-methoxy-3-((8-methoxy-2-(1-methyl-1H-pyrazol-4-yl)-2,3-dihydrobenzo[b][1,4]dioxin-6-yl)methyl)-3H-imidazo[4,5-b]pyridine | 0.36 | 0.41 |
| Ex. 1-207 | 3-((2-(1,5-dimethyl-1H-pyrazol-4-yl)-8-methoxy-2,3-dihydrobenzo[b][1,4]dioxin-6-yl)methyl)-6-methoxy-3H-imidazo[4,5-b]pyridine | 0.31 | 0.3 |
| Ex. 1-208 | 3-((2-(1,3-dimethyl-1H-pyrazol-4-yl)-8-methoxy-2,3-dihydrobenzo[b][1,4]dioxin-6-yl)methyl)-6-methoxy-3H-imidazo[4,5-b]pyridine | 0.46 | 0.51 |
| Ex. 1-209 | 3-((2-(1-(cyclopropylmethyl)-1H-pyrazol-4-yl)-8-methoxy-2,3-dihydrobenzo[b][1,4]dioxin-6-yl)methyl)-6-methoxy-3H-imidazo[4,5-b]pyridine | 0.025 | 0.033 |
| Ex. 1-210 | 3-((2-(1-cyclobutyl-1H-pyrazol-4-yl)-8-methoxy-2,3-dihydrobenzo[b][1,4]dioxin-6-yl)methyl)-6-methoxy-3H-imidazo[4,5-b]pyridine | 0.02 | 0.012 |
| Ex. 1-211 | 6-methoxy-3-((8-methoxy-2-(6-(methoxymethyl)pyridin-3-yl)-2,3-dihydrobenzo[b][1,4]dioxin-6-yl)methyl)-3H-imidazo[4,5-b]pyridine | 0.063 | 0.13 |
| Ex. 1-212 | 3-((2-butyl-8-methoxy-2,3-dihydrobenzo[b][1,4]dioxin-6-yl)methyl)-6-methoxy-3H-imidazo[4,5-b]pyridine | 0.12 | 0.27 |
| Ex. 1-213 | 6-(azetidin-1-yl)-3-((8-methoxy-2-(1-methyl-1H-pyrazol-4-yl)-2,3-dihydrobenzo[b][1,4]dioxin-6-yl)methyl)-3H-imidazo[4,5-b]pyridine | 0.36 | 0.39 |
| Ex. 1-214 | 3-((8-methoxy-2-(1-methyl-1H-pyrazol-4-yl)-2,3-dihydrobenzo[b][1,4]dioxin-6-yl)methyl)-6-(3-methoxyazetidin-1-yl)-3H-imidazo[4,5-b]pyridine | 0.13 | 0.2 |
| Ex. 1-215 | 6-cyclopropyl-3-((8-methoxy-2-(1-methyl-1H-pyrazol-4-yl)-2,3-dihydrobenzo[b][1,4]dioxin-6-yl)methyl)-3H-imidazo[4,5-b]pyridine | 0.27 | 0.26 |
| Ex. 1-216 | 6-cyclopropyl-3-((8-methoxy-2-(6-(methoxymethyl)pyridin-3-yl)-2,3-dihydrobenzo[b][1,4]dioxin-6-yl)methyl)-3H-imidazo[4,5-b]pyridine | 0.046 | 0.091 |
| Ex. 1-217 | 6-(difluoromethyl)-3-((8-methoxy-2-(6-(methoxymethyl)pyridin-3-yl)-2,3-dihydrobenzo[b][1,4]dioxin-6-yl)methyl)-3H-imidazo[4,5-b]pyridine | 0.23 | 0.28 |
| Ex. 1-218 | (3-((2-(1-cyclobutyl-1H-pyrazol-4-yl)-8-methoxy-2,3-dihydrobenzo[b][1,4]dioxin-6-yl)methyl)-3H-imidazo[4,5-b]pyridin-6-yl)methanol | 0.035 | 0.072 |
| Ex. 1-219 | 3-((8-methoxy-2-(6-methylpyridin-3-yl)-2,3-dihydrobenzo[b][1,4]dioxin-6-yl)methyl)-6-(trifluoromethyl)-3H-imidazo[4,5-b]pyridine | 0.096 | 0.15 |
| Ex. 1-220 | 1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)azetidin-2-one | 0.014 | 0.17 |
| Ex. 1-221 | 7-((8-methoxy-2-(6-methoxypyridin-3-yl)-2,3-dihydrobenzo[b][1,4]dioxin-6-yl)methyl)-5H-pyrrolo[2,3-b]pyrazine | 0.007 | 0.011 |
| Ex. 1-222 | 4-((8-methoxy-2-(6-methoxypyridin-3-yl)-2,3-dihydrobenzo[b][1,4]dioxin-6-yl)methyl)-1H-pyrrolo[2,3-b]pyridine | 0.031 | 0.036 |

TABLE 1-continued

In vitro Results of Representative CSF-1R Inhibitors [c-FMS and Phospho c-FMS IC$_{50}$]

| Example No. | Compound Name | c-FMS IC$_{50}$ (μM) | Phospho c-FMS IC$_{50}$ (μM) |
|---|---|---|---|
| Ex. 1-223 | 4-(3-((2-(6-methoxypyridin-3-yl)chroman-6-yl)methyl)-3H-imidazo[4,5-b]pyridin-6-yl)-2-methylbut-3-yn-2-amine | 0.21 | 0.5 |
| Ex. 1-224 | 4-(3-((8-methoxy-2-(4-methoxyphenyl)chroman-6-yl)methyl)-3H-imidazo[4,5-b]pyridin-6-yl)-2-methylbut-3-yn-2-amine | 0.029 | 0.066 |
| Ex. 1-225 | 6-fluoro-3-((8-methoxy-2-(6-methoxypyridin-3-yl)chroman-6-yl)methyl)-3H-imidazo[4,5-b]pyridine | 0.9 | 0.67 |
| Ex. 1-226 | 4-(3-((8-methoxy-2-(6-methoxypyridin-3-yl)chroman-6-yl)methyl)-3H-imidazo[4,5-b]pyridin-6-yl)-2-methylbut-3-yn-2-amine | 0.062 | 0.11 |
| Ex. 1-227 | 4-(3-((8-methoxy-2-(6-methoxypyridin-3-yl)chroman-6-yl)methyl)-3H-imidazo[4,5-b]pyridin-6-yl)morpholine | 0.081 | 0.16 |
| Ex. 1-228 | 3-((8-methoxy-2-(6-methoxypyridin-3-yl)chroman-6-yl)methyl)-6-(2-methyl-1H-imidazol-1-yl)-3H-imidazo[4,5-b]pyridine | 0.19 | 0.19 |
| Ex. 1-229 | 3-((8-methoxy-2-(6-methoxypyridin-3-yl)chroman-6-yl)methyl)-3H-imidazo[4,5-b]pyridine | 0.79 | 0.66 |
| Ex. 1-230 | 4-(3-((8-methoxy-2-(6-methoxypyridin-3-yl)chroman-6-yl)methyl)pyrazolo[1,5-a]pyrimidin-6-yl)-2-methylbut-3-yn-2-amine | 0.016 | 0.052 |
| Ex. 1-231 | 4-(3-((8-methoxy-2-(6-methoxypyridin-3-yl)chroman-6-yl)methyl)pyrazolo[1,5-a]pyrimidin-6-yl)morpholine | 0.017 | 0.023 |
| Ex. 1-232 | 3-((8-methoxy-2-(6-methoxypyridin-3-yl)chroman-6-yl)methyl)-6-(2-methyl-1H-imidazol-1-yl)pyrazolo[1,5-a]pyrimidine | 0.089 | 0.16 |
| Ex. 1-233 | 4-(3-((8-methoxy-2-(6-methoxypyridin-3-yl)chroman-6-yl)methyl)pyrazolo[1,5-a]pyridin-6-yl)-2-methylbut-3-yn-2-amine | 0.017 | 0.135 |
| Ex. 1-234 | 4-(3-((8-methoxy-2-(6-methoxypyridin-3-yl)chroman-6-yl)methyl)pyrazolo[1,5-a]pyridin-6-yl)morpholine | 0.05 | 0.076 |
| Ex. 1-235 | 3-((8-methoxy-2-(6-methoxypyridin-3-yl)chroman-6-yl)methyl)-6-(2-methyl-1H-imidazol-1-yl)pyrazolo[1,5-a]pyridine | 0.19 | 0.2 |
| Ex. 1-236 | 4-(3-((8-methoxy-2-(6-methoxypyridin-3-yl)chroman-6-yl)methyl)imidazo[1,2-b]pyridazin-7-yl)-2-methylbut-3-yn-2-amine | 0.024 | 0.13 |
| Ex. 1-237 | 4-(3-((8-methoxy-2-(6-methoxypyridin-3-yl)chroman-6-yl)methyl)imidazo[1,2-b]pyridazin-7-yl)morpholine | 0.035 | 0.11 |
| Ex. 1-238 | 4-(3-((8-fluoro-2-(6-methoxypyridin-3-yl)chroman-6-yl)methyl)-3H-imidazo[4,5-b]pyridin-6-yl)-2-methylbut-3-yn-2-amine | 0.27 | 0.57 |
| Ex. 1-239 | 4-(3-((8-methoxy-2-(6-methylpyridin-3-yl)chroman-6-yl)methyl)-3H-imidazo[4,5-b]pyridin-6-yl)-2-methylbut-3-yn-2-amine | 0.61 | 0.44 |
| Ex. 1-240 | 4-(3-((8-methoxy-2-(6-methylpyridin-3-yl)chroman-6-yl)methyl)-3H-imidazo[4,5-b]pyridin-6-yl)morpholine | 0.53 | 0.49 |
| Ex. 1-241 | 3-((8-methoxy-2-(6-methylpyridin-3-yl)chroman-6-yl)methyl)-6-(2-methyl-1H-imidazol-1-yl)-3H-imidazo[4,5-b]pyridine | 0.99 | 0.64 |
| Ex. 1-242 | 6-cyclopropyl-3-((8-methoxy-2-(6-methylpyridin-3-yl)chroman-6-yl)methyl)-3H-imidazo[4,5-b]pyridine | 0.8 | 0.48 |
| Ex. 1-243 | 4-(3-((2-(6-ethylpyridin-3-yl)-8-methoxychroman-6-yl)methyl)-3H-imidazo[4,5-b]pyridin-6-yl)-2-methylbut-3-yn-2-amine | 0.49 | 0.14 |
| Ex. 1-244 | 4-(3-((2-(6-ethylpyridin-3-yl)-8-methoxychroman-6-yl)methyl)-3H-imidazo[4,5-b]pyridin-6-yl)morpholine | 0.058 | 0.13 |
| Ex. 1-245 | 3-((2-(6-ethylpyridin-3-yl)-8-methoxychroman-6-yl)methyl)-6-(2-methyl-1H-imidazol-1-yl)-3H-imidazo[4,5-b]pyridine | 0.13 | 0.18 |
| Ex. 1-246 | 4-(3-((8-methoxy-2-(2-methylthiazol-4-yl)chroman-6-yl)methyl)-3H-imidazo[4,5-b]pyridin-6-yl)-2-methylbut-3-yn-2-amine | 0.72 | 0.59 |
| Ex. 1-247 | 4-(3-((8-methoxy-2-(2-methylthiazol-4-yl)chroman-6-yl)methyl)-3H-imidazo[4,5-b]pyridin-6-yl)morpholine | 0.83 | 0.52 |
| Ex. 1-248 | 2-methyl-4-(3-((4-methyl-2-(4-(trifluoromethyl)phenyl)-3,4-dihydro-2H-benzo[b][1,4]oxazin-6-yl)methyl)-3H-imidazo[4,5-b]pyridin-6-yl)but-3-yn-2-amine | 0.23 | 0.94 |
| Ex. 1-249 | 4-methyl-6-((6-(1-methyl-1H-pyrazol-4-yl)-3H-imidazo[4,5-b]pyridin-3-yl)methyl)-2-(4-(trifluoromethyl)phenyl)-3,4-dihydro-2H-benzo[b][1,4]oxazine | 0.12 | 0.054 |
| Ex. 1-250 | 6-bromo-3-((2-(6-methoxypyridin-3-yl)-2,3-dihydrobenzo[b][1,4]oxathiin-6-yl)methyl)-3H-imidazo[4,5-b]pyridine | 0.97 | 0.59 |
| Ex. 1-251 | 4-(3-((2-(6-methoxypyridin-3-yl)-2,3-dihydrobenzo[b][1,4]oxathiin-6-yl)methyl)-3H-imidazo[4,5-b]pyridin-6-yl)-2-methylbut-3-yn-2-amine | n/a | 0.3 |

TABLE 1-continued

In vitro Results of Representative CSF-1R Inhibitors [c-FMS and Phospho c-FMS IC$_{50}$]

| Example No. | Compound Name | c-FMS IC$_{50}$ (µM) | Phospho c-FMS IC$_{50}$ (µM) |
|---|---|---|---|
| Ex. 1-252 | 3-(3-methoxy-4-((6-methoxypyridin-3-yl)methoxy)benzyl)-6-(piperidin-3-ylethynyl)-3H-imidazo[4,5-b]pyridine | 0.005 | 0.008 |
| Ex. 1-253 | 3-(3-methoxy-4-((6-methoxypyridin-3-yl)methoxy)benzyl)-6-(pyrrolidin-3-ylethynyl)-3H-imidazo[4,5-b]pyridine | 0.003 | 0.014 |
| Ex. 1-254 | 3-(3-methoxy-4-((6-methoxypyridin-3-yl)methoxy)benzyl)-6-(4-methylpiperazin-1-yl)-3H-imidazo[4,5-b]pyridine | 0.016 | 0.021 |
| Ex. 1-255 | 4-(3-(3-methoxy-4-((6-methylpyridin-3-yl)methoxy)benzyl)-3H-imidazo[4,5-b]pyridin-6-yl)-2-methylbut-3-yn-2-amine | 0.015 | 0.036 |
| Ex. 1-256 | 4-(3-((5-ethoxy-6-((6-methylpyridin-3-yl)methoxy)pyridin-3-yl)methyl)-3H-imidazo[4,5-b]pyridin-6-yl)-2-methylbut-3-yn-2-amine | 0.025 | 0.026 |
| Ex. 1-257 | 3-((5-ethoxy-6-((6-methylpyridin-3-yl)methoxy)pyridin-3-yl)methyl)pyrazolo[1,5-a]pyrimidine | 0.029 | 0.046 |
| Ex. 1-258 | 3-((5-ethoxy-6-((6-(trifluoromethyl)pyridin-3-yl)methoxy)pyridin-3-yl)methyl)-N,N-dimethylimidazo[1,2-b]pyridazine-7-carboxamide | 0.02 | 0.019 |
| Ex. 1-259 | 4-((6-((6-cyclopropylpyridin-3-yl)methoxy)-5-ethoxypyridin-3-yl)methyl)-N-methylpicolinamide | 0.013 | 0.031 |
| Ex. 1-260 | 6-((3H-imidazo[4,5-b]pyridin-3-yl)methyl)-4-methoxy-2-((6-methoxypyridin-3-yl)methyl)benzo[d]oxazole | 0.086 | 0.151 |
| Ex. 1-261 | 3-((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine | 0.019 | 0.013 |
| Ex. 1-262 | 4-((6-((6-cyclopropylpyridin-3-yl)methoxy)-5-ethoxypyridin-3-yl)oxy)-N-methylpicolinamide | 0.014 | 0.031 |
| Ex. 1-263 | 4-((6-((6-cyclopropylpyridin-3-yl)methoxy)-5-fluoropyridin-3-yl)oxy)-N-methylpicolinamide | 0.11 | 0.22 |

Example 2-3: Activity of CSF-1R Inhibitors in Murine Bone Marrow-Derived Macrophage Proliferation Assay The objective of the murine bone marrow macrophage proliferation assay was to assess the inhibitory activity of select CSF-1R inhibitors.

On day 0, bone marrow cells are collected under sterile conditions and cultured overnight in tissue culture flasks at $1 \times 10^6$ cells/mL in Dulbecco's modified Eagle's medium (DMEM)/15% fetal bovine serum (FBS)/1%penicillin-streptomycin/1%l-glutamine/50 ng/mL recombinant mouse colony stimulating factor (rmM-CSF). On day 1, the flasks are tapped, and all floating and loosely adherent cells are collected. The cells are counted and resuspended in fresh medium +50 ng/mL rmM-CSF at $1 \times 10^6$ cell/mL and transferred to 10 cm or 15 cm tissue culture dishes. On days 4 and 7, the medium is removed and replaced with fresh medium +50 ng/mL rmM-CSF. On day 8, adherent cells are washed with phosphate buffered saline (PBS), collected, counted and resuspended in fresh medium without rmM-CSF at $2 \times 10^5$ cells/mL. One hundred microliters of cells ($2 \times 10^4$ cells) are then added to the assay wells. After overnight starvation of rmM-CSF, serial dilutions of the CSF-1R inhibitors are prepared and added to the appropriate assay wells. The compounds are initially diluted in dimethyl sulfoxide (DMSO) to yield serial 4-fold dilutions ranging from 1 mM to 0.46 uM. Each concentration of each compound is then diluted 1:167 in medium to yield concentrations from 6 uM to 0.003 uM. Twenty-five microliters of each concentration of each compound is then added in triplicate to the assay wells yielding final concentrations of 1 uM to 0.06 nM and 0.1% DMSO. Twenty-five microliters of rmM-CSF are also added to each assay well, except the background wells, at a final concentration of 5 ng/mL. At the end of day 9, 1 uCi of $^3$H-thymidine is added to each assay well, and the plates are allowed to incubate at 5% $CO_2$ and 37C for an additional 16 hours. On day 10, cells are harvested onto a filter plate using a 96-well plate harvester then allowed to dry overnight. Once dry, 25 µL of Beta-Count scintillation fluid is added to each well, and the plate is counted on the Trilux counter. Results were analyzed in GraphPad Prism.

Murine bone marrow-derived macrophages (BMDMs) were treated with CSF-1R inhibitors and CSF-1 for 22 hours prior to harvesting. CSF-1R inhibitors were tested for inhibitory activity of CSF-1-induced proliferation of BMDMs in multiple groups:

BMDM Group 1: Genz-882706, RA10600053, RA10607080, RA10651967, and RA10813949 (FIG. 1);

BMDM Group 2: Genz-882706, RA10680889, RA10813661, RA10846843, and RA10848270 (FIG. 2); and BMDM Group 3: RA03546849 (Genz-882706), RA10651967, RA10940752, RA10947016, RA10963700, and RA10982908 (FIG. 3).

The CSF-1R inhibitors tested in this assay were potent inhibitors of CSF-1-induced proliferation of murine bone marrow-derived macrophages with IC$_{50}$s in the nM range.

Example 2-4: Effect CSF-1R Inhibitors on Phagocytic Activity of Murine Bone Marrow-Derived Macrophages The objective of this assay was to determine the effect of CSF-1R inhibitors on phagocytic activity of murine bone marrow derived macrophages in vitro. Phagocytosis is a beneficial activity of macrophages that should be preserved in the presence of CSF-1R inhibitors.

On day 0, bone marrow cells are collected under sterile conditions and cultured overnight in tissue culture flasks at $1 \times 10^6$ cells/mL in DMEM/15%FBS/1%penicillin-streptomycin/1%l-glutamine/50 ng/mL rmM-CSF. On day 1, the flasks are tapped, and all floating and loosely adherent cells are collected. The cells are counted and resuspended in fresh medium +50ng/mL rmM-CSF at $1\times10^6$cell/mL and transferred to 15 cm tissue culture dishes. On days 3 and 6, the medium is removed and replaced with fresh medium +50 ng/mL rmM-CSF. On day 8, adherent cells are washed with PBS, collected, counted and resuspended in fresh medium at $1\times10^6$cells/mL without rmM-CSF. One hundred microliters of cells are then added in triplicate to a 96-well flat bottom tissue culture plate. After overnight incubation, DMSO at 0.1% or CSF-1R inhibitors at 100 nM are added to the appropriate wells 60 minutes prior to the addition of lipopolysaccharide (LPS) at 10 ng/mL as an activation stimulus. The cells are incubated overnight and the phagocytosis assay is run the following day.

Following a 24 hour incubation with LPS and DMSO or CSF-1R inhibitors, the phagocytic activity of murine bone marrow derived macrophages was measured using the CytoSelect 96-well Phagocytosis Assay (Cell Biolabs, Inc.). In this colorimetric assay, labeled Zymosan particles act as the target for phagocytosis. The plated cells are incubated with Zymosan particles for 1 hour at 37° C., 5% $CO_2$ and then washed. The cells are fixed for 5 minutes and then washed again. Blocking reagent is added to all wells in order to block any labeled Zymosan particles bound to the outside of the cells from reacting with the substrate. After a 1 hour incubation, the cells are again washed. The cells are permeabilized then incubated with a detection reagent for 1 hour. Permeabilization of the cells allows the colorimetric substrate to reach the engulfed labeled Zymosan particles inside the cells. After washing, detection buffer and a colorimetric substrate are added to each assay well. The reaction is stopped by adding acid to each well. Assay plates are then read on a Vmax ELISA Plate Reader (Molecular Devices) at 405 nm. The optical density (O.D.) is directly proportional to the number of cells that have engulfed the labeled Zymosan particles.

The addition of CSF-1R inhibitors had no effect on unstimulated cells when compared to cells alone (FIG. 4). Stimulation of the murine bone marrow derived macrophages with lipopolysaccharide (LPS) for 24 hours resulted in a significant increase in phagocytic activity when compared to unstimulated cells alone in this experiment. Treatment with the CSF-1R inhibitors tested in this experiment had no significant impact on phagocytic activity of murine bone marrow derived macrophages after stimulation with LPS.

Each bar in FIG. 4 represents the mean and standard deviation of 3 wells. A one-way ANOVA followed by a Dunnett's multiple comparison was done to determine significance compared to DMSO control. An unpaired t-test was done to determine any significance between cells alone and DMSO control and unstimulated cells and LPS stimulated cells.

Treatment with the CSF-1R inhibitors tested in this experiment had no significant impact on the phagocytic activity of resting or stimulated murine bone marrow derived macrophages.

Example 2-5: Effect CSF-1R Inhibitors on Phagocytic Activity of Primary Murine Microglial Cells The objective of this assay was to determine the effect of CSF-1R inhibitors on phagocytic activity of primary murine microglial cells in vitro. Phagocytosis is a beneficial activity of microglial cells that should be preserved in the presence of CSF-1R inhibitors.

Brains from seventeen 3-4 day old C57Bl/6 mice were harvested and pooled in DMEM/F12-Glutamax/10%FBS/1%Pen/Strep/100 uM non-essential amino acids/2 mM sodium pyruvate ("complete DMEM/F12") and kept on ice until processing. Upon arrival in the lab, the brains were transferred into warm 0.25% trypsin (2 mL/brain) and incubated at 37C while rotating for 30 minutes. The dissociation reaction was quenched with an equal volume of complete DMEM/F12. The tissue was centrifuged at 300× g for 7 minutes, and the supernatant was then carefully removed. The tissue pellet was washed 3 times with complete DMEM/F12 and centrifuged at 300× g for 7 minutes. Supernatant was carefully removed after each wash step with a pipet rather than by vacuum aspiration. After the final wash, the tissue was brought up in complete DMEM/F12, slowly triturated until no chunks were visible, and filtered through a 70 uM cell strainer. The resultant single-cell suspension was washed with complete DMEM/F12, centrifuged at 200× g for 7 minutes and resuspended with complete DMEM/F12. The cells were distributed evenly amongst T150 tissue culture flasks (1 flask/mouse), and the final volume was brought up to 35 mL with complete DMEM/F12. The cells were fed with a complete medium change 5, 8 and 11 days later.

On day 12, each flask was washed with 10 mL PBS. Five milliliters 0.25% trypsin were added to each flask, and the flasks were placed on a rocking platform at room temperature for 15 minutes. Ten milliliters complete DMEM/F12 were added to each flask, and the cells were gently triturated to break up cell aggregates. The single cell suspensions were then filtered through 70 μM cell strainers and centrifuged at 200× g for 6 minutes. The cells were then pooled, counted and resuspended at $1\times10^8$ cells/mL in PBS/2%FBS/1 mM EDTA ("separation media"). The cells were transferred to 5 mL polystyrene FACS tubes, and the CD11b-PE+FcR block reagent provided in the Mouse CD11b Positive Selection Kit (StemCell catalog #18770) was added to the tubes and incubated at room temperature for 15 minutes. The PE selection cocktail was then added to the FACS tubes and mixed well with a pipet tip. The sample again incubated for 15 minutes at room temperature. The EasySep Magnetic Nanoparticles provided in the kit were gently mixed and added to the tubes and incubated at room temperature for 10 minutes. The tubes were placed in the EasySep Magnets (StemCell catalog #18000) and allowed to sit for 7 minutes. In one fluid motion, the unlabeled cells in the buffer were poured off while the tube was still in the magnet. The tube was then removed from the magnet, separation medium was added to the tube, and the tube was placed back in the magnet for another 7 minutes. This washing process was done for a total of 4 times to remove all unlabeled cells. After the last wash, the labeled CD11b+ cells were resuspended in complete DMEM/F12, counted and resuspended at $1\times10^6$ cells/mL. One hundred microliters of cells were plated in 96-well flat-bottom tissue culture plates and allowed to rest overnight.

Following a 24 hour incubation with LPS and DMSO or CSF-1R inhibitors, the phagocytic activity of primary murine microglial cells was measured using the CytoSelect 96-well Phagocytosis Assay (Cell Biolabs, Inc.), as described above.

Stimulation of the primary murine microglial cells with LPS for 24 hours resulted in a significant increase in phagocytic activity when compared to unstimulated microglial cells alone in this experiment. FIG. 5 provides a graphical representation of the phagocytic activity of primary murine microglial following a 24 hr incubation with DMSO or CSF-1R inhibitors with LPS. Each graphical bar represents the mean and standard deviation of 3 wells. A one-way ANOVA followed by a Dunnett's multiple comparison was done to determine significance compared to DMSO control. An unpaired t-test was done to determine any significance between cells alone and DMSO control and unstimulated cells and LPS stimulated cells.

Treatment with the CSF-1R inhibitors tested in this experiment had no significant impact on phagocytic activity of stimulated primary murine microglial cells.

Example 2-6: Evaluation of the CSF-1R Inhibitors on Phagocytic Activity of Primary Murine Microglial Cells The objective of this study was to determine the effect of additional CSF-1R inhibitors on phagocytic activity of primary murine microglia cells in vitro.

Brains from twenty-five 3-4 day old C57Bl/6 mice were harvested and pooled in DMEM/F12-Glutamax/10%FBS/1%Pen/Strep/100 uM non-essential amino acids/2 mM sodium pyruvate ("complete DMEM/F12") and kept on ice until processing. Upon arrival in the lab, the brains were transferred into warm 0.25% trypsin (2 mL/brain) and incubated at 37C while rotating for 30 minutes. The dissociation reaction was quenched with an equal volume of complete DMEM/F12. The tissue was centrifuged at 300× g for 7 minutes, and the supernatant was then carefully removed. The tissue pellet was washed 3 times with complete DMEM/F12 and centrifuged at 300× g for 7 minutes. Supernatant was carefully removed after each wash step with a pipet rather than by vacuum aspiration. After the final wash, the tissue was brought up in complete DMEM/F12, slowly triturated until no chunks were visible, and filtered through a 70 uM cell strainer. The resultant single-cell suspension was washed with complete DMEM/F12, centrifuged at 200× g for 7 minutes and resuspended with complete DMEM/F12. The cells were distributed evenly amongst T150 tissue culture flasks (1 flask/mouse), and the final volume was brought up to 35 mL with complete DMEM/F12. The cells were fed with a complete medium change 5, 8 and 11 days later.

On day 12, each flask was washed with 10 mL PBS. Five milliliters 0.25% trypsin were added to each flask, and the flasks were placed on a rocker at room temperature for 15 minutes. Ten milliliters complete DMEM/F12 were added to each flask, and the cells were gently triturated to break up cell aggregates. The single cell suspensions were then filtered through 70 µM cell strainers and centrifuged at 200× g for 6 minutes. The cells were then pooled, counted and resuspended at $1 \times 10^8$ cells/mL in PBS/2%FBS/1 mM EDTA ("separation media"). The cells were transferred to 5 mL polystyrene FACS tubes, and the CD11b-PE+FcR block reagent provided in the Mouse CD11b Positive Selection Kit (StemCell catalog #18770) was added to the tubes and incubated at room temperature for 15 minutes. The PE selection cocktail was then added to the FACS tubes and mixed well with a pipet tip. The sample again incubated for 15 minutes at room temperature. The EasySep Magnetic Nanoparticles provided in the kit were gently mixed and added to the tubes and incubated at room temperature for 10 minutes. The tubes were placed in the EasySep Magnets (StemCell catalog #18000) and allowed to sit for 7 minutes. In one fluid motion, the unlabeled cells in the buffer were poured off while the tube was still in the magnet. The tube was then removed from the magnet, separation media was added to the tube, and the tube was placed back in the magnet for another 7 minutes. This washing process was done for a total of 4 times to remove all unlabeled cells. After the last wash, the labeled CD11b+ cells were resuspended in complete DMEM/F12, counted and resuspended at $1 \times 10^6$ /mL. One hundred microliters of cells were plated in 96-well flat-bottom tissue culture plates and allowed to rest overnight.

Following a 24 hour incubation with LPS and DMSO or CSF-1R inhibitors, the phagocytic activity of primary murine microglial cells was measured using the CytoSelect 96-well Phagocytosis Assay (Cell Biolabs, Inc.), as described above.

Some of the CSF-1R inhibitors did have a statistically significant impact on phagocytosis by unstimulated microglial cells compared to DMSO control: treatment with 0.1% DMSO significantly increased phagocytic activity of unstimulated cells but treatment with CSF-1R inhibitors resulted in phagocytic activity comparable to microglial cells alone. Stimulation of the primary murine microglial cells with LPS for 24 hours resulted in a significant increase in phagocytic activity when compared to unstimulated microglial cells alone in this experiment. None of the CSF-1R inhibitors affected the phagocytic activity of stimulated microglial cells.

The phagocytic activity of primary murine microglial following a 24 hour incubation with DMSO or CSF-1R inhibitors with LPS is displayed in FIG. 6. Each bar of the figure represents the mean and standard deviation of 3 wells. A one-way ANOVA followed by a Dunnett's multiple comparison was done to determine significance compared to DMSO control. An unpaired t-test was done to determine any significance between cells alone and DMSO control and unstimulated cells and LPS stimulated cells.

Treatment with the CSF-1R inhibitors tested in this experiment had no significant impact on the phagocytic activity of stimulated primary murine microglial cells.

Example 2-7: Effect of CSF-1R Inhibitors on the Proliferative Response of Primary Murine Microglial Cells The objectives of this study were to determine the optimal conditions for an LPS or CSF-1-induced proliferation assay with primary murine microglial cells and the effect of small molecule CSF-1R inhibitors and Laquinimod (multiple sclerosis drug active comparator) on the proliferation of primary murine microglial cells following LPS or CSF-1 stimulation.

Brains from fifty-six 2-3 day old C57Bl/6 mice were harvested and pooled in DMEM/F12-Glutamax/10%FBS/1%Pen/Strep/100 uM non-essential amino acids/2 mM sodium pyruvate ("complete DMEM/F12") and kept on ice until processing. Upon arrival in the lab, the brains were transferred into warm 0.25% trypsin (2 mL/brain) and incubated at 37C while rotating for 30 minutes. The dissociation reaction was quenched with an equal volume of complete DMEM/F12. The tissue was centrifuged at 300× g for 7 minutes, and the supernatant was then carefully removed. The tissue pellet was washed 3 times with complete DMEM/F12 and centrifuged at 300× g for 7 minutes. Supernatant was carefully removed after each wash step with a pipet rather than by vacuum aspiration. After the final wash, the tissue was brought up in complete DMEM/F12, slowly triturated until no chunks were visible, and filtered through a 70 uM cell strainer. The resultant single-cell suspension was washed with complete DMEM/F12, centrifuged at 200× g for 7 minutes and resuspended with complete DMEM/F12. The cells were distributed evenly amongst 15 T150 tissue culture flasks (1 flask/mouse), and the final volume was brought up to 35 mL with complete DMEM/F12. The cells were fed with a complete medium change 5, 8 and 12 days later.

On day 13, each flask was washed with 10 mL PBS. Five milliliters 0.25% trypsin were added to each flask, and the flasks were placed on a rocking platform at room temperature for 15 minutes. Ten milliliters complete DMEM/F12 were added to each flask, and the cells were gently triturated to break up cell aggregates. The single cell suspensions were then filtered through 70 µM cell strainers and centrifuged at 200× g for 6 minutes. The cells were then pooled, counted and resuspended at $1\times10^8$ cells/mL in PBS/2%FBS/1 mM EDTA ("separation media"). The cells were transferred to three 5 mL polystyrene FACS tubes, and the CD11b-PE+ FcR block reagent provided in the Mouse CD11b Positive Selection Kit (StemCell catalog #18770) was added to the tubes and incubated at room temperature for 15 minutes. The PE selection cocktail was then added to the FACS tubes and mixed well with a pipet tip. The sample again incubated for 15 minutes at room temperature. The EasySep Magnetic Nanoparticles provided in the kit were gently mixed and added to the tubes and incubated at room temperature for 10 minutes. The tubes were placed in the EasySep Magnets (StemCell catalog #18000) and allowed to sit for 7 minutes. In one fluid motion, the unlabeled cells in the buffer were poured off while the tube was still in the magnet. The tube was then removed from the magnet, separation media was added to the tube, and the tube was placed back in the magnet for another 7 minutes. This washing process was done for a total of 4 times to remove all unlabeled cells. After the last wash, the labeled CD11b+ cells were resuspended in complete DMEM/F12, counted and resuspended at $5\times10^5$ cells/mL and $1\times10^6$ cells/mL. One hundred microliters of cells were plated in 96-well flat-bottom tissue culture plates and allowed to rest overnight.

After resting overnight, 25 uL DMSO diluted 1:167 in medium alone or containing CSF-1R inhibitors or Laquinimod at a final concentration of 500 nM were added to appropriate assay wells. Twenty-five microliters medium were also added to all cells only wells at this time. Twenty-five microliters of LPS at 10 ng/mL or 100 ng/mL or CSF-1 at 100 ng/mL were then added to appropriate wells. Twenty-five microliters of medium were added to wells not receiving LPS or CSF-1 to bring the final volume of all assay wells to 150 uL. The assay plates then incubated at 37C and 5% $CO_2$ for up to 48 hours. A total of 8 assay plates were set up for this experiment. 1 uCi/well of $^3$H-thymidine was added to the first 2 plates immediately after assay set-up and harvested 8 hours later. Plates 3 and 4 were pulsed 8 hours after assay set-up and harvested 16 hours later. Plates 5 and 6 were pulsed 24 hours post assay set-up and harvested 8 hours later, and the last 2 plates were pulsed 32 hours post set-up and harvested at the 48 hour time point. The following assay conditions were set up for this experiment:

Controls:
Cells+25 µL media+25 µL medium
Cells+25 µL media+25 µL LPS or CSF-1
Cells+25 µL DMSO+25 µL medium
Cells+25 µL DMSO+25 µL LPS or CSF-1
CSF-1R Inhibitors:
Cells+25 µL 500 nM Genz-669195+25 µL medium
Cells+25 µL 500 nM Genz-669195+25 µL LPS or CSF-1
Cells+25 µL 500 nM Genz-666367+25 µL medium
Cells+25 µL 500 nM Genz-666367+25 µL LPS or CSF-1
Cells+25 µL 500 nM Genz-872171+25 µL medium
Cells+25 µL 500 nM Genz-872171+25 µL LPS or CSF-1
Cells+25 µL 500 nM Genz-882706+25 µL medium
Cells+25 µL 500 nM Genz-882706+25 µL LPS or CSF-1
Cells+25 µL 500 nM Genz-1007942+25 µL medium
Cells+25 µL 500 nM Genz-1007942+25 µL LPS or CSF-1
Cells+25 µL 500 nM Laquinimod+25 µL medium
Cells+25 µL 500 nM Laquinimod+25 µL LPS or CSF-1

LPS stimulation of primary murine microglial cells in vitro did not result in increased proliferative activity at any of the time points tested in this assay (data not shown). Some of the compounds tested in this experiment, Genz-872171, Genz-882706 and Laquinimod, actually induced an increased level of proliferative activity on unstimulated cells 48 hours post treatment, and the reason for this effect is unclear at this time (FIG. 7). CSF-1 stimulation of primary murine microglial cells in vitro resulted in a significant increase in proliferative activity compared to unstimulated cells at 24, 32 and 48 hours post-stimulation (FIG. 8). No increase in proliferation was detected 8 hours after stimulation (data not shown). All small molecule CSF-1R inhibitors tested significantly reduced proliferation of the microglial cells 32 and 48 hours post CSF-1 stimulation (FIG. 8). Conversely, Laquinimod had no effect or increased the proliferative activity of the microglia at those time points compared to the DMSO control.

Isolated microglial cells plated at $1\times10^5$cells/well were pulsed 32 hours after addition of test compounds and harvested 8 hours later. The columns of FIG. 7 represent the mean and SD of biological triplicates for each assay condition. A 1-way ANOVA followed by a Dunnett's comparison to the DMSO control was utilized for statistical analyses. Unpaired t-tests were also performed comparing each test compound to the DMSO control.

Isolated microglial cells plated at $1\times10^5$cells/well were stimulated with 100 ng/mL CSF-1, and the proliferative activity 8, 24, 32 and 48 hours post-stimulation was measured. The columns of FIG. 8 represent the mean and SD of biological triplicates for each assay condition. A 1-way ANOVA followed by a Dunnett's comparison to the DMSO control was utilized for statistical analyses. Unpaired t-tests were also performed comparing each test compound to the DMSO control.

LPS stimulation of murine primary microglia did not induce an increase in proliferative activity. CSF-1 stimulation, however, did induce a significant increase in proliferation, and treatment with all small molecule CSF-1R inhibitors tested significantly reduced the proliferative activity of the cells.

Example 3: In Vivo Studies

Example 3-1: Efficacy and Mechanism of Action of Genz-882706 CSF-1R Inhibitor in the MOG-Induced NOD Progressive EAE Model The objective of this study was to evaluate the efficacy and mechanism of action of Genz-882706 CSF-1R inhibitor in the MOG (myelin oligodendrocyte glycoprotein)-induced NOD progressive EAE (experimental autoimmune encephalomyelitis) model by measuring inflammatory/neurotoxic mediators in the CNS through protein analysis in homogenate and gene expression.

Female NOD mice (8 weeks of age) were assigned to one of three treatment groups; the test articles and dosages administered to each treatment group are outlined in Table 2 below.

TABLE 2

MOG-Induced NOD Progressive EAE Model
Treatment Groups (Mechanism of Action)

| Group No. | Treatment Groups | Dosing and Administration | Animals/group |
|---|---|---|---|
| 1 | MOG 35-55 peptide (150 µg in 2 mg/mL CFA) | 0.1 mL/site subcutaneously to 2 sites in abdomen | 18 |
|  | Pertussis toxin (150 ng in 200 µL PBS) | 150 ng/mouse intraperitoneally |  |
|  | Vehicle | BID oral gavage |  |
| 2 | MOG 35-55 peptide (150 µg in 2 mg/mL CFA) | 100 µL/site subcutaneously to 2 sites in abdomen | 18 |
|  | Pertussis toxin (150 ng in 200 µL PBS) | 150 ng/mouse intraperitoneally |  |
|  | GENZ-882706 (25 mg/kg/day) | QD oral gavage |  |
| 3 | Naïve | — | 6 |

EAE Induction and Scoring:

Female NOD/ShlTJ mice were immunized with an emulsion of MOG35-55 peptide (150 µg/mouse) in complete Freund's adjuvant (CFA) containing 0.6 mg *Mycobacterium tuberculosis*. The emulsion was delivered in a volume of 0.2 mL per mouse by subcutaneous injection to two sites. *Bordetella pertussis* toxin (PTX) in PBS was administered on Days 0 and 2, at a dose of 150 ng/animal via an intraperitoneal (i.p.) route. Mice were monitored daily for paralytic symptoms of EAE. The mice were scored for clinical symptoms using a progressive scoring system between 0-5. Score 0: no disease; Score 1: flaccid tail; Score 2; hind limb weakness; Score 3: hind limb paralysis; Score 4: Front limb weakness/partial paralysis; Score 5; death.

Gene Expression/QPCR:

RNA was extracted using the RNeasy kit from Qiagen (following the manufacturer's protocol) and then transcribed to cDNA using the QuantiTect kit from Qiagen (following the manufacturer's protocol.) Samples were loaded (in triplicate) on a 384-well plate. There were 6 targets and one internal control. The targets were TNFα, CSF-1R, Arg1, IL-6, Ym1 and MCP-1. RPL37A was the housekeeping gene, multiplexed in each well. The plates were run according to manufacturer's protocol on the Applied Biosystems 7900 machine. Data are calculated as relative expression to the internal control.

Results:

Disease was induced in a secondary progressive EAE model in NOD mice with an emulsion of MOG 35-55 and CFA. Therapeutic treatment with Genz-882706 (25 mg/kg/day) or vehicle control was started on Day 27 post-disease induction when mice began to enter the progressive stage of disease. The group treated with the CSF-1R inhibitor, Genz-882706 exhibited significantly decreased disease scores compared to vehicle control on Days 32, 34, and Days 41 through 43 (FIG. 9); the data show mean±SEM of disease scores. There was a trend towards lower scores, with Genz-882706 treatment overall.

Changes in gene expression of several inflammatory (IL-6, MCP-1 and TNF-α) and anti-inflammatory (Ym-1 and Arg-1) markers in spinal cord were observed in this study. Spinal cords were harvested from mice 4weeks post-induction and RNA was harvested and evaluated for changes in gene expression. Relative expression refers to the internal control, RPL37A.

With the exception of CSF1R, animals that were induced with MOG 35-55 showed up-regulation of gene expression in all targets in spinal tissue compared to naïve animals. There was a trend towards decreased gene expression of Arg1, TNFα, IL-6 and MCP-1 in spinal tissue of animals treated with Genz-882706 compared to vehicle controls, but it was not statistically significant. Also, a trend towards up-regulation of Ym-1 was seen in Genz-882706 treated animals compared to controls but that was not significant either (FIG. 10).

Daily treatment with Genz-882706 CSF-1R inhibitor compound significantly reduced mean disease scores compared to vehicle treated animals. This was accompanied by a trend in decreased gene expression of inflammatory markers in the spinal cord with reduced mRNA levels of MCP-1, TNFα, and IL-6.

Example 3-2: Assessment of Cytokine Levels in Spinal Cord After Treatment with Genz-882706 CSF-1R Inhibitor in the MOG-Induced NOD Progressive EAE Model The objective of this study was to evaluate differences in cytokine levels in the spinal cords of NOD MOG EAE mice following treatment with the small molecule CSF-1R inhibitor, Genz-882706.

Female NOD mice (8 weeks of age) were assigned to one of three treatment groups; the test articles and dosages administered to each treatment group are outlined in Table 3 below.

TABLE 3

MOG-Induced NOD Progressive EAE Model
Treatment Groups (Cytokine Levels)

| Group No. | Treatment Groups | Dosing and Administration | Animals/group |
|---|---|---|---|
| 1 | MOG 35-55 peptide (150 µg in 2 mg/mL CFA) | 100 µL/site subcutaneously to 2 sites in abdomen | 9 |
|  | Pertussis toxin (150 ng in 200 µL PBS) | 150 ng/mouse intraperitoneally |  |
|  | Vehicle | QD oral gavage |  |
| 2 | MOG 35-55 peptide (150 µg in 2 mg/mL CFA) | 100 µL/site subcutaneously to 2 sites in abdomen | 9 |
|  | Pertussis toxin (150 ng in 200 µL PBS) | 150 ng/mouse intraperitoneally |  |
|  | GENZ-882706 (25 mg/kg/day) | QD oral gavage |  |
| 3 | Naïve | — | 3 |

Homogenate Preparation:

Frozen spinal cord tissues collected on day 43 were thawed, and 700 µL of Bioplex cell lysis buffer (BioRad catalog #171-304011) containing factors 1 and 2 (protease and phosphatase inhibitors, respectively; BioRad catalog #171-304012), and the protease inhibitor phenyl-methyl-sulfonyl fluoride (PMSF, 500 mM; Sigma-Aldrich) were added. Tissue was homogenized using zirconium beads and shaken on the Omni Bead Ruptor and then centrifuged at 4° C. at 6000× g for 20 minutes. The supernatant was removed and aliquotted. Aliquots were stored at −20° C. until assay. The protein content of each sample was determined using the bicinchoninic acid (BCA) assay (Pierce catalog #23225, Rockford, Ill.), with bovine serum albumin (BSA) as a standard, according to the manufacturer's protocol. Sample absorbances were read at 560 nm using a spectrophotometer (Molecular Devices Versa Max, Sunnyvale, Calif.). The sample concentrations were calculated as mg/mL of protein. Results from the following assays were normalized to protein concentration, and cytokine/chemokine levels were reported as pg of cytokine/mg of tissue protein.

Mouse Brain-Derived Neurotrophic Factor (BDNF) ELISA:

Homogenates were assayed using the Insight Genomics murine BDNF ELISA kit. Samples were diluted 1:5 with diluent buffer. One hundred microliters of the diluted samples and standards were added to a pre-coated 96 well plate, covered and incubated at 37° C. for 90 minutes. After incubation, samples and standards were discarded and the plate was gently blotted on paper towels. One hundred microliters of biotinylated anti-mouse BDNF antibody working solution were added into each well and incubated at 37° C. for 60 minutes. The plate was then washed 3 times, and 100 ul of ABC working solution were added and the plate incubated at 37° C. for 30 minutes. The plate was then washed 5 times and 90 ul of TMB substrate were added, and the plate was allowed to incubate in the dark for 8-12 minutes. The reaction was stopped by adding 100 ul of stop solution. The plates were then read on the plate reader at 450 nm.

Mouse TNF-α ELISA:

Homogenates were assayed with the Quantikine Mouse TNF-α ELISA kit from R&D Systems. Samples were diluted 1:5 with Calibrator Diluent. Fifty microliters of Assay Diluent were first added to each well. Fifty microliters of Standards, Assay Control and diluted Sample were then added to the wells. The plate was mixed by gently tapping the frame, and sealed with an adhesive strip. The plate was incubated for 2 hours at room temperature. After incubation, the plate was washed five times with approximately 400 ul of Wash Buffer using a squirt bottle. After the last wash, the plate was gently tapped on paper towels to remove excess moisture. One hundred microliters of mouse TNF-α conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm-560 nm.

Mouse Interferon Gamma Inducible Protein (IP-10) ELISA:

Homogenates were assayed with the Quantikine Mouse IP-10 ELISA kit from R&D Systems. Samples were diluted 1:5 with Calibrator Diluent. Fifty microliters of Assay Diluent were first added to each well. Fifty microliters of Standards, Assay Control and diluted Sample were then added to the wells. The plate was mixed by gently tapping the frame, and sealed with an adhesive strip. The plate incubated for 2 hours at room temperature. After incubation, the plate was washed with approximately 400 ul of Wash Buffer using a squirt bottle 5 times. After the last wash, the plate was gently tapped on paper towels to remove excess moisture. One hundred microliters of mouse IP-10 conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm-560 nm.

Mouse IL-10 ELISA:

Homogenates were assayed with the Quantikine Mouse IL-10 ELISA kit from R&D Systems. Samples were diluted 1:5 with Calibrator Diluent. Fifty microliters of Assay Diluent were first added to each well. Fifty microliters of Standards, Assay Control and diluted Sample were then added to the wells. The plate was mixed by gently tapping the frame, and sealed with an adhesive strip. The plate incubated for 2 hours at room temperature. After incubation, the plate was washed with approximately 400 ul of Wash Buffer using a squirt bottle 5 times. After the last wash, the plate was gently tapped on paper towels to remove excess moisture. One hundred microliters of mouse IL-10 conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm-560 nm.

Mouse RANTES ELISA:

Homogenates were assayed with the Quantikine Mouse RANTES ELISA kit from R&D Systems. Samples were diluted 1:5 with Calibrator Diluent. Fifty microliters of Assay Diluent were first added to each well. Fifty microliters of Standards, Assay Control and diluted Sample were then added to the wells. The plate was mixed by gently tapping the frame, and sealed with an adhesive strip. The plate incubated for 2 hours at room temperature. After incubation, the plate was washed with approximately 400 ul of Wash Buffer using a squirt bottle 5 times. After the last wash, the plate was gently tapped on paper towels to remove excess moisture. One hundred microliters of mouse RANTES conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm-560 nm.

Mouse IL-12p40 ELISA:

Homogenates were assayed with the Quantikine Mouse IL-12p40 ELISA kit from R&D Systems. Samples were diluted 1:5 with Calibrator Diluent. Fifty microliters of Assay Diluent were first added to each well. Fifty microliters of Standards, Assay Control and diluted Sample were then added to the wells. The plate was mixed by gently tapping the frame, and sealed with an adhesive strip. The plate incubated for 2 hours at room temperature. After incubation, the plate was washed with approximately 400 ul of Wash Buffer using a squirt bottle 5 times. After the last wash, the plate was gently tapped on paper towels to remove excess moisture. One hundred microliters of mouse IL-12p40 conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm-560 nm.

Mouse IL-6 ELISA:

Homogenates were assayed with the Quantikine Mouse IL-6 ELISA kit from R&D Systems. Samples were diluted 1:4 with Calibrator Diluent. Fifty microliters of Assay Diluent were first added to each well. Fifty microliters of Standards, Assay Control and diluted Sample were then added to the wells. The plate was mixed by gently tapping the frame, and sealed with an adhesive strip. The plate incubated for 2 hours at room temperature. After incubation, the plate was washed with approximately 400 ul of Wash Buffer using a squirt bottle 5 times. After the last wash, the plate was gently tapped on paper towels to remove excess moisture. One hundred microliters of mouse IL-6 conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm-560 nm.

Mouse MCP-1 ELISA:

Homogenates were assayed with the Quantikine Mouse MCP-1 ELISA kit from R&D Systems. Samples were diluted 1:5 with Calibrator Diluent. Fifty microliters of Assay Diluent were first added to each well. Fifty microliters of Standards, Assay Control and diluted Sample were then added to the wells. The plate was mixed by gently tapping the frame, and sealed with an adhesive strip. The plate incubated for 2 hours at room temperature. After incubation, the plate was washed with approximately 400 ul of Wash Buffer using a squirt bottle 5 times. After the last wash, the plate was gently tapped on paper towels to remove excess moisture. One hundred microliters of mouse MCP-1 conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm-560 nm.

Murine TGF-β1 ELISA:

Homogenates were assayed in the Quantikine TGF-β1 ELISA kit from R&D Systems. The latent TGF-β1 in the samples was activated by an acid activation and neutralization step, and diluted in calibrator diluent yielding a dilution factor of 1:7.5. Fifty microliters of Assay Diluent were first added to each well. Fifty microliters of Standards, Assay Control and diluted Sample were then added to the appropriate wells. The plate was mixed by gently tapping the frame and sealed with an adhesive strip and incubated for 2 hours at room temperature. After incubation, the plate was washed 4 times with wash buffer. After the last wash, the plate was gently tapped on paper towels to remove excess moisture. One hundred microliters of human TGF-β1 conjugate were added to each well and incubated at room temperature for 2 hours. After incubation, the plate was washed as described above. TMB substrate solution was then added to each well and incubated for 30 minutes at room temperature in the dark. After incubation, the acid stop solution was added to each well, and the plate was read on the ELISA plate reader at 450 nm-560 nm.

Mouse IL-1β ELISA:

Homogenates were assayed with the Quantikine Mouse IL-1β ELISA kit from R&D Systems. Samples were diluted 1:3 with Calibrator Diluent. Fifty microliters of Assay Diluent were first added to each well. Fifty microliters of Standards, Assay Control and diluted Sample were then added to the wells. The plate was mixed by gently tapping the frame, and sealed with an adhesive strip. The plate incubated for 2 hours at room temperature. After incubation, the plate was washed with approximately 400 ul of Wash Buffer using a squirt bottle 5 times. After the last wash, the plate was gently tapped on paper towels to remove excess moisture. One hundred microliters of mouse IL-1β conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm-560 nm.

Mouse Nitric Oxide (NO) Assay:

Homogenates were assayed with the OxiSelect In Vitro Nitric Oxide (Nitrite/Nitrate) Assay Kit from Cell Biolabs. Samples were diluted 1:2 with media. Fifty microliters of the nitrate standards, samples, or blanks were added to the 96-well microtiter plate. Fifty microliters of Enzyme Reaction Mixture were added to each well (already containing 50 μL of nitrate standard or sample). The plate was covered and incubated at room temperature for 1 hour on an orbital shaker. Fifty microliters of Griess Reagent A were added to each well immediately followed by 50 μL of Griess Reagent B. The plate incubated for 10 minutes, allowing color development. The plate was then read on the microplate reader at 540 nm, and the concentrations were calculated by comparing the sample absorbance to the standard curve.

Mouse Chitinase 3-Like 3/ECF-L (YM-1):

Homogenates were assayed in the DuoSet Development kit from R&D Systems. The capture antibody was diluted to its working concentration in PBS and 100 μL per well was added to a 96 well microplate and allowed to incubate at room temperature overnight. After the overnight incubation, coat buffer was flicked out and plates were washed three times with Wash Buffer. Excess moisture was removed from wells by tapping dry on paper towels. Plates were then blocked by adding 300 μL of Reagent Dilution buffer to each well and incubated at room temperature for 1 hour. While plates were incubating, the samples and standards were prepared. Homogenates were diluted 1:50 in Reagent Diluent. Standard was reconstituted with 0.5 ml of Reagent Diluent and allowed to sit for a minimum of 15 minutes before making dilutions. A seven point standard curve using 2-fold serial dilutions was generated using Reagent Dilution with a high standard of 5000 pg/ml. After blocking for one hour, plates were washed as described above. One hundred microliters of samples and standards were added to the appropriate wells. The plates were sealed and allowed to incubate for 2 hours at room temperature. After incubation, the plates were washed 3 times with Wash Buffer. One hundred microliters of the working dilution of Detection Antibody was added to each well. The plates were covered and allowed to incubate for 2 hours at room temperature. The plates were washed as described above following incubation. 100 μL of the working dilution of Streptavidin-HRP was added to each well and allowed to incubate at room temperature for 20 minutes in the dark. The plates were then washed after incubation. One hundred microliters of Substrate Solution was added to each well and plates were incubated in the dark for 20 minutes. Fifty microliters of Stop solution was added to each well and plates were read on a microplate reader set at 450-560 nm.

Results:

Treatment with Genz-882706 in EAE mice resulted in significant decreases in MCP-1, IL-6, IL-1β and IP-10 levels in spinal cord homogenates when compared to Vehicle treated animals (FIG. 11); the columns represent the mean and SEM. Unpaired T-tests between the naïve and vehicle groups as well as between the vehicle and Genz-882706 groups were utilized for statistical analyses.

Although not statistically significant, Genz-882706 treated MOG induced EAE animals showed a trend towards decreased levels of TGF-β. Treatment with the CSF-1R small molecule inhibitor Genz-882706 showed a significant increase in TNF-α levels in the spinal cord when compared to the vehicle treated group. It is unclear as to why this increase occurred. There were no effects on MCSF, RANTES or IL-12p40 levels after treatment with the CSF-1R small molecule inhibitor. IL-10 levels were significantly decreased in diseased, vehicle treated animals compared to naïve control animals (FIG. 12); the columns represent the mean and SEM. Unpaired T-tests between the naïve and vehicle groups as well as between the vehicle and Genz-882706 groups were utilized for statistical analyses. Treatment with Genz-882706 at 25 mg/kg/day showed a trend towards increased IL-10 levels when compared to the vehicle treated group. Diseased animals treated with the vehicle control had significantly increased Ym-1 levels when compared to either the naïve control or Genz-882706 treated groups. BDNF levels were not affected by treatment with the CSF-1R small molecule inhibitor. Total Nitric Oxide levels could not be measured with either filtered or unfiltered samples.

Treatment with Genz-882706 in EAE mice resulted in significant decreases in levels of the inflammatory cytokines MCP-1, IL-6, IL-1β and IP-10 in the spinal cord when compared to vehicle treated animals. Treatment with Genz-882706 showed a significant increase in TNF-α levels in the spinal cord when compared to the vehicle treated group. It is unclear as to why this increase occurred. With regard to anti-inflammatory cytokines, there was a trend towards decreased levels of TGF-β following treatment with the cFMS small molecule inhibitor but a trend for increased IL-10 levels compared to vehicle control. Diseased animals treated with the vehicle control had significantly increased Ym-1 levels when compared to either the Naïve control or Genz-882706 treated groups. Overall, treatment with Genz-882706 appeared to have a general anti-inflammatory effect in the spinal cord of NOD EAE mice.

Example 3-3: Effect of Prophylactic Treatment with Genz-882706 in an LPS-Induced Microglial Activation Model The objectives of this study were to assess the effect of a novel CNS-penetrant CSF-1R inhibitor, Genz-882706, on microglial cell activation markers and monocyte, macrophage and microglial populations in the brain.

Female C57BL/6 mice (7-8 weeks of age) were assigned to one of eleven treatment groups; the test articles and dosages administered to each treatment group are outlined in Table 4 below. Mice were challenged with LPS daily for four days and dosed with CSF-1R inhibitor, Genz-882706, once a day one hour prior to LPS injection. CNS tissue samples and blood were collected on Day 5, one hour post the final dose of the CSF-1R inhibitor.

TABLE 4

LPS-Induced Microglial Activation Model Treatment Groups (Prophylactic Treatment, Genz-882706)

| Group No. | Treatment Groups | Dosing and Administration | Animals/group |
|---|---|---|---|
| 1 | Naïve | — | 9 |
| 2 | LPS (0.2 mg LPS/mL PBS) | 20 µg or 1 mg/kg/mouse intraperitoneally | 9 |
| 3 | Vehicle (15% PEG400/5% Solutol HS 15 in 30 mM citrate buffer in water, pH 3) | 200 µL QD oral | 9 |
|  | LPS (0.2 mg LPS/mL PBS) | 20 µg or 1 mg/kg/mouse intraperitoneally |  |
| 4 | GENZ-882706 (30 mg/kg in 200 µL Vehicle)) | QD oral gavage | 9 |
|  | LPS (0.2 mg LPS/mL PBS) | 20 µg or 1 mg/kg/mouse intraperitoneally |  |
| 5 | GENZ-882706 (100 mg/kg) | QD oral gavage | 9 |
|  | LPS (0.2 mg LPS/mL PBS) | 20 µg or 1 mg/kg/mouse intraperitoneally |  |
| 6 | GENZ-882706 (30 mg/kg) | QD oral gavage | 4 |
|  | LPS (0.2 mg LPS/mL PBS) | 20 µg or 1 mg/kg/mouse intraperitoneally |  |
| 7 | GENZ-882706 (30 mg/kg) | QD oral gavage | 4 |
|  | LPS (0.2 mg LPS/mL PBS) | 20 µg or 1 mg/kg/mouse intraperitoneally |  |
| 8 | GENZ-882706 (100 mg/kg) | QD oral gavage | 4 |
|  | LPS (0.2 mg LPS/mL PBS) | 20 µg or 1 mg/kg/mouse intraperitoneally |  |
| 9 | GENZ-882706 (100 mg/kg) | QD oral gavage | 4 |
|  | LPS (0.2 mg LPS/mL PBS) | 20 µg or 1 mg/kg/mouse intraperitoneally |  |
| 10 | Vehicle (15% PEG400/5% Solutol HS 15 in 30 mM citrate buffer in water, pH 3) | 200 µL QD oral | 4 |
|  | LPS (0.2 mg LPS/mL PBS) | 20 µg or 1 mg/kg/mouse intraperitoneally |  |
| 11 | Vehicle (15% PEG400/5% Solutol HS 15 in 30 mM citrate buffer in water, pH 3) | 200 µL QD oral | 4 |
|  | LPS (0.2 mg LPS/mL PBS) | 20 µg or 1 mg/kg/mouse intraperitoneally |  |

Brains and spinal cords were collected at sacrifice, pooled and kept in RPMI on ice until processing. Tissues were removed from RPMI and diced into ~1 mm by 1 mm pieces with a razor blade. 2 mL dissociation media (HBSS+2.5 mg/mL Collagenase D+1 mg/mL DNase) were added to each sample pool, mixed well and incubated on a rocking platform at 37° C. for 45 minutes. Each sample was then triturated with glass pipettes for approximately 1 minute and transferred to a 15 mL conical tube. The tissue was washed with PBS and centrifuged for 5 minutes at 2000 rpm. 10 mL PBS was added to each resulting tissue pellet then filtered through a 70 µm cell strainer. The cell strainers and cell suspensions were washed with PBS and centrifuged at 2000 rpm for 5 minutes. The supernatants were then discarded, and the cell pellets were resuspended with room temperature 30% Percoll/HBSS (4 mL/tissue pool) and transferred to a 15 mL conical tube with a glass pipet. The conical tubes were centrifuged at 700× g rpm for 10 minutes at room temperature with the centrifuge brake off. After centrifugation, the myelin layer and Percoll were aspirated, and the resultant cell pellets were resuspended with 1 mL PBS and transferred to clean 15 mL conical tubes with a glass pipet. The cells were washed with 15 mL PBS and centrifuged at 2000 rpm for 5 minutes. The supernatants were removed, and the cell pellets were resuspended in 300 µL PBS. 250 µL cells were then transferred to the appropriate wells of a round-bottom 96-well plate for staining.

The round-bottom 96-well plate containing cells was centrifuged at 2000 rpm for 1 minute, and the supernatants were flicked out. 50 µL of mouse block was added to each well, mixed well with pipet tips and allowed to incubate for 10 minutes at room temperature. 20 µL/sample of the following antibody cocktail were added to the wells:

CD11b-PCP Cy5.5 (BD 550993)
CD45-FITC (BD 553080)
CD80-BV421 (BD 562611)
CD86-PE (BD 553692).

Compensation control tubes were also set up with the beads and the individual antibodies. The antibodies and cells or beads then incubated for 20 minutes at room temperature in the dark. Two hundred microliters of protein blocking agent (PBA) were added to the cells in the staining plate, and the plate was centrifuged for 1 minute at 2000 rpm. The cell pellets were resuspended with 230 uL 1% methanol free-formaldehyde (MFF), mixed well with pipet tips and stored at 4° C. until run on an LSR flow cytometer. Twenty µL counting beads were then added to each sample well for quantitation. The compensation beads were then washed by adding 1 mL PBA to each tube and were centrifuged at 2400 rpm for 5 minutes. The compensation control beads were resuspended with 250 µL PBA and stored until acquisition. Once sample acquisition was completed, sample results were analyzed using FlowJo FACS analysis software.

Blood was collected at sacrifice by retro-orbital bleed, and 100 µL were added to FACS tubes. 50 µL of mouse block were then added to each tube and incubated for 10 minutes at room temperature. A cocktail containing the following antibodies in PBS/1%BSA/0.05%Sodium Azide (PBA) were added to the sample tubes in a final volume of 20 µL/sample:

CD11b-PCP Cy5.5 (BD 550993)
CD11c-PE (BD557401)
F4/80-APC (eBioscience 17-4801-82)

The antibodies incubated for 20 minutes at room temperature in the dark. 1 mL 1× FACS Lysing solution was then added to each tube to lyse the red blood cells, and the tubes again incubated for 10 minutes in the dark at room temperature. The sample tubes were centrifuged at 2000 rpm for 1 minute, and the cell pellets were washed by resuspending with 1 mL PBA and centrifuging at 2000 rpm for 1 minute. The resultant cell pellet was then resuspended with 200 uL 1% Methanol-Free formaldehyde (MFF). Once staining of CNS in the 96-well round-bottom plate was completed, 50 µL counting beads were added to each blood sample, and the samples were transferred to empty wells of the plate for acquisition.

Initially, an unpaired t-test was performed between the naïve group and LPS-treated group to determine changes in cell populations induced by LPS challenge. An unpaired t-test between the vehicle control group and each CSF-1R inhibitor treated group was performed to determine the effect of treatment with the small molecule inhibitor on the various cell populations.

As can be seen in FIG. 13, significant increases in the numbers of microglia, monocytes/macrophages and lymphocytes were seen in the brain and spinal cord following LPS challenge. Treatment with the small molecule CSF-1R inhibitor Genz-882706 at both the 30 mg/kg and the 100 mg/kg dose significantly reduced the number of microglia and monocytes/macrophages in the brain and spinal cord compared to the vehicle and LPS controls. No effect on lymphocyte numbers was observed following once daily dosing in this study.

Activation markers on the microglia and monocyte/macrophage populations were also evaluated in this study. The levels of expression by mean fluorescence intensity (MFI) are reported. CD80 expression was only slightly increased on both the microglia and monocyte/macrophage populations in the brain and spinal cord, respectively, upon LPS challenge (FIG. 14 and FIG. 15.) Treatment with Genz-882706 modestly reduced CD80 expression on monocytes/macrophages in the brain compared to the vehicle control. No significant effects on CD86 expression were observed. It is important to note that CD80 and CD86 expression on cells from the naïve mice was approximately 2-fold higher in this study than in previous studies.

Treatment with Genz-882706 at 30 mg/kg, but not 100 mg/kg, significantly increased the numbers of circulating monocytes and macrophages compared to the vehicle control (FIG. 16). Although not significant, treatment with the 100 mg/kg dose of Genz-882706 reduced the number of circulating myeloid DCs by >30%. In previous studies, a significant decrease in circulating myeloid DCs has consistently occurred with twice daily dosing with CSF-1R inhibitors.

Four daily doses of LPS resulted in significant increases in the numbers of microglia, monocytes/macrophages and lymphocytes in the brain and spinal cord of C57Bl/6 mice. Treatment with Genz-882706 decreased the number of microglia and monocytes/macrophages in both the brain and spinal cord following LPS challenge. Once daily dosing with Genz-882706 also decreased expression of the CD80 activation marker on the monocyte/macrophage populations in the brain. No significant reductions of circulating monocytes or macrophages were observed but there was a decrease in myeloid DCs at the 100 mg/kg dose.

Example 3-4: Evaluation of CSF-1R Inhibitors in the MOG-Induced NOD Progressive EAE Model The objective of this study was to assess the impact of therapeutic treatment of a known cFMS kinase inhibitor, Inhibitor A (Proc Natl Acad Sci U S A. 2005 November 1;102(44):16078-83.), and Genz-882706 CSF-1R inhibitor treatment in the MOG NOD progressive EAE model, a model of human secondary progressive MS. Evaluation included mean disease scores, CNS inflammation, CNS demyelination and axonal loss.

TABLE 5

| MOG-Induced NOD Progressive EAE Model Treatment Groups | | | |
|---|---|---|---|
| Group No. | Treatment Groups | Dosing and Administration | Animals/group |
| 1 | MOG 35-55 peptide (150 µg in 2 mg/mLCFA) | 0.1 mL/site subcutaneously to 2 sites in abdomen | 11 |
| | Pertussis toxin (150 ng in 200 µL PBS) | 150 ng/mouse intraperitoneally | |

TABLE 5-continued

MOG-Induced NOD Progressive EAE Model Treatment Groups

| Group No. | Treatment Groups | Dosing and Administration | Animals/group |
|---|---|---|---|
| | Vehicle A (0.5% methocel in water) | BID oral gavage | |
| 2 | MOG 35-55 peptide (150 µg in 2 mg/mLCFA) | 0.1 mL/site subcutaneously to 2 sites in abdomen | 11 |
| | Pertussis toxin (150 ng in 200 µL PBS) | 150 ng/mouse intraperitoneally | |
| | Inhibitor A (150 mg/kg) | BID oral gavage | |
| 3 | MOG 35-55 peptide (150 µg in 2 mg/mL CFA) | 100 µL/site subcutaneously to 2 sites in abdomen | 12 |
| | Pertussis toxin (150 ng in 200 µL PBS) | 150 ng/mouse intraperitoneally | |
| | Vehicle B | BID oral gavage | |
| 4 | MOG 35-55 peptide (150 µg in 2 mg/mL CFA) | 100 µL/site subcutaneously to 2 sites in abdomen | 10 |
| | Pertussis toxin (150 ng in 200 µL PBS) | 150 ng/mouse intraperitoneally | |
| | Genz-882706 (100 mg/kg) | BID oral gavage | |
| 5 | MOG 35-55 peptide (150 µg in 2 mg/mL CFA) | 100 µL/site subcutaneously to 2 sites in abdomen | 12 |
| | Pertussis toxin (150 ng in 200 µL PBS) | 150 ng/mouse intraperitoneally | |
| | Genz-882706 (25 mg/kg) | BID oral gavage | |
| 6 | MOG 35-55 peptide (150 µg in 2 mg/mL CFA) | 100 µL/site subcutaneously to 2 sites in abdomen | 13 |
| | Pertussis toxin (150 ng in 200 µL PBS) | 150 ng/mouse intraperitoneally | |
| | No treatment (Untreated) | — | |
| 7 | Naïve | — | 6 |

EAE Induction and Scoring:

Female NOD/ShlTJ mice were immunized with an emulsion of MOG35-55 peptide (150 µg/mouse) in complete Freund's adjuvant (CFA) containing 0.6 mg *Mycobacterium tuberculosis*. The emulsion was delivered in a volume of 0.2 mL per mouse by subcutaneous injection to two sites. *Bordetella pertussis* toxin (PTX) in PBS was administered on Days 0 and 2, at a dose of 150 ng/animal via an intraperitoneal (i.p.) route. Mice were monitored daily for paralytic symptoms of EAE. The mice were scored for clinical symptoms using a disease scoring system between 0-5. Score 0: no disease; Score 1: flaccid tail; Score 2; hind limb weakness; Score 3: hind limb paralysis; Score 4: Front limb weakness/partial paralysis; Score 5; death.

Histology and Immunohistochemistry:

At the end of the treatment period (36 days of dosing) mice were anesthetized with isoflurane, perfused, euthanized with CO2, and spinal cord was collected in 10% buffered neutral formalin for histopathology. Spinal cord (cervical and thoracic) samples were step-sectioned and mounted on slides at Mass Histology Labs. Spinal cord sections were stained for myelin with luxol fast blue (LFB) to detect demyelination, and Bielchowsky's silver stain (silver) to detect axonal loss, SMI-32 (neurofilament detection) to detect axonal damage, and Iba-1 to detect macrophage/monocyte/microglia. Tissue sections on the slides were evaluated by light microscopy. All evaluations used a scale of 0 (no change/finding) to 5 (severe change/finding).

Results:

Secondary progressive EAE was induced in NOD mice with an emulsion of MOG 35-55 and CFA. Therapeutic treatment with Genz-882706 (100 mg/kg or 25 mg/kg), or vehicle control was started on Day 26 post-disease induction. On Day 26 mice began the progressive stage of disease. The group treated with internal CSF-1R inhibitor, Genz-882706, at 100 mg/kg exhibited significantly decreased disease scores compared to vehicle control on Day 30, and Days 37 through 62 (FIG. 17). The lower dose of Genz-882706 (25 mg/kg) significantly reduced scores compared to vehicle on Days 43-49, 57-59 and 62.

Genz-882706 CSF-1R inhibitor at 100 mg/kg and 25 mg/kg doses significantly reduced axonal loss and proliferation/infiltration of macrophages/microglia in the spinal cord compared with the vehicle control group (FIG. 18). Data also showed a >40% reduction in axonal damage and demyelination in both the 25 mg/kg and 100 mg/kg 882706 CSF-1R inhibitor treated groups compared with the vehicle control group.

Daily treatment with Genz-882706 CSF-1R inhibitor compound significantly reduced mean disease scores and CNS damage compared to vehicle treated and untreated animals.

Example 3-5: Effect of Prophylactic Treatment with RA10651967 in an LPS-Induced Microglial Activation/CNS Inflammation Model The objectives of this study were to assess the effect of RA10651967 on microglial cell activation markers and monocyte, macrophage and microglial populations in the brain and spinal cord.

Female C57BL/6 mice (7-8 weeks of age) were assigned to one of six treatment groups; the test articles and dosages administered to each treatment group are outlined in Table 6 below.

TABLE 6

LPS-Induced Microglial Activation Model Treatment Groups (Prophylactic Treatment, RA10651967)

| Group No. | Treatment Groups | Dosing and Administration | Animals/group |
|---|---|---|---|
| 1 | Naïve | — | 8 |
| 2 | LPS (0.2 mg LPS/mL PBS) | 20 µg or 1 mg/kg/mouse intraperitoneally | 8 |
| 3 | Vehicle (20% PEG400/10% SBEβCD in 15 in 30 mM citrate buffer in water, pH 3) | 200 µL QD oral | 8 |
| | LPS (0.2 mg LPS/mL PBS) | 20 µg or 1 mg/kg/mouse intraperitoneally | |
| 4 | RA10651967 (25 mg/kg in 200 µL Vehicle)) | BID oral gavage | 8 |
| | LPS (0.2 mg LPS/mL PBS) | 20 µg or 1 mg/kg/mouse intraperitoneally | |
| 5 | RA10651967 (25 mg/kg in 200 µL Vehicle)) | BID oral gavage | 4 |
| | LPS (0.2 mg LPS/mL PBS) | 20 µg or 1 mg/kg/mouse intraperitoneally | |
| 6 | Vehicle (20% PEG400/10% SBEβCD in 15 in 30 mM citrate buffer in water, pH 3) | 200 µL QD oral | 4 |
| | LPS (0.2 mg LPS/mL PBS) | 20 µg or 1 mg/kg/mouse intraperitoneally | |

Brains were collected at sacrifice, pooled and kept in RPMI on ice until processing. Tissues were removed from RPMI and diced into ~1 mm by 1 mm pieces with a razor blade. 2 mL dissociation media (HBSS+2.5 mg/mL Collagenase D+1 mg/mL DNase) were added to each sample pool, mixed well and incubated on a rocker at 37° C. for 45 minutes. Each sample was then triturated with glass pipettes for approximately 1 minute and transferred to a 15 mL conical tube. The tissue was washed with PBS and centrifuged for 5 minutes at 2000 rpm. 10 mL PBS was added to each resulting tissue pellet then filtered through a 70 um cell strainer. The cell strainers and cell suspensions were washed with PBS and centrifuged at 2000 rpm for 5 minutes. The supernatants were then discarded, and the cell pellets were resuspended with room temperature 30% Percoll/HBSS (4 mL/tissue pool) and transferred to a 15 mL conical tube with a glass pipet. The conical tubes were centrifuged at 700× g rpm for 10 minutes at room temperature with the centrifuge brake off. After centrifugation, the myelin layer and Percoll were aspirated, and the resultant cell pellets were resuspended with 1 mL PBS and transferred to clean 15 mL conical tubes with a glass pipet. The cells were washed with 15 mL PBS and centrifuged at 2000 rpm for 5 minutes. The supernatants were removed, and the cell pellets were resuspended in 300 µL PBS. 250 µL cells were then transferred to the appropriate wells of a round-bottom 96-well plate for staining.

The round-bottom 96-well plate containing cells was centrifuged at 2000 rpm for 1 minute, and the supernatants were flicked out. 50 µL of mouse block was added to each well, mixed well with pipet tips and allowed to incubate for 10 minutes at room temperature. 20 µL/sample of the following antibody cocktail were added to the wells:
CD11b-PCP Cy5.5 (BD 550993)
CD45-FITC (BD 553080)
CD8O-BV421 (BD 562611)
Compensation control tubes were also set up with the beads and the individual antibodies. The antibodies and cells or beads then incubated for 20 minutes at room temperature in the dark. Two hundred microliters of PBA were added to the cells in the staining plate, and the plate was centrifuged for 1 minute at 2000 rpm. The cell pellets were resuspended with 230 uL MFF, mixed well with pipet tips and stored at 4° C. until run on the LSR. 20 uL counting beads were then added to each sample well for quantitation. The compensation beads were then washed by adding 1 mL PBA to each tube and were centrifuged at 2400 rpm for 5 minutes. The compensation control beads were resuspended with 250 uL PBA and stored until acquisition. Once sample acquisition was completed, sample results were analyzed using FlowJo FACS analysis software.

Blood was collected at sacrifice by retro-orbital bleed, and 100 µL were added to FACS tubes. 50 µL of mouse block were then added to each tube and incubated for 10 minutes at room temperature. A cocktail containing the following antibodies in PBS/1%BSA/0.05%Sodium Azide (PBA) were added to the sample tubes in a final volume of 20 µL/sample:
CD11b-PCP Cy5.5 (BD 550993)
CD11c-PE (BD557401)
F4/80-APC (eBioscience 17-4801-82)
The antibodies incubated for 20 minutes at room temperature in the dark. 1 mL 1× FACS Lysing solution was then added to each tube to lyse the red blood cells, and the tubes again incubated for 10 minutes in the dark at room temperature. The sample tubes were centrifuged at 2000 rpm for 1 minute, and the cell pellets were washed by resuspending with 1 mL PBA and centrifuging at 2000 rpm for 1 minute. The resultant cell pellet was then resuspended with 200 uL 1% Methanol-Free formaldehyde (MFF). Once staining of CNS in the 96-well round-bottom plate was completed, 50 µL counting beads were added to each blood sample, and the samples were transferred to empty wells of the plate for acquisition.

Initially, an unpaired t-test was performed between the naïve group and LPS-treated group to determine changes in cell populations induced by LPS challenge. An unpaired t-test between the vehicle control group and each CSF-1R inhibitor treated group was performed to determine the effect of treatment with the small molecule inhibitor on the various cell populations.

As can be seen in FIG. 19, significant increases in the numbers of monocytes/macrophages and lymphocytes were seen in the brain following LPS challenge. Treatment with the small molecule CSF-1R inhibitor RA10651967 at 25 mg/kg significantly reduced the number of microglia and monocytes/macrophages compared to the vehicle control.

The activation marker CD80 on the microglia and monocyte/macrophage populations was also evaluated in this study. In FIG. 20, the levels of expression by mean fluorescence intensity (MFI) are reported. CD80 expression was significantly increased on only the microglial cell population in the brain upon LPS challenge. Treatment with RA10651967 significantly increased CD80 expression on the microglia by 40% compared to the vehicle control. This is the first time that this has occurred in this model with a small molecule CSF-1R inhibitor.

In the blood, LPS administration significantly decreased circulating monocytes, macrophages and mDCs (FIG. 21). Typically in this model, significant increases in mDCs are observed following LPS administration. RA10651967 increased all circulating cell populations analyzed compared to the vehicle control.

Treatment with the small molecule CSF-1R inhibitor RA10651967 significantly reduced the number of microglia and monocytes/macrophages in the brain following LPS challenge compared to the vehicle control. Unexpectedly, expression of the activation marker CD80 was significantly increased on the microglia following treatment with the compound.

The invention claimed is:
1. A compound of Formula (VII):

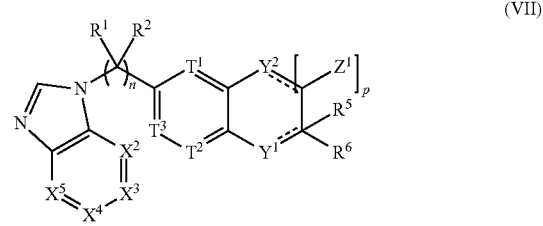

(VII)

or the pharmaceutically acceptable salt thereof, wherein:
the dashed lines represent optional double bonds;
p is 1;
n is 1;
$X^2$ is N,
$X^3$, $X^4$, and $X^5$, are each independently selected from $CR^7$,
wherein each $R^7$ is independently selected from the group consisting of H, $(C_1$-$C_{10})$alkyl, $(C_3$-$C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, $(C_1-C_{10})$alkyl-C(O)O—, $(C_2-C_9)$heteroalkyl-C(O)—, COOH—$(C_1-C_{10})$alkyl-, COOH—$(C_3-C_{10})$cycloalkyl-, $(C_1-C_{10})$alkoxy-, $(C_1-C_{10})$alkoxy-$(C_2-C_9)$heterocycloalkyl-, $R^8$-$(C_1-C_{10})$alkyl-, $R^8$-$(C_3-C_{10})$cycloalkyl, $R^8$-$(C_2-C_9)$heterocycloalkyl, $R^8$-$(C_6-C_{14})$aryl, $R^8$-$(C_2-C_9)$heteroaryl, $R^8$-$(C_2-C_{10})$alkylnyl, $R^8$-$(C_1-C_{10})$alkylamine, $R^8$-$((C_1-C_{10})$alkyl$)_2$amine, $R^8$-$(C_2-C_{10})$alkynylamine, $R^8$—C(O)—, $R^8$-$(C_1-C_{10})$alkyl-C(O)O—, $R^8$-$(C_1-C_{10})$-alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^8$-$(C_3-C_{10})$cycloalkyl-O—, $R^8$-$(C_2-C_9)$heterocycloalkyl-O—, $R^8$-$(C_6-C_{14})$aryl-O—, $R^8$-$(C_2-C_9)$heteroaryl-O—, HO—, halo, cyano, $H_2N$—, $(CH_3)HN$—, $(CH_3)_2N$—, $R^8R^9N$—, $R^8R^9N(O)C$—, $R^8(R^9C(O))N$—, $R^8R^9NC(O)O$—, $R^8C(O)$—, $R^8R^9NC(O)R^8N$—, $(C_1-C_{10})$alkyl-OC(O)$R^8N$—, $(C_3-C_{10})$cycloalkyl-OC(O)$R^8N$—, $(C_2-C_9)$heterocycloalkyl-OC(O)$R^8N$—, $(C_6-C_{14})$aryl-OC(O)$R^8N$—, $(C_2-C_9)$heteroaryl-OC(O)$R^8N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S-$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^8R^9NS(O)_2$—, $(C_1-C_{10})$alkyl-S(O)$_2R^8N$—, $(C_3-C_{10})$cycloalkyl-S(O)$_2R^8N$—, $(C_6-C_{14})$aryl-S(O)$_2R^8N$—, $(C_2-C_9)$heterocycloalkyl-SO$_2R^8N$—, and $(C_2-C_9)$heteroaryl-S(O)$_2R^8N$—;

wherein $R^8$ and $R^9$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $(CH_3)_2N$—, and $H_2N$—;

or $R^8$ and $R^9$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—;

$T^1$, $T^2$, and $T^3$ are each independently selected from N or $CR^{10}$, wherein each $R^{10}$ is independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{10A}$-$(C_1-C_{10})$alkyl-, $R^{10A}$-$(C_3-C_{10})$cycloalkyl, $R^{10A}$-$(C_2-C_9)$heterocycloalkyl, $R^{10A}$-$(C_6-C_{14})$aryl, $R^{10A}$-$(C_2-C_9)$heteroaryl, $R^{10A}$-$(C_2-C_{10})$alkylnyl, $R^{10A}$-$(C_1-C_{10})$alkylamine, $R^{10A}$-$((C_1-C_{10})$alkyl$)_2$amine, $R^{10A}$-$(C_2-C_{10})$alkynylamine, $R^{10A}$-C(O)—, $R^{10A}$-$(C_1-C_{10})$alkyl-C(O)O—, $R^{10A}$-$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^{10A}$-$(C_3-C_{10})$cycloalkyl-O—, $R^{10A}$-$(C_2-C_9)$heterocycloalkyl-O—, $R^{10A}$-$(C_6-C_{14})$aryl-O—, $R^{10A}$-$(C_2-C_9)$heteroaryl-O—, HO—, halo, cyano, $H_2N$—, $(CH_3)HN$—, $(CH_3)_2N$—, $R^{10A}R^{11}N$—, $R^{10A}R^{11}N(O)C$—, $R^{10A}(R^{11}C(O))N$—, $R^{10A}R^{11}NC(O)O$—, $R^{10A}C(O)$—, $R^{10A}R^{11}NC(O)R^{10A}N$—, $(C_1-C_{10})$alkyl-OC(O)$R^{10A}N$—, $(C_3-C_{10})$cycloalkyl-OC(O)$R^{10A}N$—, $(C_2-C_9)$heterocycloalkyl-OC(O)$R^{10A}N$—, $(C_6-C_{14})$aryl-OC(O)$R^{10A}N$—, $(C_2-C_9)$heteroaryl-OC(O)$R^{10A}N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S-$(C_1-C_{10})$alkyl-, $(C_3-C_{10})$cycloalkyl-S—, $(C_6-C_{14})$aryl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^{10A}R^{11}NS(O)_2$—, $(C_1-C_{10})$alkyl-S(O)$_2R^{10A}N$—, $(C_3-C_{10})$cycloalkyl-S(O)$_2R^{10A}N$—, $(C_6-C_{14})$aryl-S(O)$_2R^{10A}N$—, $(C_2-C_9)$heterocycloalkyl-SO$_2R^{10A}N$—, and $(C_2-C_9)$heteroaryl-S(O)$_2R^{10A}N$—;

wherein $R^{10A}$ and $R^{11}$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $(CH_3)_2N$—, and $H_2N$—;

or $R^{10A}$ and $R^{11}$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—

$Y^1$ is O, S, or $CR^{12}R^{13}$, wherein $R^{12}$ is absent or $R^{12}$ and $R^{13}$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, and $H_2N$—;

$R^1$ together with the carbon to which it is attached to form a carbonyl and $R^2$ is absent, or $R^1$ and $R^2$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, and $H_2N$—, or $R^1$ and $R^2$ are taken together with the carbon to which they are attached to form a 3 to 10 member ring;

$R^5$ is absent or selected from the group consisting of H, $(C_1-C_{10})$alkyl, HO—, halo, and $H_2N$—, wherein when the dashed lines at $Y^1$ are a double bond, then $R^5$ is absent; and $R^6$ is selected from the group consisting of $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{14}$-$(C_1-C_{10})$alkyl-, $R^{14}$-$(C_3-C_{10})$cycloalkyl, $R^{14}$-$(C_2-C_9)$heterocycloalkyl, $R^{14}$-$(C_6-C_{14})$aryl, $R^{14}$-$(C_2-C_9)$heteroaryl, $R^{14}$-$(C_2-C_{10})$alkylnyl, $R^{14}$-$(C_1-C_{10})$alkylamine, $R^{14}$-$((C_1-C_{10})$alkyl$)_2$amine, $R^{14}$-$(C_2-C_{10})$alkynylamine, $R^{14}$-C(O)—, $R^{14}$-$(C_1-C_{10})$alkyl-C(O)O—, $R^{14}$-$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^{14}$-$(C_3-C_{10})$cycloalkyl-O—, $R^{14}$-$(C_2-C_9)$heterocycloalkyl-O—, $R^{14}$-$(C_6-C_{14})$aryl-O—, $R^{14}$-$(C_2-C_9)$heteroaryl-O—, HO—, halo, cyano, $H_2N$—, $(CH_3)HN$—, $(CH_3)_2N$—, $R^{14}R^{15}N$—, $R^{14}R^{15}N(O)C$—, $R^{14}(R^{15}C(O))N$—, $R^{14}R^{15}NC(O)O$—, $R^{14}C(O)$—, $R^{14}R^{15}NC(O)R^{14}N$—, $(C_1-C_{10})$alkyl-OC(O)$R^{14}N$—, $(C_3-C_{10})$cycloalkyl-OC(O)$R^{14}N$—, $(C_2-C_9)$heterocycloalkyl-OC(O)$R^{14}N$—, $(C_6-C_{14})$aryl-OC(O)$R^{14}N$—, $(C_2-C_9)$heteroaryl-OC(O)$R^{14}N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S-$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^{14}R^{15}NS(O)_2$—, $(C_1-C_{10})$alkyl-S(O)$_2R^{14}N$—, $(C_3-C_{10})$cycloalkyl-S(O)$_2 R^{14}N$—, $(C_6-C_{14})$aryl-S(O)$_2R^{14}N$—, $(C_2-C_9)$heterocycloalkyl-SO$_2R^{14}N$—, and $(C_2-C_9)$heteroaryl-S(O)$_2R^{14}N$—;

wherein $R^{14}$ and $R^{15}$ are each independently selected from the group consisting of H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, $F_2HC$—O—, halo, $(CH_3)_2N$—, $H_2N$—, $F_3C$—C(O)—, $F_3C$—, and $F_2HC$—;

or $R^{14}$ and $R^{15}$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—; and $Z^1$ is selected from H, halo, $(C_1-C_{10})$alkyl, $(C_2-C_9)$heteroalkyl, $(C_1-C_{10})$alkylamine, $((C_1-C_{10})$alkyl$)_2$amine, $(C_2-C_{10})$alkynylamine, $(C_1-C_{10})$alkoxy-, or $H_2N$—;

$Y^2$ is O, S, $NR^{17}$, or $CR^{17}R^{18}$, wherein $R^{17}$ is absent or $R^{17}$ and $R^{18}$ are each independently selected from H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—.

2. A compound according to claim 1, wherein $R^1$ and $R^2$ are each independently selected from H, $(C_1-C_{10})$alkyl, $(C_1-C_{10})$alkylamine, $(C_1-C_{10})$alkoxy-, or $NH_2$.

3. A compound according to claim 1, wherein $Y^1$ is selected from O, S, and $CR^{12}R^{13}$, and $Y^2$ is selected from O, S, $NR^{17}$, or $CR^{17}R^{18}$, wherein $R^{12}$ and $R^{17}$ are each independently absent or H; and $R^{13}$ and $R^{18}$ are each independently H or $(C_1-C_{10})$alkyl.

4. A compound according to claim 1, wherein $Y^1$ and/or $Y^2$ are each independently O.

5. A compound according to claim 1, wherein $T^1$ is $CR^{10}$, $T^2$ is $CR^{10}$, and $T^3$ is $CR^{10}$.

6. A compound according to claim 1, wherein each $R^{10}$ is independently selected from H, $(C_1-C_{10})$alkyl, $(C_3-C_{10})$cycloalkyl, $(C_1-C_{10})$alkoxy, and halo.

7. A compound according to claim 1, wherein $T^1$ is $CR^{10}$, wherein $R^{10}$ is H, $T^2$ is $CR^{10}$, wherein $R^{10}$ is $(C_1-C_{10})$alkyl, and $T^3$ is $CR^{10}$, wherein $R^{10}$ is H.

8. A compound according to claim 1, wherein $Z^1$ is independently selected from H, halo, and $(C_1-C_{10})$alkyl.

9. A compound according to claim 1, wherein each $R^7$ is independently selected from H, $(C_2-C_9)$heterocycloalkyl, $(C_2-C_9)$heteroaryl, $(C_2-C_{10})$alkynylamine, $(C_1-C_{10})$alkoxy-, $(C_1-C_{10})$alkyl-$(C_2-C_9)$heterocycloalkyl, $(C_2-C_9)$heterocycloalkyl-$(C_1-C_{10})$alkoxy-, $(C_1-C_{10})$alkoxy-$(C_2-C_9)$heterocycloalkyl-, $(C_2-C_9)$heteroalkyl-C(O)—, or $F_2HC$—, wherein each $(C_1-C_{10})$alkyl, $(C_2-C_9)$heteroaryl, or $(C_2-C_9)$heterocycloalkyl are further optionally substituted by one to four groups selected from $(C_1-C_{10})$alkyl.

10. A compound according to claim 1, wherein $R^6$ is selected from $(C_1-C_{10})$alkyl, $(C_3-C_{10})$cycloalkyl, $(C_2-C_9)$heteroaryl, $R^{14}$-$(C_6-C_{14})$aryl, $R^{14}$-$(C_2-C_9)$heteroaryl, and R$^{14}$-(C$_1$-C$_{10}$)alkylamine; wherein R$^{14}$ is each independently selected from the group consisting of H, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, (C$_1$-C$_{10}$)alkoxy-, HO—, F$_2$HC—O—, F$_3$C—C(O)—, F$_3$C—, and F$_2$HC—; and wherein each (C$_1$-C$_{10}$)alkyl, (C$_6$-C$_{14}$)aryl, (C$_2$-C$_9$)heteroaryl, (C$_3$-C$_{10}$)cycloalkyl, or (C$_2$-C$_9$)heterocycloalkyl are further optionally substituted by one to four groups selected from (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, HO—, halo, or H$_2$N—.

11. A compound selected from the group consisting of:

4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine
(S)-4-(3-((2-(4-methoxyphenyl)-2,3-dihydrobenzo[b][1,4]clioxin-6-yl)methyl)-3H-imidazo[4,5-b]pyridin-6-yl)-2-methylbut-3-yn-2-amine
(R)-4-(3-((2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine
3-((2-(4-methoxyphenyl)-2,3-dihydrobenzo[b][1,4]clioxin-6-yl)methyl)-6-(4-methylpiperazin-1-yl)-3H-imidazo[4,5-b]pyridine
3-((2-(4-methoxyphenyl)-2,3-dihydrobenzo[b][1,4]clioxin-6-yl)methyl)-6-(1-methyl-1H-pyrazol-4-yl)-3H-imidazo[4,5-b]pyridine
4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine
(S)-4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine
(R)-4-(3-((2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine
3-((2-(6-methoxypyridin-3-yl)-2,3-dihydrobenzo[b][1,4]dioxin-6-yl)methyl)-6-(4-methylpiperazin-1-yl)-3H-imidazo[4,5-b]pyridine
3-((2-(6-methoxypyridin-3-yl)-2,3-dihydrobenzo[b][1,4]dioxin-6-yl)methyl)-3H-imidazo[4,5-b]pyridine-6-carbonitrile
6-(azetidin-1-yl)-3-((2-(6-methoxypyridin-3-yl)-2,3-dihydrobenzo[b][1,4]dioxin-6-yl)methyl)-3H-imidazo[4,5-b]pyridine
6-cyclopropyl-3-((2-(6-methoxypyridin-3-yl)-2,3-dihydrobenzo[b][1,4]dioxin-6-yl)methyl)-3H-imidazo[4,5-b]pyridine
4-(3-((2-(6-methoxypyridin-3-yl)-2,3-dihydrobenzo[b][1,4]dioxin-6-yl)methyl)-3H-imidazo[4,5-b]pyridin-6-yl)morpholine
6-methoxy-3-((2-(6-methoxypyridin-3-yl)-2,3-dihydrobenzo[b][1,4]dioxin-6-yl)methyl)-3H-imidazo[4,5-b]pyridine
4-(3-((2-(4-methoxyphenyl)-3-methyl-2,3-dihydrobenzo[b][1,4]dioxin-6-yl)methyl)-3H-imidazo[4,5-b]pyridin-6-yl)-2-methylbut-3-yn-2-amine
6-methoxy-3-((2-(6-methoxypyridin-3-yl)-3-methyl-2,3-dihydrobenzo[b][1,4]dioxin-6-yl)methyl)-3H-imidazo[4,5-b]pyridine
4-(3-((2-(2,4-dichlorophenyl)-2,3-dihydrobenzo[b][1,4]dioxin-6-yl)methyl)-3H-imidazo[4,5-b]pyridin-6-yl)-2-methylbut-3-yn-2-amine
2,2,2-trifluoro-N-((6-((6-(1-methyl-1H-pyrazol-4-yl)-3H-imidazo[4,5-b]pyridin-3-yl)methyl)-2,3-dihydrobenzo[b][1,4]dioxin-2-yl)methyl)acetamide
6-(3-methoxyazetidin-1-yl)-3-((2-(6-methoxypyridin-3-yl)-2,3-dihydrobenzo[b][1,4]dioxin-6-yl)methyl)-3H-imidazo[4,5-b]pyridine
2-methyl-4-(3-((2-(1-methyl-1H-pyrazol-4-yl)-2,3-dihydrobenzo[b][1,4]dioxin-6-yl)methyl)-3H-imidazo[4,5-b]pyridin-6-yl)but-3-yn-2-amine
4-(3-(1-(2-(6-methoxypyridin-3-yl)-2,3-dihydrobenzo[b][1,4]dioxin-6-yl)ethyl)-3H-imidazo[4,5-b]pyridin-6-yl)-2-methylbut-3-yn-2-amine
3-((2-(4-(difluoromethoxy)phenyl)-2,3-dihydrobenzo[b][1,4]dioxin-6-yl)methyl)-3H-imidazo[4,5-b]pyridine
6-(1,3-dimethyl-1H-pyrazol-4-yl)-3-((2-(2-fluoro-4-methoxyphenyl)-2,3-dihydrobenzo[b][1,4]dioxin-6-yl)methyl)-3H-imidazo[4,5-b]pyridine
4-(3-((8-fluoro-2-(4-(trifluoromethyl)phenyl)-2,3-dihydrobenzo[b][1,4]dioxin-6-yl)methyl)-3H-imidazo[4,5-b]pyridin-6-yl)-2-methylbut-3-yn-2-amine
3-((8-fluoro-2-(4-(trifluoromethyl)phenyl)-2,3-dihydrobenzo[b][1,4]dioxin-6-yl)methyl)-6-(4-methylpiperazin-1-yl)-3H-imidazo[4,5-b]pyridine
3-((8-fluoro-2-(4-(trifluoromethyl)phenyl)-2,3-dihydrobenzo[b][1,4]dioxin-6-yl)methyl)-6-(piperidin-3-ylethynyl)-3H-imidazo[4,5-b]pyridinehydrochloride
3-((8-fluoro-2-(4-(trifluoromethyl)phenyl)-2,3-dihydrobenzo[b][1,4]dioxin-6-yl)methyl)-6-(1-methyl-1H-pyrazol-4-yl)-3H-imidazo[4,5-b]pyridine2,2,2-trifluoroacetate
3-((8-fluoro-2-(6-methoxypyridin-3-yl)-5-methyl-2,3-dihydrobenzo[b][1,4]dioxin-6-yl)methyl)-6-iodo-3H-imidazo[4,5-b]pyridine
6-cyclopropyl-3-((8-fluoro-2-(6-methoxypyridin-3-yl)-5-methyl-2,3-dihydrobenzo[b][1,4]dioxin-6-yl)methyl)-3H-imidazo[4,5-b]pyridine
2,2,2-trifluoroacetate
4-(3-((8-fluoro-2-(6-methoxypyridin-3-yl)-5-methyl-2,3-dihydrobenzo[b][1,4]dioxin-6-yl)methyl)-3H-imidazo[4,5-b]pyridin-6-yl)-2-methylbut-3-yn-2-amine
3-((8-fluoro-2-(6-methoxypyridin-3-yl)-5-methyl-2,3-dihydrobenzo[b][1,4]dioxin-6-yl)methyl)-6-(1-methyl-1H-pyrazol-4-yl)-3H-imidazo[4,5-b]pyridine
3-((5-cyclopropyl-8-fluoro-2-(6-methoxypyridin-3-yl)-2,3-dihydrobenzo[b][1,4]dioxin-6-yl)methyl)-6-(1-methyl-1H-pyrazol-4-yl)-3H-imidazo[4,5-b]pyridine
4-(3-((8-fluoro-2-(6-methoxypyridin-3-yl)-5,7-dimethyl-2,3-dihydrobenzo[b][1,4]dioxin-6-yl)methyl)-3H-imidazo[4,5-b]pyridin-6-yl)-2-methylbut-3-yn-2-amine2,2,2-trifluoroacetate
4-(3-((8-fluoro-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine
3-((8-fluoro-2-(6-methoxypyridin-3-yl)-2,3-dihydrobenzo[b][1,4]dioxin-6-yl)methyl)-6-(piperidin-3-ylethynyl)-3H-imidazo[4,5-b]pyridine
4-(3-((8-fluoro-2-(6-methoxypyridin-3-yl)-2,3-dihydrobenzo[b][1,4]dioxin-6-yl)methyl)-3H-imidazo[4,5-b]pyridin-6-yl)morpholine
3-((8-fluoro-2-(6-methoxypyridin-3-yl)-2,3-dihydrobenzo[b][1,4]dioxin-6-yl)methyl)-6-(2-methyl-1H-imidazol-1-yl)-3H-imidazo[4,5-b]pyridine
4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine
(S)-4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine
(R)-4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-amine
3-((8-methoxy-2-(6-methoxypyridin-3-yl)-2,3-dihydrobenzo[b][1,4]dioxin-6-yl)methyl)-6-(1-methyl-1H-pyrazol-4-yl)-3H-imidazo[4,5-b]pyridine
4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)morpholine
6-cyclopropyl-3-((8-methoxy-2-(6-methoxypyridin-3-yl)-2,3-dihydrobenzo[b][1,4]dioxin-6-yl)methyl)-3H-imidazo[4,5-b]pyridine
4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-methylbut-3-yn-2-ol
6-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-2-oxa-6-azaspiro[3.3]heptane
3-((8-methoxy-2-(6-methoxypyridin-3-yl)-2,3-dihydrobenzo[b][1,4]dioxin-6-yl)methyl)-6-(3-methoxyprop-1-yn-1-yl)-3H-imidazo[4,5-b]pyridine
4-(3-((8-methoxy-2-(6-methoxypyridin-3-yl)-2,3-dihydrobenzo[b][1,4]dioxin-6-yl)methyl)-3H-imidazo[4,5-b]pyridin-6-yl)isoxazole
6-methoxy-3-((8-methoxy-2-(6-methoxypyridin-3-yl)-2,3-dihydrobenzo[b][1,4]dioxin-6-yl)methyl)-3H-imidazo[4,5-b]pyridine
(S)-6-methoxy-3-((8-methoxy-2-(6-methoxypyridin-3-yl)-2,3-dihydrobenzo[b][1,4]dioxin-6-yl)methyl)-3H-imidazo[4,5-b]pyridine
(R)-6-methoxy-3-((8-methoxy-2-(6-methoxypyridin-3-yl)-2,3-dihydrobenzo[b][1,4]dioxin-6-yl)methyl)-3H-imidazo[4,5-b]pyridine
3-((8-methoxy-2-(6-methoxypyridin-3-yl)-2,3-dihydrobenzo[b][1,4]dioxin-6-yl)methyl)-6-(3-methoxyazetidin-1-yl)-3H-imidazo[4,5-b]pyridine
6-(azetidin-1-yl)-3-((8-methoxy-2-(6-methoxypyridin-3-yl)-2,3-dihydrobenzo[b][1,4]dioxin-6-yl)methyl)-3H-imidazo[4,5-b]pyridine
2-((3-((8-methoxy-2-(6-methoxypyridin-3-yl)-2,3-dihydrobenzo[b][1,4]dioxin-6-yl)methyl)-3H-imidazo[4,5-b]pyridin-6-yl)oxy)-N,N-dimethylethan-1-amine
3-((8-methoxy-2-(6-methoxypyridin-3-yl)-2,3-dihydrobenzo[b][1,4]dioxin-6-yl)methyl)-6-(oxetan-3-yloxy)-3H-imidazo[4,5-b]pyridine
3-((8-methoxy-2-(6-methoxypyridin-3-yl)-2,3-dihydrobenzo[b][1,4]dioxin-6-yl)methyl)-N,N-dimethyl-3H-imidazo[4,5-b]pyridin-6-amine
1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-3-methylazetidin-3-ol
3-((8-methoxy-2-(6-methoxypyridin-3-yl)-2,3-dihydrobenzo[b][1,4]dioxin-6-yl)methyl)-6-(1H-1,2,4-triazol-1-yl)-3H-imidazo[4,5-b]pyridine
3-((8-methoxy-2-(6-methoxypyridin-3-yl)-2,3- dihydrobenzo[b][1,4]dioxin-6-yl)methyl)-6-(1H-pyrazol-1-yl)-3H-imidazo[4,5-b]pyridine
6-(1H-imidazol-1-yl)-3-((8-methoxy-2-(6-methoxypyridin-3-yl)-2,3-dihydrobenzo[b][1,4]dioxin-6-yl)methyl)-3H-imidazo[4,5-b]pyridine
3-((8-methoxy-2-(6-methoxypyridin-3-yl)-2,3-dihydrobenzo[b][1,4]dioxin-6-yl)methyl)-6-(2-methyl-1H-imidazol-1-yl)-3H-imidazo[4,5-b]pyridine
6-(2,4-dimethyl-1H-imidazol-1-yl)-3-((8-methoxy-2-(6-methoxypyridin-3-yl)-2,3-dihydrobenzo[b][1,4]dioxin-6-yl)methyl)-3H-imidazo[4,5-b]pyridine
3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine
3-((8-methoxy-2-(6-methoxypyridin-3-yl)-2,3-dihydrobenzo[b][1,4]dioxin-6-yl)methyl)-6-methyl-3H-imidazo[4,5-b]pyridine
3-((8-methoxy-2-(6-methoxypyridin-3-yl)-2,3-dihydrobenzo[b][1,4]dioxin-6-yl)methyl)-N-methyl-3H-imidazo[4,5-b]pyridin-6-amine
6-(1,3-dimethyl-1H-pyrazol-4-yl)-3-((8-methoxy-2-(6-methoxypyridin-3-yl)-2,3-dihydrobenzo[b][1,4]dioxin-6-yl)methyl)-3H-imidazo[4,5-b]pyridine
6-(6-fluoropyridin-3-yl)-3-((8-methoxy-2-(6-methoxypyridin-3-yl)-2,3-dihydrobenzo[b][1,4]dioxin-6-yl)methyl)-3H-imidazo[4,5-b]pyridine
1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)azetidin-3-ol
3-((8-methoxy-2-(6-methoxypyridin-3-yl)-2,3-dihydrobenzo[b][1,4]dioxin-6-yl)methyl)-6-(4-methylpiperazin-1-yl)-3H-imidazo[4,5-b]pyridine
1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)-3-methylazetidin-3-amine
6-(3-fluoroazetidin-1-yl)-3-((8-methoxy-2-(6-methoxypyridin-3-yl)-2,3-dihydrobenzo[b][1,4]dioxin-6-yl)methyl)-3H-imidazo[4,5-b]pyridine
6-fluoro-3-((8-methoxy-2-(6-methoxypyridin-3-yl)-2,3-dihydrobenzo[b][1,4]dioxin-6-yl)methyl)-3H-imidazo[4,5-b]pyridine
3-((8-methoxy-2-(6-methoxypyridin-3-yl)-2,3-dihydrobenzo[b][1,4]dioxin-6-yl)methyl)-3H-imidazo[4,5-b]pyridine
azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone
(S)-azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone
(R)-azetidin-1-yl(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanone
(3-((8-methoxy-2-(6-methoxypyridin-3-yl)-2,3-dihydrobenzo[b][1,4]dioxin-6-yl)methyl)-3H-imidazo[4,5-b]pyridin-6-yl)methanol
3-((8-methoxy-2-(6-methoxypyridin-3-yl)-2,3-dihydrobenzo[b][1,4]dioxin-6-yl)methyl)-6-(methoxymethyl)-3H-imidazo[4,5-b]pyridine
6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine
(S)-6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine
(R)-6-(difluoromethyl)-3-((8-methoxy-2-(6-methoxypyridin-3-yl)-2,3-dihydrobenzo[b][1,4]dioxin-6-yl)methyl)-3H-imidazo[4,5-b]pyridine
6-methoxy-3-((8-methoxy-2-(6-methoxypyridin-3-yl)-2,3-dihydrobenzo[b][1,4]dioxin-6-yl)methyl)-2-methyl-3H-imidazo[4,5-b]pyridine
6-(azetidin-3-yl)-3-((8-methoxy-2-(6-methoxypyridin-3-yl)-2,3-dihydrobenzo[b][1,4]dioxin-6-yl)methyl)-3H-imidazo[4,5-b]pyridine 2,2,2-trifluoroacetate
6-(1H-imidazol-2-yl)-3-((8-methoxy-2-(6-methoxypyridin-3-yl)-2,3-dihydrobenzo[b][1,4]dioxin-6-yl)methyl)-3H-imidazo[4,5-b]pyridine formate
3-((8-methoxy-2-(6-methoxypyridin-3-yl)-2,3-dihydrobenzo[b][1,4]dioxin-6-yl)methyl)-6-(4-methyl-1H-imidazol-2-yl)-3H-imidazo[4,5-b]pyridine
3-((8-methoxy-2-(6-methoxypyridin-3-yl)-2,3-dihydrobenzo[b][1,4]dioxin-6-yl)methyl)-3H-imidazo[4,5-b]pyridine
3-(((2R,3S)-8-methoxy-2-(6-methoxypyridin-3-yl)-3-methyl-2,3-dihydrobenzo[b][1,4]dioxin-6-yl)methyl)-3H-imidazo[4,5-b]pyridine
3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine
3-(((2S,3R)-8-methoxy-2-(6-methoxypyridin-3-yl)-3-methyl-2,3-dihydrobenzo[b][1,4]dioxin-6-yl)methyl)-3H-imidazo[4,5-b]pyridine
3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine
6-methoxy-3-((8-methoxy-2-(6-methoxypyridin-3-yl)-3-methyl-2,3-dihydrobenzo[b][1,4]dioxin-6-yl)methyl)-3H-imidazo[4,5-b]pyridine
6-methoxy-3-(((2R,3S)-8-methoxy-2-(6-methoxypyridin-3-yl)-3-methyl-2,3-dihydrobenzo[b][1,4]dioxin-6-yl)methyl)-3H-imidazo[4,5-b]pyridine
4-(3-((8-methoxy-2-(6-methoxypyridin-3-yl)-2-methyl-2,3-dihydrobenzo[b][1,4]dioxin-6-yl)methyl)-3H-imidazo[4,5-b]pyridin-6-yl)-2-methylbut-3-yn-2-amine
3-((2-(6-cyclopropylpyridin-3-yl)-8-methoxy-2,3-dihydrobenzo[b][1,4]dioxin-6-yl)methyl)-3H-imidazo[4,5-b]pyridine
3-((2-(6-cyclopropylpyridin-3-yl)-8-methoxy-2,3-dihydrobenzo[b][1,4]dioxin-6-yl)methyl)-5-methyl-3H-imidazo[4,5-b]pyridine
3-((2-(6-cyclopropylpyridin-3-yl)-8-methoxy-2,3-dihydrobenzo[b][1,4]dioxin-6-yl)methyl)-6-((1-methylazetidin-3-yl)oxy)-3H-imidazo[4,5-b]pyridine
(3-((2-(6-cyclopropylpyridin-3-yl)-8-methoxy-2,3-dihydrobenzo[b][1,4]dioxin-6-yl)methyl)-3H-imidazo[4,5-b]pyridin-6-yl)methanol
4-(3-((8-methoxy-2-(6-methylpyridin-3-yl)-2,3-dihydrobenzo[b][1,4]dioxin-6-yl)methyl)-3H-imidazo[4,5-b]pyridin-6-yl)-2-methylbut-3-yn-2-amine
3-((8-methoxy-2-(6-methylpyridin-3-yl)-2,3-dihydrobenzo[b][1,4]dioxin-6-yl)methyl)-6-(2-methyl-1H-imidazol-1-yl)-3H-imidazo[4,5-b]pyridinehydrochloride
6-methoxy-3-((8-methoxy-2-(6-methylpyridin-3-yl)-2,3-dihydrobenzo[b][1,4]dioxin-6-yl)methyl)-3H-imidazo[4,5-b]pyridine
3-((8-methoxy-2-(6-methylpyridin-3-yl)-2,3-dihydrobenzo[b][1,4]dioxin-6-yl)methyl)-3H-imidazo[4,5-b]pyridine
3-((8-methoxy-2-(6-methylpyridin-3-yl)-2,3-dihydrobenzo[b][1,4]dioxin-6-yl)methyl)-6-(3-methoxyazetidin-1-yl)-3H-imidazo[4,5-b]pyridine
1-(3-((8-methoxy-2-(6-methylpyridin-3-yl)-2,3-dihydrobenzo[b][1,4]dioxin-6-yl)methyl)-3H-imidazo[4,5-b]pyridin-6-yl)azetidin-3-ol
3-((8-methoxy-2-(6-propylpyridin-3-yl)-2,3-dihydrobenzo[b][1,4]dioxin-6-yl)methyl)-3H-imidazo[4,5-b]pyridine
3-((2-(6-ethylpyridin-3-yl)-8-methoxy-2,3-dihydrobenzo[b][1,4]dioxin-6-yl)methyl)-3H-imidazo[4,5-b]pyridine
4-(3-((2-(6-ethylpyridin-3-yl)-8-methoxy-2,3-dihydrobenzo[b][1,4]dioxin-6-yl)methyl)-3H-imidazo[4,5-b]pyridin-6-yl)morpholine
3-((2-(6-ethylpyridin-3-yl)-8-methoxy-2,3-dihydrobenzo[b][1,4]dioxin-6-yl)methyl)-6-((1-methylazetidin-3-yl)oxy)-3H-imidazo[4,5-b]pyridine
3-((2-(6-ethylpyridin-3-yl)-8-methoxy-2,3-dihydrobenzo[b][1,4]dioxin-6-yl)methyl)-6-methoxy-3H-imidazo[4,5-b]pyridine
3-((8-methoxy-2-(6-methylpyridin-3-yl)-2,3-dihydrobenzo[b][1,4]dioxin-6-yl)methyl)-6-(trifluoromethyl)-3H-imidazo[4,5-b]pyridine
3-((2-(4,6-dimethylpyridin-3-yl)-8-methoxy-2,3-dihydrobenzo[b][1,4]dioxin-6-yl)methyl)-6-methoxy-3H-imidazo[4,5-b]pyridine
3-((2-(4,6-dimethylpyridin-3-yl)-8-methoxy-2,3-dihydrobenzo[b][1,4]dioxin-6-yl)methyl)-6-(3-methoxyazetidin-1-yl)-3H-imidazo[4,5-b]pyridine
4-(3-((8-methoxy-2-(4-methoxyphenyl)-2,3-dihydrobenzo[b][1,4]dioxin-6-yl)methyl)-3H-imidazo[4,5-b]pyridin-6-yl)-2-methylbut-3-yn-2-amine
3-((8-methoxy-2-(4-methoxyphenyl)-2,3-dihydrobenzo[b][1,4]dioxin-6-yl)methyl)-6-(1-methyl-1H-imidazol-4-yl)-3H-imidazo[4,5-b]pyridine
6-bromo-3-((2-(4-(difluoromethoxy)phenyl)-8-methoxy-2,3-dihydrobenzo[b][1,4]dioxin-6-yl)methyl)-3H-imidazo[4,5-b]pyridine hydrochloride
3-((2-(4-(difluoromethoxy)phenyl)-8-methoxy-2,3-dihydrobenzo[b][1,4]dioxin-6-yl)methyl)-3H-imidazo[4,5-b]pyridine hydrochloride
4-(3-((2-(4-(difluoromethoxy)phenyl)-8-methoxy-2,3-dihydrobenzo[b][1,4]dioxin-6-yl)methyl)-3H-imidazo[4,5-b]pyridin-6-yl)-2-methylbut-3-yn-2-amine
1-(3-((2-(4-(difluoromethoxy)phenyl)-8-methoxy-2,3-dihydrobenzo[b][1,4]dioxin-6-yl)methyl)-3H-imidazo[4,5-b]pyridin-6-yl)-N,N-dimethylazetidin-3-amine
3-((2-(4-(difluoromethoxy)phenyl)-8-methoxy-2,3-dihydrobenzo[b][1,4]dioxin-6-yl)methyl)-N-methyl-3H-imidazo[4,5-b]pyridin-6-amine
4-(3-((8-methoxy-2-(pyridin-3-yl)-2,3-dihydrobenzo[b][1,4]dioxin-6-yl)methyl)-3H-imidazo[4,5-b]pyridin-6-yl)-2-methylbut-3-yn-2-amine
6-(1H-imidazol-1-yl)-3-((8-methoxy-2-(pyridin-3-yl)-2,3- dihydrobenzo[b][1,4]dioxin-6-yl)methyl)-3H-imidazo[4,5-b]pyridine
4-(3-((8-methoxy-2-(2-methylthiazol-4-yl)-2,3-dihydrobenzo[b][1,4]dioxin-6-yl)methyl)-3H-imidazo[4,5-b]pyridin-6-yl)-2-methylbut-3-yn-2-amine
4-(6-((6-(3-(1H-imidazol-1-yl)prop-1-yn-1-yl)-3H-imidazo[4,5-b]pyridin-3-yl)methyl)-8-methoxy-2,3-dihydrobenzo[b][1,4]dioxin-2-yl)-2-methylthiazole
4-(3-((8-methoxy-2-(2-methylthiazol-4-yl)-2,3-dihydrobenzo[b][1,4]dioxin-6-yl)methyl)-3H-imidazo[4,5-b]pyridin-6-yl)morpholine
4-(64(3H-imidazo[4,5-b]pyridin-3-yl)methyl)-8-methoxy-2,3-dihydrobenzo[b][1,4]dioxin-2-yl)-2-cyclopropylthiazole
4-(3-((2-(2-cyclopropylthiazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine
2-cyclopropyl-4-(8-methoxy-6-((6-methoxy-3H-imidazo[4,5-b]pyridin-3-yl)methyl)-2,3-dihydrobenzo[b][1,4]dioxin-2-yl)thiazole
4-(3-((2-(2,5-dimethylthiazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine
4-(3-((8-methoxy-2-(2-methyloxazol-4-yl)-2,3-dihydrobenzo[b][1,4]dioxin-6-yl)methyl)-3H-imidazo[4,5-b]pyridin-6-yl)-2-methylbut-3-yn-2-amine
4-(3-((2-(2,5-dimethyloxazol-4-yl)-8-methoxy-2,3-dihydrobenzo[b][1,4]dioxin-6-yl)methyl)-3H-imidazo[4,5-b]pyridin-6-yl)-2-methylbut-3-yn-2-amine
3-((8-methoxy-2-(6-(2-methoxyethoxy)pyridin-3-yl)-2,3-dihydrobenzo[b][1,4]dioxin-6-yl)methyl)-3H-imidazo[4,5-b]pyridine
4-(3-((8-methoxy-2-(6-(2-methoxyethoxy)pyridin-3-yl)-2,3-dihydrobenzo[b][1,4]dioxin-6-yl)methyl)-3H-imidazo[4,5-b]pyridin-6-yl)-2-methylbut-3-yn-2-amine
3-((8-methoxy-2-(6-(2-methoxyethoxy)pyridin-3-yl)-2,3-dihydrobenzo[b][1,4]dioxin-6-yl)methyl)-6-(1-methyl-1H-imidazol-4-yl)-3H-imidazo[4,5-b]pyridine
6-methoxy-3-((8-methoxy-2-(6-(2-methoxyethoxy)pyridin-3-yl)-2,3-dihydrobenzo[b][1,4]dioxin-6-yl)methyl)-3H-imidazo[4,5-b]pyridine
3-(2-(6-ethoxypyridin-3-yl)-8-methoxy-2,3-dihydrobenzo[b][1,4]dioxin-6-yl)methyl)-3H-imidazo[4,5-b]pyridine
3-((2-(6-ethoxypyridin-3-yl)-8-methoxy-2,3-dihydrobenzo[b][1,4]dioxin-6-yl)methyl)-6-methoxy-3H-imidazo[4,5-b]pyridine
(3-((2-(6-ethoxypyridin-3-yl)-8-methoxy-2,3-dihydrobenzo[b][1,4]dioxin-6-yl)methyl)-3H-imidazo[4,5-b]pyridin-6-yl)methanol
3-((2-(6-(difluoromethoxy)pyridin-3-yl)-8-methoxy-2,3-dihydrobenzo[b][1,4]dioxin-6-yl)methyl)-6-methoxy-3H-imidazo[4,5-b]pyridine
1-(3-((2-(6-(difluoromethoxy)pyridin-3-yl)-8-methoxy-2,3-dihydrobenzo[b][1,4]dioxin-6-yl)methyl)-3H-imidazo[4,5-b]pyridin-6-yl)-3-methylazetidin-3-ol
3-((2-(6-(difluoromethoxy)pyridin-3-yl)-8-methoxy-2,3-dihydrobenzo[b][1,4]dioxin-6-yl)methyl)-3H-imidazo[4,5-b]pyridine
3-((8-methoxy-2,3-dihydrobenzo[b][1,4]dioxin-6-yl)methyl)-6-(1-(piperidin-4-yl)-1H-pyrazol-4-yl)-3H-imidazo[4,5-b]pyridine
3-((8-methoxy-2-methyl-2,3-dihydrobenzo[b][1,4]dioxin-6-yl)methyl)-6-(1-(piperidin-4-yl)-1H-pyrazol-4-yl)-3H-imidazo[4,5-b]pyridine
3-((8-methoxy-2-methyl-2,3-dihydrobenzo[b][1,4]dioxin-6-yl)methyl)-6-(pyridin-3-yl)-3H-imidazo[4,5-b]pyridineformate
3-((8-methoxy-2-methyl-2,3-dihydrobenzo[b][1,4]dioxin-6-yl)methyl)-6-(1-methyl-1H-pyrazol-4-yl)-3H-imidazo[4,5-b]pyridineformate
3-((2-cyclopropyl-8-methoxy-2,3-dihydrobenzo[b][1,4]dioxin-6-yl)methyl)-6-(1-(piperidin-4-yl)-1H-pyrazol-4-yl)-3H-imidazo[4,5-b]pyridine
3-((2-cyclopropyl-8-methoxy-2,3-dihydrobenzo[b][1,4]dioxin-6-yl)methyl)-6-(1-methyl-1H-imidazol-4-yl)-3H-imidazo[4,5-b]pyridine
4-(3-((2-cyclopropyl-8-methoxy-2,3-dihydrobenzo[b][1,4]dioxin-6-yl)methyl)-3H-imidazo[4,5-b]pyridin-6-yl)-2-methylbut-3-yn-2-amine
3-((2-isopropyl-8-methoxy-2,3-dihydrobenzo[b][1,4]dioxin-6-yl)methyl)-6-(1-methyl-1H-pyrazol-4-yl)-3H-imidazo[4,5-b]pyridine formate
4-(3-((2-isopropyl-8-methoxy-2,3-dihydrobenzo[b][1,4]dioxin-6-yl)methyl)-3H-imidazo[4,5-b]pyridin-6-yl)-3,5-dimethylisoxazole
3-((2-cyclopropyl-8-methoxy-3-methyl-2,3-dihydrobenzo[b][1,4]dioxin-6-yl)methyl)-6-(1-methyl-1H-pyrazol-4-yl)-3H-imidazo[4,5-b]pyridine
3-((2-(6-(difluoromethyl)pyridin-3-yl)-8-methoxy-2,3-dihydrobenzo[b][1,4]dioxin-6-yl)methyl)-3H-imidazo[4,5-b]pyridine
3-((2-(2-cyclopropylpyrimidin-5-yl)-8-methoxy-2,3-dihydrobenzo[b][1,4]dioxin-6-yl)methyl)-3H-imidazo[4,5-b]pyridine
3-((8-methoxy-2-(6-methoxy-2-methylpyridin-3-yl)-2,3-dihydrobenzo[b][1,4]dioxin-6-yl)methyl)-3H-imidazo[4,5-b]pyridine
3-((8-methoxy-2-(6-methoxy-2-methylpyridin-3-yl)-2,3-dihydrobenzo[b][1,4]dioxin-6-yl)methyl)-6-(3-methoxyazetidin-1-yl)-3H-imidazo[4,5-b]pyridine
6-methoxy-3-((8-methoxy-2-(6-methoxy-2-methylpyridin-3-yl)-2,3-dihydrobenzo[b][1,4]dioxin-6-yl)methyl)-3H-imidazo[4,5-b]pyridine
3-((2-(2,6-dimethoxypyridin-3-yl)-8-methoxy-2,3-dihydrobenzo[b][1,4]dioxin-6-yl)methyl)-3H-imidazo[4,5-b]pyridine
3-((2-(2,6-dimethoxypyridin-3-yl)-8-methoxy-2,3-dihydrobenzo[b][1,4]dioxin-6-yl)methyl)-6-methoxy-3H-imidazo[4,5-b]pyridine
3-((2-(2,6-dimethoxypyridin-3-yl)-8-methoxy-2,3-dihydrobenzo[b][1,4]dioxin-6-yl)methyl)-6-(3-methoxyazetidin-1-yl)-3H-imidazo[4,5-b]pyridine
3-((8-methoxy-2-(6-(trifluoromethyl)pyridin-3-yl)-2,3-dihydrobenzo[b][1,4]dioxin-6-yl)methyl)-3H-imidazo[4,5-b]pyridine
(S)-3-((8-methoxy-2-(6-(trifluoromethyl)pyridin-3-yl)-2,3-dihydrobenzo[b][1,4]dioxin-6-yl)methyl)-3H-imidazo[4,5-b]pyridine
(R)-3-((8-methoxy-2-(6-(trifluoromethyl)pyridin-3-yl)-2,3-dihydrobenzo[b][1,4]dioxin-6-yl)methyl)-3H-imidazo[4,5-b]pyridine
6-methoxy-3-((8-methoxy-2-(6-methoxy-4-methylpyridin-3-yl)-2,3-dihydrobenzo[b][1,4]dioxin-6-yl)methyl)-3H-imidazo[4,5-b]pyridine
3-((8-methoxy-2-(6-methoxy-4-methylpyridin-3-yl)-2,3-dihydrobenzo[b][1,4]dioxin-6-yl)methyl)-3H-imidazo[4,5-b]pyridine
5-(6-((3H-imidazo[4,5-b]pyridin-3-yl)methyl)-8-methoxy-2,3-dihydrobenzo[b][1,4]dioxin-2-yl)-N,N-diethylpyridin-2-amine
4-(5-(6-((3H-imidazo[4,5-b]pyridin-3-yl)methyl)-8-methoxy-2,3-dihydrobenzo[b][1,4]dioxin-2-yl)pyridin-2-yl)morpholine
3-((8-methoxy-2-(1-methyl-1H-pyrazol-4-yl)-2,3-dihydrobenzo[b][1,4]dioxin-6-yl)methyl)-3H-imidazo[4,5-b]pyridine
3-((2-(1-cyclobutyl-1H-pyrazol-4-yl)-8-methoxy-2,3-dihydrobenzo[b][1,4]dioxin-6-yl)methyl)-3H-imidazo[4,5-b]pyridine
3-((2-(1-isopropyl-1H-pyrazol-4-yl)-8-methoxy-2,3-dihydrobenzo[b][1,4]dioxin-6-yl)methyl)-3H-imidazo[4,5-b]pyridine
3-((8-methoxy-2-(6-(methoxymethyl)pyridin-3-yl)-2,3-dihydrobenzo[b][1,4]dioxin-6-yl)methyl)-3H-imidazo[4,5-b]pyridine
3-((8-methoxy-2-(5-methoxypyrazin-2-yl)-2,3-dihydrobenzo[b][1,4]dioxin-6-yl)methyl)-3H-imidazo[4,5-b]pyridine
3-((8-methoxy-2-(2-methoxypyrimidin-5-yl)-2,3-dihydrobenzo[b][1,4]dioxin-6-yl)methyl)-3H-imidazo[4,5-b]pyridine
3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine
(R)-3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine
(S)-3-((2-(6-(1,1-difluoroethyl)pyridin-3-yl)-8-methoxy-2,3-dihydrobenzo[b][1,4]dioxin-6-yl)methyl)-3H-imidazo[4,5-b]pyridine
5-(6-((3H-imidazo[4,5-b]pyridin-3-yl)methyl)-8-methoxy-2,3-dihydrobenzo[b][1,4]dioxin-2-yl)furo[2,3-b]pyridine
5-(6-((3H-imidazo[4,5-b]pyridin-3-yl)methyl)-8-methoxy-2,3-dihydrobenzo[b][1,4]dioxin-2-yl)-2,3-dihydrofuro[2,3-b]pyridine
3-((2-(1-(cyclopropylmethyl)-1H-pyrazol-4-yl)-8-methoxy-2,3-dihydrobenzo[b][1,4]dioxin-6-yl)methyl)-3H-imidazo[4,5-b]pyridine
3-((2-(4,4-difluorocyclohexyl)-8-methoxy-2,3-dihydrobenzo[b][1,4]dioxin-6-yl)methyl)-3H-imidazo[4,5-b]pyridine
3-((8-methoxy-2-(1-(2-methoxyethyl)-1H-pyrazol-4-yl)-2,3-dihydrobenzo[b][1,4]dioxin-6-yl)methyl)-3H-imidazo[4,5-b]pyridine
3-((2-butyl-8-methoxy-2,3-dihydrobenzo[b][1,4]dioxin-6-yl)methyl)-3H-imidazo[4,5-b]pyridine
6-methoxy-3-((8-methoxy-2-(1-methyl-1H-pyrazol-4-yl)-2,3-dihydrobenzo[b][1,4]dioxin-6-yl)methyl)-3H-imidazo[4,5-b]pyridine
3-((2-(1,5-dimethyl-1H-pyrazol-4-yl)-8-methoxy-2,3-dihydrobenzo[b][1,4]dioxin-6-yl)methyl)-6-methoxy-3H-imidazo[4,5-b]pyridine
3-((2-(1,3-dimethyl-1H-pyrazol-4-yl)-8-methoxy-2,3-dihydrobenzo[b][1,4]dioxin-6-yl)methyl)-6-methoxy-3H-imidazo[4,5-b]pyridine
3-((2-(1-(cyclopropylmethyl)-1H-pyrazol-4-yl)-8-methoxy-2,3-dihydrobenzo[b][1,4]dioxin-6-yl)methyl)-6-methoxy-3H-imidazo[4,5-b]pyridine
3-((2-(1-cyclobutyl-1H-pyrazol-4-yl)-8-methoxy-2,3-dihydrobenzo[b][1,4]dioxin-6-yl)methyl)-6-methoxy-3H-imidazo[4,5-b]pyridine
6-methoxy-3-((8-methoxy-2-(6-(methoxymethyl)pyridin-3-yl)-2,3-dihydrobenzo[b][1,4]dioxin-6-yl)methyl)-3H-imidazo[4,5-b]pyridine
3-((2-butyl-8-methoxy-2,3-dihydrobenzo[b][1,4]dioxin-6-yl)methyl)-6-methoxy-3H-imidazo[4,5-b]pyridine
6-(azetidin-1-yl)-3-((8-methoxy-2-(1-methyl-1H-pyrazol-4-yl)-2,3-dihydrobenzo[b][1,4]dioxin-6-yl)methyl)-3H-imidazo[4,5-b]pyridine
3-((8-methoxy-2-(1-methyl-1H-pyrazol-4-yl)-2,3- dihydrobenzo[b][1,4]dioxin-6-yl)methyl)-6-(3-methoxyazetidin-1-yl)-3H-imidazo[4,5-b]pyridine
6-cyclopropyl-3-((8-methoxy-2-(1-methyl-1H-pyrazol-4-yl)-2,3-dihydrobenzo[b][1,4]dioxin-6-yl)methyl)-3H-imidazo[4,5-b]pyridine
6-cyclopropyl-3-((8-methoxy-2-(6-(methoxymethyl)pyridin-3-yl)-2,3-dihydrobenzo[b][1,4]dioxin-6-yl)methyl)-3H-imidazo[4,5-b]pyridine
6-(difluoromethyl)-3-((8-methoxy-2-(6-(methoxymethyl)pyridin-3-yl)-2,3-dihydrobenzo[b][1,4]dioxin-6-yl)methyl)-3H-imidazo[4,5-b]pyridine
(3-((2-(1-cyclobutyl-1H-pyrazol-4-yl)-8-methoxy-2,3-dihydrobenzo[b][1,4]dioxin-6-yl)methyl)-3H-imidazo[4,5-b]pyridin-6-yl)methanol
3-((8-methoxy-2-(6-methylpyridin-3-yl)-2,3-dihydrobenzo[b][1,4]dioxin-6-yl)methyl)-6-(trifluoromethyl)-3H-imidazo[4,5-b]pyridine
1-(3-((8-methoxy-2-(6-methoxypyridin-3-yl)-2,3-dihydrobenzo[b][1,4]dioxin-6-yl)methyl)-3H-imidazo[4,5-b]pyridin-6-yl)azetidin-2-one
4-(3-((2-(6-methoxypyridin-3-yl)chroman-6-yl)methyl)-3H-imidazo[4,5-b]pyridin-6-yl)-2-methylbut-3-yn-2-amine
4-(3-((8-methoxy-2-(4-methoxyphenyl)chroman-6-yl)methyl)-3H-imidazo[4,5-b]pyridin-6-yl)-2-methylbut-3-yn-2-amine
6-fluoro-3-((8-methoxy-2-(6-methoxypyridin-3-yl)chroman-6-yl)methyl)-3H-imidazo[4,5-b]pyridine
4-(3-((8-methoxy-2-(6-methoxypyridin-3-yl)chroman-6-yl)methyl)-3H-imidazo[4,5-b]pyridin-6-yl)-2-methylbut-3-yn-2-amine
4-(3-((8-methoxy-2-(6-methoxypyridin-3-yl)chroman-6-yl)methyl)-3H-imidazo[4,5-b]pyridin-6-yl)morpholine
3-((8-methoxy-2-(6-methoxypyridin-3-yl)chroman-6-yl)methyl)-6-(2-methyl-1H-imidazol-1-yl)-3H-imidazo[4,5-b]pyridine
3-((8-methoxy-2-(6-methoxypyridin-3-yl)chroman-6-yl)methyl)-3H-imidazo[4,5-b]pyridine
4-(3-((8-fluoro-2-(6-methoxypyridin-3-yl)chroman-6-yl)methyl)-3H-imidazo[4,5-b]pyridin-6-yl)-2-methylbut-3-yn-2-amine
4-(3-((8-methoxy-2-(6-methylpyridin-3-yl)chroman-6-yl)methyl)-3H-imidazo[4,5-b]pyridin-6-yl)-2-methylbut-3-yn-2-amine
4-(3-((8-methoxy-2-(6-methylpyridin-3-yl)chroman-6-yl)methyl)-3H-imidazo[4,5-b]pyridin-6-yl)morpholine
3-((8-methoxy-2-(6-methylpyridin-3-yl)chroman-6-yl)methyl)-6-(2-methyl-1H-imidazol-1-yl)-3H-imidazo[4,5-b]pyridine
6-cyclopropyl-3-((8-methoxy-2-(6-methylpyridin-3-yl)chroman-6-yl)methyl)-3H-imidazo[4,5-b]pyridine
4-(3-((2-(6-ethylpyridin-3-yl)-8-methoxychroman-6-yl)methyl)-3H-imidazo[4,5-b]pyridin-6-yl)-2-methylbut-3-yn-2-amine
4-(3-((2-(6-ethylpyridin-3-yl)-8-methoxychroman-6-yl)methyl)-3H-imidazo[4,5-b]pyridin-6-yl)morpholine
3-((2-(6-ethylpyridin-3-yl)-8-methoxychroman-6-yl)methyl)-6-(2-methyl-1H-imidazol-1-yl)-3H-imidazo[4,5-b]pyridine
4-(3-((8-methoxy-2-(2-methylthiazol-4-yl)chroman-6-yl)methyl)-3H-imidazo[4,5-b]pyridin-6-yl)-2-methylbut-3-yn-2-amine
4-(3-((8-methoxy-2-(2-methylthiazol-4-yl)chroman-6-yl)methyl)-3H-imidazo[4,5-b]pyridin-6-yl)morpholine
2-methyl-4-(3-((4-methyl-2-(4-(trifluoromethyl)phenyl)-3,4-dihydro-2H-benzo[b][1,4]oxazin-6-yl)methyl)-3H-imidazo[4,5-b]pyridin-6-yl)but-3-yn-2-amine
4-methyl-6-((6-(1-methyl-1H-pyrazol-4-yl)-3H-imidazo[4,5-b]pyridin-3-yl)methyl)-2-(4-(trifluoromethyl)phenyl)-3,4-dihydro-2H-benzo[b][1,4]oxazine
6-bromo-3-((2-(6-methoxypyridin-3-yl)-2,3-dihydrobenzo[b][1,4]oxathiin-6-yl)methyl)-3H-imidazo[4,5-b]pyridine
4-(3-((2-(6-methoxypyridin-3-yl)-2,3-dihydrobenzo[b][1,4]oxathiin-6-yl)methyl)-3H-imidazo[4,5-b]pyridin-6-yl)-2-methylbut-3-yn-2-amine
3-((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine
6-((3H-imidazo[4,5-b]pyridin-3-yl)methyl)-4-methoxy-2-((6-methoxypyridin-3-yl)methyl)benzo[d]oxazole
(S)-3-((2-(6-cyclopropylpyridin-3-yl)-8-methoxy-2,3-dihydrobenzo[b][1,4]dioxin-6-yl)methyl)-3H-imidazo[4,5-b]pyridine
(R)-3-((2-(6-cyclopropylpyridin-3-yl)-8-methoxy-2,3-dihydrobenzo[b][1,4]dioxin-6-yl)methyl)-3H-imidazo[4,5-b]pyridine
(R)-3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine
(S)-3-((8-methoxy-2-(6-methoxypyridin-3-yl)-2,3-dihydrobenzo[b][1,4]dioxin-6-yl)methyl)-6-((1-methylazetidin-3-yl)oxy)-3H-imidazo[4,5-b]pyridine
(S)-3-((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine
(R)-3-((2-(6-(2-fluoropropan-2-yl)pyridin-3-yl)-8-methoxy-2,3-dihydrobenzo[b][1,4]dioxin-6-yl)methyl)-3H-imidazo[4,5-b]pyridine and/or stereoisomers, optical isomers, racemic and diastereomeric mixtures, and/or pharmaceutically acceptable salts thereof.

12. A compound chosen from 3-((8-methoxy-2-(6-methoxypyridin-3-yl)-3-methyl-2,3-dihydrobenzo[b][1,4]dioxin-6-yl)methyl)-3H-imidazo[4,5-b]pyridine, and/or stereoisomers, optical isomers, racemic and diastereomeric mixtures, and/or pharmaceutically acceptable salts thereof.

13. A compound of claim 12, which is 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine.

14. A pharmaceutical composition comprising a pharmaceutically acceptable excipient and a compound of claim 1 and/or a pharmaceutically acceptable salt thereof.

15. A pharmaceutical composition comprising a pharmaceutically acceptable excipient and a compound of claim 11 and/or a pharmaceutically acceptable salt thereof.

* * * * *

UNITED STATES PATENT AND TRADEMARK OFFICE
CERTIFICATE OF CORRECTION

PATENT NO. : 11,274,108 B2  
APPLICATION NO. : 15/745223  
DATED : March 15, 2022  
INVENTOR(S) : John L. Kane et al.

Page 1 of 1

It is certified that error appears in the above-identified patent and that said Letters Patent is hereby corrected as shown below:

In the Claims

Claim 1, Column 287, Line 12, "alkyl C(O)O-, R8 (C1 C10)-alkoxy-, (C3 C10)", should be -- alkyl C(O)O-, R8 (C1 C10)alkoxy-, (C3 C10) --

Claim 11, Column 291, Line 17, "(S)-4-(3-((2-(4-methoxyphenyl)-2,3-dihydrobenzo[b][1,4]clioxin-6-", should be -- (S)-4-(3-((2-(4-methoxyphenyl)-2,3-dihydrobenzo[b][1,4]dioxin-6- --

Claim 11, Column 291, Line 20, "3-((2-(4-methoxyphenyl)-2,3-dihydrobenzo[b][1,4]clioxin-6-yl)methyl)-", should be -- 3-((2-(4-methoxyphenyl)-2,3-dihydrobenzo[b][1,4]dioxin-6-yl)methyl)- --

Claim 11, Column 291, Line 22, "3-((2-(4-methoxyphenyl)-2,3-dihydrobenzo[b][1,4]clioxin-6-yl)methyl)-", should be -- 3-((2-(4-methoxyphenyl)-2,3-dihydrobenzo[b][1,4]dioxin-6-yl)methyl)- --

Claim 11, Column 291, Line 58, "imidazo[4,5-b]pyridinehydrochloride", should be -- imidazo[4,5-b]pyridine hydrochloride --

Claim 11, Column 294, Line 24, "yl)-3H-imidazo[4,5-b]pyridinehydrochloride", should be -- yl)-3H-imidazo [4,5-b]pyridine hydrochloride --

Claim 11, Column 295, Line 11, "4-(64(3H-imidazo[4,5-b]pyridin-3-yl)methyl)-8-methoxy-2,3-", should be -- 4-(6-((3H-imidazo[4,5-b]pyridin-3-yl)methyl)-8-methoxy-2,3- --

Claim 11, Column 295, Line 48, "(pyridin-3-yl)-3H-imidazo[4,5-b]pyridineformate", should be -- (pyridin-3-yl)-3H-imidazo[4,5-b]pyridine formate --

Claim 11, Column 295, Line 50, "(1-methyl-1H-pyrazol-4-yl)-3H-imidazo[4,5-b]pyridineformate" should be -- (1-methyl-1H-pyrazol-4-yl)-3H-imidazo[4,5-b]pyridine formate --

Signed and Sealed this  
Eighteenth Day of April, 2023

Katherine Kelly Vidal  
*Director of the United States Patent and Trademark Office*